(12) United States Patent
Blum et al.

(10) Patent No.: US 7,972,390 B2
(45) Date of Patent: Jul. 5, 2011

(54) METHODS FOR CONTROLLING CRYSTAL GROWTH, CRYSTALLIZATION, STRUCTURES AND PHASES IN MATERIALS AND SYSTEMS

(75) Inventors: Bentley J. Blum, Fisher Island, FL (US); Juliana H. J. Brooks, North East, MD (US); Mark G. Mortenson, North East, MD (US)

(73) Assignee: GR Intellectual Reserve, LLC, Havre de Grace, MD (US)

( * ) Notice: Subject to any disclaimer, the term of this patent is extended or adjusted under 35 U.S.C. 154(b) by 795 days.

(21) Appl. No.: 10/508,462

(22) PCT Filed: Mar. 21, 2003

(86) PCT No.: PCT/US03/08904
§ 371 (c)(1),
(2), (4) Date: Jun. 6, 2005

(87) PCT Pub. No.: WO03/089692
PCT Pub. Date: Oct. 30, 2003

(65) Prior Publication Data
US 2006/0037177 A1  Feb. 23, 2006

(51) Int. Cl.
*C13K 1/10* (2006.01)

(52) U.S. Cl. .................. 23/295 R; 23/296
(58) Field of Classification Search .......... 23/295 R, 23/296
See application file for complete search history.

(56) References Cited

U.S. PATENT DOCUMENTS

| 2,876,083 | A | * | 3/1959 | Prietl | ............... | 23/295 R |
| 3,867,496 | A | * | 2/1975 | Mlavsky et al. | ............... | 264/71 |
| 5,338,519 | A | * | 8/1994 | Jancic et al. | ............... | 422/253 |

* cited by examiner

*Primary Examiner* — Edward M Johnson
(74) *Attorney, Agent, or Firm* — Mark G. Mortenson

(57) ABSTRACT

This invention relates to novel methods for affecting, and/or directing various crystal formation, structure formation or phase formation/phase change reaction pathways or systems by exposing one or more components in a holoreaction system to at least one spectral energy pattern. In a first aspect of the invention, at least one spectral energy pattern can be applied to a crystallization reaction system. In a second aspect of the invention, at least one spectral energy conditioning pattern can be applied to a conditioning reaction system. The spectral energy conditioning pattern can, for example, be applied at a separate location from the reaction vessel (e.g., in a conditioning reaction vessel) or can be applied in (or to) the reaction vessel, but prior to other (or all) crystallization reaction system participants being introduced into the reaction vessel.

3 Claims, 100 Drawing Sheets

Initial Frequencies (Hz)

| | | |
|---|---|---|
| 400 | and | 100 |
| 400 + 100 = 500 | and | 400 - 100 = 300 |
| 500 + 300 = 800 | and | 500 - 300 = 200 |
| 800 + 200 = 1000 | and | 800 - 200 = 600 |
| 1000 + 600 = 1600 | and | 1000 - 600 = 400 |

| Sum (Added) Frequencies (Hz) | Difference (Subtracted) Frequencies (Hz) |
|---|---|
| 400 | 100 |
| 500 | 300 |
| 800 | 200 |
| 1000 | 600 |
| 1600 | 400 |
| 2000 | 1200 |
| 3200 | 800 |

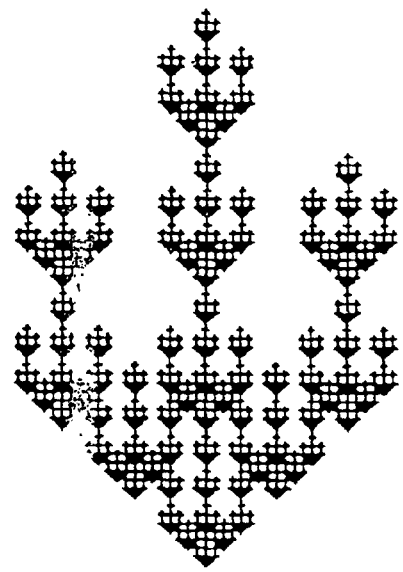
Fig. 6a  Fig. 6b  Fig. 6c  Fig. 6d
Fig. 7a
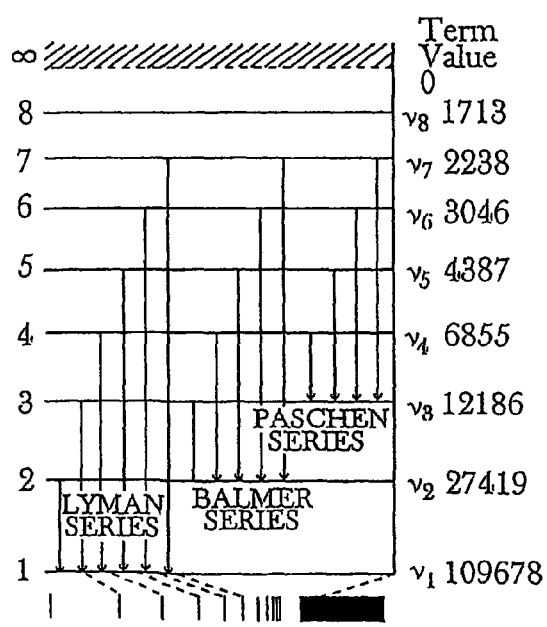
Fig. 7b
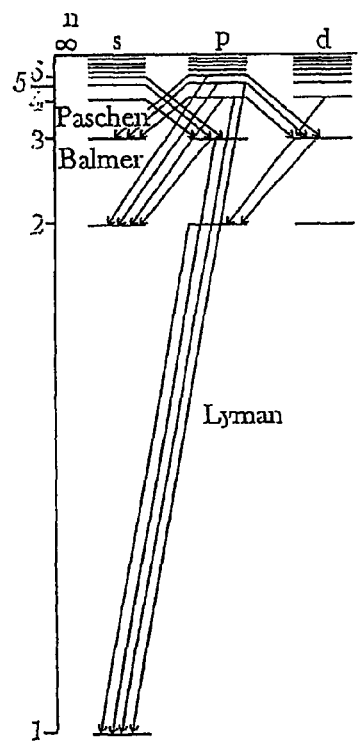

Frequency Curves - THz (relative intensity)

| V | IV | III | II | I |
|---|---|---|---|---|
| 40 (6) | 74 (15) | 160 (40) | 456 (300) | 2466 (1000) |
| 64 (4) | 114 (8) | 234 (20) | 616 (80) | 2923 (300) |
| | 138 (5) | 274 (12) | 690 (30) | 3082 (100) |
| | | 298 (7) | 731 (15) | 3156 (50) |
| | | 314 (5) | 755 (8) | 3196 (30) |
| | | | 770 (6) | 3220 (20) |
| | | | 781 (5) | 3236 (15) |

Resonance curve with high Q

Resonance curve with low Q

Spectral pattern at low temperature

Spectral pattern at moderate temperature

Spectral pattern at high temperature

Separate and distinct spectral curves at low temperature

Overlapping spectral curves at higher temperature, allowing resonant energy transfer ○ Oxygen
● Aluminum or silicon Emission spectrum
T = 50K High resolution spectrum Rotational and Vibrational Frequencies for LiF

| Rotational Transition | | | | |
|---|---|---|---|---|
| 0→1 | 89,740.46 | 88,319.18 | 86,921.20 | |
| 1→2 | 179,470.35 | 176,627.91 | 173,832.04 | 171,082.27 |
| 2→3 | 269,179.18 | 264,915.79 | 260,722.24 | 256,597.84 |
| 3→4 | 358,856.19 | 353,172.23 | 347,581.39 | 342,082.66 |
| 4→5 | 448,491.07 | | | |
| Vibrational Level | 0 | 1 | 2 | 3 |

Fig. 43a

Rotational and Vibrational Frequencies for LiF

Differences Between Rotational And Vibrational Frequencies (MHz) For LiF

| Rotational Transition | | | |
|---|---|---|---|
| 0→1 | 1,421.28 | 1,397.98 | |
| 1→2 | 2,842.44 | 2,795.87 | 2,749.77 |
| 2→3 | 4,263.39 | 4,193.55 | 4,124.40 |
| 3→4 | 5,683.96 | 5,590.84 | 5,498.73 |
| 4→5 | 7,104.24 | | |
| Vibrational Level | 0 | 1 | 2 | 3 |

Fig. 43b

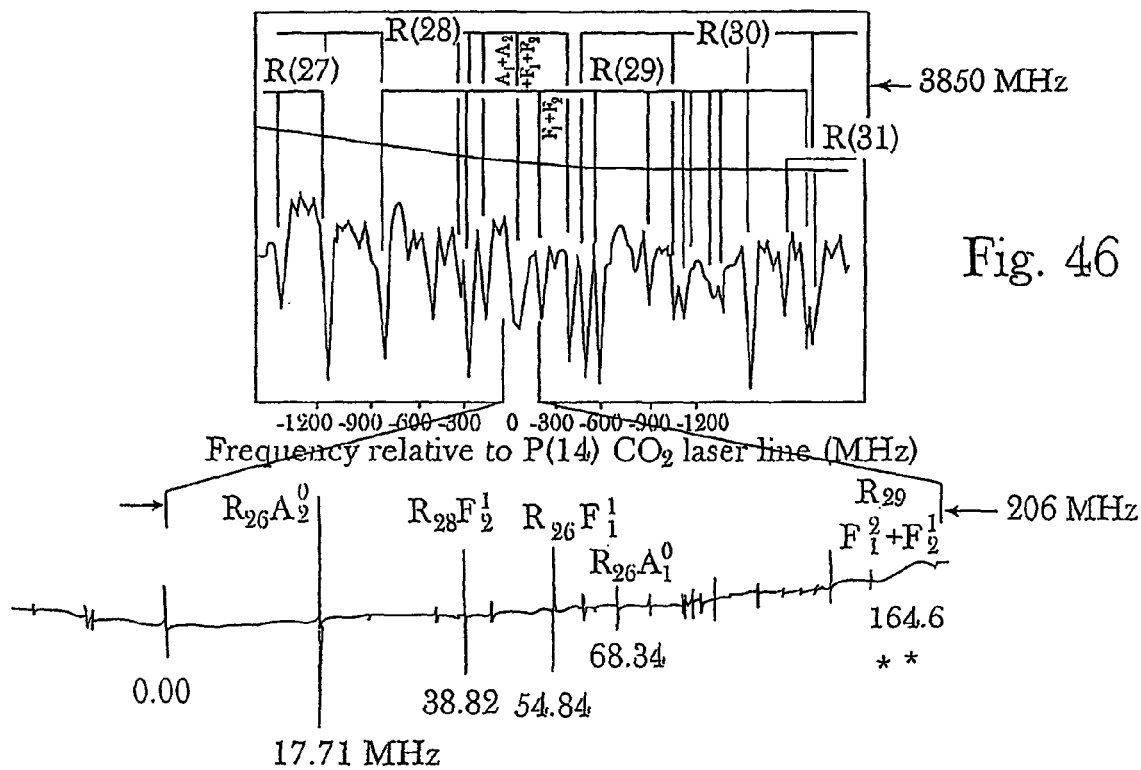
Fig. 46
Fig. 48
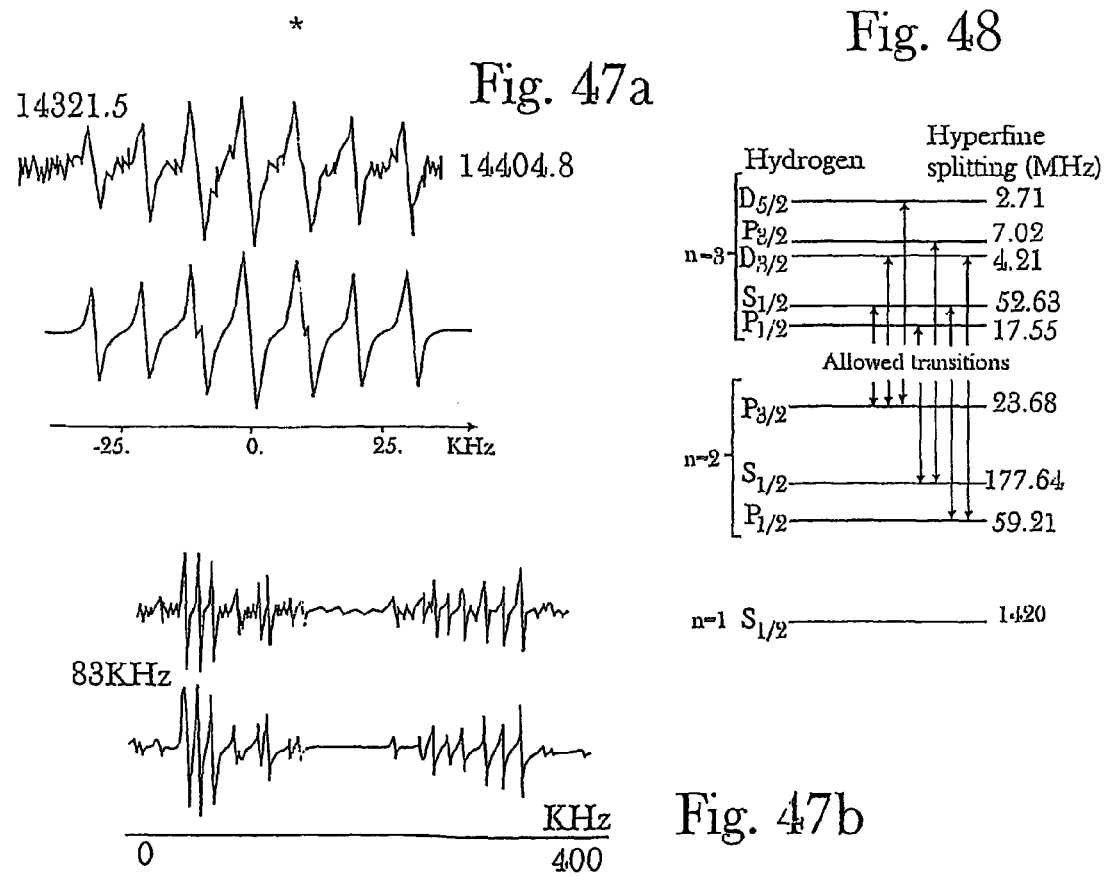
Fig. 47a
Fig. 47b

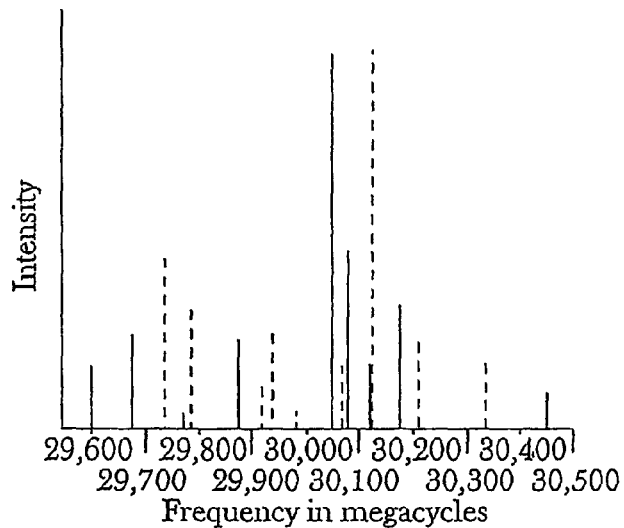

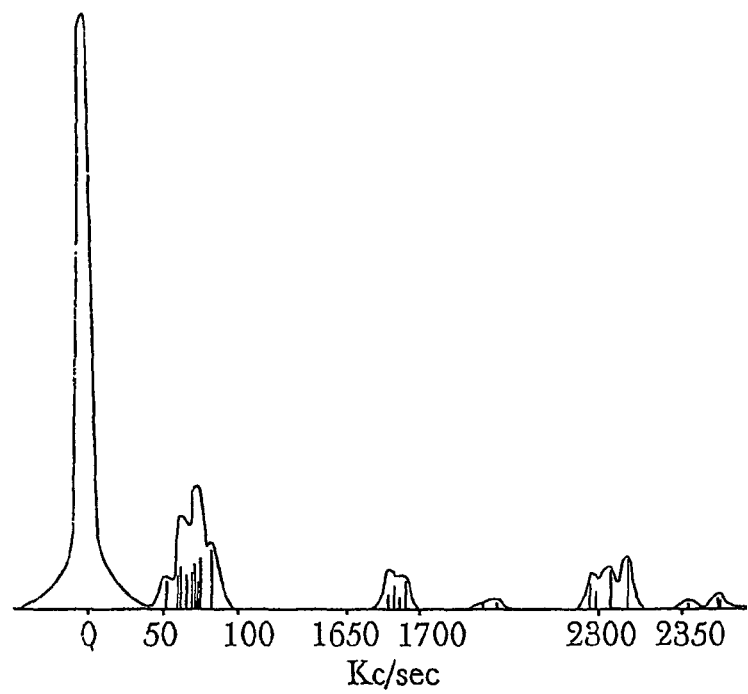
Fig. 52
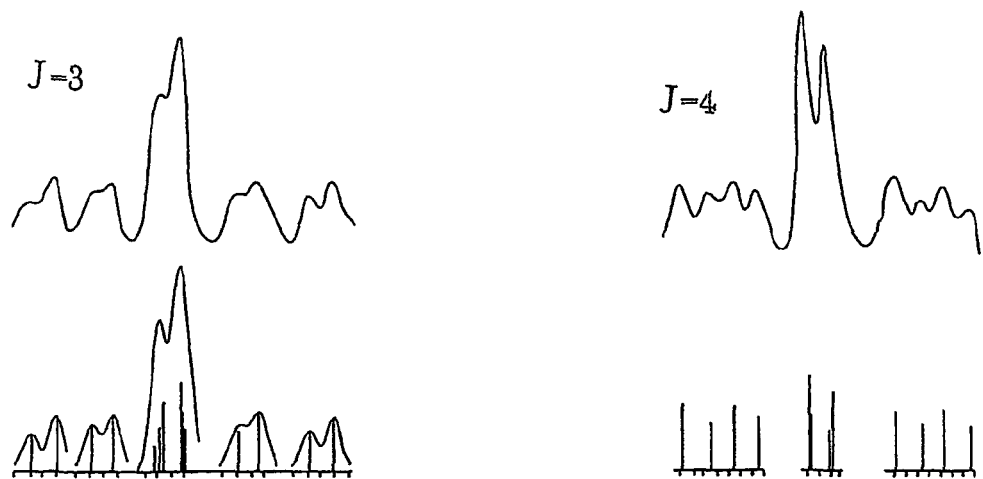
Fig. 53
Fig. 54

| | Field |
|---|---|
| | No field |
Fig. 62a
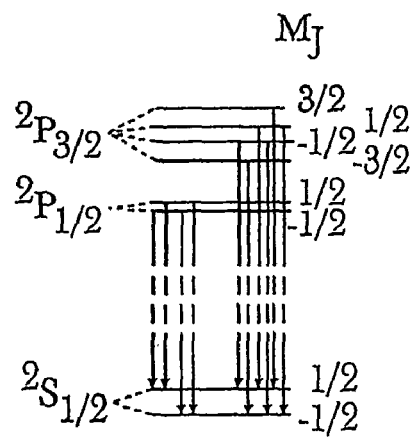
Fig. 62b
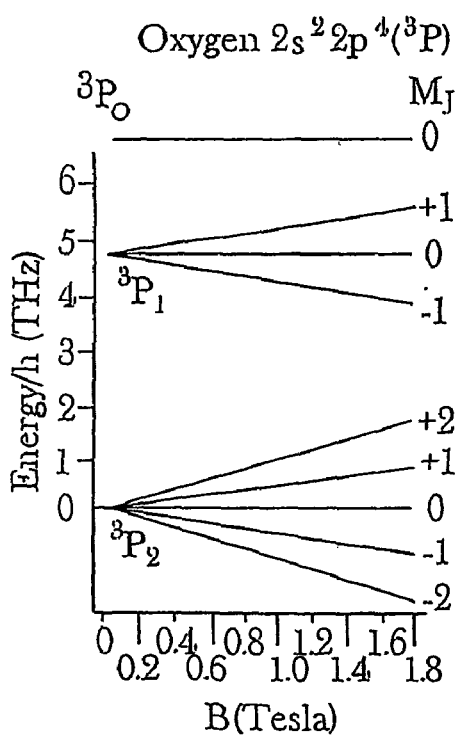
Fig. 63
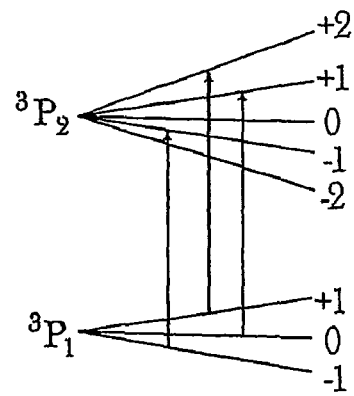
Fig. 64

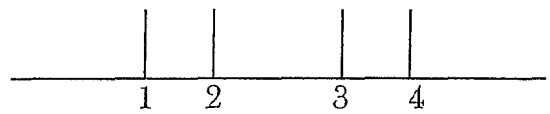
Fig. 67a
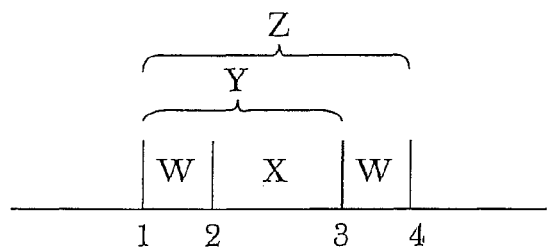
Fig. 67b
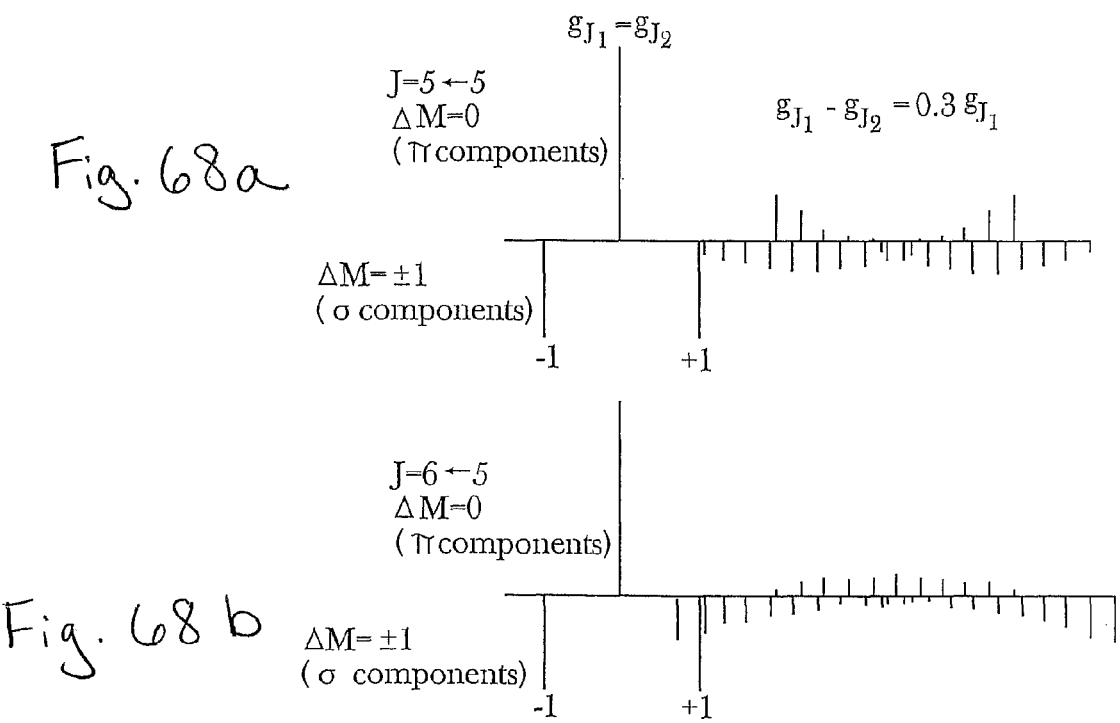
Fig. 68a
Fig. 68b

| 100 | 7.7144 | 10.786 | 15.732 | 24.2362 | 40.1985 | 64.4353 | 74.0016 | 111.2 | 138.428 | 159.881 | 233.882 | 274.031 | 293.319 | 314.051 | 456.811 |
|---|---|---|---|---|---|---|---|---|---|---|---|---|---|---|---|
| 364.501 | 0 | 0 | 0 | 0 | 0 | 0 | 0 | 0 | 0 | 0 | 0 | 0 | 0 | 0 | 0 |
| 421.428 | 0 | 0 | 0 | 0 | 0 | 0 | 0 | 0 | 0 | 0 | 0 | 0 | 0 | 0 | 0 |
| 438.127 | 0 | 0 | 0 | 0 | 0 | 0 | 0 | 0 | 0 | 0 | 0 | 0 | 0 | 0 | 0 |
| 443.127 | 0 | 0 | 0 | 0 | 0 | 0 | 0 | 0 | 0 | 0 | 0 | 0 | 0 | 0 | 0 |
| 443.479 | 0 | 0 | 0 | 0 | 0 | 0 | 5.99283 | 0 | 0 | 0 | 0 | 0 | 0 | 0 | 0 |
| 449.757 | 0 | 0 | 0 | 0 | 0 | 0 | 0 | 0 | 0 | 0 | 0 | 0 | 0 | 0 | 0 |
| 459.561 | 0 | 0 | 0 | 0 | 0 | 0 | 0 | 0 | 0 | 0 | 0 | 0 | 0 | 0 | 1.00602 |
| 473.052 | 0 | 0 | 0 | 0 | 0 | 0 | 0 | 0 | 0 | 0 | 0 | 0 | 0 | 0 | 0 |
| 474.476 | 0 | 43.9902 | 0 | 0 | 0 | 0 | 0 | 0 | 0 | 0 | 0 | 0 | 0 | 0 | 0 |
| 497.435 | 0 | 0 | 0 | 0 | 0 | 0 | 0 | 0 | 0 | 0 | 0 | 0 | 0 | 0 | 0 |
| 512.918 | 0 | 0 | 0 | 0 | 0 | 0 | 0 | 0 | 0 | 0 | 0 | 0 | 0 | 0 | 0 |
| 513.333 | 0 | 0 | 0 | 0 | 0 | 0 | 0 | 0 | 0 | 0 | 0 | 0 | 0 | 0 | 0 |
| 520.151 | 0 | 0 | 0 | 0 | 0 | 0 | 0 | 0 | 0 | 0 | 0 | 0 | 0 | 0 | 0 |
| 547.216 | 0 | 0 | 0 | 0 | 0 | 0 | 0 | 0 | 0 | 0 | 0 | 1.99655 | 0 | 0 | 0 |
| 547.489 | 0 | 0 | 0 | 0 | 0 | 0 | 0 | 0 | 0 | 0 | 0 | 1.99754 | 0 | 0 | 0 |
| 556.12 | 0 | 0 | 0 | 0 | 0 | 0 | 0 | 0 | 0 | 0 | 0 | 0 | 0 | 0 | 0 |
| 558.378 | 0 | 0 | 0 | 0 | 0 | 0 | 0 | 0 | 0 | 0 | 0 | 0 | 0 | 0 | 0 |
| 565.537 | 0 | 0 | 0 | 0 | 0 | 0 | 0 | 0 | 0 | 0 | 0 | 0 | 0 | 0 | 0 |
| 573.474 | 0 | 0 | 0 | 0 | 0 | 0 | 0 | 0 | 0 | 0 | 0 | 0 | 0 | 0 | 0 |
| 592.536 | 0 | 0 | 0 | 0 | 0 | 0 | 8.00707 | 0 | 0 | 0 | 0 | 0 | 0 | 0 | 0 |
| 594.35 | 0 | 0 | 0 | 0 | 0 | 0 | 0 | 0 | 0 | 0 | 0 | 0 | 1.99233 | 0 | 0 |
| 614.388 | 0 | 0 | 0 | 0 | 0 | 0 | 0 | 0 | 0 | 0 | 0 | 0 | 0 | 0 | 0 |
| 658.534 | 0 | 0 | 0 | 0 | 0 | 0 | 0 | 0 | 0 | 0 | 0 | 0 | 0 | 0 | 0 |
| 663.126 | 0 | 0 | 0 | 0 | 0 | 0 | 0 | 0 | 0 | 0 | 0 | 0 | 0 | 0 | 0 |
| 666.389 | 0 | 0 | 0 | 0 | 0 | 0 | 9.00586 | 0 | 0 | 0 | 0 | 0 | 0 | 0 | 0 |
| 674.305 | 0 | 0 | 0 | 0 | 0 | 0 | 0 | 0 | 0 | 0 | 0 | 0 | 0 | 0 | 0 |
| 674.821 | 0 | 0 | 0 | 0 | 0 | 0 | 0 | 0 | 0 | 0 | 0 | 0 | 0 | 0 | 0 |
| 682.614 | 0 | 0 | 0 | 0 | 0 | 0 | 0 | 0 | 0 | 0 | 0 | 0 | 0 | 0 | 0 |
| 692.832 | 0 | 0 | 0 | 0 | 0 | 0 | 0 | 0 | 5.00464 | 0 | 0 | 0 | 0 | 0 | 0 |
| 715.081 | 0 | 0 | 0 | 0 | 0 | 0 | 0 | 0 | 0 | 0 | 0 | 0 | 0 | 0 | 0 |
| 719.866 | 0 | 0 | 0 | 0 | 0 | 0 | 0 | 0 | 0 | 0 | 0 | 0 | 0 | 0 | 0 |
| 727.883 | 0 | 0 | 0 | 0 | 0 | 0 | 0 | 0 | 0 | 0 | 0 | 0 | 0 | 0 | 0 |
| 750.124 | 0 | 0 | 0 | 0 | 0 | 0 | 0 | 0 | 0 | 0 | 0 | 0 | 0 | 0 | 0 |
| 755.838 | 0 | 0 | 0 | 0 | 0 | 0 | 0 | 0 | 0 | 0 | 0 | 0 | 0 | 0 | 0 |
| 759.276 | 0 | 0 | 0 | 0 | 0 | 0 | 0 | 0 | 0 | 0 | 0 | 0 | 0 | 0 | 0 |
| 764.2 | 0 | 0 | 0 | 0 | 0 | 0 | 0 | 0 | 0 | 0 | 0 | 0 | 0 | 0 | 0 |
| 768.555 | 0 | 0 | 0 | 0 | 0 | 0 | 0 | 0 | 0 | 0 | 0 | 0 | 0 | 0 | 0 |
| 785.066 | 0 | 0 | 0 | 0 | 0 | 0 | 0 | 0 | 0 | 0 | 0 | 0 | 0 | 0 | 0 |
| 808.623 | 0 | 0 | 0 | 0 | 0 | 0 | 0 | 0 | 0 | 0 | 0 | 0 | 0 | 0 | 0 |
| 810.27 | 0 | 0 | 0 | 0 | 0 | 0 | 0 | 0 | 0 | 0 | 0 | 0 | 0 | 0 | 0 |
| 815.975 | 0 | 0 | 0 | 0 | 0 | 0 | 0 | 0 | 0 | 0 | 0 | 0 | 0 | 0 | 0 |
| 816.431 | 0 | 0 | 0 | 0 | 0 | 0 | 0 | 0 | 0 | 0 | 0 | 0 | 0 | 0 | 0 |
| 818.412 | 0 | 0 | 0 | 0 | 0 | 0 | 0 | 0 | 0 | 0 | 0 | 0 | 0 | 0 | 0 |
| 822.889 | 0 | 0 | 0 | 0 | 0 | 0 | 0 | 0 | 0 | 0 | 0 | 3.00236 | 0 | 0 | 0 |
| 823.68 | 0 | 0 | 0 | 0 | 0 | 0 | 0 | 0 | 0 | 0 | 0 | 1.00597 | 0 | 0 | 0 |
| 826.305 | 0 | 0 | 0 | 33.991 | 0 | 0 | 0 | 0 | 0 | 0 | 0 | 0 | 0 | 0 | 0 |
| 860.17 | 0 | 0 | 0 | 0 | 0 | 0 | 0 | 0 | 0 | 0 | 0 | 0 | 0 | 0 | 0 |
| 880.624 | 0 | 0 | 0 | 0 | 0 | 0 | 0 | 0 | 0 | 0 | 0 | 0 | 0 | 0 | 0 |
| 874.556 | 0 | 0 | 0 | 0 | 0 | 0 | 0 | 0 | 0 | 0 | 0 | 0 | 0 | 0 | 0 |
| 879.639 | 0 | 0 | 0 | 0 | 0 | 0 | 0 | 0 | 0 | 0 | 0 | 0 | 0 | 0 | 0 |
| 901.957 | 0 | 0 | 0 | 0 | 0 | 13.9976 | 0 | 0 | 0 | 0 | 0 | 0 | 0 | 0 | 0 |
| 904.338 | 0 | 0 | 0 | 0 | 0 | 0 | 0 | 0 | 0 | 0 | 0 | 0 | 0 | 0 | 0 |
| 907.95 | 0 | 0 | 0 | 0 | 0 | 0 | 0 | 0 | 0 | 0 | 0 | 0 | 0 | 0 | 0 |
| 911.162 | 0 | 0 | 0 | 0 | 0 | 0 | 0 | 0 | 0 | 0 | 0 | 0 | 0 | 0 | 1.99461 |
| 913.453 | 0 | 0 | 0 | 0 | 0 | 0 | 7.99871 | 0 | 0 | 0 | 0 | 0 | 0 | 0 | 1.99563 |
| 917.24 | 0 | 0 | 0 | 0 | 0 | 0 | 0 | 0 | 0 | 0 | 0 | 0 | 0 | 0 | 2.00792 |
| 920.761 | 0 | 0 | 0 | 0 | 0 | 0 | 0 | 0 | 0 | 0 | 0 | 0 | 0 | 0 | 0 |
| 921.877 | 0 | 0 | 0 | 0 | 0 | 0 | 0 | 0 | 0 | 0 | 0 | 0 | 0 | 0 | 0 |
| 922.336 | 0 | 0 | 0 | 0 | 0 | 0 | 0 | 0 | 0 | 0 | 0 | 0 | 0 | 0 | 0 |
| 927.169 | 0 | 0 | 0 | 0 | 0 | 0 | 0 | 0 | 0 | 0 | 0 | 0 | 0 | 0 | 0 |
| 929.067 | 0 | 0 | 58.9923 | 0 | 0 | 0 | 0 | 0 | 0 | 0 | 0 | 0 | 0 | 0 | 0 |
| 935.67 | 0 | 0 | 0 | 0 | 0 | 0 | 0 | 0 | 0 | 0 | 4.00061 | 0 | 0 | 0 | 0 |
| 936.044 | 0 | 0 | 0 | 0 | 0 | 0 | 0 | 0 | 0 | 0 | 4.00471 | 0 | 0 | 0 | 0 |
| 949.744 | 0 | 0 | 0 | 0 | 0 | 0 | 0 | 0 | 0 | 0 | 0 | 0 | 0 | 0 | 0 |
| 954.939 | 0 | 0 | 0 | 0 | 0 | 0 | 0 | 0 | 0 | 0 | 0 | 0 | 0 | 0 | 0 |
| 967.06 | 0 | 0 | 0 | 0 | 0 | 15.0079 | 0 | 0 | 0 | 0 | 0 | 0 | 0 | 0 | 0 |
| 975.906 | 0 | 0 | 0 | 0 | 0 | 0 | 0 | 0 | 0 | 0 | 0 | 0 | 0 | 0 | 0 |
| 978.208 | 0 | 0 | 0 | 0 | 0 | 0 | 0 | 0 | 0 | 0 | 0 | 0 | 0 | 0 | 0 |
| 985.304 | 0 | 0 | 0 | 0 | 0 | 0 | 0 | 0 | 0 | 0 | 0 | 0 | 0 | 0 | 0 |
| 987.312 | 0 | 0 | 0 | 0 | 0 | 0 | 0 | 0 | 0 | 0 | 0 | 0 | 0 | 0 | 0 |
| 993.388 | 0 | 0 | 0 | 0 | 0 | 0 | 0 | 0 | 0 | 0 | 0 | 0 | 0 | 0 | 0 |
| 998.553 | 0 | 0 | 0 | 0 | 0 | 0 | 0 | 0 | 0 | 0 | 0 | 0 | 0 | 0 | 0 |
| 999.885 | 0 | 0 | 0 | 0 | 0 | 0 | 0 | 0 | 0 | 0 | 0 | 0 | 0 | 0 | 0 |
| 1012.56 | 0 | 0 | 0 | 0 | 0 | 0 | 0 | 0 | 0 | 0 | 0 | 0 | 0 | 0 | 0 |
| 1013.12 | 0 | 0 | 0 | 0 | 0 | 0 | 0 | 0 | 0 | 0 | 0 | 0 | 0 | 0 | 0 |
| 1018.06 | 0 | 0 | 0 | 42.0023 | 0 | 0 | 0 | 0 | 0 | 0 | 0 | 0 | 0 | 0 | 0 |

Fig. 69a

| 109 | 2.7144 | 10.786 | 15.732 | 24.2392 | 49.1985 | 64.4367 | 74.0016 | 114.2 | 139.428 | 159.881 | 233.882 | 274.091 | 298.319 | 314.051 | 456.911 |
|---|---|---|---|---|---|---|---|---|---|---|---|---|---|---|---|
| 1018.75 | 0 | 0 | 0 | 0 | 0 | 0 | 0 | 0 | 0 | 0 | 0 | 0 | 0 | 0 | 0 |
| 1023.26 | 0 | 0 | 0 | 0 | 0 | 0 | 0 | 0 | 0 | 0 | 0 | 0 | 0 | 0 | 0 |
| 1026.2 | 0 | 0 | 0 | 0 | 0 | 0 | 0 | 0 | 0 | 0 | 0 | 0 | 0 | 0 | 0 |
| 1026.92 | 0 | 0 | 0 | 0 | 0 | 0 | 0 | 8.99229 | 0 | 0 | 0 | 0 | 0 | 0 | 0 |
| 1028.96 | 0 | 0 | 0 | 0 | 0 | 0 | 0 | 0 | 0 | 0 | 0 | 0 | 0 | 0 | 0 |
| 1029.42 | 0 | 0 | 0 | 0 | 0 | 0 | 0 | 0 | 0 | 0 | 0 | 0 | 0 | 0 | 0 |
| 1031.67 | 0 | 0 | 0 | 0 | 0 | 0 | 0 | 0 | 0 | 0 | 0 | 0 | 0 | 0 | 0 |
| 1034.53 | 0 | 0 | 0 | 0 | 0 | 0 | 0 | 0 | 0 | 0 | 0 | 0 | 0 | 0 | 0 |
| 1035.96 | 0 | 0 | 0 | 0 | 0 | 0 | 13.9992 | 0 | 0 | 0 | 0 | 0 | 0 | 0 | 0 |
| 1036.19 | 0 | 0 | 0 | 0 | 0 | 0 | 14.0023 | 0 | 0 | 0 | 0 | 0 | 0 | 0 | 0 |
| 1037.99 | 0 | 0 | 0 | 0 | 0 | 0 | 0 | 0 | 0 | 0 | 0 | 0 | 0 | 0 | 0 |
| 1050.76 | 0 | 0 | 0 | 0 | 0 | 0 | 0 | 0 | 0 | 0 | 0 | 0 | 0 | 0 | 0 |
| 1057.58 | 0 | 0 | 0 | 0 | 0 | 0 | 0 | 0 | 0 | 0 | 0 | 0 | 0 | 0 | 0 |
| 1059.23 | 0 | 0 | 0 | 0 | 0 | 0 | 0 | 0 | 0 | 0 | 0 | 0 | 0 | 0 | 0 |
| 1063.75 | 0 | 0 | 0 | 0 | 0 | 0 | 0 | 0 | 0 | 0 | 0 | 0 | 0 | 0 | 0 |
| 1067.44 | 0 | 0 | 0 | 0 | 0 | 0 | 0 | 0 | 0 | 0 | 0 | 0 | 0 | 0 | 0 |
| 1069.45 | 0 | 0 | 0 | 0 | 0 | 0 | 0 | 0 | 0 | 0 | 0 | 0 | 0 | 0 | 0 |
| 1073.27 | 0 | 0 | 0 | 0 | 0 | 0 | 0 | 0 | 0 | 0 | 0 | 0 | 0 | 0 | 0 |
| 1080.72 | 0 | 0 | 0 | 0 | 0 | 0 | 0 | 0 | 0 | 0 | 0 | 0 | 0 | 0 | 0 |
| 1081.82 | 0 | 0 | 0 | 0 | 0 | 0 | 0 | 0 | 0 | 0 | 0 | 0 | 0 | 0 | 0 |
| 1081.63 | 0 | 0 | 0 | 0 | 0 | 0 | 0 | 0 | 0 | 0 | 0 | 0 | 0 | 0 | 0 |
| 1082.35 | 0 | 0 | 0 | 0 | 0 | 0 | 0 | 0 | 0 | 0 | 0 | 0 | 0 | 0 | 0 |
| 1088.21 | 0 | 0 | 0 | 0 | 0 | 0 | 0 | 0 | 0 | 0 | 0 | 0 | 0 | 0 | 0 |
| 1088.63 | 0 | 0 | 0 | 0 | 0 | 0 | 0 | 0 | 0 | 0 | 0 | 0 | 0 | 0 | 0 |
| 1091.1 | 0 | 0 | 0 | 0 | 0 | 0 | 0 | 0 | 0 | 0 | 0 | 0 | 0 | 0 | 0 |
| 1094.74 | 0 | 0 | 0 | 0 | 0 | 0 | 0 | 0 | 0 | 0 | 0 | 3.99422 | 0 | 0 | 0 |
| 1096.55 | 0 | 0 | 0 | 0 | 0 | 0 | 0 | 0 | 0 | 0 | 0 | 4.00082 | 0 | 0 | 0 |
| 1098.17 | 0 | 0 | 0 | 0 | 0 | 0 | 0 | 0 | 0 | 0 | 0 | 4.00674 | 0 | 0 | 0 |
| 1102.57 | 0 | 0 | 0 | 0 | 0 | 0 | 0 | 0 | 0 | 0 | 0 | 0 | 0 | 0 | 0 |
| 1104.97 | 0 | 0 | 0 | 0 | 0 | 0 | 0 | 0 | 0 | 0 | 0 | 0 | 0 | 0 | 0 |
| 1107.93 | 0 | 0 | 0 | 0 | 0 | 0 | 0 | 0 | 8.00308 | 0 | 0 | 0 | 0 | 0 | 0 |
| 1109.36 | 0 | 0 | 0 | 0 | 0 | 0 | 14.991 | 0 | 0 | 0 | 0 | 0 | 0 | 0 | 0 |
| 1110.93 | 0 | 103.003 | 0 | 0 | 0 | 0 | 0 | 0 | 0 | 0 | 0 | 0 | 0 | 0 | 0 |
| 1119.82 | 0 | 0 | 0 | 0 | 0 | 0 | 0 | 0 | 0 | 7.00408 | 0 | 0 | 0 | 0 | 0 |
| 1120.9 | 0 | 0 | 0 | 0 | 0 | 0 | 0 | 0 | 0 | 0 | 0 | 0 | 0 | 0 | 0 |
| 1127.27 | 0 | 0 | 0 | 0 | 0 | 0 | 0 | 0 | 0 | 0 | 0 | 0 | 0 | 0 | 0 |
| 1127.82 | 0 | 0 | 0 | 0 | 0 | 0 | 0 | 0 | 0 | 0 | 0 | 0 | 0 | 0 | 0 |
| 1130.93 | 0 | 0 | 0 | 0 | 0 | 0 | 0 | 0 | 0 | 0 | 0 | 0 | 0 | 0 | 0 |
| 1132.62 | 0 | 105.008 | 71.9947 | 0 | 0 | 0 | 0 | 0 | 0 | 0 | 0 | 0 | 0 | 0 | 0 |
| 1135.86 | 0 | 0 | 0 | 0 | 0 | 0 | 0 | 0 | 0 | 0 | 0 | 0 | 0 | 0 | 0 |
| 1140.75 | 0 | 0 | 0 | 0 | 0 | 0 | 0 | 0 | 0 | 0 | 0 | 0 | 0 | 0 | 0 |
| 1144.43 | 0 | 0 | 0 | 0 | 0 | 0 | 0 | 0 | 0 | 0 | 0 | 0 | 0 | 0 | 0 |
| 1151.66 | 0 | 0 | 0 | 0 | 0 | 0 | 0 | 0 | 0 | 0 | 0 | 0 | 0 | 0 | 0 |
| 1154.82 | 0 | 0 | 0 | 0 | 0 | 0 | 0 | 0 | 0 | 0 | 0 | 0 | 0 | 0 | 0 |
| 1174.62 | 0 | 0 | 0 | 0 | 0 | 0 | 0 | 0 | 0 | 0 | 0 | 0 | 0 | 0 | 0 |
| 1175.91 | 0 | 0 | 0 | 0 | 0 | 0 | 0 | 0 | 0 | 0 | 0 | 0 | 0 | 0 | 0 |
| 1180.66 | 0 | 0 | 0 | 0 | 0 | 0 | 0 | 0 | 0 | 0 | 0 | 0 | 0 | 0 | 0 |
| 1181.02 | 0 | 0 | 0 | 0 | 0 | 0 | 0 | 0 | 0 | 0 | 0 | 0 | 0 | 0 | 0 |
| 1185.23 | 0 | 0 | 0 | 0 | 0 | 0 | 0 | 0 | 0 | 0 | 0 | 0 | 0 | 0 | 0 |
| 1187.63 | 0 | 0 | 0 | 48.9383 | 0 | 0 | 0 | 0 | 0 | 0 | 0 | 0 | 0 | 0 | 0 |
| 1191.74 | 0 | 0 | 0 | 0 | 0 | 0 | 0 | 0 | 0 | 0 | 0 | 0 | 3.99495 | 0 | 0 |
| 1192 | 0 | 0 | 0 | 0 | 0 | 0 | 0 | 0 | 0 | 0 | 0 | 0 | 3.99572 | 0 | 0 |
| 1192.46 | 0 | 0 | 0 | 0 | 0 | 0 | 0 | 0 | 0 | 0 | 0 | 0 | 3.99726 | 0 | 0 |
| 1195.11 | 0 | 0 | 0 | 0 | 0 | 0 | 0 | 0 | 0 | 0 | 0 | 0 | 4.00615 | 0 | 0 |
| 1196.33 | 0 | 0 | 0 | 0 | 0 | 0 | 0 | 0 | 0 | 0 | 0 | 0 | 0 | 0 | 0 |
| 1198.89 | 0 | 0 | 0 | 0 | 0 | 0 | 0 | 0 | 0 | 0 | 0 | 0 | 0 | 0 | 0 |
| 1201.19 | 0 | 0 | 0 | 0 | 0 | 0 | 0 | 0 | 0 | 0 | 0 | 0 | 0 | 0 | 0 |
| 1203.93 | 0 | 0 | 0 | 0 | 0 | 0 | 0 | 0 | 0 | 0 | 0 | 0 | 0 | 0 | 0 |
| 1205.36 | 0 | 0 | 0 | 0 | 0 | 0 | 0 | 0 | 0 | 0 | 0 | 0 | 0 | 0 | 0 |
| 1213.24 | 0 | 0 | 0 | 0 | 0 | 0 | 0 | 0 | 0 | 0 | 0 | 0 | 0 | 0 | 0 |
| 1214.99 | 0 | 0 | 0 | 0 | 0 | 0 | 0 | 0 | 0 | 0 | 0 | 0 | 0 | 0 | 0 |
| 1223.16 | 0 | 0 | 0 | 0 | 0 | 0 | 0 | 0 | 0 | 0 | 0 | 0 | 0 | 0 | 0 |
| 1228.63 | 0 | 0 | 0 | 0 | 0 | 0 | 0 | 0 | 0 | 0 | 0 | 0 | 0 | 0 | 0 |
| 1230.33 | 0 | 0 | 0 | 0 | 0 | 0 | 0 | 0 | 0 | 0 | 0 | 0 | 0 | 0 | 0 |
| 1234.17 | 0 | 0 | 0 | 0 | 0 | 0 | 0 | 0 | 0 | 0 | 0 | 0 | 0 | 0 | 0 |
| 1234.63 | 0 | 0 | 0 | 0 | 0 | 0 | 0 | 0 | 0 | 0 | 0 | 0 | 0 | 0 | 0 |
| 1234.71 | 0 | 0 | 0 | 0 | 0 | 0 | 0 | 0 | 0 | 0 | 0 | 0 | 0 | 0 | 0 |
| 1239.81 | 0 | 0 | 0 | 0 | 0 | 0 | 0 | 0 | 0 | 0 | 0 | 0 | 0 | 0 | 0 |
| 1247.53 | 0 | 0 | 0 | 0 | 0 | 0 | 0 | 0 | 0 | 0 | 0 | 0 | 0 | 0 | 0 |
| 1248.16 | 0 | 0 | 0 | 0 | 0 | 0 | 0 | 0 | 0 | 0 | 0 | 0 | 0 | 0 | 0 |
| 1251.13 | 0 | 115.9360 | 0 | 0 | 0 | 0 | 0 | 0 | 0 | 0 | 0 | 0 | 0 | 0 | 0 |
| 1254.61 | 0 | 0 | 0 | 0 | 0 | 0 | 0 | 0 | 0 | 0 | 0 | 0 | 0 | 3.99492 | 0 |
| 1256.04 | 0 | 0 | 0 | 0 | 0 | 0 | 10.5986 | 0 | 0 | 0 | 0 | 0 | 0 | 3.99948 | 0 |
| 1257.71 | 0 | 0 | 0 | 0 | 0 | 16.9957 | 0 | 0 | 0 | 0 | 0 | 0 | 0 | 4.0048 | 0 |
| 1265.67 | 0 | 0 | 0 | 0 | 0 | 0 | 0 | 0 | 0 | 0 | 0 | 0 | 0 | 0 | 0 |
| 1271.87 | 0 | 0 | 0 | 0 | 0 | 0 | 0 | 0 | 0 | 0 | 0 | 0 | 0 | 0 | 0 |

Fig. 69b

| 100 | 7.7144 | 10.786 | 15.732 | 24.2382 | 40.1985 | 64.4367 | 74.0016 | 114.2 | 138.438 | 159.881 | 233.892 | 274.061 | 298.319 | 314.051 | 456.811 |
|---|---|---|---|---|---|---|---|---|---|---|---|---|---|---|---|
| 1281.07 | 0 | 0 | 0 | 0 | 0 | 0 | 0 | 0 | 0 | 0 | 0 | 0 | 0 | 0 | 0 |
| 1288.82 | 0 | 0 | 0 | 0 | 0 | 20.0013 | 0 | 0 | 0 | 0 | 0 | 0 | 0 | 0 | 0 |
| 1292.16 | 0 | 0 | 0 | 0 | 0 | 0 | 0 | 0 | 0 | 0 | 0 | 0 | 0 | 0 | 0 |
| 1294.72 | 0 | 0 | 0 | 0 | 0 | 0 | 0 | 0 | 0 | 0 | 0 | 0 | 0 | 0 | 0 |
| 1298.91 | 0 | 0 | 0 | 0 | 0 | 0 | 0 | 0 | 0 | 0 | 0 | 0 | 0 | 0 | 0 |
| 1307.77 | 0 | 0 | 0 | 0 | 0 | 0 | 0 | 0 | 0 | 0 | 0 | 0 | 0 | 0 | 0 |
| 1309.56 | 0 | 0 | 0 | 0 | 0 | 0 | 0 | 0 | 0 | 0 | 0 | 0 | 0 | 0 | 0 |
| 1318.13 | 0 | 0 | 0 | 0 | 0 | 0 | 0 | 0 | 0 | 0 | 0 | 0 | 0 | 0 | 0 |
| 1321.35 | 0 | 0 | 83.9912 | 0 | 0 | 0 | 0 | 0 | 0 | 0 | 0 | 0 | 0 | 0 | 0 |
| 1332.83 | 0 | 0 | 0 | 0 | 0 | 0 | 0 | 0 | 0 | 0 | 0 | 0 | 0 | 0 | 0 |
| 1348.83 | 0 | 0 | 0 | 0 | 0 | 0 | 0 | 0 | 0 | 0 | 0 | 0 | 0 | 0 | 0 |
| 1351.32 | 0 | 0 | 0 | 0 | 0 | 0 | 0 | 0 | 0 | 0 | 0 | 0 | 0 | 0 | 0 |
| 1378.57 | 0 | 0 | 0 | 0 | 0 | 0 | 0 | 0 | 0 | 0 | 0 | 0 | 0 | 0 | 0 |
| 1384.61 | 0 | 0 | 0 | 0 | 0 | 0 | 0 | 0 | 10.0017 | 0 | 0 | 0 | 0 | 0 | 0 |
| 1386.14 | 0 | 0 | 0 | 0 | 0 | 0 | 0 | 0 | 0 | 0 | 0 | 0 | 0 | 0 | 0 |
| 1406.04 | 0 | 0 | 0 | 0 | 0 | 0 | 0 | 0 | 0 | 0 | 0 | 0 | 0 | 0 | 0 |
| 1425.32 | 0 | 0 | 0 | 0 | 0 | 0 | 0 | 0 | 0 | 0 | 0 | 0 | 0 | 0 | 0 |
| 1438.14 | 0 | 0 | 0 | 0 | 0 | 0 | 0 | 0 | 0 | 8.9550 | 0 | 0 | 0 | 0 | 0 |
| 1450.02 | 0 | 0 | 0 | 0 | 0 | 0 | 0 | 0 | 0 | 0 | 0 | 0 | 0 | 0 | 0 |
| 1462.85 | 0 | 0 | 0 | 0 | 0 | 0 | 0 | 0 | 0 | 0 | 0 | 0 | 0 | 0 | 0 |
| 1475.06 | 0 | 0 | 0 | 0 | 0 | 0 | 0 | 0 | 0 | 0 | 0 | 0 | 0 | 0 | 0 |
| 1476.35 | 0 | 0 | 0 | 0 | 0 | 0 | 0 | 0 | 0 | 0 | 0 | 0 | 0 | 0 | 0 |

| 109 | 456.816 | 616.638 | 690.691 | 730.691 | 755.131 | 778.063 | 781.649 | 2466 | 2923 | 3083 | 3157 | 3197 | 3221 | 3236.7 |
|---|---|---|---|---|---|---|---|---|---|---|---|---|---|---|
| 1018.75 | 0 | 0 | 0 | 0 | 0 | 0 | 0 | 0 | 0 | 0 | 0 | 0 | 0 | 0 |
| 1023.26 | 0 | 0 | 0 | 0 | 0 | 0 | 0 | 0 | 0 | 0 | 0 | 0 | 0 | 0 |
| 1026.2 | 0 | 0 | 0 | 0 | 0 | 0 | 0 | 0 | 0 | 0 | 0 | 0 | 0 | 0 |
| 1026.92 | 0 | 0 | 0 | 0 | 0 | 0 | 0 | 0 | 0 | 0 | 0 | 0 | 0 | 0 |
| 1028.95 | 0 | 0 | 0 | 0 | 0 | 0 | 0 | 0 | 0 | 0 | 0 | 0 | 0 | 0 |
| 1029.42 | 0 | 0 | 0 | 0 | 0 | 0 | 0 | 0 | 0 | 0 | 0 | 0 | 0 | 0 |
| 1031.61 | 0 | 0 | 0 | 0 | 0 | 0 | 0 | 0 | 0 | 0 | 0 | 0 | 0 | 0 |
| 1034.53 | 0 | 0 | 0 | 0 | 0 | 0 | 0 | 0 | 0 | 0 | 0 | 0 | 0 | 0 |
| 1035.96 | 0 | 0 | 0 | 0 | 0 | 0 | 0 | 0 | 0 | 0 | 0 | 0 | 0 | 0 |
| 1036.19 | 0 | 0 | 0 | 0 | 0 | 0 | 0 | 0 | 0 | 0 | 0 | 0 | 0 | 0 |
| 1037.99 | 0 | 0 | 0 | 0 | 0 | 0 | 0 | 0 | 0 | 0 | 0 | 0 | 0 | 0 |
| 1050.76 | 0 | 0 | 0 | 0 | 0 | 0 | 0 | 0 | 0 | 0 | 0 | 0 | 0 | 0 |
| 1057.58 | 0 | 0 | 0 | 0 | 0 | 0 | 0 | 0 | 0 | 0 | 0 | 0 | 0 | 0 |
| 1059.23 | 0 | 0 | 0 | 0 | 0 | 0 | 0 | 0 | 0 | 0 | 0 | 0 | 0 | 0 |
| 1063.75 | 0 | 0 | 0 | 0 | 0 | 0 | 0 | 0 | 0 | 0 | 0 | 0 | 0 | 0 |
| 1067.44 | 0 | 0 | 0 | 0 | 0 | 0 | 0 | 0 | 0 | 0 | 0 | 0 | 0 | 0 |
| 1069.45 | 0 | 0 | 0 | 0 | 0 | 0 | 0 | 0 | 0 | 0 | 0 | 0 | 0 | 0 |
| 1073.27 | 0 | 0 | 0 | 0 | 0 | 0 | 0 | 0 | 0 | 0 | 0 | 0 | 0 | 0 |
| 1080.72 | 0 | 0 | 0 | 0 | 0 | 0 | 0 | 0 | 0 | 0 | 0 | 0 | 0 | 0 |
| 1081.02 | 0 | 0 | 0 | 0 | 0 | 0 | 0 | 0 | 0 | 0 | 0 | 0 | 0 | 0 |
| 1081.63 | 0 | 0 | 0 | 0 | 0 | 0 | 0 | 0 | 0 | 0 | 0 | 0 | 0 | 0 |
| 1082.15 | 0 | 0 | 0 | 0 | 0 | 0 | 0 | 0 | 0 | 0 | 0 | 0 | 0 | 0 |
| 1088.21 | 0 | 0 | 0 | 0 | 0 | 0 | 0 | 0 | 0 | 0 | 0 | 0 | 0 | 0 |
| 1089.63 | 0 | 0 | 0 | 0 | 0 | 0 | 0 | 0 | 0 | 0 | 0 | 0 | 0 | 0 |
| 1091.1 | 0 | 0 | 0 | 0 | 0 | 0 | 0 | 0 | 0 | 0 | 0 | 0 | 0 | 0 |
| 1094.74 | 0 | 0 | 0 | 0 | 0 | 0 | 0 | 0 | 0 | 0 | 0 | 0 | 0 | 0 |
| 1096.55 | 0 | 0 | 0 | 0 | 0 | 0 | 0 | 0 | 0 | 0 | 0 | 0 | 0 | 0 |
| 1098.17 | 0 | 0 | 0 | 0 | 0 | 0 | 0 | 0 | 0 | 0 | 0 | 0 | 0 | 0 |
| 1102.57 | 0 | 0 | 0 | 0 | 0 | 0 | 0 | 0 | 0 | 0 | 0 | 0 | 0 | 0 |
| 1104.97 | 0 | 0 | 0 | 0 | 0 | 0 | 0 | 0 | 0 | 0 | 0 | 0 | 0 | 0 |
| 1107.93 | 0 | 0 | 0 | 0 | 0 | 0 | 0 | 0 | 0 | 0 | 0 | 0 | 0 | 0 |
| 1109.36 | 0 | 0 | 0 | 0 | 0 | 0 | 0 | 0 | 0 | 0 | 0 | 0 | 0 | 0 |
| 1110.99 | 0 | 0 | 0 | 0 | 0 | 0 | 0 | 0 | 0 | 0 | 0 | 0 | 0 | 0 |
| 1119.82 | 0 | 0 | 0 | 0 | 0 | 0 | 0 | 0 | 0 | 0 | 0 | 0 | 0 | 0 |
| 1120.9 | 0 | 0 | 0 | 0 | 0 | 0 | 0 | 0 | 0 | 0 | 0 | 0 | 0 | 0 |
| 1127.27 | 0 | 0 | 0 | 0 | 0 | 0 | 0 | 0 | 0 | 0 | 0 | 0 | 0 | 0 |
| 1127.82 | 0 | 0 | 0 | 0 | 0 | 0 | 0 | 0 | 0 | 0 | 0 | 0 | 0 | 0 |
| 1130.93 | 0 | 0 | 0 | 0 | 0 | 0 | 0 | 0 | 0 | 0 | 0 | 0 | 0 | 0 |
| 1132.62 | 0 | 0 | 0 | 0 | 0 | 0 | 0 | 0 | 0 | 0 | 0 | 0 | 0 | 0 |
| 1135.86 | 0 | 0 | 0 | 0 | 0 | 0 | 0 | 0 | 0 | 0 | 0 | 0 | 0 | 0 |
| 1140.75 | 0 | 0 | 0 | 0 | 0 | 0 | 0 | 0 | 0 | 0 | 0 | 0 | 0 | 0 |
| 1144.43 | 0 | 0 | 0 | 0 | 0 | 0 | 0 | 0 | 0 | 0 | 0 | 0 | 0 | 0 |
| 1151.66 | 0 | 0 | 0 | 0 | 0 | 0 | 0 | 0 | 0 | 0 | 0 | 0 | 0 | 0 |
| 1154.82 | 0 | 0 | 0 | 0 | 0 | 0 | 0 | 0 | 0 | 0 | 0 | 0 | 0 | 0 |
| 1174.62 | 0 | 0 | 0 | 0 | 0 | 0 | 0 | 0 | 0 | 0 | 0 | 0 | 0 | 0 |
| 1175.91 | 0 | 0 | 0 | 0 | 0 | 0 | 0 | 0 | 0 | 0 | 0 | 0 | 0 | 0 |
| 1180.66 | 0 | 0 | 0 | 0 | 0 | 0 | 0 | 0 | 0 | 0 | 0 | 0 | 0 | 0 |
| 1181.92 | 0 | 0 | 0 | 0 | 0 | 0 | 0 | 0 | 0 | 0 | 0 | 0 | 0 | 0 |
| 1185.23 | 0 | 0 | 0 | 0 | 0 | 0 | 0 | 0 | 0 | 0 | 0 | 0 | 0 | 0 |
| 1187.63 | 0 | 0 | 0 | 0 | 0 | 0 | 0 | 0 | 0 | 0 | 0 | 0 | 0 | 0 |
| 1191.74 | 0 | 0 | 0 | 0 | 0 | 0 | 0 | 0 | 0 | 0 | 0 | 0 | 0 | 0 |
| 1192 | 0 | 0 | 0 | 0 | 0 | 0 | 0 | 0 | 0 | 0 | 0 | 0 | 0 | 0 |
| 1192.46 | 0 | 0 | 0 | 0 | 0 | 0 | 0 | 0 | 0 | 0 | 0 | 0 | 0 | 0 |
| 1195.11 | 0 | 0 | 0 | 0 | 0 | 0 | 0 | 0 | 0 | 0 | 0 | 0 | 0 | 0 |
| 1196.33 | 0 | 0 | 0 | 0 | 0 | 0 | 0 | 0 | 0 | 0 | 0 | 0 | 0 | 0 |
| 1199.85 | 0 | 0 | 0 | 0 | 0 | 0 | 0 | 0 | 0 | 0 | 0 | 0 | 0 | 0 |
| 1201.18 | 0 | 0 | 0 | 0 | 0 | 0 | 0 | 0 | 0 | 0 | 0 | 0 | 0 | 0 |
| 1203.93 | 0 | 0 | 0 | 0 | 0 | 0 | 0 | 0 | 0 | 0 | 0 | 0 | 0 | 0 |
| 1205.36 | 0 | 0 | 0 | 0 | 0 | 0 | 0 | 0 | 0 | 0 | 0 | 0 | 0 | 0 |
| 1213.24 | 0 | 0 | 0 | 0 | 0 | 0 | 0 | 0 | 0 | 0 | 0 | 0 | 0 | 0 |
| 1214.99 | 0 | 0 | 0 | 0 | 0 | 0 | 0 | 0 | 0 | 0 | 0 | 0 | 0 | 0 |
| 1223.16 | 0 | 0 | 0 | 0 | 0 | 0 | 0 | 0 | 0 | 0 | 0 | 0 | 0 | 0 |
| 1228.63 | 0 | 1997.3 | 0 | 0 | 0 | 0 | 0 | 0 | 0 | 0 | 0 | 0 | 0 | 0 |
| 1230.11 | 0 | 1999.06 | 0 | 0 | 0 | 0 | 0 | 0 | 0 | 0 | 0 | 0 | 0 | 0 |
| 1234.17 | 0 | 2001.29 | 0 | 0 | 0 | 0 | 0 | 0 | 0 | 0 | 0 | 0 | 0 | 0 |
| 1234.63 | 0 | 2002.03 | 0 | 0 | 0 | 0 | 0 | 0 | 0 | 0 | 0 | 0 | 0 | 0 |
| 1234.71 | 0 | 2002.16 | 0 | 0 | 0 | 0 | 0 | 0 | 0 | 0 | 0 | 0 | 0 | 0 |
| 1239.81 | 0 | 0 | 0 | 0 | 0 | 0 | 0 | 0 | 0 | 0 | 0 | 0 | 0 | 0 |
| 1247.53 | 0 | 0 | 0 | 0 | 0 | 0 | 0 | 0 | 0 | 0 | 0 | 0 | 0 | 0 |
| 1248.16 | 0 | 0 | 0 | 0 | 0 | 0 | 0 | 0 | 0 | 0 | 0 | 0 | 0 | 0 |
| 1251.13 | 0 | 0 | 0 | 0 | 0 | 0 | 0 | 0 | 0 | 0 | 0 | 0 | 0 | 0 |
| 1254.61 | 0 | 0 | 0 | 0 | 0 | 0 | 0 | 0 | 0 | 0 | 0 | 0 | 0 | 0 |
| 1256.04 | 0 | 0 | 0 | 0 | 0 | 0 | 0 | 0 | 0 | 0 | 0 | 0 | 0 | 0 |
| 1257.31 | 0 | 0 | 0 | 0 | 0 | 0 | 0 | 0 | 0 | 0 | 0 | 0 | 0 | 0 |
| 1265.87 | 0 | 0 | 0 | 0 | 0 | 0 | 0 | 0 | 0 | 0 | 0 | 0 | 0 | 0 |
| 1271.87 | 0 | 0 | 0 | 0 | 0 | 0 | 0 | 0 | 0 | 0 | 0 | 0 | 0 | 0 |

Fig. 69e

| 100 | 456.816 | 616.609 | 690.691 | 730.891 | 755.131 | 770.963 | 781.649 | 2466 | 2923 | 3093 | 3157 | 3197 | 3221 | 3236.7 |
|---|---|---|---|---|---|---|---|---|---|---|---|---|---|---|
| 1281.07 | 0 | 0 | 0 | 0 | 0 | 0 | 0 | 0 | 0 | 0 | 0 | 0 | 0 | 0 |
| 1288.82 | 0 | 0 | 0 | 0 | 0 | 0 | 0 | 0 | 0 | 0 | 0 | 0 | 0 | 0 |
| 1291.16 | 0 | 0 | 0 | 0 | 0 | 0 | 0 | 0 | 0 | 0 | 0 | 0 | 0 | 0 |
| 1294.72 | 0 | 0 | 0 | 0 | 0 | 0 | 0 | 0 | 0 | 0 | 0 | 0 | 0 | 0 |
| 1298.91 | 0 | 0 | 0 | 0 | 0 | 0 | 0 | 0 | 0 | 0 | 0 | 0 | 0 | 0 |
| 1307.17 | 0 | 0 | 0 | 0 | 0 | 0 | 0 | 0 | 0 | 0 | 0 | 0 | 0 | 0 |
| 1309.56 | 0 | 0 | 0 | 0 | 0 | 0 | 0 | 0 | 0 | 0 | 0 | 0 | 0 | 0 |
| 1318.13 | 0 | 0 | 0 | 0 | 0 | 0 | 0 | 0 | 0 | 0 | 0 | 0 | 0 | 0 |
| 1321.35 | 0 | 0 | 0 | 0 | 0 | 0 | 0 | 0 | 0 | 0 | 0 | 0 | 0 | 0 |
| 1332.83 | 0 | 0 | 0 | 0 | 0 | 0 | 0 | 0 | 0 | 0 | 0 | 0 | 0 | 0 |
| 1348.83 | 0 | 0 | 0 | 0 | 0 | 0 | 0 | 0 | 0 | 0 | 0 | 0 | 0 | 0 |
| 1361.32 | 0 | 0 | 0 | 0 | 0 | 0 | 0 | 0 | 0 | 0 | 0 | 0 | 0 | 0 |
| 1378.57 | 0 | 0 | 1.99593 | 0 | 0 | 0 | 0 | 0 | 0 | 0 | 0 | 0 | 0 | 0 |
| 1384.61 | 0 | 0 | 2.00467 | 0 | 0 | 0 | 0 | 0 | 0 | 0 | 0 | 0 | 0 | 0 |
| 1393.14 | 0 | 0 | 0 | 0 | 0 | 0 | 0 | 0 | 0 | 0 | 0 | 0 | 0 | 0 |
| 1403.04 | 0 | 0 | 0 | 0 | 0 | 0 | 0 | 0 | 0 | 0 | 0 | 0 | 0 | 0 |
| 1425.32 | 0 | 0 | 0 | 0 | 0 | 0 | 0 | 0 | 0 | 0 | 0 | 0 | 0 | 0 |
| 1438.14 | 0 | 0 | 0 | 0 | 0 | 0 | 0 | 0 | 0 | 0 | 0 | 0 | 0 | 0 |
| 1450.02 | 0 | 0 | 0 | 0 | 0 | 0 | 0 | 0 | 0 | 0 | 0 | 0 | 0 | 0 |
| 1462.85 | 0 | 0 | 0 | 2.00146 | 0 | 0 | 0 | 0 | 0 | 0 | 0 | 0 | 0 | 0 |
| 1475.06 | 0 | 0 | 0 | 0 | 0 | 0 | 0 | 0 | 0 | 0 | 0 | 0 | 0 | 0 |
| 1476.35 | 0 | 0 | 0 | 0 | 0 | 0 | 0 | 0 | 0 | 0 | 0 | 0 | 0 | 0 |

Fig. 69f

A line of equally spaced
points as a one dimensional lattice.

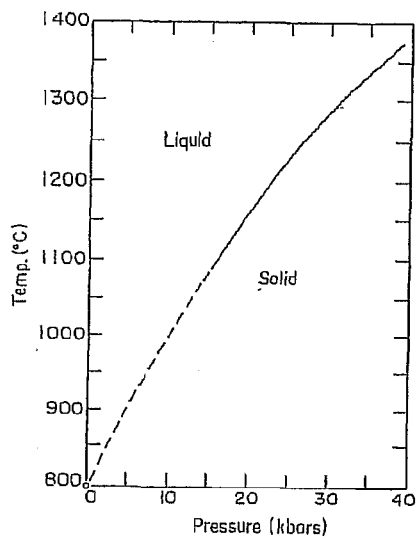

FIG. 75

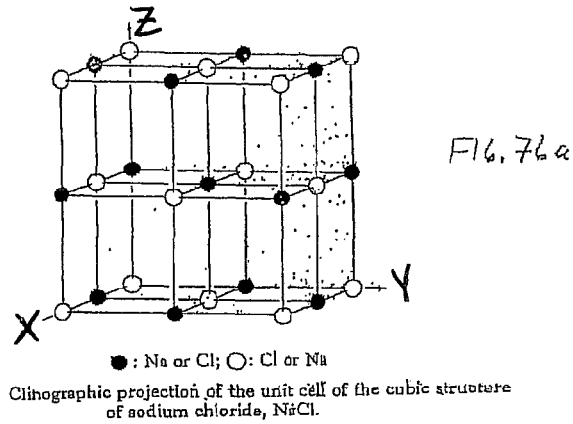

● : Na or Cl; ○ : Cl or Na

Clinographic projection of the unit cell of the cubic structure of sodium chloride, NaCl.

FIG. 76a

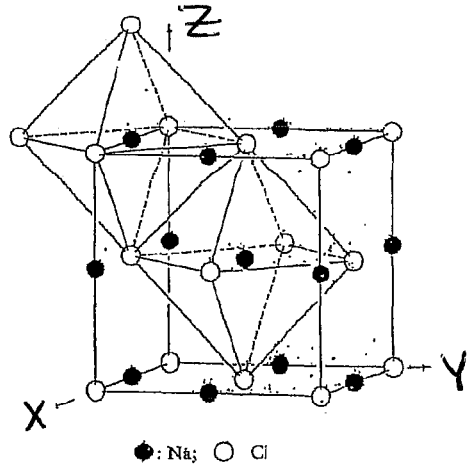

● : Na; ○ Cl

Clinographic projection of the cubic structure of sodium chloride, NaCl, showing the co-ordinating octahedra of anions round the cations.

FIG. 76b

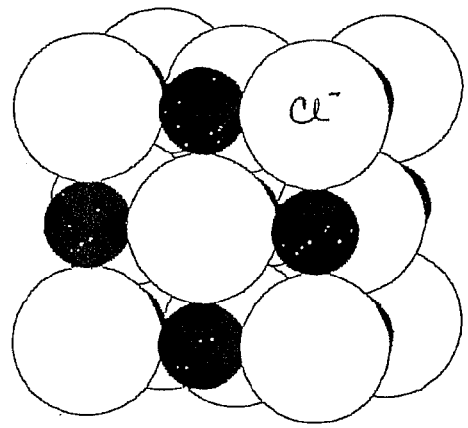

FIG. 77

Clinographic projection of the unit cell of the cubic structure of sodium chloride showing the ions in their correct relative sizes for NaCl. The solid circles represent sodium ions.

Simple binary diagram.

Example of a Solubility Curve

Clinographic projection of the hexagonal structure of graphite.
The unit cell is indicated by broken lines.

Clinographic projection of the unit cell of the
cubic structure of diamond, C.

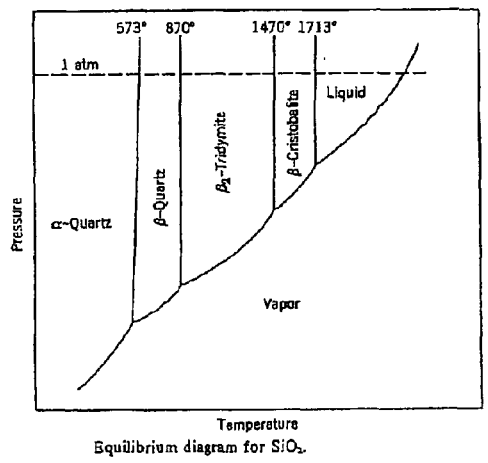

Equilibrium diagram for SiO₂.

FIG. 81a

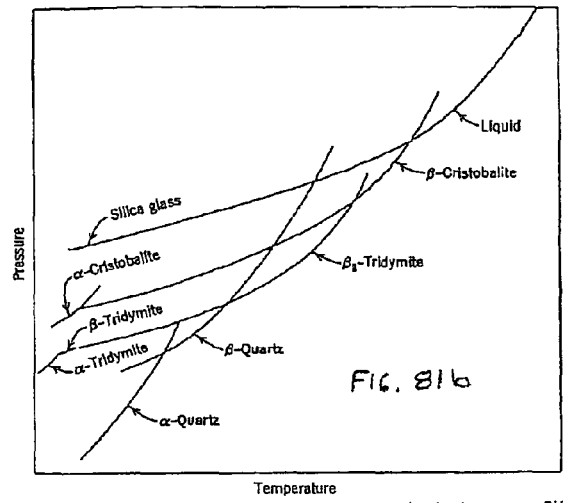

Diagram including metastable phases occurring in the system SiO₂.

FIG. 81b

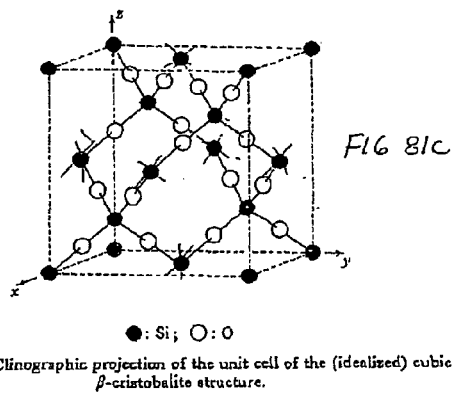

●: Si; ○: O

Clinographic projection of the unit cell of the (idealized) cubic β-cristobalite structure.

FIG 81c

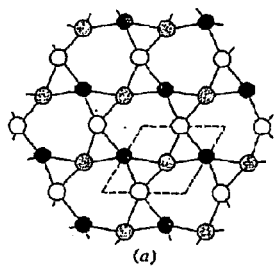

FIG 81d

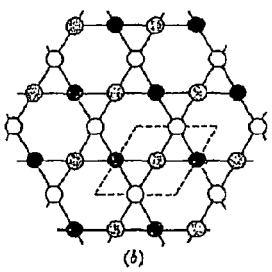

(a) Plan of the rhombohedral structure of α-quartz, SiO₂, projected on a plane perpendicular to the principal axis. (b) Plan of the hexagonal structure of β-quartz projected on a plane perpendicular to the z axis. In both diagrams only silicon atoms are shown; the oxygen atoms are tetrahedrally disposed about those of silicon in such a way that all corners of the [SiO₄] tetrahedra are shared.

Perovskite structure (idealized).

I. Water

● : H;  ◯ : O

Clinographic projection of the hexagonal structure of ice. The unit cell is indicated by broken lines. The distribution of the hydrogen atoms is arbitrary (see text).

The binary system MgO–SiO₂.

○: Mg in plane of paper    ●: Mg at height ½a
◉: O at height ½a    ○: O at height ¼a Plan of the idealized orthorhombic structure of forsterite, $Mg_2SiO_4$, projected on a plane perpendicular to the $x$ axis. The silicon atoms lie at the centres of the tetrahedra of oxygen atoms, and are not shown.

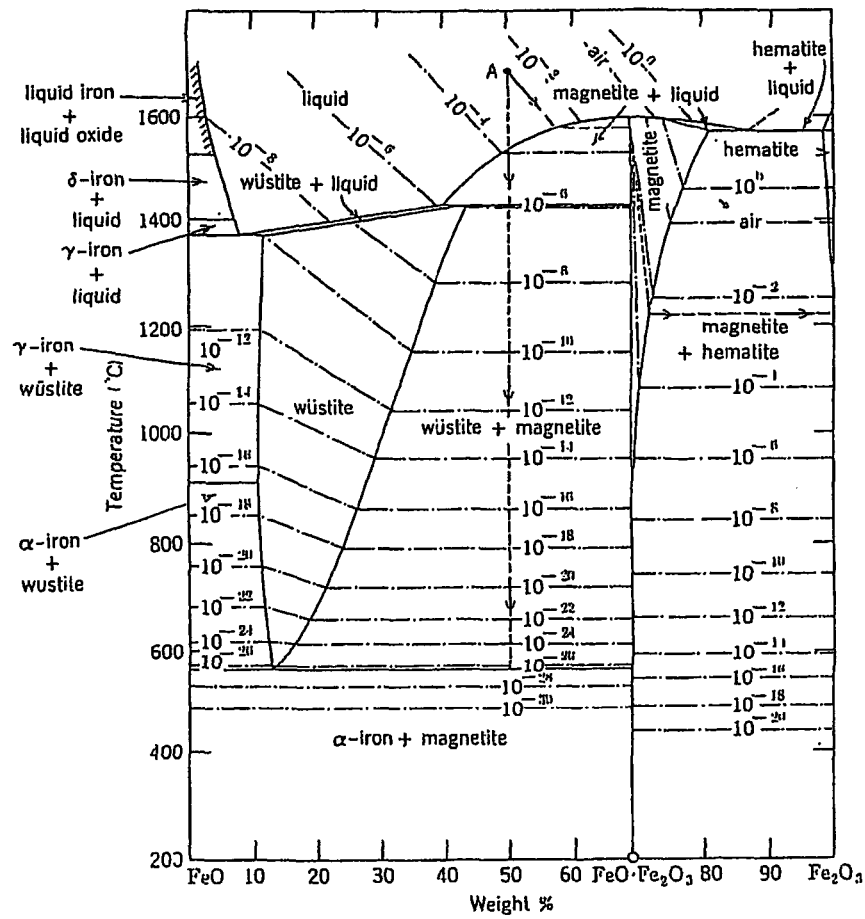

(a) Phase relations in the FeO–Fe$_2$O$_3$ system. Dash-dot lines are oxygen isobars. Alternate solidification paths for composition A are discussed in text. From A. Muan and E. F. Osborn; *Phase Equilibria among Oxides in Steelmaking*, Addison-Wesley Publishing Company, Inc., Reading, Mass., 1965.

FIG. 85a

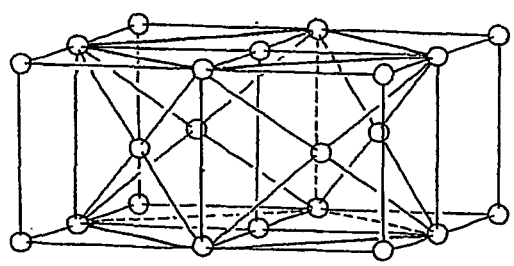

Clinographic projection of four unit cells of the cubic body-centred structure of α-iron showing the all-face-centred tetragonal unit cell in terms of which the structure may alternatively be described.

FIG. 85b

Space diagram of (a) ternary eutectic and (b) complete series of solid solutions.

Crystallization path illustrated in Fig. 86a.

A molecular model of γ-α transformation observed in oleic acid, erucic acid, asclepic acid, and palmitoleic acid.

Single-crystal morphology of α form and γ form of gondoic acid (scale bar, 100 mm).

Raman scattering C-C stretching bands of α form and γ form of gondoic acid.

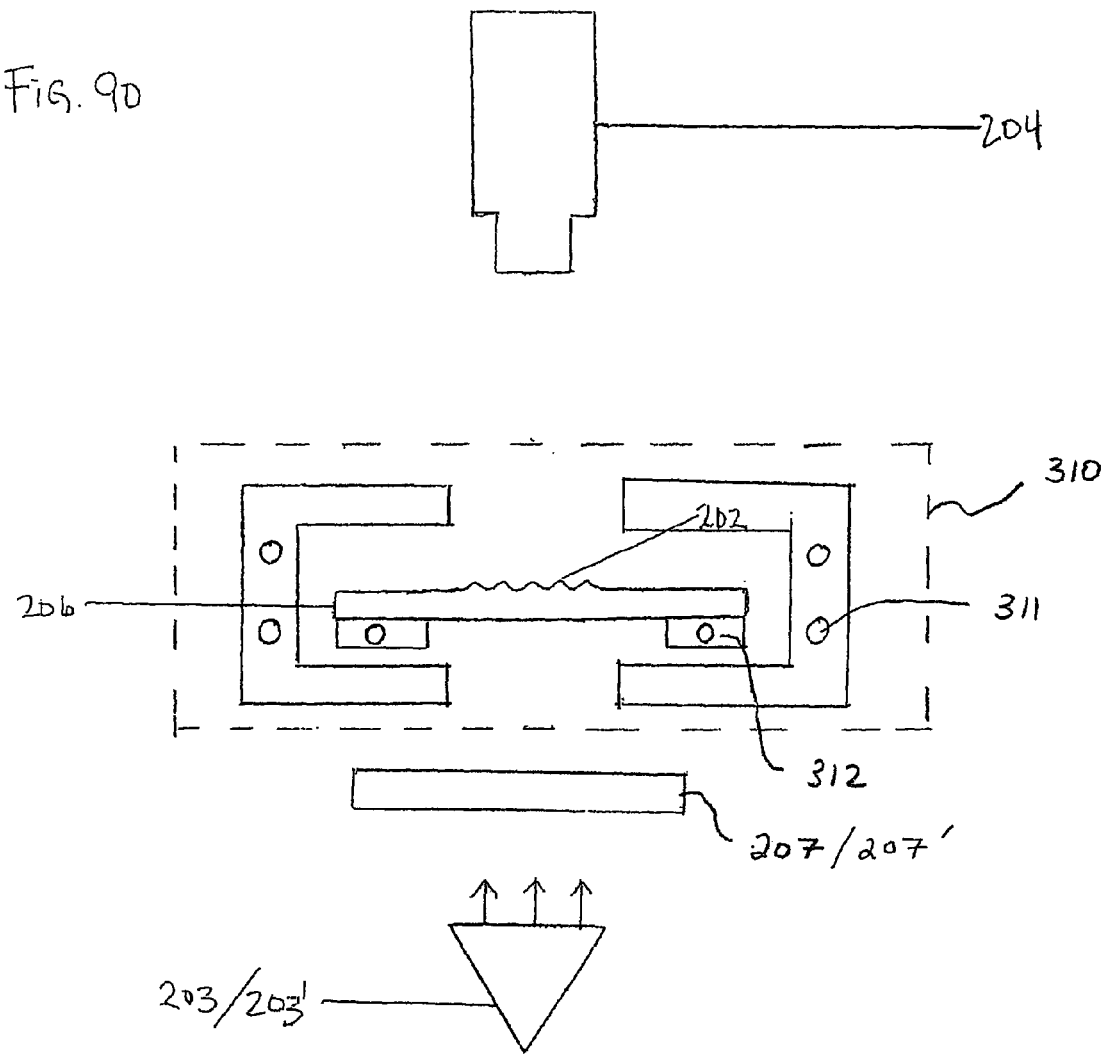

Magnifying Glass View of Control NaCl Crystals Grown in 18 hours

Spectral Crystallization from Saturated Solution
(At Room Temperature, 22° C)

Spectral Crystallization from Thermally Unsaturated Solution (3° above Room Temperature)

Spectral Crystallization from Thermally Unsaturated Solution – Altered Morpholgoy

NaCl Crystals Grown Spectrally From 3% UnSaturated Solution

NaCl Crystals Grown in 18 Hours Using 4 Overhead Na Lamps Angled at 45°

10 mm

Largest Crystal Enlarged
13 X 13 X 7 mm

Effects of Spectral Conditions During Preparation of Saturated NaCl Solutions on Subsequent Crystallization

98ad
98ae

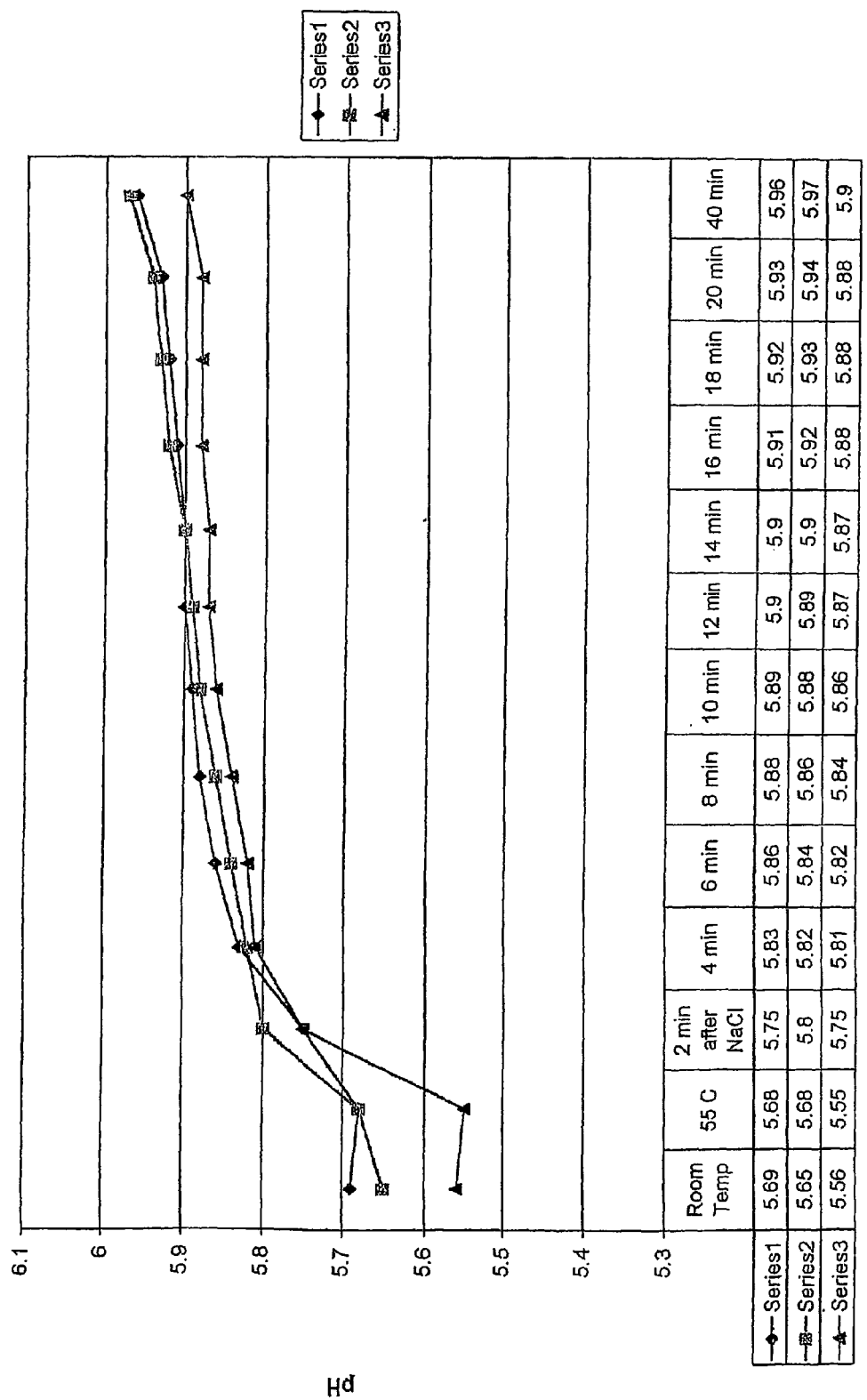
FIG. 1039

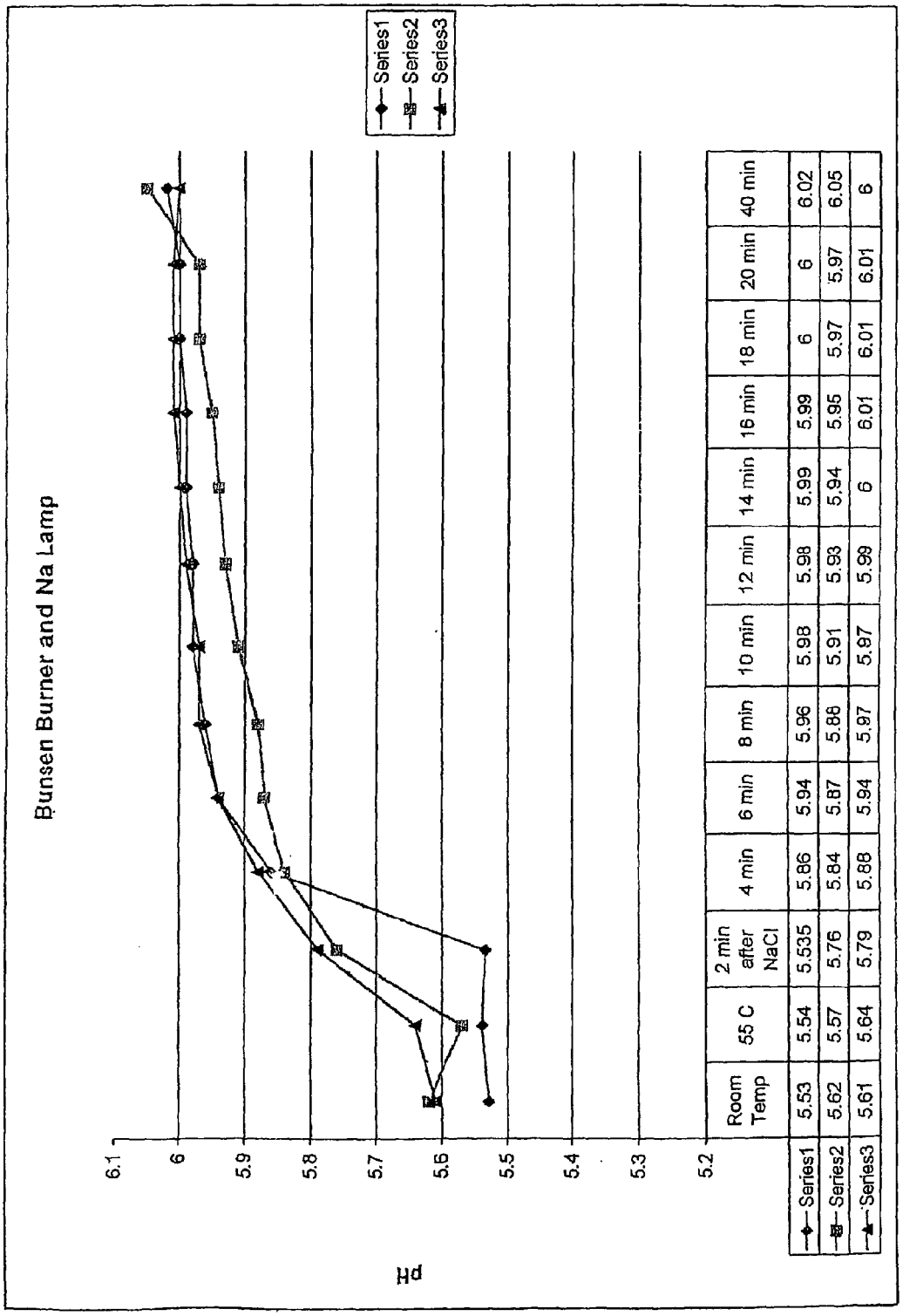
FIG. 103.6

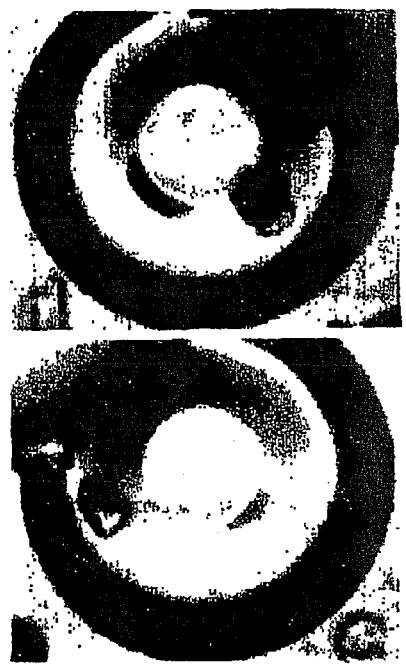 
FIG. 105d
Single large crystals of lysozyme grown under a sodium lamp, in Sodium Grid Screen A4.
 
FIG. 105e
Multiple small crystals of lysozyme grown in an incubator, in Sodium Grid Screen A4.

Microwave Crystals (60X magnification)
Many cubic crystals, some flat sheets.

Shielded Control (60X magnification)
Many flat sheets, some cubic crystals.

Sodium Lamp Crystals (60X magnification)
Mostly cubic crystals.

Incubator Control (60X magnification)
Mostly flat sheets.

Enhancement of Sodium Chloride Electrolyte With Sodium Spectral Irradiation

US 7,972,390 B2

METHODS FOR CONTROLLING CRYSTAL GROWTH, CRYSTALLIZATION, STRUCTURES AND PHASES IN MATERIALS AND SYSTEMS

TECHNICAL FIELD

This invention relates to novel methods for affecting, controlling and/or directing various crystal formation, structure formation or phase formation/phase change reaction pathways or systems by exposing one or more components in a holoreaction system to at least one spectral energy pattern. In a first aspect of the invention, at least one spectral energy pattern can be applied to a crystallization reaction system. In a second aspect of the invention, at least one spectral energy conditioning pattern can be applied to a conditioning reaction system. The spectral energy conditioning pattern can, for example, be applied at a separate location from the reaction vessel (e.g., in a conditioning reaction vessel) or can be applied in (or to) the reaction vessel, but prior to other (or all) crystallization reaction system participants being introduced into the reaction vessel.

The techniques of the present invention are applicable to certain reactions in various crystallization reaction systems, including but not limited to, inorganic reactions (e.g., oxides, nitrides, carbides, borides, chlorides, bromides, carbonates, organometallics, mixes phases, metals, metal alloys, single crystal structures, complex crystalline structures, amorphous structures, etc.), organic reactions (e.g., monomers, oligomers and/or polymers made of one component or many different components), and/or biologic reactions (e.g., protein, fatty acids or cellular). The invention also relates to mimicking various mechanisms of action of various catalysts and components in crystallization reaction systems under various environmental reaction conditions. The invention specifically discloses different means for achieving the control of energy dynamics (e.g., matching or non-matching) between, for example, applied energy and matter (e.g., solids, liquids, gases, plasmas and/or combinations or portions thereof), to achieve (or to prevent) and/or increase energy transfer to, for example, at least one participant (or at least one conditionable participant) in a holoreaction system by taking into account various energy considerations in the holoreaction system. The invention further discloses different techniques and different means for delivery of at least one spectral energy pattern (or at least one spectral energy conditioning pattern) to at least a portion of a holoreaction system. The invention also discloses an approach for designing or determining appropriate catalyst components, environmental reaction conditions and/or conditioned participants to be used in a crystallization reaction system.

DISCUSSION OF RELATED AND COMMONLY OWNED PATENT APPLICATIONS

The subject matter of the present invention is related to the subject matter contained in two (2) co-pending U.S. Provisional Application Ser. Nos. 60/366,755 and 60/403,225, both entitled, "Methods for Controlling Crystal Growth, Crystallization and Phases in Biologic, Organic and Inorganic Systems", the first being filed on Mar. 21, 2002, and the second being filed on Aug. 13, 2002.

The subject matter of the present invention is also related to the subject matter contained in co-pending U.S. Provisional Application Ser. No. 60/403,251, entitled "Spectral Chemistry", which was filed on Aug. 13, 2002.

The subject matter of the present invention is also related to the subject matter contained in co-pending U.S. Provisional Application Ser. No. 60/439,223, entitled "Spectral Conditioning", which was filed on Jan. 10, 2003.

The subject matter of the present invention is related to the subject matter contained in co-pending U.S. application Ser. No. 10/203,797, entitled "Spectral Chemistry", which entered the National Phase on Aug. 12, 2002.

The subject matter of each of the aforementioned Patent Applications is herein expressly incorporated by reference.

BACKGROUND OF THE INVENTION

The physical structures of various materials (e.g., organic, inorganic and/or biologic) are vital for determining, for example, physical properties (e.g., functionality, size, physical properties, electrical properties, mechanical properties, dielectric properties, thermal properties, etc.) of various materials (e.g., solids, liquids, gasses and/or plasmas). In this regard, certain materials may have similar chemical compositions, but very different physical properties due to, for example: (1) different arrangements of ions, atoms, molecules and/or macromolecules of various sizes and/or shapes; (2) different bonding angles between atoms, ions, molecules and/or macromolecules; and/or (3) different types of bonds holding together ions, atoms, molecules and/or macromolecules, etc. The prior art refers generally to the formation and/or control of structures in the areas of biology, inorganic chemistry and/or organic chemistry as crystal growth, crystallization, crystal engineering and/or structural or phase engineering of materials.

Crystal growth or crystallization begins with, for example, primary nucleation, followed by secondary nucleation. However, in crystal systems that do not appear to require primary nucleation (e.g., some type of seed is typically provided) then only secondary nucleation may occur.

There are numerous crystallization models postulated in the prior art which attempt to explain crystallization reactions in certain material systems. These models include: (1) the broken band model which focuses on the energy of dissociated atoms being proportional to the number of bonds between nearest neighbors; (2) the free energy model which focuses on the free energies associated with various structural configurations in lattices; (3) the step-step interactions which focus on dipole-dipole interactions; (4) Wulff's construction, which focuses on minimization of surface free energies to obtain crystalline shapes; (5) Frank's model which theorizes that the velocity of growth or dissolution depends on surface orientation; (6) the BCF (Burton, Cabrera, Frank) model which focuses on step flow or a series of growth stages occurring due to the presence of a series of steps or ledges; (7) the Schwoebel Effect which discusses adatoms overcoming a potential energy maximum prior to adhering; and (8) various other crystallization models which take into account, for example, impurities, electric field effects, liquid field theory and/or morphology, etc. None of the various proposed models or theories for crystal growth explain satisfactorily the relevant mechanisms of crystal growth. Accordingly, detailed control of crystal growth or crystallization in many different areas of science remains an empirical science with numerous trials and errors often occurring to achieve desirable crystalline growth or engineering and/or desirable phases, structures or phase transformations.

It is well known that certain ions or atoms have an affinity for other atoms and/or ions, and thus, may be capable of bonding to each other by the well-known techniques of ionic bonding, covalent bonding, polar-covalent bonding, metallic bonding, hydrogen bonding, Van der Waal forces, etc., and/or hybrids or combinations of the same. The particular types of bonds which hold together atoms, ions, molecules and/or macromolecules, influence, for example, the positioning of ions, atoms, molecules and/or macromolecules, relative to each other (e.g., including such factors as separation, distances, bond angles, coordination number, etc.). Moreover, molecules (e.g., combinations of atoms) can be bonded to other molecules or molecular ions (e.g., proteins composed of molecules of amino acids) and also exhibit various spacings and angular displacements relative to each other. Still further, there are certain materials that have mixtures of atoms and molecules, whereby the atoms and molecules are bonded together by more than one of the bonding techniques mentioned above, and are also thereby located at certain distances and angles with respect to each other. Further, there are numerous macromolecules (e.g., viruses which are composed of different proteins, water, etc.) that contain various structural and angular relationships between different molecules of the same (or substantially the same) chemical composition.

One of the most basic structures that is used to refer structurally to arrangements of atoms, ions, molecules, etc., is the unit cell. For example, the unit cells of seven (7) different crystal systems are shown in FIG. 70. In particular, FIG. 70a shows a cubic unit cell structure; FIG. 70b shows a tetragonal unit cell structure; FIG. 70c shows an orthorhombic unit cell structure; FIG. 70d shows a monoclinic unit cell structure; FIG. 70e shows a triclinic unit cell structure; FIG. 70f shows a rhombohedral unit cell structure; and FIG. 70g shows a hexagonal unit cell structure. Moreover, Table A shows relationships between the various unit cell dimensions and angles shown in FIG. 70 as well as certain examples of certain inorganic materials which exhibit the aforementioned unit cell structures.

TABLE A

| Unit Cell Dimensions | Crystal Class | Example |
| --- | --- | --- |
| $a = b = c\ a = \beta = \gamma = 90°$ | Cubic | $NaCl, MgAl_2O_4,$ $C_{60}K_3$ |
| $a = b \neq c\ a = \beta = \gamma = 90°$ | Tetragonal | $K_2NiF_4, TiO2,$ $BaTiO_3$ (298K) |
| $a \neq b \neq c\ a = \beta = \gamma = 90°$ | Orthorhombic | $YBa_2, Cu_3O_7$ |
| $a \neq b \neq c\ a = \gamma = 90°\ \beta \neq 90°$ | Monoclinc | $KH_2PO_4$ |
| $a \neq b \neq c\ a \neq \beta \neq \gamma \neq 90°$ | Triclinic | |
| $a = b \neq c\ a = \beta = 90°\ \gamma = 120°$ | Hexagonal | $LiNbO_3$ |
| $a = b = c\ a = \beta = \gamma \neq 90°$ | Trigonal/ Rhombohedral | $BaTiO_3$ below ($-80°$ C.) |

Various known inorganic, biologic and/or organic atoms, ions, molecules and/or macromolecules may adopt one or more of the unit cell arrangements shown in FIGS. 70a-70g. There are various known rules and experimental determinations that assist in predicting the various unit cells and/or macrostructures which may result from combinations of various ions, atoms, molecules and/or macromolecules of similar or different chemical compositions. For example, with specific reference to inorganic systems, different types of bonds that can be used to bond species together include covalent bonding, ionic bonding, Van der Waals bonding, metallic bonding, etc. For example, in covalently bonded crystals, the covalency of the atom(s) or ion(s) and the characteristics of the spatial distribution of the bonds in which the atoms form are the primary factors for determining the coordination or bonding or the particular assembly of atoms or ions in a structure.

In contrast, electrostatic bonding or ionic bonding is governed by several different rules. Specifically:

(1) The first rule, as an approximation, treats ions as rigid spheres and the way in which the spherical ions are packed together is determined by the relative sizes of the ions. In particular, a coordinated polyhedron of anions is formed around each cation, the cation-anion distance being determined by the radius sum and the coordination number of the cation by the radius ratio.

(2) The second rule is known as the electrostatic valency principle. This rule causes a charge balancing to occur. In particular, in a stable coordinated structure, the total strength of the valency bonds which reach an anion from all neighboring cations is equal to the charge of the anion. This rule causes structures to assume configurations of minimum potential energies in which the ions try to achieve electrical neutrality in their locality (e.g., in their unit cells).

(3) The third rule references the existence of edges and faces which may be common to two anion polyhedra in a coordinated structure. In particular, stabilities of polyhedra are decreased by the existence of edges and faces. This effect can be large for cations with high valency and small coordination numbers, and can be especially large when the radius ratio approaches the lower limit of stability of the polyhedron. This rule is due to the fact that an edge, or a face, which is common to two anion and polyhedra, will result in the close approach of two cations, and a corresponding increase in the potential energy of the system as compared with a state in which only corners are shared and thus, the cations are spaced apart as far as possible.

(4) The fourth rule is that in crystals containing different cations, those of high valency and small coordination number typically do not share polyhedron elements with each other. This rule follows the third rule stated above.

(5) The final general rule is that the number of different kinds of constituents in a crystal tends to be small in number.

The five aforementioned general rules also have certain applicability in organic and biologic systems, but have been specifically referenced with regard to inorganic systems to simplify the discussion thereof.

By following each of the aforementioned rules, different crystalline structures (or phases or patterns) may be obtainable in similar (or exactly the same) chemical systems. This aspect of obtaining different crystalline structures but having the same (or substantially the same) chemical structure is known as polymorphism. A substance is typically referred to as being polymorphous when it is capable of existing in two or more forms having different crystalline structures or patterns. Examples of well-known polymorphs include, carbon, selenium, quartz ($SiO_2$), certain metals, barium titanate, zinc sulfide, ferric oxide, silica, proteins, prions, lipids, hydrocarbons, glycine, etc. In certain polymorphs, a first crystalline form can be found under a first set of physical conditions and a reversible transition may exist between different forms, said reversible transition being capable of occurring by, for example, one or more changes in certain of the physical conditions (e.g., environmental conditions to which the polymorphs are exposed) or by introduction of a catalyst. These types of materials are said to be enantiotropic. When transitions between crystalline forms or states is irreversible, the forms are said to be monotropic. An example of an enantiomer is iron which has a cubic packed structure between the temperatures of about 906° C.-1401° C., and a cubic body-centered structure with temperatures outside this range. Water also exhibits different structural forms (e.g., microclusters, macroclusters, etc.) and there are at least 13 different crystalline $H_2O$ structures that are known to exist in relatively modest pressure and temperature regimes. A third example are certain proteins, which when exposed to a polymorphic prion, change structure to match that of the prion via an autocatlytic transition.

There are various rules that assist in identifying relationships that exist between polymorphous forms of different substances. Specifically, the prior art has attempted to classify polymorphic changes into the following areas. For example, the recognized polymorphs that exist include one or more of the following relationships:

(1) changes in which the immediate coordination number of the ions/atoms is not significantly altered;

(2) changes in which a change in immediate coordination occurs;

(3) changes involving a transition between an ideal structure and a defect structure; and (4) changes in which a change in bond-type occurs.

Each of the four (4) aforementioned polymorph relationships may be mutually exclusive, or may contain features of the other. However, it should be understood that various different configurations, such as unit cell, protein folding, or DNA twisting, exist for a large number of materials of substantially similar composition or compositions which are substantially identical.

In addition to the unit cells shown in FIGS. 70a-70g, there are different lattices available for use in combination with the unit cells. In particular, a lattice is known as an array of equivalent points in one, two, or more typically, three dimensions. Lattices typically do not provide any information regarding the actual positions of atoms or molecules in any particular spatial relationship, but show the various translational symmetries of the various atoms, ions or molecules by locating equivalent positions within the lattice. The environment of any atom or ion placed on one of the lattice points will be identical to the environment of a similar atom or ion placed on a corresponding different lattice point. The simplest illustration of this concept is a one-dimensional lattice consisting of an infinite series of equally spaced points along a line (see, for example, FIG. 71). However, the more realistic uses of lattices occurs in three-dimensional crystal structures. The simplest lattice type is known as a primitive (represented by the symbol "P"), and a unit cell with a primitive lattice contains a single lattice point.

A second lattice-type is body-centered (represented by the symbol "I"). FIG. 72 shows a body-centered cubic structure.

A lattice which has lattice points at the center of all unit faces as well as at the corners is known as a face-centered lattice and is represented by the symbol "F". This lattice is shown in FIG. 73.

A final lattice which contains points in just one of the faces is known as face-centered, but can be given any one of the symbols "A", "B" or "C". A "C-type" lattice refers to the situation where additional translational symmetry places lattice points at the centers of the faces; whereas the A and B face-centered lattices are obtained in an identical manner but the additional lattice points occur in different planes. An example of a face-centered lattice is given in FIG. 74. It is noted that the "A" and "B" face-centered lattices are obtained in identical manner but the additional lattice points in the bc and ac planes respectively are obtained. Accordingly, face-entered cubic lattice structures are typically referred to by the letter "C".

The four different lattice types discussed above (i.e., P, I, F and C) can be combined with the seven unit cell or crystal classes which gives rise to all possible variations. All the possible variations are known as the "Bravais" lattices. In particular, for example, in inorganic systems, the seven different crystal systems match up with particular Bravais lattices. Table B shows the 14 Bravais lattices that are possible.

TABLE B

| Crystal system | Bravais lattices |
|---|---|
| Cubic | P, I, F |
| Tetragonal | P, I |
| Orthorhombic | P, C, I, F |
| Monoclinic | P, C |
| Triclinic | P |
| Hexagonal | P |
| Trigonal/Rhombohedral | P(R)* |

*The primitive description of the rhombohedral lattice is normally given the symbol "R".

A variety of techniques exist for achieving crystal growth or structure in organic, inorganic, biologic, etc., systems. For example: (1) the high vacuum techniques of molecular beam epitaxy and atomic layer epitaxy cause atoms or molecules to be projected onto a surface of a substrate where the atoms or molecules become incorporated thereon (e.g., adatoms); (2) growth from solutions (e.g., epitaxial growth); (3) vapor phase growth onto one or more substrates or seed crystals; (4) growth from a liquid metal; (5) growth from a solution (e.g., aqueous, molten salts or other solvents); (6) growth from a saturated or supersaturated solution (e.g., aqueous, or other solvents); (7) growth from a melt, also known as solidification; (8) precipitation growth; (9) growth under high pressure conditions (e.g., hydrothermal); (10) chemical vapor transport reaction growth; (11) growth through electrochemical reactions (e.g., electrocrystallization); (12) growth from the solid phase (e.g., strain annealing); (13) acoustocrystallization techniques; (14) biologic techniques (e.g., sitting drop, hanging drop, containerless, etc.); and (15) numerous postgrowth treatments that affect already formed structures (e.g., annealing, heat treatment, laser treatment, etching processes (e.g., chemical, thermal, etc.), etc.). Phase-diagrams are often employed to assist in understanding what potential crystalline phases or structures can be achieved by these various crystal growth, crystallization or ordering techniques and postgrowth treatment techniques.

Much experimental and empirical work has been performed to determine systems and/or phases which various atoms, ions, molecules and/or macromolecules assemble into. For example, thousands and thousands of phase diagrams exist describing various organic, biologic and/or inorganic systems. Phase diagrams show equilibrium conditions for systems and exhibit, typically, the lowest known free energy states for composition, temperature, pressure and/or other conditions imposed upon the system. In particular, the traditional belief is that under a given set of fixed parameters, there will be only one mixture of phases that can be present. Phase-equilibrium diagrams provide a precise method of graphically representing equilibrium situations and are important for characterizing various organic, inorganic and/or biologic systems. The phase-equilibrium diagrams record the composition of each phase present, the number of phases present and the amounts of each phase, at equilibrium. It is noted that equilibrium conditions are rarely achieved in most systems. However, even though non-equilibrium conditions (e.g., metastable equilibrium conditions) typically prevail in real-life systems, phase-diagrams are still important to practitioners in each of their respective fields to assist in determining what phases may be present, influenced, and/or controlled, etc., in various crystallization systems.

Phase-diagrams are regularly utilized to determine phase and composition changes occurring under varying environmental conditions. For example, changes in environmental gasses present in a system, changes in partial pressures of environmental gasses, changes in temperature, changes in pressure, changes in composition, etc., are all known factors that are capable of influencing the resultant product (e.g., crystalline or structural species present) in any given crystallization reaction system.

There are numerous phase-diagrams for each of the aforementioned systems including, for example, one-component phase diagrams, two-component phase diagrams, three-component phase diagrams, etc. A good example of a single component, single-solid phase system is sodium chloride. In particular, FIG. 75 shows the relationship between temperature and pressure for the ionically bonded material known as NaCl. In addition, FIGS. 76a and 76b shown clinographic projections of the unit cell of the cubic structure for sodium chloride. FIG. 77 shows a clinographic projection of the cubic unit cell structure of sodium chloride, where the ions are shown in approximately correct relative sizes. The solid circles represent the sodium ions, whereas the hollow circles represent the chlorine ions.

Phase-diagrams can be interpreted by the phase rule (known as the Gibbs Phase Rule) which is shown in the following relationship for a single component system:

$$P+V=C+2.$$

The phase rule listed above uses P for the number of phases present in equilibrium, V for the variance or number of degrees of freedom and C for the number of components. This phase rule relationship is the basis for preparing and utilizing phase-equilibrium diagrams. For example, FIG. 78 shows a perspective view of a simple binary phase-diagram. This two-component system adds an additional variable of composition to the phase rule. Thus, application of the phase rule is as follows: for the point "A" one phase is present and both temperature and composition can be arbitrarily varied. However, in areas in which two phases are present at equilibrium, the composition of each phase is indicated by lines on the diagram. The intersection of a constant-temperature line with phase boundaries gives the compositions of the phases in equilibrium at temperature "T". Thus, with two phases present, the following phase rule relationship exists:

$$P+V=C+2, 2+V=2+2, V=2.$$

Thus, at an arbitrarily fixed pressure, any arbitrary change in either temperature or composition of one of the phases present requires a corresponding change in the other variable. Accordingly, the maximum number of phases that can be present where pressure is arbitrarily fixed (i.e., where V=1) is as follows:

$$P+V=C+2, P+1=2+2, P=3.$$

The solid horizontal line indicated by the letter C in FIG. 78, represents a situation where three phases are present and the composition of each phase and the temperature are fixed. Accordingly, phase-diagrams can be utilized to determine what phases are present, what conditions can result in certain phases being present and the compositions of certain phases.

In particular, defect crystallization pathways exist in each crystallization reaction system, and the precise crystalline pathway that is chosen is a function of many factors known to the art. For example, a representative ternary phase diagram is shown in FIG. 86a (which is representative of a ternary eutectic) and in FIG. 86b (which is representative of a ternary solid solution). Further, FIG. 86c shows one precise crystallization pathway followed by the composition "A" shown in FIG. 86a. A brief description of the crystallization pathway is as follows: a liquid having a composition A falls into a first primary field of component "X". As the temperature in the ternary liquid is decreased to $T_1$, a solid having a composition "X" begins to crystallize from the melt. The composition of the remaining liquid changes along the line AB due to some of the solid "X" crystallizing out therefrom. A concept known as the "lever principle" (i.e., a concept for determining relative amounts and compositions of materials which crystallize from a melt) applies along the line AB. Further, as cooling continues and the temperature reaches $T_2$, the crystallization pathway reaches a boundary condition representing the equilibrium between the composition of the remaining liquid and the two solid phases "X" and "Z". At this point, "Z" begins to crystallize as well as "X" and the remaining liquid changes in composition along the path CD. However, at the point "L" the phases that exist in equilibrium comprise a liquid having a composition "L", and the solids "X" and "Z", whereas the overall composition of the entire system is "A". Cooling continues until a ternary eutectic occurs at TE at the point D. At the point D, composition "Y" is also capable of crystallizing.

Accordingly, various crystalline species are capable of crystallizing from, for example, the solidification of one or more species from a melt, whether the melt is under equilibrium or non-equilibrium conditions.

Another example of a phase diagram is contained in FIG. 79, which shows an example of a solubility curve. This general solubility curve is for a solid that forms a hydrate (i.e., one or more compounds that has one or more water molecules attached to it) as a system is cooled. For example, FIG. 79 could be any solid that forms hydrates such as, for example, $Na_2S_2O_3$. The number of hydrate molecules shown in FIG. 79 is arbitrary and will vary for each substance.

Further, FIG. 79a shows several solubility curves for different solutes in water. Most of these materials show increased solubility as a function of temperature. Sodium chloride is one of those solutes that shows a gradually increasing solubility in water as a function of increasing temperature. Specifically, for example, the solubility plot for NaCl shows that a saturated solution of NaCl at 20° C., will comprise about 36 grams of NaCl dissolved in 100 grams of water.

Accordingly, it should be apparent that the various bonding mechanisms for bonding together ions, atoms, molecules, macromolecules, etc., result in various possibilities for crystalline and structural configurations (e.g., the different unit cells shown in FIG. 70 and the different Bravais lattices shown in FIG. 72-74). While much work has been done to categorize different chemical configurations and/or structures, as well as many theories or explanations being set forth in an attempt to explain the mechanisms of crystallization, including the initiation of crystallization as well as secondary nucleation or growth, much remains unknown regarding the ability to control various crystalline structures within, for example, one or more given species. However, it is clear that various reactions, including various bonding and chemical reactions, are important in determining certain crystalline structures.

In this regard, chemical reactions are driven by energy. The energy comes in many different forms including chemical, thermal, mechanical, acoustic, and electromagnetic. Various features of each type of energy are thought to contribute in different ways to the driving of chemical reactions. Irrespective of the type of energy involved, chemical reactions are undeniably and inextricably intertwined with the transfer and combination of energy. An understanding of energy is, therefore, vital to an understanding of chemical reactions and hence, certain structural transformations.

A chemical reaction can be controlled and/or directed either by the addition of energy to the reaction medium in the form of thermal, mechanical, acoustic and/or electromagnetic energy or by means of transferring energy through a physical catalyst. These methods are traditionally not that energy efficient and can produce, for example, either unwanted by-products, decomposition of required transients, and/or intermediates and/or activated complexes and/or insufficient quantities of preferred products of a reaction.

It has been generally believed that chemical reactions occur as a result of collisions between reacting molecules. In terms of the collision theory of chemical kinetics, it has been expected that the rate of a reaction is directly proportional to the number of the molecular collisions per second:

$$\text{rate} \propto \text{number of collisions/sec}$$

This simple relationship has been used to explain the dependence of reaction rates on concentration. Additionally, with few exceptions, reaction rates have been believed to increase with increasing temperature because of increased collisions.

The dependence of the rate constant k of a reaction can be expressed by the following equation, known as the Arrhenius equation:

$$k = Ae^{-E_a/RT}$$

where $E_a$ is the activation energy of the reaction which is the minimum amount of energy required to initiate a chemical reaction, R is the gas constant, T is the absolute temperature and e is the base of the natural logarithm scale. The quantity A represents the collision rate and shows that the rate constant is directly proportional to A and, therefore, to the collision rate. Furthermore, because of the minus sign associated with the exponent $E_a/RT$, the rate constant decreases with increasing activation energy and increases with increasing temperature.

Normally, only a small fraction of the colliding molecules, typically the fastest-moving ones, have enough kinetic energy to exceed the activation energy, therefore, the increase in the rate constant k has been explained with the temperature increase. Since more high-energy molecules are present at a higher temperature, the rate of product formation is also greater at the higher temperature. But, with increased temperatures there are a number of problems which can be introduced into the reaction system. With thermal excitation other competing processes, such as bond rupture, may occur before the desired energy state can be reached. Also, there are a number of decomposition products which often produce fragments that are extremely reactive, but they can be so short-lived because of their thermodynamic instability, that a preferred reaction may be dampened.

Radiant or light energy is another form of energy that may be added to the reaction medium that also may have negative side effects but which may be different from (or the same as) those side effects from thermal energy. Addition of radiant energy to a system produces electronically excited molecules that are capable of undergoing chemical reactions.

A molecule in which all the electrons are in stable orbitals is said to be in the ground electronic state. These orbitals may be either bonding or non-bonding. If a photon of the proper energy collides with the molecule the photon may be absorbed and one of the electrons may be promoted to an unoccupied orbital of higher energy. Electronic excitation results in spatial redistribution of the valence electrons with concomitant changes in internuclear configurations. Since chemical reactions and bonding are controlled to a great extent by these factors, an electronically excited molecule undergoes a chemical reaction or bond transformation that may be distinctly different from those of its ground-state counterpart.

The energy of a photon is defined in terms of its frequency or wavelength, $$E = h\nu = hc/\lambda$$

where E is energy; h is Plank's constant, $6.6 \times 10^{-34}$ J·sec; $\nu$ is the frequency of the radiation, $\sec^{-1}$; c is the speed of light; and $\lambda$ is the wavelength of the radiation. When a photon is absorbed, all of its energy is typically imparted to the absorbing species. The primary act following absorption depends on the wavelength of the incident light. Photochemistry studies photons whose energies lie in the ultraviolet region (e.g., 100 Å-4000 Å) and in the visible region (e.g., 4000 Å-7000 Å) of the electromagnetic spectrum. Such photons are primarily a cause of electronically excited molecules.

Since the molecules are imbued with electronic energy upon absorption of light, reactions and structural transformations occur from different potential-energy surfaces from those encountered in thermally excited systems. However, there are several drawbacks of using the known techniques of photochemistry, that being, utilizing a broad band of frequencies thereby causing unwanted side reactions, undue experimentation, and poor quantum yield. The area of photocrystallization is still in its infancy and the known techniques are trial and error, empirical approaches, with no cohesive or comprehensive understanding of the underlying mechanisms. Some good examples of photochemistry are shown in the following patents.

In particular, U.S. Pat. No. 5,174,877 issued to Cooper, et al. al., (1992) discloses an apparatus for the photocatalytic treatment of liquids. In particular, it is disclosed that ultraviolet light irradiates the surface of a prepared slurry to activate the photocatalytic properties of the particles contained in the slurry. The transparency of the slurry affects, for example, absorption of radiation. Moreover, discussions of different frequencies suitable for achieving desirable photocatalytic activity are disclosed.

Further, U.S. Pat. No. 4,755,269 issued to Brumer, et al. al., (1998) discloses a photodisassociation process for disassociating various molecules in a known energy level. In particular, it is disclosed that different disassociation pathways are possible and the different pathways can be followed due to selecting different frequencies of certain electromagnetic radiation. It is further disclosed that the amplitude of electromagnetic radiation applied corresponds to amounts of product produced.

Selective excitation of different species is shown in the following three (3) patents. Specifically, U.S. Pat. No. 4,012,301 to Rich, et al. al., (1977) discloses vapor phase chemical reactions that are selectively excited by using vibrational modes corresponding to the continuously flowing reactant species. Particularly, a continuous wave laser emits radiation that is absorbed by the vibrational mode of the reactant species.

U.S. Pat. No. 5,215,634 issued to Wan, et al., (1993) discloses a process of selectively converting methane to a desired oxygenate. In particular, methane is irradiated in the presence of a catalyst with pulsed microwave radiation to convert reactants to desirable products. The physical catalyst disclosed comprises nickel and the microwave radiation is applied in the range of about 1.5 to 3.0 GHz.

U.S. Pat. No. 5,015,349 issued to Suib, et al. al., (1991) discloses a method for cracking a hydrocarbon to create cracked reaction products. It is disclosed that a stream of hydrocarbon is exposed to a microwave energy which creates a low power density microwave discharge plasma, wherein the microwave energy is adjusted to achieve desired results. A particular frequency desired of microwave energy is disclosed as being 2.45 GHz.

The art contains numerous well known crystallization and structure formations or modifications techniques (e.g., single crystal, polycrystalline, amorphous, etc.) as well as numerous well known post-processing techniques (e.g., annealing, chemical etching, laser etching, temperature conditioning, pressure conditioning, atmospheric conditioning, etc.) which also affect structure. The prior art techniques largely contain empirical results from many trial and error approaches that, in most cases, are not well understood at a basic level.

Physical catalysts are also well known in the art but the role that physical catalysts play in various reactions is also not well understood at a basic level. Specifically, a physical catalyst is typically regarded as a substance which alters the reaction rate of a chemical reaction without appearing in the end product. It is known that some reactions can be speeded up or controlled by the presence of substances which themselves appear to remain unchanged after the reaction has ended. By increasing the velocity of a desired reaction relative to unwanted reactions, the formation of a desired product can be maximized compared with unwanted by-products. Often only a trace of physical catalyst is necessary to accelerate the reaction. Also, it has been observed that some substances, which if added in trace amounts, can slow down the rate of a reaction. This looks like the reverse of catalysis, and, in fact, substances which slow down a reaction rate have been called negative catalysts or poisons. Known physical catalysts go through a cycle in which they are used and regenerated so that they can be used again and again. A physical catalyst operates by providing another path for the reaction which can have a higher reaction rate or slower rate than available in the absence of the physical catalyst. At the end of the reaction, because the physical catalyst can be recovered, it appears the physical catalyst is not involved in the reaction. But, the physical catalyst must somehow take part in the reaction, or else the rate of the reaction would not change. The catalytic act has historically been represented by five essential steps originally postulated by Ostwald around the late 1800's:
  1. Diffusion to the catalytic site (reactant);
  2. Bond formation at the catalytic site (reactant);
  3. Reaction of the catalyst-reactant complex;
  4. Bond rupture at the catalytic site (product); and
  5. Diffusion away from the catalytic site (product).

The exact mechanisms of catalytic actions are unknown in the art but it is known that physical catalysts can speed up a reaction that otherwise would take place too slowly to be practical.

A well known category of catalysts are the autocatalysts. In autocatalysis, the product of a reaction functions as a catalyst, speeding the rate of formation of more product. In autocatalytic reactions, it is clear that the catalyst does take part in the reaction. Nevertheless, the exact mechanisms of autocatalytic actions are also largely unknown in the art.

Accordingly, what is needed is a better understanding of the crystal growth, crystallization, structural and/or phase change processes and mechanisms so that biological, organic, and/or inorganic processes and materials, etc., can be engineered by more precisely controlling the multitude of reaction processes that exist, as well as developing completely new reaction pathways and/or new and/or desirable reaction products (e.g., crystalline phases or species).

Definitions

For the purposes of this invention, the terms and expressions below, appearing in the Specification and claims, are intended to have the following meanings:

"Activated complex", as used herein, means the assembly of atom(s) (charged or neutral) which corresponds to the maximum in the reaction profile describing the transformation of reactant(s) into reaction product(s). Either the reactant or reaction product in this definition could be an intermediate in an overall transformation involving more than one step.

"Applied spectral energy conditioning pattern", as used herein, means the totality of: (a) all spectral energy conditioning patterns that are externally applied to a conditionable participant; and/or (b) spectral conditioning environmental reaction conditions that are used to condition one or more conditionable participants to form a conditioned participant in a conditioning reaction system.

"Applied spectral energy pattern", as used herein, means the totality of: (a) all spectral energy patterns that are externally applied; and/or (b) spectral environmental reaction conditions input into a crystallization reaction system.

"Bravais lattice", as used herein, means the permissible combination of lattice types with unit cells.

"Catalytic spectral conditioning pattern", as used herein, means at least a portion of a spectral conditioning pattern of a physical catalyst which when applied to a conditionable participant can condition the conditionable participant to catalyze and/or assist in catalyzing the crystallization reaction system by the following:
  completely replacing a physical chemical catalyst;
  acting in unison with a physical chemical catalyst to increase the rate of reaction;
  reducing the rate of reaction by acting as a negative catalyst; or
  altering the reaction pathway for formation of a specific reaction product.

"Catalytic spectral energy conditioning pattern", as used herein, means at least a portion of a spectral energy conditioning pattern which when applied to a conditionable participant in the form of a beam or field can condition the conditionable participant to form a conditioned participant having a spectral energy pattern corresponding to at least a portion of a spectral pattern of a physical catalyst which catalyzes and/or assists in catalyzing the crystallization reaction system when the conditioned participant is placed into, or becomes involved with, the crystallization reaction system.

"Catalytic spectral energy pattern", as used herein, means at least a portion of a spectral energy pattern of a physical catalyst which when applied to a crystallization reaction system in the form of a beam or field can catalyze a particular reaction in the crystallization reaction system.

"Catalytic spectral pattern", as used herein, means at least a portion of a spectral pattern of a physical catalyst which when applied to a crystallization reaction system can catalyze a particular reaction by the following:
  a) completely replacing a physical chemical catalyst;
  b) acting in unison with a physical chemical catalyst to increase the rate of reaction;
  c) reducing the rate of reaction by acting as a negative catalyst; or
  d) altering the reaction pathway for formation of a specific reaction product.

"Columnar liquid crystals", as used herein, means a mesophase liquid-crystal wherein disc-like molecules stack into columns which themselves form a two-dimensional, long-range ordered hexagonal packing (e.g., columnar mesophase of cylinders in block co-polymers).

"Condition" or "conditioning", as used herein, means the application or exposure of a conditioning energy or combination of conditioning energies to at least one conditionable participant prior to the conditionable participant becoming involved (e.g., being placed into a crystallization reaction system and/or prior to being activated) in the crystallization reaction system.

"Conditionable participant", as used herein, means reactant, physical catalyst, solvent, physical catalyst support material, reaction vessel, conditioning reaction vessel, promoter and/or poison comprised of molecules, macromolecules, ions and/or atoms (or components thereof) in any form of matter (e.g., solid, liquid, gas, plasma) that can be conditioned by an applied spectral energy conditioning pattern.

"Conditioned participant", as used herein, means reactant, physical catalyst, solvent, physical catalyst support material, reaction vessel, conditioning reaction vessel, physical promoter and/or poison comprised of molecules, ions and/or atoms (or components thereof) in any form of matter (e.g., solid, liquid, gas, plasma) that has been conditioned by an applied spectral energy conditioning pattern.

"Conditioning energy", as used herein means at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions.

"Conditioning environmental reaction condition", as used herein, means and includes traditional reaction variables such as temperature, pressure, surface area of catalysts, physical catalyst size and shape, concentrations, electromagnetic radiation, electric fields, magnetic fields, mechanical forces, acoustic fields, reaction vessel size, shape and composition and combinations thereof, etc., which may be present and are capable of influencing, positively or negatively, the conditioning of at least one conditionable participant.

"Conditioning reaction system", as used herein, means the combination of reactants, physical catalysts, poisons, promoters, solvents, physical catalyst support materials, conditioning reaction vessel, reaction vessel, spectral conditioning catalysts, spectral energy conditioning catalysts, conditioned participants, environmental conditioning reaction conditions, spectral environmental conditioning reaction conditions, applied spectral energy conditioning pattern, etc., that are involved in any reaction pathway to form a conditioned participant.

"Conditioning reaction vessel", as used herein, means the physical vessel(s) or containment system(s) which contains or houses all components of the conditioning reaction system, including any physical structure or media which are contained within the vessel or system.

"Conditioning targeting", as used herein, means the application of conditioning energy to a conditionable participant to condition the conditionable participant prior to the conditionable participant being involved, and/or activated, in a holoreaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern; and spectral environmental conditioning reaction conditions, to achieve (1) direct resonance; and/or (2) harmonic resonance; and/or (3) non-harmonic heterodyne-resonance with at least a portion of at least one of the following conditionable participants: reactants; physical catalysts; promoters; poisons; solvents; physical catalyst support materials; reaction vessels; conditioning reaction vessels; conditioning reaction vessels and/or mixtures or components thereof (in any form of matter), said spectral energy conditioning provider providing conditioning energy to condition at least one conditionable participant by interacting with at least one frequency thereof, to form at least one conditioned participant which assists in producing at least one desired reaction product and/or at least one desired reaction product at a desired reaction rate, when the conditioned participant becomes involved with, and/or activated in, a crystallization reaction system.

"Coordination number", as used herein, means the number of atoms or ions in a crystalline structure that are nearest neighbors to, typically, a different atom or ion in such a crystalline structure (e.g., FIGS. 76a and 76b shows six fold coordination for each of $Na^+$ and $Cl^-$).

"Crystal growth" or "crystallization", as used herein, means the arrangement of atoms, ions, molecules and/or macromolecules into an ordered structure (macromolecules, micromolecules, etc.) which contains at least one repeatable unit cell.

"Crystallization reaction system", as used herein, means the combination of reactants, intermediates, transients, activated complexes, physical catalysts, poisons, promoters, solvents, physical catalyst support materials, spectral catalysts, spectral energy catalysts, reaction products, seeds or seed crystals, crystal substrates, epitaxial growth substrates, environmental reaction conditions, spectral environmental reaction conditions, applied spectral energy pattern, reaction vessels, etc., that are involved in any reaction pathway and which typically results in at least some order (e.g., crystallization or structure) in a system. However, controlling a system so as to prevent order also falls within the meaning of this definition.

"Derivative structure", as used herein, means a somewhat more complex structure which is related to a basic or simple structure but has been somehow perturbed to result in a more complex arrangement or structure. Mechanisms for achieving these somewhat more complex structures include: (1) an ordered substitution of one or more species for another; (2) an ordered omission of one or more species; (3) the addition of one or more species to an unoccupied site; and/or (4) the distortion of any array of one or more species.

"Direct resonance conditioning targeting", as used herein, means the application of conditioning energy to a conditionable participant to condition the conditionable participant prior to the conditionable participant being involved, and/or activated, in a holoreaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions, to achieve direct resonance with at least a portion of at least one conditionable participant (e.g.; reactants; physical catalysts; promoters; poisons; solvents; physical catalyst support materials; reaction vessels; conditioning reaction vessels and/or mixtures or components thereof in any form of matter), said spectral energy conditioning providers providing conditioning energy to condition at least one conditionable participant(s) by interacting with at least one frequency thereof to form at least one conditioned participant, which assists in producing at least one desired reaction product and/or at least one desired reaction product at a desired reaction rate, when the conditioned participant becomes involved with, and/or activated in, a crystallization reaction system.

"Direct resonance targeting", as used herein, means the application of energy to a crystallization reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction conditions, to achieve direct resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy providers providing energy to at least one of said forms of matter by interacting with at least one frequency thereof, in said reactants, to produce at least one desired reaction product and/or at least one desired reaction product at a desired reaction rate.

"Electrochemical cell", as used herein, means a device that converts chemical energy into electrical energy. It includes two electrodes which are separated by an electrolyte. The electrodes may comprise any electrically conducting material (e.g., solid or liquid metals, semiconductors, etc.) which can communicate with each other through an electrolyte. These cells experience separate oxidation and reduction reactions at each electrode.

"Electrocrystallization", as used herein, means an electrochemical technique that results in a crystalline material (e.g., the deposition of metal on the cathode in an electrolytic cell).

"electrolytic cell", as used herein, means an electrochemical cell that converts electrical energy into chemical energy. The chemical reactions typically do not occur spontaneously at the electrodes when the electrodes are connected through an external circuit. The chemical reaction is typically forced by applying an external electric current to the electrodes. This cell is used to store electrical energy in chemical form such as in, for example, a secondary or rechargeable battery. The process of water being decomposed into hydrogen gas and oxygen is termed electrolysis and such electrolysis is performed in an electrolytic cell.

"Electrometallurgy", as used herein, means a branch of metallurgy which utilizes electrochemical processes known as electrowinning.

"Electromigration", as used herein, means the movement of ions under the influence of electrical potential difference.

"Electrophoresis", as used herein, means the movement of small-suspended particles or large molecules in a liquid, such movement being driven by an electrical potential difference.

"Electroplating", as used herein, means a process that produces a thin, metallic coating on the surface of another material (e.g., a metal or another electrically conducting material such as graphite). The substrate to be coated is situated to be the cathode in an electrolytic cell, where the cations of the electrolyte becomes the positive ions of the metal to be coated on the surface of the cathode. When a current is applied, the electrode reaction occurring on the cathode is a reduction reaction causing the metal ions to become metal on the surface of the cathode.

"Electrowinning", as used herein, means an electrochemical process that produces metals from their ores. In particular, metal oxides typically occur in nature and electrochemical reduction is one of the most economic methods for producing metals from these ores. In particular, the ore is dissolved in an acidic aqueous solution or molten salt and the resulting electrolyte solution is electrolyzed. The metal is electroplated on the cathode (e.g., either in a solid or liquid form) while oxygen is involved in the reaction at the anode. Copper, zinc, aluminum, magnesium and sodium are manufactured by this technique.

"Enantiotropic polymorph", as used herein, means a polymorph which exhibits reversible transitions between at least two different crystalline structures.

"Environmental reaction condition", as used herein, means and includes traditional reaction variables such as temperature, pressure, surface area of catalysts, physical catalyst size and shape, concentrations, electromagnetic radiation, electric fields, magnetic fields, mechanical forces, acoustic fields, reaction vessel size, shape and composition and combinations thereof, etc., which may be present and are capable of influencing, positively or negatively, reaction pathways in a crystallization reaction system.

"Epitaxial growth", as used herein, means the growth of at least one layer of atoms, ions, molecules and/or macromolecules onto at least one substrate material.

"Frequency", as used herein, means the number of times which a physical event (e.g., wave, field and/or motion) varies from the equilibrium value through a complete cycle in a unit of time (e.g., one second; and one cycle/sec=1 Hz). The variation from equilibrium can be positive and/or negative, and can be, for example, symmetrical, asymmetrical and/or proportional with regard to the equilibrium value.

"Galvanizing", as used herein, means a process for coating iron or steel with a thin layer of zinc for corrosion protection. Galvanizing is performed electrochemically by an electroplating process or by a hot-dip galvanizing process which consists of immersing the metal into a molten zinc.

"Harmonic conditioning targeting", as used herein, means the application of conditioning energy to a conditionable participant to condition the conditionable participant, prior to the conditionable participant becoming involved, and/or activated, in a holoreaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions, to achieve harmonic resonance with at least a portion of at least one conditionable participant (e.g.; reactants; physical catalysts; promoters, poisons; solvents; physical catalyst support materials; reaction vessels; conditioning reaction vessels; and/or mixtures or components thereof in any form of matter), said spectral energy conditioning provider providing conditioning energy to condition at least one conditionable participant(s) by interacting with at least one frequency thereof, to form at least one conditioned participant which assists in producing at least one desired reaction product and/or at least one desired reaction product at a desired reaction rate when the conditioned participant becomes involved with, and/or activated in, a crystallization reaction system.

"Harmonic targeting", as used herein, means the application of energy to a crystallization reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction conditions, to achieve harmonic resonance with at least one of the following forms of matter: reactants; transients; intermediates; activated complexes; physical catalysts; reaction products; promoters, poisons; solvents; physical catalyst support materials; reaction vessels; and/or mixtures or components thereof, said spectral energy providers providing energy to at least one of said forms of matter by interacting with at least one frequency thereof, in said reactants, to produce at least one desired reaction product and/or at least one desired reaction product at a desired reaction rate.

"Holoreaction system", as used herein, means all components of the crystallization reaction system and the conditioning reaction system.

"Hydrolysis", as used herein, means a chemical reaction in which water reacts with another substance and causes decomposition of other products, often including the reaction of water with a salt to create an acid or a base.

"Intermediate", as used herein, means a molecule, ion and/or atom which is present between a reactant and a reaction product in a reaction pathway or reaction profile. It corresponds to a minimum in the reaction profile of the reaction between reactant and reaction product. A reaction which involves an intermediate is typically a stepwise reaction.

"Liquid crystal", as used herein, means one or more crystalline species that have characteristics of both the liquid state (e.g., short-range translational order due to excluded volume) and the crystalline state (e.g., long-range orientational order). In addition to long-range orientational order, smectic and cholesteric liquid crystals exhibit one-dimensional long-range translational order; and columnar liquid crystals exhibit two-dimensional long-range translational order. Some higher order smectic liquid crystals exhibit two-dimensional positional order within the layers.

"Mass transport", as used herein means the movement or transportation of mass (e.g., chemical compounds, ions, etc.) from one part of a system to another. This phenomena is typically associated with diffusion, convection and electron migration, but can also occur or be promoted through spectral mechanisms.

"Monotropic polymorph", as used herein, means a polymorph which exhibits an irreversible transition between at least two different crystalline structures.

"Nematic liquid crystals", as used herein, means molecules with short-range translational order (e.g., a densely packed liquid) and long-range uniaxial orientational order.

"Non-harmonic heterodyne conditioning targeting", as used herein, means the application of conditioning energy to a conditionable participant to condition the conditionable participant prior to the conditionable participant being involved, and/or activated, in a holoreaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions, to achieve non-harmonic heterodyne resonance with at least a portion of at least one conditionable participant (e.g.; reactants; physical catalysts; promoters; poisons; solvents; physical catalyst support materials; reaction vessels; conditioning reaction vessels and/or mixtures or components thereof in any form of matter), said spectral energy conditioning provider providing conditioning energy to condition at least one conditionable participant by interacting with at least one frequency thereof, to form at least one conditioned participant which assists in producing at least one desired reaction product and/or at least one desired reaction product at a desired reaction rate when the conditioned participant becomes involved with, and/or activated in, a crystallization reaction system.

"Non-harmonic heterodyne targeting", as used herein, means the application of energy to a crystallization reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction condition to achieve non-harmonic heterodyne resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy provider providing energy to at least one of said forms of matter by interacting with at least one frequency thereof, to produce at least one desired reaction product and/or at least one desired reaction product at a desired reaction rate.

"Participant", as used herein, means reactant, transient, intermediate, activated complex, physical catalyst, promoter, poison and/or reaction product comprised of molecules, macromolecules, ions and/or atoms (or components thereof).

"Phase-diagram", as used herein, means a graphical representation of, typically, an equilibrium situation for a given set of system parameters.

"Plasma", as used herein means, an approximately electrically neutral (quasineutral) collection of electrically activated atoms or molecules, or ions (positive and/or negative) and electrons which may or may not contain a background neutral gas, and at least a portion of which is capable of responding to at least electric and/or magnetic fields.

"Plastic crystals", as used herein, means crystals which possess a three-dimensional translational order but are orientationally disordered. These types of crystals typically have opposite characteristics from nematic liquid crystals.

"Polymorphs" or "polymorphism", as used herein, means a chemical composition or arrangement of atoms, ions, molecules and/or macromolecules, which are capable of existing in at least two different crystalline structures or arrangements.

"Primary nucleation", as used herein, is a first step in a crystallization process, typically, the growth of a new crystal.

"Quasicrystals", as used herein, means a state of matter between a periodic long-range translational order of the crystalline state and the limited short-range translational order of a non-crystalline state. These types of crystals are often found in metal systems.

"Reactant", as used herein, means a starting material or starting component in a crystallization reaction system. A reactant can be any inorganic, organic and/or biologic atom, molecule, macromolecule, ion, compound, substance, and/or the like.

"Reaction coordinate", as used herein, means an intra- or inter-molecular/atom configurational variable whose change corresponds to the conversion of reactant into reaction product.

"Reaction pathway", as used herein, means those steps which lead to the formation of reaction product(s). A reaction pathway may include intermediates and/or transients and/or activated complexes. A reaction pathway may include some or all of a reaction profile.

"Reaction product", as used herein, means any product of a reaction involving a reactant. A reaction product may have a different chemical composition from a reactant or a substantially similar (or exactly the same) chemical composition but exhibit a different physical or crystalline structure and/or phase and/or properties.

"Reaction profile", as used herein means a plot of energy (e.g., molecular potential energy, molar enthalpy, or free energy) against reaction coordinate for the conversion of reactant(s) into reaction product(s).

"Reaction vessel", as used herein, means the physical vessel(s) or containment system(s) which contains or houses all components of the crystallization reaction system, including any physical structures or media which are contained within the vessel or system.

"Resultant energy conditioning pattern", as used herein, means the totality of energy interactions between the applied spectral energy conditioning pattern with at least one conditionable participant before said conditionable participant becomes involved, and/or activated, in a crystallization reaction system as a conditioned participant.

"Resultant energy pattern", as used herein, means the totality of energy interactions between the applied spectral energy pattern with all participants and/or components in the crystallization reaction system.

"Secondary nucleation", as used herein, is crystallization which achieves crystal growth by feeding a nucleated crystal (or the like) with atoms, ions, molecules and/or macromolecules that are located nearby a seed crystal (or the like).

"Smectic liquid crystal", as used herein, means a liquid crystal that exhibits long-range one-dimensional translational order in addition to long-range orientational order. Thus, in addition to orientational order, the molecules of this liquid crystal stack in layers.

"Spectral catalyst", as used herein, means electromagnetic energy which acts as a catalyst in a crystallization reaction system, for example, electromagnetic energy having a spectral pattern which affects, controls, or directs a reaction pathway.

Spectral conditioning catalyst", as used herein, means electromagnetic energy which, when applied to a conditionable participant to form a conditioned participant, assists the conditioned participant to act as a catalyst in a crystallization reaction system, for example, electromagnetic energy having a spectral conditioning pattern which causes the conditioned participant to affect, control, or direct a reaction pathway in a crystallization reaction system when the conditioned participant becomes involved with, and/or activated in, the crystallization reaction system.

"Spectral conditioning environmental reaction condition", as used herein, means at least one frequency and/or field which simulates at least a portion of at least one conditioning environmental reaction condition.

"Spectral conditioning pattern", as used herein, means a pattern formed in a conditioning reaction system by one or more electromagnetic frequencies emitted or absorbed after excitation of an atom or molecule. A spectral conditioning pattern may be formed by any known spectroscopic technique.

"Spectral energy catalyst", as used herein, means energy which acts as a catalyst in a crystallization reaction system having a spectral energy pattern which affects, controls, and/or directs a reaction pathway.

"Spectral energy conditioning catalyst", as used herein, means conditioning energy which, when applied to a conditionable participant, assists a conditionable participant, once conditioned, to act as a catalyst in a crystallization reaction system, the conditioned participant having a spectral energy conditioning pattern which affects, controls and/or directs a reaction pathway when the conditioned participant becomes involved with, and/or activated in, the crystallization reaction system.

"Spectral energy conditioning pattern", as used herein, means a pattern formed in a conditioning reaction system by one or more conditioning energies and/or components emitted or absorbed by a molecule, ion, atom and/or component(s) thereof and/or which is present by and/or within a molecule, ion, atom and/or component(s) thereof.

"Spectral energy pattern", as used herein, means a pattern formed by one or more energies and/or components emitted or absorbed by a molecule, ion, atom and/or component(s) thereof and/or which is present by and/or within a molecule, ion, atom and/or component(s) thereof. For example, the spectral energy pattern could be a series of electromagnetic frequencies designed to heterodyne with reaction intermediates, or the spectral energy pattern could be the portion of the actual spectrum emitted by a reaction intermediate.

"Spectral environmental reaction condition", as used herein, means at least one frequency and/or field which simulates at least a portion of at least one environmental reaction condition in a crystallization reaction system.

"Spectral pattern", as used herein, means a pattern formed by one or more electromagnetic frequencies emitted or absorbed after excitation of an atom or molecule. A spectral pattern may be formed by any known spectroscopic technique.

"Targeting", as used herein, means the application of energy to a crystallization reaction system by at least one of the following spectral energy providers: spectral energy catalyst; spectral catalyst; spectral energy pattern; spectral pattern; catalytic spectral energy pattern; catalytic spectral pattern; applied spectral energy pattern; and spectral environmental reaction conditions, to achieve direct resonance and/or harmonic resonance and/or non-harmonic heterodyne-resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy provider providing energy to at least one of said forms of matter by interacting with at least one frequency thereof, to produce at least one desired reaction product and/or at least one desired reaction product at a desired reaction rate.

"Transient", as used herein, means any chemical and/or physical state that exists between reactant(s) and reaction product(s) in a reaction pathway or reaction profile.

"Unit cell", as used herein, means a fundamental and repeatable assembly of atoms, ions, molecules and/or macromolecules in a crystal (e.g., in a reaction product).

SUMMARY OF THE INVENTION

The present invention, discloses a variety of novel spectral energy techniques, referred to sometimes herein as spectral crystallization, that can be utilized in a number of crystallization reactions in organic, biologic and/or inorganic systems, including very basic reactions, which may be desirable to achieve or to permit to occur (or to prevent) in the various crystallization reaction systems. These spectral energy techniques can be used in, for example, all known crystal growth or crystallization techniques including, but not limited to, evaporation, vapor diffusion, liquid diffusion, thermal gradients, gel diffusion, high vacuum techniques of molecular beam epitaxy, atomic layer epitaxy, epitaxial growth from solutions, growth from a liquid metal, growth from a solution (e.g., aqueous, molten salt or other solvent), growth from super saturated solutions, growth from a melt, precipitation growth, hydrothermal growth, chemical vapor transport reaction growth, electrocrystallization, growth from a solid phase, acoustocrystallization, co-crystals and clath rates, etc. In addition, the techniques of the present invention can be used to obtain virtually all types of crystallization by all known crystallization or crystal growth techniques including the use of defects, if desirable, or eliminating defects, if desirable. Further, the techniques of the present invention can be utilized to obtain desirable phase or structure changes in certain crystals (single or polycrystalline) that have already been formed and/or to cause certain grown crystals to behave as though certain phase changes have occurred. Examples include such post-treatment processes as annealing processes, etching processes (e.g., thermal or chemical), chemical treatments (e.g., solid, liquid, gas and/or plasma), etc. Further, the techniques of the present invention can be utilized to obtain desired structures in certain materials.

Further, the invention discloses a variety of novel spectral energy conditioning techniques, referred to sometimes herein as spectral conditioning, or conditioning energies that can be utilized to condition a conditionable participant. Once a conditionable participant has been conditioned, the conditioned participant can be used in a crystallization reaction system. These spectral energy conditioning techniques can be used to condition at least one conditionable participant which can thereafter be used in, for example, any type of organic or inorganic crystallization system, biological crystallization reaction system (e.g., plant and animal), industrial crystallization reaction system, etc. Further, the conditioned participant may itself comprise both a reactant and a reaction product, whereby, for example, the chemical composition of the conditioned participant does not substantially change (if at all) but one or more energy dynamics, physical properties or structures and/or phases is changed once the conditioned participant is involved with, and/or activated by, the crystallization reaction system.

The techniques of the present invention have utility for growing crystals (or preventing growth of crystals in certain crystallization reaction systems) that exhibit only a single crystalline species, and mixed crystals, as well as for growing crystals that exhibit at least two crystalline species, as well as for those systems that are polymorphic (i.e., where more than one crystalline phase exists for a single chemical formula). For example, the techniques of the present invention can be utilized to assist in the primary nucleation of crystals, the secondary nucleation of crystals, controlling particular compositions formed during crystallization, controlling particular phases formed during crystallization, causing crystals and/or phases to result (or preventing certain phases from forming) that do not normally result under a given set of environmental conditions, causing a formed crystal phase to change which may result in the crystal behaving as though the phase had changed, causing primary or secondary nucleation of a first material or crystalline species and subsequent primary nucleation and/or secondary nucleation of a second composition and/or crystalline species; epitaxial growth of similar or dissimilar materials on a substrate, preferential or selective crystallization of a particular species from a mixed species source, etc. The techniques of the present invention can be used for all known crystal growth or crystallization techniques whereby the techniques of the invention augment existing techniques (e.g., use of a seed crystal is augmented by at least one spectral energy provider and/or at least one spectral energy conditioning provider) or substantially completely replace certain aspects of growth (e.g., a seed crystal can be replaced completely by a spectral energy provider and/or a spectral energy conditioning provider). Moreover, the techniques of the present invention can prevent the formation of certain crystals or structures or cause, for example, one or more amorphous phases or structures to result when one or more crystallized species or structures would normally result or vice versa.

These novel spectral energy techniques (now referred to as spectral crystallization) and novel spectral energy conditioning techniques (now referred to as spectral conditioning crystallization) are possible to achieve due to the fundamental discoveries contained herein that disclose various means for achieving the transfer of energy (or preventing the transfer of energy) and/or controlling the energy dynamics and/or controlling the resonant exchange of energy between, for example, two entities. The invention teaches that the key for transferring energy between two entities (e.g., one entity sharing energy with another entity) is that when frequencies match, energy transfers. For example: (1) matching of frequencies of spectral energy patterns of two different forms of matter or matching of frequencies of a spectral energy pattern of matter with energy in the form of a spectral energy catalyst; and/or (2) matching of frequencies of spectral conditioning energy patterns of two different forms of matter or matching of frequencies of a spectral energy pattern of matter with energy in the form of a spectral conditioning catalyst. In the case of achieving the transfer of energy between, for example, a spectral energy conditioning pattern and a conditionable participant, once conditioning energy has been transferred, the conditioned participant can thereafter favorably utilize its conditioned energy pattern in a crystallization reaction system. The aforementioned entities may both be comprised of matter (solids, liquids, gases and/or plasmas and/or mixtures and/or components thereof), both comprised of various form(s) of energy, or one comprised of various form(s) of energy and the other comprised of matter (solids, liquids, gases and/or plasmas and/or mixtures and/or components thereof).

More specifically, all matter can be represented by spectral energy patterns, which can be quite simple to very complex in appearance, depending on, for example, the complexity of the matter. One example of a spectral energy pattern is a spectral pattern (or a spectral conditioning pattern) which likewise can be quite simple to quite complex in appearance, depending on, for example, the complexity of the matter. In the case of matter represented by spectral patterns (or spectral conditioning patterns), matter can exchange energy with other matter if, for example, the spectral patterns of the two forms of matter match, at least partially, or can be made to match or overlap, at least partially (e.g., spectral curves or spectral patterns (or spectral conditioning patterns) comprising one or more electromagnetic frequencies may overlap with each other). In general, but not in all cases, the greater the overlap in spectral patterns (and thus, the greater the overlap of frequencies comprising the spectral patterns or spectral conditioning patterns), the greater the amount of energy transferred. Likewise, for example, if the spectral pattern (or spectral conditioning pattern) of at least one form of energy can be caused to match or overlap, at least partially, with the spectral pattern of matter, (e.g., a participant or a conditionable participant) energy will also transfer to the matter. Thus, energy can be transferred to matter by causing frequencies to match.

As discussed elsewhere herein, energy (E), frequency (v) and wavelength (λ) and the speed of light (c) in a vacuum are interrelated through, for example, the following equation:

$$E = hv = hc/\lambda$$

When a frequency or set of frequencies corresponding to at least a first form of matter can be caused to match with a frequency or set of frequencies corresponding to at least a second form of matter, energy can transfer between the different forms of matter and permit at least some interaction and/or reaction to occur involving at least one of the two different forms of matter. For example, solid, liquid, gas and/or plasma (and/or mixtures and/or portions thereof) forms of matter can interact and/or react and form a desirable reaction product or result. Any combination(s) of the above forms of matter (e.g., solid/solid, solid/liquid, solid/gas, solid/plasma, solid/gas/plasma, solid/liquid/gas, etc., and/or mixtures and/or portions thereof) are possible to achieve for desirable interactions and/or reactions to occur in various crystallization reaction systems in biologic, organic and/or inorganic systems.

In particular, for example, the present invention has applicability in the following exemplary systems: (1) graphite/diamond; (2) the phases associated with $SiO_2$; (3) the phases associated with $BaTiO_3$, (4) the phases of water/ice; (5) the solubility of materials in solvents (e.g., solutes in water); (6) the phases in the binary system $MgO/SiO_2$; (7) the phases in the $FeO/Fe_2O_3$ system; (8) the phases in a hydrate system; (9) the phases in polymers; (10) the phases in lipids; and (11) the phases in proteins. Specific experimental examples of various exemplary crystallization reaction systems are contained in the "Examples" section later herein, while the following exemplary systems give a general understanding of the applicability of the techniques of the present invention.

FIGS. 80a, 80b and 80c relate to the various phases for carbon, including graphite and diamond. A phase-diagram for carbon phases is shown in FIG. 80a. This phase-diagram shows that graphite is the predominate phase present at lower pressures and lower temperatures but that a transition to diamond occurs at higher temperatures and/or higher pressures. The clinographic projection of the hexagonal structure of diamond is shown in FIG. 80b; whereas the clinographic projection of the unit cell of the cubic structure of diamond is shown in FIG. 80c. The techniques of the present invention can be utilized to assist in phase transformations in this system and systems like this system.

FIGS. 81a and 81b show two phase-diagrams for the $SiO_2$ system. In particular, FIG. 81a shows the equilibrium diagram for $SiO_2$ whereas FIG. 81b shows metastable phases that also occur in the $SiO_2$ system. FIG. 81c shows a clinographic projection of the unit cell of an idealized cubic β-crystobalite structure. FIG. 81d shows a plan view of a rhombohedral structure of α-quartz projected on a plane perpendicular to the principal axis. FIG. 81e shows a plan view of the hexagonal structure of β-quartz projected on a plan view taken perpendicular to the z-axis. The techniques of the present invention can assist in controlling the presence of one or more phases in the $SiO_2$ system and systems like this system.

FIG. 82a shows the phase diagram for the system $Ba_2TiO_4$/$TiO_2$. Of particular interest in this phase diagram is the formation of barium titanate ($BaTiO_3$). FIG. 82b shows a clinographic projection of the unit cell of an idealized cubic structure of $BaTiO_3$. In addition, FIG. 82c shows cation displacements relative to an oxide sub-lattice in tetragonal $BaTiO_3$. Moreover, Table C shows the relationship between transition temperature and crystal structure for the phase behavior of $BaTiO_3$.

TABLE C

| | Phase Behavior of $BaTiO_3$ | | | |
| --- | --- | --- | --- | --- |
| | Transition Temperature | | | |
| | −80° C. | 5° C. | 120° C. | |
| Crystal Structure | Rhombohedral | Orthorhombic | Tetragonal<br>a = 3.995 Å<br>c = 4.034 Å | Cubic<br>a = 4.002 Å |

The techniques of the present invention can be utilized to control various phases in the barium titanate crystallographic system and systems like this system.

The various phase diagrams (e.g., showing temperature and pressure relationships) for water are shown in FIGS. 83a, 83b and 83c, with FIG. 83c being the more common phase diagram for water. In addition, FIG. 83d shows a clinographic projection of the hexagonal structure of ice. In general, there are three recognized forms of water under the temperature/pressure conditions shown in the aforementioned Figure between which a somewhat continuous transition with temperature occurs. Specifically, a first structure of water is ice-like and is stable below about 4° C.; a second phase is a quartz-like structure of water which is stable between about 4° C. and about 150° C. under the shown pressure conditions; and a third phase of water is a close-packed array which is stable above about 150° C. under the shown pressure conditions. However, water may be regarded as one of the most complex structures known to man. In particular, numerous sub-phases exist within the three general phases discussed above. The sub-phases may coincide with various micro- and macro-molecular clusters. Further, there are at least 13 recognized phases of water as a function of modest temperatures and pressures. The techniques of the present invention can be utilized to affect the behavior of water (e.g., solute/solvent relationships can be affected by the techniques of the present invention).

A binary phase diagram for the system MgO—$SiO_2$ is shown in FIG. 84a. A corresponding plan view of an idealized orthorhombic structure of forsterite (i.e., $Mg_2SiO_4$) is shown in FIG. 84b on a plane which is perpendicular to the x-axis. The techniques of the present invention can be utilized to control various phases in the MgO—$SiO_2$ system.

The system $FeO/Fe_2O_3$ is shown in phase-diagram form in FIG. 85a. A clinographic projection of four unit cells of a cubic body-centered structure of α-iron is shown in FIG. 85b. The techniques of the present invention can be utilized to obtain desirable phases in the system FeO—$Fe_2O_3$ and systems like this system (as discussed in more Still further, as shown in FIG. 79, a solubility curve for a theoretical hydrate is given. The techniques of the present invention can be utilized to modify the expected phases in the solubility curve in this system and in systems like this system (as discussed in greater detail later herein.

Further, FIG. 97a shows several solubility curves for different solvents in water. Most of these materials show increased solubility as a function of temperature. Sodium chloride is one of those solutes that shows a gradually increasing solubility in water as a function of increasing temperature. Specifically, for example, the solubility plot for NaCl shows that a saturated solution of NaCl at 20° C., will comprise about 36 grams of NaCl dissolved in 100 grams of water. Thus, for example, if 40 grams of NaCl was added to the 100 grams of water, about 4 grams of undissolved NaCl would remain as solid in the bottom of a container. Moreover, if 36 grams of NaCl was added to 100 grams of water at 20° C., as above, and the temperature of the solution was raised, then the solution would be slightly unsaturated (e.g., the solution would be capable of dissolving more NaCl at this temperature). Still further, if 36 grams of NaCl was added to 100 grams of water at 20° C., as above, and the temperature of the solution was lowered, then the solution would be "supersaturated" (e.g., at least temporarily) until the extra (i.e., 4 grams) of solute would come out of the solution (i.e., at which point the solution would again be saturated). Thus, these aforementioned selective examples are exemplary ways to utilize solubility curves to form saturated, unsaturated and supersaturated solutions. In this regard, a saturated solution is typically regarded as one where an equilibrium is established between undissolved solute and dissolved solutes. However, the techniques of the present invention can advantageously affect or change the solubility (or at least the rate that solutes can be dissolved by solvents) of known materials at known temperatures in known solutions (as discussed in grater detail later herein).

Furthermore, the techniques of the present invention are equally applicable in polymer or organic systems as well as in biologic systems. In this regard, crystalline or structural growth of, for example, proteins, fatty acids, lipids, DNA, etc., as well as crystalline or structural growth of, for examples, polymers (including monomers and oligimers) are well known. Different crystalline or structural species (e.g., phases) are also obtainable in these crystallization reaction systems. Further, the techniques of the present invention can be utilized to control quasicrystal systems, liquid crystal systems, as well as encouraging certain crystallization reaction systems to remain essentially non-crystalline (e.g., predominantly non-crystalline or only localized order) or to encourage at least only a limited order within certain crystallization reaction systems.

FIG. 87a shows a molecular model of the $\delta$-$\alpha$ transformation observed in oleic acid, erucic acid, asclepic acid and palmitoleic acid. Specifically, oleic acid is one of the principal unsaturated fatty acids. Most of the unsaturated fatty acids exhibit a polymorphic behavior. Unsaturated fatty acids play an important role in lipid molecules that correspondingly play critical roles in the functional activities of biological organisms and also in fatty products. Unsaturated fatty acids occupy about one-half of all acyl chains in bio-membrane phospholipids, promoting fluidity and permeability of the membrane through conformational flexibility of the acyl chains. Major factors which are thought to influence the physical and chemical properties of unsaturated fats and lipids are the number, position and configuration of double bonds. Thus, it is very important to have a molecular-level understanding of the structure-function relationships of unsaturated fatty acids. The techniques of the present invention can assist in controlling certain reaction products and/or reaction pathways in various organic or biologic crystallization reaction systems.

FIG. 87b shows a single crystal morphology of the $\alpha$-form and $\delta$-form of gondoic acid.

FIG. 87c shows a Raman scattering C-C stretching band of the $\alpha$-form and $\delta$-form of gondoic acid.

FIG. 87d shows a phase-diagram for mixtures of gondoic acid with asclepic acid; and FIG. 87e shows a phase-diagram for mixtures of gondoic acid with oleic acid.

In particular, FIGS. 87b-87e show important phase and structure relationships between these various biologic acids. The control of particular phases or structures within these fatty acids can be of great significance and importance in biological reactions. Accordingly, the techniques of the present invention can be utilized to assist and/or control various reaction pathways within these crystallization reaction systems (as discussed in greater detail later herein).

However, crystallization in biological crystallization reaction systems, in general, follow the basic steps of nucleation and growth. In this regard, crystallization of, for example, a fat compound typically requires supersaturation or supercooling. For fat systems, crystallization is often complex because natural fats are a mixture of various triacylglycerols. Consequently, the concentration of these triacylglycerols is typically low and, for example, increased supercooling may be required to achieve desirable nucleation of the low concentration species. Furthermore, triacylglycerols are characterized by a complex melting behavior. The triacylglycerols typically exhibit three different crystal structures of $\alpha$, $\beta'$ and $\beta$. These polymorphic crystal structures depend on, for example, the particular driving forces for crystallization. Accordingly, the understanding and techniques for controlling of these various processes to achieve desirable polymorphic phases is important in these crystallization reaction systems.

Crystallization of other organic compounds, for example, proteins, is typically accomplished using a variety of catalytic components such as salts, buffers, precipitants, reagents, additives, and temperature. Accordingly, the techniques of the present invention can be utilized to assist and/or control various reaction pathways within these crystallization reaction systems (as discussed in greater detail later herein).

In order to practice the techniques of the present invention, it has been discovered that matter (e.g., solids, liquids, gases and/or plasmas and/or mixtures and/or portions thereof) can be caused, or influenced, to interact and/or react (or be prevented from reacting and/or interacting) with other matter and/or portions thereof in, for example, a crystallization reaction system along a desired reaction pathway by applying energy, in the form of, for example, a spectral energy provider such as a catalytic spectral energy pattern, a catalytic spectral pattern, a spectral energy pattern, a spectral energy catalyst, a spectral pattern, a spectral catalyst, a spectral environmental reaction condition and/or combinations thereof, which can collectively result in an applied spectral energy pattern being applied or provided in at least a portion of the crystallization reaction system.

Likewise, matter (e.g., solids, liquids, gases and/or plasmas and/or mixtures and/or portions thereof) can be caused, or influenced, to interact and/or react with other matter and/or portions thereof in, for example, a crystallization reaction system along a desired reaction pathway by applying conditioning energy to a conditionable participant, in the form of, for example, a catalytic spectral energy conditioning pattern, a catalytic spectral conditioning pattern, a spectral energy conditioning pattern, a spectral energy conditioning catalyst, a spectral conditioning pattern, a spectral conditioning catalyst, a spectral conditioning environmental reaction condition and/or combinations thereof, which can collectively result in an applied spectral energy conditioning pattern being applied to a conditionable participant. Specifically, the applied conditioning energy results in a conditioned participant which, when exposed to, and/or activated by, a crystallization reaction system, can cause the crystallization reaction system to behave in a desirable manner (e.g., the conditioned energy pattern of the conditioned participant favorably interacts with at least one participant in a crystallization reaction system).

One aspect of the present invention is the discovery that a spectral energy pattern delivered to a crystallization reaction system can function as a form of scaffolding which effects and controls crystallization and/or structure of the reaction product. For example, a seed crystal in a crystallization reaction system can be modeled as an autocatalyst. In this model, a seed crystal emits a unique spectral energy pattern which extends a short distance into the surrounding medium. This extending energy pattern functions as a type of scaffolding which guides and catalyzes growth of the crystal. In this regard, a seed crystal can be considered to be an autocatalyst, and crystallization and autocatalytic process. A spectral energy pattern can be delivered to a crystallization reaction system which enhances the inherent energy scaffolding of a seed crystal, or which replaces it altogether. Examples if this phenomena, discussed in greater detail in the "Examples" section later herein, utilizes a sodium vapor lamp as a spectral energy pattern which results in enhanced formation of sodium halide crystals from various aqueous solutions.

Since, a seed crystal appears to behave as a catalyst in an autocatalytic process which results in the formation of one or more ordered or structured forms of matter in a crystallization reaction system, the seed crystal (or seed-crystal spectral energy pattern) is an important component to consider in a crystallization reaction system. For example, a seed crystal catalyzes at least one reaction in a crystallization reaction system leading to the formation of one or more species (e.g., crystal growth, crystallization, phase changes, etc.). In the case of a seed crystal, the spectral frequencies, which are constantly being emitted and absorbed by all matter, can act as a spectral catalyst for the formation of more crystal in the crystallization reaction system. However, these frequencies emitted are, typically, somewhat limited in intensity (i.e., are relatively weak) due to the relatively small size of most seed crystals that are utilized. Accordingly, the emanated or emitted spectral pattern may not reach very far into a crystallization reaction system. This disclosure teaches and shows that crystallization can be enhanced if the spectral signal of the seed crystal is effectively amplified. In many respects, the electric and/or magnetic fields emitted by the seed crystal may act as, for example, electromagnetic scaffolding for the rapid and orderly formation of more crystalline layers. However, if the signal is small (e.g., the "scaffolding" does not extend very far into the reactants or participants in the crystallization reaction system) then crystal growth may be relatively slow. However, if the size of the "scaffolding" could be effectively increased (e.g., by applying a spectral energy provider of sufficient strength so as to increase the effective size of the spectral pattern emitted by the seed crystal) then, for example, the rate of crystallization or the rate of crystal growth can be effectively increased. Moreover, directional patterning of the electromagnetic scaffolding can also influence, for example, shape, morphology, phase, etc., of crystalline growth or formation in the crystallization reaction system.

In particular, an existing seed crystal produces an electromagnetic "scaffolding" effect comprising a combination of standing waves and nodes which are produced by, for example, the interaction of spectral patterns of the crystallized species. These electromagnetic waves include electronic, vibrational, rotational, librational, translational, gyrational and torsional frequencies, as well as fine splitting frequencies, hyperfine splitting frequencies, Stark frequencies and Zeeman frequencies. These particular electromagnetic nodes and waves extend, typically, only a short distance from the surface of the seed crystal (or epitaxial substrate or nucleation site). When, for example, adatoms approach the seed crystal, the adatoms can resonate sympathetically with the standing wave pattern emitted by the seed crystal (e.g., the presence of the scaffolding) and may be attracted, through, for example, the process of beading, to form additional layers on the seed crystal (i.e., a growth of one or more crystalline species now occurs).

Accordingly, by augmenting or supplementing a naturally occurring standing wave pattern of electromagnetic energy existing in, for example, a seed crystal, layer-by-layer growth can be accelerated, as well as growth being capable of being controlled with greater specificity. Particular control of growth includes controlling the lattice vibrations for atomic or mixed crystals; controlling librational, vibrational or translational frequencies in the case of molecular crystals such as water; controlling torsional or hydrogen bonding frequencies in the case of, for example, organic macromolecules; and/or controlling electronic or other frequencies.

In addition to supplementing the electromagnetic patterns of a seed crystal, a complete substitution of electromagnetic patterns (e.g., use of a spectral provider) can also be utilized.

In these cases, interactions and/or reactions may also be caused to occur when the applied spectral energy pattern (or the applied spectral energy conditioning pattern) results in, for example, some type of modification to the spectral energy pattern of one or more of the forms of matter in the crystallization reaction system. The various forms of matter include reactants; transients; intermediates; activated complexes; physical catalysts; reaction products; promoters; poisons; solvents; physical catalyst support materials; reaction vessels; and/or mixtures of components thereof. For example, the applied spectral energy provider (i.e., at least one of spectral energy catalyst; spectral catalyst; spectral energy pattern; spectral pattern; catalytic spectral energy pattern; catalytic spectral pattern; applied spectral energy pattern and spectral environmental reaction conditions) when targeted appropriately to, for example, a participant and/or component in the crystallization reaction system, can result in the generation of, and/or desirable interaction (e.g., primary nucleation and/or secondary nucleation) with one or more participants for enhanced nucleation (or if desired, primary and/or secondary nucleation can be prevented or substantially completely eliminated). Specifically, the applied spectral energy provider can be targeted to achieve very specific desirable results and/or reaction product and/or reaction product at a desired rate and/or along a desired reaction pathway (e.g., along a desired crystallization reaction pathway).

The targeting in many cases can occur by a direct resonance approach, (i.e., direct resonance targeting), a harmonic resonance approach (i.e., harmonic targeting) and/or a non-harmonic heterodyne resonance approach (i.e., non-harmonic heterodyne targeting). The spectral energy provider can be targeted to, for example, interact with at least one frequency of an atom or molecule, including, but not limited to, electronic frequencies, vibrational frequencies, rotational frequencies, rotational-vibrational frequencies, librational frequencies, translational frequencies, gyrational frequencies, fine splitting frequencies, hyperfine splitting frequencies, magnetic field induced frequencies, electric field induced frequencies, natural oscillating frequencies, and all components and/or portions thereof (discussed in greater detail later herein). These approaches may result in, for example, the mimicking of at least one mechanism of action of a physical catalyst, environmental factor and/or a seed crystal, etc., in a crystallization reaction system.

Similar concepts also apply to utilizing an applied spectral energy conditioning pattern in a conditioning reaction system to form a conditioned participant. In the case where one applied spectral energy conditioning pattern is utilized, interactions and/or reactions may be caused to occur in the conditioning reaction system when the applied spectral energy conditioning pattern results in, for example, some type of modification to the spectral energy pattern of one or more conditionable participants prior to such participant(s) being involved in, and/or activated by, the crystallization reaction system. The various forms of matter that can be used as a conditionable participant include reactants; physical catalysts; reaction products; promoters; poisons; solvents; physical catalyst support materials; reaction vessels; conditioning reaction vessels; and/or mixtures of components thereof. For example, the applied spectral energy conditioning provider (e.g., at least one of a: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions) when targeted appropriately to, for example, a conditionable participant and/or component thereof prior to the conditionable participant and/or component thereof becoming involved in, and/or activated by, the crystallization reaction system, can result in the generation of a desirable reaction product, and/or desirable interaction with one or more participants in the crystallization reaction system. Specifically, the applied spectral energy conditioning provider can be targeted to a conditionable participant to achieve very specific desirable results (e.g., a very specific conditioned energy pattern). The desirable conditioned energy pattern can thereafter result in a desirable reaction pathway, a desirable reaction product and/or at a desired rate in a crystallization reaction system, when the conditioned participant becomes involved in the crystallization reaction system. Further, the conditioned participant may itself comprise both a reactant and a reaction product, whereby, for example, the chemical composition of the conditioned participant does not substantially change (if at all) but one or more physical properties or structures or phases or relationships in one or more of the energy structure(s) is changed once the conditioned participant is involved with, and/or activated by, the crystallization reaction system.

The conditioning targeting can occur by a direct resonance conditioning approach, (i.e., direct resonance conditioning targeting), a harmonic resonance conditioning approach (i.e., harmonic conditioning targeting), non-harmonic heterodyne conditioning resonance approach (i.e., non-harmonic heterodyne conditioning targeting). The spectral energy conditioning provider can be targeted to, for example, interact with the conditionable participant by interacting with at least one frequency of an atom or molecule, including, but not limited to, electronic frequencies, vibrational frequencies, rotational frequencies, rotational-vibrational frequencies, fine splitting frequencies, hyperfine splitting frequencies, magnetic field induced frequencies, electric field induced frequencies, natural oscillating frequencies, and all components and/or portions thereof (discussed in greater detail later herein). Some examples of known sources of spectral energy conditioning providers include, but are not limited to, ELF sources, VLF sources, radio sources, microwave sources, infrared sources, visible light sources, ultraviolet sources, x-ray sources and gamma ray sources.

The following Table D lists examples of various possible sources of spectral energy patterns and of spectral energy conditioning patterns.

TABLE D

ELF, VLF, and Radio Sources

Electron tubes
(e.g. oscillators such as regenerative, Meissner, Harley, Colpitts, Ultraudion, Tuned-Grid Tuned Plate, Crystal, Dynatron, Transitron, Beat-requency, R-C Transitron, Phase-Shift, Multivibrator, Inverse-Feedback, Sweep-Circuit, Thyratron Sweep)
Glow tube
Thyratron
Electron-ray tube
Cathode-ray tube
Phototube
Ballast tube
Hot body
Magnetron
Klystron
Crystals
(e.g. microprocessor, piezoelectric, quartz, quartz strip, SAW resonator, semiconductor)
Oscillators
(e.g. crystal, digitally compensated crystal, hybrid, IC, microcomputer compensated crystal, oven controlled crystal OCXO, positive emitter-coupled logic, pulse, RC, RF, RFXO, SAW, sinusoidal, square wave, temperature compensated TCXO, trigger coherent, VHF/UHF, voltage controlled crystal VCXO, voltage controlled VCO, dielectric resonator DRO)

Microwave Sources

Hot body
Spark discharge
Electronic tubes (e.g. triode)
Klystrons
Klystron plus multipliers
Magnetrons
Magnetron harmonics
Traveling-wave and backward wave tubes
Spark oscillator
Mass oscillator
Vacuum tube
Multipliers
Microwave tube
Microwave solid-state device
(e.g. transistors, bipolar transistors, field-effect transistors, transferred electron (Gunn) devices, avalanche diodes, tunnel diodes)
Maser
Oscillators
(e.g. crystal, digitally compensated crystal, hybrid, IC, microcomputer compensated crystal, oven controlled crystal OCXO, positive emitter-coupled logic, pulse, RC, RF, RFXO, SAW, sinusoidal, square wave, temperature compensated TCXO, trigger coherent, VHF/UHF, voltage controlled crystal VCXO, voltage controlled VCO, dielectric resonator DRO)

Infrared Sources

Filaments (e.g. Nernst, refractory, Globar)
Gas mantle
Lamp (e.g. mercury, neon)
Hot body
Infrared light emitting diode ILED, arrays Visible Light Sources Flame
Electric arc
Spark electrode
Gaseous discharge (e.g. sodium, mercury)
Planar Gas discharge
Plasma
Hot body
Filament, Incandescence
Laser, laser diodes (e.g. multiple quantum well types, double heterostructured)

TABLE D-continued

Lamps
(e.g. arc, cold cathode, fluorescent, electroluminescent, fluorescent, high intensity discharge, hot cathode, incandescent, mercury, neon, tungsten-halogen, deuterium, tritium, hollow cathode, xenon, high pressure, photoionization, zinc)
Light-emitting diode LED, LED arrays
Organic Light-emitting diode OLED (e.g. small molecule, polymer)
Luminescence (e.g. electro-, chemi-)
Charge coupled devices CCD
Cathode ray tube CRT
Cold cathode
Field emission
Liquid crystal LCD
Liquid crystal on silicon LcoS
Low Temperature polycrystalline silicon LTPS
Metal-Insulated-Metal (MIM) Active Matrix
Active Matrix Liquid Crystal
Chip on Glass COG
Twist Nematic TN
Super Twist Nematic STN
Thin film transistor TNT
Fluorescence (e.g. vacuum, chemi-)
Ultraviolet Sources Spark discharge
Arc discharge
Hot body
Lamps (e.g. gaseous discharge, mercury vapor, neon, fluorescence, mercury-xenon)
Light emiting diode LED, LED arrays
Laser
X-ray Sources Atomic inner shell
Positron-electron annihilation
Electron impact on a solid
Spark discharge
Hot body
Tubes (e.g. gas, high vacuum)
γ-ray Sources Radioactive nuclei
Hot body The techniques of the present invention can be utilized to achieve preferred characteristics, such as growth and/or orientation and/or morphology, etc., which is/are not normally attainable by known systems. For example, if a seed crystal is utilized, electromagnetic energy may be preferentially directed to one or more faces of the seed crystal to result in a larger "scaffolding" extending from one or more selected sides of the seed crystal to result in preferential growth from those side(s). Moreover, rather than simply applying a spectral energy provider which simulates the "scaffolding" or energy pattern of a seed crystal, a spectral energy provider such as spectral environmental reaction condition could be applied. In this regard, environmental factors such as temperature, pressure, concentration, etc., can also favorably influence crystal growth or crystallization. Accordingly, for example, spectral patterns corresponding to, for example, temperature and/or pressure could be applied instead of, or in addition to, those spectral energy patterns corresponding to the "scaffolding" of the seed crystal.

Further, for example, a spectral energy conditioning pattern may be applied to a conditionable participant which may by itself, or when used with a spectral energy pattern, favorably influence the formation of desirable reaction product(s) at one or more specific locations in a crystallization reaction system when the conditioned participant becomes involved in the crystallization reaction system. For example, the conditioned participant may itself function as a seed crystal, or may complement the energy pattern of one or more participants in the crystallization reaction system. Depending on a particular crystallization reaction system, a spectral energy pattern and a spectral energy conditioning pattern may be substantially similar to each other, or very different from each other. Examples of this phenomenon, discussed in greater detail in the "Examples" section later herein, utilize a sodium vapor light as a spectral energy conditioning pattern for conditioning water prior to solute being dissolved therein.

As stated above, a spectral energy provider can be used to augment a system, or to replace, for example, a seed crystal. In this regard, when a critical size for nucleation is provided by the use of, for example, seed crystals, crystallization occurs on the provided nucleation sites. There are a number of critical factors associated with these nucleation sites. However, rather than using such seed crystals, a spectral energy provider could be input into a crystallization reaction system to function effectively as a seed crystal.

The techniques of the present invention can also be utilized to grow crystals (e.g., epitaxial growth) onto other materials (e.g., epitaxial substrates), which differ in crystalline form from those materials which are desired to be grown. In particular, by providing appropriate spectral energy providers to, for example, a substrate, an appropriate "scaffolding" can emanate from a surface of a substrate resulting in the attraction of desirable ions, atoms, molecules and/or macromolecules, etc., onto at least one surface of a substrate.

Further, by substantially matching, for example, a spectral energy pattern of a substrate with a spectral energy provider, atoms, ions, molecules and/or macromolecules can be encouraged to bond or attach themselves to the substrate in a desirable manner. If, for example, the desired substrate creates a spectral energy pattern (e.g., an electromagnetic energy pattern), which does not match sufficiently to, for example, the spectral energy patterns of atoms, ions, molecules and/or macromolecules which are to be bonded onto the substrate, then the substrate can be caused to emit a spectral energy pattern which differs from the normal (i.e., inherent) spectral energy pattern emitted therefrom. In this regard, for example, particular frequencies could be heterodyned (e.g., externally or internally) with the substrate to cause the substrate to behave in a different manner spectrally (i.e., a different and more favorable spectral energy pattern can be created). These techniques of causing the substrate to behave in a different manner spectrally could be advantageously utilized to, for example: (1) attract ions, atoms, molecules and/or macromolecules (or portions thereof) that would not normally be attracted; (2) attract ions, atoms, molecules and/or macromolecules (or portions thereof) that subsequently remain fixed to the substrate; (3) attract ions, atoms, molecules and/or macromolecules (or portions thereof) which subsequently detach themselves from the substrate and form a free-standing body; and/or (4) repel ions, atoms, molecules and/or macromolecules (or portions thereof) that would not normally be repelled that, for example, may correspond to certain impurities or defects in a particular structure or material. These particular techniques can enhance the production of many difficult, and/or economically undesirable products, to be formed in an efficient, economical and desirable manner. Moreover, these techniques could be used to form patterns or designs of similar or dissimilar atoms, ions, molecules and/or macromolecules on at least a portion of a substrate. Specifically, designs of particular utility could be placed permanently or temporarily on various substrate materials (e.g., forming a circuit pattern on a chip, etc.) to achieve a variety of functional effects.

Still further, the techniques of the present invention can be used to form composite crystals (e.g., the formation of superlattices). In this regard, if a first spectral energy provider was utilized in a crystallization reaction system a first crystalline growth could be achieved. Thereafter, a different spectral energy provider (and/or conditioned participant) could be introduced into the same crystallization reaction system, thereby resulting in a different crystalline species growing on, for example, the first produced crystalline species. Accordingly, alternating layers of different crystal materials could be achieved. An example of alternating layers that would be useful in the inorganic crystallization art would be layers of CdTe followed by layers of ZnTe. Moreover, one or more alternating layers of an amorphous species could be included with one more crystalline species. Accordingly, many additional unmentioned permutations should occur to those of ordinary skill in the art once armed with the teachings contained herein. Examples of this phenomenon, discussed in greater detail in the "Examples" section later herein, utilize various spectral energy patterns which result in enhanced formation of particular crystalline species in composite crystals.

Further, composite crystals could be achieved where different growth patterns are achieved in different directions. In this regard, for example, a first crystalline species could be achieved in an XY direction, and an alternative crystalline species could be achieved in, for example, a Z direction.

The techniques of the present invention could also enhance the evaporation crystallization process. In this regard, when materials typically flow from the vapor phase, a crystallization growth rate is approximately equal to the difference of the flux of atoms from the vapor compared to the evaporation rate. The incoming flux is proportional to the vapor pressure (and thus to the vapor density). The present invention can effectively reduce the evaporation rate by applying, for example, a spectral energy provider (and/or a spectral energy conditioning provider) which corresponds to, for example, electronic frequencies or frequencies of individual components in the crystal lattice to assist in stabilizing each atom which is, for example, evaporated onto a surface or, generally, is within a crystallization reaction system. This effective stabilization could limit, for example, reabsorption of atoms into the gas and/or accelerate the deposition of adatoms.

The techniques of the present invention can also be utilized to eliminate certain derivative structures, if desired, or to achieve certain derivative structures. In this regard, various defects exist in crystals. These defects include: point defects (e.g., lattice vacancies, interstitials, impurities, etc.); line defects (e.g., dislocations); surface defects (e.g., grain boundaries, stacking faults, etc.); and three-dimensional defects (e.g., striations, cellular growth, voids, inclusions, etc.). In many cases a perfect crystal would be desirable to achieve because, for example, such crystals would be very strong mechanically. Such crystals could be very useful for abrasion or wear applications. However, when crystalline defects such as lattice vacancies, interstitials, dislocations, grain boundaries, stacking faults, etc., occur, all such defects degrade mechanical performance. In order to minimize defects, an appropriate spectral energy provider could be utilized and create, for example, a "gettering", "getting" or "scavenging" standing wave pattern or "scaffolding" for any impurities in the system at a location which is apart from the area where crystallization is occurring. The provision of such a "gettering" spectral pattern could minimize the inclusion of undesirable defects. Alternatively, if certain defects are desirable to be included, then a particular spectral energy provider could be utilized to mimic such defects and the mechanism of action of, for example, the impurity could be copied by utilizing an appropriate spectral energy provider. Still further, certain derivative structures or defects may also be minimized or eliminated by utilizing an appropriate spectral energy provider which creates an effective repulsion or repulsive wave pattern at or near a location where crystallization is occurring. The provision of such a "repulsing" spectral pattern could minimize the inclusion of undesirable impurities or defects. One example of such a "repulsing" wave pattern would be the rotational frequency of a crystalline species causing increased rotational motion of the species in the crystallization reaction system thereby slowing or preventing, for example, its bonding to a growing crystal.

Still further, for most materials, $E_I$ (i.e., the energy required to form an interstitial), is greater than $E_v$, (i.e., the energy require to form a vacancy). Vacancies tend to be a dominant entity in defect structures. Typically, near the melting point, a crystal may have a vacancy concentration of up to 0.1%. The presence of vacancies and interstitial atoms in a crystal provides a mechanism by which mass transport (i.e., diffusion) can occur in the crystalline lattice. The vacancy provides a missing site into which a neighboring atom can jump. When the atom jumps, the vacancy has moved, now occupying the original site of the neighbor. Interstitals may move in a similar manner. Both of these motions result in an energization of the lattice as the atoms move. Moreover, the jump rate for a defect (as well as the rate of atomic diffusion) in a crystal is proportional to temperature. Accordingly, the techniques of the present invention can be applied to control the number of interstitials and/or vacancies in a crystal by including and/or excluding the spectral pattern of the vacancies and/or interstitials, in a controlled manner, by controlling the energy provided by the spectral energy provider. Further, diffusion of foreign substances can be controlled either positively or negatively, by, for example: (1) controlling the number or lack thereof of vacancies/interstitials; (2) using spectral energy providers which mimic the mechanisms of action of lattice patterns to increase the jump rates of the point defects, and hence diffusion rates, of the foreign substance; and/or (3) energizing the foreign substances directly by controlling their energy structure, etc. For example, foreign substances such as heavy metals (tungsten, mercury, etc.) are often infiltrated as interstitials into protein crystals to assist in the x-ray analysis of those crystals. The techniques of the present invention can be used to enhance interstitial formation, for example, by applying a mercury lamp emitting the mercury electronic frequencies, to a protein crystal bathed in a solution of mercury salts, thereby enhancing mercury infiltration into the protein crystal.

In non-metals, vacancies and interstitials may also be activated in crystallization reaction systems by applying an appropriate spectral energy provider, thus producing electrical conductivity. The presence of vacancies and/or interstitials in semiconductors can alter the electronic properties of the material in that they serve to trap and scatter free electrons and holes. The techniques of the present invention can be used to reduce the random chaos of current crystallization techniques, with their subsequent random placement of point defects, to produce a semiconductor with a more evenly spaced group of point defects, thus refining the electrical conduction properties of the material.

Electronic transitions of the trapped charges may also give rise to optical absorption and luminescence bands in semiconductors and insulators. Thus, by controlling, for example, the placement and number of point defects, (i.e., by utilizing an appropriate spectral energy provider) these properties can also be tailored.

The somewhat chaotic manner in which atoms fall into place during growth (e.g., adatoms) makes the formation of lattice dislocations likely. Once such lattice dislocations are formed on a small scale, the dislocations can propagate as the crystal grows. Thus, applied shear stress allows one atom plane to slip past another as the dislocations move which may, in some cases, significantly alter one or more properties of a material in a negative manner. Further, work hardening, resulting in pinned dislocations, is currently used to minimize dislocation problems and strengthen materials. By applying the spectral energy techniques of the present invention, the chaos of current crystallization techniques can be minimized, resulting in, for example, the minimizing of dislocations in a crystal structure and a corresponding increase in various physical properties including, for example, the strength of materials formed by such techniques. Further, as shown in the "Examples" Section later herein, modified crystal growth can be achieved from solutions that have not yet reached their saturation point (e.g., sodium chloride aqueous solutions which result in the production of NaCl crystals from solutions that are not completely saturated).

Surface defects also can be a problem in crystal growth. As with the other defects, the chaos of random crystallization methods allow grain boundary and stacking faults to occur. Reducing the chaos of the crystallization process will diminish, if desired, these defects as well.

Cellular structure can occur in alloys and is thought to be due to impurities. The impurities diffuse rather slowly in the liquid melt, and even more slowly in the solid. Consequently, the impurities which remain trapped in the pockets cannot escape and the pockets become infinitely deep, leading to the formation of cellular structures. Thus cellular formations occur with rapid growth velocities. The techniques of the present invention can cause a spectral energy provider to be applied to speed the rate of diffusion of impurities (e.g., via heterodyning between the impurity and lattice frequencies) applying the rotational frequency of impurity, or encouraging crystallization immediately around the impurity thus avoiding the usually undesirable formation of deep pockets and cellular structures.

The current techniques for controlling defects include, for example, using temperature gradients applied during directional solidification to remove constitutional supercooling and prevent cellular growth by morphological instability. Also, they control dislocation density by use of a bottlenecked seed at which dislocations may emerge on the crystal surfaces. These techniques or mechanisms of action could be at least partially duplicated by the application of at least one spectral energy provider. For example, a vibrational frequency may be applied to duplicate certain of the effects of a higher temperature atomic and/or molecular motion, without actually raising the temperature.

The techniques of the present invention are also useful for controlling step bunching as well as annealing. For example, step bunching may result in macrostops. This macrostop process can occur during growth of crystals from a liquid phase or from a vapor phase. Defects occur in formed crystals due to, for example, the inclusion of physical impurities. Further, in annealing processes, crystals are heated to, for example, reduce surface roughening. The techniques of the present invention could be utilized to enhance both of these general processes.

The techniques of the present invention can also be utilized to affect the myriad of electrochemical crystallization systems. For example, the techniques of the present invention are applicable to affecting the structure of materials formed in any of the following processes or techniques: electrocrystallization; electrometallurgy; electromigration; electrophoresis; electroplating; electrowinning; galvanizing; and mass transport reactions.

In some cases, desirable results in the aforementioned crystallization reaction systems may be achieved by utilizing a single applied spectral energy pattern targeted to a single participant or component or to multiple participants or components; while in other cases, more than one applied spectral energy pattern may be targeted to a single participant or component or to multiple participants or components, by, for example, multiple approaches in a single crystallization reaction system. Specifically, combinations of direct resonance targeting, harmonic targeting and non-harmonic heterodyne targeting, which can be made to interact with one or more frequencies occurring in atoms and/or molecules, could be used sequentially or substantially continuously. Further, in certain cases, the spectral energy provider targeting may result in various interactions at predominantly the upper energy levels of one or more of the various forms of matter present in a crystallization reaction system.

Further, in another preferred embodiment of the invention, the aforementioned approaches for creating a conditioned participant may result in, for example, the conditioned participant mimicking of at least one mechanism of action of a physical or environmental reaction condition once the conditioned participant is exposed to (e.g., activated in) a crystallization reaction system and/or the conditioned participant may enhance certain reaction pathways and/or reaction rates (e.g., kinetics of a reaction may be increased or decreased; or reaction products may be altered, increased or decreased). For example, in some cases, desirable results may be achieved by utilizing a single applied spectral energy conditioning pattern targeted to a single conditionable participant; while in other cases, more than one applied spectral energy conditioning pattern may be targeted to a single participant or to multiple conditionable participants, by, for example, multiple approaches. Specifically, combinations of direct resonance conditioning targeting, harmonic conditioning targeting and non-harmonic heterodyne conditioning targeting, which can be made to interact with one or more frequencies occurring in atoms and/or molecules of a conditionable participant, could be used sequentially or substantially continuously to create desirable conditioned participants. Further, in certain cases, the spectral energy conditioning provider targeting may result in various interactions at predominantly the upper energy levels of one or more of the various forms of matter present as a conditionable participant.

Still further, numerous combinations of the aforementioned applied spectral energy patterns and applied spectral energy conditioning patterns could be used in a crystallization reaction system to target participants and/or conditionable participants. For example, applied spectral energy patterns could be directed to one or more participants; and/or applied spectral energy conditioning patterns could be directed to one or more conditionable participants. In some crystallization reaction systems, a spectral energy pattern and a spectral energy conditioning pattern may be substantially similar to each other (e.g., exactly the same or at least comprising similar portions of the electromagnetic spectrum) or very different from each other (e.g., comprising similar or very different portions of the electromagnetic spectrum). The combination of one or more spectral energy patterns with one or more spectral energy conditioning patterns could have significant implications for control or growth of specific structures or phases and/or rates of reaction(s).

The invention further recognizes and explains that various environmental reaction conditions are capable of influencing reaction pathways in a crystallization reaction system when using a spectral energy catalyst such as a spectral catalyst. The invention teaches specific methods for controlling various environmental reaction conditions in order to achieve desirable results in a reaction (e.g., desirable reaction product(s) in one or more desirable reaction pathway(s)) and/or interactions. The invention further discloses an applied spectral energy approach which permits the simulation, at least partially, of desirable environmental reaction conditions by the application of at least one, for example, spectral environmental reaction conditions. Thus, environmental reaction conditions can be controlled and used in combination with at least one spectral energy pattern to achieve a desired reaction pathway (e.g., a desired phase or phases or a desired crystalline form or species). Alternatively, traditionally utilized environmental reaction conditions can be modified in a desirable manner (e.g., application of a reduced temperature and/or reduced pressure) by supplementing and/or replacing the traditional environmental reaction condition(s) with at least one spectral environmental reaction condition. One example of such a spectral environmental reaction pattern, is the delivery of vibrational overtones to water, thereby causing water to behave, in its solvent capacity, as though it were at higher temperatures, as discussed in greater detail in the "Examples" section later herein.

Similarly, the invention further recognizes and explains that various conditioning environmental reaction conditions are capable of influencing the resultant energy pattern of a conditionable participant, which, when such conditioned participant becomes involved with, and/or activated in, a crystallization reaction system, can influence reaction pathways in a crystallization reaction system. The invention teaches specific methods for controlling various conditioning environmental reaction conditions in order to achieve desirable conditioning of at least one conditionable participant which in turn can achieve desirable results (e.g., desirable reaction product(s) and/or one or more desirable reaction pathway(s) and/or desirable interactions and/or desirable reaction rates) in a crystallization reaction system. The invention further discloses an applied spectral energy conditioning approach which permits the simulation, at least partially, of desirable environmental reaction conditions by the application of at least one, for example, spectral conditioning environmental reaction condition. Thus, conditioning environmental reaction conditions can be controlled and used in combination with at least one spectral energy conditioning pattern to achieve a desired conditioned energy pattern in a conditioned participant. Alternatively, traditionally utilized environmental reaction conditions can be modified in a desirable manner (e.g., application of a reduced temperature and/or reduced pressure) by supplementing and/or replacing the traditional environmental reaction condition(s) with at least one spectral conditioning environmental reaction condition.

The invention also provides a method for determining desirable physical catalysts (i.e., comprising previously known materials or materials not previously known to function as a physical catalyst such as a new or different seed crystal) which can be utilized in a crystallization reaction system to achieve a desired reaction pathway and/or desired reaction rate. In this regard, the invention may be able to provide a recipe for a physical and/or spectral catalyst for a particular reaction in a crystallization reaction system where no physical catalyst previously existed. In this embodiment of the invention, spectral energy patterns are determined or calculated by the techniques of the invention and corresponding physical catalysts (e.g., seed crystal) can be supplied or manufactured and thereafter included in the crystallization reaction system to generate the calculated required spectral energy patterns. In certain cases, one or more existing physical species could be used or combined in a suitable manner, if a single physical species was deemed to be insufficient, to obtain the appropriate calculated spectral energy pattern to achieve a desired reaction pathway and/or desired reaction rate. Such catalysts can be used alone, in combination with other physical catalysts, spectral energy catalysts, controlled environmental reaction conditions and/or spectral environmental reaction conditions to achieve a desired resultant energy pattern and consequent reaction pathway and/or desired reaction rate.

Similarly, the invention also provides a method for determining desirable physical catalysts (e.g., comprising previously known materials or materials not previously known to function as a physical catalyst or seed crystal) which can be utilized in a crystallization reaction system by appropriately conditioning at least one conditionable participant to achieve a desired reaction pathway and/or desired reaction rate and/or desired reaction product when the conditioned participant becomes involved with (e.g., is added to or activated in) the crystallization reaction system. In this regard, the invention may be able to provide a recipe for a physical and/or spectral catalyst for a particular crystallization reaction system where no physical catalyst previously existed. In this embodiment of the invention, spectral energy conditioning patterns are determined or calculated by the techniques of the invention and corresponding conditionable participants can be supplied or manufactured and thereafter included in the crystallization reaction system to generate the calculated required spectral energy patterns. In certain cases, one or more existing physical species of a conditionable participant could be used or combined in a suitable manner, if a single physical species was deemed to be insufficient, to obtain the appropriate calculated spectral energy conditioning pattern to achieve a desired reaction pathway and/or desired reaction rate. Such conditionable participants, once conditioned, can be used alone, in combination with other physical catalysts, spectral energy catalysts, spectral energy catalysts, controlled environmental reaction conditions, spectral environmental reaction conditions and/or spectral environmental reaction conditions to achieve a desired reaction pathway and/or desired reaction rate. Thus, once a desired conditioned energy pattern is achieved in a conditionable participant, the conditioned participant becomes involved with, and/or activated in, the crystallization reaction system.

The invention discloses many different permutations of one important theme of the invention, namely, that when frequencies of components in a crystallization reaction system match, or can be made to match, energy transfers between the components, participants or conditioned participants in the crystallization reaction system. Depending on how the energy dynamics of the component(s) are controlled or directed, the crystallization reaction system will be likewise controlled or directed. It should be understood that the many different permutations can be used alone to achieve desirable results (e.g., desired reaction pathways and/or a desired reaction rates and/or desired reaction products) or can be used in a limitless combination of permutations, to achieve desired results (e.g., desired reaction pathways, desired reaction products and/or desired reaction rates). However, in a first preferred embodiment of the invention, so long as a participant, or conditioned participant has one or more of its frequencies that match with at least one frequency of at least one other component in a crystallization reaction system (e.g., spectral patterns overlap), energy can be transferred. If energy is transferred, desirable interactions and/or reactions can result in the crystallization reaction system. Further, the conditioned participant may itself comprise both a reactant and a reaction product, whereby, for example, the chemical composition of the conditioned participant does not substantially change (if at all) but one or more energy dynamics, physical properties, structures, or phases is changed once the conditioned participant is involved with, and/or activated by, the reaction system.

Further, the same targeted frequency or energy can be used with different power amplitudes, in the same crystallization reaction system, to achieve dramatically different results. For example, the vibrational frequency of a liquid solvent may be input at low power amplitudes to improve the solvent properties of the liquid without causing any substantial change in the chemical composition of the liquid. At higher power levels, the same vibrational frequency can be used to dissociate the liquid solvent, thereby changing its chemical composition. Thus, there is a continuum of effects that can be obtained with a single targeted frequency, ranging from changes in the energy dynamics of a participant, to changes in the actual chemical or physical structure of a participant.

A targeted frequency or energy can also be used with different power amplitudes on a formed material in post-formation treatment processes that also could achieve dramatically different structural results with the formed material. For example, post-treatment processes such as annealing, thermal etching, chemical etching (e.g., using liquids, solids, gases and/or plasmas), etc., can all be used to selectively alter one or more properties in a formed material. A targeted frequency or energy could also result in desirable structural, physical and/or chemical changes (e.g., permit certain reactions to occur, locally or globally) within at least a portion of (or on at least a portion of a surface of) a formed material (e.g., solid, liquid, gas or plasma). These techniques could be useful for interactions including metal formation, semiconductor manufacturing, sintering, biological processes, plastics formation, hydrocarbon manufacturing, etc.

Moreover, the concept of frequencies matching can also be used in the reverse. Specifically, if a reaction in a crystallization reaction system is occurring because frequencies match, the reaction can be slowed or stopped by causing the frequencies to no longer match or at least to match to a lesser degree. In this regard, one or more crystallization reaction system components (e.g., environmental reaction condition, spectral environmental reaction condition and/or an applied spectral energy pattern) can be modified and/or applied so as to minimize, reduce or eliminate frequencies from matching. This also permits reactions to be started and stopped with ease providing for novel control in a myriad of reactions in a crystallization reaction system including preventing the formation of certain crystalline species, controlling the amount of crystallization in a crystallization reaction system, etc. Further, if a source of, for example, electromagnetic radiation includes a somewhat larger spectrum of wavelengths or frequencies (i.e., energies) than those which are needed to optimize (or prevent) a particular reaction in a crystallization reaction system, then some of the unnecessary (or undesirable) wavelengths can be prevented from coming into contact with the crystallization reaction system (e.g., can be blocked, reflected, absorbed, etc.) by an appropriate filtering, absorbing and/or reflecting technique as discussed in greater detail later herein.

Moreover, the concept of frequencies matching can also be used in the reverse for conditionable participants. Specifically, if a reaction is occurring because frequencies match, the reaction can be slowed or stopped by causing the frequencies to no longer match or at least match to a lesser degree. In this regard, one or more crystallization reaction system components (e.g., environmental reaction condition, spectral environmental reaction condition and/or an applied spectral energy pattern) can be modified by introducing a conditionable participant, once conditioned, so as to minimize, reduce or eliminate frequencies from matching in the crystallization reaction system. This also permits reactions to be started and stopped with ease providing for novel control in a myriad of reactions in a crystallization reaction system including preventing the formation of certain crystalline species, controlling the amount of product formed in a crystallization reaction system, etc. Further, if a source of, for example, electromagnetic radiation includes a somewhat larger spectrum of wavelengths or frequencies (i.e., energies) than those which are needed to optimize (or prevent) a particular reaction in a crystallization reaction system, then some of the unnecessary (or undesirable) wavelengths can be prevented from coming into contact with the crystallization reaction system (e.g., can be blocked, reflected, absorbed, etc.) by an appropriate filtering, absorbing and/or reflecting technique as discussed in greater detail later herein.

It should also be apparent that various conditionable participants, once conditioned, can be used in combination with various participants and/or spectral energy providers in a crystallization reaction system to control numerous reaction pathways. Also, the conditioning of reaction vessels, or portions thereof, can also result in desirable control of numerous reaction pathways.

Further, a conditionable participant may be conditioned by removing at least a portion of its spectral pattern prior to the conditionable participant being introduced into a crystallization reaction system. Also, removing (or blocking) at least a portion of a spectral pattern of a reaction vessel, or portion(s) thereof, can also result in desirable control of various reaction pathways.

To simplify the disclosure and understanding of the invention, specific categories or sections have been created in the "Summary of the Invention" and in the "Detailed Description of the Preferred Embodiments". However, it should be understood that these categories are not mutually exclusive and that some overlap exists. Accordingly, these artificially created sections should not be used in an effort to limit the scope of the invention defined in the appended claims.

Further, in the following Sections, attempts have been made to simplify discussions and reduce the overall length of this disclosure. For example, in many instances, "participants" in a crystallization reaction system or holoreaction system are exclusively referred to. However, it should be understood that "conditionable participants" could also be separately addressed in the disclosure, even though not always expressly referred to herein. Thus, when the various general mechanisms of the invention are referred to herein, even if reference is made directly or indirectly to "participants" only, it should be understood that the discussion also applies to "conditionable participants" with similar relevancy. Efforts have been made throughout the disclosure to refer expressly to all of the novel phenomenon associated with conditionable participants only when required for clarification purposes.

I. Wave Energies

In general, thermal energy has traditionally been used to drive chemical reactions by applying heat and increasing the temperature of a reaction system. The addition of heat increases the kinetic (motion) energy of the chemical reactants. It has been believed that a reactant with more kinetic energy moves faster and farther, and is more likely to take part in a chemical reaction. Mechanical energy likewise, by stirring and moving the chemicals, increases their kinetic energy and thus their reactivity. The addition of mechanical energy often increases temperature, by increasing kinetic energy.

Acoustic energy is applied to chemical reactions as orderly mechanical waves. Because of its mechanical nature, acoustic energy can increase the kinetic energy of chemical reactants, and can also elevate their temperature(s). Electromagnetic (EM) energy consists of waves of electric and magnetic fields. EM energy may also increase the kinetic energy and heat in reaction systems. It also may energize electronic orbitals or vibrational motion in some reactions.

Both acoustic and electromagnetic energy consist of waves. Energy waves and frequency have some interesting properties, and may be combined in some interesting ways. The manner in which wave energy transfers and combines, depends largely on the frequency. For example, when two waves of energy, each having the same amplitude, but one at a frequency of 400 Hz and the other at 100 Hz are caused to interact, the waves will combine and their frequencies will add, to produce a new frequency of 500 Hz (i.e., the "sum" frequency). The frequency of the waves will also subtract when they combine to produce a frequency of 300 Hz (i.e., the "difference" frequency). All wave energies typically add and subtract in this manner, and such adding and subtracting is referred to as heterodyning. Common results of heterodyning are familiar to most as harmonics in music. The importance of heterodyning will be discussed in greater detail later herein.

Another concept important to the invention is wave interactions or interference. In particular, wave energies are known to interact constructively and destructively. This phenomena is important in determining the applied spectral energy pattern. FIGS. 1a-1c show two different incident sine waves 1 (FIG. 1a) and 2 (FIG. 1b) which correspond to two different spectral energy patterns having two different wavelengths $\lambda_1$ and $\lambda_2$ (and thus different frequencies) which could be applied to a reaction system. Assume arguendo that the energy pattern of FIG. 1a corresponds to an electromagnetic spectral pattern (or an electromagnetic spectral conditioning pattern) and that FIG. 1b corresponds to one spectral environmental reaction condition (or a spectral conditioning environmental reaction condition). Each of the sine waves 1 and 2 has a different differential equation which describes its individual motion. However, when the sine waves are combined into the resultant additive wave 1+2 (FIG. 1c), the resulting complex differential equation, which describes the totality of the combined energies (i.e., the applied spectral energy pattern; or the applied spectral energy conditioning pattern) actually results in certain of the input energies being high (i.e., constructive interference shown by a higher amplitude) at certain points in time, as well as being low (i.e., destructive interference shown by a lower amplitude) at certain points in time.

Specifically, the portions "X" represent areas where the electromagnetic spectral pattern of wave 1 has constructively interfered with the spectral environmental reaction condition wave 2, whereas the portions "Y" represent areas where the two waves 1 and 2 have destructively interfered. Depending upon whether the portions "X" corresponds to desirable or undesirable wavelengths, frequencies or energies (e.g., causing the applied spectral energy pattern (or the applied spectral energy conditioning pattern) to have positive or negative interactions with, for example, one or more participants and/or components in the crystallization reaction system), then the portions "X" could enhance a positive effect in the reaction system or could enhance a negative effect in the crystallization reaction system. Similarly, depending on whether the portions "Y" correspond to desirable or undesirable wavelengths, frequencies, or energies, then the portions "Y" may correspond to the effective loss of either a positive or negative effect.

Further, if a source of, for example, electromagnetic radiation includes a somewhat larger spectrum of wavelengths or frequencies (i.e., energies) than those which are needed to optimize a particular reaction, then some of the unnecessary (or undesirable) wavelengths can be prevented from coming into contact with the crystallization reaction system (e.g., blocked, reflected, absorbed, etc.). Accordingly in the simplified example discussed immediately above, by permitting only desirable wavelengths $\lambda_1$ to interact in a crystallization reaction system (e.g., filtering out certain wavelengths or frequencies of a broader spectrum electromagnetic emitter) the possibilities of negative effects resulting from the combination of waves 1 (FIG. 1a) and 2 (FIG. 1b) would be minimized or eliminated. In this regard, it is noted that in practice many desirable incident wavelengths can be made to be incident on at least a portion of a crystallization reaction system. Moreover, it should also be clear that positive or desirable effects include, but are not limited to, those effects resulting from an interaction (e.g., heterodyne, resonance, additive wave, subtractive wave, constructive or destructive interference) between a wavelength or frequency of incident light and a wavelength (e.g., atomic and/or molecular, etc.), frequency or property (e.g., Stark effects, Zeeman effects, etc.) inherent to the crystallization reaction system itself. Thus, by maximizing the desirable wavelengths (or minimizing undesirable wavelengths), crystallization reaction system efficiencies never before known (e.g., crystal growth rates, crystal morphologies, crystal phases, crystal purities, etc.) can be achieved. Alternatively stated, certain destructive interference effects resulting from the combinations of different energies, frequencies and/or wavelengths can reduce certain desirable results in a crystallization reaction system. The present invention attempts to mask or screen (e.g., filter) as many of such undesirable energies (or wavelengths) as possible (e.g., when a somewhat larger spectrum of wavelengths is available to be incident on a crystallization reaction system) from becoming incident on a crystallization reaction system and thus strive for, for example, the synergistic results that can occur due to, for example, desirable constructive interference effects between the incident wavelengths of, for example, electromagnetic energy.

It should be clear from this particular analysis that constructive interferences (i.e., the points "X") could, for example, maximize both positive and negative effects in a crystallization reaction system. Accordingly, this simplified example shows that by combining, for example, certain frequencies from a spectral pattern (or a spectral conditioning pattern) with one or more other frequencies from, for example, at least one spectral environmental reaction condition (or at least one spectral environmental conditioning reaction condition), that the applied spectral energy pattern (or applied spectral energy conditioning pattern) that is actually applied to the crystallization reaction system can be a combination of constructive and destructive interference(s). The degree of interference can also depend on the relative phases of the waves. Accordingly, these factors should also be taken into account when choosing appropriate spectral energy patterns (or applied spectral energy conditioning patterns) that are to be applied to a crystallization reaction system. In this regard, it is noted that in practice many desirable incident wavelengths can be applied to a crystallization reaction system or undesirable incident wavelengths removed from a source which is incident upon at least a portion of a crystallization reaction). Moreover, it should also be clear that wave interaction effects include, but are not limited to, heterodyning, direct resonance, indirect resonance, additive waves, subtractive waves, constructive or destructive interference, etc. Further, as discussed in detail later herein, additional effects such as electric effects and/or magnetic field effects can also influence spectral energy patterns or spectral energy conditioning patterns (e.g., spectral patterns or spectral conditioning patterns, respectively).

II. Spectral Catalysts, Spectral Conditioning Catalysts and Spectroscopy

A wide variety of reactions can be advantageously affected and directed with the assistance of a spectral energy catalyst (or spectral energy conditioning catalyst) having a specific spectral energy pattern (e.g., spectral pattern, spectral conditioning pattern or electromagnetic pattern) which transfers targeted energy to initiate, control and/or promote desirable reaction pathways (e.g., desirable crystallization pathways in a single or multiple component crystallization system) and/or desirable reaction rates within a crystallization reaction system. This section discusses spectral catalysts (and spectral conditioning catalysts) in more detail and explains various techniques for using spectral catalysts (and/or spectral conditioning catalysts) in various crystallization reaction systems (and holoreaction systems). For example, a spectral catalyst can be used in a crystallization reaction system to replace and provide the additional energy normally supplied by a physical catalyst (e.g., a seed crystal, a substrate used for epitaxial growth, a crystallization agent, promoter or inhibitor, etc.). The spectral catalyst can actually mimic or copy the mechanisms of action of a physical catalyst. The spectral catalyst can act as both a positive catalyst to increase the rate of a reaction or as a negative catalyst or poison to decrease the rate of reaction. Furthermore, the spectral catalyst can augment a physical catalyst by utilizing both a physical catalyst and a spectral catalyst to achieve, for example a desired crystallization pathway in a crystallization reaction system. The spectral catalyst can improve the activity of a physical catalyst. Also, the spectral catalyst can partially replace a specific quantity or amount of the physical catalyst, thereby reducing and/or eliminating many of the difficulties associated with, for example, primary and/or secondary nucleation, selectivity, and/or morphology.

Moreover, a conditionable participant can be conditioned by a spectral conditioning catalyst to form a conditioned participant which can thereafter be used in a crystallization reaction system, alone or in combination with a spectral catalyst. The spectral conditioning catalyst can energize a conditionable participant to result in a conditioned participant which can likewise, for example, replace, augment or otherwise provide additional energy normally provided by a physical catalyst in a crystallization reaction system, as discussed immediately above with regard to a spectral catalyst.

Further, in the present invention, the spectral energy catalyst provides targeted energy (e.g., electromagnetic radiation comprising a specific frequency or combination of frequencies), in a sufficient amount for a sufficient duration to initiate and/or promote and/or direct a reaction (e.g., follow a particular reaction pathway). The total combination of targeted energy applied at any point in time to the crystallization reaction system is referred to as the applied spectral energy pattern. The applied spectral energy pattern may be comprised of a single spectral catalyst, multiple spectral catalysts and/or other spectral energy catalysts as well. With the absorption of targeted energy into a crystallization reaction system (e.g., electromagnetic energy from a spectral catalyst), a reactant may be caused to proceed through one or several reaction pathways including: energy transfer which can, for example, excite electrons to higher energy states for initiation of a reaction, by causing frequencies to match; ionize or dissociate reactants which may participate in a reaction; stabilize reaction products; energize and/or stabilize intermediates and/or transients and/or activated complexes that participate in a reaction pathway; cause one or more components in a crystallization reaction to have spectral patterns which at least partially overlap; alter the energy dynamics of one or more components causing them to have altered properties; and/or alter the resonant exchange of energy within the holoreaction system.

Moreover, in the present invention, the spectral energy conditioning catalyst provides targeted conditioning energy (e.g., electromagnetic radiation comprising a specific frequency or combination of frequencies), in a sufficient amount for a sufficient duration to condition a conditionable participant to form a conditioned participant and to permit the conditioned participant to initiate and/or promote and/or direct a reaction (e.g., follow a particular reaction pathway) once the conditioned participant is initiated or activated in the crystallization reaction system. The total combination of targeted conditioning energy applied at any point in time to the conditioning reaction system is referred to as the applied spectral energy conditioning pattern. The applied spectral energy conditioning pattern may be comprised of a single spectral conditioning catalyst, multiple spectral conditioning catalysts and/or other spectral energy conditioning catalysts. With the absorption of targeted conditioning energy into a conditioning reaction system (e.g., electromagnetic energy from a spectral conditioning catalyst), a conditioned participant may cause one or more reactants to proceed through one or several reaction pathways including: energy transfer which can for example, excite electrons to higher energy states for initiation of chemical reaction, by causing frequencies to match; ionize or dissociate reactants which may participate in a chemical reaction; stabilize reaction products; energize and/or stabilize intermediates and/or transients and/or activated complexes that participate in a reaction pathway; cause one or more components in a crystallization reaction system to have spectral patterns which at least partially overlap; and/or alter the energy dynamics of one or more components causing them to have altered properties; and/or alter the resonant exchange of energy within the holoreaction system.

For example, in a simple crystallization reaction system, if a chemical reaction provides for at least one reactant "A" to be converted into at least one reaction product "B", a physical catalyst "C" (or a conditioned participant "C") may be utilized. In contrast, a portion of the catalytic spectral energy pattern (e.g., in this section the catalytic spectral pattern) of the physical catalyst "C" may be applied in the form of, for example, an electromagnetic beam (as discussed elsewhere herein) to catalyze the crystallization reaction.

Substances A and B=unknown frequencies, and C=30 Hz;

Therefore, Substance $A+30\ HZ \rightarrow$ Substance $B$.

In the present invention, for example, the spectral pattern (e.g., electromagnetic spectral pattern) of the physical catalyst "C" can be determined by known methods of spectroscopy. Utilizing spectroscopic instrumentation, the spectral pattern of the physical catalyst is preferably determined under conditions approximating those occurring in the crystallization reaction system using the physical catalyst (e.g., spectral energy patterns as well as spectral patterns can be influenced by environmental reaction conditions, as discussed later herein). In the case of crystallization, which can be an auto-catalytic process, B and C can be identical such that:

C=B; and thus

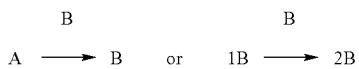

Spectroscopy is a process in which the energy differences between allowed states of any system are measured by determining the frequencies of the corresponding electromagnetic energy which is either being absorbed or emitted. Electromagnetic spectroscopy in general deals with the interaction of electromagnetic radiation with matter. When photons interact with, for example, atoms or molecules, changes in the properties of atoms and molecules are observed.

Atoms and molecules are associated with several different types of motion. The entire molecule rotates, the bonds vibrate, and even the electrons move, albeit so rapidly that electron density distributions have historically been the primary focus of the prior art. Each of these kinds of motion is quantified. That is, the atom, molecule or ion can exist only in distinct states that correspond to discrete energy amounts. The energy difference between the different quantum states depends on the type of motion involved. Thus, the frequency of energy required to bring about a transition is different for the different types of motion. That is, each type of motion corresponds to the absorption of energy in different regions of the electromagnetic spectrum and different spectroscopic instrumentation may be required for each spectral region. The total motion energy of an atom or molecule may be considered to be at least the sum of its electronic, vibrational and rotational energies.

In both emission and absorption spectra, the relation between the energy change in the atom or molecule and the frequency of the electromagnetic energy emitted or absorbed is given by the so-called Bohr frequency condition:

$$\Delta E = h\nu$$

where h is Planck's constant; $\nu$ is the frequency; and $\Delta E$, is the difference of energies in the final and initial states.

Electronic spectra are the result of electrons moving from one electronic energy level to another in an atom, molecule or ion. A molecular physical catalyst's spectral pattern includes not only electronic energy transitions but also may involve transitions between rotational and vibrational energy levels. As a result, the spectra of molecules are much more complicated than those of atoms. The main changes observed in the atoms or molecules after interaction with photons include excitation, ionization and/or rupture of chemical bonds, all of which may be measured and quantified by spectroscopic methods including emission or absorption spectroscopy which give the same information about energy level separation.

In emission spectroscopy, when an atom or molecule is subjected to a flame or an electric discharge, such atoms or molecules may absorb energy and become "excited." On their return to their "normal" state they may emit radiation. Such an emission is the result of a transition of the atom or molecule from a high energy or "excited" state to one of lower state. The energy lost in the transition is emitted in the form of electromagnetic energy. "Excited" atoms usually produce line spectra while "excited" molecules tend to produce band spectra.

In absorption spectroscopy, the absorption of nearly monochromatic incident radiation is monitored as it is swept over a range of frequencies. During the absorption process the atoms or molecules pass from a state of low energy to one of high energy. Energy changes produced by electromagnetic energy absorption occur only in integral multiples of a unit amount of energy called a quantum, which is characteristic of each absorbing species. Absorption spectra may be classified into four types: rotational; rotation-vibration; vibrational; and electronic.

The rotational spectrum of a molecule is associated with changes which occur in the rotational states of the molecule. The energies of the rotational states differ only by a relatively small amount, and hence, the frequency which is necessary to effect a change in the rotational levels is very low and the wavelength of electromagnetic energy is very large. The energy spacing of molecular rotational states depends on bond distances and angles. Pure rotational spectra are observed in the far infrared and microwave and radio regions (See Table 1).

Rotation-vibrational spectra are associated with transitions in which the vibrational states of the molecule are altered and may be accompanied by changes in rotational states. Absorption occurs at higher frequencies or shorter wavelength and usually occurs in the middle of the infrared region (See Table 1).

Vibrational spectra from different vibrational energy levels occur because of motion of bonds. A stretching vibration involves a change in the interatomic distance along the axis of the bond between two atoms. Bending vibrations are characterized by a change in the angle between two bonds. The vibrational spectra of a molecule are typically in the near-infrared range. It should be understood that the term vibrational spectra means all manner of bond motion spectra including, but not limited to, stretching, bending, librational, translational, torsional, etc.

Electronic spectra are from transitions between electronic states for atoms and molecules and are accompanied by simultaneous changes in the rotational and vibrational states in molecules. Relatively large energy differences are involved, and hence absorption occurs at rather large frequencies or relatively short wavelengths. Different electronic states of atoms or molecules correspond to energies in the infrared, ultraviolet-visible or x-ray region of the electromagnetic spectrum (see Table 1).

TABLE 1

| | Approximate Boundaries | | |
|---|---|---|---|
| Region Name | Energy, J | Wavelength | Frequency, Hz |
| X-ray | $2 \times 10^{-14}$-$2 \times 10^{-17}$ | 10–2-10 nm | $3 \times 10^{19}$-$3 \times 10^{16}$ |
| Vacuum Ultraviolet | $2 \times 10^{-17}$-$9.9 \times 10^{-19}$ | 10-200 nm | $3 \times 10^{16}$-$1.5 \times 10^{15}$ |

TABLE 1-continued

Approximate Boundaries

| Region Name | Energy, J | Wavelength | Frequency, Hz |
|---|---|---|---|
| Near ultraviolet | $9.9 \times 10^{-19}$-$5 \times 10^{-19}$ | 200-400 nm | $1.5 \times 10^{15}$-$7.5 \times 10^{14}$ |
| Visible | $5 \times 10^{-19}$-$2.5 \times 10^{-19}$ | 400-800 nm | $7.5 \times 10^{14}$-$3.8 \times 10^{14}$ |
| Near Infrared | $2.5 \times 10^{-19}$-$6.6 \times 10^{-20}$ | 0.8-2.5 um | $3.8 \times 10^{14}$-$1 \times 10^{14}$ |
| Fundamental Infrared | $6.6 \times 10^{-20}$-$4 \times 10^{-21}$ | 2.5-50 um | $1 \times 10^{14}$-$6 \times 10^{12}$ |
| Far infrared | $4 \times 10^{-21}$-$6.6 \times 10^{-22}$ | 50-300 um | $6 \times 10^{12}$-$1 \times 10^{12}$ |
| Microwave | $6.6 \times 10^{-22}$-$4 \times 10^{-25}$ | 0.3 mm-0.5 m | $1 \times 10^{12}$-$6 \times 10^{8}$ |
| Radiowave | $4 \times 10^{-25}$-$6.6 \times 10^{-34}$ | $0.5$-$300 \times 10^{6}$ m | $6 \times 10^{8}$-1 |

Electromagnetic radiation as a form of energy can be absorbed or emitted, and therefore many different types of spectroscopy may be used in the present invention to determine a desired spectral pattern of a spectral catalyst (e.g., a spectral pattern of a physical catalyst) including, but not limited to, x-ray, ultraviolet, infrared, microwave, atomic absorption, flame emissions, atomic emissions, inductively coupled plasma, DC argon plasma, arc-source emission, spark-source emission, high-resolution laser, radio, Raman and the like.

In order to study the electronic transitions, the material to be studied may need to be heated to a high temperature, such as in a flame, where the molecules are atomized and excited. Another very effective way of atomizing gases is the use of gaseous discharges. When a gas is placed between charged electrodes, causing an electrical field, electrons are liberated from the electrodes and from the gas atoms themselves and may form a plasma or plasma-like conditions. These electrons will collide with the gas atoms which will be atomized, excited or ionized. By using high frequency fields, it is possible to induce gaseous discharges without using electrodes. By varying the field strength, the excitation energy can be varied. In the case of a solid material, excitation by electrical spark or arc can be used. In the spark or arc, the material to be analyzed is evaporated and the atoms are excited.

The basic scheme of an emission spectrophotometer includes a purified silica cell containing the sample which is to be excited. The radiation of the sample passes through a slit and is separated into a spectrum by means of a dispersion element. The spectral pattern can be detected on a screen, photographic film or by a detector.

An atom will most strongly absorb electromagnetic energy at the same frequencies it emits. Measurements of absorption are often made so that electromagnetic radiation that is emitted from a source passes through a wavelength-limiting device, and impinges upon the physical catalyst sample that is held in a cell. When a beam of white light passes through a material, selected frequencies from the beam are absorbed. The electromagnetic radiation that is not absorbed by the physical catalyst passes through the cell and strikes a detector. When the remaining beam is spread out in a spectrum, the frequencies that were absorbed show up as dark lines in the otherwise continuous spectrum. The position of these dark lines correspond exactly to the positions of lines in an emission spectrum of the same molecule or atom. Both emission and absorption spectrophotometers are available through regular commercial channels.

In 1885, Balmer discovered that hydrogen vibrates and produces energy at frequencies in the visible light region of the electromagnetic spectrum which can be expressed by a simple formula:

$$1\lambda = R(1/2^2 - 1/m^2)$$

when $\lambda$ is the wavelength of the light, R is Rydberg's constant and m is an integer greater than or equal to 3 (e.g., 3, 4, or 5, etc.). Subsequently, Rydberg discovered that this equation could be adapted to result in all the wavelengths in the hydrogen spectrum by changing the $1/2^2$ to $1/n^2$, as in, $$1/\lambda = R(1/n^2 - 1/m^2)$$

where n is an integer$\geq 1$, and m is an integer$\geq n+1$. Thus, for every different number n, the result is a series of numbers for wavelength, and the names of various scientists are assigned to each such series which resulted. For instance, when n=2 and m$\geq$3, the energy is in the visible light spectrum and the series is referred to as the Balmer series. The Lyman series is in the ultraviolet spectrum with n=1, and the Paschen series is in the infrared spectrum with n=3.

In the prior art, energy level diagrams were the primary means used to describe energy levels in the hydrogen atom (see FIGS. 7a and 7b).

After determining the electromagnetic spectral pattern of a desired catalyst (e.g., a physical catalyst such as a seed crystal), the catalytic spectral pattern may be duplicated, at least partially, and applied to the crystallization reaction system. Any generator of one or more frequencies within an acceptable approximate range of, for example, frequencies of electromagnetic radiation may be used in the present invention. When duplicating one or more frequencies of, for example, a spectral pattern (or a spectral conditioning pattern), it is not necessary to duplicate the frequency exactly. For instance, the effect achieved by a frequency of 1,000 THz, can also be achieved by a frequency very close to it, such as 1,001 or 999 THz. Thus, there will be a range above and below each exact frequency which will also catalyze a reaction. Specifically, FIG. 12 shows a typical bell-curve "B" distribution of frequencies around the desired frequency $f_o$, wherein desirable frequencies can be applied which do not correspond exactly to $f_o$, but are close enough to the frequency $f_o$ to achieve a desired effect, such as those frequencies between and including the frequencies within the range of $f_1$ and $f_2$. Note that $f_1$ and $f_2$ correspond to about one half the maximum amplitude, $a_{max}$, of the curve "B". Thus, whenever the term "exact" or specific reference to "frequency" or the like is used, it should be understood to have this meaning. In addition, harmonics of spectral catalyst (or spectral conditioning catalyst) frequencies, both above and below the exact spectral catalyst frequency (or spectral conditioning catalyst frequency), will cause sympathetic resonance with the exact frequency and will catalyze the reaction. Finally, it is possible to catalyze reactions by duplicating one or more of the mechanisms of action of the exact frequency, rather than using the exact frequency itself. For example, platinum catalyzes the formation of water from hydrogen and oxygen, in part, by energizing the hydroxyl radical at its frequency of roughly 1,060 THz. The desired reaction can also be catalyzed by energizing the hydroxy radical with its microwave frequency, thereby duplicating platinum's mechanism of action.

An electromagnetic radiation-emitting source should have the following characteristics: high intensity of the desired wavelengths; long life; stability; and the ability to emit the electromagnetic energy in a pulsed and/or continuous mode. Moreover, in certain crystallization reaction systems, it may be desirable for the electromagnetic energy emitted to be capable of being directed to an appropriate point (or area) within at least a portion of the crystallization reaction system. Suitable techniques include optical waveguides, optical fibers, etc.

Irradiating sources can include, but are not limited to, arc lamps, such as xenon-arc, hydrogen and deuterium, krypton-arc, high-pressure mercury, platinum, silver; plasma arcs, discharge lamps, such as As, Bi, Cd, Cs, Ge, Hg, K, Na, P, Pb, Rb, Sb, Se, Sn, Ti, Tl and Zn; hollow-cathode lamps, either single or multiple elements such as Cu, Pt, and Ag; and sunlight and coherent electromagnetic energy emissions, such as masers and lasers. A more complete list of irradiating sources are located in Table D.

Masers are devices which amplify or generate electromagnetic energy waves with great stability and accuracy. Masers operate on the same principal as lasers, but produce electromagnetic energy in the radio and microwave, rather than visible range of the spectrum. In masers, the electromagnetic energy is produced by the transition of molecules between rotational energy levels.

Lasers are powerful coherent photon sources that produce a beam of photons having the same frequency, phase and direction, that is, a beam of photons that travel exactly alike. Accordingly, for example, the predetermined spectral pattern of a desired catalyst can be generated by a series or grouping of lasers producing one or more required frequencies.

Any laser capable of emitting the necessary electromagnetic radiation with a frequency or frequencies of the spectral energy provider may be used in the present invention. Lasers are available for use throughout much of the spectral range. They can be operated in either a continuous or a pulsed mode. Lasers that emit lines and lasers that emit a continuum may be used in the present invention. Line sources may include argon ion laser, ruby laser, the nitrogen laser, the Nd:YAG laser, the carbon dioxide laser, the carbon monoxide laser and the nitrous oxide-carbon dioxide laser. In addition to the spectral lines that are emitted by lasers, several other lines are available, by addition or subtraction in a crystal of the frequency emitted by one laser to or from that emitted by another laser. Devices that combine frequencies and may be used in the present invention include difference frequency generators and sum frequency mixers. Other lasers that may be used in this invention include, but are not limited to: crystal, such as $Al_2O_3$ doped with $Cr^{3+}$, $Y_3Al_5O_{12}$ doped with $Nd^{3+}$; gas, such as He—Ne, Kr-ion; glass, chemical, such as vibrationally excited HCL and HP; dye, such as Rhodamine 6G in methanol; and semiconductor lasers, such as $Ga_{1-x}Al_xAs$. Many models can be tuned to various frequency ranges, thereby providing several different frequencies from one instrument and applying them to the crystallization reaction system (See Examples in Table 2).

TABLE 2

SEVERAL POPULAR LASERS

| Medium | Type | Emitted wavelength, nm |
|---|---|---|
| Ar | Gas | 334, 351.1, 363.8, 454.5, 457.9, 465.8, 472.7, 476.5, 488.0, 496.5, 501.7, 514.5, 528.7 |
| Kr | Gas | 350.7, 356.4, 406.7, 413.1, 415.4, 468.0, 476.2, 482.5, 520.8, 530.9, 568.2, 647.1, 676.4, 752.5, 799.3 |
| He—Ne | Gas | 632.8 |
| He—Cd | Gas | 325.0, 441.6 |
| $N_2$ | Gas | 337.1 |
| XeF | Gas | 351 |
| KrF | Gas | 248 |
| ArF | Gas | 193 |
| Ruby | Solid | 693.4 |
| Nd:YAG | Solid | 266, 355, 532 |
| $Pb_{1-x}Cd_xS$ | Solid | $2.9 \times 10^3\text{-}2.6 \times 10^4$ |
| $Pb_{1-x}Se_x$ | Solid | $2.9 \times 10^3\text{-}2.6 \times 10^4$ |
| $Pb_{1-x}Sn_xSe$ | Solid | $2.9 \times 10^3\text{-}2.6 \times 10^4$ |
| Dyes | Liquid | 217-1000 |

The coherent light from a single laser or a series of lasers is simply brought to focus or introduced to the region of the crystallization reaction system where a desired reaction is to take place. The light source should be close enough to avoid a "dead space" in which the light does not reach the desired area in the crystallization reaction system, but far enough apart to assure complete incident-light absorption. Since ultraviolet sources generate heat, such sources may need to be cooled to maintain efficient operation. Irradiation time, causing excitation of one or more components in the crystallization reaction system, may be individually tailored for each reaction: some short-term for a continuous reaction with large surface exposure to the light source; or long light-contact time for other systems. In addition, exposure times and energy amplitudes or intensities may be controlled depending on the desired effect (e.g., altered energy dynamics, ionizations, bond rupture, species selection, directional growth etc.).

An object of this invention is to provide a spectral energy pattern (e.g., a spectral pattern of electromagnetic energy) to one or more reactants in a crystallization reaction system by applying at least a portion of (or substantially all of) a required spectral energy catalyst (e.g., a spectral catalyst) determined and calculated by, for example, waveform analysis of the spectral patterns of, for example, the reactant(s) and the reaction product(s). Accordingly, in the case of a spectral catalyst, a calculated electromagnetic pattern will be a spectral pattern or will act as a spectral catalyst to generate a preferred reaction pathway and/or preferred reaction rate. In basic terms, spectroscopic data for identified substances can be used to perform a simple waveform calculation to arrive at, for example, the correct electromagnetic energy frequency, or combination of frequencies, needed to catalyze a reaction. In simple terms,

A→B

Substance A=50 Hz, and Substance B=80 Hz

80 Hz–50 Hz=30 Hz:

Therefore, Substance $A$+30 Hz→Substance $B$.

The spectral energy pattern (e.g., spectral patterns) of both the reactant(s) and reaction product(s) can be determined. In the case of a spectral catalyst, this can be accomplished by the spectroscopic means mentioned earlier. Once the spectral patterns are determined (e.g., having a specific frequency or combination of frequencies) within an appropriate set of environmental reaction conditions, the spectral energy pattern(s)

(e.g., electromagnetic spectral pattern(s)) of the spectral energy catalyst (e.g., spectral catalyst) can be determined. Using the spectral energy pattern(s) (e.g., spectral patterns) of the reactant(s) and reaction product(s), a waveform analysis calculation can determine the energy difference between the reactant(s) and reaction product(s) and at least a portion of the calculated spectral energy pattern (e.g., electromagnetic spectral pattern) in the form of a spectral energy pattern (e.g., a spectral pattern) of a spectral energy catalyst (e.g., a spectral catalyst) can be applied to the desired reaction in a crystallization reaction system to cause the desired reaction to follow along the desired crystallization reaction pathway. The specific frequency or frequencies of the calculated spectral energy pattern (e.g., spectral pattern) corresponding to the spectral energy catalyst (e.g., spectral catalyst) will provide the necessary energy input into the desired reaction in the crystallization reaction system to affect and initiate a desired crystallization reaction pathway.

Performing the waveform analysis calculation to arrive at, for example, the correct electromagnetic energy frequency or frequencies can be accomplished by using complex algebra, Fourier transformation or Wavelet Transforms, which is available through commercial channels under the trademark Mathematica® and supplied by Wolfram, Co. It should be noted that only a portion of a calculated spectral energy catalyst (e.g., spectral catalyst) may be sufficient to catalyze a reaction or a substantially complete spectral energy catalyst (e.g., spectral catalyst) may be applied depending on the particular circumstances.

In addition, at least a portion of the spectral energy pattern (e.g., electromagnetic pattern of the required spectral catalyst) may be generated and applied to the crystallization reaction system by, for example, the electromagnetic radiation emitting sources defined and explained earlier.

Another object of this invention is to provide a spectral energy conditioning pattern (e.g., a spectral conditioning pattern of electromagnetic energy) to one or more conditionable participants in a conditioning crystallization reaction system by applying at least a portion of (or substantially all of) a required spectral energy conditioning catalyst (e.g., a spectral conditioning catalyst) determined and calculated by, for example, waveform analysis of the spectral patterns of, for example, the conditionable participant(s), and the conditioned participant. Accordingly, in the case of a spectral conditioning catalyst, a calculated electromagnetic conditioning pattern will be a spectral conditioning pattern which, when applied to a conditionable participant, will permit the conditioned participant to act as a spectral catalyst to generate a preferred reaction pathway and/or preferred reaction rate in a crystallization reaction system. In basic terms, spectroscopic data for identified substances can be used to perform a simple waveform calculation to arrive at, for example, the correct electromagnetic energy frequency, or combination of frequencies, needed to catalyze a reaction. In simple terms,

A→B

Conditionable substance A=50 Hz, and conditioned Substance B=80 Hz

80 Hz−50 Hz=30 Hz:

Therefore, Substance $A$+30 Hz=Substance $B$.

The spectral energy conditioning pattern (e.g., spectral conditioning pattern) of both the conditionable participant and the conditioned participant can be determined. In the case of a spectral conditioning catalyst, this can be accomplished by the spectroscopic means mentioned earlier. Once the spectral patterns are determined (e.g., having a specific frequency or combination of frequencies) within an appropriate set of conditioning environmental reaction conditions, the spectral energy conditioning pattern(s) (e.g., electromagnetic spectral conditioning pattern(s)) of the spectral energy conditioning catalyst (e.g., spectral conditioning catalyst) can be determined. Using the spectral energy conditioning pattern(s) (e.g., spectral conditioning patterns) of the conditionable participant and the conditioned participant, a waveform analysis calculation can determine the energy difference between the conditioned participant and reactant(s) or product(s) and at least a portion of the calculated spectral energy conditioning pattern (e.g., electromagnetic spectral conditioning pattern) in the form of a spectral energy conditioning (e.g., a spectral conditioning pattern) of a spectral energy conditioning catalyst (e.g., a spectral conditioning catalyst) can be applied to the desired conditionable participant in a conditioning reaction system to subsequently result in the desired reaction in the crystallization reaction system once the conditioned participant is introduced to the crystallization reaction system. The specific frequency or frequencies of the calculated spectral energy conditioning pattern (e.g., a spectral conditioning pattern) corresponding to the spectral energy conditioning catalyst (e.g., spectral conditioning catalyst) required to form a conditioned participant will provide the necessary energy input into the desired reaction in the crystallization reaction system to affect and initiate a desired reaction pathway.

Performing the waveform analysis calculation to arrive at, for example, the correct electromagnetic energy frequency or frequencies can be accomplished by using complex algebra, Fourier transformation or Wavelet Transforms, which is available through commercial channels under the trademark Mathematica® and supplied by Wolfram, Co. It should be noted that only a portion of a calculated spectral energy conditioning catalyst (e.g., spectral conditioning catalyst) may be sufficient to catalyze a reaction or a substantially complete spectral energy conditioning catalyst (e.g., spectral conditioning catalyst) may be applied depending on the particular circumstances.

In addition, at least a portion of the spectral energy conditioning pattern (e.g., electromagnetic pattern of the required spectral catalyst) may be generated and applied to the holoreaction system by, for example, the electromagnetic radiation emitting sources defined and explained earlier.

The specific physical catalysts (e.g., seed crystals, epitaxial substrates, crystallization agent, promoter or inhibitor, etc.) that may be replaced or augmented in the present invention may include any solid, liquid, gas or plasma catalyst, having either homogeneous or heterogeneous catalytic activity.

III. Targeting

The frequency and wave nature of energy has been discussed herein. Additionally, Section I entitled "Wave Energies" disclosed the concepts of various potential interactions between different waves. The general concepts of "targeting", "direct resonance targeting", "harmonic targeting" and "non-harmonic heterodyne targeting" (all defined terms herein) build on these and other understandings.

Targeting has been defined generally as the application of a spectral energy provider (e.g., spectral energy catalyst, spectral catalyst, spectral energy pattern, spectral pattern, catalytic spectral energy pattern, catalytic spectral pattern, spectral environmental reaction conditions and applied spectral energy pattern) to a desired reaction in a crystallization reaction system. The application of these types of energies to a desired reaction can result in interaction(s) between the applied spectral energy provider(s) and matter (including all components thereof) in the crystallization reaction system. This targeting can result in at least one of direct resonance, harmonic resonance, and/or non-harmonic heterodyne resonance with at least a portion, for example, of at least one form of matter in a crystallization reaction system. In this invention, targeting should be generally understood as meaning applying a particular spectral energy provider (e.g., a spectral energy pattern) to another entity comprising matter (or any component thereof) to achieve a particular desired result (e.g., desired reaction product and/or desired reaction product at a desired reaction rate).

Further, the invention provides techniques for achieving such desirable results without the production of, for example, undesirable transients, intermediates, activated complexes and/or reaction products (e.g., derivative structures, impurities, defects, etc.). In this regard, some limited prior art techniques exist which have applied certain forms of energies (as previously discussed) to various non-crystallization reactions. These certain forms of energies have been limited to direct resonance and harmonic resonance with some electronic frequencies and/or vibrational frequencies of some reactants. These limited forms of energies used by the prior art were due to the fact that the prior art lacked an adequate understanding of the spectral energy mechanisms and techniques disclosed herein. Further, crystallization prior art has typically applied general processing conditions such as temperature, pressure, etc., to achieve desired goals. Moreover, it has often been the case in the prior art that at least some undesirable intermediate, transient, activated complex and/or reaction product was formed, and/or a less than optimum reaction rate for a desired crystallization reaction pathway occurred. The present invention overcomes the limitations of the prior art by specifically targeting, for example, various forms of matter (e.g., seed crystals) in a crystallization reaction system (and/or components thereof), with, for example, an applied spectral energy pattern. Heretofore, such selective targeting of the invention was never disclosed or suggested. Specifically, at best, the prior art has been reduced to using random, trial and error environmental factors.

Accordingly, whenever use of the word "targeting" is made herein, it should be understood that targeting does not correspond to undisciplined energy bands being applied to a crystallization reaction system; but rather to a targeted, applied spectral energy pattern.

IV. Conditioning Targeting

Conditioning targeting has been defined generally as the application of a spectral energy conditioning provider (e.g., spectral energy conditioning catalyst, spectral conditioning catalyst, spectral energy conditioning pattern, spectral conditioning pattern, catalytic spectral energy conditioning pattern, catalytic spectral conditioning pattern, spectral conditioning environmental reaction conditions and applied spectral energy conditioning pattern) to a conditionable participant to form at least one conditioned participant prior to the conditioned participant becoming involved in (e.g., introduced into and/or activated in) a crystallization reaction system. The application of these types of conditioning energies to conditionable participants to form conditioned participants, prior to the conditioned participants being introduced to a crystallization reaction system, can result in interaction(s) between the conditioned participant matter and other components in the crystallization reaction system (including all components thereof) so that the conditioned matter can then initiate and/or direct desirable reaction pathways and/or desirable reaction rates within a crystallization reaction system. This conditioning targeting can result in at least one of direct conditioning resonance, harmonic conditioning resonance, non-harmonic conditioning heterodyne resonance and/or non-resonance influencing with at least a portion of, for example, at least one form of conditionable participant matter (of any form) to form conditioned participant matter which is later introduced into, or activated in, a crystallization reaction system. In this invention, conditioning targeting should be generally understood as meaning applying a particular spectral energy conditioning provider (e.g., a spectral energy conditioning pattern) to another conditionable entity comprising conditionable matter (or any component thereof) to achieve a particular desired result (e.g., ultimately achieve a desired reaction product and/or desired reaction product at a desired reaction rate due to the conditioned matter being introduced into the crystallization reaction system.). It should be noted that introduction into the crystallization reaction system should not be construed as meaning only a physical introduction of a conditioned participant that has been conditioned in a conditioning reaction vessel, but should also be understood as meaning that a conditionable participant can be conditioned in situ in a crystallization reaction vessel (or the reaction vessel per se can be conditioned) and the crystallization reaction system thereafter is initiated, activated, or turned on (e.g., initiated by the application of, for example, temperature, pressure, etc.) once the conditioned participant is present in the crystallization reaction vessel. Thus, the invention provides techniques for achieving such desirable results without the production of, for example, undesirable transients, intermediates, activated complexes and/or reaction products (e.g., defects, impurities, etc.). The present invention teaches that by specifically targeting, for example, various forms of conditionable matter (and/or components thereof) prior to the conditioned matter being involved with reactions in a crystallization reaction system desirable results can be achieved.

Accordingly, whenever use of the word "conditioning targeting" is made herein, it should be understood that conditioning targeting does not correspond to undisciplined energy bands being applied to a conditionable participant to form a conditioned participant which then becomes involved in a crystallization reaction system; but rather to well defined, targeted, applied spectral energy conditioning patterns, each of which has a particular desirable purpose to form a conditioned participant so that the conditioned participant can, for example, permit a desired reaction pathway to be followed, and/or achieve a desired result and/or a desired result at a desired reaction rate in a crystallization reaction system. These results include conditioning targeting a single form of conditionable participant matter to form conditioned matter which, when such conditioned matter is activated or initiated in a crystallization reaction system, causes the conditioned matter to behave favorably, or conditioning targeting multiple forms of conditionable participant matter to achieve desirable results.

V. Environmental Reaction Conditions

Environmental reaction conditions are important to understand because they can influence, positively or negatively, crystallization reaction pathways in a crystallization reaction system. Traditional environmental reaction conditions include temperature, pressure, surface area of catalysts, catalyst size and shape, solvents, support materials, poisons, promoters, concentrations, electromagnetic radiation, electric fields, magnetic fields, mechanical forces, acoustic fields, reaction vessel size, shape and composition and combinations thereof, etc.

The following reaction can be used to discuss the effects of environmental reaction conditions which may need to be taken into account in order to cause the reaction to proceed along the simple reaction pathway shown below.

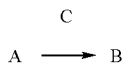

Specifically, in some instances, reactant A will not form into reaction product B in the presence of any catalyst C unless the environmental reaction conditions in the crystallization reaction system include certain maximum or minimum conditions of environmental reaction conditions such as pressure and/or temperature. In this regard, many reactions will not occur in the presence of a physical catalyst unless the environmental reactions conditions include, for example, an elevated temperature and/or an elevated pressure. In the present invention, such environmental reaction conditions should be taken into consideration when applying a particular spectral energy catalyst (e.g., a spectral catalyst). Many specifics of the various environmental reaction conditions are discussed in greater detail in the Section herein entitled "Description of the Preferred Embodiments".

VI. Conditioning Environmental Reaction Conditions

Conditioning environmental reaction conditions are also important to understand because they can also influence, positively or negatively, the conditioning of a conditionable participant and can ultimately lead to different reaction pathways in a crystallization reaction system when a conditioned participant is introduced into, or activated in, the crystallization reaction system. The same traditional environmental reaction conditions listed above also apply here, namely temperature, pressure, surface area of catalysts, catalyst size and shape, solvents, support materials, poisons, promoters, concentrations, electromagnetic radiation, electric fields, magnetic fields, mechanical forces, acoustic fields, reaction vessel size, shape and composition and combinations thereof, etc.

In the present invention, such conditioning environmental reaction conditions should be taken into consideration when applying a particular spectral energy catalyst (e.g., a spectral conditioning catalyst) to a conditionable participant. Similar environmental considerations need to be taken into account when the conditioned participant is introduced into a crystallization reaction system. Many specifics of the various environmental and/or conditioning environmental reaction conditions are discussed in greater detail in the Section herein entitled "Description of the Preferred Embodiments".

VII. Spectral Environmental Reaction Conditions

If it is known that certain reaction pathways will not occur within a crystallization reaction system (or not occur at a desirable rate) even when a catalyst is present unless, for example, certain minimum or maximum environmental reaction conditions are present (e.g., the temperature is lowered or pressure is elevated), then an additional frequency or combination of frequencies (i.e., an applied spectral energy pattern) can be applied to the crystallization reaction system. In this regard, spectral environmental reaction condition(s) can be applied instead of, or to supplement, those environmental reaction conditions that are naturally present, or need to be present, in order for a desired crystallization reaction pathway and/or desired reaction rate to be followed. The environmental reaction conditions that can be supplemented or replaced with spectral environmental reaction conditions include, for example, temperature, pressure, surface area of catalysts, catalyst size and shape, solvents, support materials, poisons, promoters, concentrations, electric fields, magnetic fields, etc.

Still further, a particular frequency or combination of frequencies and/or fields that can produce one or more spectral environmental reaction conditions can be combined with one or more spectral energy catalysts and/or spectral catalysts to generate an applied spectral energy pattern which can be focused on a particular area in a crystallization reaction system. Accordingly, various considerations can be taken into account for what particular frequency or combination of frequencies and/or fields may be desirable to combine with (or replace) various environmental reaction conditions, for example.

As an example, in a simple reaction, assume that a first reactant "A" has a frequency or simple spectral pattern of 3 THz and a second reactant "B" has a frequency or simple spectral pattern of 7 THz. At room temperature, no reaction occurs. However, when reactants A and B are exposed to high temperatures, their frequencies, or simple spectral patterns, both shift to 5 THz. Since their frequencies match, they transfer energy and a reaction occurs. By applying a frequency of 2 THz, at room temperature, the applied 2 THz frequency will heterodyne with the 3 THz pattern to result in, both 1 Thz and 5 THz heterodyned frequencies; while the applied frequency of 2 THz will heterodyne with the spectral pattern of 7 THz of reactant "B" and result in heterodyned frequencies of 5 THz and 9 THz in reactant "B". Thus, the heterodyned frequencies of 5 THz are generated at room temperature in each of the reactants "A" and "B". Accordingly, frequencies in each of the reactants match and thus energy can transfer between the reactants "A" and "B". When the energy can transfer between such reactants, all desirable reactions along a reaction pathway may be capable of being achieved. However, in certain reactions, only some desirable reactions along a reaction pathway are capable of being achieved by the application of a singular frequency. In these instances, additional frequencies and/or fields may need to be applied to result in all desirable steps along a reaction pathway being met, including but not limited to, the formation of all required reaction intermediates and/or transients.

Thus, by applying a frequency, or combination of frequencies and/or fields (i.e., creating an applied spectral energy pattern) which corresponds to at least one spectral environmental reaction condition, the spectral energy patterns (e.g., spectral patterns of, for example, reactant(s), intermediates, transients, catalysts, etc.) can be effectively modified which may result in broader spectral energy patterns (e.g., broader spectral patterns), in some cases, or narrower spectral energy patterns (e.g., spectral patterns) in other cases. Such broader or narrower spectral energy patterns (e.g., spectral patterns) may correspond to a broadening or narrowing of line widths in a spectral energy pattern (e.g., a spectral pattern). As stated throughout herein, when frequencies match, energy transfers. In this particular embodiment, frequencies can be caused to match by, for example, broadening the spectral pattern of one or more participants in a crystallization reaction system. For example, as discussed in much greater detail later herein, the application of temperature to a crystallization reaction system typically causes the broadening of one or more spectral patterns (e.g., line width broadening) of, for example, one or more reactants in the crystallization reaction system. It is this broadening of spectral patterns that can cause spectral patterns of one or more reactants to, for example, overlap. The overlapping of the spectral patterns can cause frequencies to match, and thus energy to transfer. When energy is transferred, reactions can occur. The scope of reactions which occur, include all of those reactions along any particular crystallization reaction pathway. Thus, the broadening of spectral pattern(s) can result in, for example, formation of reaction product, formation of and/or stimulation and/or stabilization of reaction intermediates and/or transients, catalyst frequencies, poisons, promoters, etc. All of the environmental reaction conditions that are discussed in detail in the section entitled "Detailed Description of the Preferred Embodiments" can be at least partially stimulated in a crystallization reaction system by the application of a spectral environmental reaction condition.

Similarly, spectral patterns can be caused to become non-overlapping by changing, for example, at least one spectral environmental reaction condition, and thus changing the applied spectral energy pattern. In this instance, energy will not transfer (or the rate at which energy transfers can be reduced) and reactions will not occur (or the rates of reactions can be slowed).

Finally, by controlling spectral environmental reaction conditions, the energy dynamics within a holoreaction system may be controlled. For example, with a first spectral environmental reaction condition, a first set of frequencies may match and hence energy may transfer at a first set of energy levels and types. When the spectral environmental reaction condition is changed, a second set of frequencies may match, resulting in transfer of energy at different levels or types.

Spectral environmental reaction conditions can be utilized to start and/or stop reactions in a reaction pathway. Thus, certain reactions can be started, stopped, slowed and/or speeded up by, for example, applying different spectral environmental reaction conditions at different times during a reaction and/or at different intensities. Thus, spectral environmental reaction conditions are capable of influencing, positively or negatively, reaction pathways and/or reaction rates in a crystallization reaction system.

VII. Spectral Conditioning Environmental Reaction Conditions

Similarly, spectral conditioning environmental reaction conditions considerations apply in a parallel manner in this section as well. Specifically, if it is known that certain conditioning of a conditioned participant will not occur (or not occur at a desirable rate), unless for example, certain minimum or maximum conditioning environmental reaction conditions are present (e.g., the temperature and/or pressure is/are elevated), then an additional frequency or combination of frequencies (i.e., an applied spectral energy conditioning pattern) can be applied to the conditionable participant. In this regard, spectral conditioning environmental reaction condition(s) can be applied instead of, or to supplement, those conditioning environmental reaction conditions that are naturally present, or need to be present, in order for a desired conditioning of a conditionable participant to occur (i.e., to form a desired conditioned participant). The conditioning environmental reaction conditions that can be supplemented or replaced with spectral conditioning environmental reaction conditions include, for example, temperature, pressure, surface area of catalysts, catalyst size and shape, solvents, support materials, poisons, promoters, concentrations, electric fields, magnetic fields, etc.

Still further, a particular frequency or combination of frequencies and/or fields that can produce one or more spectral conditioning environmental reaction conditions can be combined with one or more spectral energy conditioning catalysts and/or spectral conditioning catalysts to generate an applied spectral energy conditioning pattern. Accordingly, various considerations can be taken into account for what particular frequency or combination of frequencies and/or fields may be desirable to combine with (or replace) various conditioning environmental reaction conditions, for example.

Thus, by applying a frequency, or combination of frequencies and/or fields (i.e., creating an applied spectral energy conditioning pattern) which corresponds to at least one spectral environmental conditioning reaction condition, the spectral energy conditioning patterns of a conditionable participant can be effectively modified which may result in broader spectral energy conditioning patterns (e.g., broader spectral conditioning patterns), in some cases, or narrower spectral energy conditioning patterns (e.g., spectral conditioning patterns) in other cases. Such broader or narrower spectral energy patterns (e.g., spectral conditioning patterns) may correspond to a broadening or narrowing of line widths in a spectral conditioning energy pattern (e.g., a spectral conditioning pattern). As stated throughout herein, when frequencies match, energy transfers. In this particular embodiment, frequencies can be caused to match by, for example, broadening the spectral conditioning pattern of one or more participants in a cell reaction system. For example, as discussed in much greater detail later herein, the application of temperature to a conditioning reaction system typically causes the broadening of one or more spectral conditioning patterns (e.g., line width broadening) of, for example, one or more conditionable participants in a conditioning reaction system. It is this broadening of spectral conditioning patterns that can cause spectral conditioning patterns of one or more constituents in a conditioning reaction system to, for example, overlap. The overlapping of the spectral conditioning patterns can cause frequencies to match, and thus energy to transfer to result in a conditioned participant. The same conditionable participant may be conditioned with different spectral energy patterns or amounts to result in conditioned participants with different energy dynamics (e.g., energized electronic level versus energized rotation). The scope of reactions which occur once a conditioned participant is introduced into a crystallization reaction system, include all of those reactions along any particular reaction pathway. Thus, the broadening of spectral conditioned pattern(s) in a conditioned participant can result in, for example, formation of reaction product, formation of and/or stimulation and/or stabilization of reaction intermediates and/or transients, catalyst frequencies, poisons, promoters, etc., in a crystallization reaction system. All of the conditioning environmental reaction conditions that are discussed in detail in the section entitled "Detailed Description of the Preferred Embodiments" can be at least partially simulated in a conditioning reaction system by the application of a spectral conditioning environmental reaction condition.

Spectral conditioning environmental reaction conditions can be utilized to start direct, contain and/or appropriately condition a conditionable participant so that the conditioned participant can stop reactions or reaction pathways in a crystallization reaction system. Thus, certain reactions can be started, stopped, slowed and/or speeded up in a crystallization reaction system by, for example, applying different spectral conditioning environmental reaction conditions to a conditionable participant and introducing the conditioned participant into a crystallization reaction system at different times during a reaction and/or at different intensities. Thus, spectral conditioning environmental reaction conditions are capable of influencing, positively or negatively, reaction pathways and/or reaction rates in a crystallization reaction system by providing different spectral energy patterns in one or more conditioned participants.

Moreover, by utilizing the above techniques to design (e.g., calculate or determine) a desirable spectral energy pattern, such as a desirable spectral pattern for a spectral energy catalyst (e.g., a spectral catalyst corresponding to, for example, a seed crystal or an epitaxial substrate) rather than applying the spectral energy catalyst (e.g., spectral catalyst) per se, for example, the designed spectral pattern can be used to design and/or determine an optimum physical and/or spectral catalyst that could be used in the crystallization reaction system to obtain a particular crystallization result. Further, the invention may be able to provide a recipe for a physical and/or spectral catalyst for a particular crystallization reaction where no catalyst previously existed (e.g., certain atoms, ions, molecules and/or macromolecules can be influenced to crystallize in a manner which does not normally occur). For example in a reaction where:

where A=reactant, B=product and I=known intermediate, and there is no known catalyst, either a physical or spectral catalyst could be designed which, for example, resonates with the intermediate "I", thereby catalyzing the formation of one or more desirable crystallization reaction product(s).

As a first step, the designed spectral pattern could be compared to known spectral patterns for existing materials to determine if similarities exist between the designed spectral pattern and spectral patterns of known materials. If the designed spectral pattern at least partially matches against a spectral pattern of a known material, then it is possible to utilize the known material as a physical catalyst to obtain a desired crystallization reaction and/or desired crystallization reaction pathway in a crystallization reaction system. In this regard, it may be desirable to utilize the known material alone or in combination with a spectral energy catalyst and/or a spectral catalyst. Still further, it may be possible to utilize environmental reaction conditions and/or spectral environmental reaction conditions to cause the known material to behave in a manner which is even closer to the designed energy pattern or spectral pattern. Further, the application of different spectral energy patterns may cause the designed catalyst to behave in different manners, such as, for example, encouraging a first crystallization reaction pathway with the application of a first spectral energy pattern and encouraging a second crystallization reaction pathway with the application of a second spectral energy pattern. Likewise, the changing of one or more environmental reaction conditions could have a similar effect.

Further, this designed catalyst has applications in all types of reactions including, but not limited to, chemical (organic and inorganic), biological, physical, energy, etc.

Still further, in certain cases, one or more physical species could be used or combined in a suitable manner, for example, physical mixing or by a chemical reaction, to obtain a physical catalyst material exhibiting the appropriate designed spectral energy pattern (e.g., spectral pattern) to achieve a desired reaction pathway. Accordingly, a combination of designed catalyst(s) (e.g., a physical catalyst which is known or manufactured expressly to function as a physical catalyst such as a seed crystal), spectral energy catalyst(s) and/or spectral catalyst(s) can result in a resultant energy pattern (e.g., which in this case can be a combination of physical catalyst(s) and/or spectral catalyst(s)) which is conducive to forming desired reaction product(s) and/or following a desired reaction pathway at a desired reaction rate. In this regard, various line width broadening and/or narrowing of spectral energy pattern(s) and/or spectral pattern(s) may occur when the designed catalyst is combined with various spectral energy patterns and/or spectral patterns.

It is important to consider the energy interactions between all components involved in the desired reaction in a crystallization reaction system when calculating or determining an appropriate designed catalyst. There will be a particular combination of specific energy pattern(s) (e.g., electromagnetic energy) that will interact with the designed catalyst to form an applied spectral energy pattern. The particular frequencies, for example, of electromagnetic radiation that should be caused to be applied to a crystallization reaction system should be as many of those frequencies as possible, when interacting with the frequencies of the designed catalyst, that can result in desirable effects to one or more participants in the crystallization reaction system, while eliminating as many of those frequencies as possible which result in undesirable effects within the crystallization reaction system.

X. Designing Conditionable Participants

Moreover, by utilizing the above techniques to design (e.g., calculate or determine) a desirable spectral energy pattern, such as a desirable spectral pattern for a spectral energy catalyst rather than applying the spectral energy catalyst (e.g., spectral catalyst) per se, for example, the designed spectral pattern can be used to design and/or determine an optimum physical and/or spectral catalyst that could be used in the crystallization reaction system to obtain a particular result. Further, the invention may be able to provide a recipe for a physical and/or spectral catalyst for a particular crystallization reaction where no catalyst previously existed. For example in a reaction where:

where A=reactant, B=product and I=known intermediate, and there is no known catalyst, either a physical or spectral catalyst could be designed which, for example, resonates with the intermediate "I", thereby catalyzing the formation of one or more desirable reaction product(s).

As a first step, the designed spectral pattern could be compared to known spectral patterns for existing materials to determine if similarities exist between the designed spectral pattern and spectral patterns of known materials. If the designed spectral pattern at least partially matches against a spectral pattern of a known material, then it is possible to utilize the known material as a physical catalyst to obtain a desired reaction and/or desired reaction pathway or rate in a crystallization reaction system. In this regard, it may be desirable to utilize the known material alone or in combination with a spectral energy catalyst and/or a spectral catalyst. Still further, it may be possible to utilize environmental reaction conditions and/or spectral environmental reaction conditions to cause the known material to behave in a manner which is even closer to the designed energy pattern or spectral pattern. Further, the application of different spectral energy patterns may cause the designed catalyst to behave in different manners, such as, for example, encouraging a first reaction pathway with the application of a first spectral energy pattern and encouraging a second reaction pathway with the application of a second spectral energy pattern. Likewise, the changing of one or more environmental reaction conditions could have a similar effect.

Further, this designed catalyst has applications in all types of reactions including, but not limited to, chemical (organic and inorganic), biological, physical, energy, etc.

Still further, in certain cases, one or more physical species could be used or combined in a suitable manner, for example, physical mixing or by a chemical reaction, to obtain a physical catalyst material exhibiting the appropriate designed spectral energy pattern (e.g., spectral pattern) to achieve a desired reaction pathway. Accordingly, a combination of designed catalyst(s) (e.g., a physical catalyst which is known or manufactured expressly to function as a physical catalyst), spectral energy catalyst(s) and/or spectral catalyst(s) can result in a resultant energy pattern (e.g., which in this case can be a combination of physical catalyst(s) and/or spectral catalyst(s)) which is conducive to forming desired reaction product(s) and/or following a desired reaction pathway at a desired reaction rate. In this regard, various line width broadening and/or narrowing of spectral energy pattern(s) and/or spectral pattern(s) may occur when the designed catalyst is combined with various spectral energy patterns and/or spectral patterns.

It is important to consider the energy interactions between all components involved in the desired reaction in a crystallization reaction system when calculating or determining an appropriate designed catalyst. There will be a particular combination of specific energy pattern(s) (e.g., electromagnetic energy) that will interact with the designed catalyst to form an applied spectral energy pattern. The particular frequencies, for example, of electromagnetic radiation that should be caused to be applied to a crystallization reaction system should be as many of those frequencies as possible, when interacting with the frequencies of the designed catalyst, that can result in desirable effects to one or more participants in the cell reaction system, while eliminating as many of those frequencies as possible which result in undesirable effects within the crystallization reaction system.

XI. Objects of the Invention

All of the above information disclosing the invention should provide a comprehensive understanding of the main aspects of the invention. However, in order to understand the invention further, the invention shall now be discussed in terms of some of the representative objects or goals to be achieved.

1. One object of this invention is to control or direct a crystallization reaction pathway in a crystallization reaction system by applying a spectral energy pattern in the form of a spectral catalyst having at least one electromagnetic energy frequency which may initiate, activate, and/or affect at least one of the participants involved in the crystallization reaction system.

2. Another object of the invention is to provide an efficient, selective and economical process for replacing a known physical catalyst (e.g., a seed crystal, an epitaxial growth promoter, etc.) in a crystallization reaction system comprising the steps of:

duplicating at least a portion of a spectral pattern of a physical catalyst (e.g., at least one frequency of a spectral pattern of a physical catalyst) to form a catalytic spectral pattern; and applying to at least a portion of the crystallization reaction system (e.g. to a melt, to a solution, and/or to an epitaxial plasma) at least a portion of the catalytic spectral pattern.

3. Another object of the invention is to provide a method to augment a physical catalyst (e.g., a seed crystal, an epitaxial substrate, etc.) in a crystallization reaction system with its own catalytic spectral pattern comprising the steps of:

determining an electromagnetic spectral pattern of the physical catalyst; and duplicating at least one frequency of the spectral pattern of the physical catalyst with at least one electromagnetic energy emitter source to form a catalytic spectral pattern; and applying to at least a portion of the crystallization reaction system at least one frequency of the catalytic spectral pattern at a sufficient intensity and for a sufficient duration to catalyze the formation of reaction product(s) in a desired portion of the crystallization reaction system. Said at least one frequency can be applied by at least one of: (1) an electromagnetic wave guide: (2) an optical fiber array; (3) at least one element added to the crystallization reaction system which permits electromagnetic energy to be radiated therefrom; (4) an electric field; (5) a magnetic field; and/or (6) an acoustic field.

4. Another object of the invention is to provide an efficient, selective and economical process for replacing a known physical catalyst in a crystallization reaction system comprising the steps of:

duplicating at least a portion of a spectral pattern of a physical catalyst (e.g., at least one frequency of a spectral pattern of a physical catalyst such as a seed crystal or an epitaxial substrate) to form a catalytic spectral pattern; and applying to the crystallization reaction system at least a portion of the catalytic spectral pattern; and, applying at least one additional spectral energy pattern which forms an applied spectral energy pattern when combined with said catalytic spectral pattern.

5. Another object of the invention is to provide a method to replace a physical catalyst in a crystallization reaction system comprising the steps of:

determining an electromagnetic spectral pattern of the physical catalyst;

duplicating at least one frequency of the electromagnetic spectral pattern of the physical catalyst with at least one electromagnetic energy emitter source to form a catalytic spectral pattern;

applying to the crystallization reaction system at least one frequency of the catalytic spectral pattern; and applying at least one additional spectral energy pattern to form an applied spectral energy pattern, said applied spectral energy pattern being applied at a sufficient intensity and for a sufficient duration to catalyze the formation of at least one crystallization reaction product in the crystallization reaction system.

6. Another object of this invention is to provide a method to affect and/or direct a particular crystallization reaction pathway in a crystallization reaction system with a spectral catalyst (e.g., the spectral pattern of a seed crystal and/or an epitaxial substrate) by augmenting a physical catalyst comprising the steps of:

duplicating at least a portion of a spectral pattern of a physical catalyst (e.g., at least one frequency of a spectral pattern of the physical catalyst) with at least one energy emitter source to form a catalytic spectral pattern;

applying to the crystallization reaction system, (e.g., irradiating) at least a portion of the catalytic spectral pattern (e.g., an electromagnetic spectral pattern having a frequency range of from about radio frequency to about ultraviolet frequency) at a sufficient intensity and for a sufficient duration to catalyze one or more particular reactions in the crystallization reaction system; and introducing the physical catalyst (e.g., seed crystal) into the crystallization reaction system.

The above method may be practiced by introducing the physical catalyst into the crystallization reaction system before, and/or during, and/or after applying said catalytic spectral pattern to the crystallization reaction system.

7. Another object of this invention is to provide a method to affect and/or direct a particular reaction in a crystallization reaction system with a spectral energy catalyst by augmenting a physical catalyst (e.g., a seed crystal and/or an epitaxial substrate) comprising the steps of:

applying at least one spectral energy catalyst at a sufficient intensity and for a sufficient duration to catalyze the particular crystallization reaction in the crystallization reaction system;

introducing the physical catalyst into the crystallization reaction system.

The above method may be practiced by introducing the physical catalyst into the crystallization reaction system before, and/or during, and/or after applying the spectral energy catalyst to the crystallization reaction system.

8. Another object of this invention is to provide a method to affect and/or direct a desired crystallization reaction pathway in a crystallization reaction system with a spectral catalyst and a spectral energy catalyst by augmenting a physical catalyst (e.g., a seed crystal and/or an epitaxial substrate) comprising the steps of:

applying at least one spectral catalyst at a sufficient intensity and for a sufficient duration to at least partially catalyze the desired crystallization reaction system;

applying at least one spectral energy catalyst at a sufficient intensity and for a sufficient duration to at least partially catalyze the desired crystallization reaction system; and introducing the physical catalyst into the crystallization reaction system.

The above method may be practiced by introducing the physical catalyst into the crystallization reaction system before, and/or during, and/or after applying the spectral catalyst and/or the spectral energy catalyst to the crystallization reaction system. Moreover, the spectral catalyst and spectral energy catalyst may be applied simultaneously to form an applied spectral energy pattern or they may be applied sequentially either at the same time or at different times from when the physical catalyst is introduced into the crystallization reaction system.

9. Another object of this invention is to provide a method to affect and/or direct a desired reaction into a crystallization reaction system with a spectral catalyst and a spectral energy catalyst and a spectral environmental reaction condition, with or without a physical catalyst (e.g., a seed crystal and/or an epitaxial substrate), comprising the steps of:

applying at least one spectral catalyst at a sufficient intensity and for a sufficient duration to catalyze a crystallization reaction pathway;

applying at least one spectral energy catalyst at a sufficient intensity and for a sufficient duration to catalyze a crystallization reaction pathway;

applying at last one spectral environmental reaction condition at a sufficient intensity and for a sufficient duration to catalyze a crystallization reaction pathway, whereby when any of said at least one spectral catalyst, said at least one spectral energy catalyst and/or at least one spectral environmental reaction condition are applied at the same time, they form an applied spectral energy pattern; and introducing the physical catalyst into the crystallization reaction system.

The above method may be practiced by introducing the physical catalyst into the crystallization reaction system before, and/or during, and/or after applying any one of, or any combination of, the spectral catalyst and/or the spectral energy catalyst and/or the spectral environmental reaction condition to the crystallization reaction system. Likewise, the spectral catalyst and/or the spectral energy catalyst and/or the spectral environmental reaction condition can be provided sequentially or continuously.

10. Another object of this invention is to provide a method to affect and direct a crystallization reaction system with an applied spectral energy pattern and a spectral energy catalyst comprising the steps of:

applying at least one applied spectral energy pattern at a sufficient intensity and for a sufficient duration to catalyze a particular reaction in a crystallization reaction system, whereby said at least one applied spectral energy pattern comprises at least two members selected from the group consisting of catalytic spectral energy pattern, catalytic spectral pattern, spectral catalyst, spectral energy catalyst, spectral energy pattern, spectral environmental reaction condition and spectral pattern; and applying at least one spectral energy catalyst to the crystallization reaction system.

The above method may be practiced by introducing the applied spectral energy pattern into the crystallization reaction system before, and/or during, and/or after applying the spectral energy catalyst to the crystallization reaction system. Moreover, the spectral energy catalyst and the applied spectral energy pattern can be provided sequentially or continuously. If applied continuously, a new applied spectral energy pattern is formed.

11. Another object of this invention is to provide a method to affect and/or direct a crystallization reaction system with a spectral energy catalyst comprising the steps of:

determining at least a portion of a spectral energy pattern for starting reactant(s) in a particular reaction in said crystallization reaction system;

determining at least a portion of a spectral energy pattern for reaction product(s) in said particular reaction in said crystallization reaction system;

calculating an additive and/or subtractive spectral energy pattern (e.g., at least one electromagnetic frequency) from said reactant(s) and reaction product(s) spectral energy patterns to determine a required spectral energy catalyst (e.g., a spectral catalyst);

generating at least a portion of the required spectral energy catalyst (e.g., at least one electromagnetic frequency of the required spectral catalyst); and applying to the particular reaction in said crystallization reaction system (e.g., irradiating with electromagnetic energy) said at least a portion of the required spectral energy catalyst (e.g., spectral catalyst) to form at least one desired crystallization reaction product(s).

12. Another object of the invention is to provide a method to affect and/or direct a crystallization reaction system with a spectral energy catalyst comprising the steps of:

targeting at least one participant in said crystallization reaction system with at least one spectral energy catalyst to cause the formation and/or stimulation and/or stabilization of at least one transient and/or at least one intermediate to result in desired reaction product(s).

13. Another object of the invention is to provide a method for catalyzing a crystallization reaction system with a spectral energy pattern to result in at least one reaction product comprising:

applying at least one spectral energy pattern for a sufficient time and at a sufficient intensity to cause the formation and/or stimulation and/or stabilization of at least one transient and/or at least one intermediate to result in desired reaction product(s) at a desired reaction rate.

14. Another object of the invention is to provide a method to affect and direct a crystallization reaction system with a spectral energy catalyst and at least one of the spectral environmental reaction conditions comprising the steps of:

applying at least one applied spectral energy catalyst to at least one participant in said crystallization reaction system; and applying at least one spectral environmental reaction condition to said crystallization reaction system to cause the formation and/or stimulation and/or stabilization of at least one transient and/or at least one intermediate to permit desired crystallization reaction product(s) to form.

15. Another object of the invention is to provide a method for catalyzing a crystallization reaction system with a spectral energy catalyst to result in at least one reaction product comprising:

applying at least one frequency (e.g., electromagnetic) which heterodynes with at least one reactant frequency to cause the formation of and/or stimulation and/or stabilization of at least one transient and/or at least one intermediate to result in desired crystallization reaction product(s).

16. Another object of the invention is to provide a method for catalyzing a crystallization reaction system with at least one spectral energy pattern resulting in at least one reaction product comprising:

applying a sufficient number of frequencies (e.g., electromagnetic) and/or fields (e.g., electric, magnetic and/or acoustic) to result in an applied spectral energy pattern which stimulates all transients and/or intermediates required in a crystallization reaction pathway to result in desired crystallization reaction product(s).

17. Another object of the invention is to provide a method for catalyzing a crystallization reaction system with a spectral energy catalyst resulting in at least one reaction product comprising:

targeting at least one participant in said crystallization reaction system with at least one frequency and/or field to form, indirectly, at least one transient and/or at least one intermediate, whereby formation of said at least one transient and/or at least one intermediate results in the formation of an additional at least one transient and/or at least one additional intermediate.

18. It is another object of the invention to provide a method for catalyzing a crystallization reaction system with a spectral energy catalyst resulting in at least one reaction product comprising:

targeting at least one spectral energy catalyst to at least one participant in said crystallization reaction system to form indirectly at least one transient and/or at least one intermediate, whereby formation of said at least one transient and/or at least one intermediate results in the formation of an additional at least one transient and/or at least one additional intermediate.

19. It is a further object of the invention to provide a method for directing a crystallization reaction system along a desired reaction pathway comprising:

applying at least one targeting approach selected from the group of approaches consisting of direct resonance targeting, harmonic targeting and non-harmonic heterodyne targeting.

In this regard, these targeting approaches can cause the formation and/or stimulation and/or stabilization of at least one transient and/or at least one intermediate in at least a portion of said crystallization reaction system to result in desired reaction product(s).

20. It is another object of the invention to provide a method for catalyzing a crystallization reaction system comprising:

applying at least one frequency to at least one participant and/or at least one component in said crystallization reaction system to cause the formation and/or stimulation and/or stabilization of at least one transient and/or at least one intermediate to result in desired reaction product(s), whereby said at least one frequency comprises at least one frequency selected from the group consisting of direct resonance frequencies, harmonic resonance frequencies, non-harmonic heterodyne resonance frequencies, electronic frequencies, vibrational frequencies, rotational frequencies, rotational-vibrational frequencies, librational frequencies, translational frequencies, gyrational frequencies, fine splitting frequencies, hyperfine splitting frequencies, electric field induced frequencies, magnetic field induced frequencies, cyclotron resonance frequencies, orbital frequencies, acoustic frequencies and/or nuclear frequencies.

In this regard, the applied frequencies can include any desirable frequency or combination of frequencies which resonates directly, harmonically or by a non-harmonic heterodyne technique, with at least one participant and/or at least one component in said crystallization reaction system.

21. It is another object of the invention to provide a method for directing a crystallization reaction system along with a desired crystallization reaction pathway with a spectral energy pattern comprising:

applying at least one frequency and/or field to cause the spectral energy pattern (e.g., spectral pattern) of at least one participant and/or at least one component in said crystallization reaction system to at least partially overlap with the spectral energy pattern (e.g., spectral pattern) of at least one other participant and/or at least one other component in said crystallization reaction system to permit the transfer of energy between said at least two participants and/or components.

22. It is another object of the invention to provide a method for catalyzing a crystallization reaction system with a spectral energy pattern resulting in at least one crystallization reaction product comprising:

applying at least one spectral energy pattern to cause the spectral energy pattern of at least one participant and/or component in said crystallization reaction system to at least partially overlap with a spectral energy pattern of at least one other participant and/or component in said crystallization reaction system to permit the resonant transfer of energy between the at least two participants and/or components, thereby causing the formation of said at least one reaction product.

23. It is a further object of the invention to provide a method for catalyzing a crystallization reaction system with a spectral energy catalyst resulting in at least one crystallization reaction product comprising:

applying at least one frequency and/or field to cause spectral energy pattern (e.g., spectral pattern) broadening of at least one participant (e.g., at least one reactant) and/or component in said crystallization reaction system to cause a transfer of energy to occur resulting in transformation (e.g., chemically, physically, phase, property or otherwise) of at least one participant and/or at least one component in said crystallization reaction system.

In this regard, the transformation may result in a reaction product which is of a different chemical composition and/or different physical or crystalline composition and/or phases than any of the chemical and/or physical or crystalline compositions and/or phases of any starting reactant. Thus, only transients may be involved in the conversion of a reactant into a reaction product.

24. It is a further object of the invention to provide a method for catalyzing a crystallization reaction system with a spectral energy catalyst resulting in at least one reaction product comprising:

applying an applied spectral energy pattern to cause spectral energy pattern (e.g., spectral pattern) broadening of at least one participant (e.g., at least one reactant) and/or component in said crystallization reaction system to cause a resonant transfer of energy to occur resulting in transformation (e.g., chemically, physically, phase, property or otherwise) of at least one participant and/or at least one component in said crystallization reaction system.

In this regard, the transformation may result in a reaction product which is of a different chemical composition and/or different physical or crystalline composition and/or phase and/or exhibits different properties than the chemical and/or physical or crystalline compositions and/or phases of any starting reactant. Thus, only transients may be involved in the conversion of a reactant into a reaction product.

25. Another object of the invention is to provide a method for controlling a reaction and/or directing a reaction pathway in a crystallization reaction system by utilizing at least one spectral environmental reaction condition, comprising:

forming a crystallization reaction system; and applying at least one spectral environmental reaction condition to direct said crystallization reaction system along at least one desired crystallization reaction pathway.

In this regard, the applied spectral environmental reaction condition can be used alone or in combination with other environmental reaction conditions to achieve desired results. Further, additional spectral energy patterns may also be applied, simultaneously and/or continuously with said spectral environmental reaction condition.

26. Another object of the invention is to provide a method for designing a catalyst (e.g., a seed catalyst and/or an epitaxial substrate) where no catalyst previously existed (e.g., a physical catalyst and/or spectral energy catalyst), to be used in a crystallization reaction system, comprising:

determining a required spectral pattern to obtain a desired crystallization reaction and/or desired reaction pathway and/or desired crystallization reaction rate; and designing a catalyst (e.g., material or combination of materials, and/or spectral energy catalysts) that exhibit(s) a spectral pattern that approximates the required spectral pattern.

In this regard, the designed catalyst material (e.g., a seed crystal and/or an epitaxial substrate, etc.) may comprise a physical admixing of one or more materials and/or more materials that have been combined by an appropriate reaction, such as a chemical reaction. The designed material may be enhanced in function by one or more spectral energy patterns that may also be applied to the crystallization reaction system. Moreover, the application of different spectral energy patterns may cause the designed material to behave in different manners, such as, for example, encouraging a first crystallization reaction pathway with the application of a first spectral energy pattern and encouraging a second crystallization reaction pathway with the application of a second spectral energy pattern. Likewise, the changing of one or more environmental reaction conditions could have a similar effect.

Further, this designed material has applications in all types of reactions including, but not limited to, chemical (organic and inorganic), biological, physical, etc.

27. Another object of the invention is to provide a method for controlling a reaction and/or directing a reaction pathway in a crystallization reaction system by preventing at least a portion of certain undesirable spectral energy from interacting with a crystallization reaction system comprising:

providing at least one control means for absorbing, filtering, trapping, reflecting, etc., spectral energy incident thereon;

permitting desirable spectral energy emitted from said control means and contacting at least a portion of a crystallization reaction system with said emitted spectral energy; and causing said emitted spectral energy from said control means to desirably interact with said crystallization reaction system thereby directing said crystallization reaction system along at least one desired crystallization reaction pathway.

28. It should be understood that in each of the aforementioned 27 Objects of the Invention, that crystallization reaction systems also include preventing certain crystallization phenomena from occurring, when desirable.

29. One object of this invention is to control or direct a reaction pathway in a crystallization reaction system with a conditioned participant, and forming the conditioned participant by applying a spectral energy conditioning pattern (e.g., a spectral conditioning catalyst) to at least one conditionable participant, said conditionable participant thereafter having at least one conditioned energy frequency (e.g., electromagnetic energy frequency) which may initiate, activate, and/or affect at least one of the participants involved in the crystallization reaction system and/or may itself be affected by a subsequent application of spectral energy in the crystallization reaction system.

30. Another object of the invention is to provide an efficient, selective and economical process for replacing a known physical catalyst in a crystallization reaction system comprising the steps of:

duplicating at least a portion of a spectral pattern of a physical catalyst (e.g., at least one frequency of a spectral pattern of a physical catalyst) by modifying a conditionable participant so that the conditionable participant forms a catalytic spectral pattern; and applying or introducing to the crystallization reaction system the conditioned participant.

31. Another object of the invention is to provide a method to augment a physical catalyst in a crystallization reaction system with its own catalytic spectral pattern comprising the steps of:

determining an electromagnetic spectral pattern of the physical catalyst; and duplicating at least one frequency of the spectral pattern of the physical catalyst by conditioning a conditionable participant with at least one electromagnetic energy emitter source to form a catalytic spectral pattern in the conditioned participant; and applying or introducing to the crystallization reaction system the conditioned participant.

32. Another object of the invention is to provide an efficient, selective and economical process for replacing a known physical catalyst in a crystallization reaction system comprising the steps of:

duplicating at least a portion of a spectral pattern of a physical catalyst (e.g., at least one frequency of a spectral pattern of a physical catalyst) by conditioning a conditionable participant to form a catalytic spectral pattern in the conditioned participant;

applying or introducing to the crystallization reaction system the conditioned participant; and applying at least one additional spectral energy pattern which forms an applied spectral energy pattern when combined with said catalytic spectral pattern of the conditioned participant.

33. Another object of the invention is to provide a method to replace a physical catalyst in a crystallization reaction system comprising the steps of:

determining an electromagnetic spectral pattern of the physical catalyst;

duplicating at least one frequency of the electromagnetic spectral pattern of the physical catalyst by conditioning a conditionable participant with at least one electromagnetic energy emitter conditioning source to form a catalytic spectral pattern in the conditioned participant;

applying or introducing to the crystallization reaction system the conditioned participant; and applying at least one additional spectral energy pattern to form an applied spectral energy pattern, said applied spectral energy pattern being applied at a sufficient intensity and for a sufficient duration to catalyze the formation of at least one reaction product in the crystallization reaction system.

34. Another object of this invention is to provide a method to affect and/or direct a crystallization reaction system with a spectral catalyst by augmenting a physical catalyst comprising the steps of:

duplicating at least a portion of a spectral pattern of a physical catalyst (e.g., at least one frequency of a spectral pattern of the physical catalyst) by conditioning a conditionable participant with at least one electromagnetic energy emitter source to form a catalytic spectral pattern in the conditioned participant;

applying or introducing to the crystallization reaction system, the conditioned participant; and introducing the physical catalyst into the crystallization reaction system.

The above method may be practiced by introducing the physical catalyst into the crystallization reaction system before, and/or during, and/or after applying said conditioned participant to the crystallization reaction system.

35. Another object of this invention is to provide a method to affect and/or direct a crystallization reaction system with a conditioned participant by augmenting a physical catalyst comprising the steps of:

applying or introducing at least one conditioned participant to the crystallization reaction system; and introducing the physical catalyst into the crystallization reaction system.

The above method may be practiced by introducing the physical catalyst into the crystallization reaction system before, and/or during, and/or after applying the conditioned participant to the crystallization reaction system.

36. Another object of this invention is to provide a method to affect and/or direct a crystallization reaction system with a conditioned participant and a spectral energy catalyst by augmenting a physical catalyst comprising the steps of:

applying or introducing at least one conditioned participant to the crystallization reaction system;

applying at least one spectral energy catalyst at a sufficient intensity and for a sufficient duration to at least partially catalyze the crystallization reaction system; and introducing the physical catalyst into the crystallization reaction system.

The above method may be practiced by introducing the physical catalyst into the crystallization reaction system before, and/or during, and/or after applying the conditioned participant and/or the spectral energy catalyst to the crystallization reaction system. Moreover, the conditioned participant and spectral energy catalyst may be applied simultaneously to form an applied spectral energy pattern or they may be applied sequentially either at the same time or at different times from when the physical catalyst is introduced into the crystallization reaction system.

37. Another object of this invention is to provide a method to affect and/or direct a reaction system with a conditioned participant and a spectral energy catalyst and a spectral environmental reaction condition, with or without a physical catalyst, comprising the steps of:

applying or introducing at least one conditioned participant to the crystallization reaction system;

applying at least one spectral energy catalyst at a sufficient intensity and for a sufficient duration to catalyze a reaction pathway;

applying at last one spectral environmental reaction condition at a sufficient intensity and for a sufficient duration to catalyze a reaction pathway, whereby when any of said at least one conditioned participant, said at least one spectral energy catalyst and/or at least one spectral environmental reaction condition are applied at the same time, they form an applied spectral energy pattern; and introducing the physical catalyst into the crystallization reaction system.

The above method may be practiced by introducing the physical catalyst into the crystallization reaction system before, and/or during, and/or after applying any one of, or any combination of, the conditioned participant and/or the spectral energy catalyst and/or the spectral environmental reaction condition to the crystallization reaction system. Likewise, the conditioned participant and/or the spectral energy catalyst and/or the spectral environmental reaction condition can be provided sequentially or continuously.

38. Another object of this invention is to provide a method to condition a conditionable participant with an applied spectral energy conditioning pattern and/or a spectral energy conditioning catalyst comprising the steps of:

applying at least one applied spectral energy conditioning pattern at a sufficient intensity and for a sufficient duration to condition the conditionable participant, whereby said at least one applied spectral energy conditioning pattern comprises at least one member selected from the group consisting of catalytic spectral energy conditioning pattern, catalytic spectral conditioning pattern, spectral conditioning catalyst, spectral energy conditioning catalyst, spectral energy conditioning pattern, spectral conditioning environmental reaction condition and spectral conditioning pattern.

The above method may be combined with introducing an applied spectral energy pattern into a crystallization reaction system before, and/or during, and/or after introducing a conditioned participant into the crystallization reaction system. Moreover, the conditioned participant and the applied spectral energy pattern can be provided sequentially or continuously. If applied continuously, a new applied spectral energy pattern is formed.

The above method may also comprise conditioning the conditionable participant in a conditioning reaction vessel and/or in a reaction vessel. If the conditionable participant is first conditioned in a reaction vessel, the conditioning occurs prior to some or all other components comprising the cell reaction system being introduced into the cell reaction system.

Further, the reaction vessel and/or conditioning reaction vessel per se may be treated with conditioning energy. In the case of the reaction vessel being treated with conditioning energy, such conditioning treatment occurs prior to some or all other components comprising the cell reaction system being introduced into the reaction vessel.

39. Another object of this invention is to provide a method to affect and direct a crystallization reaction system with a conditioned participant comprising the steps of:

determining at least a portion of a spectral energy pattern for starting reactant(s) in said crystallization reaction system;

determining at least a portion of a spectral energy pattern for reaction product(s) in said crystallization reaction system;

calculating an additive spectral energy pattern (e.g., at least one electromagnetic frequency) from said reactant(s) and reaction product(s) spectral energy patterns to determine a required conditioned participant (e.g., a spectral conditioned catalyst);

generating at least a portion of the required spectral energy conditioning catalyst (e.g., at least one electromagnetic frequency of the required spectral conditioning catalyst); and applying to the conditionable participant (e.g., irradiating with electromagnetic energy) said at least a portion of the required spectral energy conditioning catalyst (e.g., spectral conditioning catalyst) to form desired conditioned participant; and introducing the conditioned participant to the reaction system to form a desired reaction product and/or desired reaction product at a desired reaction rate.

40. Another object of the invention is to provide a method to affect and direct a crystallization reaction system with a conditioned participant comprising the steps of:

targeting at least one conditionable participant in said conditioning reaction system with at least one spectral energy conditioning catalyst to cause the formation and/or stimulation and/or stabilization of at least one conditioned participant; and applying or introducing the conditioned participant to the crystallization reaction system to result in at least one desired reaction product and/or desired or controlled reaction rate in said crystallization reaction system.

41. Another object of the invention is to provide a method for catalyzing a crystallization reaction system with a conditioned participant to result in at least one reaction product and/or at least one desired reaction rate comprising:

applying at least one spectral energy conditioning pattern for a sufficient time and at a sufficient intensity to cause the formation and/or stimulation and/or stabilization of at least one conditioned participant, so as to result in desired reaction product(s) at a desired reaction rate when said conditioned participant communicates with said crystallization reaction system.

42. Another object of the invention is to provide a method to affect and direct a crystallization reaction system with a conditioned participant and at least one spectral environmental reaction condition comprising the steps of:

applying or introducing at least one conditioned participant to the crystallization reaction system; and applying at least one spectral environmental reaction condition to said crystallization reaction system to cause the formation and/or stimulation and/or stabilization of at least one transient and/or at least one intermediate to permit desired reaction product(s) to form.

43. Another object of the invention is to provide a method for forming a conditioned participant with a spectral energy conditioning catalyst to result in at least one conditioned participant comprising:

applying at least one frequency (e.g., electromagnetic) which heterodynes with at least one conditionable participant frequency to cause the formation of and/or stimulation and/or stabilization of at least one conditioned participant.

44. Another object of the invention is to provide a method for forming a conditioned participant with at least one spectral energy conditioning pattern resulting in at least one conditioned participant comprising:

applying a sufficient number of frequencies (e.g., electromagnetic) and/or fields (e.g., electric and/or magnetic) to result in an applied spectral energy conditioning pattern which results in the formation of at least one conditioned participant.

45. Another object of the invention is to provide a method for forming a conditioned participant with a spectral energy conditioning catalyst resulting in at least one conditioned participant comprising:

conditioning targeting at least one conditionable participant prior to being introduced to said crystallization reaction system with at least one frequency and/or field to form a conditioned participant, whereby formation of said at least one conditioned participant results in the formation of at least one transient and/or at least one intermediate when said conditioned participant is introduced into said crystallization reaction system.

46. It is another object of the invention to provide a method for catalyzing a crystallization reaction system with a conditioned participant resulting in at least one reaction product comprising:

conditioning targeting at least one spectral energy conditioning catalyst to form at least one conditioned participant (e.g., at least one spectral energy catalyst) which is present in said crystallization reaction system when at least one reaction in said crystallization reaction system is initiated, such that at least one transient and/or at least one intermediate, and/or at least one reaction product is formed in the crystallization reaction system.

47. It is a further object of the invention to provide a method for directing a crystallization reaction system along a desired reaction pathway comprising:

applying at least one conditioning targeting approach to at least one conditionable participant, said at least one conditioning targeting approach being selected from the group of approaches consisting of direct resonance conditioning targeting, harmonic conditioning targeting and non-harmonic heterodyne conditioning targeting.

In this regard, these conditioning targeting approaches can result in the formation of a conditioned participant which can cause the formation and/or stimulation and/or stabilization of at least one transient and/or at least one intermediate to result in desired reaction product(s) at a desired reaction rate.

48. It is another object of the invention to provide a method for conditioning at least one conditionable participant comprising:

applying at least one conditioning frequency to at least one conditionable participant to cause the formation and/or stimulation and/or stabilization of at least one conditioned participant, whereby said at least one frequency comprises at least one frequency selected from the group consisting of direct resonance conditioning frequencies, harmonic resonance conditioning frequencies, non-harmonic heterodyne conditioning resonance frequencies, electronic conditioning frequencies, vibrational conditioning frequencies, rotational conditioning frequencies, rotational-vibrational conditioning frequencies, fine splitting conditioning frequencies, hyperfine splitting conditioning frequencies, electric field splitting conditioning frequencies, magnetic field splitting conditioning frequencies, cyclotron resonance conditioning frequencies, orbital conditioning frequencies and nuclear conditioning frequencies.

In this regard, the applied conditioning frequencies can include any desirable conditioning frequency or combination of conditioning frequencies which resonates directly, harmonically or by a non-harmonic heterodyne technique, with at least one conditionable participant and/or at least one component of said conditionable participant.

49. It is another object of the invention to provide a method for directing a crystallization reaction system along with a desired reaction pathway with a conditioned participant comprising:

applying at least one conditioning frequency and/or conditioning field to cause the conditioned spectral energy pattern (e.g., spectral conditioning pattern) of at least one conditioned participant to at least partially overlap with the spectral energy pattern (e.g., spectral pattern) of at least one participant and/or at least one other component in said crystallization reaction system to permit the transfer of energy between said conditioned participant and said participant and/or other components.

50. It is another object of the invention to provide a method for catalyzing a crystallization reaction system with a conditioned participant resulting in at least one reaction product comprising:

applying at least one spectral energy conditioning pattern to at least one conditionable participant to cause the conditioned spectral energy pattern of at least one conditioned participant in said crystallization reaction system to at least partially overlap with a spectral energy pattern of at least one other participant and/or component in said crystallization reaction system to permit the transfer of energy between the said conditioned participant and said participant and/or components, thereby causing the formation of said at least one reaction product.

51. It is a further object of the invention to provide a method for catalyzing a crystallization reaction system with a conditioned participant resulting in at least one reaction product comprising:

applying at least one frequency and/or field to cause a conditioned spectral energy pattern (e.g., conditioned spectral pattern) broadening of said conditioned participant to cause a transfer of energy to occur between the conditioned participant and at least one participant in the crystallization reaction system, resulting in transformation (e.g., chemically, physically, phase or otherwise) of at least one participant and/or at least one component in said crystallization reaction system.

In this regard, the transformation may result in a reaction product which is of a different chemical composition and/or different physical or crystalline composition and/or phases than any of the chemical and/or physical or crystalline compositions and/or phases of any starting reactant and/or conditioned participant. Thus, only transients may be involved in the conversion of a reactant into a reaction product.

52. Another object of the invention is to provide a method for controlling a reaction and/or directing a reaction pathway by utilizing at least one conditioned participant and at least one spectral environmental reaction condition, comprising:

forming a crystallization reaction system comprising said conditioned participant; and applying at least one spectral environmental reaction condition to direct said crystallization reaction system along a desired reaction pathway.

In this regard, the applied spectral environmental reaction condition can be used alone or in combination with other environmental reaction conditions to achieve desired results. Further, additional spectral energy patterns may also be applied, simultaneously and/or continuously with said spectral environmental reaction condition.

53. Another object of the invention is to provide a method for designing a conditionable participant to be used as a catalyst, once conditioned, in a crystallization reaction system where no catalyst previously existed (e.g., a physical catalyst and/or spectral energy catalyst), to be used in a crystallization reaction system, comprising:

determining a required spectral pattern to obtain a desired reaction and/or desired reaction pathway and/or desired reaction rate; and designing a conditionable participant (e.g., material or combination of materials), that exhibit(s) a conditioned spectral pattern that approximates the required spectral pattern, when exposed to a suitable spectral energy conditioning pattern.

In this regard, the designed conditionable participant may comprise a physical admixing of one or more materials and/or more materials that have been combined by an appropriate reaction, such as a chemical reaction. The designed conditionable participant material may be enhanced in function by one or more spectral energy conditioning patterns that may also be applied to the conditioning reaction system. Moreover, the application of different spectral energy conditioning patterns may cause the designed conditionable material, once conditioned, to behave in different manners in a crystallization reaction system, such as, for example, encouraging a first reaction pathway in a crystallization reaction system with the application of a first spectral energy conditioning pattern, and encouraging a second reaction pathway with the application of a second spectral energy conditioning pattern. Likewise, the changing of one or more environmental reaction conditions could have a similar effect.

Further, this designed conditionable participant or material has applications in all types of reactions including, but not limited to, chemical (organic and inorganic), biological, physical, etc.

54. It should be understood that in each of 29-53 Objects of the Invention, that crystallization reaction systems also include preventing certain crystallization phenomena from occurring, when desirable.

55. Another object of the invention is to use at least one conditioned participant with each of the techniques set forth in Objects 1-28 above; and to use at least one additional spectral energy pattern with each of the techniques set forth in Objects 29-54 above.

While not wishing to be bound by any particular theory or explanation of operation, it is believed that when frequencies match, energy transfers. The transfer of energy can be a sharing of energy between two entities and, for example, a transfer of energy from one entity into another entity. The entities may both be, for example, matter, or one entity may be matter and the other energy (e.g. energy may be a spectral energy pattern such as electromagnetic frequencies, and/or an electric field and/or a magnetic field).

BRIEF DESCRIPTION OF THE FIGURES

FIG. 2a shows a low amplitude wave and FIG. 2b shows a high amplitude wave.

FIG. 3a shows a time vs. amplitude plot and FIG. 3b shows a frequency vs. amplitude plot.

FIG. 6 shows fractal diagrams.

FIGS. 7a and 7b show hydrogen energy level diagrams.

FIG. 13a shows a narrow resonance curve with a high Q and FIG. 13b shows a broad resonance curve with a low Q.

FIG. 15a is at a low temperature, FIG. 15b is at a moderate temperature and FIG. 15c is at a high temperature.

FIG. 17a shows distinct spectral curves at low temperature; and FIG. 17b shows overlapping of spectral curves at a higher temperature.

FIG. 21a corresponds to a spectral pattern representing the absorption of water vapor in air and FIG. 21b is a spectral pattern which corresponds to the absorption of $NH_3$ at one atmosphere pressure.

FIG. 23a is a standard spectral curve not showing any self-absorption; FIG. 23b shows the shifting of resonant frequency due to self absorption; FIG. 23c shows a self-reversal spectral pattern due to self-absorption; and FIG. 23d shows an attenuation example of a self-reversal spectral pattern.

FIG. 39b shows the same spectrum of FIG. 39a at a lower resolution (i.e., not showing any fine frequencies).

FIG. 43a shows rotational and vibrational frequencies (MHz) for LiF. FIG. 43b shows differences between rotational and vibrational frequencies for LiF.

FIG. 46 shows a fine structure spectrum for $SF_6$ from zero to 300 being magnified.

FIGS. 47a and 47b show the magnification of two curves from fine structure of $SF_6$ showing hyperfine structure frequencies. Note the regular spacing of the hyperfine structure curves. FIG. 47a shows magnification of the curve marked with a single asterisk (*) in FIG. 46 and FIG. 47b shows the magnification of the curved marked with a double asterisk (**) in FIG. 46.

FIG. 48 shows an energy level diagram corresponding to the hyperfine splitting for the hyperfine structure in the n=2 to n=3 transition for hydrogen.

FIG. 49 shows the hyperfine structure in the J=1→2 rotational transition of $CH_3I$.

FIG. 50 shows the hyperfine structure of the J=1→2 transition for ClCN in the ground vibrational state.

FIG. 52 shows a spectrum corresponding to the hyperfine frequencies for $NH_3$.

FIG. 53 shows hyperfine structure and doubling of the $NH_3$ spectrum for rotational level J=3. The upper curves in FIG. 53 show experimental data, while the lower curves are derived from theoretical calculations. Frequency increases from left to right in 60 KHz intervals.

FIG. 54 shows a hyperfine structure and doubling of $NH_3$ spectrum for rotational level J=4. The upper curves in each of FIG. 54 show experimental data, while the lower curves are derived from theoretical calculations. Frequency increases from left to right in 60 KHz intervals.

FIG. 59a shows the J=4→5 transitions; and FIG. 59b shows the J=4→4 transitions. The electric field is large enough for complete spectral resolution.

FIG. 62a shows the Zeeman effect for sodium "D" lines; and FIG. 62b shows the energy level diagram for transitions in the Zeeman effect for sodium "D" lines.

FIG. 63 is a graph which shows the splitting of the ground term of the oxygen atom as a function of magnetic field.

FIG. 64 is a graphic which shows the dependence of the Zeeman effect on magnetic field strength for the "3P" state of silicon.

FIG. 67a shows a graphic representation of four Zeeman splitting frequencies and FIG. 67b shows a graphic representation of four new heterodyned differences.

FIGS. 68a and 68b show graphs of typical Zeeman splitting patterns for two different transitions in a paramagnetic molecule.

FIG. 69 shows the frequencies of hydrogen listed horizontally across the Table; and the frequencies of platinum listed vertically on the Table.

FIG. 75 shows a phase-diagram exhibiting an equilibrium relationship between solid and liquid forms of sodium chloride.

FIGS. 76a and 76b show clinographic projections of the cubic structure of sodium chloride (NaCl).

FIG. 77 shows a clinographic projection of the unit cell of the cubic structure of sodium chloride as represented by circular ions of sodium and chlorine.

FIGS. 81a and 81b show two phase-diagrams for silica ($SiO_2$); FIG. 81c shows a clinographic projection of the unit cell of cubic β-crystobalite; FIG. 81d shows a plan view of the rhombohedral structure of α-quartz; and FIG. 81e shows a plan view of the hexagonal structure of β-quartz.

FIG. 85a shows phase relations for the FeO/Fe$_2$O$_3$ system; and FIG. 85b shows a clinographic projection of four unit cells of the cubic body-centered structure of α-iron.

FIG. 86c shows a crystallization path of the element "A" shown in FIG. 86a.

FIG. 90 shows a schematic of an apparatus that was utilized to grow sodium chloride crystals in accordance with Example 2.

FIGS. 98i-98v; and 98ad-ae are photomicrographs which correspond to crystals grown according to Example 4.

FIGS. 98w-98ac are photomicrographs which correspond to crystals grown in Example 6.

FIG. 99 shows a schematic of the experimental set-up which corresponds to a Bunsen burner heating a solution of sodium chloride and water on a hot plate, which is discussed in Example 7a.

FIG. 103a is a graph of the experimental data which shows pH as a function of time and corresponds to the experimental set-up of Example 7a.

FIG. 103b is a graph of the experimental data which shows pH as a function of time and corresponds to the experimental set-up of Example 7b.

FIG. 103d is a graph which shows the averages of the three (3) different experimental conditions of experiments 7a, 7b and 7c, all superimposed on a single plot.

FIG. 103e is a graph of the experimental data which shows pH as a function of time and corresponds to the experimental set-up of Example 7d.

FIG. 103f is a graph of the experimental data which shows pH as a function of time and corresponds to the experimental set-up of Example 7e.

FIG. 103g is a graph which shows the averages of the three (3) different experimental conditions of experiments 7a, 7b and 7e, all superimposed on a single plot.

FIG. 103h shows the results of three (3) separate experiments (#'s 3, 4 and 5) and represent decay curves generated by the experimental apparatus shown in FIG. 100.

FIG. 103i shows pH as a function of time for two experiments where sodium chloride solute was dissolved in water.

FIGS. 104a and 104b are graphical representations of metal alloy crystals grown according to Example 9a.

FIGS. 105a and 105b are graphical representations of metal alloy crystals grown according to Example 9b.

FIG. 105c is a photograph of exemplary crystals grown according to Example 9a.

FIGS. 105d and 105e are photomicrographs of protein crystals grown according to Example 10d.

FIG. 105f-105i are photomicrographs of mixed crystals grown according to Example 12.

FIG. 106a is a graph of the experimental data which shows conductivity as a function of time for three separate sets of Bunsen burner-only data.

FIG. 106b is a graph of the experimental data which shows conductivity as a function of temperature (two separate data points only) for Bunsen burner-only data.

Figure 106A:
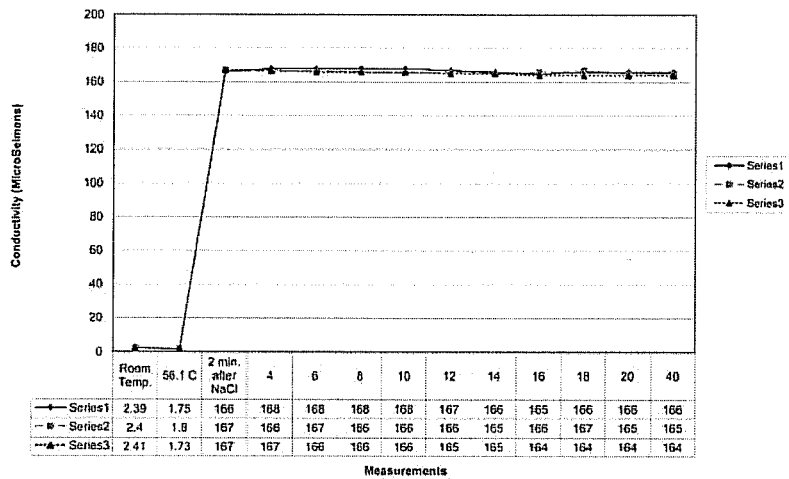
Figure 106B:
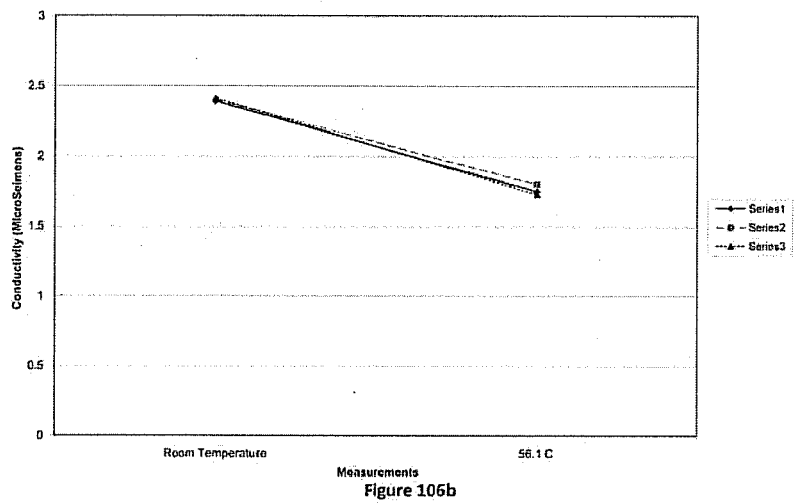
Figure 106C:
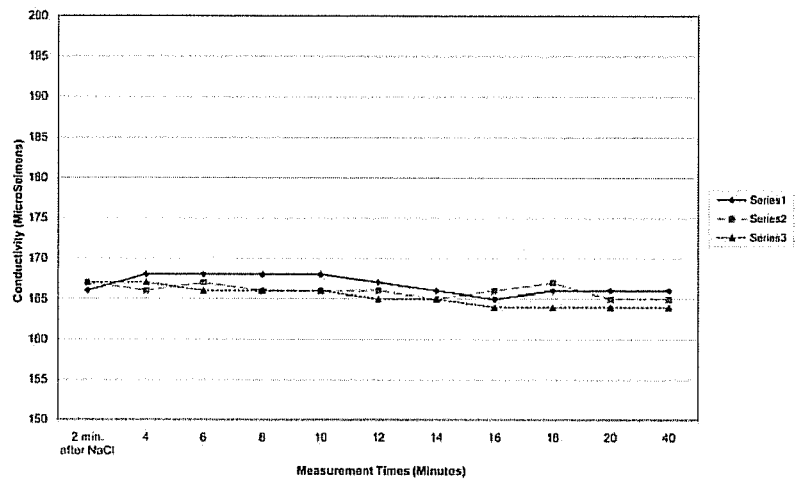

FIG. 106c is a graph of the experimental data which shows conductivity as a function of time for three separate sets of Bunsen burner-only data, the plot beginning with the data point generated two minutes after sodium chloride was added to the water.

Figure 106D:
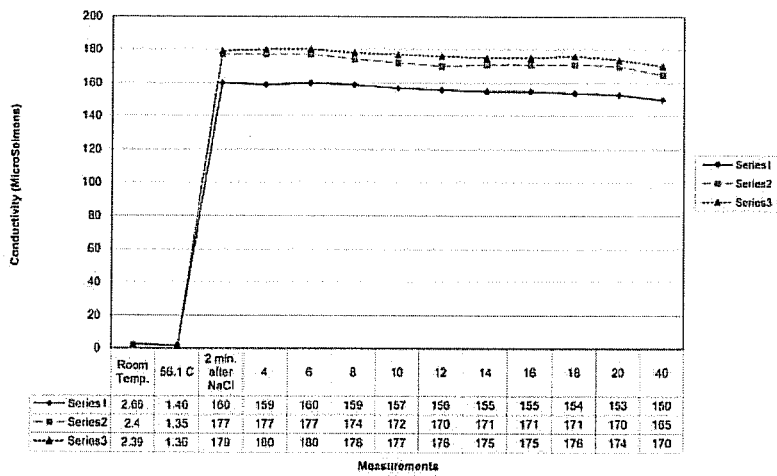

FIG. 106d is a graph of the experimental data which shows conductivity as a function of time for three separate sets of data corresponding to the water being conditioned by the sodium lamp for about 40 minutes before the sodium chloride was dissolved therein.

Figure 106E:
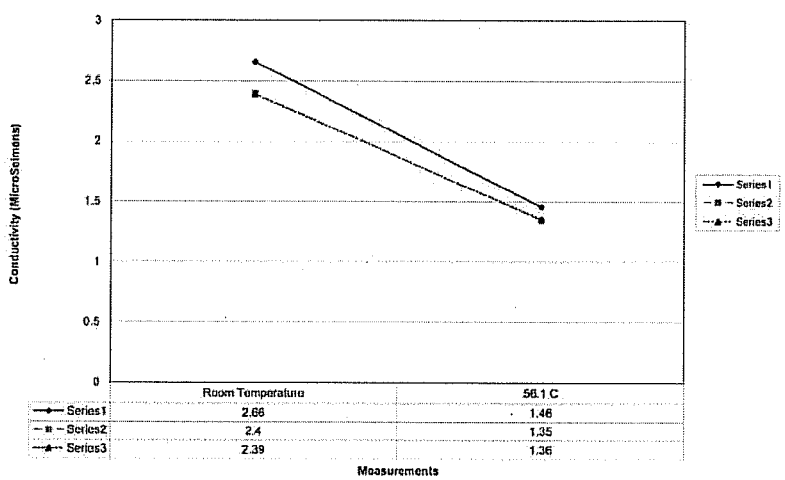

FIG. 106e is a graph of the experimental data which shows conductivity as a function of temperature (two separate data points only), corresponding to the water being conditioned by the sodium lamp for about 40 minutes before the sodium chloride was dissolved therein.

Figure 106F:
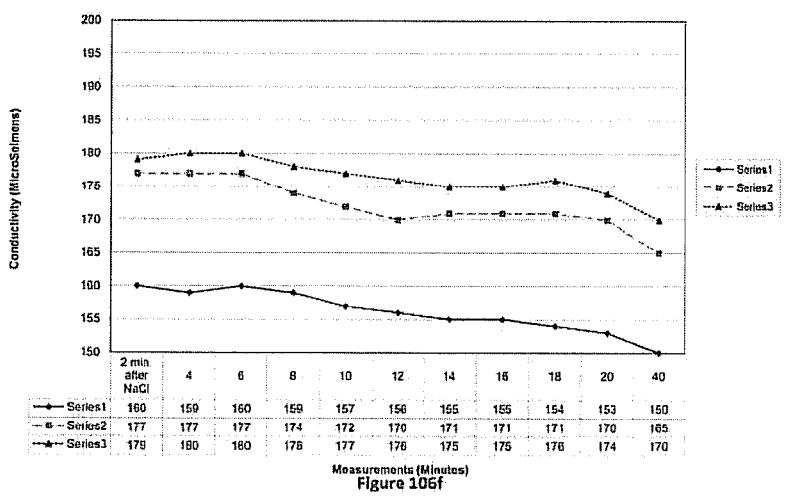

FIG. 106f is a graph of the experimental data which shows conductivity as a function of time for three separate sets of data corresponding to the water being conditioned by the sodium lamp for about 40 minutes before the sodium chloride was dissolved therein.

Figure 106G:
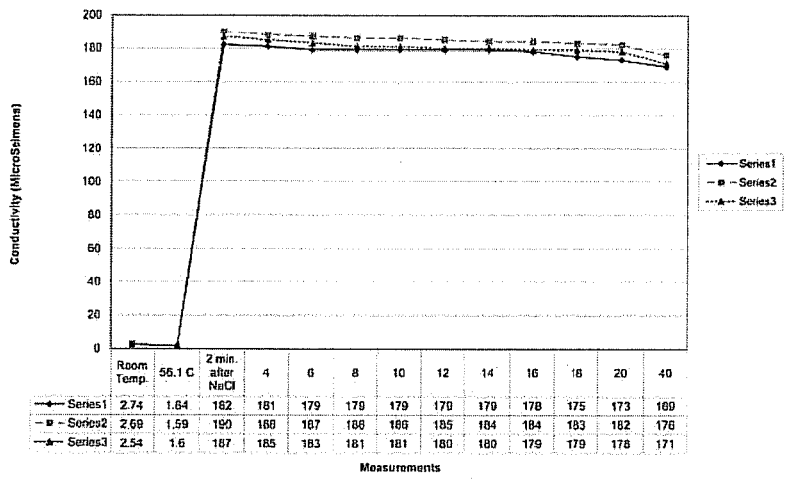

FIG. 106g is a graph of the experimental data which shows conductivity as a function of time for three separate sets of data corresponding to the solution of sodium chloride and water being irradiated with a spectral energy pattern of a sodium lamp beginning when the sodium chloride was added to the water.

Figure 106H:
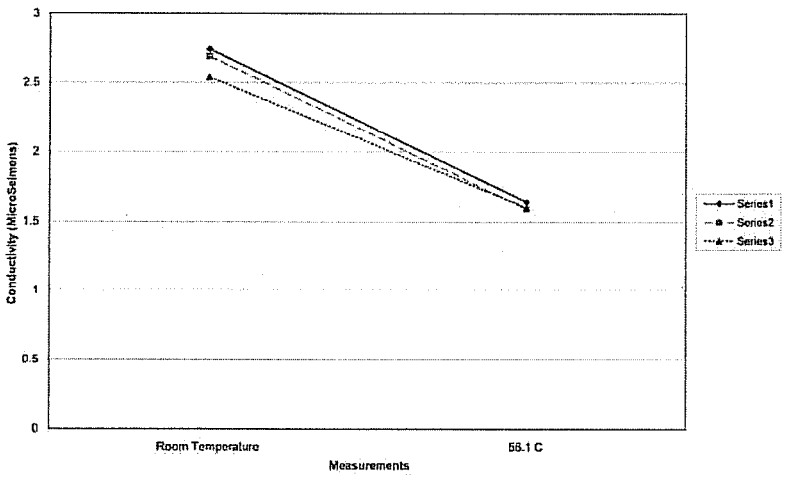

FIG. 106h is a graph of the experimental data which shows conductivity as a function of temperature (two separate data points only) corresponding to the solution of sodium chloride and water being irradiated with a spectral energy pattern of a sodium lamp beginning when the sodium chloride was added to the water.

Figure 106I:
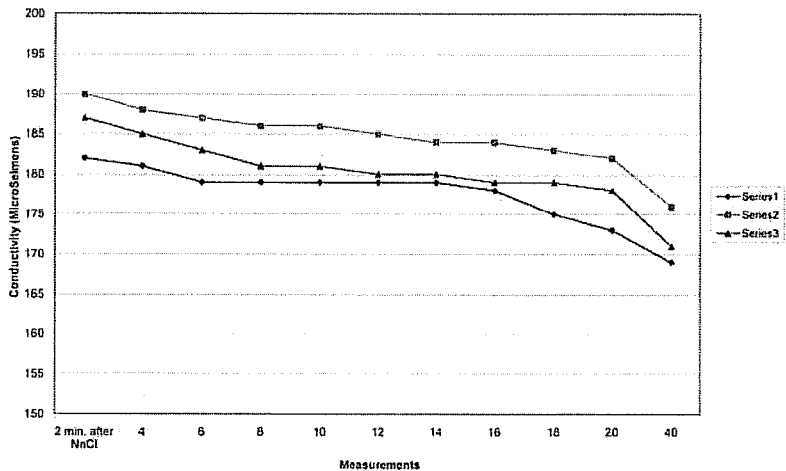
Figure 106:
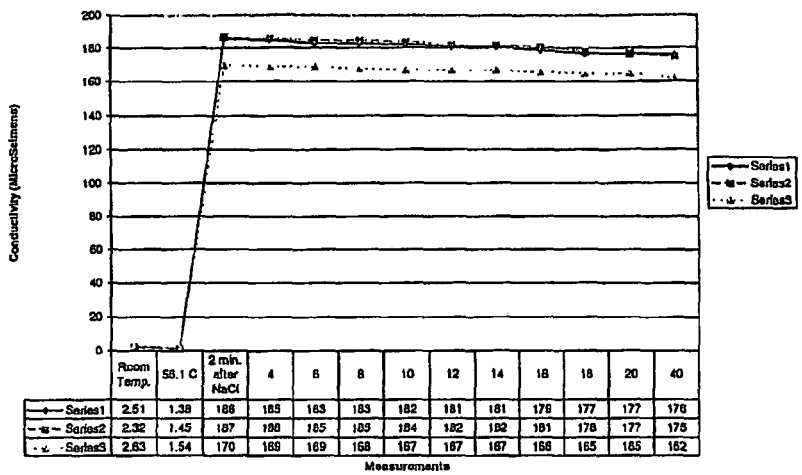
Figure 106:
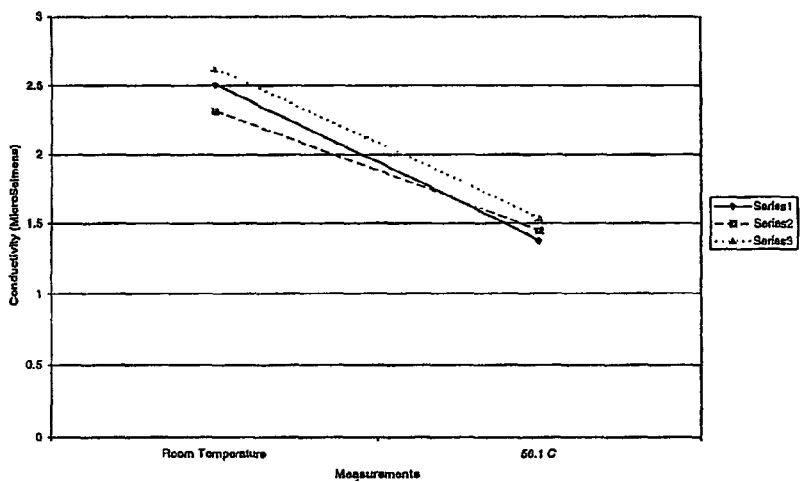
Figure 106:
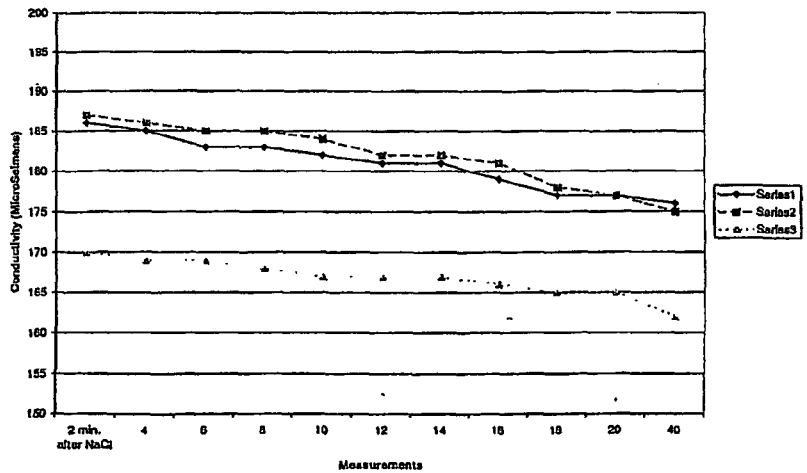
Figure 106:
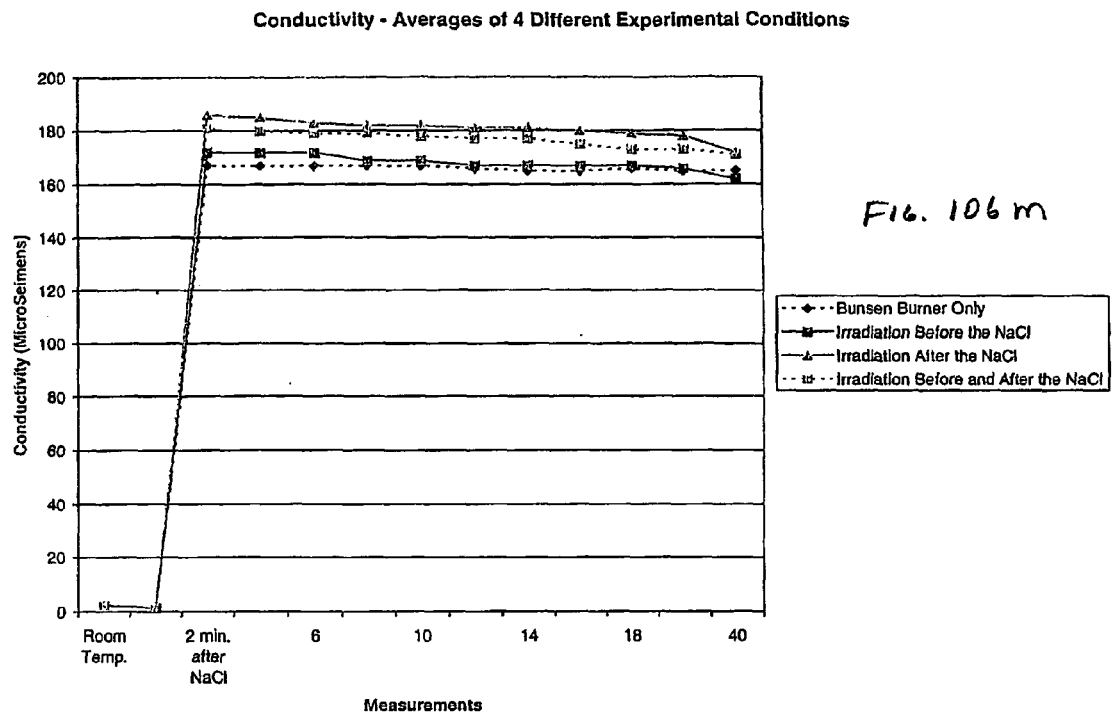
Figure 106:
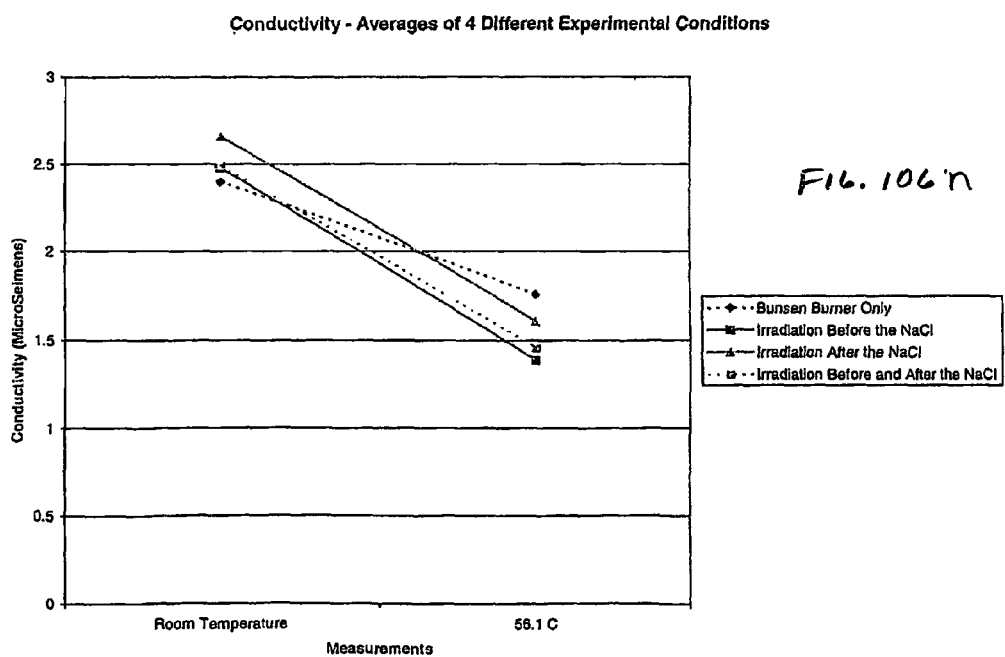
Figure 106:
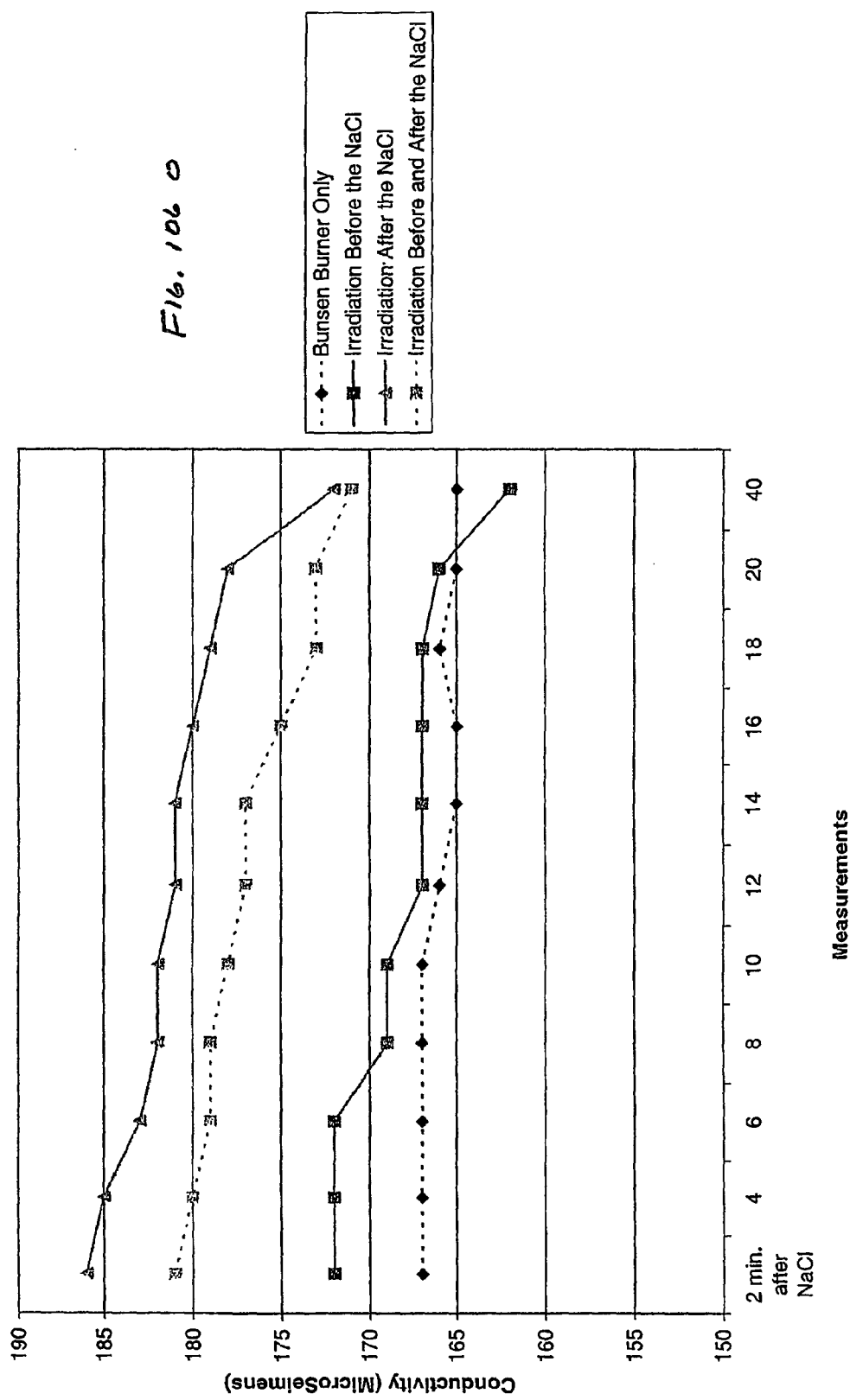

FIG. 106i is a graph of the experimental data which shows conductivity as a function of time for three separate sets of data corresponding to the solution of sodium chloride and water being irradiated with a spectral energy pattern of a sodium lamp beginning when the sodium chloride was added to the water.

FIG. 106j is a graph of the experimental data which shows conductivity as a function of time for three separate sets of data corresponding to the water being conditioned by the sodium lamp spectral conditioning pattern for about 40 minutes before the sodium chloride was added to the water; and continually irradiating the water with the sodium light spectral pattern while sodium chloride is added thereto and remaining on while all conductivity measurements were taken.

FIG. 106k is a graph of the experimental data which shows conductivity as a function of temperature (two separate data points only) for three sets of data, corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

FIG. 106l is a graph of the experimental data which shows conductivity as a function of time for three separate sets of data corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

FIG. 106m is a graph of the experimental data which superimposes averages from the data in FIGS. 106a, 106d, 106g and 106j.

FIG. 106n is a graph of the experimental data which superimposes averages from the data in FIGS. 106b, 106e, 106h and 106k.

FIG. 106o is a graph of the experimental data which superimposes averages from the data in FIGS. 106c, 106f, 106i and 106j.

Figure 107:
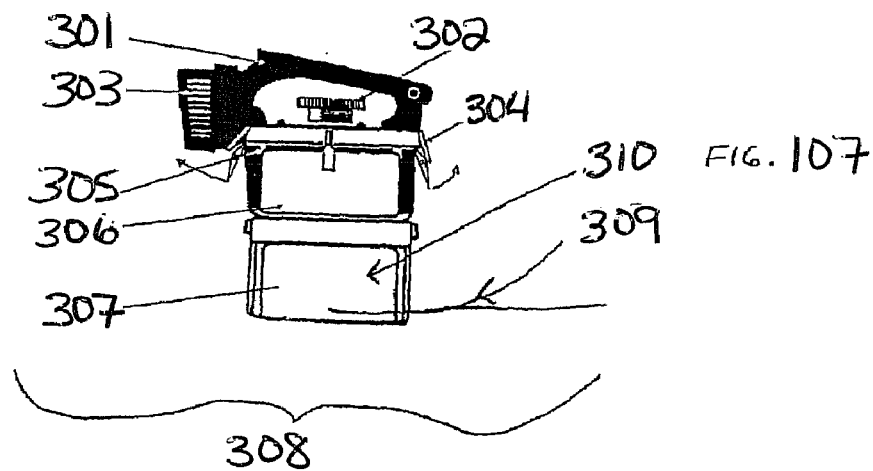

FIG. 107 shows a schematic of a flashlight battery assembly used in Example 14.

Figure 108:
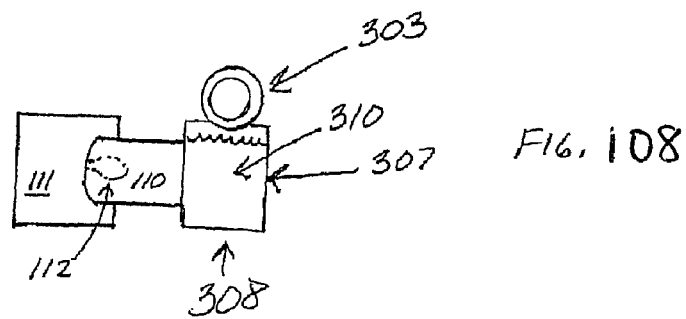

FIG. 108 shows a schematic of a sodium light used in Example 14.

Figure 109:
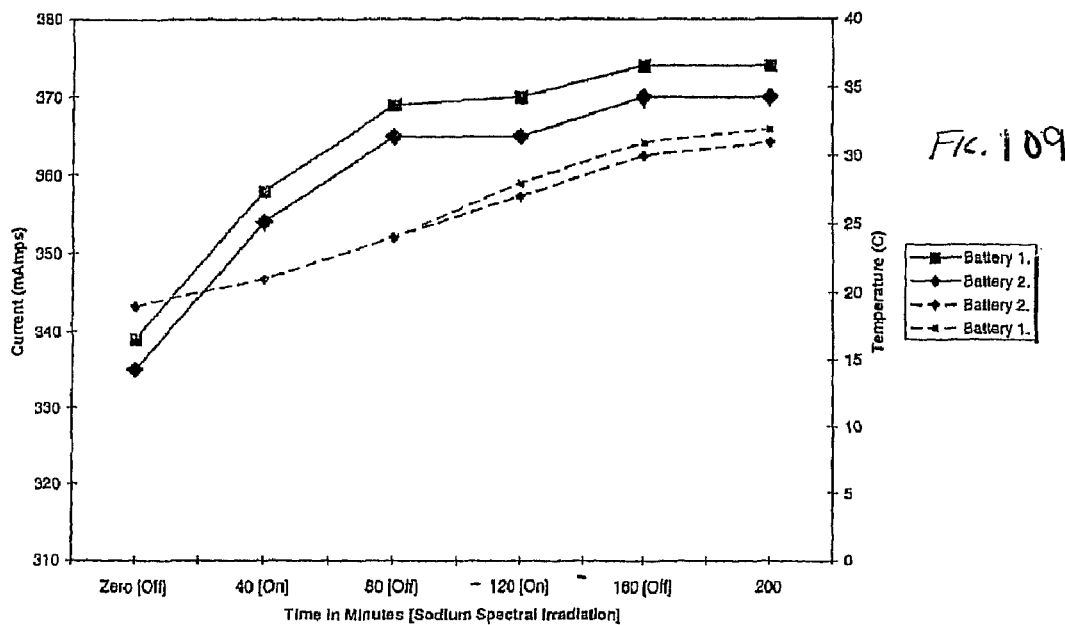

FIG. 109 shows a graph of the change in current as a function of time.

Figure 110:
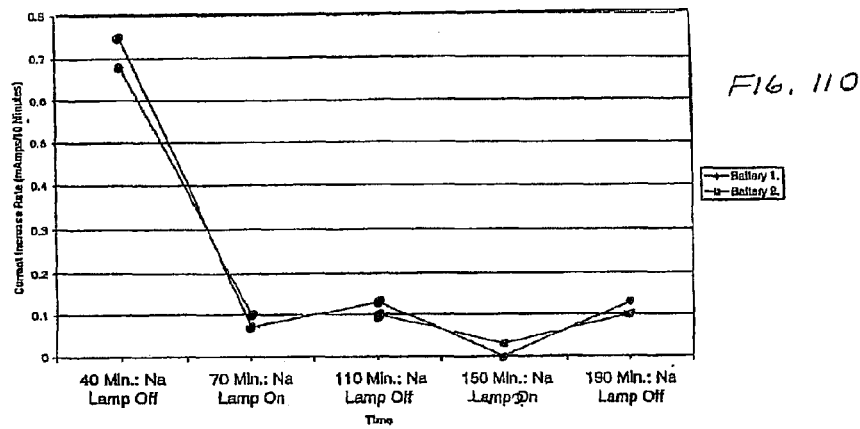

FIG. 110 shows a graph of the change in current as a function of time.

Figure 111:
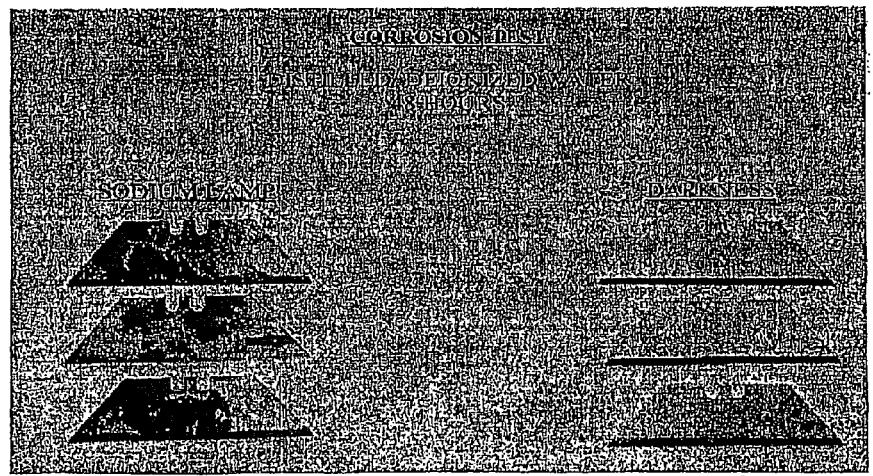

FIG. 111 shows the corrosion/non-corrosion on steel razor blades according to Example 15.

DESCRIPTION OF THE PREFERRED EMBODIMENTS

In general, thermal energy is used to drive chemical reactions by applying heat and increasing the temperature. The addition of heat increases the kinetic (motion) energy of the chemical reactants. A reactant with more kinetic energy moves faster and farther, and is more likely to take part in a chemical reaction. Mechanical energy likewise, by stirring and moving the chemicals, increases their kinetic energy and thus their reactivity. The addition of mechanical energy often increases temperature, by increasing kinetic energy.

Acoustic energy is applied to chemical reactions as orderly mechanical waves. Because of its mechanical nature, acoustic energy can increase the kinetic energy of chemical reactants, and can also elevate their temperature(s). Electromagnetic (M) energy consists of waves of electric and magnetic fields. Electromagnetic energy may also increase the kinetic energy and heat in crystallization reaction systems. It may energize electronic orbitals or vibrational motion in some reactions.

Figure 1A:
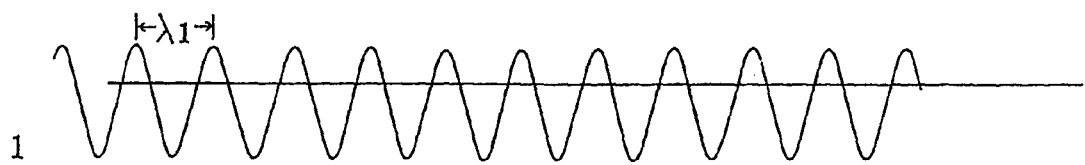
FIGS. 1a and 1b show a graphic representation of an acoustic or electromagnetic wave.
Figure 1B:
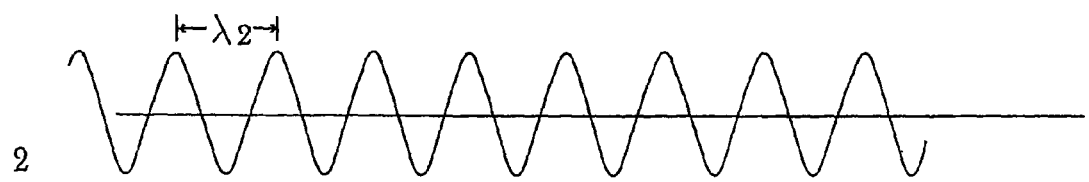
Figure 1C:
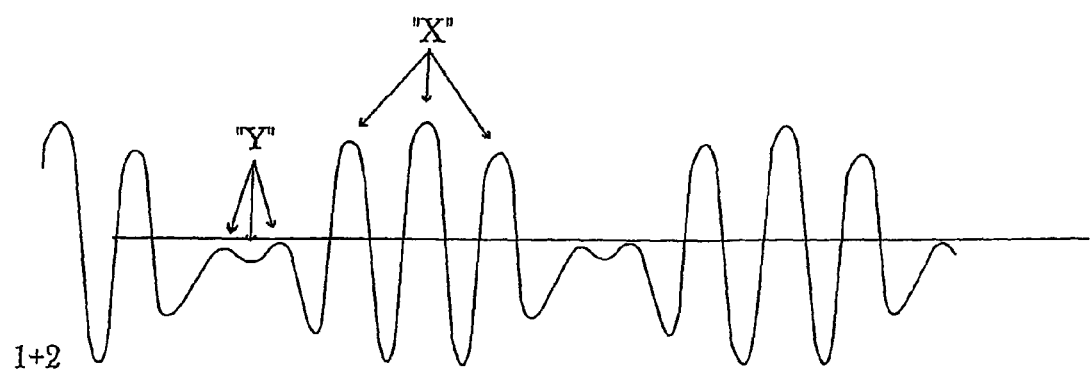
FIG. 1c shows the combination wave which results from the combining of the waves in FIG. 1a and FIG. 1b.
Figure 2A:
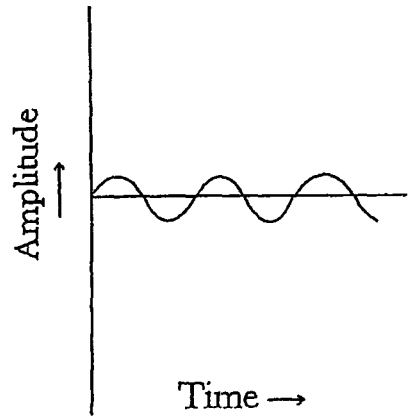
FIGS. 2a and 2b show waves of different amplitudes but the same frequency.
Figure 2B:
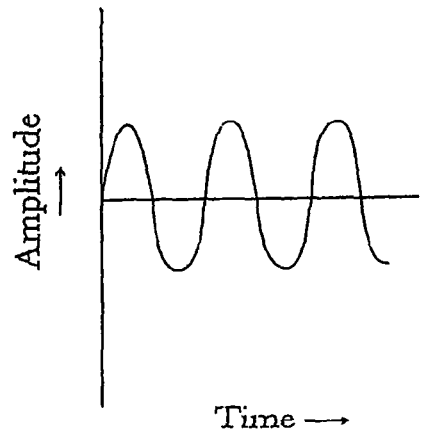

Both acoustic and electromagnetic energy may consist of waves. The number of waves in a period of time can be counted. Waves are often drawn, as in FIG. 1a. Usually, time is placed on the horizontal X-axis. The vertical Y-axis shows the strength or intensity of the wave. This is also called the amplitude. A weak wave will be of weak intensity and will have low amplitude (see FIG. 2a). A strong wave will have high amplitude (see FIG. 2b).

Traditionally, the number of waves per second is counted, to obtain the frequency.

Frequency=Number of waves/time=Waves/second=Hz.

Figure 3A:
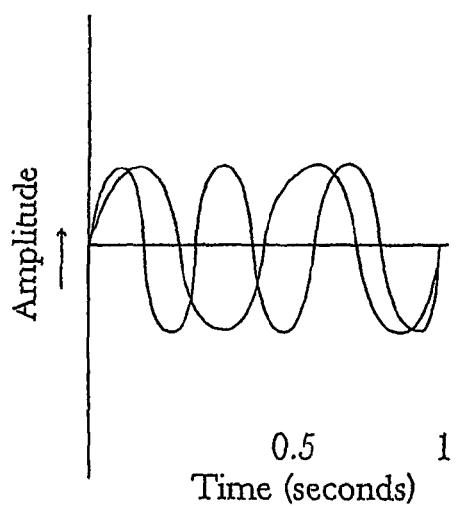
FIGS. 3a and 3b show frequency diagrams.
Figure 3B:
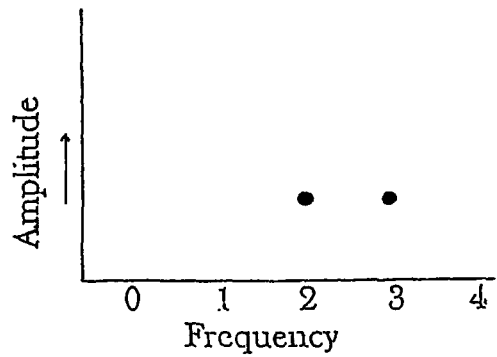

Another name for "waves per second", is "hertz" (abbreviated "Hz"). Frequency is drawn on wave diagrams by showing a different number of waves in a period of time (see FIG. 3a which shows waves having a frequency of 2 Hz and 3 Hz). It is also drawn by placing frequency itself, rather than time, on the X-axis (see FIG. 3b which shows the same 2 Hz and 3 Hz waves plotted differently).

Energy waves and frequency have some interesting properties, and may interact in some interesting ways. The manner in which wave energies interact, depends largely on the frequency. For example, when two waves of energy interact, each having the same amplitude, but one at a frequency of 400 Hz and the other at 100 Hz, the waves will add their frequencies, to produce a new frequency of 500 Hz (i.e., the "sum" frequency). The frequency of the waves will also subtract to produce a frequency of 300 HZ (i.e., the "difference" frequency). All wave energies typically add and subtract in this manner, and such adding and subtracting is referred to as heterodyning. Common results of heterodyning are familiar to most as harmonics in music.

Figures 4, 5:
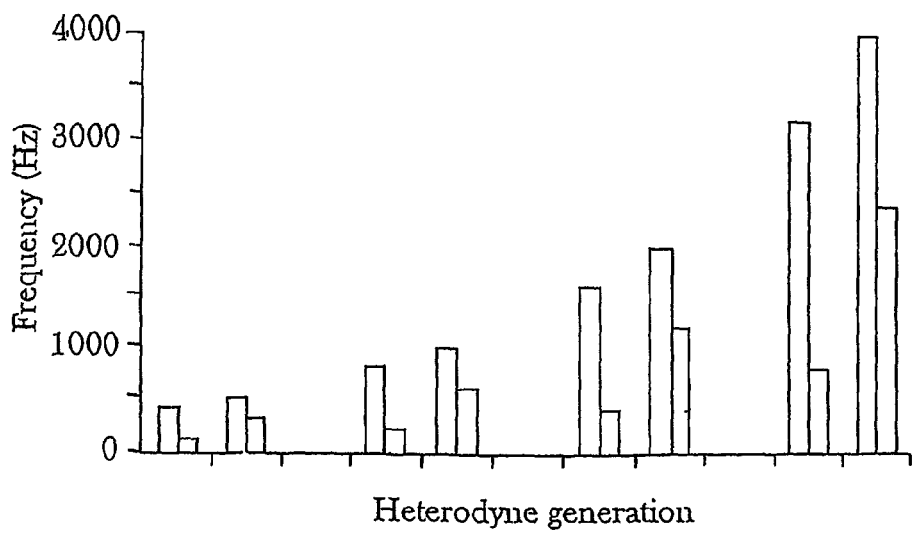
FIG. 4 shows a specific example of a heterodyne progression.
FIG. 5 shows a graphical example of the heterodyned series from FIG. 4.

There is a mathematical, as well as musical basis, to the harmonics produced by heterodyning. Consider, for example, a continuous progression of heterodyned frequencies. As discussed above, beginning with 400 Hz and 100 Hz, the sum frequency is 500 Hz and the difference frequency is 300 Hz. If these frequencies are further heterodyned (added and subtracted) then new frequencies of 800 (i.e., 500+300) and 200 (i.e., 500-300) are obtained. The further heterodyning of 800 and 200 results in 1,000 and 600 Hz as shown in FIG. 4.

A mathematical pattern begins to emerge. Both the sum and the difference columns contain alternating series of numbers that double with each set of heterodynes. In the sum column, 400 Hz, 800 Hz, and 1,600 Hz, alternates with 500 Hz, 1000 Hz, and 2000 Hz. The same sort of doubling phenomenon occurs in the difference column.

Heterodyning of frequencies is the natural process that occurs whenever waveform energies interact. Heterodyning results in patterns of increasing numbers that are mathematically derived. The number patterns are integer multiples of the original frequencies. These multiples are called harmonics. For example, 800 Hz and 1600 Hz are harmonics of 400 Hz. In musical terms, 800 Hz is one octave above 400 Hz, and 1600 Hz is two octaves higher. It is important to understand the mathematical heterodyne basis for harmonics, which occurs in all waveform energies, and thus in all of nature.

The mathematics of frequencies is very important. Frequency heterodynes increase mathematically in visual patterns (see FIG. 5). Mathematics has a name for these visual patterns of FIG. 5. These patterns are called fractals. A fractal is defined as a mathematical function which produces a series of self-similar patterns or numbers. Fractal patterns have spurred a great deal of interest historically because fractal patterns are found everywhere in nature. Fractals can be found in the patterning of large expanses of coastline, all the way down to microorganisms. Fractals are found in the behavior of organized insects and in the behavior of fluids. The visual patterns produced by fractals are very distinct and recognizable. A typical fractal pattern is shown in FIG. 6.

A heterodyne is a mathematical function, governed by mathematical equations, just like a fractal. A heterodyne also produces self-similar patterns of numbers, like a fractal. If graphed, a heterodyne series produces the same familiar visual shape and form which is so characteristic of fractals. It is interesting to compare the heterodyne series in FIG. 5, with the fractal series in FIG. 6.

Heterodynes are fractals; the conclusion is inescapable. Heterodynes and fractals are both mathematical functions which produce a series of self-similar patterns or numbers. Wave energies interact in heterodyne patterns. Thus, all wave energies interact as fractal patterns. Once it is understood that the fundamental process of interacting energies is itself a fractal process, it becomes easier to understand why so many creatures and systems in nature also exhibit fractal patterns. The fractal processes and patterns of nature are established at a fundamental or basic level.

Accordingly, since energy interacts by heterodyning, matter should also be capable of interacting by a heterodyning process. All matter whether in large or small forms, has what is called a natural oscillatory frequency. The natural oscillatory frequency ("NOF") of an object, is the frequency at which the object prefers to vibrate, once set in motion. The NOF of an object is related to many factors including size, shape, dimension, and composition. The smaller an object is, the smaller the distance it has to cover when it oscillates back and forth. The smaller the distance, the faster it can oscillate, and the higher its NOF.

For example, consider a wire composed of metal atoms. The wire has a natural oscillatory frequency. The individual metal atoms also have unique natural oscillatory frequencies. The NOF of the atoms and the NOF of the wire heterodyne by adding and subtracting, just the way energy heterodynes.

$$NOF_{atom} + NOF_{wire} = \text{Sum Frequency}_{atom+wire}$$

and $$NOF_{atom} - NOF_{wire} = \text{Difference Frequency}_{atom-wire}$$

If the wire is stimulated with the Difference Frequency$_{atom-wire}$, the difference frequency will heterodyne (add) with the NOF$_{wire}$ to produce NOF$_{atom}$, (natural oscillatory frequency of the atom) and the atom will absorb with the energy, thereby becoming stimulated to a higher energy level. Cirac and Zoeller reported this phenomenon in 1995, and they used a laser to generate the Difference Frequency.

$$\text{Difference Frequency}_{atom-wire} + NOF_{wire} = NOF_{atom}$$

Matter heterodynes with matter in a manner similar to the way in which wave energies heterodyne with other wave energies. This means that matter in its various states may also interact in fractal processes. This interaction of matter by fractal processes assists in explaining why so many creatures and systems in nature exhibit fractal processes and patterns. Matter, as well as energy, interacts by the mathematical equations of heterodynes, to produce harmonics and fractal patterns. That is why there are fractals everywhere around us.

Thus, energy heterodynes with energy, and matter heterodynes with matter. However, perhaps even more important is that matter can heterodyne with energy (and visa versa). In the metal wire discussion above, the Difference Frequency$_{atom-wire}$ in the experiment by Cirac and Zoeller was provided by a laser which used electromagnetic wave energy at a frequency equal to the Difference Frequency$_{atom-wire}$. The matter in the wire, via its natural oscillatory frequency, heterodyned with the electromagnetic wave energy frequency of the laser to produce the frequency of an individual atom of matter. This shows that energy and matter do heterodyne with each other.

In general, when energy encounters matter, one of three possibilities occur. The energy either bounces off the matter (i.e., is reflected energy), passes through the matter (i.e., is transmitted energy), or interacts and/or combines with the matter (e.g., is absorbed or heterodynes with the matter). If the energy heterodynes with the matter, new frequencies of energy and/or matter will be produced by mathematical processes of sums and differences. If the frequency thus produced matches an NOF of the matter, the energy will be, at least partially, absorbed, and the matter will be stimulated to, for example, a higher energy level, (i.e., it possesses more energy). A crucial factor which determines which of these three possibilities will happen is the frequency of the energy compared to the frequency of the matter. If the frequencies do not match, the energy will either be reflected, or will pass on through as transmitted energy. If the frequencies of the energy and the matter match either directly (e.g., are close to each other, as discussed in greater detail later herein), or match indirectly (e.g., heterodynes), then the energy is capable of interacting and/or combining with the matter.

Another term often used for describing the matching of frequencies is resonance. In this invention, use of the term resonance will typically mean that frequencies of matter and/or energy match. For example, if the frequency of energy and the frequency of matter match, the energy and matter are in resonance and the energy is capable of combining with the matter. Resonance, or frequency matching, is merely an aspect of heterodyning that permits the coherent transfer and combination of energy with matter.

In the example above with the wire and atoms, resonance could have been created with the atom, by stimulating the atom with a laser frequency exactly matching the NOF of the atom. In this case, the atom would be energized with its own resonant frequency and the energy would be transferred to the atom directly. Alternatively, as was performed in the actual wire/laser experiment, resonance could also have been created with the atom by using the heterodyning that naturally occurs between differing frequencies. Thus, the resonant frequency of the atom ($NOF_{atom}$) can be produced indirectly, as an additive (or subtractive) heterodyned frequency, between the resonant frequency of the wire ($NOF_{wire}$) and the applied frequency of the laser. Either direct resonance, or indirect resonance through heterodyned frequency matching, produces resonance and thus permits the combining of matter and energy. When frequencies match, energy transfers and amplitudes may increase.

Heterodyning produces indirect resonance. Heterodyning also produces harmonics, (i.e., frequencies that are integer multiples of the resonant (NOF) frequency. For example, the music note "A" is approximately 440 Hz. If that frequency is doubled to about 880 Hz, the note "A" is heard an octave higher. This first octave is called the first harmonic. Doubling the note or frequency again, from 880 Hz to 1,760 Hz (i.e., four times the frequency of the original note) results in another "A", two octaves above the original note. This is called the third harmonic. Every time the frequency is doubled another octave is achieved, so these are the even integer multiples of the resonant frequency.

In between the first and third harmonic is the second harmonic, which is three times the original note. Musically, this is not an octave like the first and third harmonics. It is an octave and a fifth, equal to the second "E" above the original "A". All of the odd integer multiples are fifths, rather than octaves. Because harmonics are simply multiples of the fundamental natural oscillatory frequency, harmonics stimulate the NOF or resonant frequency indirectly. Thus by playing the high "A" at 880 Hz on a piano, the string for middle "A" at 440 Hz should also begin to vibrate due to the phenomenon of harmonics.

Matter and energy in chemical reactions respond to harmonics of resonant frequencies much the way musical instruments do. Thus, the resonant frequency of the atom ($NOF_{atom}$) can be stimulated indirectly, using one or more of its' harmonic frequencies. This is because the harmonic frequency heterodynes with the resonant frequency of the atom itself ($NOF_{atom}$). For example, in the wire/atom example above, if the laser is tuned to 800 THz and the atom resonates at 400 THz, heterodyning the two frequencies results in:

800 THz−400 THz=400 THz

The 800 THz (the atom's first harmonic), heterodynes with the resonant frequency of the atom, to produce the atom's own resonant frequency. Thus the first harmonic indirectly resonates with the atom's NOF, and stimulates the atom's resonant frequency as a first generation heterodyne.

Of course, the two frequencies will also heterodyne in the other direction, producing:

800 THz+400 THz=1,200 THz

The 1,200 THz frequency is not the resonant frequency of the atom. Thus, part of the energy of the laser will heterodyne to produce the resonant frequency of the atom. The other part of the energy of the laser heterodynes to a different frequency, that does not itself stimulate the resonant frequency of the atom. That is why the stimulation of an object by a harmonic frequency of particular strength of amplitude, is typically less than the stimulation by its' own resonant (NOF) frequency at the same particular strength.

Although it appears that half the energy of a harmonic is wasted, that is not necessarily the case. Referring again to the exemplary atom vibrating at 400 THz, exposing the atom to electromagnetic energy vibrating at 800 THz will result in frequencies subtracting and adding as follows:

800 THz−400 THz=400 THz and

800 THz+400 THz=1,200 THz

Figure 14:
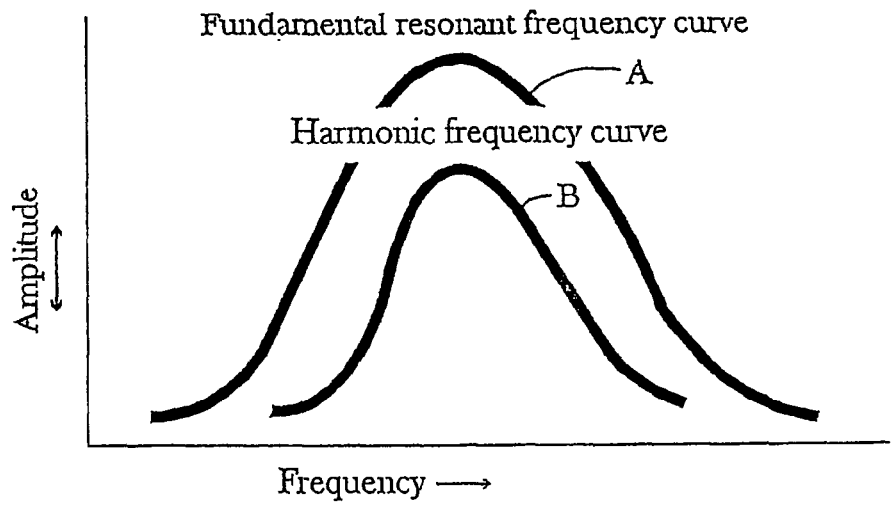
FIG. 14 shows two different energy transfer curves at fundamental resonance frequencies (curve A) and a harmonic frequency (curve B).

The 1,200 THz heterodyne, for which about 50% of the energy appears to be wasted, will heterodyne with other frequencies also, such as 800 THz. Thus, 1,200 THz−800 THz=400 THz Also, the 1,200 THz will heterodyne with 400 THz:

1,200 THz−400 THz=800 THz, thus producing 800 THz, and the 800 THz will heterodyne with 400 THz:

800 THz−400 THz=400 THz, thus producing 400 THz frequency again. When other generations of heterodynes of the seemingly wasted energy are taken into consideration, the amount of energy transferred by a first harmonic frequency is much greater than the previously suggested 50% transfer of energy. There is not as much energy transferred by this approach when compared to direct resonance, but this energy transfer is sufficient to produce a desired effect (see FIG. 14).

As stated previously, Ostwald's theories on catalysts and bond formation were based on the kinetic theories of chemistry from the turn of the century. However, it should now be understood that chemical reactions are interactions of matter, and that matter interacts with other matter through resonance and heterodyning of frequencies; and energy can just as easily interact with matter through a similar processes of resonance and heterodyning. With the advent of spectroscopy (discussed in more detail elsewhere herein), it is evident that matter produces, for example, electromagnetic energy at the same or substantially the same frequencies at which it vibrates. Energy and matter can move about and recombine with other energy or matter, as long as their frequencies match, because when frequencies match, energy transfers. In many respects, both philosophically and mathematically, both matter and energy can be fundamentally construed as corresponding to frequency. Accordingly, since chemical reactions are recombinations of matter driven by energy, chemical reactions are in effect, driven just as much by frequency.

Analysis of a typical chemical reaction should be helpful in understanding the normal processes disclosed herein. A representative reaction to examine is the formation of water from hydrogen and oxygen gases, catalyzed by platinum. Platinum has been known for some time to be a good hydrogen catalyst, although the reason for this has not been well understood.

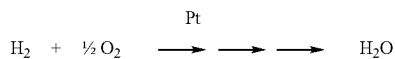

This reaction is proposed to be a chain reaction, depending on the generation and stabilization of the hydrogen and hydroxy intermediates. The proposed reaction chain is:

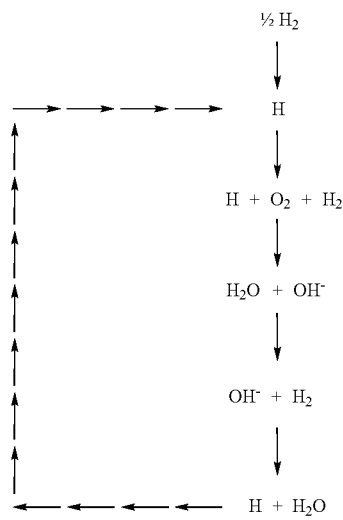

Generation of the hydrogen and hydroxy intermediates are thought to be crucial to this reaction chain. Under normal circumstances, hydrogen and oxygen gas can be mixed together for an indefinite amount of time, and they will not form water. Whenever the occasional hydrogen molecule splits apart, the hydrogen atoms do not have adequate energy to bond with an oxygen molecule to form water. The hydrogen atoms are very short-lived as they simply re-bond again to form a hydrogen molecule. Exactly how platinum catalyzes this reaction chain is a mystery to the prior art.

The present invention teaches that an important step to catalyzing this reaction is the understanding now provided that it is crucial not only to generate the intermediates, but also to energize and/or stabilize (i.e., maintain the intermediates for a longer time), so that the intermediates have sufficient energy to, for example, react with other components in the reaction system. In the case of platinum, the intermediates react with the reactants to form product and more intermediates (i.e., by generating, energizing and stabilizing the hydrogen intermediate, it has sufficient energy to react with the molecular oxygen reactant, forming water and the hydroxy intermediate, instead of falling back into a hydrogen molecule). Moreover, by energizing and stabilizing the hydroxy intermediates, the hydroxy intermediates can react with more reactant hydrogen molecules, and again water and more intermediates result from this chain reaction. Thus, generating energizing and/or stabilizing the intermediates, influences this reaction pathway. Paralleling nature in this regard would be desirable (e.g., nature can be paralleled by increasing the energy levels of the intermediates). Specifically, desirable, intermediates can be energized and/or stabilized by applying at least one appropriate electromagnetic frequency resonant with the intermediate, thereby stimulating the intermediate to a higher energy level. Interestingly, that is what platinum does (e.g., various platinum frequencies resonate with the intermediates on the reaction pathway for water formation). Moreover, in the process of energizing and stabilizing the reaction intermediates, platinum fosters the generation of more intermediates, which allows the reaction chain to continue, and thus catalyzes the reaction.

As a catalyst, platinum takes advantage of many of the ways that frequencies interact with each other. Specifically, frequencies interact and resonate with each other: 1) directly, by matching a frequency; or 2) indirectly, by matching a frequency through harmonics or heterodynes. In other words, platinum vibrates at frequencies which both directly match the natural oscillatory frequencies of the intermediates, and which indirectly match their frequencies, for example, by heterodyning harmonics with the intermediates.

Further, in addition to the specific intermediates of the reaction discussed above herein, it should be understood that in this reaction, like in all reactions, various transients or transient states also exist. In some cases, transients or transient states may only involve different bond angles between similar chemical species or in other cases transients may involve completely different chemistries altogether. In any event, it should be understood that numerous transient states exist between any particular combination of reactant and reaction product.

Figure 8A:
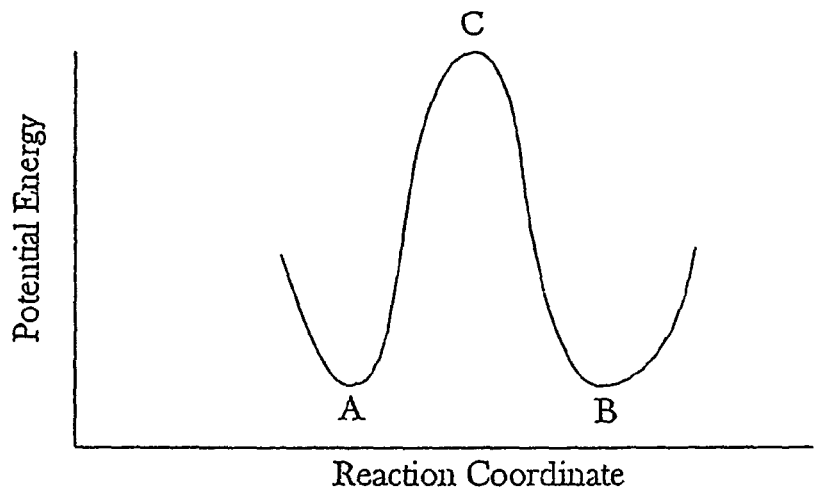
FIGS. 8a-8c show three different simple reaction profiles.

It should now be understood that physical catalysts produce effects by generating, energizing and/or stabilizing all manner of transients, as well as intermediates. In this regard, FIG. 8a shows a single reactant and a single product. The point "A" corresponds to the reactant and the point "B" corresponds to the reaction product. The point "C" corresponds to an activated complex. Transients correspond to all those points on the curve between reactant "A" and product "B", and can also include the activated complex "C".

Figure 8B:
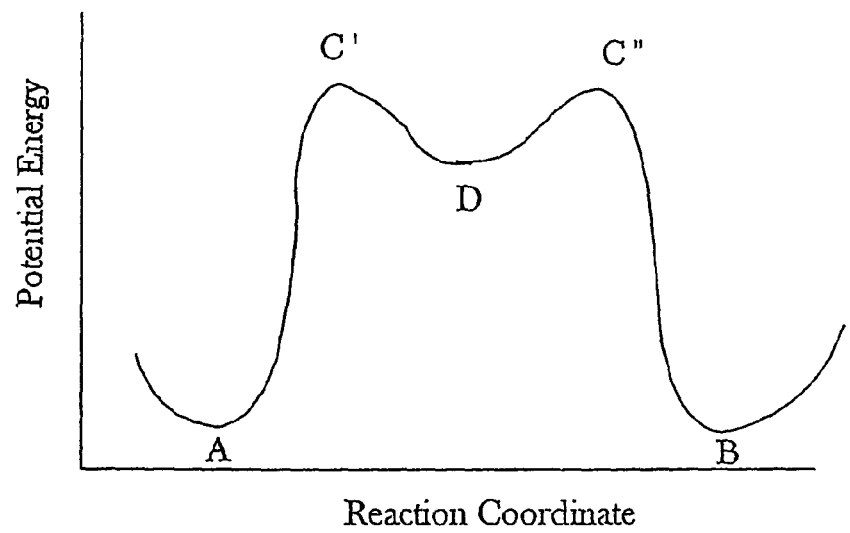
Figure 8C:
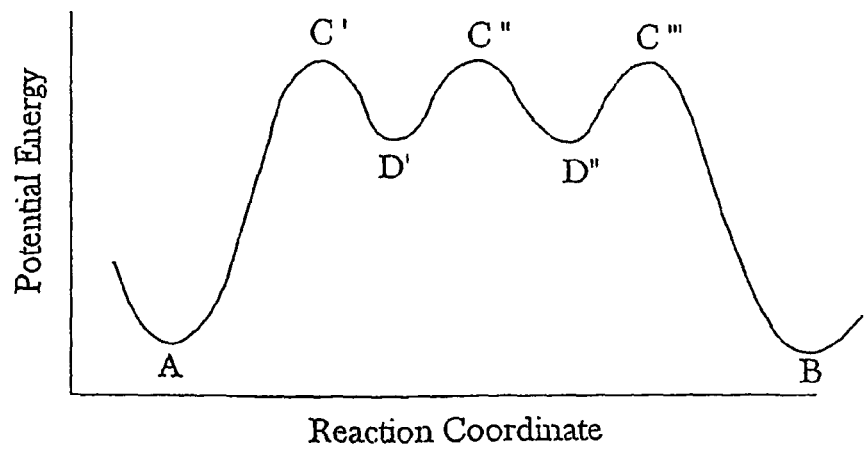

In a more complex reaction which involves formation of at least one intermediate, the reaction profile looks somewhat different. In this regard, reference is made to FIG. 8b, which shows reactant "A", product "B", activated complex "C' and C", and intermediate "D". In this particular example, the intermediate "D" exists as a minimum in the energy reaction profile of the reaction, while it is surrounded by the activated complexes C' and C". However, again, in this particular reaction, transients correspond to anything between the reactant "A" and the reaction product "B", which in this particular example, includes the two activated complexes "C'" and "C"," as well as the intermediate "D". In the particular example of hydrogen and oxygen combining to form water, the reaction profile is closer to that shown in FIG. 8c. In this particular reaction profile, "D'" and "D''" could correspond generally to the intermediates of the hydrogen atom and hydroxy molecule.

Figure 69D:
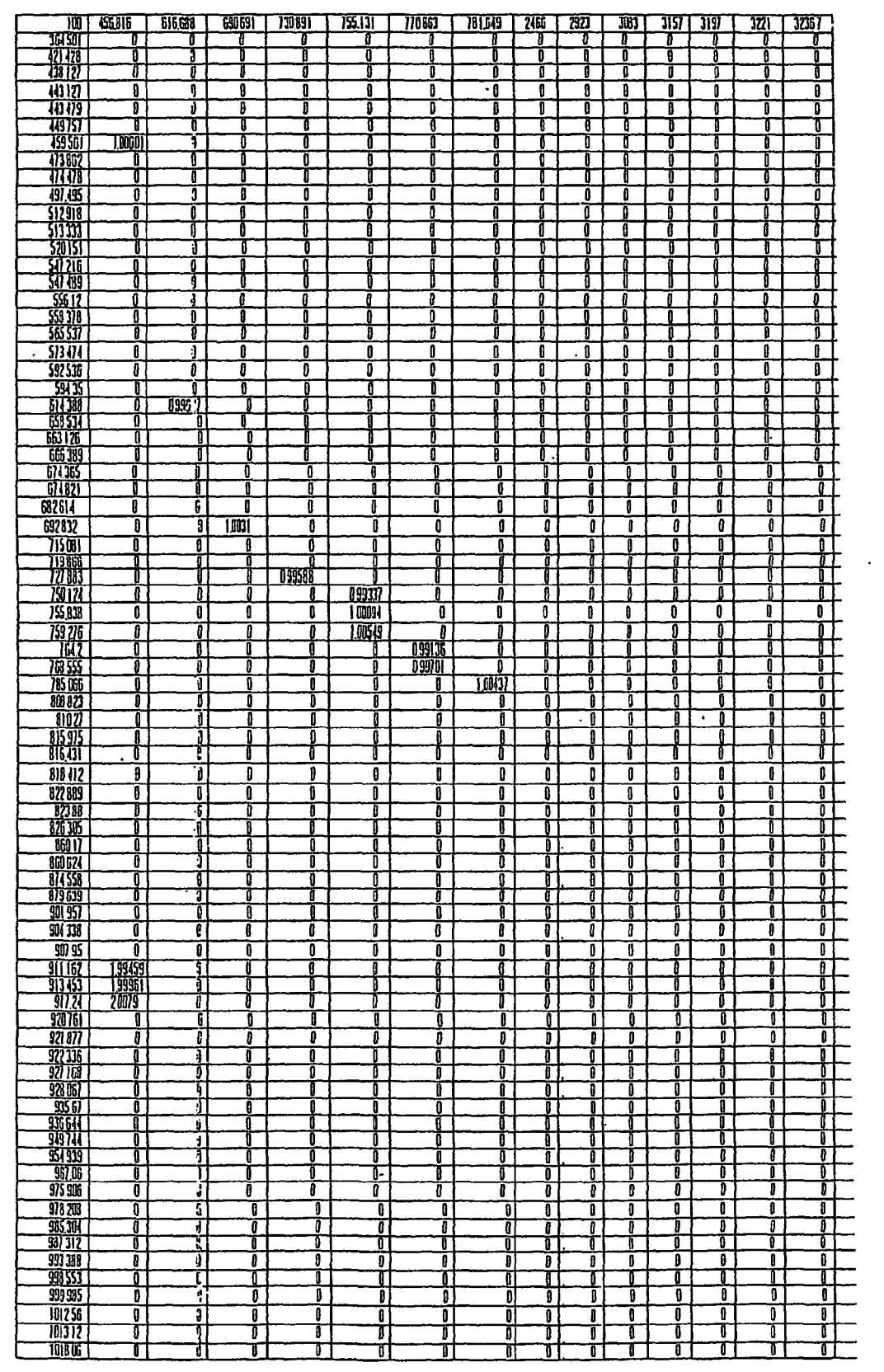

Now, with specific reference to the reaction to form water, both intermediates are good examples of how platinum produces resonance in an intermediate by directly matching a frequency. Hydroxy intermediates vibrate strongly at frequencies of 975 THz and 1,060 THz. Platinum also vibrates at 975 THz and 1,060 THz. By directly matching the frequencies of the hydroxy intermediates, platinum can cause resonance in hydroxy intermediates, enabling them to be energized, stimulated and/or stabilized long enough to take part in chemical reactions. Similarly, platinum also directly matches frequencies of the hydrogen intermediates. Platinum resonates with about 10 out of about 24 hydrogen frequencies in its electronic spectrum (see FIG. 69). Specifically, FIG. 69 shows the frequencies of hydrogen listed horizontally across the Table and the frequencies of platinum listed vertically on the Table. Thus, by directly resonating with the intermediates in the above-described reaction, platinum facilitates the generation, energizing, stimulating, and/or stabilizing of the intermediates, thereby catalyzing the desired reaction.

Platinum's interactions with hydrogen are also a good example of matching frequencies through heterodyning. It is disclosed herein, and shown clearly in FIG. 69, that many of the platinum frequencies resonate indirectly as harmonics with the hydrogen atom intermediate (e.g., harmonic heterodynes). Specifically, fifty-six (56) frequencies of platinum (i.e., 33% of all its frequencies) are harmonics of nineteen (19) hydrogen frequencies (i.e., 80% of its 24 frequencies). Fourteen (14) platinum frequencies are first harmonics (2×) of seven (7) hydrogen frequencies. And, twelve (12) platinum frequencies are third harmonics (4×) of four (4) hydrogen frequencies. Thus, the presence of platinum causes massive indirect harmonic resonance in the hydrogen atom, as well as significant direct resonance.

Figure 9A:
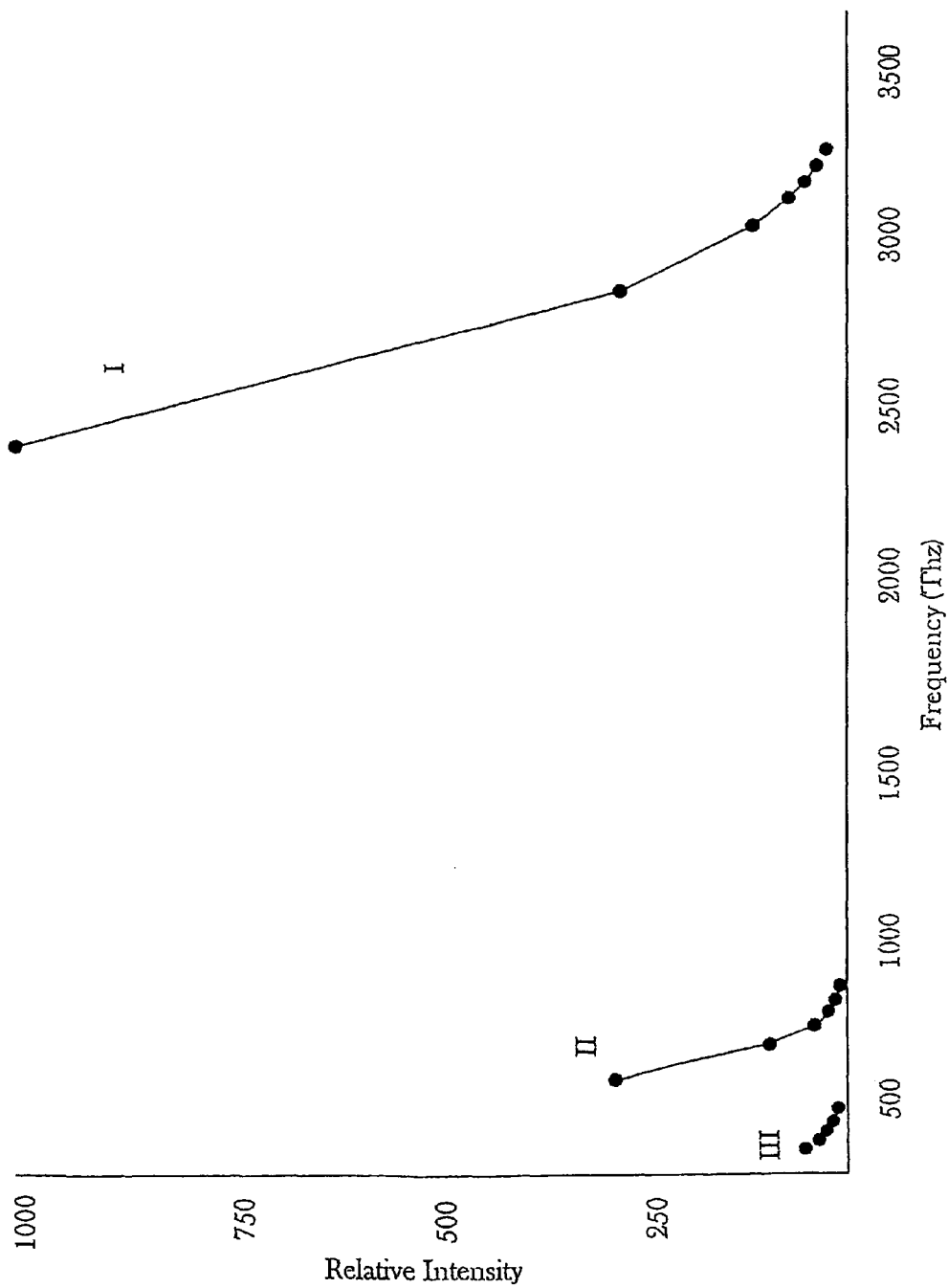
FIGS. 9a and 9b show fine frequency diagram curves for hydrogen.
Figures 9B, 10:
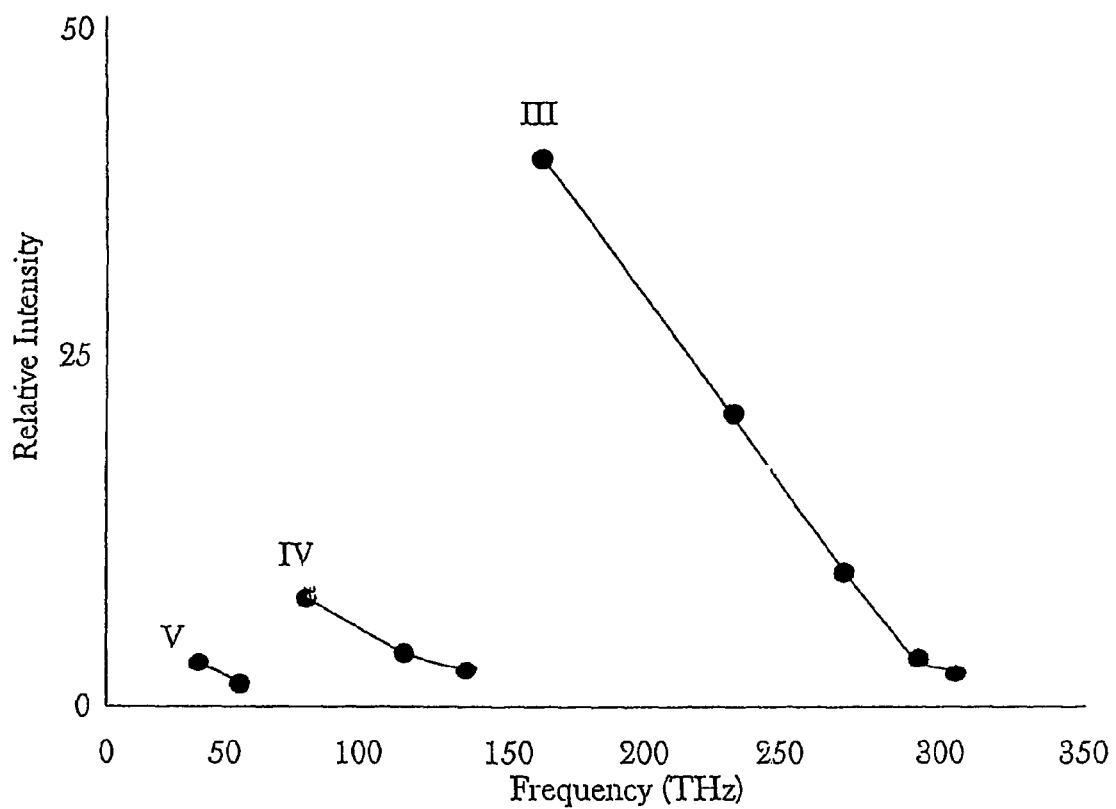
FIG. 10 shows various frequencies and intensities for hydrogen.

Further focus on the individual hydrogen frequencies is even more informative. FIGS. 9-10 show a different picture of what hydrogen looks like when the same information used to make energy level diagrams is plotted as actual frequencies and intensities instead. Specifically, the X-axis shows the frequencies emitted and absorbed by hydrogen, while the Y-axis shows the relative intensity for each frequency. The frequencies are plotted in terahertz (THz, $10^{12}$ Hz) and are rounded to the nearest THz. The intensities are plotted on a relative scale of 1 to 1,000. The highest intensity frequency that hydrogen atoms produce is 2,466 THz. This is the peak of curve I to the far right in FIG. 9a. This curve I shall be referred to as the first curve. Curve I sweeps down and to the right, from 2,466 THz at a relative intensity of 1,000 to 3,237 THz at a relative intensity of only about 15.

The second curve in FIG. 9a, curve II, starts at 456 THz with a relative intensity of about 300 and sweeps down and to the right. It ends at a frequency of 781 Thz with a relative intensity of five (5). Every curve in hydrogen has this same downward sweep to the right. Progressing from right to left in FIG. 9, the curves are numbered I through V; going from high to low frequency and from high to low intensity.

The hydrogen frequency chart shown in FIG. 10 appears to be much simpler than the energy level diagrams. It is thus easier to visualize how the frequencies are organized into the different curves shown in FIG. 9. In fact, there is one curve for each of the series described by Rydberg. Curve "I" contains the frequencies in the Lyman series, originating from what quantum mechanics refers to as the first energy level. The second curve from the right, curve "II", equates to the second energy level, and so on.

The curves in the hydrogen frequency chart of FIG. 9 are composed of sums and differences (i.e., they are heterodyned). For example, the smallest curve at the far left, labeled curve "V", has two frequencies shown, namely 40 THz and 64 THz, with relative intensities of six (6) and four (4), respectively (see also FIG. 10). The next curve, IV, begins at 74 THz, proceeds to 114 THz and ends with 138 THz. The summed heterodyne calculations are thus:

40+74=114

64+74=138.

The frequencies in curve IV are the sum of the frequencies in curve V plus the peak intensity frequency in curve IV.

Alternatively, the frequencies in curve IV, minus the frequencies in curve V, yield the peak of curve IV:

114−40=74

138−64=74.

This is not just a coincidental set of sums or differences in curves IV and V. Every curve in hydrogen is the result of adding each frequency in any one curve, with the highest intensity frequency in the next curve.

These hydrogen frequencies are found in both the atom itself, and in the electromagnetic energy it radiates. The frequencies of the atom and its energy, add and subtract in regular fashion. This is heterodyning. Thus, not only matter and energy heterodyne interchangeably, but matter heterodynes its' own energy within itself.

Moreover, the highest intensity frequencies in each curve are heterodynes of heterodynes. For example, the peak frequency in Curve I of FIG. 9 is 2,466 THz, which is the third harmonic of 616 THz;

4×616 Thz=2,466 THz.

Thus, 2,466 THz is the third harmonic of 616 THz (Recall that for heterodyned harmonics, the result is even multiples of the starting frequency, i.e., for the first harmonic 2× the original frequency and the third harmonic is 4× the original frequency. Multiplying a frequency by four (4) is a natural result of the heterodyning process.) Thus, 2,466 THz is a fourth generation heterodyne, namely the third harmonic of 616 THz.

The peak of curve II of FIG. 9, a frequency corresponding to 456 THz, is the third harmonic of 114 THz in curve IV. The peak of curve III, corresponding to a frequency of 160 THz, is the third harmonic of 40 THz in curve V. The peaks of the curves shown in FIG. 9 are not only heterodynes between the curves but are also harmonics of individual frequencies which are themselves heterodynes. The whole hydrogen spectrum turns out to be an incestuously heterodyned set of frequencies and harmonics.

Theoretically, this heterodyne process could go on forever. For example, if 40 is the peak of a curve, that means the peak is four (4) times a lower number, and it also means that the peak of the previous curve is 24 (64-40=24). It is possible to mathematically extrapolate backwards and downwards this way to derive lower and lower frequencies. Peaks of successive curves to the left are 24.2382, 15.732, and 10.786 THz, all generated from the heterodyne process. These frequencies are in complete agreement with the Rydberg formula for energy levels 6, 7 and 8, respectively. Not much attention has historically been given by the prior art to these lower frequencies and their heterodyning.

This invention teaches that the heterodyned frequency curves amplify the vibrations and energy of hydrogen. A low intensity frequency on curve IV or V has a very high intensity by the time it is heterodyned out to curve I. In many respects, the hydrogen atom is just one big energy amplification system. Moving from low frequencies to high frequencies, (i.e., from curve V to curve I in FIG. 9), the intensities increase dramatically. By stimulating hydrogen with 2,466 THz at an intensity of 1,000, the result will be 2,466 THz at 1,000 intensity. However, if hydrogen is stimulated with 40 THz at an intensity of 1,000, by the time it is amplified back out to curve I of FIG. 9, the result will be 2,466 THz at an intensity of 167,000. This heterodyning turns out to have a direct bearing on platinum, and on how platinum interacts with hydrogen. It all has to do with hydrogen being an energy amplification system. That is why the lower frequency curves are perceived as being higher energy levels. By understanding this process, the low frequencies of low intensity suddenly become potentially very significant.

Platinum resonates with most, if not all, of the hydrogen frequencies with one notable exception, the highest intensity curve at the far right in the frequency chart of FIG. 9 (i.e., curve I) representing energy level 1, and beginning with 2,466 THz. Platinum does not appear to resonate significantly with the ground state transition of the hydrogen atom. However, it does resonate with multiple upper energy levels of lower frequencies.

With this information, one ongoing mystery can be solved. Ever since lasers were developed, the prior art chemists believed that there had to be some way to catalyze a reaction using lasers. Standard approaches involved using the single highest intensity frequency of an atom (such as 2,466 THz of hydrogen) because it was apparently believed that the highest intensity frequency would result in the highest reactivity. This approach was taken due to considering only the energy level diagrams. Accordingly, prior art lasers are typically tuned to a ground state transition frequency. This use of lasers in the prior art has been minimally successful for catalyzing chemical reactions. It is now understood why this approach was not successful. Platinum, the quintessential hydrogen catalyst, does not resonate with the ground state transition of hydrogen. It resonates with the upper energy level frequencies, in fact, many of the upper level frequencies. Without wishing to be bound by any particular theory or explanation, this is probably why platinum is such a good hydrogen catalyst.

Platinum resonates with multiple frequencies from the upper energy levels (i.e., the lower frequencies). There is a name given to the process of stimulating many upper energy levels, it is called a laser.

Einstein essentially worked out the statistics on lasers at the turn of the century when atoms at the ground energy level ($E_1$) are resonated to an excited energy level ($E_2$). Refer to the number of atoms in the ground state as "$N_1$" and the number of excited atoms as "$N_2$", with the total "$N_{total}$". Since there are only two possible states that atoms can occupy:

$$N_{total} = N_1 + N_2.$$

After all the mathematics are performed, the relationship which evolves is:

$$\frac{N_2}{N_{total}} = \frac{N_2}{N_1 + N_2} < \frac{1}{2}$$

In a two level system, it is predicted that there will never by more than 50% of the atoms in the higher energy level, $E_2$, at the same time.

If, however, the same group of atoms is energized at three (3) or more energy levels (i.e., a multi-level system), it is possible to obtain more than 50% of the atoms energized above the first level. By referring to the ground and energized levels as $E_1$, $E_2$, and $E_3$, respectively, and the numbers of atoms as $N_{total}$, $N_1$, $N_2$, and $N_3$, under certain circumstances, the number of atoms at an elevated energy level ($N_3$) can be more than the number at a lower energy level ($N_2$). When this happens, it is referred to as a "population inversion". Population inversion means that more of the atoms are at higher energy levels that at the lower energy levels.

Figure 11A:
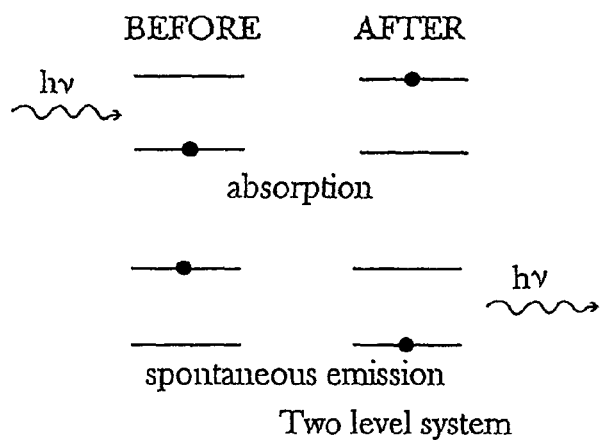
FIGS. 11a and 11b show two light amplification diagrams with stimulated emission/population inversions.
Figure 11B:
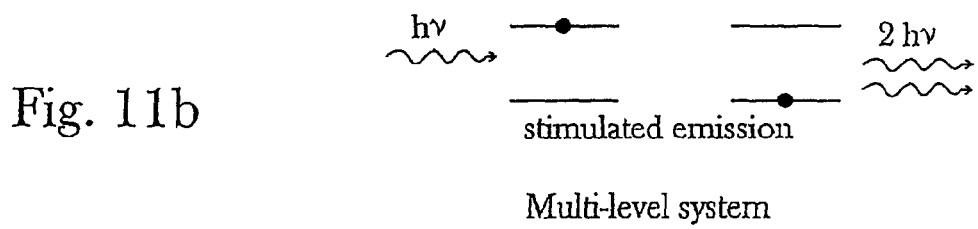

Population inversion in lasers is important. Population inversion causes amplification of light energy. For example, in a two-level system, one photon in results in one photon out. In a system with three (3) or more energy levels and population inversion, one photon in may result in 5, 10, or 15 photons out (see FIG. 11). The amount of photons out depends on the number of levels and just how energized each level becomes. All lasers are based on this simple concept of producing a population inversion in a group of atoms, by creating a multi-level energized system among the atoms. Lasers are simply devices to amplify electromagnetic wave energy (i.e., light). Laser is actually an abbreviation for Light Amplification System for Emitting Radiation.

By referring back to the interactions discussed herein between platinum and hydrogen, platinum energizes 19 upper level frequencies in hydrogen (i.e., 80% of the total hydrogen frequencies). But only three frequencies are needed for a population inversion. Hydrogen is stimulated at 19. This is a clearly multi-level system. Moreover, consider that seventy platinum frequencies do the stimulating. On average, every hydrogen frequency involved is stimulated by three or four (i.e., 70/19) different platinum frequencies; both directly resonant frequencies and/or indirectly resonant harmonic frequencies. Platinum provides ample stimulus, atom per atom, to produce a population inversion in hydrogen. Finally, consider the fact that every time a stimulated hydrogen atom emits some electromagnetic energy, that energy is of a frequency that matches and stimulates platinum in return.

Platinum and hydrogen both resonate with each other in their respective multi-level systems. Together, platinum and hydrogen form an atomic scale laser (i.e., an energy amplification system on the atomic level). In so doing, platinum and hydrogen amplify the energies that are needed to stabilize both the hydrogen and hydroxy intermediates, thus catalyzing the reaction pathway for the formation of water. Platinum is such a good hydrogen catalyst because it forms a lasing system with hydrogen on the atomic level, thereby amplifying their respective energies.

Further, this reaction hints that in order to catalyze a crystallization reaction system and/or control the reaction pathway in a crystallization reaction system it is possible for only a single transient and/or intermediate to be formed and/or energized by an applied frequency (e.g., a spectral catalyst) and that by forming and/or stimulating at least one transient and/or at least one intermediate that is required to follow for a desired reaction pathway (e.g., either a complex reaction or a simple reaction), then a frequency, or combination of frequencies, which result in such formation or stimulation of only one of such required transients and/or intermediates may be all that is required. Accordingly, the present invention recognizes that in some crystallization reaction systems, by determining at least one required transient and/or intermediate, and by applying at least one frequency which generates, energizes and/or stabilizes said at least one transient and/or intermediate, then all other transients and/or intermediates required for a reaction to proceed down a desired reaction pathway may be self-generated. However, in some cases, the reaction could be increased in rate by applying the appropriate frequency or spectral energy pattern, which directly stimulates all transients and/or intermediates that are required in order for a reaction to proceed down a desired reaction pathway. Accordingly, depending upon the particulars of any crystallization reaction system, it may be desirable for a variety of reasons, including equipment, environmental reaction conditions, etc., to provide or apply a frequency or spectral energy pattern which results in the formation and/or stimulation and/or stabilization of any required transients and/or intermediates. Thus, in order to determine an appropriate frequency or spectral energy pattern, it is first desirable to determine which transients and/or intermediates are present in any reaction pathway. Similarly, a conditioned participant could be formulated to accomplish a similar task.

Specifically, once all known required transients and/or intermediates are determined, then, one can determine experimentally or empirically which transients and/or intermediates are essential to a reaction pathway and then determine, which transients and or intermediates can be self-generated by the stimulation and/or formation of a different transient or intermediate. Once such determinations are made, appropriate spectral energies (e.g., electromagnetic frequencies) can then be applied to the crystallization reaction system to obtain the desirable reaction product and/or desirable reaction pathway.

It is known that an atom of platinum interacts with an atom of hydrogen and/or a hydroxy intermediate. And, that is exactly what modern chemistry has taught for the last one hundred years, based on Ostwald's theory of catalysis. However, the prior art teaches that catalysts must participate in the reaction by binding to the reactants, in other words, the prior art teaches a matter:matter bonding interaction is required for physical catalysts. As previously stated, these reactions follow these steps:

1. Reactant diffusion to the catalyst site;
2. Bonding of reactant to the catalyst site;
3. Reaction of the catalyst-reactant complex;
4. Bond rupture at the catalytic site (product); and
5. Diffusion of the product away from the catalyst site.

However, according to the present invention, for example, energy:energy frequencies can interact as well as energy:matter frequencies. Moreover, matter radiates energy, with the energy frequencies being substantially the same as the matter frequencies. So platinum vibrates at the frequency of 1,060 THz, and it also radiates electromagnetic energy at 1,060 THz. Thus, according to the present invention, the distinction between energy frequencies and matter frequencies starts to look less important.

Resonance can be produced in, for example, the reaction intermediates by permitting them to come into contact with additional matter vibrating at substantially the same frequencies, such as those frequencies of a platinum atom (e.g., platinum stimulating the reaction between hydrogen and oxygen to form water). Alternatively, according to the present invention, resonance can be produced in the intermediates by introducing electromagnetic energy corresponding to one or more platinum energies, which also vibrate at the same frequencies, thus at least partially mimicking (an additional mechanism of platinum is resonance with the $H_2$ molecule, a pathway reactant) the mechanism of action of a platinum catalyst. Matter, or energy, it makes no difference as far as the frequencies are concerned, because when the frequencies match, energy transfers. Thus, physical catalysts are not required. Rather, the application of at least a portion of the spectral pattern of a physical catalyst may be sufficient (i.e. at least a portion of the catalytic spectral pattern). However, in another preferred embodiment, substantially all of a spectral pattern can be applied.

Still further, by understanding the catalyst mechanism of action, particular frequencies can be applied to, for example, one or more reactants in a reaction system and, for example, cause the applied frequencies to heterodyne with existing frequencies in the matter itself to result in frequencies which correspond to one or more platinum catalyst or other relevant spectral frequencies. For example, both the hydrogen atom and the hydrogen molecule have unique frequencies. By heterodyning the frequencies a subtractive frequency can be determined:

$$NOF_{H\,atom} - NOF_{H\,molecule} = Difference_{H\,atom-molecule}$$

The Difference $H_{atom-molecule}$ frequency applied to the $H_2$ molecule reactant will heterodyne with the molecule and energize the individual hydrogen atoms as intermediates. Similarly, any reaction participant can serve as the heterodyning backboard for stimulation of another participant. For example, $$Difference_{H\,atom-Oxygen\,molecule} + NOF_{oxygen\,molecule} = NOF_{H\,atom}$$

or $$Difference_{OH-water} + NOF_{water} = NOF_{OH}$$

This approach enables greater flexibility for choice of appropriate equipment to apply appropriate frequencies. However, the key to this approach is understanding catalyst mechanisms of action and the reaction pathway so that appropriate choices for application of frequencies can be made.

Specifically, whenever reference is made to, for example, a spectral catalyst duplicating at least a portion of a physical catalyst's spectral pattern, this reference is to all the different frequencies produced by a physical catalyst; including, but not necessarily limited to, electronic, vibrational, rotational, and NOF frequencies. To catalyze, control, and/or direct a chemical reaction then, all that is needed is to duplicate one or more frequencies from a physical catalyst, with, for example, an appropriate electromagnetic energy. The actual physical presence of the catalyst is not necessary. A spectral catalyst can substantially completely replace a physical catalyst, if desired.

A spectral catalyst can also augment or promote the activity of a physical catalyst. The exchange of energy at particular frequencies, between hydrogen, hydroxy, and platinum is primarily what drives the conversion to water. These participants interact and create a miniature atomic scale lasing system that amplify their respective energies. The addition of these same energies to a crystallization reaction system, using a spectral catalyst, does the same thing. The spectral catalyst amplifies the participant energies by resonating with them and when frequencies match, energy transfers and the chemicals (matter) can absorb the energy. Thus, a spectral catalyst can augment a physical catalyst, as well as replace it. In so doing, the spectral catalyst may increase the reaction rate, enhance specificity, and/or allow for the use of less physical catalyst.

Figure 12:
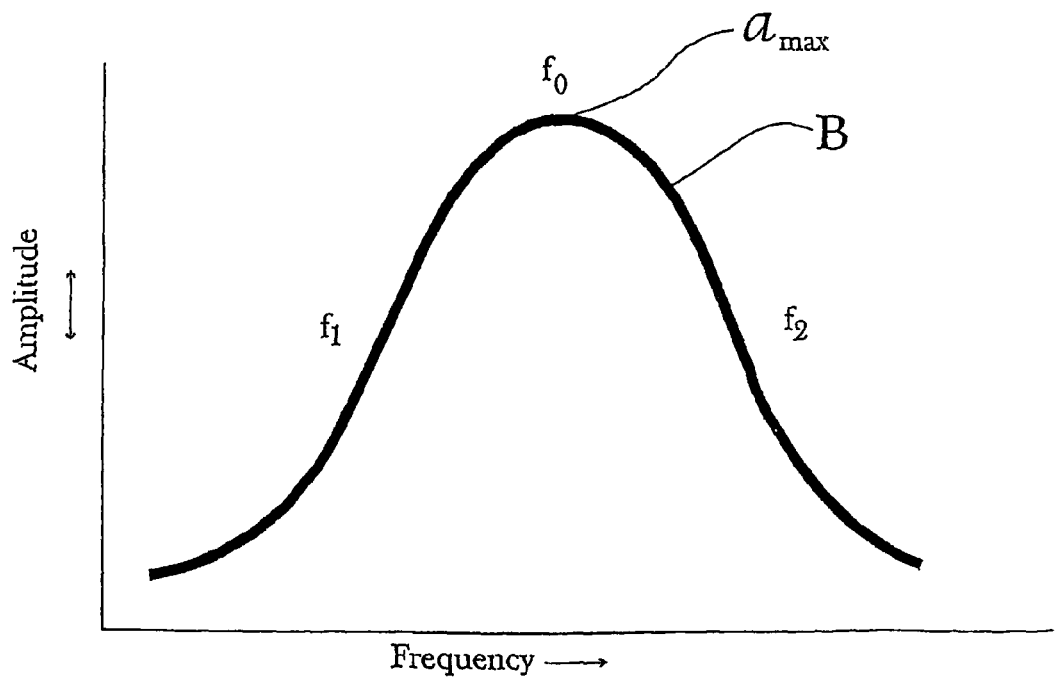
FIG. 12 shows a resonance curve where the resonance frequency is $f_0$, an upper frequency=$f_2$ and a lower frequency=$f_1$, wherein $f_1$ and $f_2$ are at about 50% of the amplitude of $f_0$.

FIG. 12 shows a basic bell-shaped curve produced by comparing how much energy an object absorbs, as compared to the frequency of the energy. This curve is called a resonance curve. As elsewhere herein stated, the energy transfer between, for example, atoms or molecules, reaches a maximum at the resonant frequency ($f_o$). The farther away an applied frequency is from the resonant frequency, $f_o$, the lower the energy transfer (e.g., matter to matter, energy to matter, etc.). At some point the energy transfer will fall to a value representing only about 50% of that at the resonant frequency $f_o$. The frequency higher than the resonant frequency, at which energy transfer is only about 50% is called "$f_2$." The frequency lower than the resonant frequency, at which about 50% energy transfer occurs, is labeled "$f_1$."

The resonant characteristics of different objects can be compared using the information from the simple exemplary resonance curve shown in FIG. 12. One such useful characteristic is called the "resonance quality" or "Q" factor. To determine the resonance quality for an object the following equation is utilized:

$$Q = \frac{f_o}{(f_2 - f_1)}$$

Figure 13A:
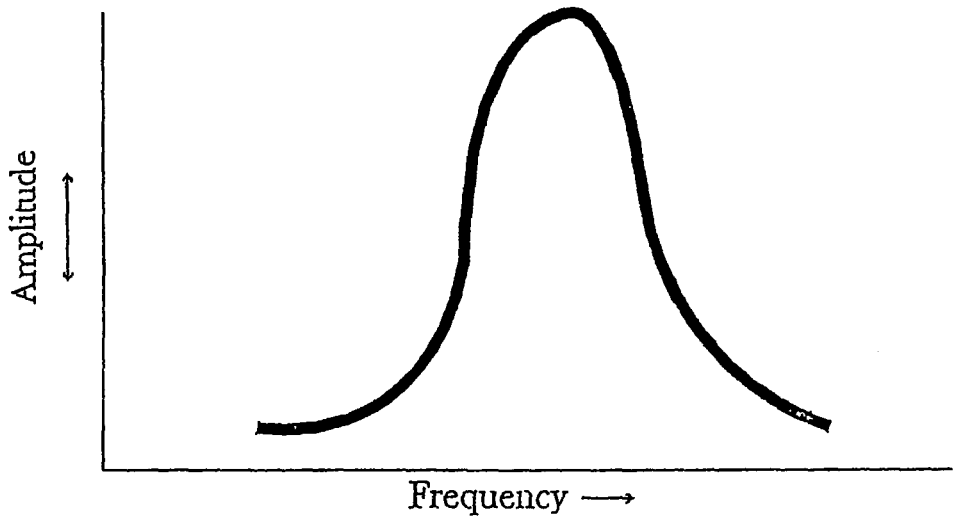
FIGS. 13a and 13b show two different resonance curves having different quality factors.
Figure 13B:
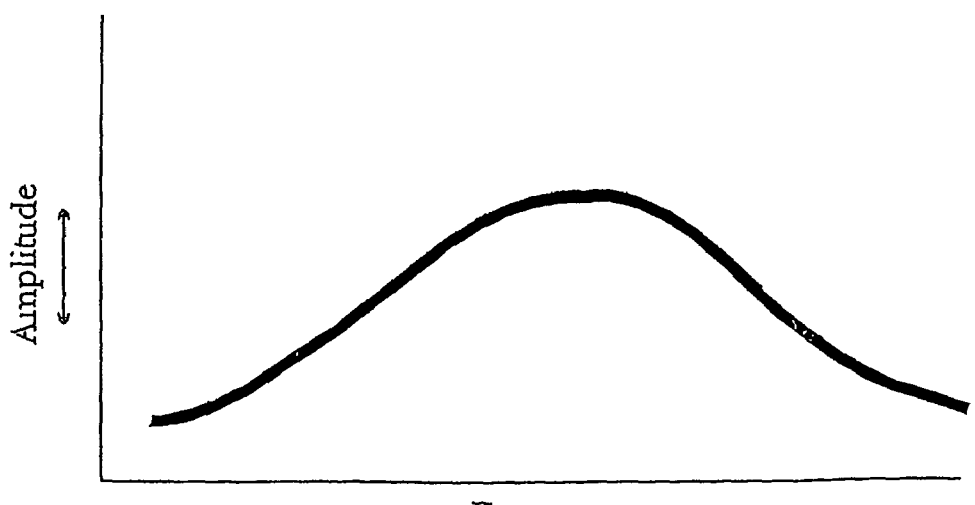

Accordingly, as shown from the equation, if the bell-shaped resonance curve is tall and narrow, then ($f_2-f_1$) will be a very small number and Q, the resonance quality, will be high (see FIG. 13a). An example of a material with a high "Q" is a high quality quartz crystal resonator. If the resonance curve is low and broad, then the spread or difference between $f_2$ and $f_1$ will be relatively large. An example of a material with a low "Q" is a marshmallow. The dividing of the resonant frequency by this large number will produce a much lower Q value (see FIG. 13b).

Atoms and molecules, for example, have resonance curves which exhibit properties similar to larger objects such as quartz crystals and marshmallows. If the goal is to stimulate atoms in a reaction (e.g., hydrogen in the reaction to produce water as mentioned previously) a precise resonant frequency produced by a crystallization reaction system component or environmental reaction condition (e.g., hydrogen) can be used. It is not necessary to use the precise frequency, however. Use of a frequency that is near a resonant frequency of, for example, one or more crystallization reaction system components or environmental reaction conditions is adequate. There will not be quite as much of an effect as using the exact resonant frequency, because less energy will be transferred, but there will still be an effect. The closer the applied frequency is to the resonant frequency, the more the effect. The farther away the applied frequency is from the resonant frequency, the less effect that is present (i.e., the less energy transfer that occurs).

Harmonics present a similar situation. As previously stated, harmonics are created by the heterodyning (i.e., adding and subtracting) of frequencies, allowing the transfer of significant amounts of energy. Accordingly, for example, desirable results can be achieved in chemical reactions if applied frequencies (e.g., at least a portion of a spectral catalyst) are harmonics (i.e., matching heterodynes) with one or more resonant frequency(ies) of one or more crystallization reaction system components or environmental reaction conditions.

Further, similar to applied frequencies being close to resonant frequencies, applied frequencies which are close to the harmonic frequency can also produce desirable results. The amplitude of the energy transfer will be less relative to a harmonic frequency, but an effect will still occur. For example, if the harmonic produces 70% of the amplitude of the fundamental resonant frequency and by using a frequency which is merely close to the harmonic, for example, about 90% on the harmonic's resonance curve, then the total effect will be 90% of 70%, or about 63% total energy transfer in comparison to a direct resonant frequency. Accordingly, according to the present invention, when at least a portion of the frequencies of one or more crystallization reaction system components or environmental reaction conditions at least partially match, then at least some energy will transfer and at least some reaction will occur (i.e., when frequencies match, energy transfers).

Duplicating the Catalyst Mechanism of Action

As stated previously, to catalyze, control, and/or direct a chemical reaction, a spectral catalyst can be applied. The spectral catalyst may correspond to at least a portion of a spectral pattern of a physical catalyst or the spectral catalyst may correspond to frequencies which form or stimulate required participants (e.g., heterodyned frequencies) or the spectral catalyst may substantially duplicate environmental reaction conditions such as temperature or pressure. Thus, as now taught by the present invention, the actual physical presence of a catalyst is not required to achieve the desirable chemical reactions, phase transformations, or structural control. The obsoleting of a physical catalyst is accomplished by understanding the underlying mechanism inherent in catalysis, namely that desirable energy can be exchanged (i.e., transferred) between, for example, (1) at least one participant (e.g., reactant, transient, intermediate, activated complex, reaction product, promoter and/or poison) and/or at least one component in a crystallization reaction system and (2) an applied spectral energy (e.g., spectral catalyst) when such energy is present at one or more specific frequencies. In other words, the targeted mechanism that nature has built into the catalytic process can be copied according to the teachings of the present invention. Nature can be further mimicked because the catalyst process reveals several opportunities for duplicating catalyst mechanisms of action, and hence improving the use of spectral catalysts, as well as the control of countless chemical reactions and transformations.

For example, the previously discussed reaction of hydrogen and oxygen to produce water, which used platinum as a catalyst, is a good starting point for understanding catalyst mechanisms of action. For example, this invention discloses that platinum catalyzes the reaction in several ways not contemplated by the prior art:

Platinum directly resonates with and energizes reaction intermediates and/or transients (e.g., atomic hydrogen and hydroxy radicals);

Platinum harmonically resonates with and energizes at least one reaction intermediate and or transient (e.g., atomic hydrogen); and Platinum energizes multiple upper energy levels of at least one reaction intermediate and or transient (e.g., atomic hydrogen).

This knowledge can be utilized to improve the functioning of the spectral catalyst and/or spectral energy catalyst, to design spectral catalysts and spectral energy catalysts which differ from actual catalytic spectral patterns, to design physical catalysts (or conditionable participants that can be conditioned to function as physical catalysts), and to optimize environmental reaction conditions in crystallization holoreaction systems. For example, the electronic frequencies of potassium are in the visible light regions of the electromagnetic spectrum. The electronic spectra of virtually all atoms are in the ultraviolet, visible light, and infrared regions. However, these very high electromagnetic frequencies can be a problem for large-scale and industrial applications because wave energies having high frequencies typically do not penetrate matter very well (i.e., do not penetrate far into matter). The tendency of wave energy to be absorbed rather than transmitted, can be referred to as attenuation. High frequency wave energies have a high attenuation, and thus do not penetrate far into a typical industrial scale reaction vessel containing typical reactants for a chemical reaction. Thus, the duplication and application of at least a portion of the spectral pattern of platinum into a commercial scale reaction vessel will typically be a slow process because a large portion of the applied spectral pattern of the spectral catalysts may be rapidly absorbed near the edges of the reaction vessel.

Thus, in order to input energy into a large industrial-sized commercial reaction vessel, a lower frequency energy could be used that would penetrate farther into the reactants housed within the reaction vessel. The present invention teaches that this can be accomplished in a unique manner by copying nature. As discussed herein, the spectra of atoms and molecules are broadly classified into three (3) different groups: electronic, vibrational, and rotational. The electronic spectra of atoms and small molecules are said to result from transitions of electrons from one energy level to another, and have the corresponding highest frequencies, typically occurring in the ultraviolet (UV), visible, and infrared (IR) regions of the EM spectrum. The vibrational spectra are said to result primarily from this movement of bonds between individual atoms within molecules, and typically occur in the infrared and microwave regions. Rotational spectra occur primarily in the microwave and radiowave regions of the EM spectrum due, primarily, to the rotation of the molecules.

Microwave or radiowave radiation could be an acceptable frequency to be used to spectrally control a chemical reaction or transformation because it would penetrate well into a large reaction vessel. Unfortunately, potassium atoms do not produce frequencies in the microwave or radiowave portions of the electromagnetic spectrum because they do not have vibrational or rotational spectra. However, by understanding the mechanism of action of electronic potassium frequencies in phase transformations, selected potassium frequencies can be used as a model for a spectral catalyst in the microwave portion of the spectrum. Specifically, as previously discussed by an analogy of platinum, one mechanism of action of potassium in the mixed KCl halide crystallization reaction system to produce only KCl solid crystals involves energizing the potassium atoms to produce resonant attraction and solid growth of the potassium atoms. Atomic potassium has a high frequency electronic spectrum without vibrational or rotational spectra. The NaCl and KCl crystals, on the other hand, are molecules and have vibrational and rotational spectra as well as electronic spectra. Thus, the NaCl and KCl molecules absorb and heterodyne frequencies in the microwave portion of the electromagnetic spectrum.

Thus, to copy the mechanism of action of potassium in the reaction to form solid KCl, namely resonating with at least one reaction participant, the potassium atom can be specifically targeted via resonance. However, instead of resonating with the potassium in its electronic spectrum, as the KCl seed crystal does, at least one NaCl frequency in the microwave portion of the electromagnetic spectrum can be used to resonate with the NaCl nuclei. NaCl molecules resonate at a microwave frequency of about 13.0737 GHz. Energizing a mixed crystallization Na, K, and Cl with a spectral catalyst at about 13.0737 GHz will catalyze the formation of KCl. In this instance, the mechanism of action of the physical catalyst potassium has been partially copied and reversed and the mechanism has been shifted to a different region of the electromagnetic spectrum. In other words, by engineering the NaCl vibrational frequency, small NaCl molecules are energized and prevented from bonding to the KCl solid. Thus, by understanding the resonant mechanisms involved in phase transformations, the mechanisms can be copied in desired regions of the electromagnetic spectrum.

According to the present invention, by again copying the mechanism of action, physical catalysts (e.g., seed crystals) frequencies can be adapted or selected to be convenient and/or efficient for the equipment available. Specifically, harmonic frequencies can be utilized. The potassium atom has resonant frequencies which are harmonics of the sodium spectral frequencies. Thus, a K spectral light source can resonate harmonically with the sodium (in a sodium crystallization system) and visa versa to enhance phase transformations. Similarly, harmonic overtones of materials can be used to alter and control those material properties. In summary, a mechanism of action of a physical catalyst can be copied, duplicated or mimicked while moving the relevant energy frequencies, to a portion of the electromagnetic spectrum that matches equipment available for the holoreaction system and the application of electromagnetic energy.

The third method discussed above for platinum catalyzing this reaction involves energizing at least one reaction component multiple upper energy levels. Again, assume that the only spectral energy source available produces frequencies in the infra-red region, where many of the upper energy level electronic frequencies for atoms are located. These infra-red frequencies, for example for potassium, can be used to produce resonant attraction and solid growth of the potassium atom in, for example, a potassium covalent crystal. Specifically, the present invention has discovered that a mechanism of action that physical catalysts use is to resonate with multiple upper energy levels of at least one reaction participant. It is now understood that the use of upper energy levels can affect and control transformations of matter. Once again, nature can be mimicked by duplicating one naturally occurring mechanism of action by specifically targeting multiple energy levels with a spectral catalyst to achieve energy transfer in a novel manner.

The preceding discussion on duplicating catalyst mechanisms of action is just the beginning of an understanding of many variables associated with the use of spectral catalysts. These additional variables should be viewed as potentially very useful tools for enhancing the performance of spectral energy, and/or physical catalysts. There are many factors and variables that affect both catalyst performance, and chemical reactions in general. For example, when the same catalyst (or conditioned participant) is mixed with the same reactant, but exposed to different environmental reaction conditions such as temperature or pressure, different products can be produced. Consider the following example:

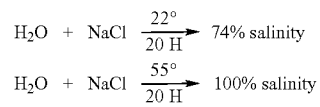

The same reactants produces quite different products in these two reactions, namely 74% salinity or 100% salinity, depending on the reaction temperature.

Many factors are known in the art which affect the direction and intensity and rate at a which a reaction proceeds in general. Temperature is but one of these factors. Other factors include pressure, volume, surface area of physical catalysts, solvents, support materials, contaminants, catalyst size and shape and composition, reactor vessel size, shape and composition, electric fields, magnetic fields, acoustic fields and whether a conditioning energy was introduced to a conditioned participant prior to the conditioned participant being involved or activated in a crystallization reaction system. The present invention teaches that these factors all have one thing in common. These factors are capable of changing the spectral patterns (i.e., frequency pattern) of, for example, participants and/or crystallization reaction system components. Some changes in spectra are very well studied and thus much information is available for consideration and application thereof. The prior art does not contemplate, however, the spectral chemistry basis for each of these factors, and how they relate to catalyst mechanisms of action, and chemical reactions in general. Further, alternatively, effects of the aforementioned factors can be enhanced or diminished by the application of additional spectral, spectral energy, and/or physical catalyst frequencies. Moreover, these environmental reaction conditions can be at least partially simulated in a crystallization reaction system by the application of one or more corresponding spectral environmental reaction conditions (e.g., a spectral energy pattern which duplicates at least a portion of one or more environmental reaction conditions). Alternatively, one spectral environmental reaction condition (e.g., a spectral energy pattern corresponding to temperature) could be substituted for another (e.g., spectral energy pattern corresponding to pressure) so long as the goal of matching of frequencies was met.

Temperature

Figure 15A:
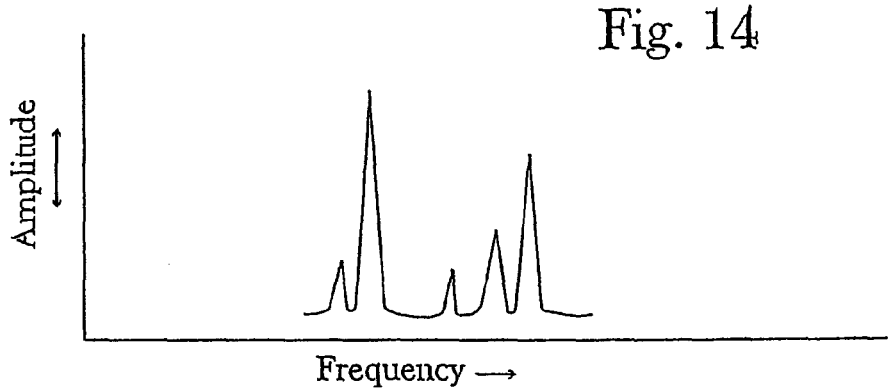
FIGS. 15a-c show how a spectral pattern varies at three different temperatures.
Figure 15B:
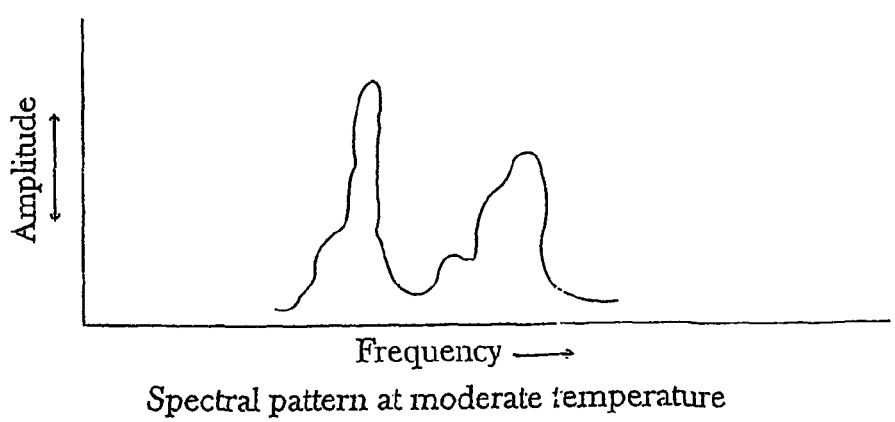
Figure 15C:
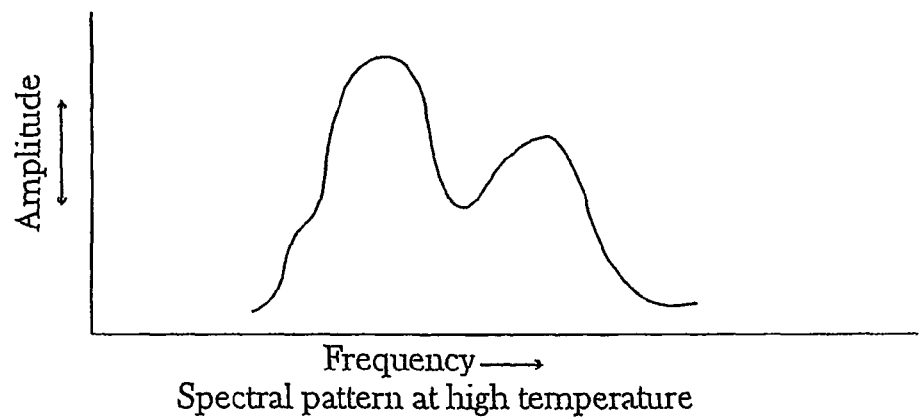

At very low temperatures, the spectral pattern of an atom or molecule has clean, crisp peaks (see FIG. 15a). As the temperature increases, the peaks begin to broaden, producing a bell-shaped curve of a spectral pattern (see FIG. 15b). At even higher temperatures, the bell-shaped curve broadens even more, to include more and more frequencies on either side of the primary frequency (see FIG. 15c). This phenomenon is called "broadening".

These spectral curves are very much like the resonance curves discussed in the previous section. Spectroscopists use resonance curve terminology to describe spectral frequency curves for atoms and molecules (see FIG. 16). The frequency at the top of the curve, $f_o$, is called the resonance frequency. There is a frequency ($f_2$) above the resonance frequency and another ($f_1$) below it (i.e., in frequency), at which the energy or intensity (i.e., amplitude) is 50% of that for the resonance frequency $f_o$. The quantity $f_2-f_1$ is a measure of how wide or narrow the spectral frequency curve is. This quantity ($f_2-f_1$) is the "line width". A spectrum with narrow curves has a small line width, while a spectrum with wide curves has a large line width.

Figure 17A:
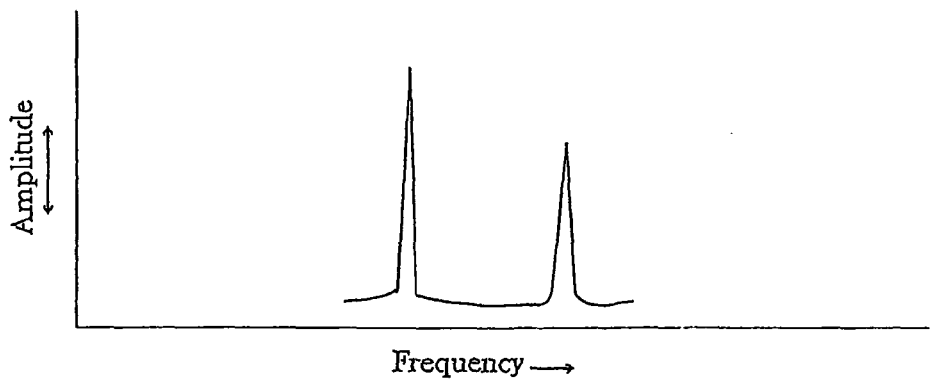
FIGS. 17a and 17b show two amplitude vs. frequency curves.
Figure 17B:
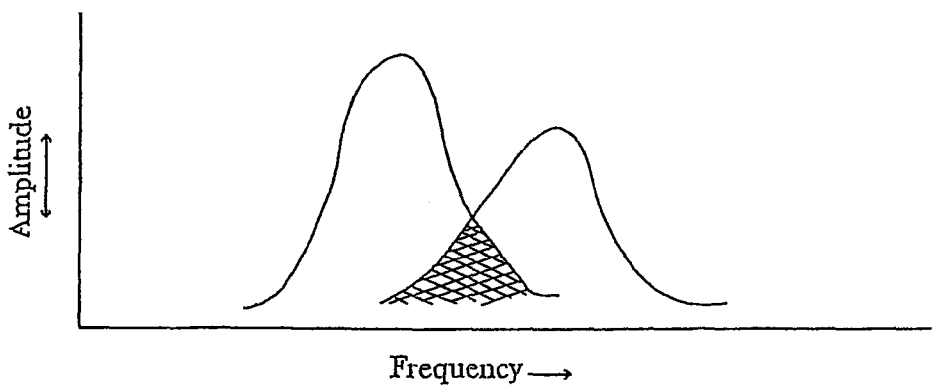

Temperature affects the line width of spectral curves. Line width can affect catalyst performance, chemical reactions and/or reaction pathways. At low temperatures, the spectral curves of chemical species will be separate and distinct, with a lesser possibility for the transfer of resonant energy between potential crystallization reaction system components (see FIG. 17a). However, as the line widths of potentially reactive chemical species broaden, their spectral curves may start to overlap with spectral curves of other chemical species (see FIG. 17b). When frequencies match, or spectral energy patterns overlap, energy transfers. Thus, when temperatures are low, frequencies do not match and reactions are slow. At higher temperatures, resonant transfer of energy can take place and reactions can proceed very quickly or proceed along a different reaction pathway than they otherwise would have at a lower temperature.

Figure 18A:
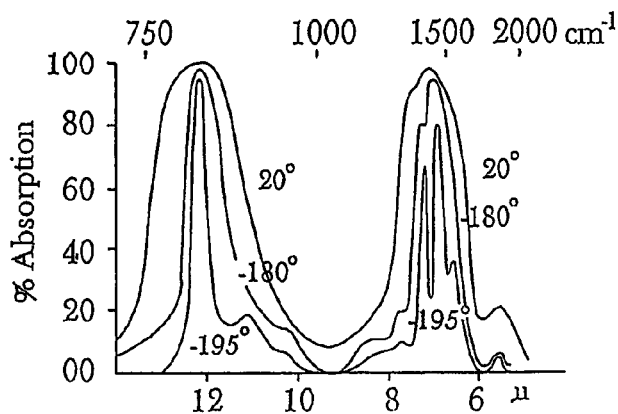
FIG. 18a shows the influence of temperature on the resolution of infrared absorption spectra.
Figure 18B:
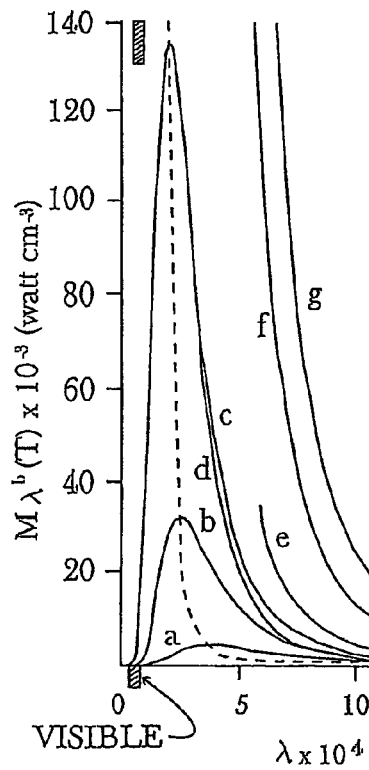
FIG. 18b shows blackbody radiation.
Figure 18C:
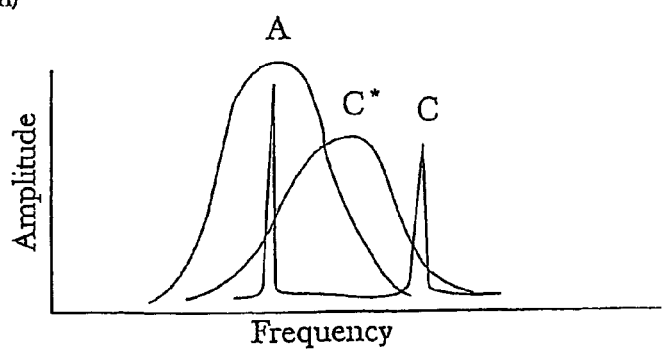
FIG. 18c shows curves A and C at low temperature, and broadened curves A and C* at higher temperature, with C* also shifted.

Besides affecting the line width of the spectral curves, temperature also can change, for example, the resonant frequency of holoreaction system components. For some chemical species, the resonant frequency will shift as temperature changes. This can be seen in the infrared absorption spectra in FIG. 18a and blackbody radiation graphs shown in FIG. 18b. Further, atoms and molecules do not all shift their resonant frequencies by the same amount or in the same direction, when they are at the same temperature. This can also affect catalyst performance. For example, if a catalyst resonant frequency shifts more with increased temperature than the resonant frequency of its targeted chemical species, then the catalyst could end up matching the frequency of a chemical species, and resonance may be created where none previously existed (see FIG. 18c). Specifically, FIG. 18c shows catalyst "C" at low temperature and "C*" at high temperature. The catalyst "C*" resonates with reactant "A" at high temperatures, but not at low temperatures.

The amplitude or intensity of a spectral line may be affected by temperature also. For example, linear and symmetric rotor molecules will have an increase in intensity as the temperature is lowered while other molecules will increase intensity as the temperature is raised. These changes of spectral intensity can also affect catalyst performance. Consider the example where a low intensity spectral curve of a catalyst is resonant with one or more frequencies of a specific chemical target. Only small amounts of energy can be transferred from the catalyst to the target chemical (e.g., a hydroxy intermediate). As temperature increases, the amplitude of the catalyst's curve increases also. In this example, the catalyst can transfer much larger amounts of energy to the chemical target when the temperature is raised.

If the chemical target is the intermediate chemical species for an alternative reaction route, the type and ratio of end products may be affected. By examining the above cyclohexene/palladium reaction again, at temperatures below 300° C., the products are benzene and hydrogen gas. However, when the temperature is above 300° C., the products are benzene and cyclohexane. Temperature is affecting the palladium and/or other constituents in the holoreaction system (including, for example, reactants, intermediates, and/or products) in such a way that an alternative reaction pathway leading to the formation of cyclohexane is favored above 300° C. This could be a result of, for example, increased line width, altered resonance frequencies, or changes in spectral curve intensities for any of the components in the holoreaction system.

It is important to consider not only the spectral catalyst frequencies one may wish to use to catalyze a reaction, but also the reaction conditions under which those frequencies are supposed to work. For example, in the palladium/cyclohexene reaction at low temperatures, the palladium may match frequencies with an intermediate for the formation of hydrogen molecules ($H_2$). At temperatures above 300° C. the reactants and transients may be unaffected, but the palladium may have an increased line width, altered resonant frequency and/or increased intensity. The changes in the line width, resonant frequency and/or intensity may cause the palladium to match frequencies and transfer energy to an intermediate in the formation of cyclohexane instead. If a spectral catalyst was to be used to assist in the formation of cyclohexane at room temperature, the frequency for the cyclohexane intermediate would be more effective if used, rather than the spectral catalyst frequency used at room temperature.

Thus, it may be important to understand the holoreaction system dynamics in designing and selecting an appropriate spectral catalyst. The transfer of energy between different crystallization reaction system components will vary, depending on temperature. Once understood, this allows one to knowingly adjust temperature to optimize a reaction, reaction product, interaction and/or formation of reaction product at a desirable reaction rate, without the trial and error approaches of prior art. Further, it allows one to choose catalysts such as physical catalysts, spectral catalysts, and/or spectral energy patterns to optimize a desired reaction pathway. This understanding of the spectral impact of temperature allows one to perform customarily high temperature (and, sometimes high danger) chemical processes at safer, room temperatures. It also allows one to design physical catalysts which work at much broader temperature ranges (e.g., frigid arctic temperatures or hot furnace temperatures), as desired.

Pressure

Figure 19:
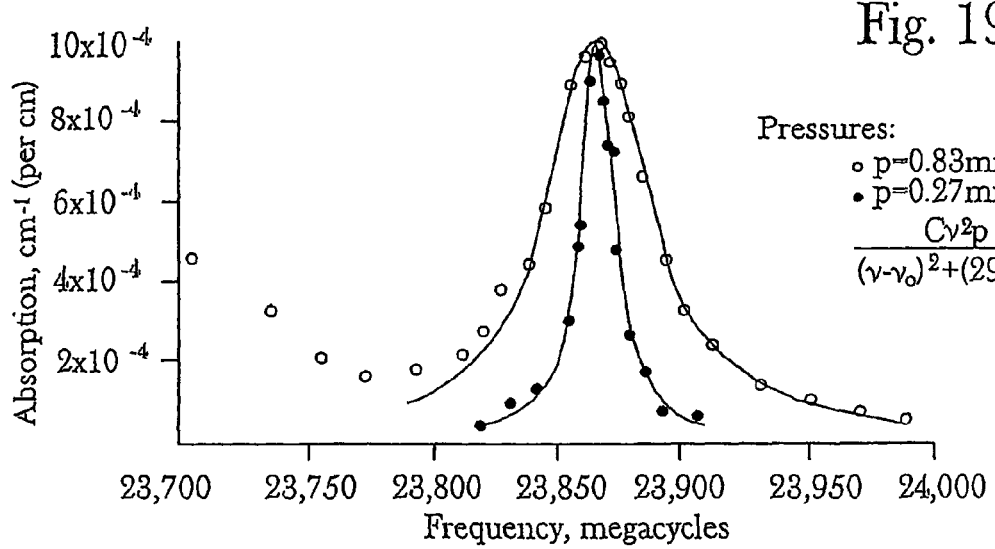
FIG. 19 shows spectral patterns which exhibit the effect of pressure broadening on the compound $NH_3$.

Pressure and temperature are directly related to each other. Specifically, from the ideal gas law, we know that $$PV=nRT$$

where P is pressure, V is volume, n is the number of moles of gas, R is the gas constant, and T is the absolute temperature. Thus, at equilibrium, an increase in temperature will result in a corresponding increase in pressure. Pressure also has an effect on spectral patterns. Specifically, increases in pressure can cause broadening and changes in spectral curves, just as increases in temperature do (see FIG. 19 which shows the pressure broadening effects on the $NH_3$ 3.3 absorption line).

Mathematical treatments of pressure broadening are generally grouped into either collision or statistical theories. In collision theories, the assumption is made that most of the time an atom or molecule is so far from other atoms or molecules that their energy fields do not interact. Occasionally, however, the atoms or molecules come so close together that they collide. In this case, the atom or molecule may undergo a change in wave phase (spectral) function, or may change to a different energy level. Collision theories treat the matter's emitted energy as occurring only when the atom or molecule is far from others, and is not involved in a collision. Because collision theories ignore spectral frequencies during collisions, collision theories fail to predict accurately chemical behavior at more than a few atmospheres of pressure, when collisions are frequent.

Statistical theories, however, consider spectral frequencies before, during and after collisions. They are based on calculating the probabilities that various atoms and/or molecules are interacting with, or perturbed by other atoms or molecules. The drawback with statistical treatments of pressure effects is that the statistical treatments do not do a good job of accounting for the effects of molecular motion. In any event, neither collision nor statistical theories adequately predict the rich interplay of frequencies and heterodynes that take place as pressure is increased. Experimental work has demonstrated that increased pressure can have effects similar to those produced by increased temperature, by:

1) broadening of the spectral curve, producing increased line width; and
2) shifting of the resonant frequency ($f_o$).

Figure 20:
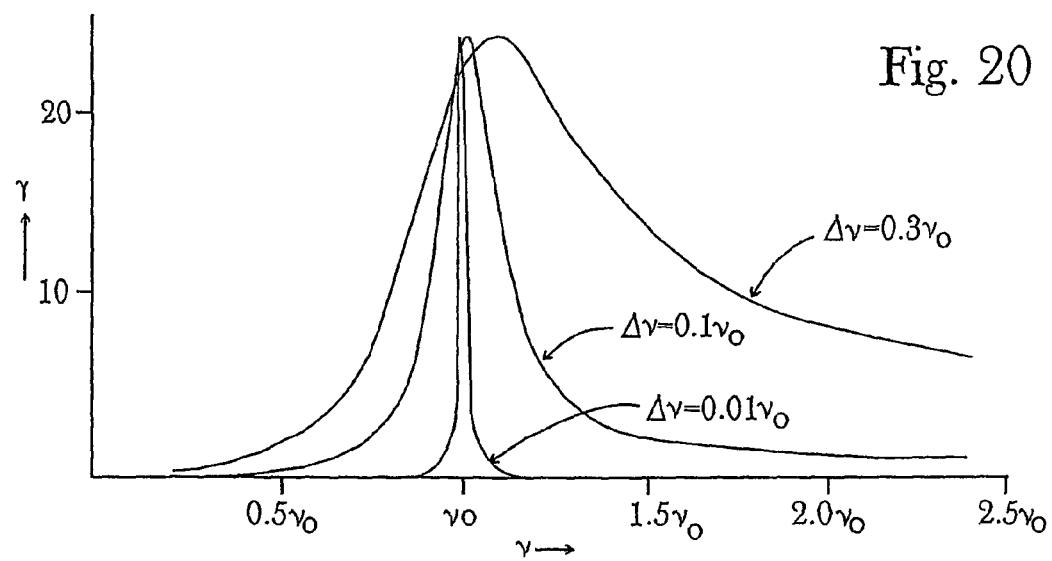
FIG. 20 shows the theoretical shape of pressure-broadened lines at three different pressures for a single compound.
Figure 21A:
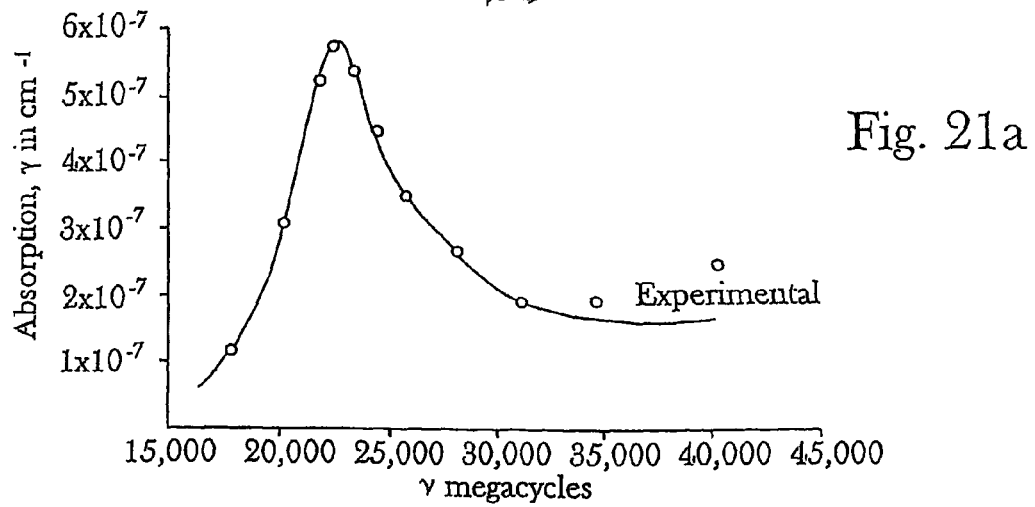
FIGS. 21a and 21b are two graphs which show experimental confirmation of changes in spectral patterns at increased pressures.
Figure 21B:
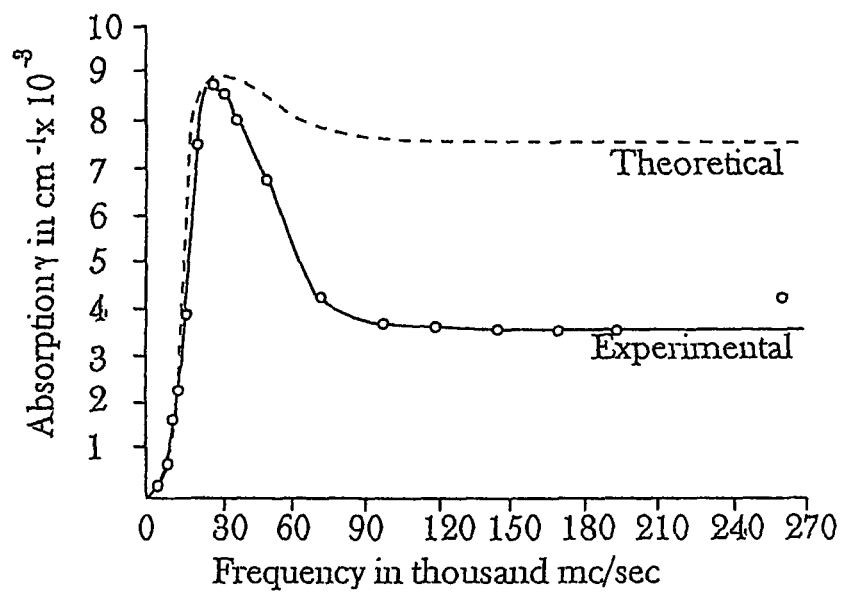

Pressure effects different from those produced by temperatures are: (1) pressure changes typically do not affect intensity, (see FIG. 20 which shows a theoretical set of curves exhibiting an unchanged intensity for three applied different pressures) as with temperature changes; and (2) the curves produced by pressure broadening are often less symmetric than the temperature affected curves. Consider the shape of the three theoretical curves shown in FIG. 20. As the pressure increases, the curves become less symmetrical. A tail extending into the higher frequencies develops. This upper frequency extension is confirmed by the experimental work shown in FIG. 21. Specifically, FIG. 21a shows a pattern for the absorption by water vapor in air (10 g of $H_2O$ per cubic meter); and FIG. 21b shows the absorption in $NH_3$ at 1 atmosphere pressure.

Pressure broadening effects on spectral curves are broadly grouped into two types: resonance or "Holtsmark" broadening, and "Lorentz" broadening. Holtsmark broadening is secondary to collisions between atoms of the same element, and thus the collisions are considered to be symmetrical. Lorentz broadening results from collisions between atoms or molecules which are different. The collisions are asymmetric, and the resonant frequency, $f_o$, is often shifted to a lower frequency. This shift in resonant frequency is shown in FIG. 20. The changes in spectral curves and frequencies that accompany changes in pressure can affect catalysts, both physical and spectral, and chemical reactions and/or reaction pathways. At low pressures, the spectral curves tend to be fairly narrow and crisp, and nearly symmetrical about the resonant frequency. However, as pressures increase, the curves may broaden, shift, and develop high frequency tails.

At low pressures the spectral frequencies in the crystallization reaction system might be so different for the various atoms and molecules that there may be little or no resonant effect, and thus little or no energy transfer. At higher pressures, however, the combination of broadening, shifting and extension into higher frequencies can produce overlapping between the spectral curves, resulting in the creation of resonance, where none previously existed, and thus, the transfer of energy. The crystallization reaction system may proceed down one reaction pathway or another, depending on the changes in spectral curves produced by various pressure changes. One reaction pathway may be resonant and proceed at moderate pressure, while another reaction pathway may be resonant and predominate at higher pressures. As with temperature, it is important to consider the crystallization reaction system frequencies and mechanisms of action of various catalysts under the environmental reaction conditions one wishes to duplicate. Specifically, in order for an efficient transfer of energy to occur between, for example, a spectral catalyst and at least one reactant in a crystallization reaction system, there must be at least some overlap in frequencies.

For example, a reaction with a physical catalyst seed crystal at 400 THz and a key covalent adatom at 500 THz may proceed slowly at atmospheric pressure. Where the pressure is raised to about five (5) atmospheres, the catalyst broadens out through the 500 THz, for example, of the adatom. This allows the transfer of energy between the catalyst and adatom by, for example, energizing and stimulating the adatom. The crystallization reaction then proceeds very quickly. Without wishing to be bound by any particular theory or explanation, it appears that, the speed of the reaction has much less to do with the number of collisions (as taught by the prior art) than it has to do with the spectral patterns of the crystallization reaction system components. In the above example, the reaction could be energized at low pressures by applying the 500 THz frequency to directly stimulate and attract the key adatom. This could also be accompanied indirectly using various heterodynes, (e.g., @ 1,000 THz harmonic, or a 100 THz non-harmonic heterodyne between the catalyst and transient (500 THz−400 THz=100 THz.).

As shown herein, the transfer of energy between different crystallization reaction system components will vary, depending on pressure. Once understood, this allows one to knowingly adjust pressure to optimize a reaction, without the trial and error approaches of prior art. Further, it allows one to choose catalysts such as physical catalysts, seed crystals, epitaxial substrates, spectral catalysts, and/or spectral energy patterns to optimize one or more desired reaction pathways. This understanding of the spectral impact of pressure allows one to perform customarily high pressure (and thus, typically, high danger) chemical processes at safer, room pressures. It also allows one to design physical catalysts which work over a large range of acceptable pressures (e.g., low pressures approaching a vacuum to several atmospheres of pressure).

Surface Area

Traditionally, the surface area of a catalyst has been considered to be important because the available surface area controls the number of available binding sites. Supposedly, the more exposed binding sites, the more catalysis. In light of the spectral mechanisms disclosed in the present invention, surface area may be important for another reason.

Many of the spectral catalyst frequencies that correspond to physical catalysts are electronic frequencies in the visible light and ultraviolet regions of the spectrum. These high frequencies have relatively poor penetrance into, for example, large reaction vessels that contain one or more reactants. The high frequency spectral emissions from a catalyst such as a seed crystal will thus not travel very far into such a crystallization reaction system before such spectral emissions are absorbed. Thus, for example, an atom or molecule must be fairly close to a physical catalyst so that their respective electronic frequencies can interact.

Thus, surface area primarily affects the probability that a particular chemical species, will be close enough to the physical catalyst to interact with its electromagnetic spectra emission(s) and in the case of crystallization, be attracted to the catalyst as an adatom. With small surface area, few atoms or molecules will be close enough to interact. However, as surface area increases, so too does the probability that more atoms or molecules will be within range for reaction. Thus, in addition to increasing the available number of binding sites, larger surface area probably increases the volume of the crystallization reaction system exposed to the spectral catalyst frequencies or patterns. This is similar to the concept of assuring adequate penetration of a spectral catalyst into a crystallization reaction system (e.g., assuming that there are adequate opportunities for species to interact with each other).

An understanding of the effects of surface area on catalysts and crystallization reaction system components allows one to knowingly adjust surface area, spectral emission, and other crystallization reaction system components to optimize a reaction, reaction pathway and/or formation of reaction product(s), at a desirable reaction rate, without the drawbacks of the prior art. For instance, surface area is currently optimized by making traditional chemical catalyst particles as small as possible, thereby maximizing the overall surface area. The small particles have a tendency to, for example, sinter (merge or bond together) which decreases the overall surface area and catalytic activity. Rejuvenation of a large surface area catalyst can be a costly and time-consuming process. This process can be avoided with an understanding of the herein presented invention in the field of spectral chemistry. For example, assume a reaction is quickly catalyzed by a 3 m² catalyst bed (in a transfer of energy from catalyst to a key reactant and product). After sintering takes place, however, the surface area is reduced to 1 m². Thus, the transfer of energy from the catalyst is dramatically reduced, and the reaction slows down. The costly and time-consuming process of rejuvenating the surface area can be avoided (or at least delayed) by inhibiting the crystallization reaction system (i.e., sintering) with one or more desirable spectral energy patterns. In addition, because spectral energy patterns can affect the final physical form or phase of a material, as well as its chemical formula, the sintering process itself may be reduced or eliminated.

Further, the penetrance of spectral frequencies into a crystallization reaction system can be enhanced, creating a "virtually" enlarged surface. For example, in a metal alloy crystallization reaction system, spectral frequencies of a desired metal in the alloy can be transmitted onto the seed crystal. These spectral frequencies may act to extent the effective spectral emissions of the metal many times further than would normally occur with typical attenuation. Crystallizing species will be attracted by resonance from much further away, enhancing formation of the alloy. These same methods can be used to control selectivity of crystallization, such as ratios or symmetry of species within a material, such as an alloy.

Catalyst Size and Shape

In a related line of reasoning, catalyst size and shape are classically thought to affect physical catalyst activity. Crystallization controlled by critical nucleus size has historically been used to steer transformation pathways. As with surface area, certain particle sizes (e.g., critical nuclei) are thought to provide a stable structure and thus maximize the transformation rate and amount. The relationship between size and surface area has been previously discussed.

Figure 22A:
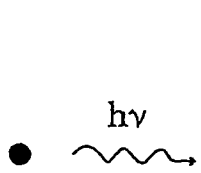
FIG. 22a shows a representation of radiation from a single atom and FIG. 22b shows a representation of radiation from a group of atoms.
Figure 22B:
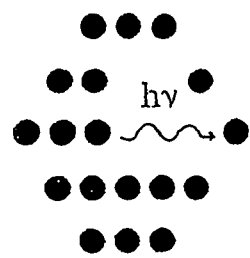
Figure 23A:
FIGS. 23a-d show four different spectral curves, three of which exhibit self-absorption patterns.
Figure 23B:
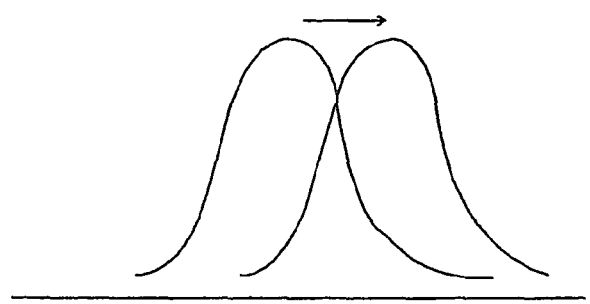
Figure 23C:
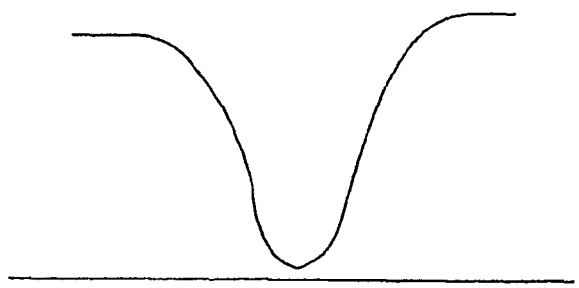
Figure 23D:
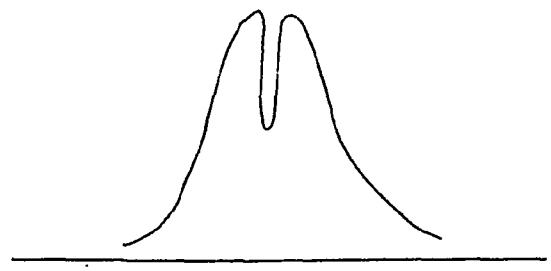

In light of the current understanding of the spectral mechanisms underlying the activity of physical catalysts and transformations in general, catalyst size and shape may be important for other reasons. One of those reasons is a phenomenon called "self absorption". When a single atom or molecule produces its' classical spectral pattern it radiates electromagnetic energy which travels outward from the atom or molecule into neighboring space. FIG. 22a shows radiation from a single atom versus radiation from a group of atoms as shown in FIG. 22b. As more and more atoms or molecules group together, radiation from the center of the group is absorbed by its' neighbors and may never make it out into space. Depending on the size and shape of the group of atoms, self absorption can cause a number of changes in the spectral emission pattern (see FIG. 23). Specifically, FIG. 23a shows a normal spectral curve produced by a single atom; FIG. 23b shows a resonant frequency shift due to self absorption; FIG. 23c shows a self-reversal spectral pattern produced by self absorption in a group of atoms and FIG. 23d shows a self-reversal spectral pattern produced by self absorption in a group of atoms. These changes include a shift in resonant frequency and self-reversal patterns.

The changes in spectral curves and frequencies that accompany changes in catalyst (e.g., seed crystal) size and shape can affect catalysts, chemical transformations and/or reaction pathways. For example, atoms or molecules of a physical catalyst may produce spectral frequencies in the crystallization reaction system which resonate with a key intermediate and/or reaction product. With larger groups of atoms, such as in a forming crystal, the combination of resonant frequency shifting and self-reversal may eliminate overlapping between the spectral curves of chemical species, thereby minimizing or destroying conditions of resonance, and for example slowing the rate of crystallization.

A crystallization reaction system may proceed down one reaction pathway or another, depending on the changes in spectral curves produced by the particle sizes. For example, a catalyst (or conditioned participant) having a moderate particle size may proceed down a first reaction pathway while a larger size catalyst may direct the reaction down another reaction pathway.

The changes in spectral curves and frequencies that accompany changes in catalyst size and shape are relevant for practical applications The use of spectral catalysts according to the present invention allows for much finer tuning of these processes. For example, the high level of catalyst activity obtained with a smaller catalyst size can still be obtained by, for example, augmenting the physical catalyst with at least a portion of one or more spectral catalyst(s).

For example, assume that a 10 μm average particle size catalyst (e.g., seed crystal) has 50% of the activity of a 5 μm average particle size catalyst. One approach to maintain desired rates of crystallization is to use the 10 μm physical catalyst and augment the physical catalyst with at least a portion of at least one spectral catalyst. Catalyst activity can be effectively doubled (or increased even more) by the spectral catalyst, resulting in approximately the same degree of activity (or perhaps even greater activity) as with the 5 μm catalyst. Thus, the present invention permits the size of the catalyst to be changed, while retaining favorable conditions so that the reaction can be performed economically, compared to traditional prior art approaches.

Another manner to approach the issue is to eliminate the physical catalyst completely. For example, in another embodiment of the invention, a fiberoptic sieve, (e.g., one with very large pores) can be used in a flow-through reactor vessel. According to the present invention, the spectral catalyst can be emitted through the fiberoptic sieve, thus catalyzing the reacting species as they flow by. This improvement over the prior art approaches has significant processing implications including lower costs, higher rates and improved safety, to mention only a few.

Materials are also manufactured in a range of shapes, as well as sizes. Shapes include spheres, irregular granules, pellets, extrudate, and rings. Some shapes are more expensive to manufacture than others, while some shapes have superior properties (e.g., material activity, strength, etc.) than others. While spheres are inexpensive to manufacture, a packed bed of spheres produces high-pressure drops and the spheres are typically not very strong. Traditional physical catalyst rings on the other hand, have superior strength and activity and produce very little pressure drop, but they are also relatively expensive to produce.

Spectral energy catalysts permit a greater flexibility in choosing shape, for example, in a traditional chemical catalyst. For example, instead of using a packed bed of inexpensive spheres, with the inevitable high pressure drop and resulting mechanical damage to the catalyst particles, catalyst rings can be used while obtaining the same or greater catalyst activity. Using the spectral crystallization techniques described herein, particularly those related to directional growth, the shape of formed materials can be more easily controlled.

The use of spectral energy catalysts and/or spectral environmental reaction conditions to control shape of materials has the following advantages:
- permit the use of less expensive shaped material particles;
- permit the use of fewer particles overall;
- permit the use of stronger shapes of particles; and
- permit the use of particle shapes with more desirable performance characteristics.

Their use to replace existing physical catalysts has similar advantages:
- eliminate the use and expense of catalyst particles (e.g., seed crystals) altogether;
- allow use of spectral catalyst delivery systems that are faster; and
- delivery systems can be designed to incorporate superior materials characteristics.

Catalyst size and shape are also important to spectral emission patterns because all objects have an NOF depending on their size and shape. The smaller an object is in dimension, the higher its NOF will be in frequency (because speed=length× frequency). Also, two (2) objects of the same size, but different shape will have different NOF's (e.g., the resonant NOF frequency of a 1.0 m diameter sphere, is different from the NOF for a 1.0 m edged cube). Wave energies (both acoustic and EM) will have unique resonant frequencies for particular objects. The objects, such as physical catalyst particles or powder granules of reactants in a slurry, will act like antennas, absorbing and emitting energies at their structurally resonant frequencies. With this understanding, one is further able to manipulate and control the size and shape of crystallization reaction system components (e.g., physical catalysts, reactants, etc.) to achieve desired effects. For example, a transient for a desired reaction pathway may produce a spectral rotational frequency of 30 GHz. Catalyst spheres 1 cm in diameter with structural EM resonant frequency of 30 GHz ($3\times10^8$ m/s $1\times10^{-2}$ m=$30\times10^9$ Hz), can be used to direct the reaction. The catalyst particles will structurally resonate with the rotational frequency of the transient, providing energy to the transient and controlling the reaction. Likewise, the structurally resonant catalyst particles may be further energized by a spectral energy catalyst, such as, for example, 30 GHz microwave radiation. Thus understood, the spectral dynamics of chemical transformations can be much more precisely controlled than in prior art trial and error approaches.

Solvents

Typically, the term solvent is applied to mixtures for which the solvent is a liquid, however, it should be understood that solvents may also comprise solids, liquids, gases or plasmas and/or mixtures and/or components thereof. The prior art typically groups liquid solvents into three broad classes: aqueous, organic, and non-aqueous. If an aqueous solvent is used, it means that the solvent is water. Organic solvents include hydrocarbons such as alcohols and ethers. Non-aqueous solvents include inorganic non-water substances. Many chemical transformations take place in solvents.

Because solvents are themselves composed of atoms, molecules and/or ions they can have pronounced effects on chemical transformations. Solvents are comprised of matter and they emit their own spectral frequencies. The present invention teaches that these solvent frequencies undergo the same basic processes discussed earlier, including heterodyning, resonance, and harmonics. Spectroscopists have known for years that a solvent can dramatically affect the spectral frequencies produced by its' solutes. Likewise, chemists have known for years that solvents can affect catalyst activity and material properties. However, the spectroscopists and chemists in the prior art have apparently not associated these long studied changes in solute frequencies with changes in catalyst activity and material properties. The present invention recognizes that these changes in solute spectral frequencies can affect catalyst activity and chemical reactions and/or reaction pathways in general. Changes of curve intensity, gradual or abrupt shifting of the resonant frequency $f_o$, and even abrupt rearrangement of resonant frequencies can occur.

Further, the present invention recognizes that one or more spectral frequencies in a solvent may be targeted by a spectral energy pattern or spectral energy conditioning pattern to change one or more properties of the solvent, and hence may change the reaction and energy dynamics in a holoreaction system. Similarly, a spectral energy pattern or a spectral energy conditioning pattern may be applied to a solute, causing a change in one or more properties of the solute, solvent, or solute/solvent system, and hence may change the reaction and energy dynamics in a holoreaction systems.

Figure 24A:
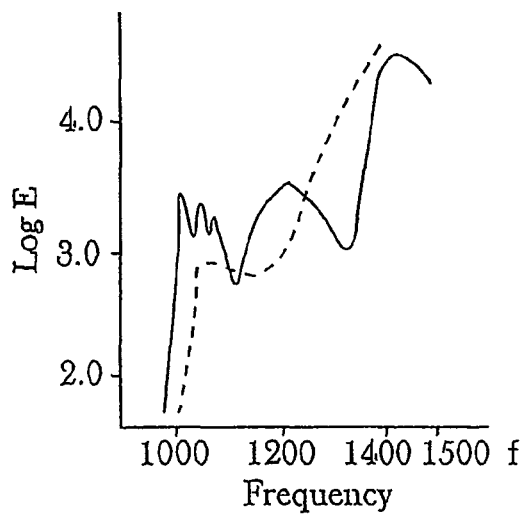
FIG. 24a shows an absorption spectra of alcohol and phthalic acid in hexane.

When reviewing FIG. 24a, the solid line represents a portion of the spectral pattern of phthalic acid in alcohol while the dotted line represents phthalic acid in the solvent hexane. Consider a phase reaction taking place in alcohol, in which the spectral catalyst resonates with phthalic acid at a frequency of 1,250, the large solid curve in the middle. If the solvent is changed to hexane, the phthalic acid no longer resonates at a frequency of 1,250 and the spectral catalyst can not stimulate and energize its phase transformation. The change in solvent will render the spectral catalyst ineffective.

Figure 24B:
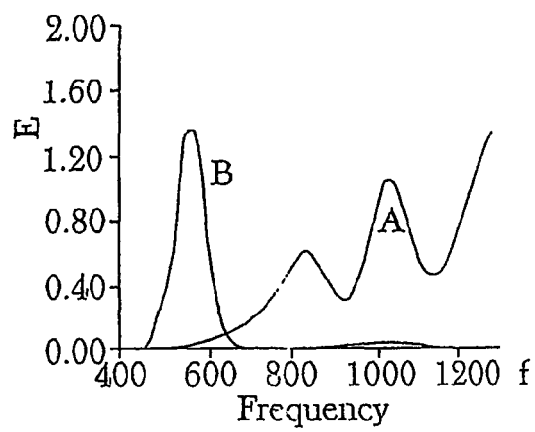
FIG. 24b shows an absorption spectra for the absorption of iodine in alcohol and carbon tetrachloride.

Similarly, in reference to FIG. 24b, iodine produces a high intensity curve at 580 when dissolved in carbon tetrachloride, as shown in curve B. In alcohol, as shown by curve A the iodine produces instead, a moderate intensity curve at 1,050 and a low intensity curve at 850. Accordingly, assume that a reaction uses a spectral catalyst that resonates directly with the iodine in carbon tetrachloride at 580 for an organohalide crystallization. If the spectral catalyst does not change and the solvent is changed to alcohol, the spectral catalyst will no longer function because frequencies no longer match and energy will not transfer. Specifically, the spectral catalyst's frequency of 580 will no longer match and resonate with the new iodine frequencies of 850 and 1,050.

There is also the possibility that the change in the solvent could bring the catalyst into resonance with a different chemical species and help the reaction proceed down an alternative reaction pathway.

Figure 24C:
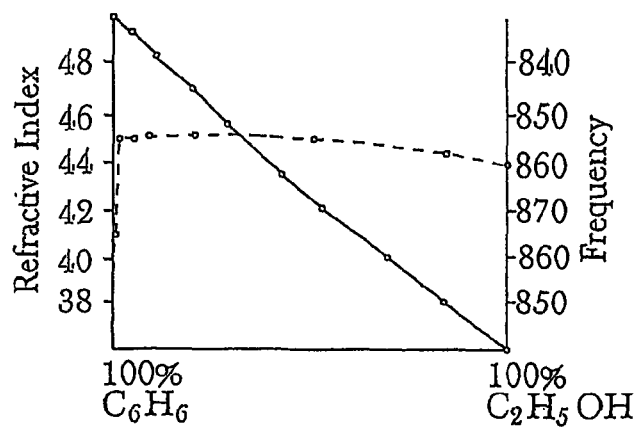
FIG. 24c shows the effect of mixtures of alcohol and benzene on the solute phenylazophenol.

Finally, consider the graph in FIG. 24c, which shows a variety of solvent mixtures ranging from 100% benzene at the far left, to a 50:50 mixture of benzene and alcohol in the center, to 100% alcohol at the far right. The solute is phenylazophenol. The phenylazophenol has a frequency of 855-860 for most of the solvent mixtures. For a 50:50 benzene:alcohol mixture the frequency is 855; or for a 98:2 benzene:alcohol mixture the frequency is still 855. However, at 99.5:0.5 benzene:alcohol mixture, the frequency abruptly changes to about 865. A spectral catalyst active in 100% benzene by resonating with the phenylazophenol at 865, will lose its activity if there is even a slight amount of alcohol (e.g., 0.5%) in the solvent.

Thus understood, the principles of spectral chemistry presented herein can be applied to catalysis, and reactions and/or reaction pathways in general. Instead of using the prior art trial and error approach to the choice of solvents and/or other crystallization reaction system components, solvents can be tailored and/or modified to optimize the spectral environmental reaction conditions. For example, a reaction may be designed to have a key reaction participant (e.g., reaction vessel) which resonates at 400 THz, while the catalyst (e.g., seed crystal) resonates at 800 THz transferring energy harmonically. A more efficient system could be designed with a different solvent that may cause the resonant frequencies of both the participant and the catalyst to abruptly shift to 600 THz. There the catalyst would resonate directly with the participant, transferring even more energy, and catalyzing the crystallization reaction system more efficiently.

Further, the properties of solvents, solutes, and solvent/solute systems may be affected by spectral energy providers. Water is the universal solvent. It is commonly known and understood that if water is heated, its kinetic energy increases, and hence, the rate at which solutes dissolve also increases. After a solute has been added to a solvent, such as water, physical properties such as pH and conductivity change at a rate related to their kinetic energy and the temperature of the solute/solvent system.

A novel aspect of the present invention is the understanding that the properties of solvents, solutes and solvent/solute systems may be affected and controlled by spectral energy providers outside the realm of simple thermal or kinetic mechanisms. For example, water at about 28° C. will dissolve salt (sodium chloride) at a particular rate. Water at about 28° C. which has been conditioned with its own vibrational overtones will dissolve salt faster, even though there is no apparent difference in temperature. Similarly, if salt is added to water, there is a predictable rate of change in the pH and conductivity of the solution. If the water is conditioned or spectrally activated with its own vibrational overtones, either before or after, respectively, the addition of the salt, the rate of change of pH and conductivity is enhanced even though there is no difference in temperature. These effects are shown in greater detail in the Examples section herein.

Further, if the salt is conditioned with some of its own electronic frequencies prior to adding it to water, the rate of change of conductivity is again enhanced, even though there is again no apparent difference in temperature. These effects are shown in greater detail in the Examples section herein.

In general, delivery of spectral energy patterns and/or spectral energy conditioning patterns to solvents, solutes: and solvent/solute systems may change the energy dynamics of the solvent and/or solute and hence their properties in a holoreaction system. These spectral techniques disclosed herein can be used to control many aspects of matter transformations such as chemical reactions, phase changes, and material properties (all of which are described in the Examples section herein).

Support Materials

Traditional physical catalysts can be either unsupported or supported. An unsupported catalyst is a formulation of the pure catalyst, with substantially no other molecules present. Unsupported catalysts are rarely used industrially because these catalysts generally have low surface area and hence low activity. The low surface area can result from, for example, sintering, or coalescence of small molecules of the catalyst into larger particles in a process which reduces surface tension of the particles. An example of an unsupported catalyst is platinum alloy gauze, which is sometimes used for the selective oxidation of ammonia to nitric oxide. Another example is small silver granules, sometimes used to catalyze the reaction of methanol with air, to form formaldehyde. When the use of unsupported catalysts is possible, their advantages include straightforward fabrication and relatively simple installation in various industrial processes.

A supported catalyst is a formulation of the catalyst with other particles, the other particles acting as a supporting skeleton for the catalyst. Traditionally, the support particles are thought to be inert, thus providing a simple physical scaffolding for the catalyst molecules. Thus, one of the traditional functions of the support material is to give the catalyst shape and mechanical strength. The support material is also said to reduce sintering rates. If the catalyst support is finely divided similar to the catalyst, the support will act as a "spacer" between the catalyst particles, and hence prevent sintering. An alternative theory holds that an interaction takes place between the catalyst and support, thereby preventing sintering. This theory is supported by the many observations that catalyst activity is altered by changes in support material structure and composition.

Supported catalysts are generally made by one or more of the following three methods: impregnation, precipitation, and/or crystallization. Impregnation techniques use preformed support materials, which are then exposed to a solution containing the catalyst or its precursors. The catalyst or precursors diffuse into the pores of the support. Heating, or another conversion process, drives off the solvent and transforms the catalyst or precursors into the final catalyst. The most common support materials for impregnation are refractory oxides such as aluminas and aluminum hydrous oxides. These support materials have found their greatest use for catalysts that must operate under extreme conditions such as steam reforming, because they have reasonable mechanical strengths.

Precipitation techniques use concentrated solutions of catalyst salts (e.g., usually metal salts). The salt solutions are rapidly mixed and then allowed to precipitate in a finely divided form. The precipitate is then prepared using a variety of processes including washing, filtering, drying, heating, and pelleting. Often a graphitic lubricant is added. Precipitated catalysts have high catalytic activity secondary to high surface area, but they are generally not as strong as impregnated catalysts.

Figure 25A:
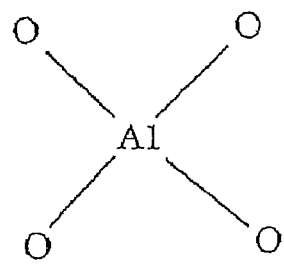
FIG. 25a shows a tetrahedral unit representation of aluminum oxide and FIG. 25b shows a representation of a tetrahedral unit for silicon dioxide.
Figure 25B:
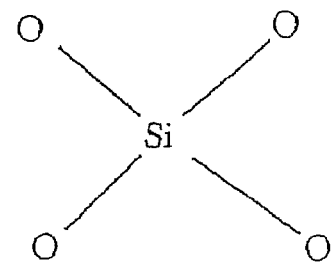
Figure 26A:
FIG. 26a shows a truncated octahedron crystal structure for aluminum or silicon combined with oxygen and FIG. 26b shows a plurality of truncated octahedrons joined together to represent zeolite.
Figure 26B:
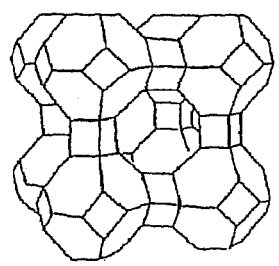
Figure 26C:
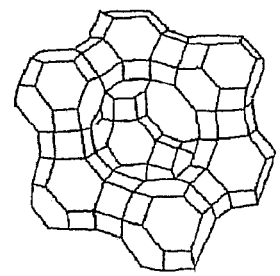
FIG. 26c shows truncated octahedrons for zeolites "X" and "Y" which are joined together by oxygen bridges.

Traditional crystallization techniques produce support materials called zeolites. The structure of these crystallized catalyst zeolites is based on $SiO_4$ and $AlO_4$ (see FIG. 25a which shows the tetrahedral units of silicon; and FIG. 25b which shows the tetrahedral units of aluminum). These units link in different combinations to form structural families, which include rings, chains, and complex polyhedra. For example, the $SiO_4$ and $AlO_4$ tetrahderal units can form truncated octahedron structures, which form the building blocks for A, X, and Y zeolites (see FIG. 26a which shows a truncated octahedron structure with lines representing oxygen atoms and corners are Al or Si atoms; FIG. 26b which shows zeolite with joined truncated octahedrons joined by oxygen bridges between square faces; and FIG. 26c which shows zeolites X and Y with joined truncated octahedrons joined by oxygen bridges between hexagonal faces).

The crystalline structure of zeolites gives them a well defined pore size and structure. This differs from the varying pore sizes found in impregnated or precipitated support materials. Zeolite crystals are made by mixing solutions of silicates and aluminates and the catalyst. Crystallization is generally induced by heating (see spectral effects of temperature in the Section entitled "Temperature"). The structure of the resulting zeolite depends on the silicon/aluminum ratio, their concentration, the presence of added catalyst, the temperature, and even the size of the reaction vessels used, all of which are environmental reaction conditions. Zeolites generally have greater specificity than other catalyst support materials (e.g., they do not just speed up the reaction). They also may steer the reaction towards a particular reaction pathway.

Spectral crystallization methods can be used to affect and control the formation of desired materials such as, for example, zeolites. The processes taught herein can, for example, crystallize materials faster, more economically, in greater numbers, with more convenient environmental factors (e.g., lower temperatures for zeolite), with more precise control of poisons or promoters, and with desired material properties, etc.

Support materials can affect the activity of a catalyst. Traditionally, the prior art has attributed these effects to geometric factors. However, according to the present invention, there are spectral factors to consider as well. It has been well established that solvents affect the spectral patterns produced by their solutes. Solvents can be liquids, solids, gases and/or plasmas Support materials can, in many cases, be viewed as nothing more than solid solvents for catalysts. As such, support materials can affect the spectral patterns produced by their solute catalysts.

Just as dissolved sugar can be placed into a solid phase solvent (ice), catalysts can be placed into support materials that are solid phase solvents. These support material solid solvents can have similar spectral effects on catalysts that liquid solvents have. Support materials can change spectral frequencies of their catalyst solutes by, for example, causing spectral curve broadening, changing of curve intensity, gradual or abrupt shifting of the resonant frequency $f_o$, and even abrupt rearrangement of resonant frequencies.

Further, uses of spectral techniques to affect matter transformations are not limited to solvent/solute or support/catalysts systems, but rather apply broadly to all material systems and phases of matter, and their respective properties (e.g., chemical, physical, electrical, magnetic, thermal, etc.).

The use of targeted spectral techniques in numerous materials systems (including solid, liquid and gas to control chemical reactions, phase changes and material properties (e.g., chemical physical, electrical, thermal, etc.) is described more fully in the Examples section later herein.

Support materials can be simply viewed as solid solvents for their catalyst solutes. The present invention teaches that spectral techniques can be used to control many aspects of matter transformation in solvent/solute systems such as chemical reactions, phase changes, and material properties. Similarly, spectral techniques can be used to control many aspects such as chemical reactions, phase changes, and material properties of support/catalyst systems. These spectral techniques can be used to affect the synthesis of support/catalyst systems, or to affect the subsequent properties of the support/catalyst system in a holoreaction system.

Additionally, in transformations of matter, substrates are often used as a base for the growth of a desired species (e.g., epitaxial substrates). The methods taught herein can be used to control and direct interactions of materials with substrates. For example, if the spectral frequencies of a crystallization reaction system participant are caused to emanate from an amorphous surface (which traditionally does not support formation of the desired crystalline species), crystals may be caused to form and adhere to that surface. In this manner, it should be understood that methods applied to support materials apply also to substrates of all kinds.

Thus, due to the disclosure herein, it should become clear to an artisan of ordinary skill that changes in support materials can have dramatic effects on catalyst activity. The support materials affect the spectral frequencies produced by the catalysts. The changes in catalyst spectral frequencies produce varying effects on chemical reactions and catalyst activity, including accelerating the rate of reaction and also guiding the reaction on a particular reaction path. Thus support materials can potentially influence the matching of frequencies and can thus favor the possibility of transferring energy between crystallization reaction system components and/or spectral energy patterns, thus permitting certain reactions to occur.

Poisoning

Poisoning of catalysts occurs when the catalyst activity is reduced by adding a small amount of another constituent, such as a chemical species. The prior art has attributed poisoning to chemical species that contain excess electrons (e.g., electron donor materials) and to adsorption of poisons onto the physical catalyst surface where the poison physically blocks reaction sites. However, neither of these theories satisfactorily explains poisoning.

Consider the case of nickel hydrogenation catalysts. These physical catalysts are substantially deactivated if only 0.1% sulphur compounds by weight are adsorbed onto them. It is difficult to believe that 0.1% sulphur by weight could contribute so many electrons as to inactivate the nickel catalyst. Likewise, it is difficult to believe that the presence of 0.1% sulphur by weight occupies so many reaction sites that it completely deactivates the catalyst. Accordingly, neither prior art explanation is satisfying.

Poisoning phenomena can be more logically understood in terms of spectral chemistry. In reference to the example in the Solvent Section using a benzene solvent and phenylazophenol as the solute, in pure benzene the phenylazophenol had a spectral frequency of 865 Hz. The addition of just a few drops of alcohol (0.5%) abruptly changed the phenylazophenol frequency to 855. If the expectation was for the phenylazophenol to resonate at 865, then the alcohol would have poisoned that particular reaction. The addition of small quantities of other chemical species can change the resonant frequencies ($f_0$) of catalysts and reacting chemicals. The addition of another chemical species can act as a poison to take the catalyst and reacting species out of resonance (i.e., the presence of the additional species can remove any substantial overlapping of frequencies and thus prevent any significant transfer of energy).

Figure 27:
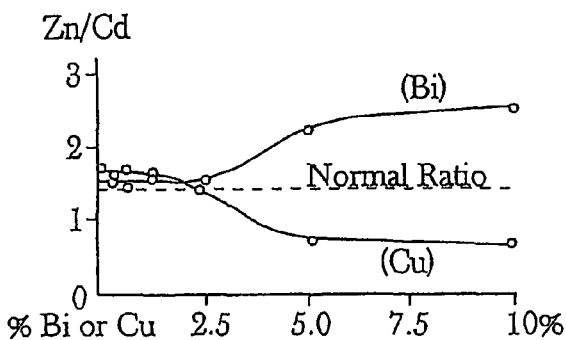
FIG. 27 is a graph which shows the influence of copper and bismuth on zinc/cadmium line ratios.

Besides changing resonant frequencies of chemical species, adding small amounts of other chemicals can also affect the spectral intensities of the catalyst and, for example, other atoms and molecules in the crystallization reaction system by either increasing or decreasing the spectral intensities. Consider cadmium and zinc mixed in an alumina-silica precipitate (see FIG. 27 which shows the influences of copper and bismuth on the zinc/cadmium line ratio). A normal ratio between the cadmium 3252.5 spectral line and the zinc 3345.0 spectral line was determined. The addition of sodium, potassium, lead, and magnesium had little or no effect on the Cd/Zn intensity ratio. However, the addition of copper reduced the relative intensity of the zinc line and increased the cadmium intensity. Conversely, addition of bismuth increased the relative intensity of the zinc line while decreasing cadmium.

Figure 28:
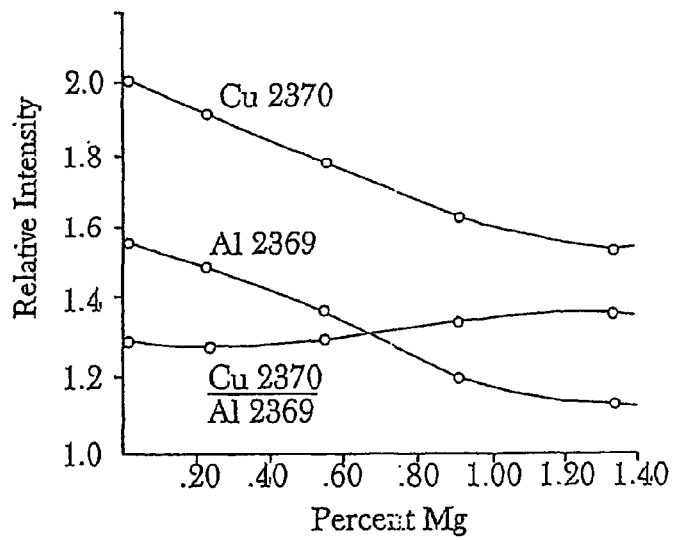
FIG. 28 is a graph which shows the influence of magnesium on copper/aluminum intensity ratio.

Also, consider the effect of small amounts of magnesium on a copper-aluminum mixture (see FIG. 28 which shows the influence of magnesium on the copper aluminum intensity ratio). Magnesium present at 0.6%, caused significant reductions in line intensity for copper and for aluminum. At 1.4% magnesium, the spectral intensities for both copper and aluminum were reduced by about a third. If the copper frequency is important for catalyzing a reaction, adding this small amount of magnesium would dramatically reduce the catalyst activity. Thus, it could be concluded that the copper catalyst had been poisoned by the magnesium.

In summary, poisoning effects on catalysts are due to spectral changes. Adding a small amount of another chemical species to a physical catalyst and/or crystallization reaction system can change the resonance frequencies or the spectral intensities of one or more chemical species (e.g., reactant). The catalyst might remain the same, while a crucial intermediate is changed. Likewise, the catalyst might change, while the intermediate stays the same. They might both change, or they might both stay the same and be oblivious to the added poison species. This understanding is important to achieving the goals of the present invention which include targeting species to cause an overlap in frequencies, or in this instance, specifically targeting one or more species so as to prevent any substantial overlap in frequencies and thus prevent reactions from occurring by blocking the transfer of energy.

Promoters

Just as adding a small amount of another chemical species to a catalyst and crystallization reaction system can poison the activity of the catalyst, the opposite can also happen. When an added species enhances the activity of a catalyst, it is called a promoter. For instance, adding a few percent calcium and potassium oxide to iron-alumina compounds promotes activity of the iron catalyst for ammonia synthesis. Promoters act by all the mechanisms discussed previously in the Sections entitled Solvents, Support Materials, and Poisoning. Not surprisingly, some support materials actually are promoters. Promoters enhance catalysts and specific reactions and/or reaction pathways by changing spectral frequencies and intensities. While a catalyst poison takes the reacting species out of resonance (i.e., the frequencies do not overlap), the promoter brings them into resonance (i.e., the frequencies do overlap). Likewise, instead of reducing the spectral intensity of crucial frequencies, the promoter may increase the crucial intensities.

Thus, if it was desired for phenylazophenol to react at 855 in a benzene solvent, alcohol could be added and the alcohol would be termed a promoter. If it was desired for the phenylazophenol too react at 865, alcohol could be added and the alcohol could be considered a poison. Thus understood, the differences between poisons and promoters are a matter of perspective, and depend on which reaction pathways and/or reaction products are desired. They both act by the same underlying spectral chemistry mechanisms of the present invention.

Similarly, in crystallization and material transformation systems, addition of small amounts of other species can change reaction dynamics. For example, NaCl structure can be modified from cubic to pyramidal or octahedral by the addition of small amounts of boron. Similarly, spectral irradiation (and hence activation) of NaCl solution through a boron containing substrate (borosilicate glass) may cause typical boron modification of NaCl structure to become pyramidal or octahedral, even though no boron is physically present in the solution. A spectral boron pattern can substitute for the effects of a boron crystallizing agent in the actual solution.

Thus understood, poisons, promoters, and all manner of crystallization agents affect crystallization reaction system pathways through spectral mechanisms, which can be duplicated, approximated, or initiated.

Concentrations

Figure 29:
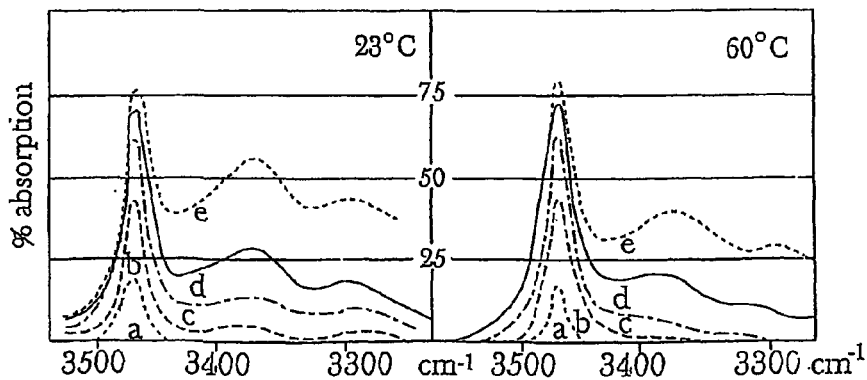
FIG. 29 shows the concentration effects on the atomic spectra frequencies of N-methyl urethane in carbon tetrachloride solutions at the following concentrations: a) 0.01M; b) 0.03M; c) 0.06M; d) 0.10M; 3) 0.15M.

Concentrations of chemical species are known to affect reaction rates and dynamics. Concentration also affects catalyst activity. The prior art explains these effects by the probabilities that various chemical species will collide with each other. At high concentrations of a particular species, there are many individual atoms or molecules present. The more atoms or molecules present, the more likely they are to collide with something else. However, this statistical treatment by the prior art does not explain the entire situation. FIG. 29 shows various concentrations of N-methyl urethane in a carbon tetrachloride solution. At low concentrations, the spectral lines have a relatively low intensity. However, as the concentration is increased, the intensities of the spectral curves increase also. At 0.01 molarity, the spectral curve at 3,460 cm$^{-1}$ is the only prominent frequency. However, at 0.15 molarity, the curves at 3,370 and 3,300 cm$^{-1}$ are also prominent.

As the concentration of a chemical species is changed, the spectral character of that species in the reaction mixture changes also. Suppose that 3,300 and 3,370 cm$^{-1}$ are important frequencies for a desired reaction pathway. At low concentrations the desired reaction pathway will not occur. However, if the concentrations are increased (and hence the intensities of the relevant frequencies) the reaction will proceed down the desired pathway. Concentration is also related to solvents, support structures, poisons and promoters, as previously discussed.

Similarly, as discussed previously, the intensity of spectral emissions in a holoreaction system affects species attraction and phase transformations. The effects of increased concentration can be mimicked spectrally. For example, crystallization can be caused to occur in unsaturated solutions, wherein crystallization does not normally occur. Further, by controlling the material transformation spectrally in the absence of the inherently chaotic process which normally takes place in a saturated solution, structure and morphology can be more easily controlled.

Fine Structure Frequencies

The field of science concerned generally with measuring the frequencies of energy and matter, known as spectroscopy, has already been discussed herein. Specifically, the three broad classes of atomic and molecular spectra were reviewed. Electronic spectra, which are due to electron transitions, have frequencies primarily in the ultraviolet (UV), visible, and infrared (IR) regions, and occur in atoms and molecules. Vibrational spectra, which are due to, for example, bond motion between individual atoms within molecules, are primarily in the IR, and occur in molecules. Rotational spectra are due primarily to rotation of molecules in space and have microwave or radiowave frequencies, and also occur in molecules.

The previous discussion of various spectra and spectroscopy has been oversimplified. There are actually at least three additional sets of spectra, which comprise the spectrum discussed above herein, namely, the fine structure spectra and the hyperfine structure spectra and the superfine structure spectra. These spectra occur in atoms and molecules, and extend, for example, from the ultraviolet down to the low radio regions. These spectra are often mentioned in prior art chemistry and spectroscopy books typically as an aside, because prior art chemists typically focus more on the traditional types of spectroscopy, namely, electronic, vibrational, and rotational.

The fine and hyperfine spectra are quite prevalent in the areas of physics and radio astronomy. For example, cosmologists map the locations of interstellar clouds of hydrogen, and collect data regarding the origins of the universe by detecting signals from outerspace, for example, at 1.420 GHz, a microwave frequency which is one of the hyperfine splitting frequencies for hydrogen. Most of the large databases concerning the microwave and radio frequencies of molecules and atoms have been developed by astronomers and physicists, rather than by chemists. This apparent gap between the use by chemists and physicists, of the fine and hyperfine spectra in chemistry, has apparently resulted in prior art chemists not giving much, if any, attention to these potentially useful spectra.

Figure 30A:
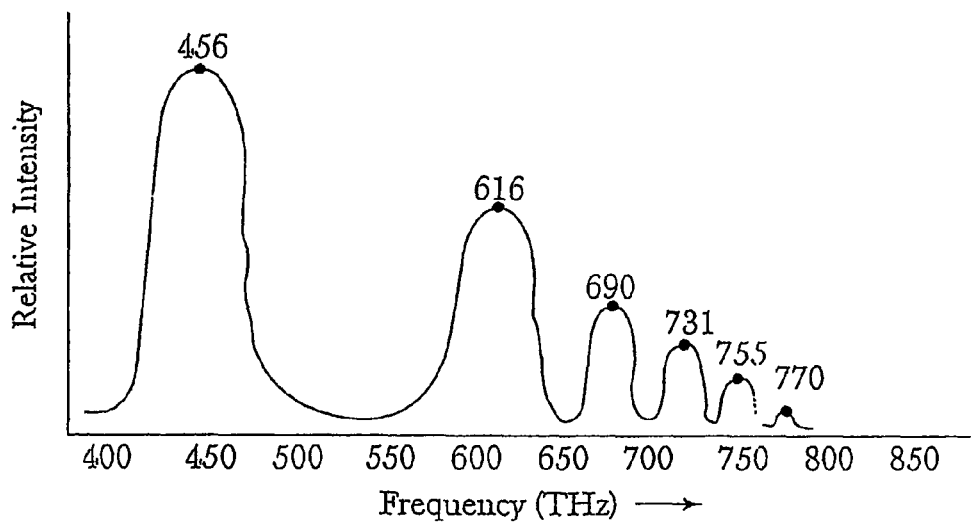
FIG. 30 shows plots corresponding to the emission spectrum of hydrogen. Specifically, FIG. 30a corresponds to Balmer Series 2 for hydrogen.
FIG. 30b corresponds to emission spectrum for the 456 THz frequency of hydrogen.
Figure 30B:
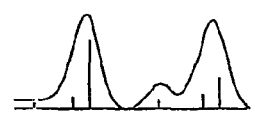
Figure 31:
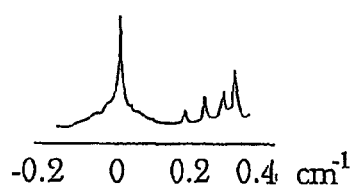
FIG. 31 corresponds to a high resolution laser saturation spectrum for the 456 THz frequency of hydrogen.

Referring again to FIGS. 9a and 9b, the Balmer series (i.e., frequency curve II), begins with a frequency of 456 THz (see FIG. 30a). Closer examination of this individual frequency shows that instead of there being just one crisp narrow curve at 456 THz, there are really seven different curves very close together that comprise the curve at 456 THz. The seven (7) different curves are fine structure frequencies. FIG. 30b shows the emission spectrum for the 456 THz curve in hydrogen. A high-resolution laser saturation spectrum, shown in FIG. 31, gives even more detail. These seven different curves, which are positioned very close together, are generally referred to as a multiplet.

Although there are seven different fine structure frequencies shown, these seven frequencies are grouped around two major frequencies. These are the two, tall, relatively high intensity curves shown in FIG. 30b. These two high intensity curves are also shown in FIG. 31 at zero cm$^{-1}$ (456.676 THz), and at relative wavenumber 0.34 cm$^{-1}$ (456.686 THz). What appears to be a single frequency of (456 THz), is actually composed predominantly of two slightly different frequencies (456.676 and 456.686 THz), and the two frequencies are typically referred to as doublet and the frequencies are said to be split. The difference or split between the two predominant frequencies in the hydrogen 456 THz doublet is 0.010 THz (100 THz) or 0.34 cm$^{-1}$ wavnumbers. This difference frequency, 10 GHz, is called the fine splitting frequency for the 456 THz frequency of hydrogen.

Figure 32:
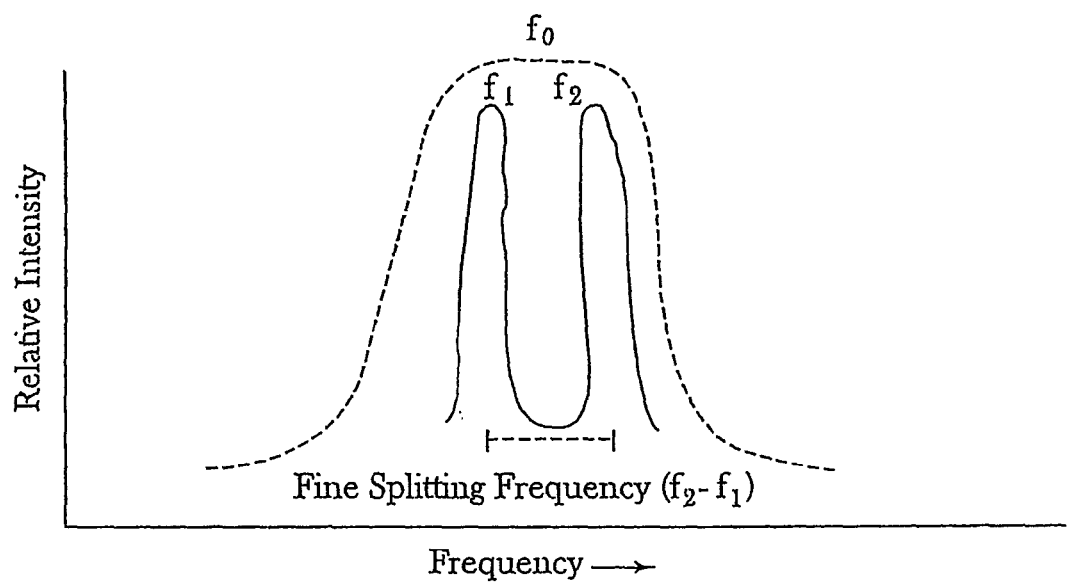
FIG. 32 shows fine splitting frequencies which exist under a typical spectral curve.

Thus, the individual frequencies that are typically shown in ordinary electronic spectra are composed of two or more distinct frequencies spaced very close together. The distinct frequencies spaced very close together are called fine structure frequencies. The difference, between two fine structure frequencies that are split apart by a very slight amount, is a fine splitting frequency (see FIG. 32 which shows $f_1$ and $f_2$ which comprise $f_0$ and which are shown as underneath $f_0$. The difference between $f_1$ and $f_2$ is known as the fine splitting frequency). This "difference" between two fine structure frequencies is important because such a difference between any two frequencies is a heterodyne.

Almost all the hydrogen frequencies shown in FIGS. 9a and 9b are doublets or multiplets. This means that almost all the hydrogen electronic spectrum frequencies have fine structure frequencies and fine splitting frequencies (which means that these heterodynes are available to be used as spectral catalysts, if desired). The present invention discloses that these "differences" or heterodynes can be quite useful for certain reactions. However, prior to discussing the use of these heterodynes, in the present invention, more must be understood about these heterodynes. Some of the fine splitting frequencies (i.e., heterodynes) for hydrogen are listed in Table 3. These fine splitting heterodynes range from the microwave down into the upper reaches of the radio frequency region.

TABLE 3

Fine Splitting Frequencies for Hydrogen

| Frequency (THz) | Orbital | Wavenumber (cm$^{-1}$) | Fine Splitting Frequency |
|---|---|---|---|
| 2,466 | 2p | 0.365 | 10.87 GHz |
| 456 | n2→3 | 0.340 | 10.02 GHz |
| 2,923 | 3p | 0.108 | 3.23 GHz |
| 2,923 | 3d | 0.036 | 1.06 GHz |
| 3,082 | 4p | 0.046 | 1.38 GHz |
| 3,082 | 4d | 0.015 | 448.00 MHz |
| 3,082 | 4f | 0.008 | 239.00 MHz |

There are more than 23 fine splitting frequencies (i.e., heterodynes) for just the first series or curve I in hydrogen. Lists of the fine splitting heterodynes can be found, for example, in the classic 1949 reference "Atomic Energy Levels" by Charlotte Moore. This reference also lists 133 fine splitting heterodyned intervals for carbon, whose frequencies range from 14.1 THz (473.3 cm$^{-1}$) down to 12.2. GHz (0.41 cm$^{-1}$). Oxygen has 287 fine splitting heterodynes listed from 15.9 THz (532.5 cm$^{-1}$) down to 3.88 GHz (0.13 cm$^{-1}$). The 23 platinum fine splitting intervals detailed are from 23.3 THz (775.9 cm$^{-1}$) to 8.62 THz in frequency (287.9 cm$^{-1}$).

Figure 33:
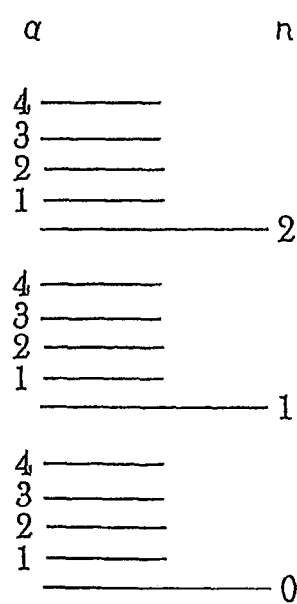
FIG. 33 corresponds to a diagram of atomic electron levels (n) in fine structure frequencies (a).
Figure 34:
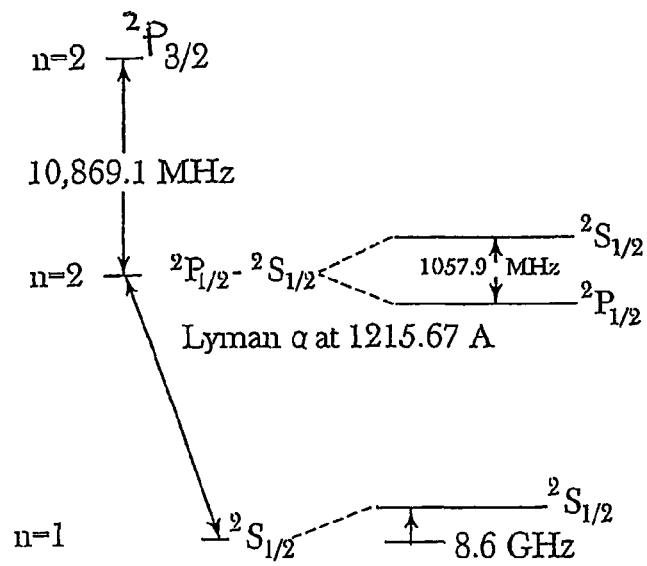
FIG. 34 shows fine structures of the n=1 and n=2 levels of a hydrogen atom.
Figure 35:
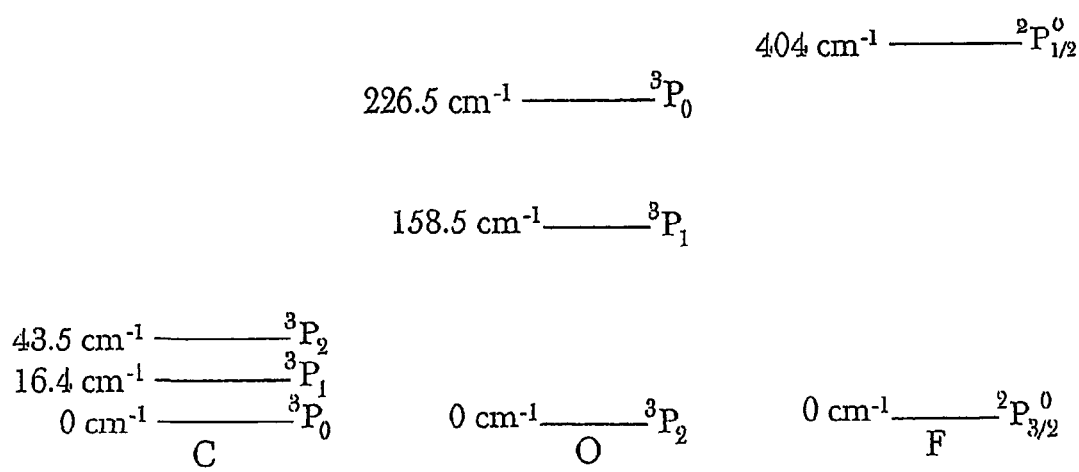
FIG. 35 shows multiplet splittings for the lowest energy levels of carbon, oxygen and fluorine: 43.5 cm=1.3 THz; 16.4 $cm^1$ 490 GHz; 226.5 $cm^{-1}$=6.77 THz; 158.5 $cm^{-1}$=4.74 THz; 404 $cm^{-1}$=12.1 THz.

Diagrammatically, the magnification and resolution of an electronic frequency into several closely spaced fine frequencies is depicted in FIG. 33. The electronic orbit is designated by the orbital number n=0, 1, 2, etc. The fine structure is designated as α. A quantum diagram for the hydrogen fine structure is shown in FIG. 34. Specifically, shown is the fine structure of the n=1 and n=2 levels of the hydrogen atom. FIG. 35 shows the multiplet splittings for the lowest energy levels of carbon, oxygen, and fluorine, as represented by "C", "O" and "F", respectively.

In addition to the fine splitting frequencies for atoms (i.e., heterodynes), molecules also have similar fine structure frequencies. The origin and derivation for molecular fine structure and splitting is different from that for atoms, however, the graphical and practical results are quite similar. In atoms, the fine structure frequencies are said to result from the interaction of the spinning electron with its' own magnetic field. Basically, this means the electron cloud of a single atomic sphere, rotating and interacting with its' own magnetic field, produces the atomic fine structure frequencies. The prior art refers to this phenomena as "spin-orbit coupling". For molecules, the fine structure frequencies correspond to the actual rotational frequencies of the electronic or vibrational frequencies. So the fine structure frequencies for atoms and molecules both result from rotation. In the case of atoms, it is the atom spinning and rotating around itself, much the way the earth rotates around its axis. In the case of molecules, it is the molecule spinning and rotating through space.

Figure 36:
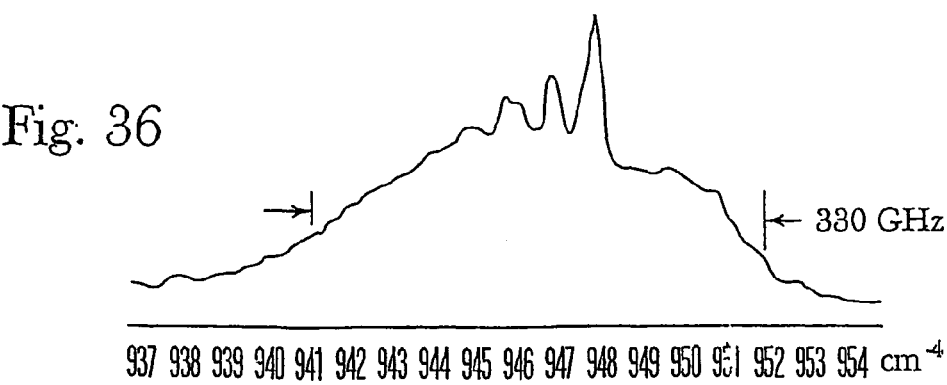
FIG. 36 shows a vibration band of $SF_6$ at a wavelength of 10 $\mu m^2$.

FIG. 36 shows the infrared absorption spectrum of the $SF_6$ vibration band near 28.3 THz (10.6 μm wavelength, wavenumber 948 $cm^{-1}$) of the $SF_6$ molecule. The molecule is highly symmetrical and rotates somewhat like a top. The spectral tracing was obtained with a high resolution grating spectrometer. There is a broad band between 941 and 952 $cm^{-1}$ (28.1 and 28.5 THz) with three sharp spectral curves at 946, 947, and 948 $cm^{-1}$ (28.3, 28.32, and 23.834 THz).

Figure 37A:
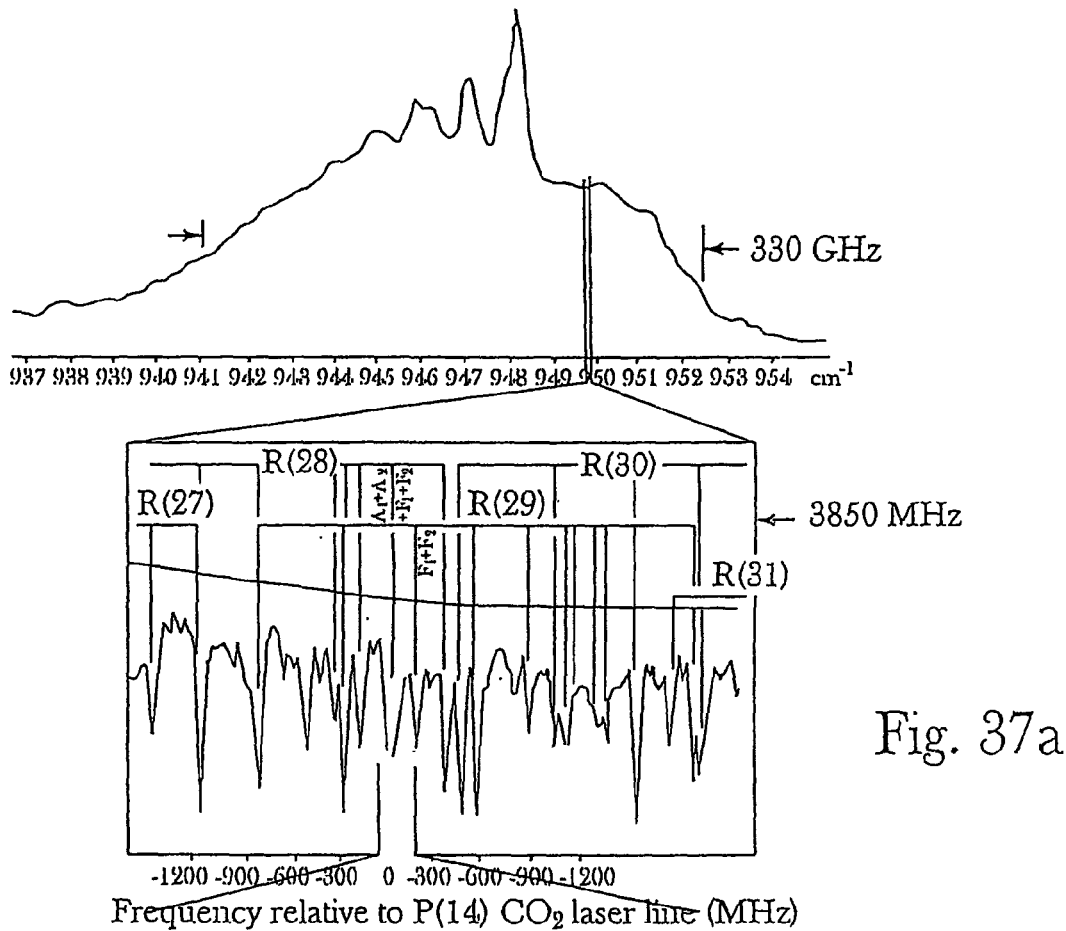
FIG. 37a shows a spectral pattern similar to that shown in FIG. 36, with a particular frequency magnified.
Figure 37B:
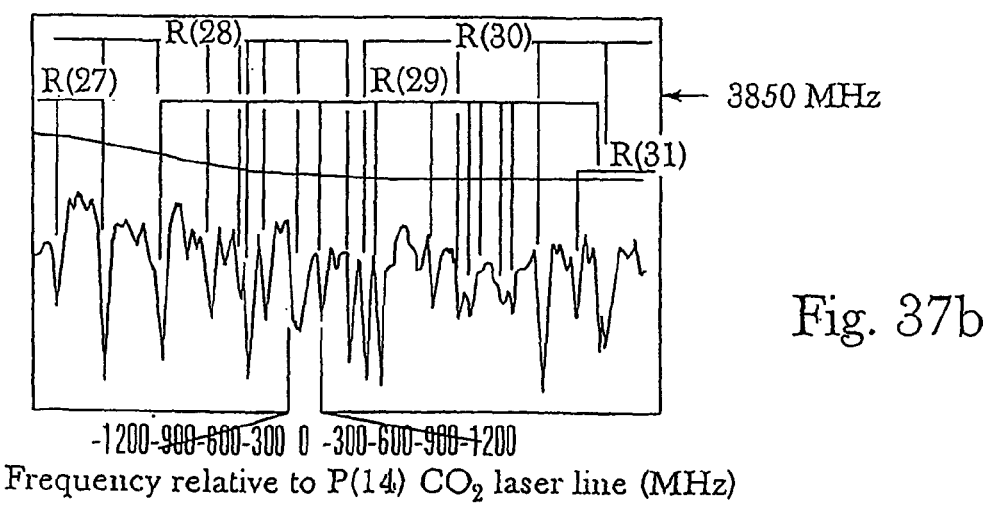
FIG. 37b shows fine structure frequencies in greater detail for the compound $SF_6$.
Figure 38:
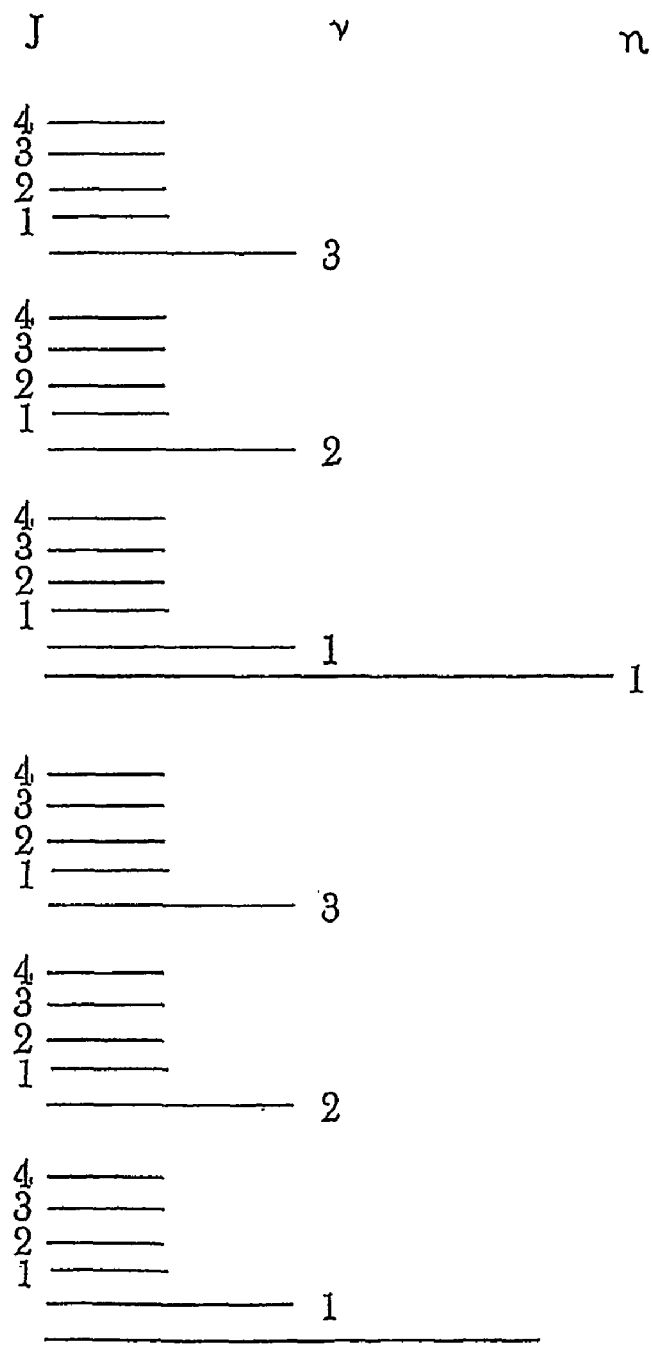
FIG. 38 shows an energy level diagram which corresponds to different energy levels for a molecule where rotational corresponds to "J", vibrational corresponds to "v" and electronic levels correspond to "n".

FIG. 37a shows a narrow slice being taken from between 949 and 950 $cm^{-1}$, which is blown up to show more detail in FIG. 37b. A tunable semiconductor diode laser was used to obtain the detail. There are many more spectral curves which appear when the spectrum is reviewed in finer detail. These curves are called the fine structure frequencies for this molecule. The total energy of an atom or molecule is the sum of its' electronic, vibrational, and rotational energies. Thus, the simple Planck equation discussed previously herein:

$$E=hv$$

can be rewritten as follows:

$$E=E_e+E_v+E_r$$

where E is the total energy, $E_e$ is the electronic energy, $E_v$ is the vibrational energy, and $E_r$ is the rotational energy. Diagrammatically, this equation is shown in FIG. 38 for molecules. The electronic energy, $E_e$, involves a change in the orbit of one of the electrons in the molecule. It is designated by the orbital number n=0, 1, 2, 3, etc. The vibrational energy, $E_v$, is produced by a change in the vibration rate between two atoms within the molecule, and is designated by a vibrational number v=1, 2, 3, etc. Lastly, the rotational energy, $E_r$, is the energy of rotation caused by the molecule rotating around its' center of mass. The rotational energy is designated by the quantum number J=1, 2, and 3, etc., as determined from angular momentum equations.

Thus, by examining the vibrational frequencies of $SP_6$ in more detail, the fine structure molecular frequencies become apparent. These fine structure frequencies are actually produced by the molecular rotations, "J", as a subset of each vibrational frequency. Just as the rotational levels "J" are substantially evenly separated in FIG. 38, they are also substantially evenly separated when plotted as frequencies.

Figure 39A:
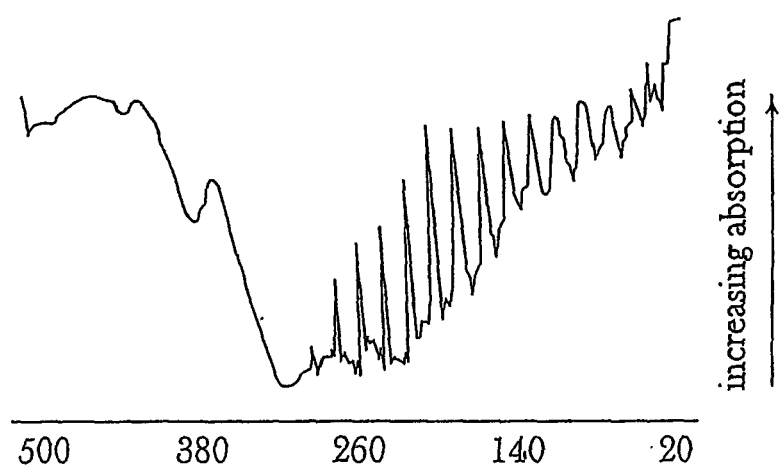
FIGS. 39a and 39b correspond to pure rotational absorption spectrum of gaseous hydrogen chloride as recorded with an interferometer.
Figure 39B:
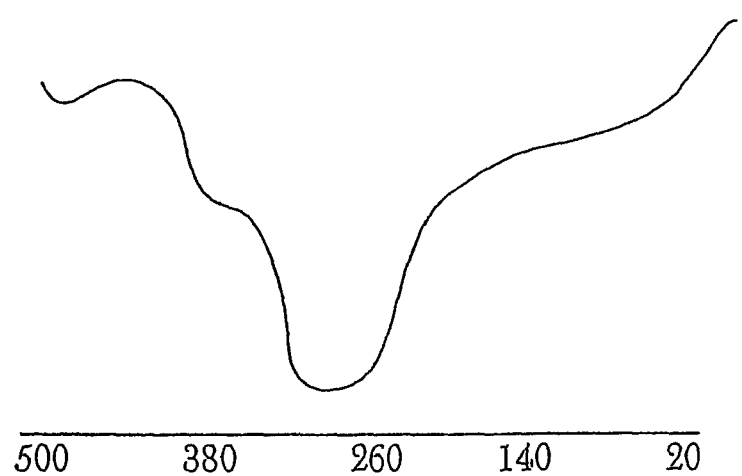

This concept may be easier to understand by viewing some additional frequency diagrams. For example, FIG. 39a shows the pure rotational absorption spectrum for gaseous hydrogen-chloride and FIG. 39b shows the same spectrum at low resolution. In FIG. 39a, the separate waves, that look something like teeth on a "comb", correspond to the individual rotational frequencies. The complete wave (i.e., that wave comprising the whole comb) that extends in frequency from 20 to 500 $cm^{-1}$ corresponds to the entire vibrational frequency. At low resolution or magnification, this set of rotational frequencies appear to be a single frequency peaking at about 20 $cm^{-1}$ (598 GHz) (see FIG. 39b). This is very similar to the way atomic frequencies such as the 456 THz hydrogen frequency appear (i.e., just one frequency at low resolution, that turn out to be several different frequencies at higher magnification).

Figure 40:
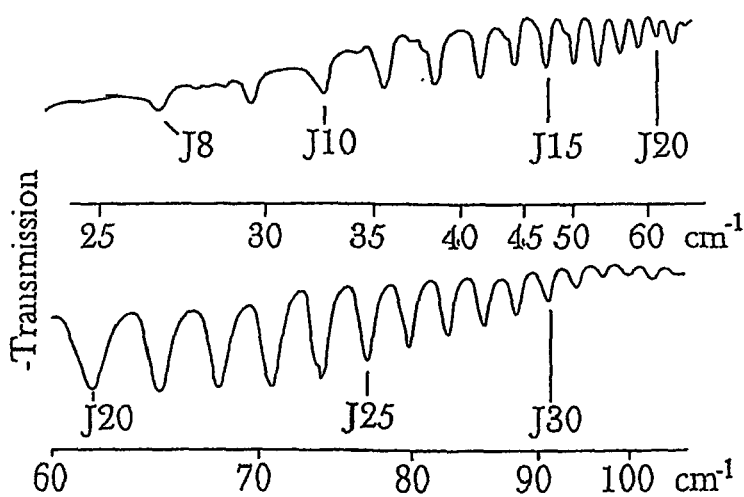
FIG. 40 corresponds to the rotational spectrum for hydrogen cyanide. "J" corresponds to the rotational level.

In FIG. 40, the rotational spectrum (i.e., fine structure) of hydrogen cyanide is shown, where "J" is the rotational level. Note again, the regular spacing of the rotational levels. (Note that this spectrum is oriented opposite of what is typical). This spectrum uses transmission rather than emission on the horizontal Y-axis, thus, intensity increases downward on the Y-axis, rather than upwards.

Figure 41:
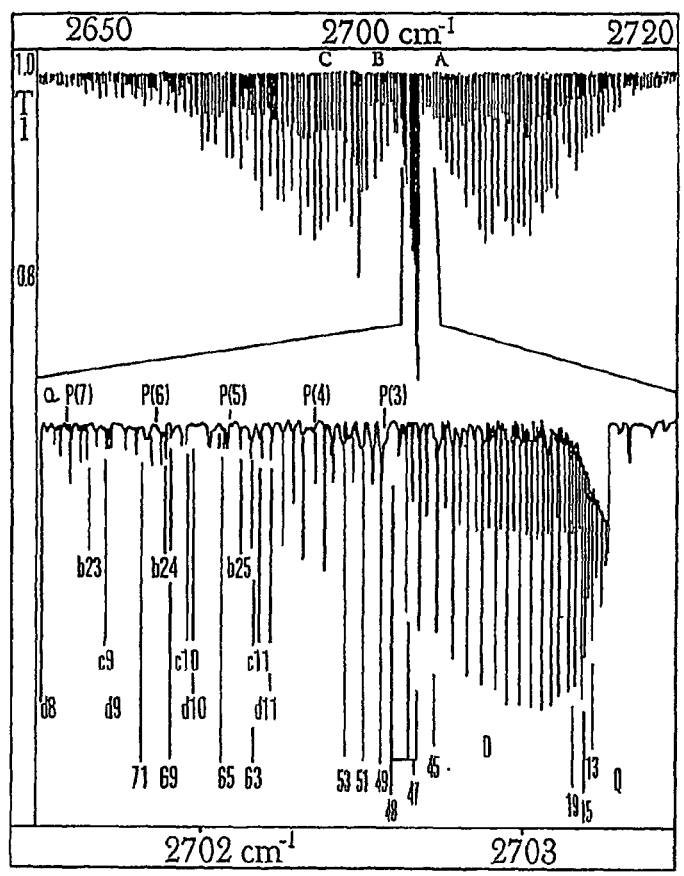
FIG. 41 shows a spectrum corresponding to the additive heterodyne of $v_1$ and $v_5$ in the spectral band showing the frequency band at A ($v_1$-v5), B=$v_1-2v_5$.

Additionally, FIG. 41 shows the $v_1$-$v_5$ vibrational bands for FCCF (where $v_1$ is vibrational level 1 and $v_5$ vibrational level 5) which includes a plurality of rotational frequencies. All of the fine sawtooth spikes are the fine structure frequencies which correspond to the rotational frequencies. Note the substantially regular spacing of the rotational frequencies. Also note, the undulating pattern of the rotational frequency intensity, as well as the alternating pattern of the rotational frequency intensities.

Consider the actual rotational frequencies (i.e., fine structure frequencies) for the ground state of carbon monoxide listed in Table 4.

TABLE 4

Rotational Frequencies and Derived Rotational Constant for CO in the Ground State

| J Transition | Frequency (MHz) | Frequency (GHz) |
|---|---|---|
| 0 → 1 | 115,271.204 | 115 |
| 1 → 2 | 230,537.974 | 230 |
| 2 → 3 | 345,795.989 | 346 |
| 3 → 4 | 461,040.811 | 461 |
| 4 → 5 | 576,267.934 | 576 |
| 5 → 6 | 691,472.978 | 691 |
| 6 → 7 | 806,651.719 | 807 |

Where; $B_o$ = 57,635.970 MHz

Each of the rotational frequencies is regularly spaced at approximately 115 GHz apart. Prior art quantum theorists would explain this regular spacing as being due to the fact that the rotational frequencies are related to Planck's constant and the moment of inertia (i.e., center of mass for the molecule) by the equation:

$$B = \frac{h}{8\pi^2 I}$$

where B is the rotational constant, h is Planck's constant, and I is the moment of inertia for the molecule. From there the prior art established a frequency equation for the rotational levels that corresponds to:

$$f=2B(J+1)$$

where f is the frequency, B is the rotational constant, and J is the rotational level. Thus, the rotational spectrum (i.e., fine structure spectrum) for a molecule turns out to be a harmonic series of lines with the frequencies all spaced or split (i.e., heterodyned) by the same amount. This amount has been referred to in the prior art as "2B", and "B" has been referred to as the "rotational constant". In existing charts and databases of molecular frequencies, "B" is usually listed as a frequency such as MHz. This is graphically represented for the first four rotational frequencies for CO in FIG. 42.

This fact is interesting for several reasons. The rotational constant "B", listed in many databases, is equal to one half of the difference between rotational frequencies for a molecule. That means that B is the first subharmonic frequency, to the fundamental frequency "2B", which is the heterodyned difference between all the rotational frequencies. The rotational constant B listed for carbon monoxide is 57.6 GHz (57,635.970 MHz). This is basically half of the 115 GHz difference between the rotational frequencies. Thus, according to the present invention, if it is desired to stimulate a molecule's rotational levels, the amount "2B" can be used, because it is the fundamental first generation heterodyne. Alternatively, the same "B" can be used because "B" corresponds to the first subharmonic of that heterodyne.

Further, the prior art teaches that if it is desired to use microwaves for stimulation, the microwave frequencies used will be restricted to stimulating levels at or near the ground state of the molecule (i.e., n=0 in FIG. 38). The prior art teaches that as you progress upward in FIG. 38 to the higher electronic and vibrational levels, the required frequencies will correspond to the infrared, visible, and ultraviolet regions. However, the prior art is wrong about this point.

By referring to FIG. 38 again, it is clear that the rotational frequencies are evenly spaced out no matter what electronic or vibrational level is under scrutiny. The even spacing shown in FIG. 38 is due to the rotational frequencies being evenly spaced as progression is made upwards through all the higher vibrational and electronic levels. Table 5 lists the rotational frequencies for lithium fluoride (LiF) at several different rotational and vibrational levels.

TABLE 5

Rotational Frequencies for Lithium Fluoride (LiF)

| Vibrational Level | Rotational Transition | Frequency (MHz) |
|---|---|---|
| 0 | 0 → 1 | 89,740.46 |
| 0 | 1 → 2 | 179,470.35 |
| 0 | 2 → 3 | 269,179.18 |
| 0 | 3 → 4 | 358,856.19 |
| 0 | 4 → 5 | 448,491.07 |
| 0 | 5 → 6 | 538,072.65 |
| 1 | 0 → 1 | 88,319.18 |
| 1 | 1 → 2 | 176,627.91 |
| 1 | 2 → 3 | 264,915.79 |
| 1 | 3 → 4 | 353,172.23 |
| 1 | 4 → 5 | 441,386.83 |
| 2 | 0 → 1 | 86,921.20 |
| 2 | 1 → 2 | 173,832.04 |
| 2 | 2 → 3 | 260,722.24 |
| 2 | 3 → 4 | 347,581.39 |
| 3 | 1 → 2 | 171,082.27 |
| 3 | 2 → 3 | 256,597.84 |
| 3 | 3 → 4 | 342,082.66 |

It is clear from Table 5 that the differences between rotational frequencies, no matter what the vibrational level, is about 86,000 to about 89,000 MHz (i.e., 86-89 GHz). Thus, according to the present invention, by using a microwave frequency between about 86,000 MHz and 89,000 MHz, the molecule can be stimulated from the ground state level all the way up to its' highest energy levels. This effect has not been even remotely suggested by the prior art. Specifically, the rotational frequencies of molecules can be manipulated in a unique manner. The first rotational level has a natural oscillatory frequency (NOF) of 89,740 MHz. The second rotational level has an NOF of 179,470 MHz. Thus, $NOF_{rotational\ 1\to 2} - NOF_{rotational\ 0\to 1} =$ Subtracted Frequency$_{rotation\ 2-1}$;

or 179,470 MHz−89,740 MHz=89,730 MHz.

Thus, the present invention has discovered that the NOF's of the rotational frequencies heterodyne by adding and subtracting in a manner similar to the manner that all frequencies heterodyne. Specifically, the two rotational frequencies heterodyne to produce a subtracted frequency. This subtracted frequency happens to be exactly twice as big as the derived rotational constant "B" listed in nuclear physics and spectroscopy manuals. Thus, when the first rotational frequency in the molecule is stimulated with the Subtracted Frequency$_{rotational\ 2-1}$, the first rotational frequency will heterodyne (i.e., in this case add) with the NOF$_{rotational\ 0\to 1}$ (i.e., first rotational frequency) to produce NOF$_{rotational\ 1\to 2}$, which is the natural oscillatory frequency of the molecule's second rotational level. In other words:

Subtracted Frequency$_{rotational\ 2-1}$+$NOF_{rotational\ 0\to 1}$=$NOF_{rotational\ 1\to 2}$;

or 89,730 MHz+89,740 MHz=179,470 MHz

Since the present invention has disclosed that the rotational frequencies are actually evenly spaced harmonics, the subtracted frequency will also add with the second level NOF to produce the third level NOF. The subtracted frequency will add with the third level NOF to produce the fourth level NOF. This procedure can be repeated over and over. Thus, according to the present invention, by using one single microwave frequency, it is possible to stimulate all the rotational levels in a vibratory band.

Moreover, if all the rotational levels for a vibrational frequency are excited, then the vibrational frequency will also be correspondingly excited. Further, if all the vibrational levels for an electronic level are excited, then the electronic level will be excited as well. Thus, according to the teachings of the present invention, it is possible to excite the highest levels of the electronic and vibrational structure of a molecule by using a single microwave frequency. This is contrary to the prior art teachings that the use of microwaves is restricted to the ground state of the molecule. Specifically, if the goal is to resonate directly with an upper vibrational or electronic level, the prior art teaches that microwave frequencies can not be used. If, however, according to the present invention, a catalytic mechanism of action is initiated by, for example, resonating with target species indirectly through heterodynes, then one or more microwave frequencies can be used to energize at least one upper level vibrational or electronic state. Accordingly, by using the teachings of the present invention in conjunction with the simple processes of heterodyning it becomes readily apparent that microwave frequencies are not limited to the ground state levels of molecules.

Figure 42:
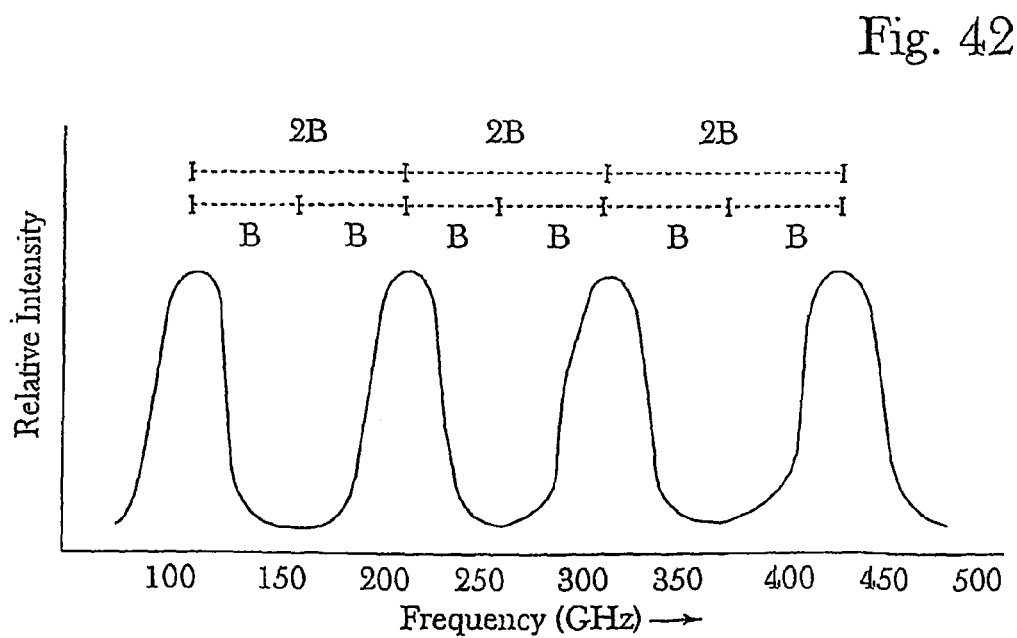
FIG. 42 shows a graphical representation of fine structure spectrum showing the first four rotational frequencies for CO in the ground state. The difference (heterodyne) between the molecular fine structure rotational frequencies is 2× the rotational constant B (i.e., $f_2-f_1$=2B). In this case, B=57.6 GHz (57,635.970 MHz).

The present invention has determined that catalysts can actually stimulate target species indirectly by utilizing at least one heterodyne frequency (e.g., harmonic). However, catalysts can also stimulate the target species by direct resonance with at least one fundamental frequency of interest. However, the rotational frequencies can result in use of both mechanisms. For example, FIG. 42 shows a graphical representation of fine structure spectrum showing the first four rotational frequencies for CO in the ground state. The first rotational frequency for CO is 115 GHz. The heterodyned difference between rotational frequencies is also 115 GHz. The first rotational frequency and the heterodyned difference between frequencies are identical. All of the upper level rotational frequencies are harmonics of the first frequency. This relationship is not as apparent when one deals only with the rotational constant "B" of the prior art. However, frequency-based spectral chemistry analyses, like those of the present invention, makes such concepts easier to understand.

Examination of the first level rotational frequencies for LiF shows that it is nearly identical to the heterodyned difference between it and the second level rotational frequency. The rotational frequencies are sequential harmonics of the first rotational frequency. Accordingly, if a molecule is stimulated with a frequency equal to 2B (i.e., a heterodyned harmonic difference between rotational frequencies) the present invention teaches that energy will resonate with all the upper rotational frequencies indirectly through heterodynes, and resonate directly with the first rotational frequency. This is an important discovery.

The prior art discloses a number of constants used in spectroscopy that relate in some way or another to the frequencies of atoms and molecule, just as the rotational constant "B" relates to the harmonic spacing of rotational fine structure molecular frequencies. The alpha ($\alpha$) rotation-vibration constant is a good example of this. The alpha rotation-vibration frequency constant is related to slight changes in the frequencies for the same rotational level, when the vibrational level changes. For example, FIG. 43a shows the frequencies for the same rotational levels, but different vibrational levels for LiF. The frequencies are almost the same, but vary by a few percent between the different vibrational levels.

Referring to FIG. 43b, the differences between all the frequencies for the various rotational transitions at different vibrational levels of FIG. 43a are shown. The rotational transition 0→1 in the top line of FIG. 43b has a frequency of 89,740.46 MHz at vibrational level 0. At vibrational level 1, the 0→1 transition is 88,319.18 MHz. The difference between these two rotational frequencies is 1,421.28 MHz. At vibrational level 2, the 0→1 transition is 86,921.20 MHz. The difference between it and the vibrational level 1 frequency (88,319.18 MHz) is 1,397.98 MHz. These slight differences for the same J rotational level between different vibrational levels are nearly identical. For the J=0→1 rotational level they center around a frequency of 1,400 MHz.

For the J=1→2 transition, the differences center around 2,800 Hz, and for the J=2→3 transition, the differences center around 4,200 Hz. These different frequencies of 1,400, 2,800 and 4,200, Hz etc., are all harmonics of each other. Further, they are all harmonics of the alpha rotation-vibration constant. Just as the actual molecular rotational frequencies are harmonics of the rotational constant B, the differences between the rotational frequencies are harmonics of the alpha rotation-vibration constant. Accordingly, if a molecule is stimulated with a frequency equal to the alpha vibration-rotation frequencies, the present invention teaches that energy will resonate with all the rotational frequencies indirectly through heterodynes. This is an important discovery.

Figure 44:
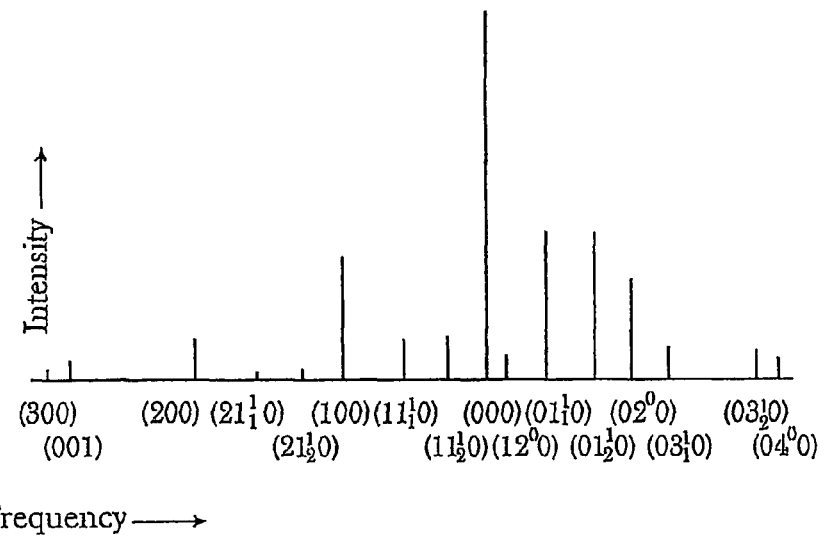
FIG. 44 shows the rotational transition J=1→2 for the triatomic molecule OCS. The vibrational state is given by vibrational quantum numbers in brackets ($v_1, v_2, v_3$), $v_2$ have a superscript [1]. In this case, l=1. A subscript 1 is applied to the lower-frequency component of the l-type doublet, and 2 to the higher-frequency components. The two lines at $(01^10)$ and $(01^10)$ are an l-type doublet, separated by $q_l$.

Consider the rotational and vibrational states for the triatomic molecule OCS shown in FIG. 44. FIG. 44 shows the same rotational level (J=1→2) for different vibrational states in the OCS molecule. For the ground vibrational (000) level, J=1→2 transition; and the excited vibrational state (100) J=1→2 transition, the difference between the two frequencies is equal to 4× alpha$_1$ (4 $\alpha_1$). In another excited state, the frequency difference between the ground vibrational (000) level, J=1→2 transition, and the center of the two l-type doublets is 4× alpha$_2$ (4$\alpha_2$). In a higher excited vibrational state, the frequency difference between (000) and (02°0) is 8× alpha$_2$ (8$\alpha_2$). Thus, it can be seen that the rotation-vibration constants "$\alpha$" are actually harmonics of molecular frequencies. Thus, according to the present invention, stimulating a molecule with an "$\alpha$" frequency, or a harmonic of "$\alpha$", will either directly resonate with or indirectly heterodyne harmonically with various rotational-vibrational frequencies of the molecule.

Another interesting constant is the l-type doubling constant. This constant is also shown in FIG. 44. Specifically, FIG. 44 shows the rotational transition J=1→2 for the triatomic molecule OCS. Just as the atomic frequencies are sometimes split into doublets or multiplets, the rotational frequencies are also sometimes split into doublets. The difference between them is called the l-type doubling constant. These constants are usually smaller (i.e., of a lower frequency) than the a constants. For the OCS molecule, the a constants are 20.56 and 10.56 MHz while the l-type doubling constant is 6.3 MHz. These frequencies are all in the radiowave portion of the electromagnetic spectrum.

As discussed previously herein, energy is transferred by two fundamental frequency mechanisms. If frequencies are substantially the same or match, then energy transfers by direct resonance. Energy can also transfer indirectly by heterodyning, (i.e., the frequencies substantially match after having been added or subtracted with another frequency). Further, as previously stated, the direct or indirect resonant frequencies do not have to match exactly. If they are merely close, significant amounts of energy will still transfer. Any of these constants or frequencies that are related to molecules or other matter via heterodynes, can be used to transfer, for example, energy to the matter and hence can directly interact with the matter.

In the reaction in which hydrogen and oxygen are combined to form water, the present invention teaches that the energizing of the reaction intermediates of atomic hydrogen and the hydroxy radical are crucial to sustaining the reaction. In this regard, the physical catalyst platinum energizes both reaction intermediates by directly and indirectly resonating with them. Platinum also energizes the intermediates at multiple energy levels, creating the conditions for energy amplification. The present invention also teaches how to copy platinum's mechanism of action by making use of atomic fine structure frequencies.

The invention has previously discussed resonating with the fine structure frequencies with only slight variations between the frequencies (e.g., 456.676 and 456.686 THz). However, indirectly resonating with the fine structure frequencies, is a significant difference. Specifically, by using the fine splitting frequencies, which are simply the differences or heterodynes between the fine structure frequencies, the present invention teaches that indirect resonance can be achieved. By examining the hydrogen 456 THz fine structure and fine splitting frequencies (see, for example, FIGS. 30 and 31 and Table 3 many heterodynes are shown). In other words, the difference between the fine structure frequencies can be calculated as follows:

$$456.686 \text{ THz} - 456.676 \text{ THz} = 0.0102 \text{ THz} = 10.2 \text{ GHz}$$

Thus, if hydrogen atoms are subjected to 10.2 GHz electromagnetic energy (i.e., energy corresponding to microwaves), then the 456 THz electronic spectrum frequency is energized by resonating with it indirectly. In other words, the 10.2 GHz will add to 456.676 THz to produce the resonant frequency of 456.686 THz. The 10.2 GHz will also subtract from the 456.686 THz to produce the resonant frequency of 456.676 THz. Thus, by introducing 10.2 GHz to a hydrogen atom, the hydrogen atom is excited at the 456 THz frequency. A microwave frequency can be used to stimulate an electronic level.

According to the present invention, it is also possible to use a combination of mimicked catalyst mechanisms. For example, it is possible to: 1) resonate with the hydrogen atom frequencies indirectly through heterodynes (i.e., fine splitting frequencies); and/or 2) resonate with the hydrogen atom at multiple frequencies. Such multiple resonating could occur using a combination of microwave frequencies either simultaneously, in sequence, and/or in chirps or bursts. For example, the individual microwave fine splitting frequencies for hydrogen of 10.87 GHz, 10.2 GHz, 3.23 GHz, 1.38 GHz, and 1.06 GHz could be used in a sequence. Further, there are many fine splitting frequencies for hydrogen that have not been expressly included herein, thus, depending on the frequency range of equipment available, the present invention provides a means for tailoring the chosen frequencies to the capabilities of the available equipment. Thus, the flexibility according to the teachings of the present invention is enormous.

Another method to deliver multiple electromagnetic energy frequencies according to the present invention, is to use a lower frequency as a carrier wave for a higher frequency. This can be done, for example, by producing 10.2 GHz EM energy in short bursts, with the bursts coming at a rate of about 239 MHz. Both of these frequencies are fine splitting frequencies for hydrogen. This can also be achieved by continuously delivering EM energy and by varying the amplitude at a rate of about 239 MHz. These techniques can be used alone or in combination with the various other techniques disclosed herein.

Thus, by mimicking one or more mechanisms of action of catalysts and by making use of the atomic fine structure and splitting frequencies, it is possible to energize upper levels of atoms using microwave and radiowave frequencies. Accordingly, by selectively energizing or targeting particular atoms, it is possible to catalyze and guide desirable reactions to desired end products. Depending on the circumstances, the option to use lower frequencies may have many advantages. Lower frequencies typically have much better penetration into large reaction spaces and volumes, and may be better suited to large-scale industrial applications. Lower frequencies may be easier to deliver with portable, compact equipment, as opposed to large, bulky equipment which delivers higher frequencies (e.g., lasers). The choice of frequencies of a spectral catalyst may be for as simple a reason as to avoid interference from other sources of EM energy. Thus, according to the present invention, an understanding of the basic processes of heterodyning and fine structure splitting frequencies confers greater flexibility in designing and applying spectral energy catalysts in a targeted manner. Specifically, rather than simply reproducing the spectral pattern of a physical catalyst, the present invention teaches that is possible to make full use of the entire range of frequencies in the electromagnetic spectrum, so long as the teachings of the present invention are followed. Thus, certain desirable frequencies can be applied while other not so desirable frequencies could be left out of an applied spectral energy catalyst targeted to a particular participant and/or component in the crystallization reaction system.

As a further example, reference is again made to the hydrogen and oxygen reaction for the formation of water. If it is desired to catalyze the water reaction by duplicating the catalyst's mechanism of action in the microwave region, the present invention teaches that several options are available. Another such option is use of the knowledge that platinum energizes the reaction intermediates of the hydroxy radical. In addition to the hydrogen atom, the B frequency for the hydroxy radical is 565.8 GHz. That means that the actual heterodyned difference between the rotational frequencies is 2B, or 1,131.6 GHz. Accordingly, such a frequency could be utilized to achieve excitement of the hydroxy radical intermediate.

Further, the a constant for the hydroxy radical is 21.4 GHz. Accordingly, this frequency could also be applied to energizing the hydroxy radical. Thus, by introducing hydrogen and oxygen gases into a chamber and irradiating the gases with 21.4 GHz, water will be formed. This particular gigahertz energy is a harmonic heterodyne of the rotational frequencies for the same rotational level but different vibrational levels. The heterodyned frequency energizes all the rotational frequencies, which energize the vibrational levels, which energize the electronic frequencies, which catalyze the reaction. Accordingly, the aforementioned reaction could be catalyzed or targeted with a spectral catalyst applied at several applicable frequencies, all of which match with one or more frequencies in one or more participants and thus permit energy to transfer.

Still further, delivery of frequencies of 565.8 GHz, or even 1,131.6 GHz, would result in substantially all of the rotational levels in the molecule becoming energized, from the ground state all the way up. This approach copies a catalyst mechanism of action in two ways. The first way is by energizing the hydroxy radical and sustaining a crucial reaction intermediate to catalyze the formation of water. The second mechanism copied from the catalyst is to energize multiple levels in the molecule. Because the rotational constant "B" relates to the rotational frequencies, heterodynes occur at all levels in the molecule. Thus, using the frequency "B" energizes all levels in the molecule. This potentiates the establishment of an energy amplification system such as that which occurs with the physical catalyst platinum.

Still further, if a molecule was energized with a frequency corresponding to an l-type doubling constant, such frequency could be used in a substantially similar manner in which a fine splitting frequency from an atomic spectrum is used. The difference between the two frequencies in a doublet is a heterodyne, and energizing the doublet with its' heterodyne frequency (i.e., the splitting frequency) would energize the basic frequency and catalyze the reaction.

A still further example utilizes a combination of frequencies for atomic fine structure. For instance, by utilizing a constant central frequency of 1,131.6 GHz (i.e., the heterodyned difference between rotational frequencies for a hydroxy radical) with a vibrato varying around the central frequency by ±21.4 GHz (i.e., the α constant harmonic for variations between rotational frequencies), use could be made of 1.131.6 GHz EM energy in short bursts, with the bursts coming at a rate of 21.4 GHz.

Since there is slight variation between rotational frequencies for the same level, that frequency range can be used to construct bursts. For example, if the largest "B" is 565.8 GHz, then a rotational frequency heterodyne corresponds to 1,131.6 GHz. If the smallest "B" is 551.2 GHz, this corresponds to a rotational frequency heterodyne of 1,102 GHz. Thus, "chirps" or bursts of energy starting at 1,100 GHz and increasing in frequency to 1,140 GHz, could be used. In fact, the transmitter could be set to "chirp" or burst at a rate of 21.4 GHz.

As previously discussed, fine and fine splitting frequencies can also be used in crystallization reaction systems to achieve desired results.

In any event, there are many ways to make use of the atomic and molecular fine structure frequencies, with their attendant heterodynes and harmonics. An understanding of catalyst mechanisms of action enables one of ordinary skill armed with the teachings of the present invention to utilize a spectral catalyst from the high frequency ultraviolet and visible light regions, down into the sometimes more manageable microwave and radiowave regions. Moreover, the invention enables an artisan of ordinary skill to calculate and/or determine the effects of microwave and radiowave energies on chemical reactions and/or reaction pathways.

Hyperfine Frequencies

Hyperfine structure frequencies are similar to the fine structure frequencies. Fine structure frequencies can be seen by magnifying a portion of a standard frequency spectrum. Hyperfine frequencies can be seen by magnifying a portion of a fine structure spectrum. Fine structure splitting frequencies occur at lower frequencies than the electronic spectra, primarily in the infrared and microwave regions of the electromagnetic spectrum. Hyperfine splitting frequencies occur at even lower frequencies than the fine structure spectra, primarily in the microwave and radio wave regions of the electromagnetic spectrum. Fine structure frequencies are generally caused by at least the electron interacting with its' own magnetic field. Hyperfine frequencies are generally caused by at least the electron interacting with the magnetic field of the nucleus.

Figure 45:
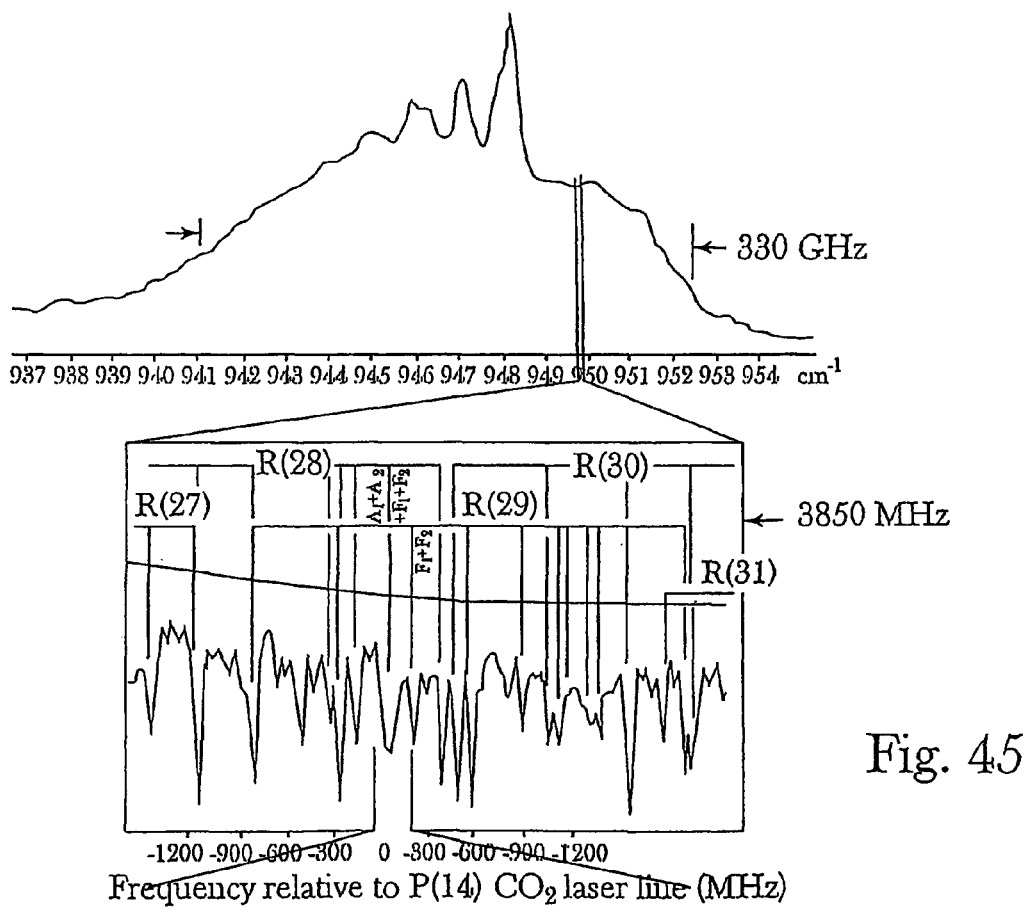
FIG. 45 shows the rotation-vibration band and fine structure frequencies for $SF_6$.

FIG. 36 shows the rotation-vibration band frequency spectra for an $SF_6$ molecule. The rotation-vibration band and fine structure are shown again in FIG. 45. However, the fine structure frequencies are seen by magnifying a small section of the standard vibrational band spectrum (i.e., the lower portion of FIG. 45 shows some of the fine structure frequencies). In many respects, looking at fine structure frequencies is like using a magnifying glass to look at a standard spectrum. Magnification of what looks like a flat and uninteresting portion of a standard vibrational frequency band shows many more curves with lower frequency splitting. These many other curves are the fine structure curves. Similarly, by magnifying a small and seemingly uninteresting portion of the fine structure spectrum of the result is yet another spectrum of many more curves known as the hyperfine spectrum.

A small portion (i.e., from zero to 300) of the $SF_6$ fine structure spectrum is magnified in FIG. 46. The hyperfine spectrum includes many curves split part by even lower frequencies. This time the fine structure spectrum was magnified instead of the regular vibrational spectrum. What is found is even more curves, even closer together. FIGS. 47a and 47b show a further magnification of the two curves marked with asterisks (i.e., "*" and "**") in FIG. 46.

What appears to be a single crisp curve in FIG. 46, turns out to be a series of several curves spaced very close together. These are the hyperfine frequency curves. Accordingly, the fine structure spectra is comprised of several more curves spaced very close together. These other curves spaced even closer together correspond to the hyperfine frequencies.

FIGS. 47a and 47b show that the spacing of the hyperfine frequency curves are very close together and at somewhat regular intervals. The small amount that the hyperfine curves are split apart is called the hyperfine splitting frequency. The hyperfine splitting frequency is also a heterodyne. This concept is substantially similar to the concept of the fine splitting frequency. The difference between two curves that are split apart is called a splitting frequency. As before, the difference between two curves is referred to as a heterodyne frequency. So, hyperfine splitting frequencies are all heterodynes of hyperfine frequencies.

Because the hyperfine frequency curves result from a magnification of the fine structure curves, the hyperfine splitting frequencies occur at only a fraction of the fine structure splitting frequencies. The fine structure splitting frequencies are really just several curves, spaced very close together around the regular spectrum frequency. Magnification of fine structure splitting frequencies results in hyperfine splitting frequencies. The hyperfine splitting frequencies are really just several more curves, spaced very close together. The closer together the curves are, the smaller the distance or frequency separating them. Now the distance separating any two curves is a heterodyne frequency. So, the closer together any two curves are, the smaller (lower) is the heterodyne frequency between them. The distance between hyperfine splitting frequencies (i.e., the amount that hyperfine frequencies are split apart) is the hyperfine splitting frequency. It can also be called a constant or interval.

The electronic spectrum frequency of hydrogen is 2,466 THz. The 2,466 THz frequency is made up of fine structure curves spaced 10.87 GHz (0.01087 THz) apart. Thus, the fine splitting frequency is 10.87 GHz. Now the fine structure curves are made up of hyperfine curves. These hyperfine curves are spaced just 23.68 and 59.21 MHz apart. Thus, 23 and 59 MHz are both hyperfine splitting frequencies for hydrogen. Other hyperfine splitting frequencies for hydrogen include 2.71, 4.21, 7.02, 17.55, 52.63, 177.64, and 1,420.0 MHz. The hyperfine splitting frequencies are spaced even closer together than the fine structure splitting frequencies, so the hyperfine splitting frequencies are smaller and lower than the fine splitting frequencies.

Thus, the hyperfine splitting frequencies are lower than the fine splitting frequencies. This means that rather than being in the infrared and microwave regions, as the fine splitting frequencies can be, the hyperfine splitting frequencies are in the microwave and radiowave regions. These lower frequencies are in the MHz ($10^6$ hertz) and Khz ($10^3$ hertz) regions of the electromagnetic spectrum. Several of the hyperfine splitting frequencies for hydrogen are shown in FIG. 48. (FIG. 48 shows hyperfine structure in the n=2 to n=3 transition of hydrogen).

FIG. 49 shows the hyperfine frequencies for $CH_3I$. These frequencies are a magnification of the fine structure frequencies for that molecule. Since fine structure frequencies for molecules are actually rotational frequencies, what is shown is actually the hyperfine splitting of rotational frequencies. FIG. 49 shows the hyperfine splitting of just the J=1→2 rotational transition. The splitting between the two tallest curves is less than 100 MHz.

FIG. 50 shows another example of the molecule ClCN. This set of hyperfine frequencies is from the J=1→2 transition of the ground vibrational state for ClCN. Notice that the hyperfine frequencies are separated by just a few megahertz, (MHz) and in a few places by less than even one megahertz.

Figure 51:
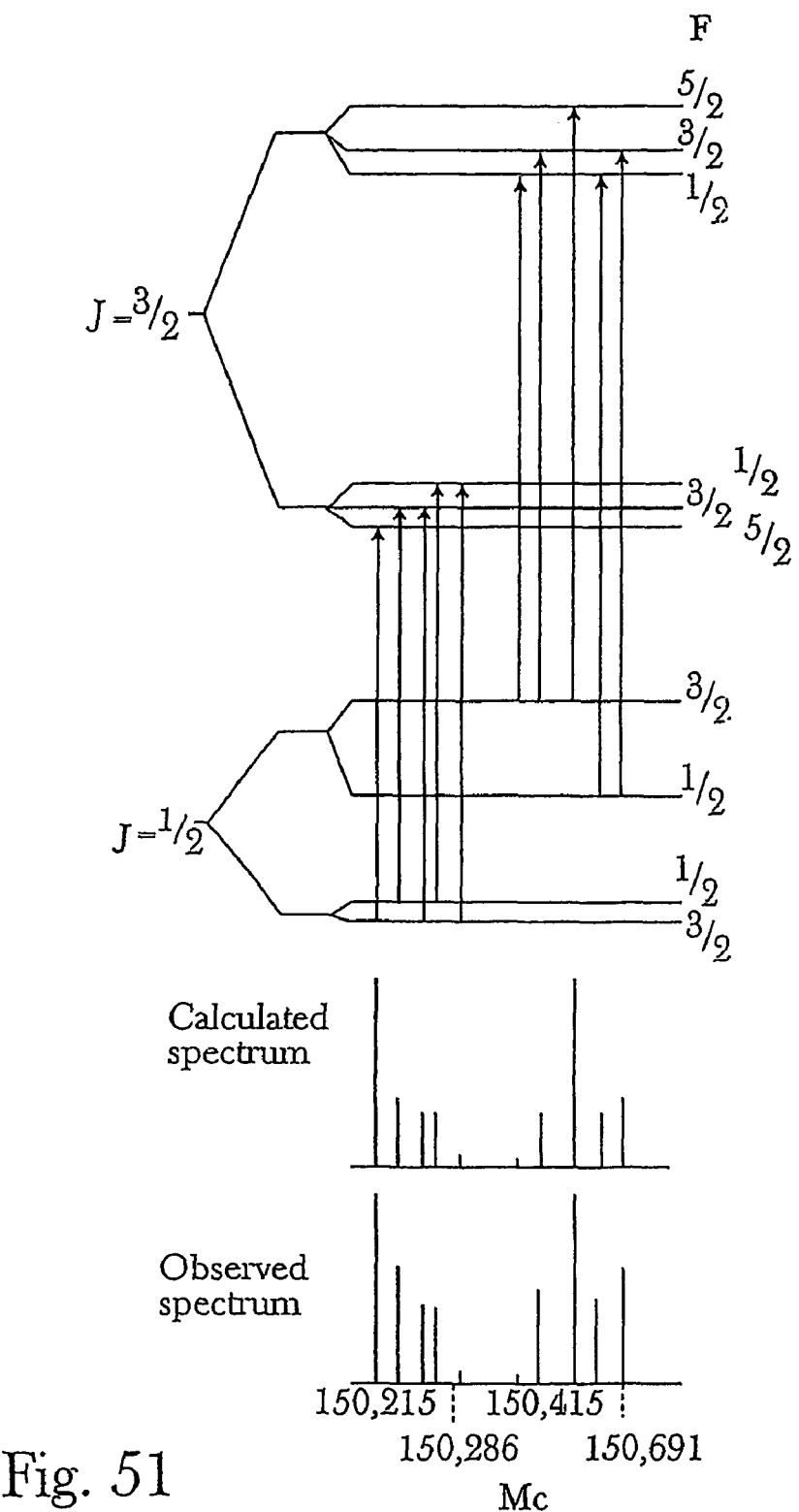
FIG. 51 shows energy level diagrams and hyperfine frequencies for the NO molecule.

The energy-level diagram and spectrum of the J=½→3/2 rotational transition for NO is shown if FIG. 51.

In FIG. 52, the hyperfine splitting frequencies for $NH_3$ are shown. Notice that the frequencies are spaced so close together that the scale at the bottom is in kilohertz (Kc/sec). The hyperfine features of the lines were obtained using a beam spectrometer.

Just as with fine splitting frequencies, the hyperfine splitting frequencies are heterodynes of atomic and molecular frequencies. Accordingly, if an atom or molecule is stimulated with a frequency equal to a hyperfine splitting frequency (a heterodyned difference between hyperfine frequencies), the present invention teaches that the energy will equal to a hyperfine splitting frequency will resonate with the hyperfine frequencies indirectly through heterodynes. The related rotational, vibrational, and/or electronic energy levels will, in turn, be stimulated. This is an important discovery. It allows one to use more radio and microwave frequencies to selectively stimulate and target specific crystallization reaction system components (e.g., atomic hydrogen intermediates can be stimulated with, for example, (2.55, 23.68 59.2 and/or 1,420 MHz).

Hyperfine frequencies, like fine frequencies, also contain features such as doublets. Specifically, in a region where one would expect to find only a single hyperfine frequency curve, there are two curves instead, typically, one on either side of the location where a single hyperfine frequency was expected. Hyperfine doubling is shown in FIGS. 53 and 54. This hyperfine spectrum is also from $NH_3$. FIG. 53 corresponds to the J=3 rotational level and FIG. 54 corresponds to the J=4 rotational level. The doubling can be seen most easily in the J=3 curves (i.e., FIG. 53). There are two sets of short curves, a tall one, and then two more short sets. Each of the short sets of curves is generally located where one would expect to find just one curve. There are two curves instead, one on either side of the main curve location. Each set of curves is a hyperfine doublet.

There are different notations to indicate the source of the doubling such as l-type doubling, K doubling, and Λ doubling, etc., and they all have their own constants or intervals. Without going into the detailed theory behind the formation of various types of doublets, the interval between any two hyperfine multiplet curves is also a heterodyne, and thus all of these doubling constants represent frequency heterodynes. Accordingly, those frequency heterodynes (i.e., hyperfine constants) can also be used as spectral energy catalysts according to the present invention.

Specifically, a frequency in an atom or molecule can be stimulated directly or indirectly. If the goal was to stimulate the 2,466 Thz frequency of hydrogen for some reason, then, for example, an ultraviolet laser could irradiate the hydrogen with 2,466 THz electromagnetic radiation. This would stimulate the atom directly. However, if such a laser was unavailable, then hydrogen's fine structure splitting frequency of 10.87 GHz could be achieved with microwave equipment. The gigahertz frequency would heterodyne (i.e., add or subtract) with the two closely spaced fine structure curves at 2,466, and stimulate the 2,466 THz frequency band. This would stimulate the atom indirectly.

Still further, the atom could be stimulated by using the hyperfine splitting frequency for hydrogen at 23.68 MHz as produced by radiowave equipment. The 23.68 MHz frequency would heterodyne (i.e., add or subtract) with the two closely spaced hyperfine frequency curves at 2,466, and stimulate the fine structure curves at the 2,466 THz. Stimulation of the fine structure curves would in turn lead to stimulation of the 2,466 THz electronic frequency for the hydrogen atom.

Still further, additional hyperfine splitting frequencies for hydrogen in the radiowave and microwave portions of the electromagnetic spectrum could also be used to stimulate the atom. For example, a radio wave pattern with 2.7 MHz, 4.2 MHz, 7 MHz, 18 MHz, 23 MHz, 52 MHz, and 59 MHz could be used. This would stimulate several different hyperfine frequencies of hydrogen, and it would stimulate them essentially all at the same time. This would cause stimulation of the fine structure frequencies, which in turn would stimulate the electronic frequencies in the hydrogen atom.

Still further, depending on available equipment and/or design, and/or processing constraints, some delivery mode variations can also be used. For example, one of the lower frequencies could be a carrier frequency for the upper frequencies. A continuous frequency of 52 MHz could be varied in amplitude at a rate of 2.7 MHz. Or, a 59 MHz frequency could be pulsed at a rate of 4.2 MHz. There are various ways in which these frequencies can be combined and/or delivered, including different wave shapes durations, intensity shapes, duty cycles, etc. Depending on which of the hyperfine splitting frequencies are stimulated, the evolution of, for example, various and specific transients may be precisely tailored and controlled, allowing precise control over holoreaction systems using the fine and/or hyperfine splitting frequencies.

Accordingly, a major point of the present invention is once it is understood the energy transfers when frequencies match, then determining which frequencies are available for matching is the next step. This invention discloses precisely how to achieve that goal. Interactions between equipment limitations, processing constraints, etc., can decide which frequencies are best suited for a particular purpose. Thus, both direct resonance and indirect resonance are suitable approaches for the use of spectral energy catalysts.

Similar to previous discussions, hyperfine and hyperfine spitting frequencies can be used to achieve desired results in crystallization reaction systems.

Electric Fields

Another means for modifying the spectral pattern of substances, is to expose a substance to an electric field. Specifically, in the presence of an electric field, spectral frequency lines of atoms and molecules can be split, shifted, broadened, or changed in intensity. The effect of an electric field on spectral lines is known as the "Stark Effect", in honor of its' discoverer, J. Stark. In 1913, Stark discovered that the Balmer series of hydrogen (i.e., curve II of FIGS. 9a and 9b) was split into several different components, while Stark was using a high electric field in the presence of a hydrogen flame. In the intervening years, Stark's original observation has evolved into a separate branch of spectroscopy, namely the study of the structure of atoms and molecules by measuring the changes in their respective spectral lines caused by an electric field.

The electric field effects have some similarities to fine and hyperfine splitting frequencies. Specifically, as previously discussed herein, fine structure and hyperfine structure frequencies, along with their low frequency splitting or coupling constants, were caused by interactions inside the atom or molecule, between the electric field of the electron and the magnetic field of the electron or nucleus. Electric field effects are similar, except that instead of the electric field coming from inside the atom, the electric field is applied from outside the atom. The Stark effect is primarily the interaction of an external electric field, from outside the atom or molecule, with the electric and magnetic fields already established within the atom or molecule.

When examining electric field effects on atoms, molecules, ions and/or components thereof, the nature of the electric field should also be considered (e.g., such as whether the electric field is static or dynamic). A static electric field may be produced by a direct current. A dynamic electric field is time varying, and may be produced by an alternating current. If the electric field is from an alternating current, then the frequency of the alternating current compared to the frequencies of the, for instance atom or molecule, should also be considered.

In atoms, an external electric field disturbs the charge distribution of the atom's electrons. This disturbance of the electron's own electric field induces a dipole moment in it (i.e., slightly lopsided charge distribution). This lopsided electron dipole moment then interacts with the external electric field. In other words, the external electric field first induces a dipole moment in the electron field, and then interacts with the dipole. The end result is that the atomic frequencies become split into several different frequencies. The amount the frequencies are split apart depends on the strength of the electric field. In other words, the stronger the electric field, the farther apart the splitting.

Figure 55:
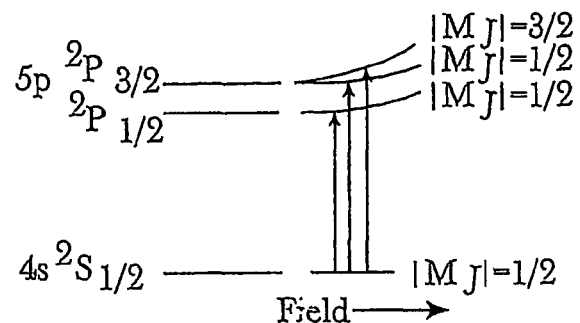
FIG. 55 shows a Stark effect for potassium. In particular, the schematic dependence of the $4_s$ and $5_p$ energy levels on the electric field.
Figure 56:
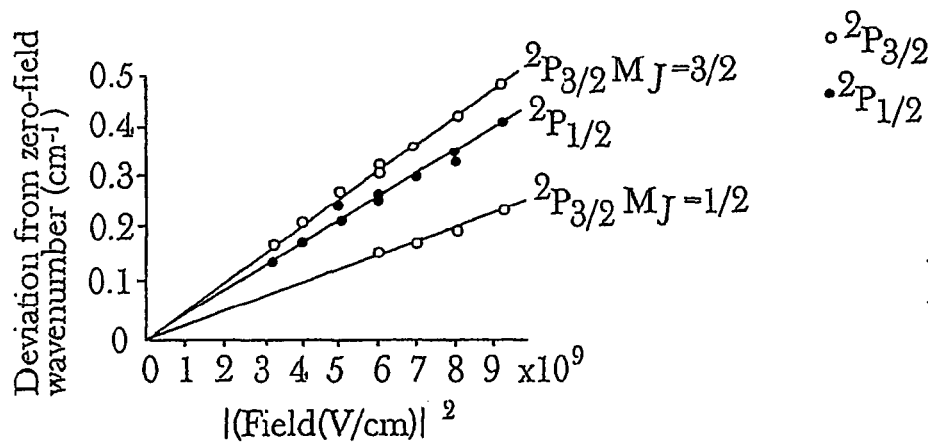
FIG. 56 shows a graph plotting the deviation from zero-field positions of the $5p^2P_{1/2} \leftarrow 4s^2S_{1/2,3/2}$ transition wavenumbers against the square of the electric field.

If the splitting varies directly with the electric field strength, then it is called first order splitting (i.e., $\Delta v=AF$ where $\Delta v$ is the splitting frequency, A is a constant and F is the electric field strength. When the splitting varies with the square of the field strength, it is called a second order or quadriatic effect (i.e., $\Delta v=BF^2$). One or both effects may be seen in various forms of matter. For example, the hydrogen atom exhibits first order Stark effects at low electric field strengths, and second order effects at high field strengths. Other electric field effects which vary with the cube or the fourth power, etc., of the electric field strength are less studied, but produce splitting frequencies nonetheless. A second order electric field effect for potassium is shown in FIGS. 55 and 56. FIG. 55 shows the schematic dependence of the 4s and 5p energy levels on the electric field. FIG. 56 shows a plot of the deviation from zero-field positions of the $5p^2$ P1/2.3/2←$4s^2$ S1/2 transition wavenumbers against the square of the electric field. Note that the frequency splitting or separation of the frequencies (i.e., deviation from zero-field wavenumber) varies with the square of the electric field strength (v/cm)$^2$.

The mechanism for the Stark effect in molecules is simpler than the effect is in atoms. Most molecules already have an electric dipole moment (i.e., a slightly uneven charge distribution). The external electric field simply interacts with the electric dipole moment already inside the molecule. The type of interaction, a first or a second order Stark effect, is different for differently shaped molecules. For example, most symmetric top molecules have first-order Stark effects. Asymmetric rotors typically have second-order Stark effects. Thus, in molecules, as in atoms, the splitting or separation of the frequencies due to the external electric field, is proportional either to the electric field strength itself, or to the square of the electric field strength.

Figure 57:
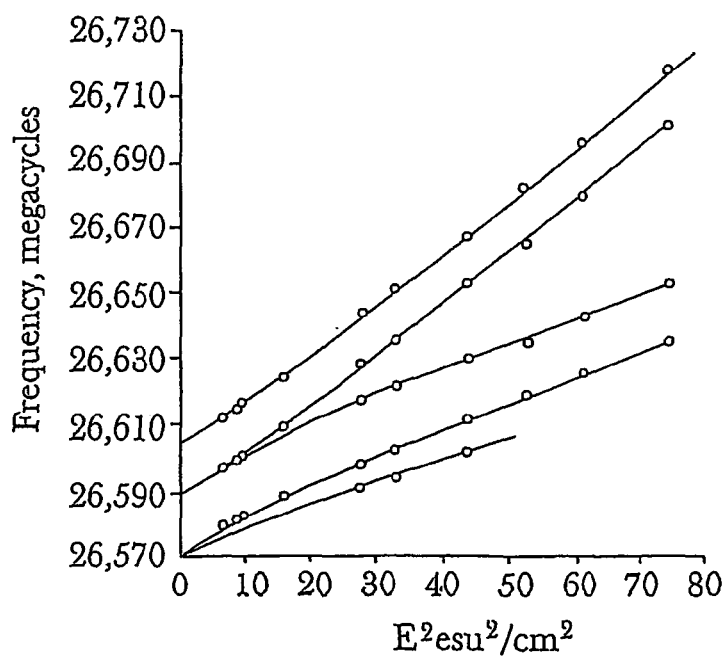
FIG. 57 shows the frequency components of the J=0→1 rotational transition for $CH_3Cl$, as a function of field strength. Frequency is given in megacycles (MHz) and electric field strength (esu cm) is given as the square of the field $E^2$, in $esu^2/cm^2$.

An example of this is shown in FIG. 57, which diagrams how frequency components of the J=0→1 rotational transition for the molecule $CH_3Cl$ respond to an external electric field. When the electric field is very small (e.g., less than $10 E^2$ esu$^2$/cm$^2$), the primary effect is shifting of the three rotational frequencies to higher frequencies. As the field strength is increased (e.g., between 10 and 20 $E^2$ esu$^2$/cm$^2$), the three rotational frequencies split into five different frequencies. With continued increases in the electric field strength, the now five frequencies continue to shift to even higher frequencies. Some of the intervals or differences between the five frequencies remain the same regardless of the electric field strength, while other intervals become progressively larger and higher. Thus, a heterodyned frequency might stimulate splitting frequencies at one electric field strength, but not at another.

Figure 58:
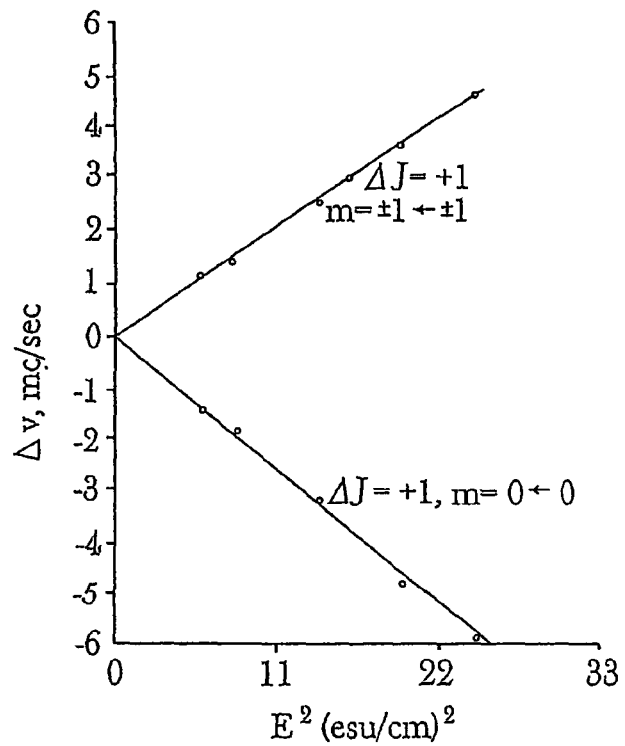
FIG. 58 shows the theoretical and experimental measurements of Stark effect in the J=1→2 transition of the molecule OCS. The unaltered absolute rotational frequency is plotted at zero, and the frequency splitting and shifting is denoted as MHz higher or lower than the original frequency.

Another molecular example is shown in FIG. 58. (This is a diagram of the Stark Effect in the same OCS molecule shown in FIG. 44 for the J=1→2). The J=1→2 rotational transition frequency is shown centered at zero on the horizontal frequency axis in FIG. 58. That frequency centered at zero is a single frequency when there is no external electric field. When an electric field is added, however, the single rotational frequency splits into two. The stronger the electric field is, the wider the splitting is between the two frequencies. One of the new frequencies shifts up higher and higher, while the other frequency shifts lower and lower. Because the difference between the two frequencies changes when the electric field strength changes, a heterodyned splitting frequency might stimulate the rotational level at one electric field strength, but not at another. An electric field can effect the spectral frequencies of reaction participants, and thus impact the spectral chemistry of a reaction.

Broadening and shifting of spectral lines also occurs with the intermolecular Stark effect. The intermolecular Stark effect is produced when the electric field from surrounding atoms, ions, or molecules, affects the spectral emissions of the species under study. In other words, the external electric field comes from other atoms and molecules rather than from a DC or AC current. The other atoms and molecules are in constant motion, and thus their electric fields are inhomogeneous in space and time. Instead of a frequency being split into several easily seen narrow frequencies, the original frequency simply becomes much wider, encompassing most, if not all, of what would have been the split frequencies, (i.e., it is broadened). Solvents, support materials, poisons, promoters, etc., are composed of atoms and molecules and components thereof. It is now understood that many of their effects are the result of the intermolecular Stark effect.

Figure 59:
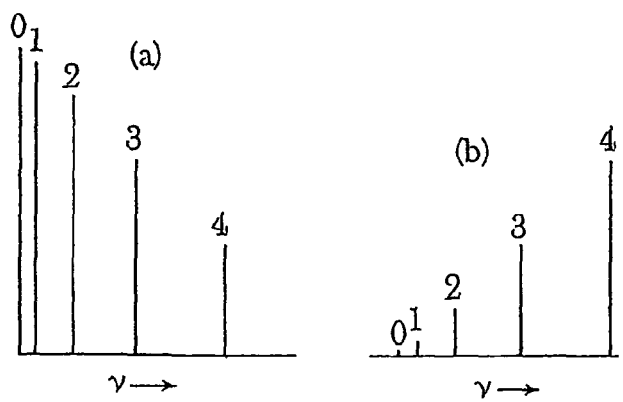
FIG. 59 shows patterns of Stark components for transitions in the rotation of an asymmetric top molecule. Specifically.

The above examples demonstrate how an electric field splits, shifts, and broadens spectral frequencies for matter. However, intensities of the lines can also be affected. Some of these variations in intensity are shown in FIGS. 59a and 59b. FIG. 59a shows patterns of Stark components for transitions in the rotation of an asymmetric top molecule for the J=4→5 transition; whereas FIG. 59b corresponds to J=4→4. The intensity variations depend on rotational transitions, molecular structure, etc., and the electric field strength.

An interesting Stark effect is shown in a structure such as a molecule, which has hyperfine (rotational) frequencies. The general rule for the creation of hyperfine frequencies is that the hyperfine frequencies result from an interaction between electrons and the nucleus. This interaction can be affected by an external electric field. If the applied external electric field is weak, then the Stark energy is much less than the energy of the hyperfine energy (i.e., rotational energy). The hyperfine lines are split into various new lines, and the separation (i.e., splitting) between the lines is very small (i.e., at radio frequencies and extra low frequencies).

If the external electric field is very strong, then the Stark energy is much larger than the hyperfine energy, and the molecule is tossed, sometimes violently, back and forth by the electric field. In this case, the hyperfine structure is radically changed. It is almost as though there no longer is any hyperfine structure. The Stark splitting is substantially the same as that which would have been observed if there were no hyperfine frequencies, and the hyperfine frequencies simply act as a small perturbation to the Stark splitting frequencies.

If the external electric field is intermediate in strength, then the Stark and hyperfine energies are substantially equivalent. In this case, the calculations become very complex. Generally, the Stark splitting is close to the same frequencies as the hyperfine splitting, but the relative intensities of the various components can vary rapidly with slight changes in the strength of the external electric field. Thus, at one electric field strength one splitting frequency may predominate, while at an electric field strength just 1% higher, a totally different Stark frequency could predominate in intensity.

All of the preceding discussion on the Stark effect has concentrated on the effects due to a static electric field, such as one would find with a direct current. The Stark effects of a dynamic, or time-varying electric field produced by an alternating current, are quite interesting and can be quite different. Just which of those affects appear, depends on the frequency of the electric field (i.e., alternating current) compared to the frequency of the matter in question. If the electric field is varying very slowly, such as with 60 Hz wall outlet electricity, then the normal or static type of electric field effect occurs. As the electric field varies from zero to maximum field strength, the matter frequencies vary from their unsplit frequencies to their maximally split frequencies at the rate of the changing electric field. Thus, the electric field frequency modulates the frequency of the splitting phenomena.

Figure 16:
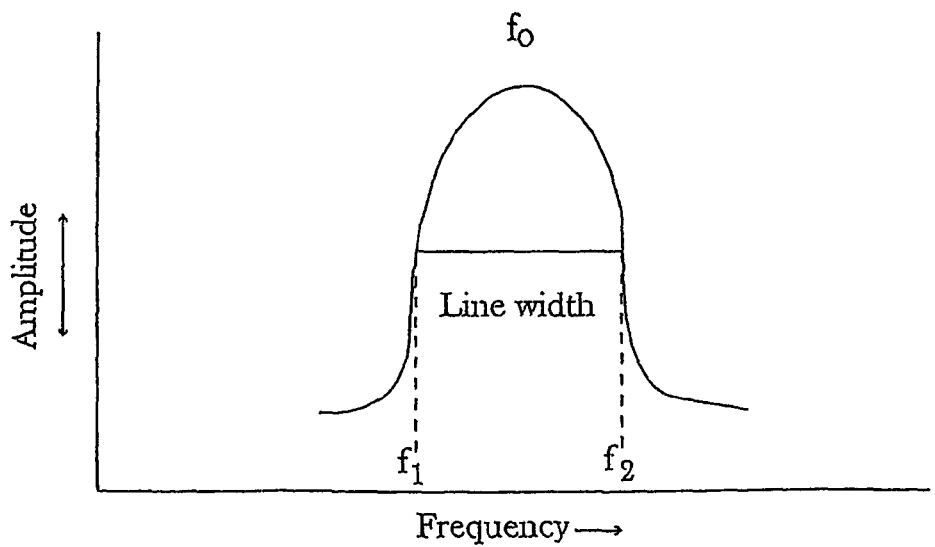
FIG. 16 is spectral curve showing a line width which corresponds to $f_2-f_1$.

However, as the electrical frequency increases, the first frequency measurement it will begin to overtake is the line width (see FIG. 16 for a diagram of line width). The line width of a curve is its' distance across, and the measurement is actually a very tiny heterodyne frequency measurement from one side of the curve to the other side. Line width frequencies are typically around 100 KHz at room temperature. In practical terms, line width represents a relaxation time for molecules, where the relaxation time is the time required for any transient phenomena to disappear. So, if the electrical frequency is significantly smaller than the line width frequency, the molecule has plenty of time to adjust to the slowly changing electric field, and the normal or static-type Stark effects occur.

Figure 60:
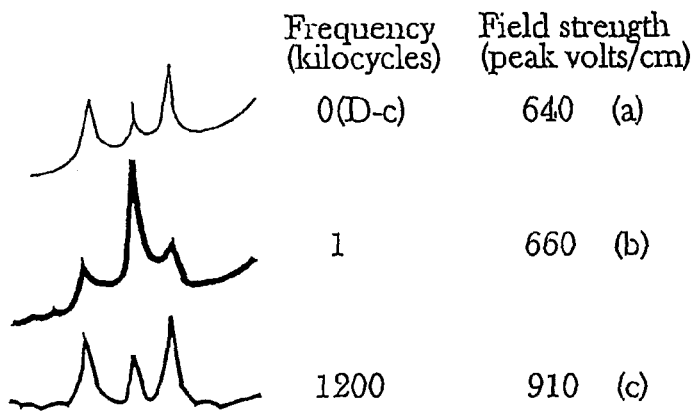
FIG. 60 shows the Stark effect for the OCS molecule on the J=1→2 transition with applied electric fields at various frequencies. The "a" curve represents the Stark effect with a static DC electric field; the "b" curve represents broadening and blurring of the Stark frequencies with a 1 KHz electric field; and the "c" curve represents normal Stark type effect with electric field of 1,200 KHz.

If the electrical frequency is slightly less than the line width frequency, the molecule changes its' frequencies substantially in rhythm with the frequency of the electric field (i.e., it entrains to the frequency of the electric field). This is shown in FIG. 60 which shows the Stark effect for OCS on the $J=1 \rightarrow 2$ transition with applied electric fields at various frequencies. The letter "a" corresponds to the Stark effect with a static DC electric field; "b" corresponds to a broadening and blurring of the Stark frequencies with a 1 KHz electric field; and "c" corresponds to a normal Stark effect with an electric field of 1,200 KHz. As the electric field frequency approaches the KHz line width range, the Stark curves vary their frequencies with the electric field frequency and become broadened and somewhat blurred. When the electric field frequency moves up and beyond the line width range to about 1,200 KHz, the normal Stark type curves again become crisp and distinguishable. In many respects, the molecule cannot keep up with the rapid electrical field variation and simply averages the Stark effect. In all three cases, the cyclic splitting of the Stark frequencies is modulated with the electrical field frequency, or its' first harmonic (i.e., 2× the electrical field frequency).

The next frequency measurement that an ever-increasing electrical frequency will overtake in a molecule is the transitional frequency between two rotational levels (i.e., hyperfine frequencies). As the electric field frequency approaches a transitional frequency between two levels, the radiation of the transitional frequency in the molecule will induce transitions back and forth between the levels. The molecule oscillates back and forth between both levels, at the frequency of the electric field. When the electric field and transition level frequencies are substantially the same (i.e., in resonance), the molecule will be oscillating back and forth in both levels, and the spectral lines for both levels will appear simultaneously and at approximately the same intensity. Normally, only one frequency level is seen at a time, but a resonant electric field causes the molecule to be at both levels at essentially the same time, and so both transitional frequencies appear in its' spectrum.

Moreover, for sufficiently large electric fields (e.g., those used to generate plasmas) additional transition level frequencies can occur at regular spacings substantially equal to the electric field frequency. Also, splitting of the transition level frequencies can occur, at frequencies of the electric field frequency divided by odd numbers (e.g., electric field frequency "$f_E$" divided by 3, or 5, or 7, i.e., $f_E/3$ or $f_E/5$, etc.).

All the varied effects of electric fields cause new frequencies, new splitting frequencies and new energy level states.

Further, when the electric field frequency equals a transition level frequency of for instance, an atom or molecule, a second component with an opposite frequency charge and equal intensity can develop. This is negative Stark effect, with the two components of equal and opposite frequency charges destructively canceling each other. In spectral chemistry terms this amounts to a negative catalyst or poison in the crystallization reaction system, if the transition thus targeted was important to the reaction pathway. Thus, electric fields cause the Stark effect, which is the splitting, shifting, broadening, or changing intensity and changing transitional states of spectral frequencies for matter, (e.g., atoms and molecules). As with many of the other mechanisms that have been discussed herein, changes in the spectral frequencies of crystallization reaction systems can affect the reaction rate and/or reaction pathway. For example, consider a crystallization reaction system like the following:

where A&B are reactants, C is a physical catalyst, I stands for the intermediates, and D&F are the products.

Assume arguendo that the reaction normally progresses at only a moderate rate, by virtue of the fact that the physical catalyst produces several frequencies that are merely close to harmonics of the intermediates. Further assume that when an electric field is added, the catalyst frequencies are shifted so that several of the catalyst frequencies are now exact or substantially exact harmonics of the intermediates. This will result in, for example, the reaction being catalyzed at a faster rate. Thus, the Stark effect can be used to obtain a more efficient energy transfer through the matching of frequencies (i.e., when frequencies match, energies transfer).

If a reaction normally progresses at only a moderate rate, many "solutions" have included subjecting the crystallization reaction system to extremely high pressures. The high pressures result in a broadening of the spectral patterns, which improves the transfer of energy through a matching of resonant frequencies. By understanding the underlying catalyst mechanisms of action, high-pressure systems could be replaced with, for example, a simple electric field which produces broadening. Not only would this be less costly to an industrial manufacturer, it could be much safer for manufacturing due to the removal of, for example, high-pressure equipment.

Some reactants when mixed together do not react very quickly at all, but when an electric field is added they react rather rapidly. The prior art may refer to such a reaction as being catalyzed by an electric field and the equations would look like this:

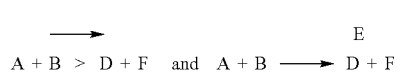

where E is the electric field. In this case, rather than applying a catalyst "C" (as discussed previously) to obtain the products "D+F", an electric field "E" can be applied. In this instance, the electric field works by changing the spectral frequencies (or spectral pattern) of one or more components in the crystallization reaction system so that the frequencies come into resonance, and the reaction can proceed along a desired reaction pathway (i.e., when frequencies match, energy is transferred). Understood in this way, the electric field becomes just another tool to change spectral frequencies of atoms and molecules, and thereby affect reaction rates in spectral chemistry.

Reaction pathways are also important. In the absence of an electrical field, a reaction pathway will progress to one set of products:

However, if an electrical field is added, at some particular strength of the field, the spectral frequencies may change so much, that a different intermediate is energized and the reaction proceeds down a different reaction pathway:

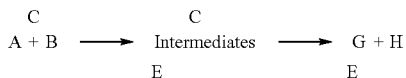

This is similar to the concept discussed earlier herein, regarding the formation of different products depending on temperature. The changes in temperature caused changes in spectral frequencies, and hence different reaction pathways were favored at different temperatures. Likewise, electric fields cause changes in spectral frequencies, and hence different reactions pathways are favored by different electric fields. By tailoring an electric field to a particular crystallization reaction system, one can control not only the rate of the reaction but also the reaction products produced.

The ability to tailor reactions, with or without a physical catalyst, by varying the strength of an electric field should be useful in many manufacturing situations. For example, it might be more cost effective to build only one physical set-up for a crystallization reaction system and to use one or more electric fields to change the reaction dynamics and products, depending on which product is desired. This would save the expense of having a separate physical set-up for production of each group of products.

Besides varying the strength of an electric field, the frequency of an electric field can also be varied. Assuming that a reaction will proceed at a much faster rate if a particular strength static electric field (i.e., direct current) is added as in the following:

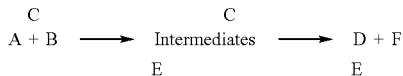

But further assume, that because of reactor design and location, it is much easier to deliver a time-varying electric field with alternating current. A very low frequency field, such as with a 60 Hz wall outlet, can produce the normal or static-type Stark effect. Thus, the reactor could be adapted to the 60 Hz electric field and enjoy the same increase in reaction rate that would occur with the static electric field.

If a certain physical catalyst produces spectral frequencies that are close to intermediate frequencies, but are not exact, it is possible that the activity of the physical catalyst in the past may have been improved by using higher temperatures. As disclosed earlier herein, the higher temperatures actually broadened the physical catalyst's spectral pattern to cause the frequency of the physical catalyst to be at least a partial match for at least one of the intermediates. What is significant here is that high temperature boilers can be minimized, or eliminated altogether, and in their stead a moderate frequency electric field which, for example, broadened the spectral frequencies, could be used. For example, a frequency of around 100 Khz, equivalent to the typical line width frequencies at room temperature, could broaden substantially all of the spectral curves and cause the physical catalyst's spectral curves to match those of, for example, required intermediates. Thus, the electric field could cause the matter to behave as though the temperature had been raised, even though it had not been. (Similarly, any spectral manipulation, (e.g., electric fields acoustics, heterodynes, etc., that cause changes in the spectral line width, may cause a material to behave as though its temperature had been changed).

The cyclic splitting of the Stark frequencies can be modulated with the electrical field frequency or its' first harmonic (i.e., first-order Stark effects are modulated with the electrical field frequency, while second-order Stark effects are modulated by two times the electrical field, frequency). Assume that a metallic platinum catalyst is used in a hydrogen reaction and it is desired to stimulate the 2.7 MHz hyperfine frequency of the hydrogen atoms. Earlier herein it was disclosed that electromagnetic radiation could be used to deliver the 2.7 MHz frequency. However, use of an alternating electric field at 2.7 MHz could be used instead. Since platinum is a metal and conducts electricity well, the platinum can be considered to be a part of the alternating current circuit. The platinum will exhibit a Stark effect, with all the frequencies splitting at a rate of 2.7 MHz. At sufficiently strong electric fields, additional transition frequencies or "sidebands" will occur at regular spacings equal to the electric field frequency. There will be dozens of split frequencies in the platinum atoms that are heterodynes of 2.7 MHz. This massive heterodyned output may stimulate the hydrogen hyperfine frequency of 2.7 MHz and direct the reaction.

Figure 61A:
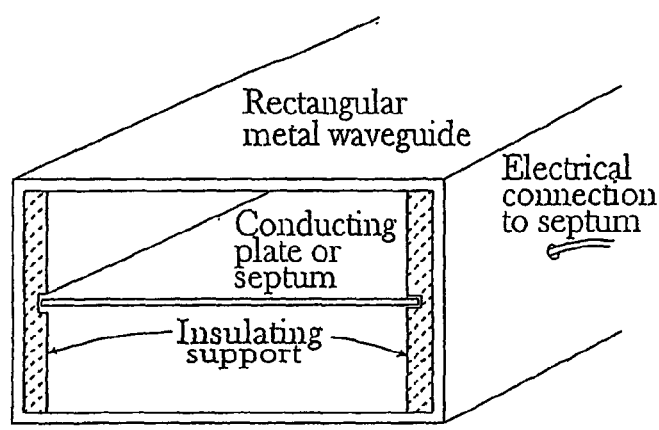
FIG. 61a shows a construction of a Stark waveguide and FIG. 61b shows a distribution of fields in the Starck waveguide.
Figure 61B:
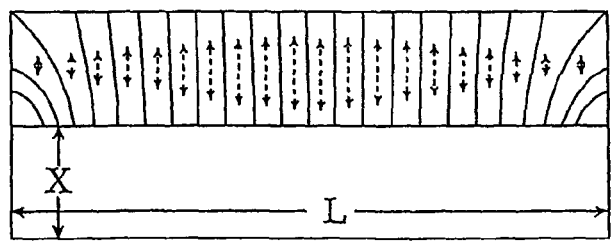

Another way to achieve this reaction, of course, would be to leave the platinum out of the reaction altogether. The 2.7 MHz field will have a resonant Stark effect on the hydrogen, separate and independent of the platinum catalyst. Copper is not normally catalytic for hydrogen, but copper could be used to construct a reaction vessel like a Stark waveguide to energize the hydrogen. A Stark waveguide is used to perform Stark spectroscopy. It is shown as FIGS. 61a and 61b. Specifically, FIG. 61a shows the construction of the Stark waveguide, whereas FIG. 61b shows the distribution of fields in the Stark waveguide. The electrical field is delivered through the conducting plate. A reaction vessel could be made for the flow-through of gases and use an economical metal such as copper for the conducting plate. When the 2.7 MHz alternating current is delivered through the electrical connection to the copper conductor plate, the copper spectral frequencies, none of which are particularly resonant with hydrogen, will exhibit a Stark effect with normal-type splitting. The Stark frequencies will be split at a rate of 2.7 MHz. At a sufficiently strong electric field strength, additional sidebands will appear in the copper, with regular spacings (i.e., heterodynes) of 2.7 MHz even though none of the actual copper frequencies matches the hydrogen frequencies, the Stark splitting or heterodynes will match the hydrogen frequency.

Dozens of the copper split frequencies may resonate indirectly with the hydrogen hyperfine frequency and direct the reaction (i.e., when frequencies match, energies transfer).

With sophisticated equipment and a good understanding of a particular system, Stark resonance can be used with a transition level frequency. For example, assume that to achieve a particular reaction pathway, a molecule needs to be stimulated with a transition level frequency of 500 MHz. By delivering the 500 MHz electrical field to the molecule, this resonant electrical field may cause the molecule to oscillate back and forth between the two levels at the rate of 500 MHz. This electrically creates the conditions for light amplification (i.e., laser via stimulation of multiple upper energy levels) and any added electromagnetic radiation at this frequency will be amplified by the molecule. In this manner, an electrical field may substitute for the laser effects of physical catalysts.

In summary, by understanding the underlying spectral mechanisms of chemical reactions, electric fields can be used as yet another tool to catalyze and modify those chemical reactions and/or reaction pathways by modifying the spectral characteristics, for example, at least one participant and/or one or more components in the crystallization reaction system. Thus, another tool for mimicking catalyst mechanisms of reactions can be utilized.

Similar to other spectral frequencies, as previously discussed, control of resonant energy exchange via manipulation of electric fields can be used in crystallization reaction systems to achieve desired results.

Magnetic Fields

In spectral terms, magnetic fields behave similar to electric fields in their effect. Specifically, the spectral frequency lines, for instance of atoms and molecules, can be split and shifted by a magnetic field. In this case, the external magnetic field from outside the atom or molecule, interacts with the electric and magnetic fields already inside the atom or molecule.

This action of an external magnetic field on spectral lines is called the "Zeeman Effect", in honor of its' discoverer, Dutch physicist Pieter Zeeman. In 1896, Zeeman discovered that the yellow flame spectroscopy "D" lines of sodium were broadened when the flame was held between strong magnetic poles. It was later discovered that the apparent broadening of the sodium spectral lines was actually due to their splitting and shifting. Zeeman's original observation has evolved into a separate branch of spectroscopy, relating to the study of atoms and molecules by measuring the changes in their spectral lines caused by a magnetic field. This in turn has evolved into the nuclear magnetic resonance spectroscopy and magnetic resonance imaging used in medicine, as well as the laser magnetic resonance and electron spin resonance spectroscopy used in physics and chemistry.

The Zeeman effect for the famous "D" lines of sodium is shown in FIGS. 62a and 62b. FIG. 62a shows the Zeeman effect for sodium "D" lines; whereas FIG. 62b shows the energy level diagram for the transitions in the Zeeman effect for the sodium "D" lines. The "D" lines are traditionally said to result from transition between the $3p^2p$ and $3s^2S$ electron orbitals. As is shown, each of the single spectral frequencies is split into two or more slightly different frequencies, which center around the original unsplit frequency.

In the Zeeman effect, the amount that the spectral frequencies are split apart depends on the strength of the applied magnetic field. FIG. 63 shows Zeeman splitting effects for the oxygen atom as a function of magnetic field. When there is no magnetic field, there are two single frequencies at zero and 4.8. When the magnetic field is at low strength (e.g., 0.2 Tesla) there is just slight splitting and shifting of the original two frequencies. However, as the magnetic field is increased, the frequencies are split and shifted farther and farther apart.

The degree of splitting and shifting in the Zeeman effect, depending on magnetic field strength, is shown in FIG. 64 for the $^3P$ state of silicon.

As with the Stark effect generated from an external electric field, the Zeeman effect, generated from an external magnetic field, is slightly different depending on whether an atom or molecule is subjected to the magnetic field. The Zeeman effect on atoms can be divided into three different magnetic field strengths: weak; moderate; and strong. If the magnetic field strength is weak, the amount that the spectral frequencies will be shifted and split apart will be very small. The shifting away from the original spectral frequency will still stimulate the shifted frequencies. This is because they will be so close to the original spectral frequency that they will still be well within its resonance curve. As for the splitting, it is so small, that it is even less than the hyperfine splitting that normally occurs. This means that in a weak magnetic field, there will be only very slight splitting of spectral frequencies, translating into very low splitting frequencies in the lower regions of the radio spectrum and down into the very low frequency region. For example, the Zeeman splitting frequency for the hydrogen atom, which is caused by the earth's magnetic field, is around 30 KHz. Larger atoms have even lower frequencies in the lower kilohertz and even hertz regions of the electromagnetic spectrum.

Without a magnetic field, an atom can be stimulated by using direct resonance with a spectral frequency or by using its fine or hyperfine splitting frequencies in the infrared through microwave, or microwave through radio regions, respectively. By merely adding a very weak magnetic field, the atom can be stimulated with an even lower radio or very low frequency matching the Zeeman splitting frequency. Thus, by simply using a weak magnetic field, a spectral catalyst range can be extended even lower into the radio frequency range. The weak magnetic field from the Earth causes Zeeman splitting in atoms in the hertz and kilohertz ranges. This means that all atoms, including those in biological organisms, are sensitive to hertz and kilohertz EM frequencies, by virtue of being subjected to the Earth's magnetic field.

At the other end of magnetic field strength, is the very strong magnetic field. In this case, the splitting apart and shifting of the spectral frequencies will be very wide. With this wide shifting of frequencies, the difference between the split frequencies will be much larger than the difference between the hyperfine splitting frequencies. This translates to Zeeman effect splitting frequencies at higher frequencies than the hyperfine splitting frequencies. This splitting occurs somewhere around the microwave region. Although the addition of a strong magnetic field does not extend the reach in the electromagnetic spectrum at one extreme or the other, as a weak magnetic field does, it still does provide an option of several more potential spectral catalyst frequencies that can be used in the microwave region.

The moderate magnetic field strength case is more complicated. The shifting and splitting caused by the Zeeman effect from a moderate magnetic field will be approximately equal to the hyperfine splitting. Although not widely discussed in the prior art, it is possible to apply a moderate magnetic field to an atom, to produce Zeeman splitting which is substantially equivalent to its' hyperfine splitting. This presents interesting possibilities. Methods for guiding atoms in chemical reactions were disclosed earlier herein by stimulating atoms with hyperfine splitting frequencies. The Zeeman effect provides a way to achieve similar effects without introducing any spectral frequencies at all. For example, by introducing a moderate magnetic field, resonance may be set-up within the atom itself, that stimulates and/or energizes and/or stabilizes the atom.

The moderate magnetic field causes low frequency Zeeman splitting that matches and hence energizes the low frequency hyperfine splitting frequency in the atom. However, the low hyperfine splitting frequencies actually correspond to the heterodyned difference between two vibrational or fine structure frequencies. When the hyperfine splitting frequency is stimulated, the two electronic frequencies will eventually be stimulated. This in turn causes the atom to be, for example, stimulated. Thus, the Zeeman effect permits a spectral energy catalyst stimulation of an atom by exposing that atom to a precise strength of a magnetic field, and the use of spectral EM frequencies is not required (i.e., so long as frequencies match, energies will transfer). The possibilities are quite interesting because an inert crystallization reaction system may suddenly spring to life upon the application of the proper moderate strength magnetic field.

Figure 65A:
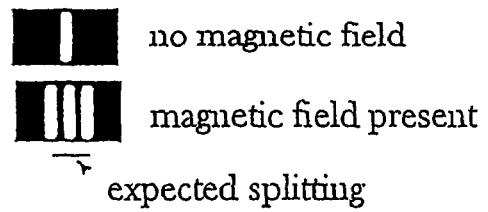
FIG. 65a is a pictorial which shows a normal Zeeman effect and FIG. 65b is a pictorial which shows an anomolous Zeeman effect.
Figure 65B:
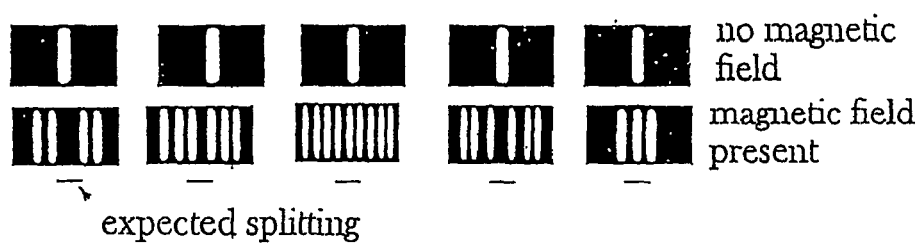

There is also a difference between the "normal" Zeeman effect and the "anomalous" Zeeman effect. With the "normal" Zeeman effect, a spectral frequency is split by a magnetic field into three frequencies, with expected even spacing between them (see FIG. 65a which shows the "normal" Zeeman effects and FIG. 65b which shows the "anomalous" Zeeman effects). One of the new split frequencies is above the original frequency, and the other new split frequency is below the original frequency. Both new frequencies are split the same distance away from the original frequency. Thus, the difference between the upper and original and the lower and original frequencies is about the same. This means that in terms of heterodyne differences, there are at most, two new heterodyned differences with the normal Zeeman effect. The first heterodyne or splitting difference is the difference between one of the new split frequencies and the original frequency. The other splitting difference is between the upper and lower new split frequencies. It is, of course, twice the frequency difference between either of the upper or lower frequencies and the original frequency.

Figure 66:
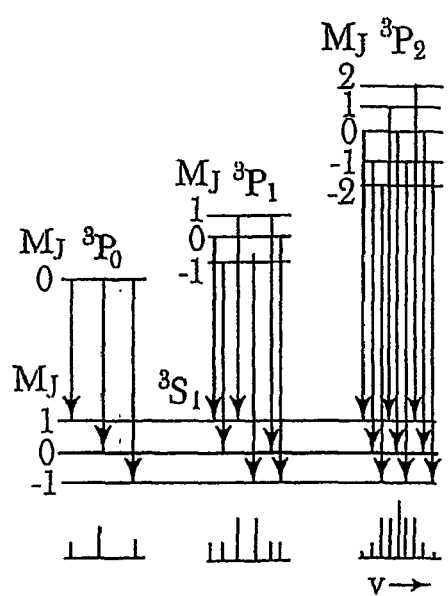
FIG. 66 shows anomalous Zeeman effect for zinc $^3P \rightarrow ^3S$.
Figure 70:
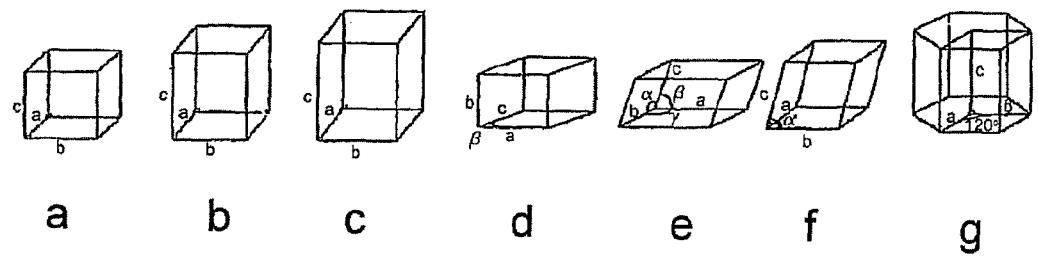
FIG. 70 shows schematics of the seven (7) different unit cells in the following order: a—cubic, b—tetragonal, c—orthorhombic, d—monoclinic, e—triclinic, f—hexagonal, g—trigonal/rhombohedral.
Figure 71:
FIG. 71 shows a one-dimensional lattice system comprising a line of equally spaced points.
Figures 72, 73, 74:
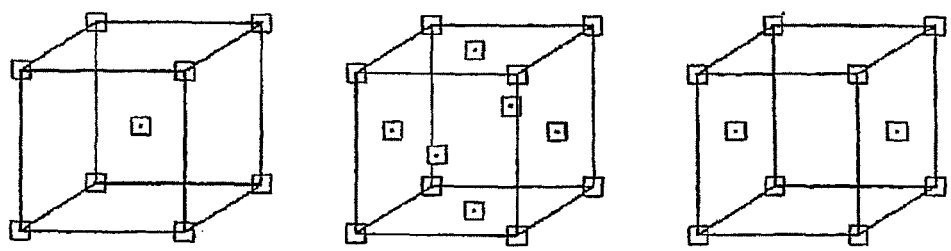
FIG. 72 shows a schematic of a body-centered cubic lattice structure.
FIG. 73 shows a schematic of a face-centered lattice structure.
FIG. 74 shows a schematic of a face-centered cubic lattice structure.
Figure 78:
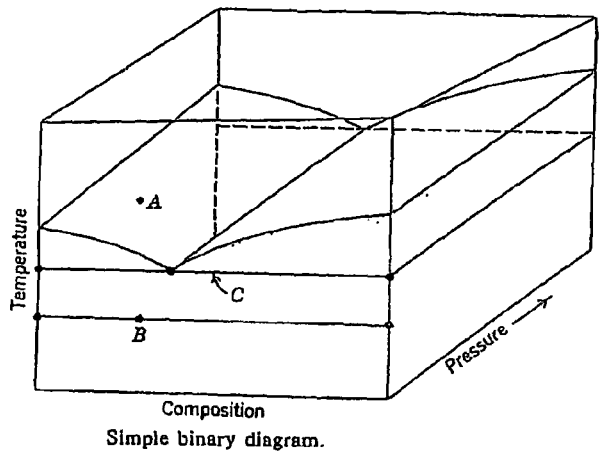
FIG. 78 shows a perspective view of a simple binary phase-diagram.
Figure 79:
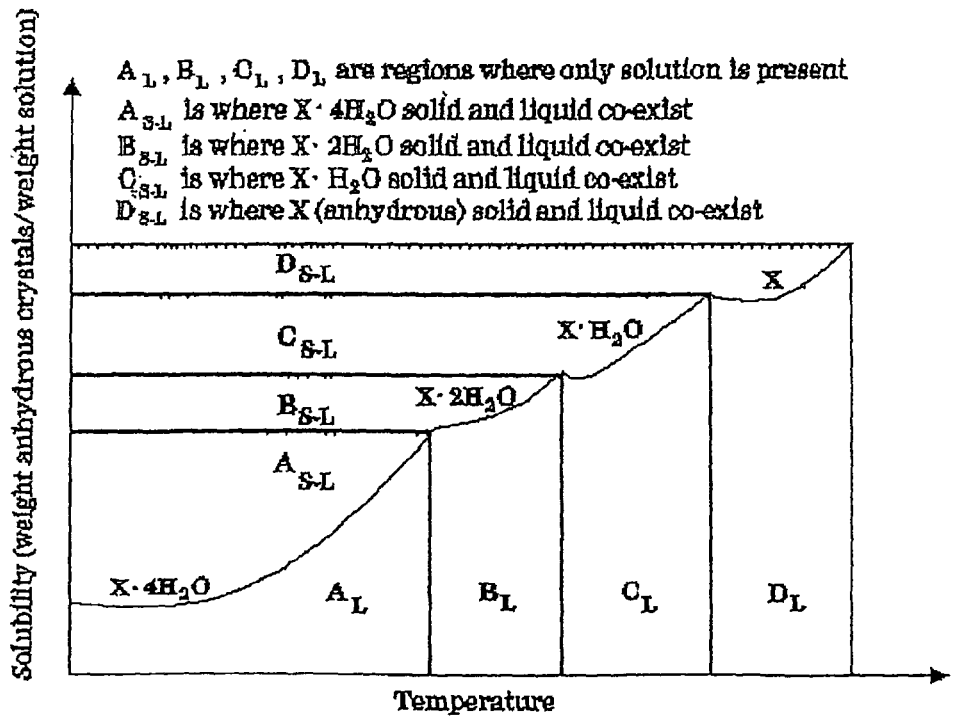
FIG. 79 shows a phase-diagram which is an example of solubility curve for a solid that forms a hydrate.
Figure 79A:
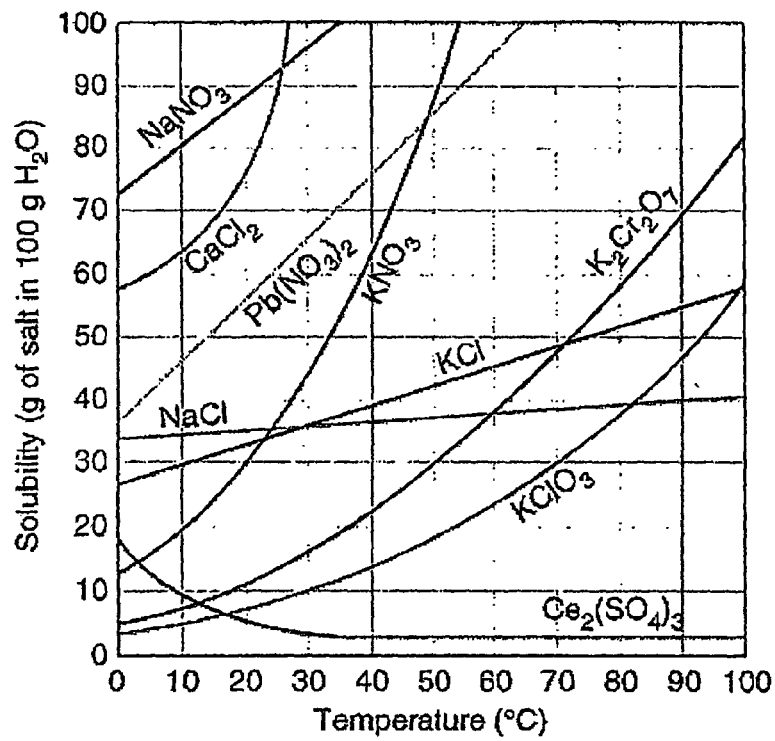
FIG. 79a shows several solubility curves for different solutions in water as a function of temperature.
Figure 80A:
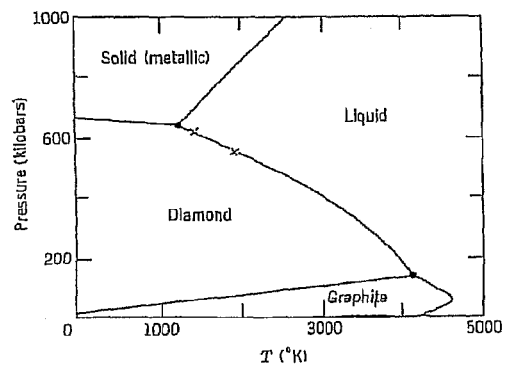
FIG. 80a shows a phase-diagram for carbon; and, FIGS. 80b and 80c shown clinographic projections of a hexagonal structure of graphite and the cubic structure of diamond, respectively.
Figure 80:
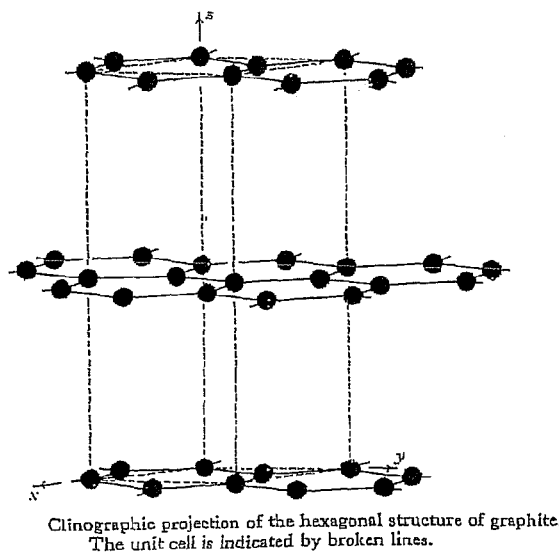
Figure 80:
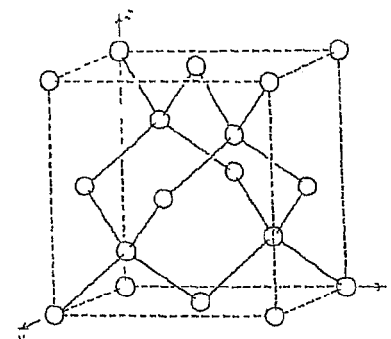
Figure 82A:
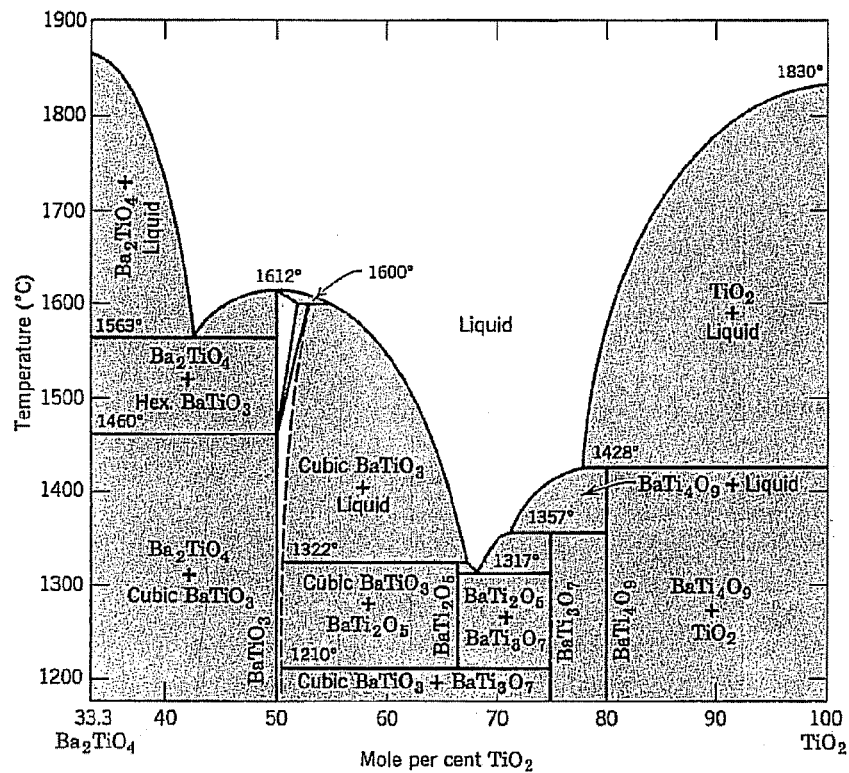
FIG. 82a shows a phase diagram for the system $Ba_2TiO_4/TiO_2$.
Figure 82B:
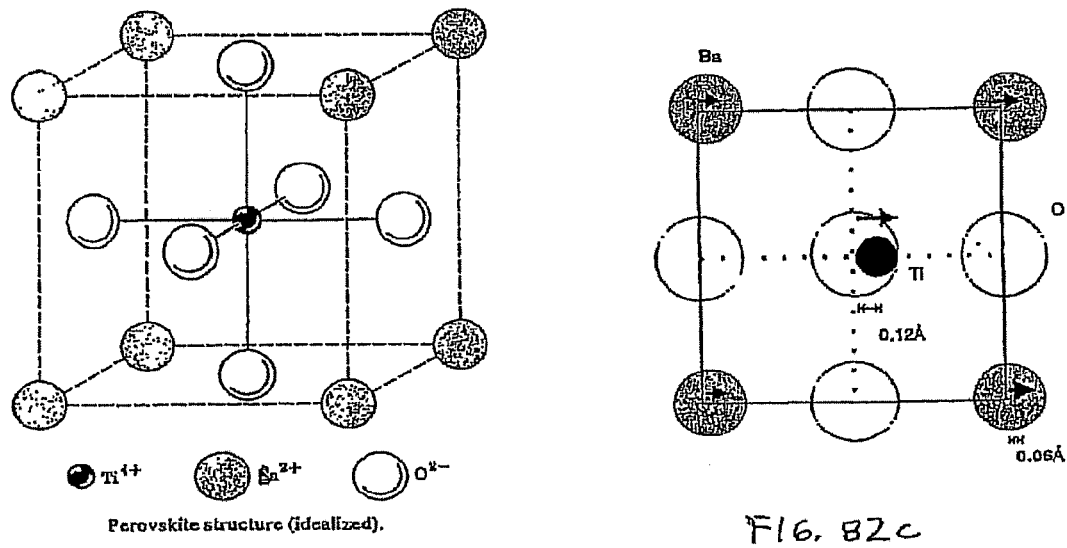
FIG. 82b shows a clinographic projection of the unit cell of an idealized cubic structure of barium titanate (i.e., the Perovskite structure)
Figure 82C:
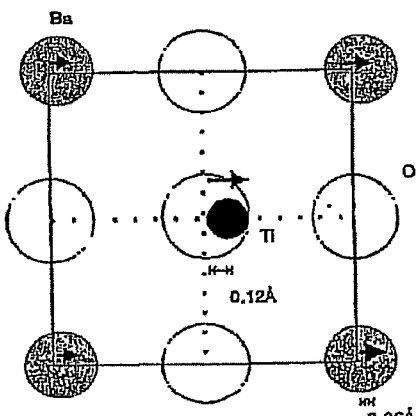
FIG. 82c shows a plan view of barium, titanium and oxygen ions in a lattice relationship, showing that the central ion of $Ti_4^+$ has room to move within its lattice positions.
Figure 83A:
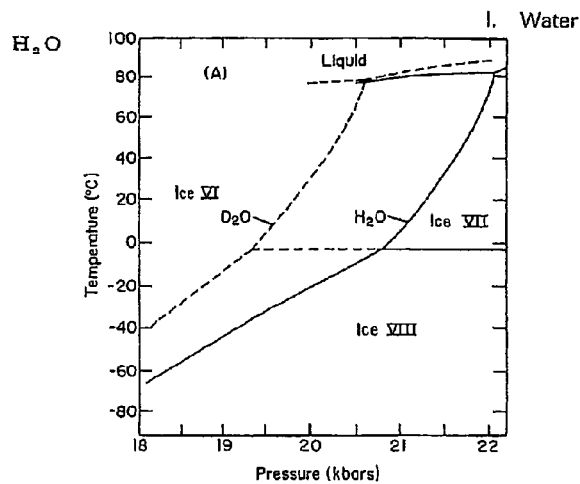
FIGS. 83a, 83b and 83c show various phase-diagrams for water.
Figure 83B:
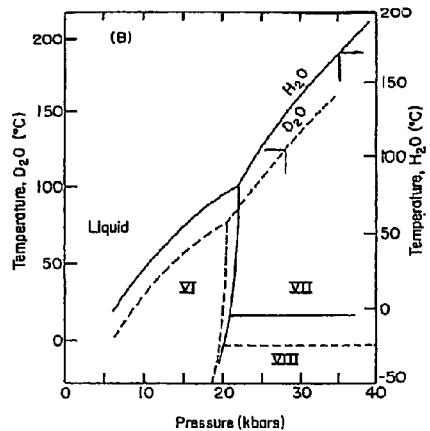
Figure 83C:
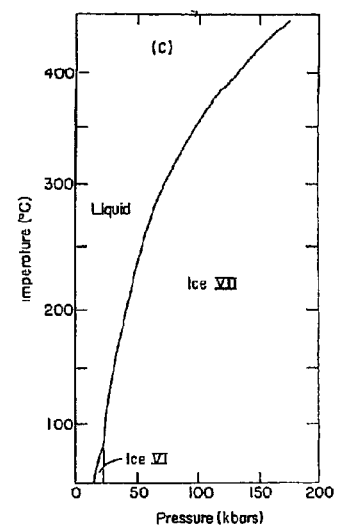
Figure 83D:
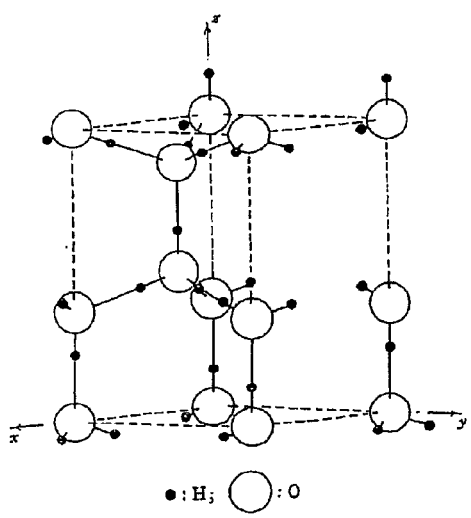
FIG. 83d shows a clinographic projection of the hexagonal structure of ice.
Figure 84:
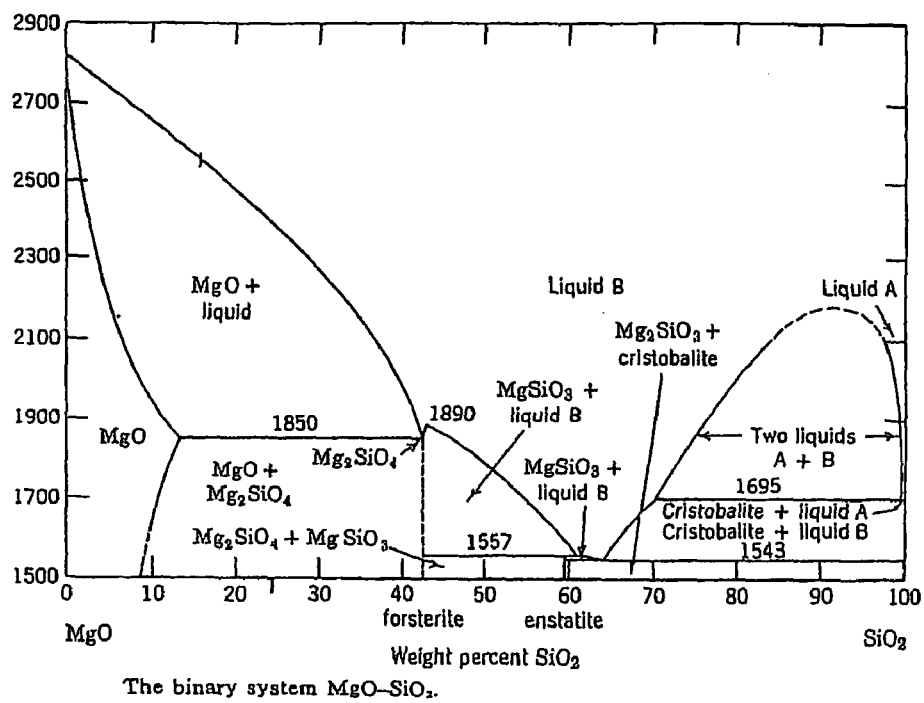
FIG. 84a shows a binary system for MgO/SiO$_2$.
FIG. 84b shows a plan view of an idealized orthorhombic structure of Mg$_2$SiO$_4$ (forsterite).
Figure 84:
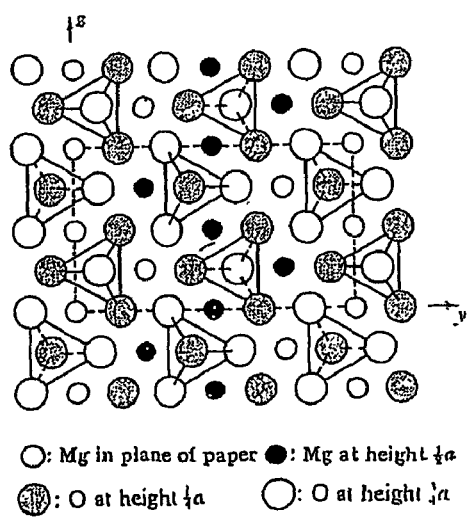
Figures 86A, 86B:
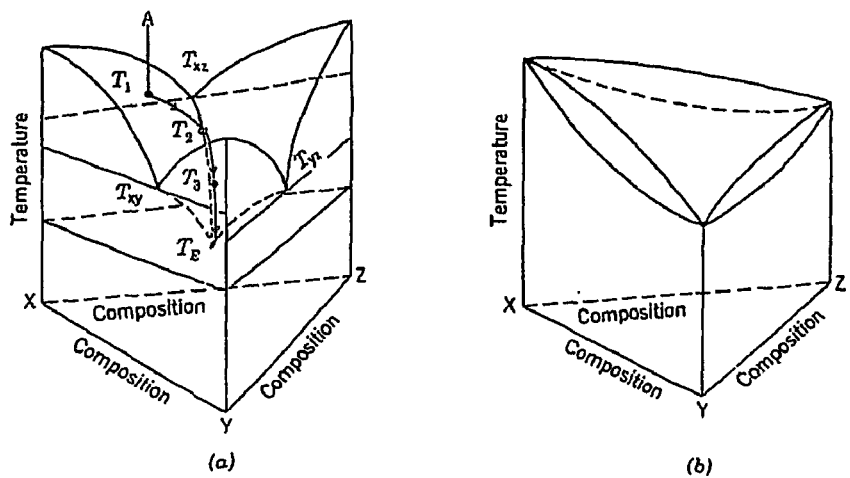
FIG. 86a shows a space diagram of a ternary eutectic composition.
FIG. 86b shows a space diagram of a complete series of solid solutions.
Figure 86C:
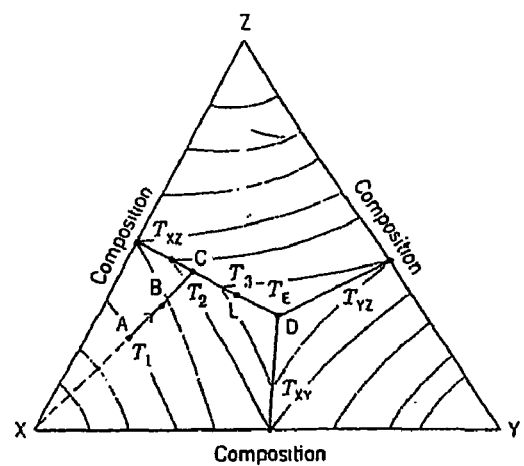
Figure 87A:
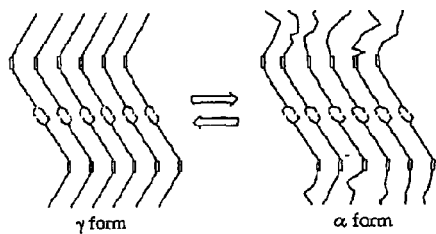
FIG. 87a shows a molecular model of the δ-α transformation observed in oleic acid, erucic acid, asclepic acid and palmitoleic acid.
Figure 87B:
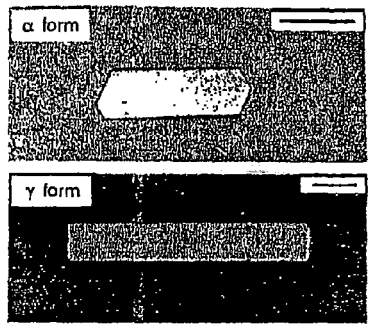
FIG. 87b shows a single crystal morphology of the α-form and δ-form of gondoic acid.
Figure 87C:
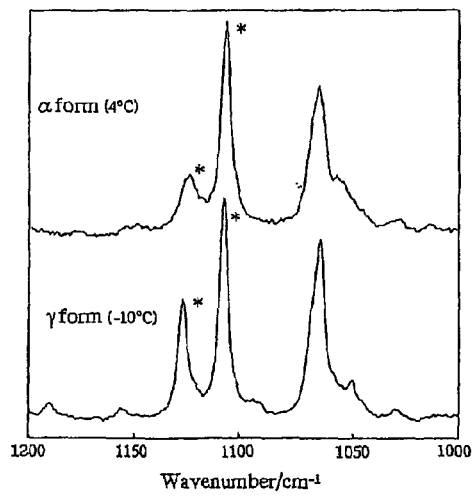
FIG. 87c shows a Raman scattering C-C stretching band of the α-form and δ-form of gondoic acid.
Figure 87D:
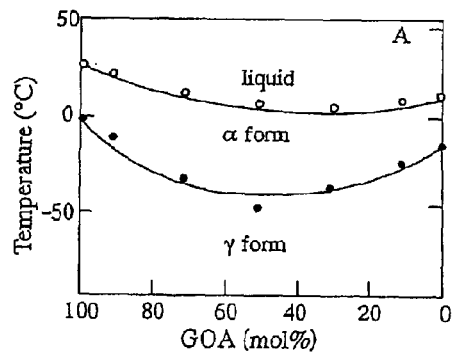
FIG. 87d shows a phase-diagram for mixtures of gondoic acid with asclepic acid.
Figure 87E:
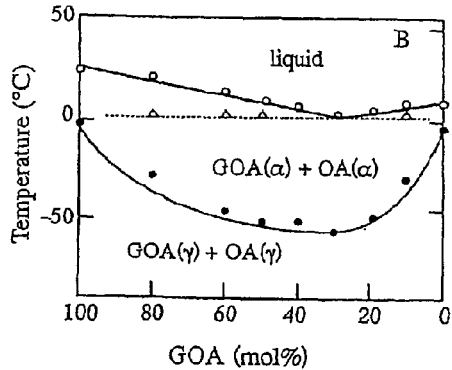
FIG. 87e shows a phase-diagram for mixtures of gondoic acid with oleic acid.

In many instances the Zeeman splitting produced by a magnetic field results in more than three frequencies, or in splitting that is spaced differently than expected. This is called the "anomalous" Zeeman effect (see FIGS. 65 and 66; wherein FIG. 66 shows an anomalous Zeeman effect for zinc 3p→3s.

If there are still just three frequencies, and the Zeeman effect is anomalous because the spacing is different than expected, the situation is similar to the normal effect. However, there are at most, two new splitting frequencies that can be used. If, however, the effect is anomalous because more than three frequencies are produced, then there will be a much more richly varied situation. Assume an easy case where there are four Zeeman splitting frequencies (see FIG. 67a and FIG. 67b). FIG. 67a shows four Zeeman splitting frequencies and FIG. 67b shows four new heterodyned differences.

In this example of anomalous Zeeman splitting, there are a total of four frequencies, where once existed only one frequency. For simplicity's sake, the new Zeeman frequencies will be labeled 1, 2, 3, and 4. Frequencies 3 and 4 are also split apart by the same difference "w". Thus, "w" is a heterodyned splitting frequency. Frequencies 2 and 3 are also split apart by a different amount "x". So far there are two heterodyned splitting frequencies, as in the normal Zeeman effect.

However, frequencies 1 and 3 are split apart by a third amount "y", where "y" is the sum of "w" and "x". And, frequencies 2 and 4 are also split apart by the same third amount "y". Finally, frequencies 1 and 4 are split even farther apart by an amount "z". Once again, "z" is a summation amount from adding "w+x+w". Thus, the result is four heterodyned frequencies: w, x, y, and z in the anomalous Zeeman effect.

If there were six frequencies present from the anomalous Zeeman effect, there would be even more heterodyned differences. Thus, the anomalous Zeeman effect results in far greater flexibility in the choice of frequencies when compared to the normal Zeeman effect. In the normal Zeeman effect the original frequency is split into three evenly spaced frequencies, with a total of just two heterodyned frequencies. In the anomalous Zeeman effect the original frequency is split into four or more unevenly spaced frequencies, with at least four or more heterodyned frequencies.

Similar Zeeman effects can occur in molecules. Molecules come in three basic varieties: ferromagnetic; paramagnetic; and diamagnetic. Ferromagnetic molecules are typical magnets. The materials typically hold a strong magnetic field and are composed of magnetic elements such as iron, cobalt, and nickel.

Paramagnetic molecules hold only a weak magnetic field. If a paramagnetic material is put into an external magnetic field, the magnetic moment of the molecules of the material are lined up in the same direction as the external magnetic field. Now, the magnetic moment of the molecules is the direction in which the molecules own magnetic field is weighted. Specifically, the magnetic moment of a molecule will tip to whichever side of the molecule is more heavily weighted in terms of its own magnetic field. Thus, paramagnetic molecules will typically tip in the same direction as an externally applied magnetic field. Because paramagnetic materials line up with an external magnetic field, they are also weakly attracted to sources of magnetic fields.

Common paramagnetic elements include oxygen, aluminum, sodium, magnesium, calcium and potassium. Stable molecules such as oxygen ($O_2$) and nitric oxide (NO) are also paramagnetic. Molecular oxygen makes up approximately 20% of our planet's atmosphere. Both molecules play important roles in biologic organisms. In addition, unstable molecules, more commonly known as free radicals, chemical reaction intermediates or plasmas, are also paramagnetic. Paramagnetic ions include hydrogen, manganese, chromium, iron, cobalt, and nickel. Many paramagnetic substances occur in biological organisms. For instance the blood flowing in our veins is an ionic solution containing red blood cells. The red blood cells contain hemoglobin, which in turn contains ionized iron. The hemoglobin, and hence the red blood cells, are paramagnetic. In addition, hydrogen ions can be found in a multitude of organic compounds and reactions. For instance, the hydrochloric acid in a stomach contains hydrogen ions. Adenosine triphosphate (ATP), the energy system of nearly all biological organisms, requires hydrogen and manganese ions to function properly. Thus, the very existence of life itself depends on paramagnetic materials.

Diamagnetic molecules, on the other hand, are repelled by a magnetic field, and line up what little magnetic moments they have away from the direction of an external magnetic field. Diamagnetic substances do not typically hold a magnetic field. Examples of diamagnetic elements include hydrogen, helium, neon, argon, carbon, nitrogen, phosphorus, chlorine, copper, zinc, silver, gold, lead, and mercury. Diamagnetic molecules include water, most gases, organic compounds, and salts such as sodium chloride. Salts are really just crystals of diamagnetic ions. Diamagnetic ions include lithium, sodium, potassium, rubidium, caesium, fluorine, chlorine, bromine, iodine, ammonium, and sulphate. Ionic crystals usually dissolve easily in water, and as such the ionic water solution is also diamagnetic. Biologic organisms are filled with diamagnetic materials, because they are carbon-based life forms. In addition, the blood flowing in our veins is an ionic solution containing blood cells. The ionic solution (i.e., blood plasma) is made of water molecules, sodium ions, potassium ions, chlorine ions, and organic protein compounds. Hence, our blood is a diamagnetic solution carrying paramagnetic blood cells.

With regard to the Zeeman effect, first consider the case of paramagnetic molecules. As with atoms, the effects can be categorized on the basis of magnetic field strength. If the external magnetic field applied to a paramagnetic molecule is weak, the Zeeman effect will produce splitting into equally spaced levels. In most cases, the amount of splitting will be directly proportional to the strength of the magnetic field, a "first-order" effect. A general rule of thumb is that a field of one (1) oersted (i.e., slightly larger than the earth's magnetic field) will produce Zeeman splittings of approximately 1.4 MHz in paramagnetic molecules. Weaker magnetic fields will produce narrower splittings, at lower frequencies. Stronger magnetic fields will produce wider splittings, at higher frequencies. In these first order Zeeman effects, there is usually only splitting, with no shifting of the original or center frequency, as was present with Zeeman effects on atoms.

In many paramagnetic molecules there are also second-order effects where the Zeeman splitting is proportional to the square of the magnetic field strength. In these cases, the splitting is much smaller and of much lower frequencies. In addition to splitting, the original or center frequencies shift as they do in atoms, proportional to the magnetic field strength.

Sometimes the direction of the magnetic field in relation to the orientation of the molecule makes a difference. For instance, $\pi$ frequencies are associated with a magnetic field parallel to an exciting electromagnetic field, while $\sigma$ frequencies are found when it is perpendicular. Both $\pi$ and $\sigma$ frequencies are present with a circularly polarized electromagnetic field. Typical Zeeman splitting patterns for a paramagnetic molecule in two different transitions are shown in FIGS. 68*a* and 68*b*. The $\pi$ frequencies are seen when $\Delta M = 0$, and are above the long horizontal line. The $\sigma$ frequencies are seen when $\Delta M = \pm 1$, and are below the long horizontal line. If a paramagnetic molecule was placed in a weak magnetic field, circularly polarized light would excite both sets of frequencies in the molecule. Thus, it is possible to control which set of frequencies are excited in a molecule by controlling its orientation with respect to the magnetic field.

When the magnetic field strength is intermediate, the interaction between the paramagnetic molecule's magnetic moments and the externally applied magnetic field produces Zeeman effects equivalent to other frequencies and energies in the molecule. For instance, the Zeeman spitting may be near a rotational frequency and disturb the end-over-end rotational motion of the molecule. The Zeeman splitting and energy may be particular or large enough to uncouple the molecule's spin from its molecular axis.

If the magnetic field is very strong, the nuclear magnetic moment spin will uncouple from the molecular angular momentum. In this case, the Zeeman effects overwhelm the hyperfine structure, and are of much higher energies at much higher frequencies. In spectra of molecules exposed to strong magnetic fields, hyperfine splitting appears as a small perturbation of the Zeeman splitting.

Next, consider Zeeman effects in so called "ordinary molecules" or diamagnetic molecules. Most molecules are of the diamagnetic variety, hence the designation "ordinary". This includes, of course, most organic molecules found in biologic organisms. Diamagnetic molecules have rotational magnetic moments from rotation of the positively charged nucleus, and this magnetic moment of the nucleus is only about $\frac{1}{1000}$ of that from the paramagnetic molecules. This means that the energy from Zeeman splitting in diamagnetic molecules is much smaller than the energy from Zeeman splitting in paramagnetic molecules. The equation for the Zeeman energy in diamagnetic molecules is:

$$Hz = -(g_J J = g_1 I) \cdot \beta H_o$$

where J is the molecular rotational angular momentum, I is the nuclear-spin angular momentum, $g_j$ is the rotational g factor, and $g_1$ is the nuclear-spin g factor. This Zeeman energy is much less, and of much lower frequency, than the paramagnetic Zeeman energy. In terms of frequency, it falls in the hertz and kilohertz regions of the electromagnetic spectrum.

Finally, consider the implications of Zeeman splitting for catalyst and chemical reactions and for spectral chemistry. A weak magnetic field will produce hertz and kilohertz Zeeman splitting in atoms and second order effects in paramagnetic molecules. Virtually any kind of magnetic field will produce hertz and kilohertz Zeeman splitting in diamagnetic molecules. All these atoms and molecules will then become sensitive to radio and very low frequency (VLF) electromagnetic waves. The atoms and molecules will absorb the radio or VLF energy and become stimulated to a greater or lesser degree. This could be used to add spectral energy to, for instance, a particular molecule or intermediate in a chemical crystallization reaction system. For instance, for hydrogen and oxygen gases turning into water over a platinum catalyst, the hydrogen atom radical is important for maintaining the reaction. In the earth's weak magnetic field, Zeeman splitting for hydrogen is around 30 KHz. Thus, the hydrogen atoms in the crystallization reaction system, could be energized by applying to them a Zeeman splitting frequency for hydrogen (e.g., 30 KHz). Energizing the hydrogen atoms in the crystallization reaction system will duplicate the mechanisms of action of platinum, and catalyze the reaction. If the reaction was moved into outer space, away from the earth's weak magnetic field, hydrogen would no longer have a 30 KHz Zeeman splitting frequency, and the 30 KHz would no longer as effectively catalyze the reaction.

The vast majority of materials on this planet, by virtue of existing within the earth's weak magnetic field, will exhibit Zeeman splitting in the hertz and kilohertz regions. This applies to biologics and organics as well as inorganic or inanimate materials. Humans are composed of a wide variety of atoms, diamagnetic molecules, and second order effect paramagnetic molecules. These atoms and molecules all exist in the earth's weak magnetic field. These atoms and molecules in humans all have Zeeman splitting in the hertz and kilohertz regions, because they are in the earth's magnetic field. Biochemical and biocatalytic processes in humans are thus sensitive to hertz and kilohertz electromagnetic radiation, by virtue of the fact that they are in the earth's weak magnetic field. As long as humans continue to exist on this planet, they will be subject to spectral energy catalyst effects from hertz and kilohertz EM waves because of the Zeeman effect from the planet's magnetic field. This has significant implications for low frequency communications, as well as chemical and biochemical reactions, diagnostics, and treatment of diseases.

A strong magnetic field will produce splitting greater than the hyperfine frequencies, in the microwave and infrared regions of the EM spectrum in atoms and paramagnetic molecules. In the hydrogen/oxygen reaction, a strong field could be added to the crystallization reaction system and transmit MHz and/or GHz frequencies into the reaction to energize the hydroxy radical and hydrogen reaction intermediates. If physical platinum was used to catalyze the reaction, the application of a particular magnetic field strength could result in both the platinum and the reaction intermediate spectra having frequencies that were split and shifted in such a way that even more frequencies matched than without the magnetic field. In this way, Zeeman splitting can be used to improve the effectiveness of a physical catalyst, by copying its mechanism of action (i.e., more frequencies could be caused to match and thus more energy could transfer).

A moderate magnetic field will produce Zeeman splitting in atoms and paramagnetic molecules at frequencies on par with the hyperfine and rotational splitting frequencies. This means that a crystallization reaction system can be energized without even adding electromagnetic energy. Similarly, by placing the crystallization reaction system in a moderate magnetic field that produces Zeeman splitting equal to the hyperfine or rotational splitting, increased reaction would occur. For instance, by using a magnetic field that causes hyperfine or rotational splitting in hydrogen and oxygen gas, that matches the Zeeman splitting in hydrogen atom or hydroxy radicals, the hydrogen or hydroxy intermediate would be energized and would proceed through the reaction cascade to produce water. By using the appropriately tuned moderate magnetic field, the magnetic field could be used to turn the reactants into catalysts for their own reaction, without the addition of physical catalyst platinum or the spectral catalyst of platinum. Although the magnetic field would simply be copying the mechanism of action of platinum, the reaction would have the appearance of being catalyzed solely by an applied magnetic field.

Finally, consider the direction of the magnetic field in relation to the orientation of the molecule. When the magnetic field is parallel to an exciting electromagnetic field, $\pi$ frequencies are produced. When the magnetic field is perpendicular to an exciting electromagnetic field, $\sigma$ frequencies are found. Assume that there is an industrial chemical crystallization reaction system that uses the same (or similar) starting reactants, but the goal is to be able to produce different products at will. By using magnetic fields combined with spectral energy or physical catalysts, the reaction can be guided to one set of products or another. For the first set of products, the electromagnetic excitation is oriented parallel to the magnetic field, producing one set of $\pi$ frequencies, which leads to a first set of products. To achieve a different product, the direction of the magnetic field is changed so that it is perpendicular to the exciting electromagnetic field. This produces a different set of $\sigma$ frequencies, and a different reaction pathway is energized, thus producing a different set of products. Thus, according to the present invention, magnetic field effects, Zeeman splitting, splitting and spectral energy catalysts can be used to fine-tune the specificity of many crystallization reaction systems.

Similar to other spectral frequencies, as previously discussed, control of resonant energy exchange via manipulation of magnetic fields can be used in crystallization reaction systems to achieve desired results.

In summary, by understanding the underlying spectral mechanism to chemical reactions, magnetic fields can be used as yet another tool to catalyze and modify those chemical reactions by modifying the spectral characteristics of at least one participant and/or at least one component in the crystallization reaction system.

Reaction Vessel and Conditioning Reaction Vessel Size, Shape and Composition

An important consideration in the use of spectral chemistry is the reaction vessel size, shape and composition. The reaction vessel size and shape can affect the vessel's NOF to various wave energies (e.g., EM, acoustic, electrical current, etc). This in turn may affect cell reaction system dynamics. For instance, a particularly small bench-top reaction vessel may have an EM NOF of 1,420 MHz related to a 25 cm dimension. When a reaction with an atomic hydrogen intermediate is performed in the small bench-top reaction the reaction proceeds quickly, due in part to the fact that the reactor vessel and the hydrogen hyperfine splitting frequencies match (1,420 MHz). This allows the reaction vessel and hydrogen intermediates to resonate, thus transferring energy to the intermediate and promoting the reaction pathway.

When the reaction is scaled up for large industrial production, the reaction would occur in a much larger reaction vessel with an EM NOF of, for example, 100 MHz. Because the reaction vessel is no longer resonating with the hydrogen intermediate, the reaction proceeds at a slower rate. This deficiency in the larger reaction vessel can be compensated for, by, for example, supplementing the reaction with 1,420 MHz radiation, thereby restoring the faster reaction rate.

Likewise, reaction vessel (or conditioning reaction vessel) composition may play a similar role in crystallization reaction system dynamics. For example, a stainless steel bench-top reaction vessel may produce vibrational frequencies which resonate with vibrational frequencies of a reactant, thus, for example, promoting disassociation of a reactant into reactive intermediates. When the reaction is scaled up for industrial production, it may be placed into, for example, a ceramic-lined metal reactor vessel. The new reaction vessel typically will not produce the reactant vibrational frequency, and the reaction will proceed at a slower rate. Once again, this deficiency in the new reaction vessel, caused by its different composition, can be compensated for either by returning the reaction to a stainless steel vessel, or by supplementing, for example, the vibrational frequency of the reactant into the ceramic-lined vessel; and/or conditioning the reaction vessel with a suitable conditioning energy prior to some or all of the other components of the reaction system being introduced into the reaction vessel.

It should now be understood that all the aspects of spectral chemistry previously discussed (resonance, targeting, poisons, promoters, supporters, electric and magnetic-fields both endogenous and exogenous to cell reaction system components, etc.) apply to the reaction vessel (or conditioning reaction vessel), as well as to, for example, any participant (or conditionable participant) placed inside it. The reaction vessel (or conditioning reaction vessel) may be comprised of matter (e.g., stainless steel, plastic, glass, and/or ceramic, etc.) or it may be comprised of a field or energy (e.g., magnetic bottle, light trapping, etc.) A reaction vessel (or conditioning reactor vessel), by possessing inherent properties such as frequencies, waves, and/or fields, may interact with other components in the cell reaction system and/or at least one participant. Likewise, holding vessels, conduits, etc., some of which may interact with the reaction system, but in which the reaction does not actually take place, may interact with one or more components in the cell reaction system and may potentially affect them, either positively or negatively. Accordingly, when reference is made to the reaction vessel, it should be understood that all portions associated therewith may also be involved in desirable reactions.

EXAMPLES

The invention will be more clearly perceived and better understood from the following specific examples.

Example 1

Enhancing the Growth of Sodium Chloride Crystals

This Example shows that the growth of crystals of NaCl was enhanced by applying electromagnetic energy from a commercially available 70-watt high-pressure sodium bulb to a saturated solution of sodium chloride. Specifically, as shown schematically in FIG. 88, a glass beaker 200 was divided substantially in half vertically by a divider or membrane 201. The divider or membrane 201 was not completely liquid-tight at the points where it contacted the glass beaker 200. Thus, ions were capable of migrating around and/or underneath the membrane 201 to permit substantially equivalent ion concentrations at any point in the beaker 200. However, the membrane 201 itself was substantially impervious to visible light frequencies. In particular, the membrane 201 was comprised of a paper-backed acetate material which is similar to the material used for creating overhead projector transparencies. A saturated solution of sodium chloride 202 was prepared by known conventional techniques. Specifically, distilled and deionized water was heated to about 45° C. and sodium chloride crystals from Fisher Chemicals (Certified A.C.S. and discussed later herein) were added until no more dissolution of the sodium chloride crystals occurred. The liquid was then decanted and filtered from any remaining undissolved sodium chloride and the resulting solution was placed into the beaker 200.

Figure 88:
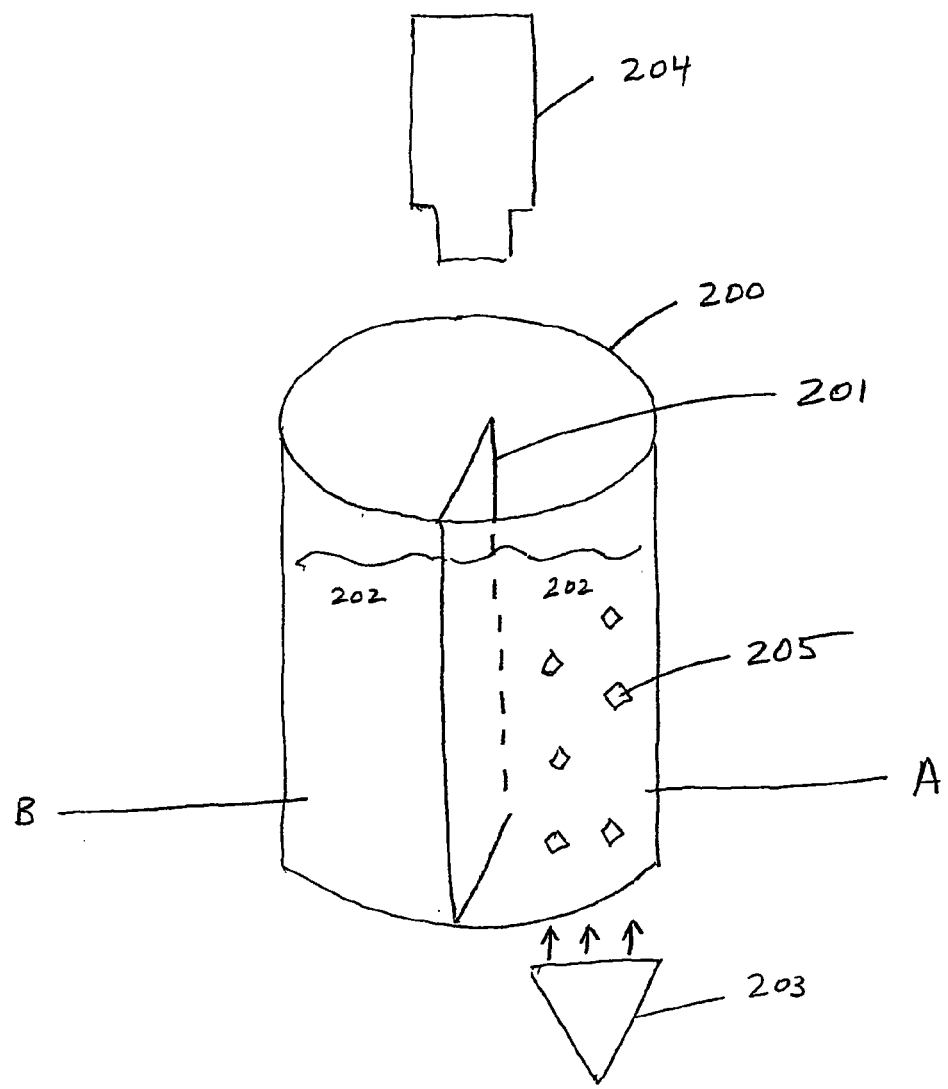
FIG. 88 shows a schematic of an apparatus that was utilized to grow sodium chloride crystals in accordance with Example 1.

A commonly available, 70 watt, high-pressure sodium lamp 203, was used to illuminate only side "A" of the beaker 200 containing the saturated NaCl solution 202. The lamp 203 was made by Philips and was sold under the Trademark CERAMALUX. The electric discharge sodium lamp 203 contained primarily sodium, but also contained some mercury, as is common in this type of discharge lamp. As shown in FIG. 88, a camera 204 was positioned on top of a magnifying microscopic assembly (not shown) so as to be able to view both of sides "A" and "B" from the top of the beaker 200 under 2× to 4× magnification.

The sodium lamp 203 was allowed to illuminate only the side "A" of the beaker 200 while the saturated solution 202 in both sides "A" and "B" was maintained at about room temperature. Even though the membrane 201 was not completely light-tight, the specific positioning of the light source 203 along with the positioning of the membrane 201 prevented almost all light from entering side "B" of the beaker 200. The temperature of the solution 202 was maintained at constant temperature (in this Example room temperature) by using a conventional heating/cooling stage (not shown in FIG. 88). In addition, all photomicrographs were taken by a computer-controlled system which permitted an instantaneous reading of temperature at the moment that the photomicrograph was taken. The entire crystal growth experiment was performed in a darkened room.

Figure 89B:
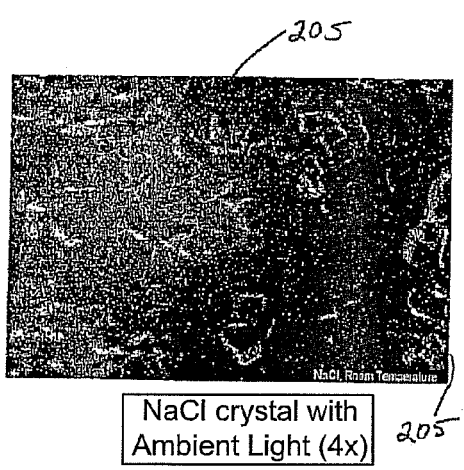
FIG. 89b is a photomicrograph taken at 4× of crystals formed under ambient light condition.
Figure 89A:
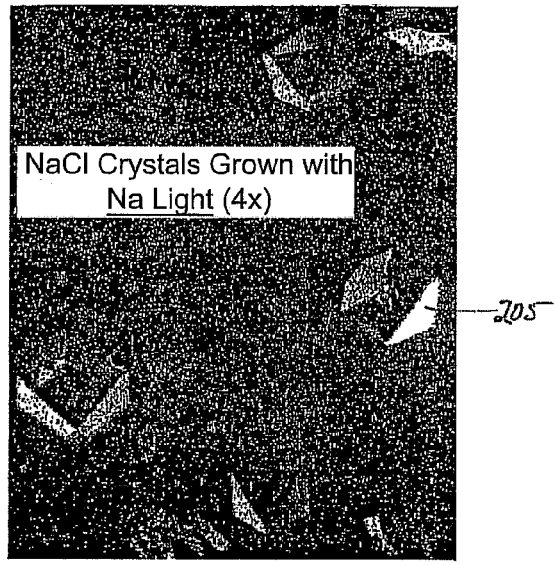
FIG. 89a is a photomicrograph taken at 4× of crystals formed on side "A" of the apparatus shown in FIG. 88.
Figure 89C:
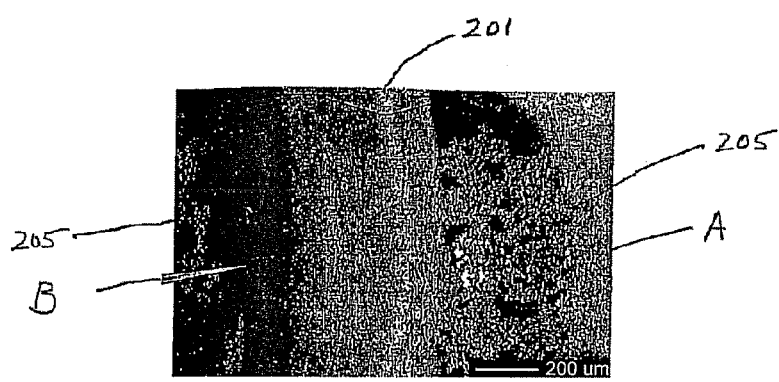
FIG. 89c shows a comparison of the amount of crystallization occurring on side "A" versus side "B" of the apparatus shown in FIG. 88.

FIG. 89*a* shows crystals 205 (magnification 4×) which were grown from the saturated solution 202 on side "A" of the beaker 200 which was illuminated by the sodium lamp 203 of FIG. 88. FIG. 89*b* shows crystals 205 (magnification 4×) which are grown from a solution corresponding to side "B" of the beaker 200. FIG. 89*c* shows an actual photomicrograph corresponding to a top view of the beaker 200 (by the microscope 204) with the divider or membrane 201 forming sides "A" and "B". It is clear that side "A" of the chamber contained a number of crystals 205, whereas side "B" of the chamber did not exhibit nearly as much crystal formation in comparison to side "A". Accordingly, the sodium discharge lamp 203 had a dramatic impact on the number, size and morphology (more precise faceting, pyramidal crystals) of crystals 205 formed from the saturated solution 202.

Example 2

Enhancing the Crystal Growth of Sodium Chloride

This Example shows that the growth of crystals of NaCl was enhanced by applying electromagnetic energy from a commercially available 70-watt high pressure sodium bulb to a saturated solution of sodium chloride; compared to crystal growth achieved with electromagnetic energy of a similar intensity but a different wavelength or frequency (e.g., provided by a tungsten light source).

Specifically, FIG. 90 shows a schematic representation of an assembly similar to that assembly used in Example 1. In particular, a slide 206, contained a small amount of a saturated solution 202 of sodium chloride thereon. The saturated solution of sodium chloride 202 was prepared by the same conventional techniques discussed in Example 1. A small amount of saturated solution 202 was placed onto the slide 206. As discussed in Example 1, the saturated solution 202 was made at a temperature about 45° C. The solution 202 was transferred to the slide 206 while its temperature was still elevated (e.g., was around 25-35° C.). The slide 206 was placed onto the same heating/cooling stage 310 discussed in Example 1. The temperature of the solution 202 was thereafter cooled by the heating and controlled channels 311 and 312 which were capable of changing temperature at a rate of about 1° C. per minute.

A light source 203 comprising the same sodium light source discussed in Example 1, and a light source 203', comprising a tungsten bulb, were sequentially exposed to different solutions 202. Specifically, a first sample of the saturated solution 202 was cooled down from about 3045° C., depending on the experiment, at a controlled rate of about 1° C. per minute while the sodium light source 203 was irradiated onto the solution 202 on the slide 206. Similarly, a second series of samples of saturated solution 202 was cooled from about 30-45° C., at the same controlled rate of about 1° C. per minute, while the tungsten light source 203' was irradiated onto the solution 202 located on the slide 206. In this instance, a 50 Å bandpass filter 207 was used which permitted only light corresponding to wavelengths of from about 4225 Å to about 4275 Å to pass therethrough. Similarly, a third sample of saturated solution 202 was cooled from about 30-45° C. at the same controlled rate of about 1° C. per minute while the filtered tungsten light source 203' was irradiated onto the solution 202 on the stage 206. In this instance, a second bandpass 50 Å filter 207' was used which permitted light corresponding to wavelengths of from about 6175 Å to about 6225 Å to pass therethrough. In each of these three different saturated solution samples series, the onset of crystallization was monitored and recorded by a computer-controlled system which permitted an instantaneous reading of temperature at the moment that the photograph was taken. It was noted that these solutions, upon cooling, may have become slightly supersaturated. However, for comparison purposes, the solutions were at the same temperatures and cooled at the same rates. Thus, the amount of crystallization observed was only a function of the spectral patterns that irradiated the solutions.

Figure 91A:
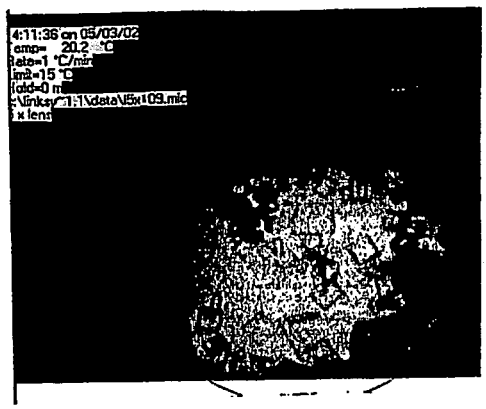
FIG. 91a shows a transmission optical micrograph of sodium chloride crystals grown with illumination by a sodium light.

FIG. 91a shows a transmission optical micrograph of the NaCl crystal growth which had resulted at a temperature of approximately 20° C. The saturated solution was illuminated by the sodium source light 203.

Figure 91B:
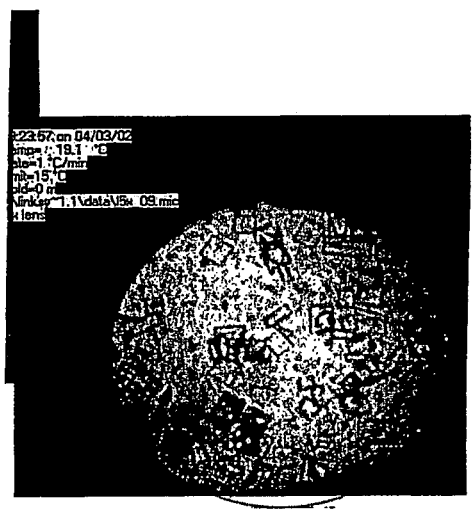
FIGS. 91b and 91c show the growth of sodium chloride crystals illuminated with tungsten light (filtered by 4250 Å) and tungsten light (filtered by 6200 Å), respectively.

FIG. 91b shows a transmission optical micrograph of the NaCl crystal growth from the saturated solution taken at about 19° C. This saturated solution was illuminated with a tungsten light filtered by the bandpass filter 207 (i.e., 4225 Å-4275 Å).

Figure 91C:
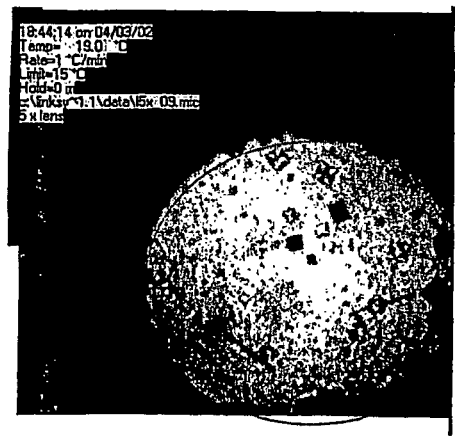

FIG. 91c shows a transmission optical micrograph of the NaCl crystal growth from saturated solution taken at about 19° C. This saturated solution was illuminated with a tungsten light filtered by the bandpass filter of 207' (i.e., 6175 Å-6225 Å).

It is clear from comparing the results in FIG. 91a, versus the results in both of FIGS. 91b and 91c, that the illumination of the saturated solution 202 with a sodium light source 203 had a dramatic increase in the amount of crystallization or crystal growth compared to illumination with the tungsten light source 203' filtered by the two filters 207/207', as shown in FIGS. 91b and 91c, respectively. In particular, the amount of field occlusion which is shown in FIG. 91a is much more dramatic than the amount of field occlusion that is shown in FIG. 91b or 91c. In this particular example, field occlusion is equivalent to the amount of crystallization that occurred. Accordingly, it is clear that the sodium light source had a dramatic impact on the number and size of crystals 205 which were formed from the saturated solution 202. It should be noted that the excessive field occlusion shown in FIG. 91a was accompanied by an onset of crystallization which began immediately upon illumination with the sodium light source. Crystallization did not begin in the experiments corresponding to FIGS. 91b and 91c until the solutions had cooled 2-3° C. Typically, in traditional crystallization experiments of this general type (e.g., growing NaCl crystals from solution) less crystallization would be expected at higher temperatures. NaCl crystal growth began at about 25° C. in the experiment corresponding to FIG. 91a; at about 23° C. in the experiment corresponding to FIG. 91b; and at about 22° C. in the experiment corresponding to FIG. 91c. Clearly the results shown in this Example 2 demonstrate that the sodium light influenced not only the amount of crystallization, but also the temperature at which the onset of crystal growth began.

Example 3

Enhancing the Growth of Potassium Dihydrogen Phosphate Cyrstals

The procedures of Example 1 were followed except for the following differences. Rather than forming a saturated solution of NaCl in water, a saturated solution of "KDP" (Potassium Dihydrogen Phosphate) was formed. The KDP (molecular weight 136.1) was obtained from Baker Analyzed Reagents (Stock #1-3246; Bakers Company in Phillipsburg, N.J.). Further, a potassium light source (Thermo Oriel, 10 W spectral line potassium lamp #65070; lamp mount #65160 and spectral lamp power supply #65150) was used rather than the sodium light source. Moreover, the membrane 201 divided the beaker 202 into four sections rather than two. The potassium source light was introduced to only one portion of the beaker 202. Growth of KDP crystals was observed only in the section of the beaker 202 which had the potassium light incident thereon. Absolutely no KDP crystal growth began in any of the three other chambers in the beaker 202 under the experimental conditions of this Example 3.

Example 4

Various Sodium Chloride and Sodium Bromide Crystallization Experiments

For the following Examples 4a-4ah, the below-listed Equipment, materials and experimental procedures were utilized (unless stated differently in each Example).

a) Equipment and Materials

Sterile water—Bio Whittaker, contained in one liter clear, plastic bottles, processed by ultrafiltration, reverse osmosis, deionization, and distillation.

Sodium Chloride, Fisher Chemicals, packaged in gray plastic 3 Kg bottles. The sodium chloride, in crystalline form, is characterized as follows:

Sodium Chloride; Certified A.C.S.
  Barium (Ba) (about 0.001%)—P.T.
  Bromide (Br)—less than 0.01%
  Calcium (Ca)—less than 0.0002%-0.0007%
  Chlorate and Nitrate (as $NO_3$)—less than 0.0006%-0.0009%
  Heavy Metals (as Pb)—less than 0.2 ppm-0.4 ppm
  Insoluble Matter—less than 0.001%-0.006%
  Iodide (I)—less than 0.0002%-0.0004%
  Iron (Fe)—less than 0.2 ppm-0.4 ppm
  Magnesium (Mg)—less than 0.001%-0.0003%
  Nitrogen Compounds (as N)—less than 0.0001%-0.0003%
  pH of 5% solution at 25° C.—5.0-9.0
  Phosphate ($PO_3$)—less than 5 ppm
  Potassium (K)—0.001%-0.005%
  Sulfate ($SO_4$)—0.003%-0.004%

Potassium Chloride, Fisher Chemicals, packaged in gray plastic 3 Kg bottles. The potassium chloride, in crystalline form, is characterized as follows:

Potassium Chloride, Certified A.C.S.
  Bromide—0.01%
  Chlorate and Nitrate (as $NO_3$)—less than 0.003%
  Nitrogen Compounds (as N)—less than 0.001%
  Phosphate—less than 5 ppm
  Sulfate—less than 0.001%
  Barium 0.001%
  Calcium and $R_2O_3$ Precipitate—less than 0.002%
  Heavy Metals (as Pb)—less than 5 ppm
  Iron—less than 2 ppm
  Sodium—less than 0.005%
  Magnesium—less than 0.001%
  Iodide—less than 0.002%
  pH of 5% solution at 25° C.—5.4 to 8.6
  Insoluble Matter—less than 0.005%

Sodium Bromide, Fisher Chemicals, packaged in small (e.g., pint-sized) brown glass jars. The sodium bromide, in crystalline form, is characterized as follows:

Sodium Bromide, Certified A.C.S.
  Barium—less than 0.002%
  Bromate—less than 0.001%
  Calcium—less than 0.002%
  Magnesium—less than 0.001%
  Chloride—less than 0.2%
  Heavy Metals (as Pb)—less than 5 ppm
  Insoluble Matter—less than 0.005%
  Iron—less than 5 ppm
  Nitrogen Compounds (as N)—less than 5 ppm
  pH of a 5% solution at 25° C.—5.5 to 8.8

Potassium—less than 0.1%

Sulfate—less than 0.002%

Humboldt Bunsen burner, with Coleman propane fuel.

One or more sodium lamps, Stonco 70 watt high-pressure sodium security wall light, fitted with a parabolic aluminum reflector directing the light away from the housing. The sodium bulb was a Type S62 lamp, 120V, 60 Hz, 1.5 A made in Hungary by Jemanamjjasond. One or more sodium lamps was/were mounted at various angles, and location(s) as specified in each experiment. Unless stated differently in the Example, the lamp was located at about 15 inches (about 38 cm) from the beakers or dishes to maintain substantially consistent intensities.

Potassium lamp, Thermo Oriel, 10 watt spectral line potassium lamp #65070 with Thermo Oriel lamp mount #65160 and Thermo Oriel spectral lamp power supply #65150. The potassium lamp was mounted overhead with the bulb oriented horizontally and about 9 inches (about 23 cm) from the experimental surface.

Full spectrum lamp, 75 watt, frosted Chromalux full spectrum lamp (containing full visible spectra of sodium, potassium, chlorine, and bromine). The full spectrum lamp was mounted overhead with the bulb oriented vertically and also, typically, about 15 inches from the beakers or dishes used in the various Examples, unless stated differently in each Example.

Figure 92:
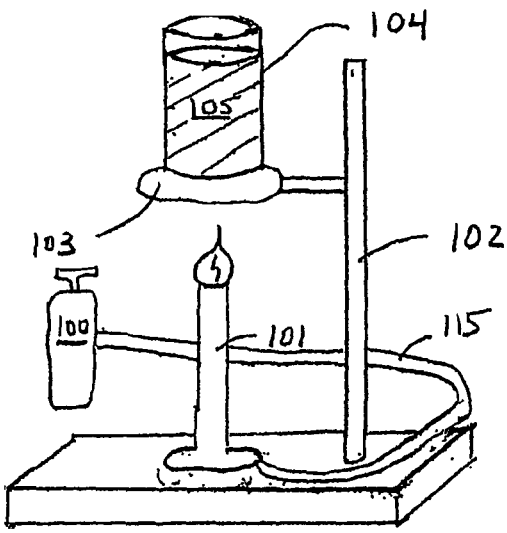
FIG. 92 shows a schematic of the apparatus used to prepare classical saturated solution.
Figure 93:
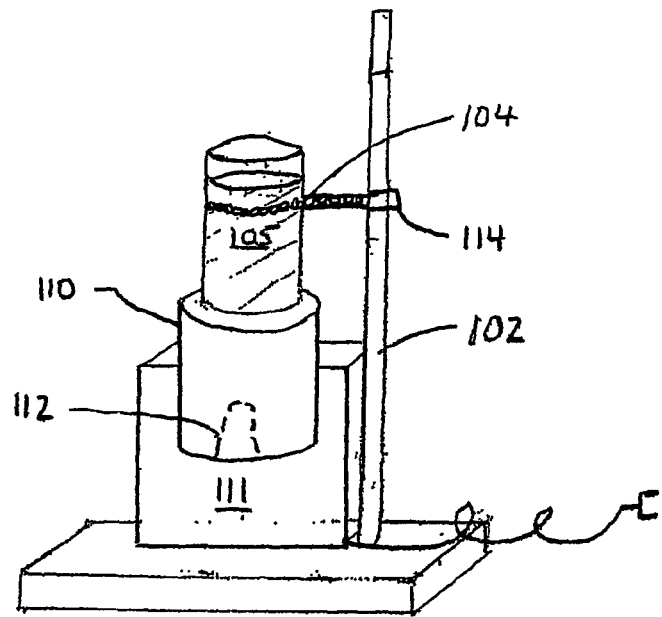
FIG. 93 shows a schematic of the apparatus used to prepare spectrally conditioned solution.

Shielded room in a dark or darkened room, Ace Shielded Room, Ace, Philadelphia, Pa., U.S. Model A6H3-16, copper mesh, with a width of about eight feet, a length of about 17 feet and a height of about eight feet (about 2.4 meters×5.2 meters×2.4 meters).

b) Preparation of Solutions i) Classical Solution—The apparatus used to make a classical solution is shown schematically in FIG. 92. Water (about 800 ml) was placed into a glass Beaker 104 and was heated with a Bunsen burner 101 from room temperature to about 55° C. in about 6-12 minutes. Salt was added in about 50 gram amounts and the solution 105 was stirred with a glass stir rod (not shown) until no more salt would dissolve and undissolved salt remained on the bottom of the Beaker 104. The solution 105 was then allowed to equilibrate overnight (about 16 hours) before being decanted for use in the various crystallization experiments discussed later herein.

ii) Conditioned Solution—The apparatus used to make a conditioned solution is shown in FIG. 93. Water (about 800 ml) was heated by the sodium lamp 112 and housing 111, which together were positioned below the Beaker 104. The light from the bulb 112 was made to be incident on the bottom of the Beaker 104 through an aluminum foil cylinder 110 which functioned as a light guide. The temperature of the solution 105 was raised to about 55° C. in about 40 minutes. Salt was added in about 50 gram amounts and the solution 105 was stirred with a glass stir rod until no more salt would dissolve and undissolved salt remained on the bottom of the Beaker 104. The solution 105 was allowed to equilibrate overnight (about 16 hours) before being decanted for use in the various crystallization experiments discussed later herein.

The D lines in the sodium electronic spectrum are resonant with vibrational overtones of water. Energizing these vibrational overtones of water changes its material properties as a solvent. Thus, the sodium lamp can be used to condition the water and change its material properties before it is used in a crystallization solution.

c) Crystallization Procedures i) Classical Crystallization—Solution was placed in a beaker or in a crystallization dish and left undisturbed in the presence of ambient overhead fluorescent lighting.

ii) Spectral Crystallization—Solution was placed in a beaker or in a crystallization dish and left undisturbed in the presence of irradiation from one or more positioned sodium or potassium lamps (as discussed in each Example). The sodium electronic spectrum produced by the spectral lamp affected metal halide phase changes.

d) Spectral Delivery Configurations i) Cone—Aluminum foil cone light guide fitted around a sodium light bulb, extending about 23 cm from the bulb, with the distal end formed around a uniform diameter of about 1.8 cm.

ii) Cylinder—Aluminum foil cylinder light guide fitted around a sodium light bulb, extending about 23 cm from the bulb, with a uniform diameter of about 6 cm.

iii) Parabolic—Aluminum dish (e.g., from a small stovetop burner) fitted around a sodium light bulb without a foil light guide.

e) Ambient Lighting

All experimental conditions described in the Examples occurred in the presence of standard fluorescent lighting. The fluorescent lamps were Sylvania Cool White Deluxe Fluorescent Lamps, 75 watts, and were each about eight (8) feet long (about 2.4 meters long). The lamps were suspended in pairs approximately 3.5 meters above the laboratory counter on which the experimental set-up was located. There were six (6) pairs of lamps present in a room which measured approximately 25 feet by 40 feet (7.6 meters×12.1 meters).

Example 4a

Sodium Chloride

Figure 94:
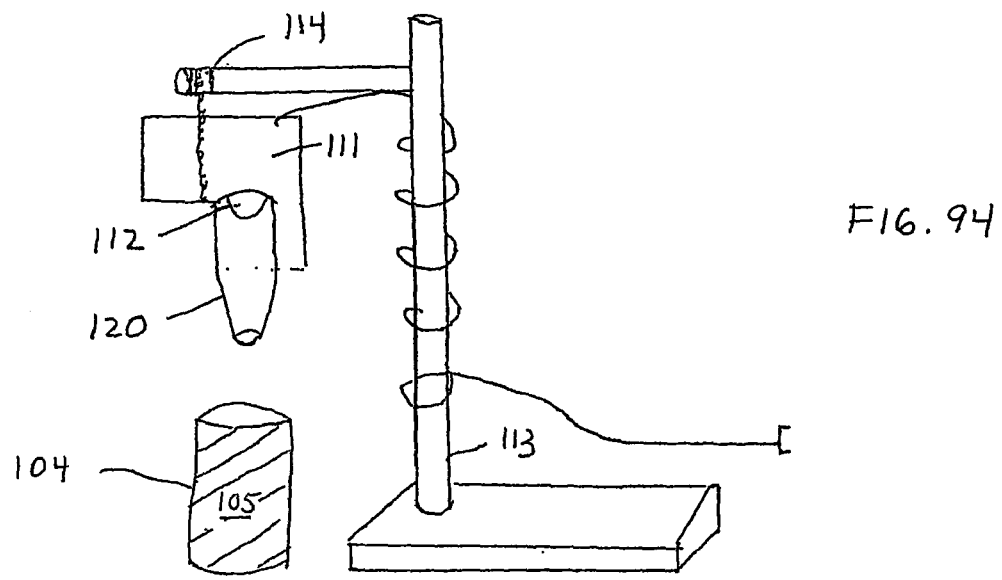
FIG. 94 shows a schematic of the experiments used to grow crystals from an overhead cone delivery system

Classical saturated NaCl solution (about 50 ml), at room temperature (22° C.), was placed into three glass beakers (200 ml). One beaker was placed in a 25° C. waterbath (making the solution slightly unsaturated) with spectral crystallization being initiated from a single overhead sodium lamp 112 with a cone delivery configuration 120 (as shown in FIG. 94). The second beaker was placed directly on the laboratory counter with spectral crystallization being irradiated from a single overhead sodium lamp 112 with a cone delivery configuration 120 (as shown in FIG. 94). The third beaker was placed into a plastic bucket as a control with no ambient light being incident on the saturated solution. Crystallization proceeded for about 21 hours under overhead fluorescent ambient lights (i.e., the first and second beakers).

Results: Both spectral crystallizations, relative to the control (crystals shown in FIG. 98a), showed more primary nucleation, and increased growth rate. The 25° C. unsaturated solution, which was spectrally irradiated, showed more crystallization (crystals shown in FIG. 98c) relative to the saturated spectral crystallization experiment (crystals shown in FIG. 98b). Moreover, the unsaturated solution showed more primary nucleation, increased sizes in NaCl crystals (e.g., about 2 mm average vs. about 1 mm average), and certain changes in morphology (rod-like structure (see FIG. 98d) in addition to cubes) and more precise faceting relative to the saturated and spectrally excited solution. Thus, the crystals from the thermally unsaturated solution shown in FIGS. 98c and 98d were larger than the crystals from the saturated solution shown in FIG. 98b.

Example 4b

Sodium Chloride

Figure 95:
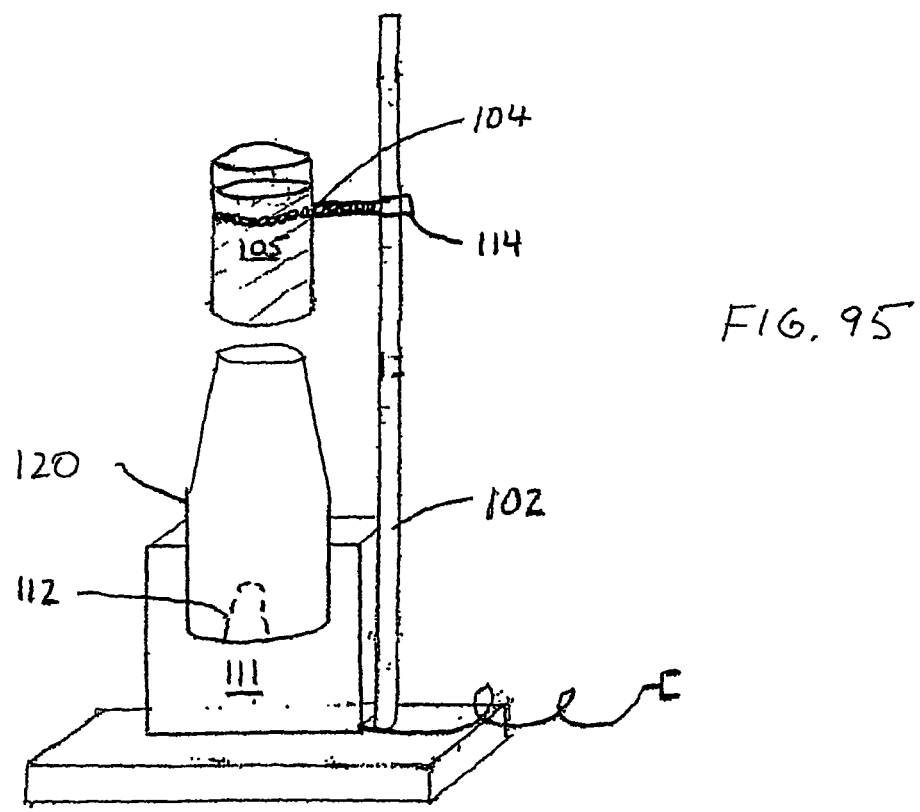
FIG. 95 shows a schematic of the experiments used to grow crystals from an underneath cone delivery system.

Classical saturated NaCl solution (about 100 ml), at room temperature (22° C.), was placed into four glass beakers (about 200 ml in size). Beaker #1 was suspended over a sodium lamp 112 with an aluminum foil cone 120 used to direct the energy from the sodium light 112 and the housing toward the Beaker 104, as shown in FIG. 95. Beaker #2, which also contained about 100 ml of classical saturated NaCl solution, had about 10 ml of water added thereto using a glass syringe (i.e., making the solution slightly unsaturated). Beaker #2 was also suspended over a sodium lamp 112 using a cone 120, as shown in FIG. 95. Beaker #3 was placed in an aluminum foil-wrapped bucket as a saturated control. After adding about 10 ml of water to beaker #4, it too was placed in the aluminum foil-wrapped bucket, but as an unsaturated control. Crystallization commenced under ambient overhead fluorescent lights. Approximately 2 hours after placing the beakers over the sodium lamps 112 (as shown in FIG. 95) it was noted that heat rising from the sodium lamps and sodium lamp housings 111 was heating the NaCl solutions in beakers 1 and 2. Solution temperatures were measured and Beaker #1 was about 56° C. The temperature of the solution 105 in Beaker #2 was about 58° C. and there were numerous small crystals on the bottom of the beaker and on the surface of the solution 105. A fan was used to cool the solutions while still delivering sodium spectra through the bottoms of the beakers. After about 21 hours, the temperature in Beaker #1 was about 22° C.; and the temperature in Beaker #2 was about 27° C.

Results: Both spectral crystallizations in Beakers #1 and #2, compared to the saturated control in Beaker #3, showed increased primary nucleation and increased crystal growth. The unsaturated control in Beaker #4 had no growth. Crystals from the unsaturated solution in Beaker #2 showed decreased primary nucleation, substantially increased growth rate (about 3-7 mm in size), and certain changes in morphology (rods) compared to the saturated solution in Beaker #1 (about 1-2 mm in size cubic crystals).

Example 4c

Sodium Chloride

Classical saturated NaCl solution (about 100 ml), at room temperature (22° C.), was placed into three beakers (about 200 ml in size). Sterile water (about 10 ml) was added to the 100 ml of classical saturated solution in Beaker #1 and Beaker #2, which were both suspended over a sodium lamp 112 with a cone delivery configuration 120, as shown in FIG. 95. Beaker #3 was placed into an aluminum foil-wrapped bucket as a saturated control. Beaker #1 was cooled with a fan. Beaker #2 was shielded from the fan until the temperature rose to about 58° C., and the shield was removed. Crystallization commenced under ambient overhead fluorescent lighting. After about 20 hours, the temperature in Beaker #1 was about 23° C. and there was no observed crystallization growth. The temperature in Beaker #2 was about 25° C.

Results: There were several cubic (approximately 3-8 mm) and a rectangular crystal (approximately 4×11 mm), similar to Example 4b, Beaker #2.

Example 4d

Sodium Chloride

Classical saturated NaCl solution (about 100 ml) at room temperature (22° C.) was placed into Beaker #1. A spectral saturated NaCl solution (about 100 ml) at room temperature (22° C.) was placed into Beaker #2. Beaker #3 with about 100 ml classical solution and Beaker #4 with about 100 ml of spectral solution were placed into an aluminum foil-wrapped bucket as controls. Beakers #1 and #2 were each placed under a single overhead sodium lamp 112 with a cone delivery configuration 120 (as shown in FIG. 94). Crystallization proceeded overnight (about 20 hours) under ambient overhead fluorescent lighting.

Results: Beakers #1 and #2 showed increased primary nucleation, and increased growth rate compared to the controls. Beaker #2, with a spectral solution, showed substantially increased primary nucleation and more overall crystallization (about 3.8 grams total) compared to the classical solution in Beaker #1 (about 3.3 grams total). In addition, crystals from the spectral solution had an altered morphology which included glass sheets, pyramid structures, and hollow pyramids inside cubic structures.

Example 4e

Sodium Chloride

Classical saturated NaCl solution (about 100 ml), at room temperature (22° C.), was placed into three beakers (about 200 ml in size). Sterile water (about 10 ml) was added to all three beakers. Beakers #1 and #2 were both suspended over a sodium lamp 112 with a cone delivery configuration 120 (FIG. 95). Beaker #3 was placed into an aluminum foil-wrapped bucket as an unsaturated control. Beaker #1 was shielded from the fan until the temperature rose to about 58° C., and the shield was removed. Beaker #2 was cooled with the fan. The tops of all three beakers were covered with plastic wrap.

Results: After about 20 hours there was no growth in any of the beakers.

Example 4f

Sodium Chloride

Classical saturated NaCl solution (about 100 ml), at room temperature (22° C.) was placed into five beakers (about 200 ml in size), and 50 ml into Beaker #6. Beakers #'s 1-5 were positioned under single overhead sodium lamps 112 with cones 120 (as shown in FIG. 94). Water was added (in the following amounts) via glass syringe to Beakers #'s 1-5 to create serial dilutions as follows: 1) zero; 2) 2 ml; 3) 4 ml; 4) 6 ml; and 5) 8 ml. Beaker #6 was placed into an aluminum foil-wrapped bucket as a saturated control. Spectral crystallization proceeded overnight (about 16 hours) at room temperature under ambient fluorescent lighting.

Results: Spectral crystallization of saturated, and 2 and 4 ml dilutions of the 100 ml saturated solution showed changes in morphology (e.g., rods, glass sheets, daisy stalks). Saturated solutions grew cubic crystals about 14 mm on a side, and a glassy sheet about 5 mm×5 mm. The 2 and 4 ml diluted solutions, relative to the saturated solution, showed approximately the same primary nucleation, and increased growth rate of individual crystals up to about 5 mm cubic. The 6 and 8 ml diluted solutions, compared to the saturated solution, showed different morphologies (e.g., pyramids), and decreased nucleation and decreased growth rate (e.g., ≦1 mm cubic crystals). The 6 and 8 ml diluted solutions showed definite spectral crystallization at decreased saturation (i.e., 103-104 ml remaining in beakers) with approximately the same primary nucleation, and approximately the same growth rate compared to the control crystallized traditionally from saturated solution. Crystals grown from the 3% unsaturated solution are shown in FIG. 98e.

Example 4g

Sodium Chloride

Figure 96:
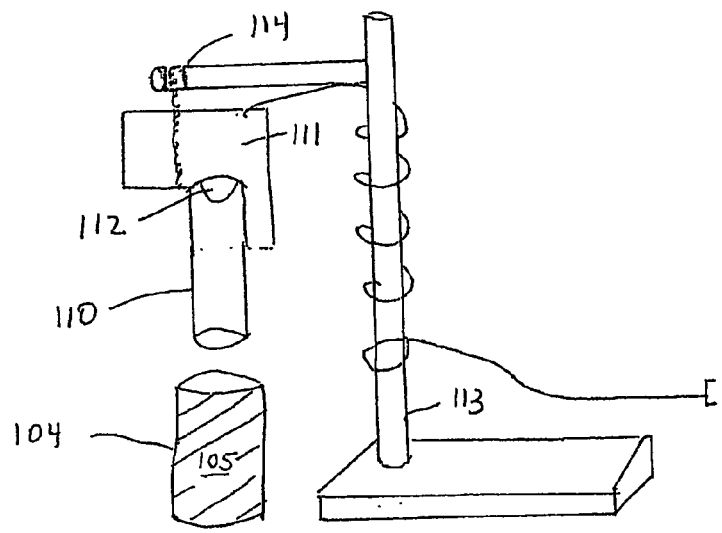
FIG. 96 shows a schematic of the apparatus used to grow crystals from an overhead cylinder delivery system FIGS. 97 a-g show various schematic representations of different apparatus used to grow crystals by causing spectral energy to be incident from different locations (and combinations of locations) according to various examples of the present invention.

Serial dilutions of classically prepared saturated NaCl solution (about 100 ml) were created as in Example 4f, with added water per 100 ml per beaker as follows: 1) zero; 2) 1 ml; 3) 2 ml; 4) 4 ml; 5) 6 ml; 6) 8 ml. Control Beakers #'s 7-10 each contained about 50 ml of classical saturated solution with added water as follows: 7) zero; 8) 0.5 ml; 9) 1 ml; 10) 2 ml. Beakers #1-6 were positioned under single overhead sodium lamps 112 with cylinder delivery configuration 110 (as shown in FIG. 96), and Beakers #'s 7-10 were placed in a closed, wooden/plastic cupboard. Crystallization proceeded at room temperature overnight (about 16 hours) with ambient fluorescent lighting on.

Figure 98A:
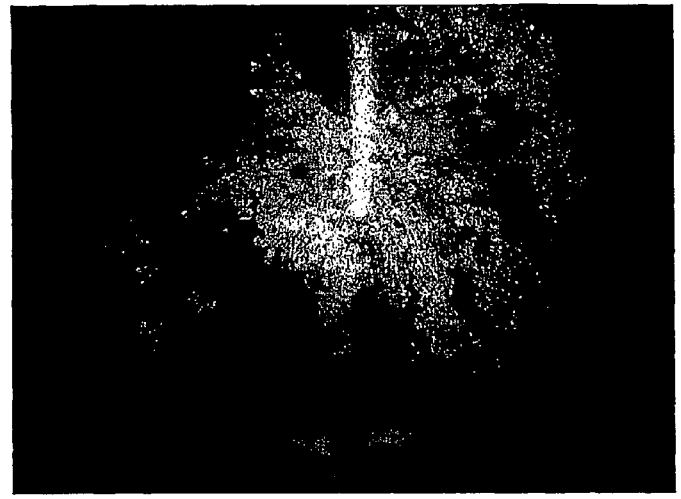
FIG. 98a shows a photomicrograph of sodium chloride crystal grown as a control from a saturated solution of sodium chloride and water after about 18 hours of growth.
Figure 98B:
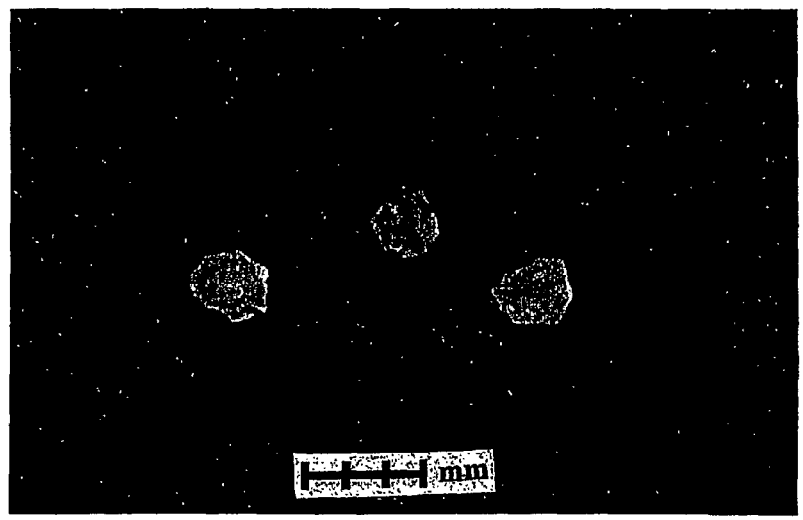
FIG. 98b shows a photomicrograph of sodium chloride crystal grown by spectral crystallization techniques from a saturated solution of sodium chloride and water.
Figure 98C:
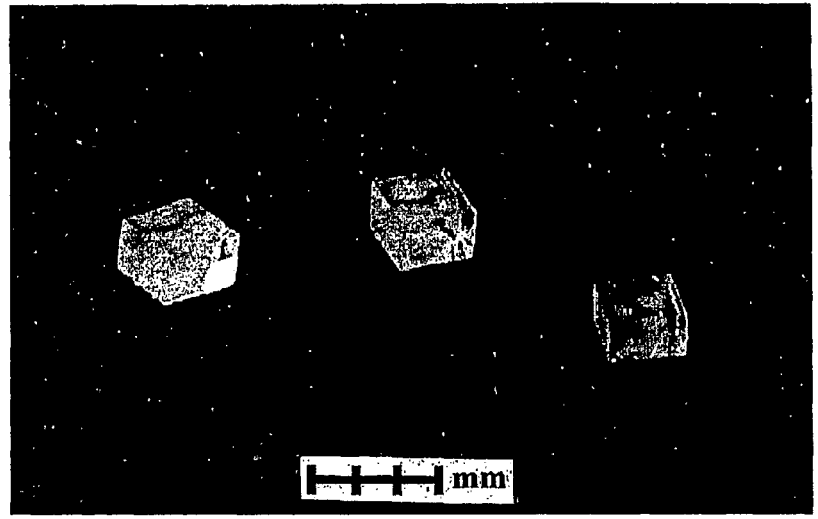
FIG. 98c shows a photomicrograph of sodium chloride crystallization grown by spectral crystallization techniques from an unsaturated solution of sodium chloride and water.
Figure 98D:
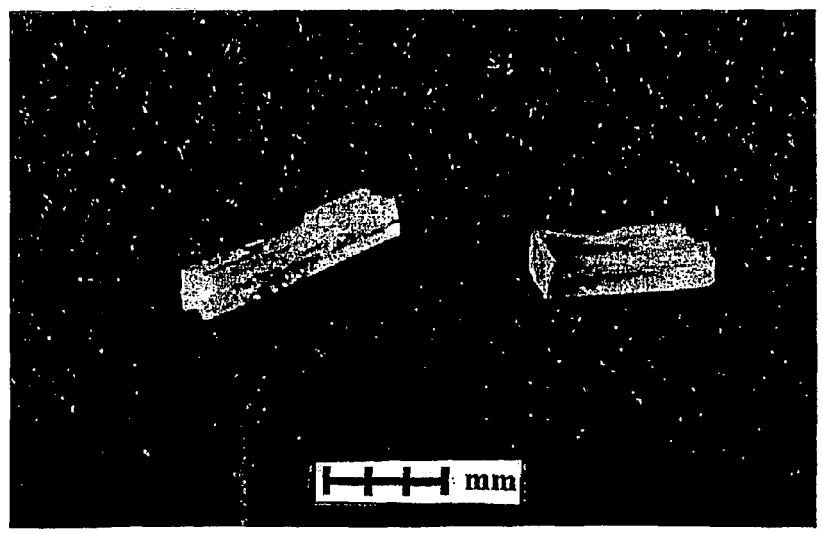
FIG. 98d shows a photomicrograph of sodium chloride crystallization grown by spectral crystallization techniques from an unsaturated solution of sodium chloride and water.
Figure 98E:
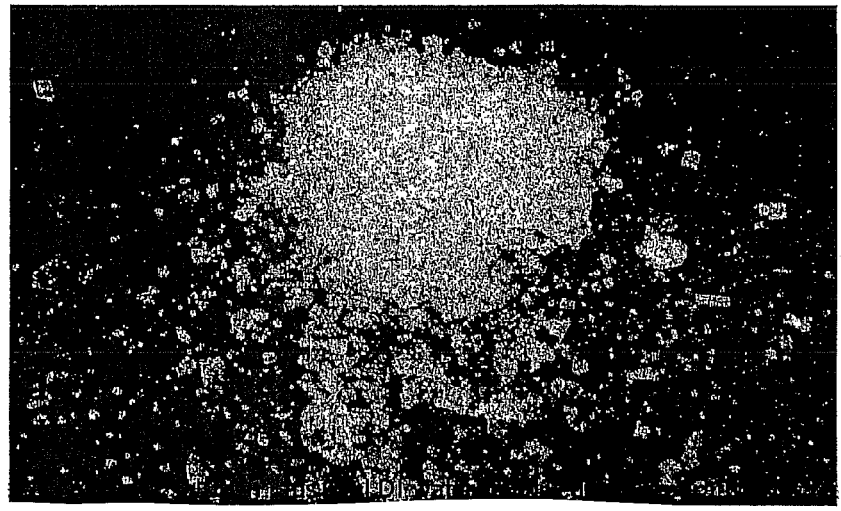
FIG. 98e shows a photomicrograph of sodium chloride crystallization grown by spectral crystallization techniques from an unsaturated solution of sodium chloride and water.

Results: All solutions in Beakers #1-6 showed substantially increased primary nucleation, increased growth rate, numerous clusters with individual cubic crystals about 3-5 mm, and increased water evaporation with overhead spectral cylinder irradiation (as shown in FIG. 96) compared to the results in Example 4f with overhead spectral cone irradiation. Beakers #1-6 also exhibited NaCl dendritic-like growth up the sides of the beakers (as shown in FIGS. 98ad and 98ae) apparently originating from NaCl crystals growing expitaxially on the beaker. By irradiating the sides of the beaker, which reflected the sodium spectral pattern, the beaker apparently functioned as an epitaxial substrate for crystallization. Approximate NaCl crystal weights for Beakers #'s 1-6 were as follows: 1) 22.9 g; 2) 10.3 g; 3) 26.4 g; 4) 22.1 g; 5) 23.4 g; 6) 13.4 g. Saturated control beaker #7 grew a few small crystals, while control Beakers #8-10 had no observable crystal growth.

Example 4h

Sodium Chloride

Serial dilutions of classically prepared saturated NaCl solution were created as in Example 15f, with added water per 100 ml per beaker as follows: 1) zero; 2) 1 ml; 3) 2 ml; 4) 3 ml; 5) 4 ml; 6) 5 ml. Beakers #1-6 were positioned under single overhead sodium lamps 112 with cylinder delivery configuration 110 (as shown in FIG. 96). Crystallization proceeded at room temperature with no ambient lighting present for about 65 hours.

Results: Compared to overnight spectral crystallizations of about 16-20 hours, all 65 hour crystallizations showed increased primary nucleation, and substantial increases in crystal size. Although crystallization began first in more saturated solutions, the largest single crystal (i.e., about 12×12×4 mm) was from the most dilute (5 ml H₂O/100 ml) solution. There were between 10 to 20 crystals greater than 1 cm on a side in each of the Beakers #1-6. Remaining saturated solution on the counter about 11 feet in front of the sodium lamps (e.g., there were 6 sodium lamps irradiating separate beakers at one time) grew many crystals (see FIGS. 98p and 98q) equal in size (i.e., about 5-7 mm and cubic in size) to those crystals grown overnight from the heated solutions in Examples 4b and 4c. Controls for Example 4g left on the counter about 12 feet behind the sodium lamps grew about 1 mm sand-like crystals in about 85 hours.

Example 4i

Sodium Chloride

Figure 97A:
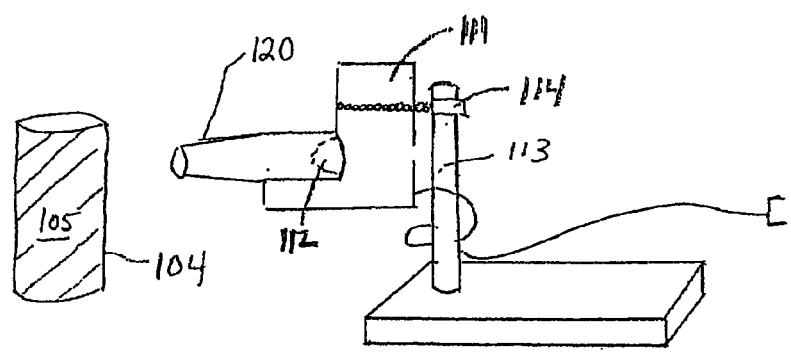
FIG. 97h is a schematic representation of an apparatus used for the solubility experiments of Example 8b.
Figure 97B:
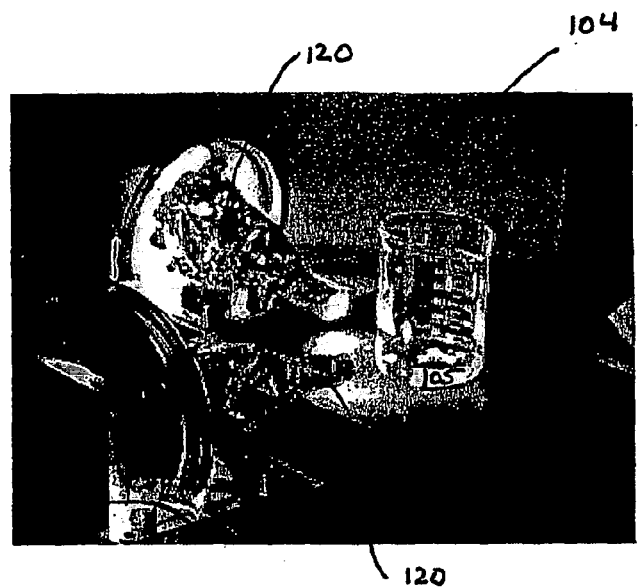
Figure 97C:
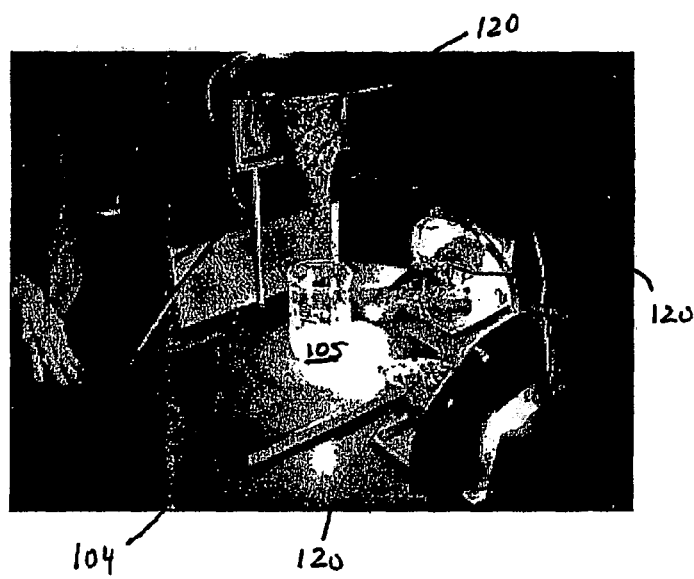

Classical saturated NaCl solution was prepared on a counter about 10 feet away from the nearest sodium lamp while Example 4h, was being conducted. Seven days later the classical saturated sodium chloride solution (about 50 ml) was placed into each of three separate beakers in a dark, shielded room. Spectral cone crystallization in various configurations, with no ambient light, proceeded overnight as follows: 1) single horizontal sodium lamp (FIG. 97a); 2) two horizontal sodium lamps at right angles to each other (FIG. 97b); and 3) two horizontal lamps at right angles to each other and one overhead lamp (FIG. 97c).

Results: Compared to classical solutions not exposed to ambient sodium spectral irradiation during their preparation, this solution grew crystals that exhibited substantially increased primary nucleation and all crystals were small (e.g., less than 1 mm) sand-like crystals.

Example 4j

Sodium Chloride

Classical saturated NaCl solution was filtered and about 50 ml was placed into each of three beakers in a dark and EM shielded room. Spectral cone crystallization (as discussed in Example 4i) with no ambient light present occurred overnight, as above.

Results—From the single horizontal sodium lamp (FIG. 97a) a single cubic crystal (about 0.27 grams) grew. From two horizontal sodium lamps at approximate right angles to each other (FIG. 97b) crystals grew (about 2.2 grams total weight) with 45° growth axes on the horizontal plane. Two horizontal lamps at approximate right angles and a third lamp overhead at approximate right angles grew hoppers and crystals with twinning on 3 planes (3.5 grams total weight). Temperature in the shielded room was about 26° C. (i.e., about 2 degrees above room temperature of the original saturated solution).

Example 4k

Sodium Chloride

Figure 97D:
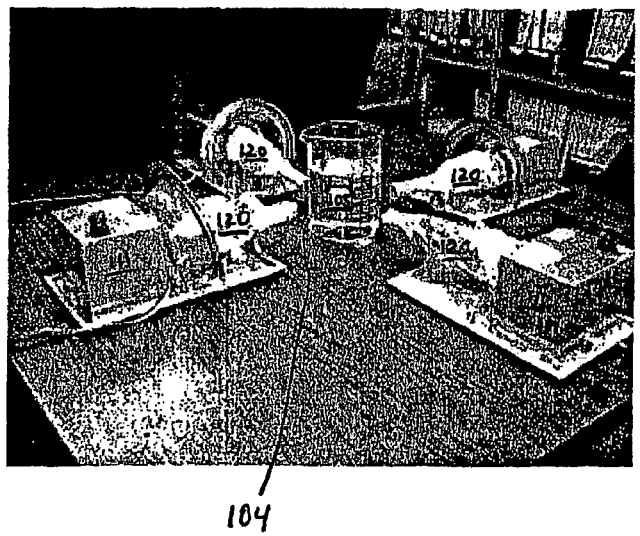
Figure 97E:
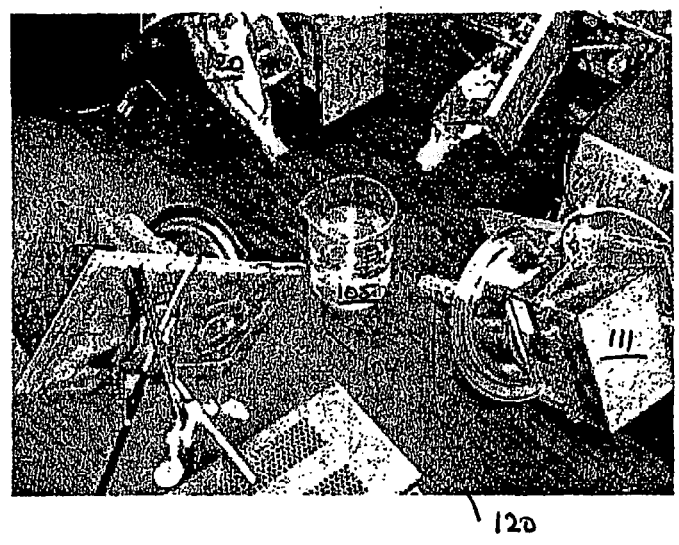

Classical saturated NaCl solution prepared as above was filtered and about 50 ml was placed into each of three beakers which were then placed into the aforementioned dark, shielded room. Beaker #1 had four horizontal sodium lamps with cones (FIG. 97d), and all at approximate right angles to each other. Beaker #2 had four overhead sodium lamps with cones, and positioned at right angles to each other and at about a 45 degree angle from the horizontal (FIG. 97e). Beaker #3 was placed in a control bucket. Crystallization proceeded overnight (about 18 hours) with no ambient light present in the shielded room.

Figure 98F:
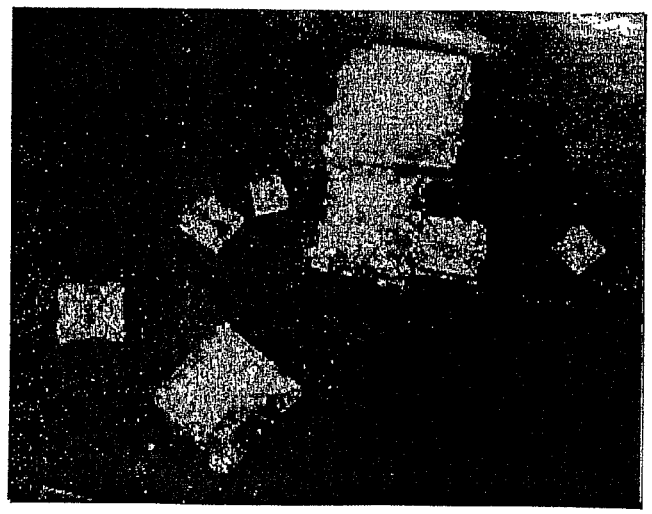
FIG. 98f shows a photomicrograph of sodium chloride crystal grown by spectral crystallization techniques from a saturated solution of sodium chloride and water.
Figure 98G:
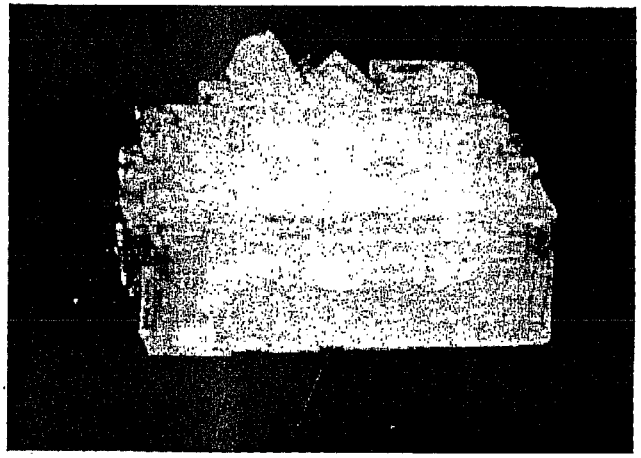
FIG. 98g is a photomicrograph which shows the largest crystal from FIG. 98f.
Figure 98H:
FIG. 98h shows a photomicrograph comparison of amounts of sodium chloride crystals formed as a function of solution properties techniques.
Figure 98I:
Figure 98J:
Figure 98K:
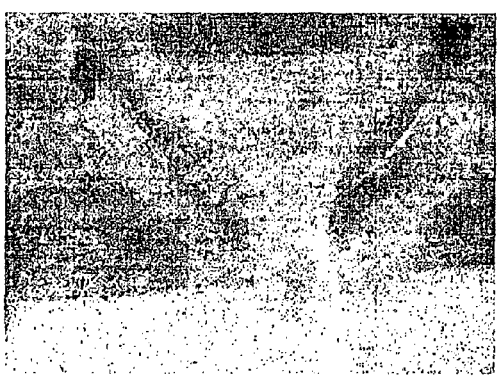
Figure 98L:
Figure 98M:
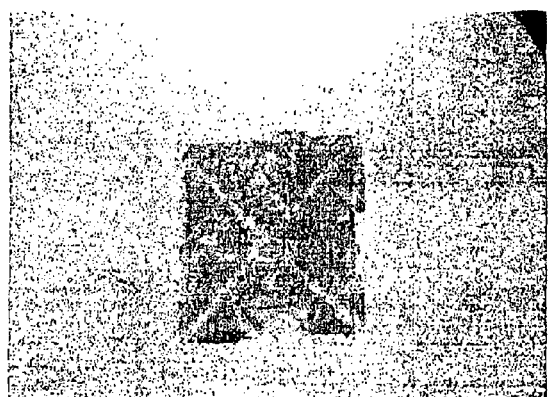
Figure 98N:
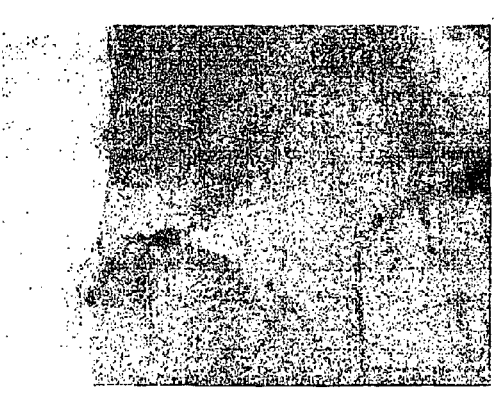
Figure 98O:
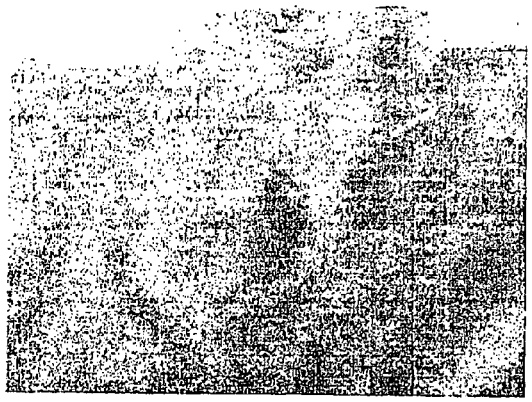
Figure 98P:
Figure 98Q:
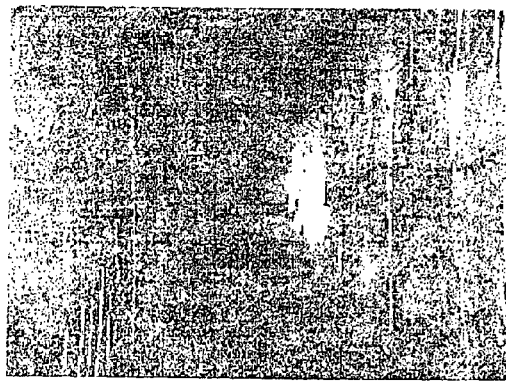
Figure 98R:
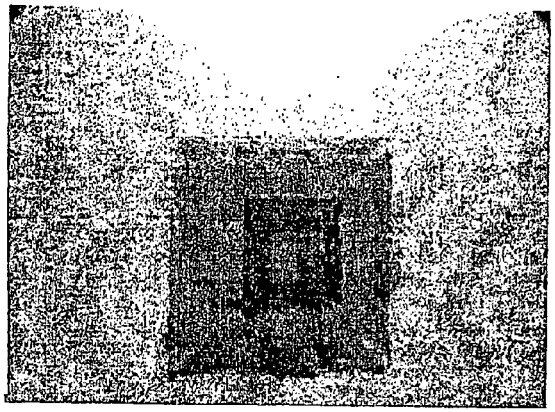
Figure 98S:
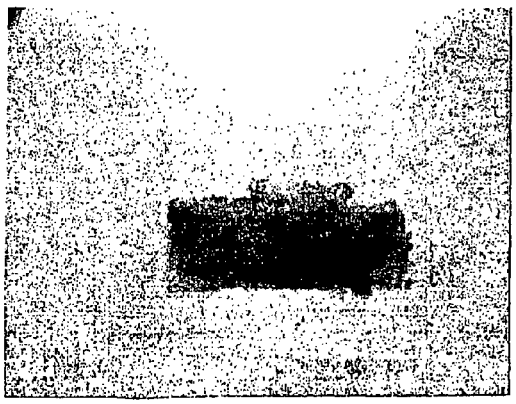

Results: Beaker #1 (four horizontal sodium lamps at right angles and as shown in FIG. 97d) grew cubes (about 4-11 mm on a side) and large crystals with significant twinning (about 16 mm on a side). Four overhead sodium lamps at approximate 45° angles (FIG. 97e), grew twinned cubes (about 5-10 mm) and large hoppers (with the largest measuring about 13×13×7 mm). FIGS. 98f and 98g show some of the crystals grown according to this Example, with FIG. 98g showing the largest crystal grown. The control in total darkness in the shielded room showed no growth. Beaker #1 also grew epitaxial crystals and dendritic formations on the side of the beaker, where the horizontal light beams intersected the glass/solution/air triple point.

Example 4l

Sodium Chloride

The experimental procedure was identical to the experimental procedure of Example 4k, except that spectral NaCl solution was used rather than classical NaCl solution.

Results: Beaker #1 (four horizontal sodium lamps at approximate right angles (FIG. 97d), grew many small twinned cubes (about 34 mm on a side). Beaker #2 (four overhead sodium lamps at approximately 45° angles from horizontal and substantially equally spaced from each other (FIG. 97e), grew many small twinned cubes (about 4-5 mm on a side) and a few twinned crystals. The control maintained in total darkness in the shielded room showed no growth. The spectral solution exhibited increased nucleation.

Twinned cubic crystals from Beakers 1 and 2 were removed and placed in fresh spectral, saturated, filtered NaCl solution in the dark, shielded room with the same spectral cone crystallization overnight.

Results: Crystals in both Beakers #1 and #2 grew pyramidal corners and rims onto the twinned cubes with substantially increased primary nucleation.

Example 4m

Sodium Chloride

Figure 97F:
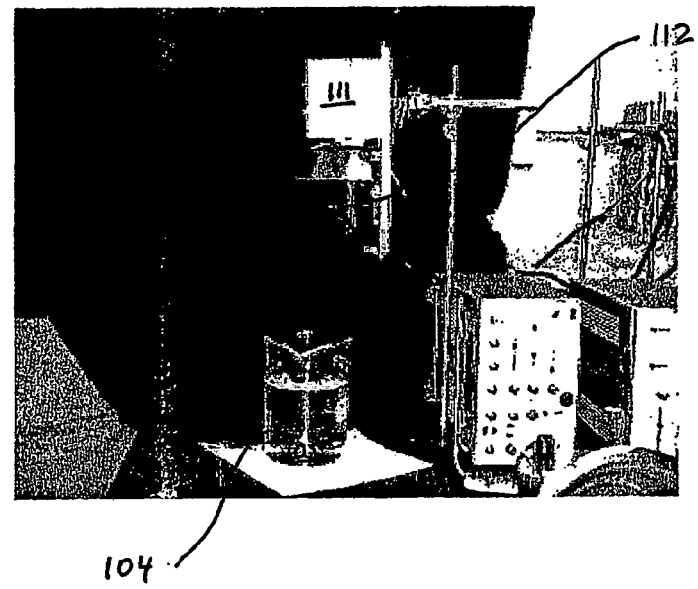

Seven beakers with different serial dilutions of classical saturated filtered NaCl solution were placed under overhead sodium lamps with parabolic dishes (FIG. 97f). The serial dilutions were 0, 1, 2, 3, 4, 5 and 6 ml of water separately added to about 100 ml of saturated solution. Four more beakers with serial dilutions (zero, 2, 4, and 6 ml) were placed in a cupboard as controls. Crystallization proceeded overnight (about 20 hours) with no ambient light.

Results: Twinned cubes and/or crystals grew in all beakers, with increased primary nucleation in the more saturated solutions and increased crystal size in the 4 ml dilution.

Spectral Crystallization—about 3-4 mm cubic; 1 ml diluted solution about 3-6 mm cubic with 1 cm polycrystalline mass; 2 ml diluted solution about 4-6 mm cubes and 16 mm diameter twinned crystal with about 1 cm rod projecting vertically at 45 degrees; 3 ml diluted solution about 5-7 mm cubes and about 14 mm polycrystalline twinned crystal; 4 ml diluted solution about 34 mm cubes and about 5×10 twinned polycrystalline mass; 5 ml diluted solution about 2-3 mm cubes; 6 ml diluted solution about 2-3 mm cubes.

Serial dilution controls had been placed in a wooden/plastic cupboard, which was later found to admit a narrow beam of light between the cupboard doors (e.g., sodium light and/or ambient fluorescent lights). The saturated control grew many small (about 1-1.5 mm cubic) primary nucleations overnight while the dilutions grew nothing. After an additional approximately 24 hours in the cupboard, the saturated and 2 ml serial dilution showed substantially increased primary nucleation with about 1-2 mm crystals; the 4 ml diluted solution grew large rods (about 4×10 mm and about 3×8 mm), a cubic corner (about 8 mm), and two twinned crystals (about 10×12 mm and about 9×9 mm); and the 6 ml diluted solution grew small sand-like crystals.

Example 4n

Sodium Chloride

Classical saturated NaCl solution was both prepared and stored in the dark. Beakers with 100 ml filtered solution were placed into the dark, shielded room with the following set-up: 1) four horizontal sodium lamps with cones at approximate right angles (FIG. 97d); 2) four overhead sodium lamps with cones at about 45° angles FIG. 97e); 3) on a table about 8 feet from the sodium lamps; and 4) in an aluminum foil-covered bucket. Crystallization proceeded overnight (about 20 hours) with no ambient light present.

Results:—Beaker #1 (four horizontal sodium lamps), FIG. 97d, grew many twinned cubes (about 34 mm), pyramids, rods, twinned crystals, and a cubic corner, with a total weight of 6.1 grams. Beaker #2 (four sodium lamps at about 45°), FIG. 97e, grew twinned cubes and crystals (about 4-5 mm on a side), and a large twinned crystal (about 18×11 mm) with a total weight of about 9.5 grams. Beaker #3 (i.e., on the about table 8 feet away) grew many small (about 1 mm) crystals, with a total weight of about 2.7 grams. Beaker #4 (aluminum foil-covered bucket) grew about 0.2 grams of very small crystals (less than about 1 mm).

Example 4o

Sodium Chloride

The experimental procedure was identical to the experimental procedure of Example 4n, except that a spectral NaCl solution prepared in the dark was used.

Results: Beaker #1 (four horizontal sodium lamps as shown in FIG. 97d), grew 15 twinned cubes (most about 5-7 mm), hoppers, a corner (about 10×10 mm), a rod (about 15×4) and polycrystals (up to about 15×12 mm). As shown in FIGS. 98i, 98j, 98k and 98l, the crystals that were grown according to this Example also exhibited modified growth planes at 45° angles to the normal axes. Beaker #2 (four sodium lamps oriented overhead at about a 45° angle, as shown in FIG. 97e), grew twinned cubes (about 7 mm), 2 large hoppers (about 10×10 mm and 12×12 mm), and 5 polycrystals with twinning ranging from about 6×10 mm to 14×18 mm. As shown in FIGS. 98m, 98n, 98o, and 98v, the crystals that were grown according to this Example also exhibited modified growth planes at 45° angles to the normal axes. The control maintained in total darkness showed no crystallization at all. This experiment demonstrates the effects of directional spectral crystallization.

Example 4p

Sodium Chloride

The experimental procedure was identical to Example 4n, except a spectral NaCl solution prepared under ambient fluorescent lighting was used.

Results—Beaker #1 (four horizontal sodium lamps; FIG. 97d) grew clear cubes and rods. Beaker #2 (four sodium lamps oriented at 45°; FIG. 97e) grew cubes and clumped crystals. The control, maintained in total darkness in the shielded room in an aluminum foil-wrapped bucket, showed no crystallization. The crystals grown from the spectral solution appear to be more clear and more perfect than crystals grown from the classical solution.

Example 4q

Sodium Chloride

The experimental procedure was identical to Example 4n, except that a spectral NaCl solution prepared in the dark was used.

Results—Beaker #1 (four horizontal Na lamps; FIG. 97*d*) grew many (greater than 50) small cubes (about 24 mm on a side). Beaker #2 (four sodium lamps oriented at 45°; FIG. 97*e*) grew fewer (approximately 30) but larger cubes (about 5-7 mm on a side) and pyramids. The crystals in both Beakers #1 and #2 were growing above a layer of sandy consistency crystals. The control, maintained in total darkness in the aluminum foil-wrapped bucket, showed no crystallization. The spectral solutions appear to produce many more nucleations and this solution preparation technique should be applicable when a polycrystalline phase or thin film may be useful.

Example 4r

Sodium Chloride

A spectral NaCl solution was prepared and filtered and about 50 ml of solution was placed into each of five different sized beakers #'s 1-5 as follows: 1) 50 ml beaker; 2) 150 ml beaker; 3) 250 ml beaker; 4) 400 ml beaker; and 5) 600 ml beaker. About 50 ml of solution was also placed into each of control Beakers #'s 6-10 as follows: 6) 50 ml beaker; 7) 150 ml beaker; 8) 250 ml beaker; 9) 400 ml beaker; and 10) 600 ml beaker. Beakers #'s 1-5 were placed under overhead sodium lamps 112 with cone delivery configuration 120, as shown in FIG. 94. Beakers #'s 6-10 were placed in a cabinet with the doors covered with aluminum foil to block light from entering into the cabinet. Crystallization proceeded overnight (about 16 hours) with no ambient light present.

Results: For the spectral crystallizations, the following results were achieved: 1) approximately 25 cubes (about 1.5-2 mm); 2) approximately 12 cubes (about 3-5 mm); 3) approximately 25 cubes (about 3-6 mm); 4) approximately 20 cubes (up to about 9 mm); 5) approximately 25 cubes (about 3-6 mm).

For the controls, the following results were achieved: 6) approximately 15 cubes (most about 1 mm); 7) approximately 10 cubes (about 1.5 mm); 8) approximately 4 cubes (about 3 mm) and a rod (about 1.5×9 mm); 9) approximately 8 cubes (about 24 mm); 10) approximately 12 cubes (about 3-6 mm). Thus, with the same solution and crystallization time, crystal yields and growth are affected by the size and/or shape of the beaker (e.g., container or reaction vessel effects).

In this Example, targeted spectral energies were used to affect phase changes, material properties, and structure in solid and liquid materials.

Example 4s

Sodium Chloride

Figure 97G:
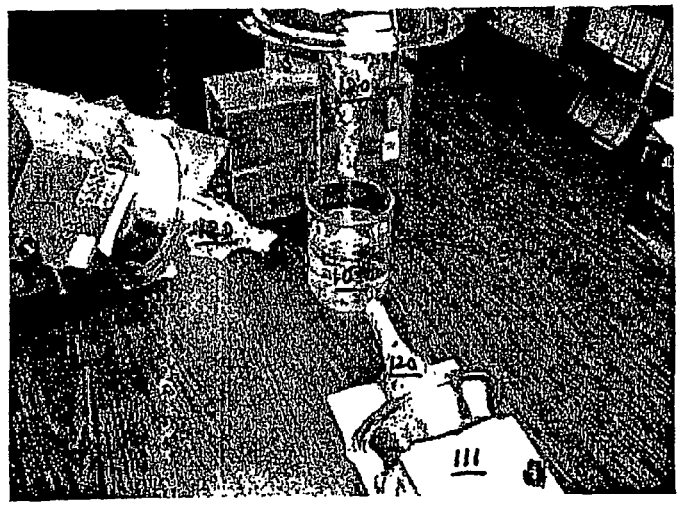

Classical NaCl solution prepared in the dark was filtered and about 100 ml placed into three separate beakers (about 600 ml in size) in the dark, shielded room. Beaker #1 was illuminated by two horizontal sodium lamps and one overhead sodium lamp (FIG. 97*c*). Beaker #2 was illuminated by one horizontal lamp, one overhead lamp at about 90 degrees to the horizontal lamp, and one lamp at about 45 degrees between the horizontal and overhead lamps (FIG. 97*g*). The control Beaker #3 was placed in an aluminum foil-wrapped bucket in the dark, shielded room. Crystallization proceeded overnight in the dark, shielded room (about 20 hours) with no ambient light present.

Figure 98T:
Figure 98:
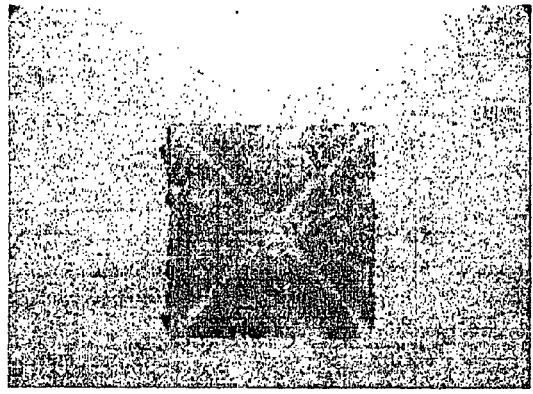
Figure 98:
Figure 98:
Figure 98:
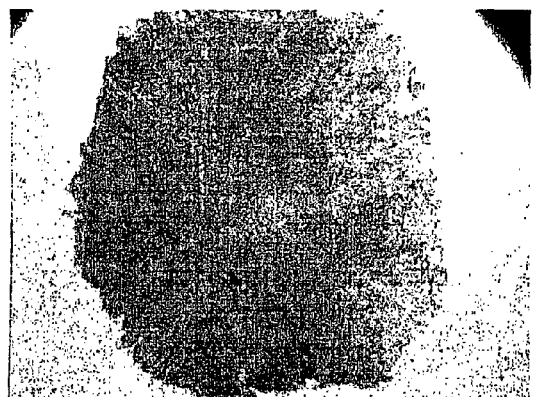
Figure 98:
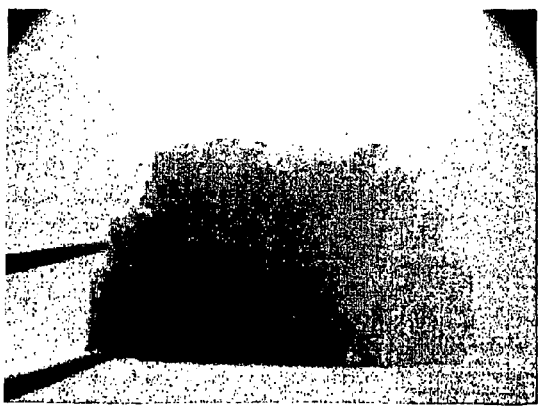
Figure 98:
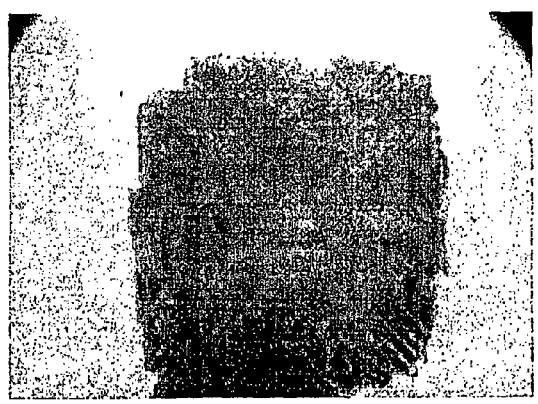
Figure 98:
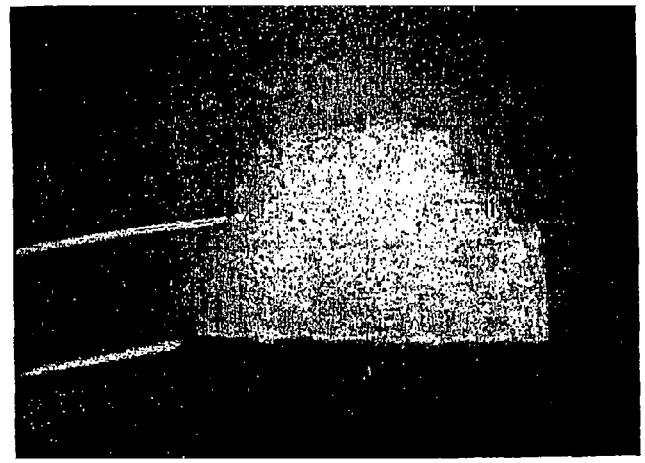
Figure 98:
Figure 98:
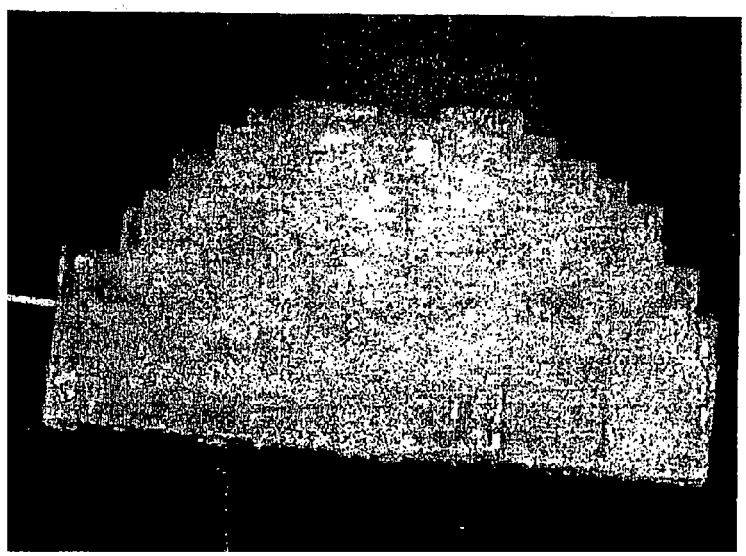

Results: The control in the aluminum foil-wrapped bucket showed no crystallization. Beaker #1 (2 horizontal/1 overhead; FIG. 97*c*) grew more than 50 cubes (2 about 4 mm) and approximately 10 rods (about 3-11 mm in length). Beaker #2 (one horizontal, one 45 degrees, one overhead; FIG. 97*g*) grew approximately 15 cubes (about 5-12 mm; see FIGS. 98*t* and 98*u*) many of which were twinned and/or hoppers, a few rods (up to about 22×2 mm) and two polycrystalline clusters. Thus, it appears that direction and orientation of the spectral input during crystallization affects crystal growth and morphology.

Example 4t

Sodium Chloride

Experimental procedures were identical to Example 4s, except that a spectral solution prepared in the dark was used. Crystallization proceeded with no ambient light present.

Results: The control in the aluminum foil-wrapped bucket showed no crystallization. Beaker #1 (2 horizontal/1 overhead; FIG. 97*c*) grew approximately 40 cubes (about 3-7 mm) many with twinning and 4-5 polycrystalline masses about 5-10 mm. Beaker #2 (horizontal, 45 degrees, overhead; FIG. 97*g*) grew approximately 30 slightly larger cubes (about 5-7 mm) and rods (about 10×3 mm). Beaker #3 (control) showed no growth.

Example 4u

Sodium Chloride

Spectral NaCl solution (stored with aluminum foil around beaker to block light) was filtered and different amounts were placed into identical 400 ml Pyrex beakers #'s 1-5 as follows: 1) 50 ml solution; 2) 75 ml solution; 3) 100 ml solution; 4) 125 ml solution; 5) 150 ml solution. Beakers #'s 6-10 (identical 400 ml Pyrex beakers) were used as controls as follows: 6) 50 ml solution; 7) 75 ml solution; 8) 100 ml solution; 9) 125 ml solution; 10) 150 ml solution. Beakers #'s 1-5 were placed under overhead sodium lamps with cones (FIG. 94). Beakers #'s 6-10 were placed in a cabinet with the doors covered with aluminum foil to block light. Crystallization proceeded overnight (about 16 hours) with no ambient light present.

Results: For the spectral crystallization in Beakers #'s 1-5 crystals were about 1.5 mm cubic in shape and weights were about as follows: 1) 1.6 gram 2) 2.0 gram; 3) 1.6 gram; 4) 1.2 gram; 5) 1.3 gram. Control Beakers #6-10 contained crystals which were less than 1 mm and weights were about as follows: 6) 0.4 gram; 7) 0.5 gram; 8) 0.4 gram; 9) 0.4 gram; 10) 0.5 gram. Accordingly, with identical size, shape, and composition of the beakers, classical crystallization was the same regardless of solution volume. However, spectral crystallization was about 3-5 times greater than classical crystallization and varied with solution volume.

Example 4v

Sodium Chloride

The experimental procedure was identical to Example 4u.
Results: For the spectral crystallization in beakers 1-5 crystals were approximately 1 mm cubic and approximate weights were: 1) 5.0 gram; 2) 4.5 gram; 3) 5.4 gram; 4) 5.2 gram; 5) 5.1 gram. Control beakers #'s 6-10 crystals were approximately 1 mm and weights were approximately: 6) 2.8 grams; 7) 3.0 grams; 8) 2.8 grams; 9) 3.1 grams; 10) 3.1 grams. With identical size, shape, and composition of the beakers, classical crystallization was the same regardless of solution volume. Spectral crystallization was about 65% greater than classical crystallization and varied with solution volume.

Example 4w

Sodium Bromide

Classical NaBr and NaCl solutions were filtered. A saturated solution of NaBr (100 ml) was placed into a 600 ml beaker, Beaker #1, and placed under an overhead sodium lamp with cone (FIG. 94). A saturated solution of NaCl (100 ml) was placed into a 600 ml beaker, Beaker #2, and placed under an overhead sodium lamp with cone (FIG. 94). Beakers #3 and #4 were controls of about 100 ml of NaBr and NaCl, respectively, placed into 600 ml Pyrex beakers. Crystallization proceeded overnight (about 18 hours) with no ambient light present.

Results: NaBr solution from Beaker #1 grew approximately 20 flat hexagonal sheets (up to about 8×15 mm) and some rods (about 2×8 mm). NaCl solution from Beaker #2 grew typical spectral NaCl cubic crystals, approximately 100, 2×2 mm. Controls of both solutions grew only a small amount of sandy type crystals overnight. The controls were left out under the ambient fluorescent lights for a weekend (about 60 hours), and after the additional 60 hours showed crystal growth similar to that in Beakers #1 and #2 in about 18 hours. While the average control NaBr crystal was slightly smaller (about 6×8 mm) the largest was in this control beaker (about 30 mm×20 mm).

Example 4x

Sodium Bromide

The spectral NaBr solution was filtered and about 100 ml was placed into four beakers (about 600 ml in size) in the dark, shielded room. Beaker #1 was illuminated by two horizontal Na lamps and one overhead Na lamp (FIG. 97c). Beaker #2 was illuminated by one horizontal lamp, one overhead lamp at approximately 90 degrees to the horizontal lamp, and one lamp approximately 45 degrees between the horizontal and overhead lamp (FIG. 97 g). The control Beaker #3 was placed in the aluminum foil-wrapped bucket. Control Beaker #4 was placed under ambient fluorescent lights in an office (i.e., slightly different ambient light intensity). Crystallization proceeded with no ambient light for Beakers #1, #2 and #3.

Results: Beaker #1 (2 horizontal/1 overhead; FIG. 97c) and Beaker #2 (horizontal, 45 degrees, overhead; FIG. 97g) grew several large, flat, hexagonal crystals (up to about 30 mm×20 mm), and weighing about 21.5 grams and 19.32 grams, respectively. Beaker #3 in the bucket grew nothing. Beaker #4 under ambient lights in an office grew crystals similar in size to Beakers #1 and #2, but fewer in number, about 4.5 grams in weight. Solution levels in Beakers #1 and #2 were about 80 ml, and about 100 ml in the control. The control Beaker #3 was next placed under ambient fluorescent lights in an office until water had evaporated to about the 80 ml level. A small number of moderately sized (about 2 mm×4 mm) flat hexagonal crystals grew. Accordingly, the increase in crystal growth rate observed with the sodium lamps is not due simply to greater evaporation, because control solutions which had water evaporated therefrom in approximately the same amount did not produce the same amount of crystal growth.

Example 4v

Sodium Bromide

A spectral NaBr solution was prepared and filtered and about 100 ml was placed into three beakers (about 400 ml in size). Beaker #1 was placed in a water bath at about 28° C. under an overhead sodium lamp 112 with cone delivery configuration 120 (FIG. 94). The room temperature was about 24° C. Beaker #2 was placed on the counter under an overhead sodium lamp 112 with cone delivery configuration 120 (FIG. 94). Crystallization proceeded overnight (about 21 hours) with no ambient light. Beaker #3 was placed in an office with overhead fluorescent ambient lighting present.

Results: Beakers #1 and #2 had polycrystalline films on the surfaces, and flat hexagonal crystals on the bottom. Beaker #1 crystals were up to about 30 mm×20 mm and weighed about 14.2 grams. Beaker #2 crystals measured up to about 25 mm×15 mm and weighed about 6.4 grams. Beaker #3 had similar morphology to Beaker #2, but a much lesser quantity of crystals.

Example 4z

Sodium Chloride

Water in its original clear plastic packaging was conditioned overnight (about 19 hours) by irradiation with a sodium lamp. Classic NaCl solution was prepared using the conditioned water under ambient fluorescent lighting. The saturated classic solution was filtered and about 100 ml was placed into three beakers (about 600 ml in size) in a dark, shielded room at about 24° C. Beaker #1 was illuminated by two horizontal sodium lamps and one overhead sodium lamp (FIG. 97c). Beaker #2 was illuminated by one horizontal lamp, one overhead lamp at about 90 degrees to the horizontal lamp, and one lamp at about 45 degrees between the horizontal and overhead lamp (FIG. 97g). The control Beaker #3 was placed in an aluminum foil-wrapped bucket. Crystallization proceeded with no ambient light for Beakers 1-3.

Results: The control in the aluminum foil-wrapped bucket showed a few pinpoints of crystallization (too little to collect and weigh). Beaker #1 (two horizontal/one overhead; FIG. 97c) grew hundreds of small cubic (about 1.5 mm) crystals and some small rods, about 5.9 grams. Beaker #1 fluid level was about 90 ml and the solution temperature was about 27° C. Beaker #2 (horizontal, 45 degrees, overhead; FIG. 97g) grew hundreds of small cubic (about 1.5 mm) crystals with some rods, total weight about 5.6 grams. The solution level was approximately 80 ml and the solution temperature was about 27° C. Thus, solutions prepared classically from irradiated water showed an increase in nucleation.

Example 4aa

Classical NaCl solution, prepared with sodium lamp-conditioned water under ambient fluorescent lights and stored in an aluminum foil-wrapped beaker, was filtered and about 100 ml was placed into two beakers (600 ml in size) in a shielded room at about 24° C. Beaker #1 was placed under an overhead sodium lamp with cone (FIG. 94), and Beaker #2 was placed in the aluminum foil-wrapped bucket. A spectral NaBr solution, prepared under ambient fluorescent lights and stored in aluminum foil, was also filtered and about 100 ml was placed in two beakers (about 600 ml in size) in a shielded room at about 24° C. Beaker #3 was placed under an overhead sodium lamp with cone (FIG. 94), and Beaker #4 was placed in an aluminum foil-wrapped bucket. Crystallization proceeded overnight (about 18 hours) with no ambient light present.

Results: Beaker #1 (conditioned water NaCl solution) had 95 ml of solution and many small, sandy crystals, a total weight of about 2 grams. Beaker #2 also grew small sandy crystals, total weight about 0.7 grams. Beaker #3 had about 95 ml solution and several flat, hexagonal crystals, up to about 8×4 mm and total weight about 6.3 grams. Beaker #4 had several smaller sized flat hexagonal crystals (most about 2×4 mm, although two were up to about 10 mm on a side) and weighing about 5.0 grams total.

Example 4ab

Sodium Chloride

Classical NaCl solution, prepared under ambient fluorescent lights and stored in aluminum foil, was filtered and about 100 ml was placed into two beakers (about 600 ml in size) in a shielded, dark room at about 25° C. Beaker #1 was placed under an overhead sodium lamp with cone (FIG. 94), and Beaker #2 was placed into an aluminum foil-wrapped bucket. Classic NaCl solution, prepared with sodium lamp-conditioned water under ambient fluorescent lights and stored in aluminum foil, was also filtered and about 100 ml was placed into two beakers (about 600 ml in size) in a shielded room at about 24° C. Beaker #3 was placed under an overhead sodium lamp with cone (FIG. 94), and Beaker #4 was placed into an aluminum foil-wrapped bucket. Crystallization proceeded overnight (about 21 hours) with no ambient light present Results: Beaker #1 with classic solution grew about 7.0 grams total of about 1 mm cubic crystals. Beaker #3 with conditioned water solution grew about 6.2 grams total of about 1.5 mm crystals. Control Beakers #2 and #4 had essentially no growth.

Example 4ac

Sodium Chloride

The procedure in Example 4ab was repeated. Results were similar.

Results: Beaker #1 with classic solution grew about 2.5 grams of about 1 mm cubic crystals. Beaker #3 with conditioned water solution grew about 2.3 grams of about 1.5 mm crystals. Control Beakers #2 and #4 had essentially no growth. Both solutions crystallized almost the same weight of NaCl, but the crystals from the irradiated water solution were larger (and hence fewer in number). Thus, it appears that sodium spectral conditioning of water prior to preparing classical saturated NaCl solutions affects subsequent crystal size and nucleation.

In this Example, targeted spectral energies were used to affect phase change, structure, and material properties of solid and liquid materials.

Example 4ad

Sodium Chloride

Classical NaCl was prepared and stored four different ways as follows: 1) wrapped in aluminum foil; 2) wax paper over the top; 3) wrapped in a black plastic bag; 4) wrapped in clear plastic. The classical NaCl solution stored in aluminum foil was filtered and about 100 ml was placed into Beakers #1, #2 and #3 (about 600 ml in size). Classical NaCl solution stored with wax paper over the top was filtered and about 100 ml was placed into Beakers #4, #5 and #6 (about 600 ml in size). Classical NaCl solution stored wrapped in a black plastic bag was filtered and about 100 ml was placed into Beakers #7, #8 and #9 (about 600 ml in size). Classical NaCl solution stored wrapped in clear plastic was filtered and about 100 ml was placed into Beakers #10, #11 and #12 (about 600 ml in size). Beakers #1, #4, #7, and #10 were placed under an overhead sodium lamp with cone (FIG. 94). Beakers #2, #5, #8, and 1#1 had about 10 ml water added and were placed under an overhead sodium lamp with cone (FIG. 94). Control beakers #3, #6, #9, and #12 were placed in a light-tight cabinet.

Results:
1. (foil, sodium lamp)—crystals less than about 1 mm, about 0.17 grams total weight
2. (foil, diluted)—no growth
3. (foil, control)—no growth
4. (wax paper, sodium lamp)—three cubes (about 2-4 mm), clusters of about 1 mm crystals, total weight about 0.26 grams
5. (wax paper, diluted)—no growth
6. (wax paper, control)—no growth
7. (black plastic, sodium lamp)—three cubes (about 2-4 mm), clusters of about 1 mm crystals, total weight about 0.44 gram
8. (black plastic, diluted)—no growth
9. (black plastic, control)—no growth
10. (clear plastic, sodium lamp)—nine cubes (about 3-6 mm) with twinning and three polycrystalline clusters, about 1.1 gram total weight
11. (clear plastic, diluted)—no growth
12. (clear plastic, control)—no growth Example 4ae Sodium Chloride Classical NaCl solution stored in aluminum foil was filtered and about 100 ml was placed into Beakers #1 and #2 (about 600 ml in size). Classical NaCl solution stored wrapped in a black plastic bag was filtered and about 100 ml was placed into Beakers #3 and #4 (about 600 ml in size). Classical NaCl solution stored wrapped in clear plastic was filtered and about 100 ml was placed into Beakers #5 and #6 (about 600 ml in size). Beakers #1, #3, and #5 were placed under an overhead sodium lamp with cone FIG. 94). Control Beakers #2, #4, and #6 were placed in a light-tight cabinet. Crystallization proceeded overnight (about 20 hours) with no ambient light present.

Results:
1. (foil, sodium lamp)—about 1 mm crystals, about 0.8 grams total weight
2. (foil, control)—no growth
3. (black plastic, sodium lamp)—about 3-7 mm cubic crystals, some twinning, about 1.2 grams total weight
4. (black plastic, control)—less than 0.4 mm crystals, about 0.25 grams total weight
5. (clear plastic, sodium lamp)—about 34 mm cubic crystals, no twinning, about 1.7 grams total weight
6. (clear plastic, control)—about 1.5 mm crystals, about 0.38 g total weight Thus, aluminum foil coverings on the outside of the Pyrex beaker during storage conditioned the saturated solution and inhibited subsequent NaCl crystal nucleation and growth.

Solutions exposed to ambient light during solution equilibration overnight have more crystal growth by weight. Accordingly, it appears that storage containers and/or spectral conditions and/or conditioning of solutions preparation before, during, and after affect subsequent crystallization from solutions.

Example af

Sodium Chloride

Classical NaCl solution stored in black plastic was filtered and about 100 ml was placed into six crystallization dishes. Room temperature was about 25° C. Dishes #1, #2, and #3 were placed under an overhead sodium lamp with cone (FIG. 94). Dishes #4, #5 and #6 were placed under an overhead full spectrum lamp with cone. Crystallization proceeded overnight (about 19 hours) with no ambient light present Results—Dishes #1, #2 and #3 (sodium lamp) grew cubes (about 2 mm) and clusters, 5.8 grams in total weight. Dishes #4, #5, and #6 (full spectrum lamp) grew cubes (about 2-3 mm), 8.1 grams total weight.

Example 4ag

Sodium Cholride

Classical NaCl solution stored in black plastic was filtered and about 100 ml was placed in six crystallization dishes. Room temperature was about 25° C. Dishes #1, #2, and #3 were placed under an overhead sodium lamp with a cone delivery configuration (FIG. 94). Dishes #4, #5, and #6 were placed under an overhead full spectrum lamp with a cone delivery configuration (similar to the configuration shown in FIG. 94). Crystallization proceeded overnight (about 19 hours) with no ambient light present.

Results—Dishes #1, #2, and #3 (sodium lamp) grew cubes (about 2-4 mm) and clusters, total weight about 5.5 grams. Dishes #4, #5, and #6 (full spectrum lamp) grew cubes (about 3-4 mm), total weight about 7.4 grams. The full spectrum lamp had higher wattage than the Na lamp and contained frequencies in the spectra for both Na and Cl.

Example 4ah

Sodium Chloride

Classical saturated NaCl solution was filtered and about 100 ml was placed into three beakers. Beaker #1 was placed in a dark, shielded room directly under an overhead potassium lamp (similar to the configuration shown in FIG. 94). Beaker #2 was placed in a shielded room behind a cardboard shield, in very low level ambient potassium spectral light. Beaker #3 was placed in an office about 3.5 feet from overhead fluorescent lights.

Results: Beaker #1 grew cubic crystals (about 34 mm), about 2.7 grams total weight. Beaker #2 grew cubic crystals (about 2-2.5 mm), about 0.5 grams total weight. Beaker #3 grew less than 1 mm crystals, about 0.7 grams total weight. It appears that the significant direct resonance between the sodium and potassium spectra allows one to influence NaCl crystal growth using the potassium spectrum alone. Moreover, NaCl growth with the potassium lamp may be modulated by spectral intensity, similar to the sodium lamp.

Observations for Examples 4a-4ah

Spectral crystallization techniques permitted the modification/control of crystals as follows:

FIGS. 98*a*-98*v* and 98*ad*-98*ae* show photomicrographs of various crystals formed according to some of the Experiments in Example 4. These photomicrographs, along with direct experimental observations, showed that spectral crystallization has the following general affects:

(1) increased primary nucleation;
(2) increased growth rate;
(3) increased temperature at which crystallization begins;
(4) controlled crystallization from a thermally unsaturated solution;
(5) controlled crystallization from a diluted unsaturated solution;
(6) altered morphologies including:
altered crystal symmetry;
altered axes;
multiple growth axes controlled by multiple axes of spectral irradiation;
altered growth axis direction controlled by spectral axis directions;
(7) altered crystallization controlled by controlling spectral conditions during solution preparation; and
(8) altered crystallization controlled by controlling ambient spectral conditions during crystallization.

Example 5

Microwaves and Sodium Chloride Crystallization

For the following Examples 5a-5c, the below-listed Equipment, materials and experimental procedures were utilized (unless stated differently in each Example).

a) Equipment and Materials

Distilled Water—the water is distilled water from American Fare, contained in one (1) gallon translucent, colorless, plastic jugs and was processed by a combination of distillation, microfiltration and ozonation. The original source for the water was the Greeneville Municipal water supply in Greeneville, Tenn. The plastic jugs were stored in a darkened and electromagnetic shielded room prior to use in the experiments described in Examples 5a, 5b and 5c.

Pyrex 1000 ml beakers.

Pyrex 400 ml beakers.

A solution of water, or of sodium chloride and water. The sodium chloride is from Fisher Chemicals, is in crystalline form and is characterized as follows:

Sodium Chloride: Certified A.C.S.
Barium (Ba) (about 0.001%)—P.T.
Bromide (Br)—less than 0.01%
Calcium (Ca)—less than 0.0002%-0.0007%
Chlorate and Nitrate (as $NO_3$)—less than 0.0006%-0.0009%
Heavy Metals (as Pb)—less than 0.2 ppm-0.4 ppm
Insoluble Matter—less than 0.001%-0.006%
Iodide (I)—less than 0.0002%-0.0004%
Iron (Fe)—less than 0.2 ppm-0.4 ppm
Magnesium (Mg)—less than 0.001%-0.0003%
Nitrogen Compounds (as N)—less than 0.0001%-0.0003%
pH of 5% solution at 25° C.—5.0-9.0
Phosphate ($PO_3$)—less than 5 ppm
Potassium (K)—0.001%-0.005%
Sulfate ($SO_4$)—0.003%-0.004%

Grounded, dark enclosure: about 6 feet by about 3 feet by about 1½ foot metal cabinet (24 gauge metal) with flat, black paint inside.

Microwave horn, Maury Microwave, Model P230B, SN# s959, 12.4-18.0 GHz (10.0-18.7), 8725 A, 3.5 mm.

Microwave spectroscopy system, Hewlett Packard; HP 83350B Sweep Oscillator, HP 8510B Network analyzer, and HP 8513A Reflection—Transmission Test set.

Sodium lamp, Stonco, 70 watt high pressure sodium security wall light fitted with a parabolic aluminum reflector directing the light down and away from the housing, oriented vertically above a flat, horizontal testing surface, with the bulb about 9 inches (about 23 cm) from the horizontal test surface.

Humboldt Bunsen burner with Bernzomatic propane fuel.

Ring stand and Fisher cast iron ring and heating plate.

1000 ml Pyrex beakers.

Crystallization dishes, Pyrex 270 ml capacity, Corning 3140, Ace Glass 8465-12.

Forma Scientific incubator; Model 3157; Water-jacketed; 28° C. internal temperature, opaque door and walls, nearly completely light blocking with internal light, average 0.82 mW/cm².

Intel computerized microscope.

Example 5a

Crystallization of Sodium Chloride Using Rotational Frequencies

The rotational constant Be of 6536.86 Mc for sodium chloride (NaCl) was obtained from "Microwave Spectroscopy: C. H. Townes and A. L. Schawlow, Dover Publ. Inc., New York". The rotational frequency used in this experiment was calculated to be 2×Be, or 13.07372 GHz.

Saturated sodium chloride solution was prepared by heating distilled water (about 800 ml) in a 1000 ml Pyrex beaker to about 55° C., and adding NaCl until no more would dissolve (about 250-300 grams), under ambient fluorescent lighting. The beaker was wrapped in black plastic, stored in a cabinet, and allowed to equilibrate overnight (about 15 hours). The saturated solution was filtered over the crystals at room temperature (22° C.).

Saturated NaCl solution (about 100 ml) was pipetted into each of six crystallization dishes. Two crystallization dishes A and B were placed in the incubator (set to about 28° C.); two crystallization dishes C and D were placed under a sodium lamp 112 as shown in FIG. 94, the temperature being about 28° C. (8.2 mW/cm²); and two crystallization dishes E and F were placed in a shielded dark enclosure for microwave irradiation at about 25° C. The microwave field was coupled through the air to the outside of microwave Dish E. Microwave Dish F was placed adjacent to microwave Dish E, in line with the microwave horn. The microwave was set in parameter $S_{11}$, sweeping from 13.0736 to 13.0738 GHz. The solutions were allowed to crystallize for about 40 hours.

Photomicrographs taken at about at 60× (Figures not shown but were used to determine "Relative Crystal Size" reported below) and total crystal weight from each crystallization dish A-F was determined. The relative sizes of formed crystals were determined from the photomicrographs by measuring the dimensions of all discernable individual crystals. For rectangular crystals, the smaller dimension was used.

Results: Crystals from the incubator at about 28° C. in dishes A and B were smaller than crystals in dishes C and D which had received sodium spectral electronic irradiation; and smaller than the crystals in dishes E and F which were grown with the sodium microwave rotational frequency. However, crystals grown in dishes E and F (microwave irradiated solutions) were inhibited relative to crystals grown in dishes C and D (sodium lamp irradiated solutions). Relative sizes and weights of formed crystals were as follows:

|  | Relative Crystal Size | Weight (g) |
|---|---|---|
| Incubator | | |
| Dish A | 14.5 | 1.4 |
| Dish B | 14.5 | 1.2 |
| Sodium lamp | | |
| Dish C | 44 | 11.4 |
| Dish D | 41 | 10.9 |
| Microwave | | |
| Dish E | 36.5 | 5.3 |
| Dish F | 34.5 | 4.6 |

Example 5b

Sodium Chloride Crystallization Using Rotational Frequencies

The rotational constant Be of 6536.86 Mc for sodium chloride (NaCl) was obtained from "Microwave Spectroscopy: C. H. Townes and A. L. Schawlow, Dover Publ. Inc., New York". The rotational frequency used in this experiment was calculated to be 2×Be, or 13.07372 GHz.

Saturated sodium chloride solution was prepared by heating distilled water (about 800 ml) in a 1000 ml Pyrex beaker to about 55° C., and adding NaCl until no more would dissolve (about 250-300 grams), under ambient fluorescent lighting. The beaker was wrapped in black plastic, stored in a cabinet, and allowed to equilibrate overnight (about 15 hours). The saturated solution was filtered over the crystals at room temperature (about 22° C.).

Saturated NaCl solution (about 100 ml) was pipetted into each of eight crystallization dishes labeled G-N. Two crystallization dishes G and H were placed in an incubator (set to about 28° C.), two crystallization dishes H and I were placed under a sodium lamp 112, as shown in FIG. 94 at about 28-30° C. (8.2 mW/cm²), two crystallization dishes K and L were placed in a shielded dark enclosure for microwave irradiation at about 25° C., and two control crystallization dishes M and N were placed in a shielded dark enclosure at about 25° C. The microwave field was coupled through the air to the outside of microwave Dish K. Microwave Dish L was placed adjacent to Dish K, in line with the microwave horn. The microwave was set in parameter $S_{11}$, sweeping from 13.073719 to 13.073721 GHz. The solutions were allowed to crystallize for about 18 hours.

The total crystal weight in each of dishes G-N was determined.

Results: Irradiation with the sodium chloride rotational microwave frequency in a shielded dark enclosure inhibited sodium chloride crystallization compared to controls in a shielded dark enclosure.

Sodium lamp spectral electronic irradiation enhanced crystallization compared to controls at the same ambient room temperature.

|  |  | Weight (g) |
|---|---|---|
| Incubator | Dish G | 0.0 |

-continued

|  | | Weight (g) |
|---|---|---|
| Na lamp | Dish H | 0.0 |
|  | Dish I | 5.4 |
|  | Dish J | 6.2 |
| Microwave | Dish K | 1.9 |
|  | Dish L | 1.8 |
| Shielded Control | Dish M | 2.1 |
|  | Dish N | 2.1 |

Example 5c

Crystallization of Sodium Chloride Using Rotational Frequencies

The rotational constant Be of 6536.86 Mc for sodium chloride (NaCl) was obtained from "Microwave Spectroscopy: C. H. Townes and A. L. Schawlow, Dover Publ. Inc., New York". The rotational frequency used in this experiment was calculated to be $2 \times B_e$, or 13.07372 GHz.

Saturated sodium chloride solution was prepared by heating distilled water (about 800 ml) in a 1000 ml Pyrex beaker to about 55° C., and adding NaCl until no more would dissolve (about 250-300 grams), under ambient fluorescent lighting. The beaker was wrapped in black plastic, stored in a cabinet, and allowed to equilibrate overnight (about 15 hours). The saturated solution was filtered over the crystals at room temperature (about 20° C.).

Saturated NaCl solution (about 100 ml) was pipetted into each of four crystallization dishes labeled) O-R, and 85 ml of saturated NaCl solution (about 100 ml) was pipetted into each of four crystallization dishes labeled S-V. Two crystallization dishes O and S were placed in an incubator (set at about 28° C.), two crystallization dishes P and T were placed under a sodium lamp 112, as shown in FIG. 94, at about 28-30° C. (8.2 mW/cm²), two crystallization dishes Q and U were placed in a shielded dark enclosure for microwave irradiation, and two control crystallization dishes R and V were placed in a shielded dark enclosure at about 25° C. The microwave field was coupled through the air to the outside of microwave Dish 0. Microwave Dish U was placed adjacent to Dish 0, in line with the microwave horn. The microwave parameter was $S_{11}$, sweeping from 13.073719 to 13.073721 GHz. Ambient room/enclosure temperatures throughout were:
1) incubator controls about 28° C.;
2) sodium lamp about 28° C.;
3) microwave irradiation about 25° C.;
4) shielded enclosure control about 25° C.

The solutions were allowed to crystallize for about 14.5 hours, after which solution temperatures were measured:
1) incubator control solutions about 26° C.;
2) sodium lamp solutions about 22° C.;
3) microwave irradiation about 21° C.; and
4) shielded enclosure control about 20° C.

The dishes O-V were photomicrographed (not shown) at about 60× magnification. The total crystal weight was determined in each of dishes O-V by being dried and weighed. Relative crystal sizes for only Dishes O-R was determined as in Example 5a.

Results: Irradiation with the sodium chloride rotational microwave frequency in a shielded dark enclosure inhibited sodium chloride crystallization compared to controls in a shielded dark enclosure.

Sodium lamp spectral electronic irradiation enhanced crystallization rate compared to controls at the same ambient room temperatures, however solution temperatures differed. The sodium lamp solutions were closest in temperature to the microwave irradiated solution. Although the size of the sodium lamp and microwave crystals was essentially the same and the sodium lamp solution was slightly warmer, about 2.5 times more salt crystallized under the sodium lamp, than with the microwave irradiation.

|  | Relative Crystal Size | Weight (g) |
|---|---|---|
| Incubator | | |
| Dish O | 10 | 0.7 |
| Dish S | — | 0.6 |
| Sodium lamp | | |
| Dish P | 21 | 5.6 |
| Dish T | — | 5.1 |
| Microwave | | |
| Dish Q | 20 | 1.9 |
| Dish U | — | 1.9 |
| Shielded Control | | |
| Dish R | 25 | 2.1 |
| Dish V | — | 1.9 |

Example 6

Various Potassium Lamp Crystallization Experiments a) Equipment and Materials
   Sterile water by Bio Whittaker (prepared by ultrafiltration, reverse osmosis, deionization, and distillation) in one liter plastic bottles.
   Sodium Chloride, Fisher Chemicals, packaged in gray plastic 3 Kg bottles. The sodium chloride, in crystalline form, is characterized as follows:
      Sodium Chloride: Certified A.C.S.
         Barium (Ba) (about 0.001%)—P.T.
         Bromide (Br)—less than 0.01%
         Calcium (Ca)—less than 0.0002%-0.0007%
         Chlorate and Nitrate (as $NO_3$)—less than 0.0006%-0.0009%
         Heavy Metals (as Pb)—less than 0.2 ppm-0.4 ppm
         Insoluble Matter—less than 0.001%-0.006%
         Iodide (I)—less than 0.0002%-0.0004%
         Iron (Fe)—less than 0.2 ppm-0.4 ppm
         Magnesium (Mg)—less than 0.001%-0.0003%
         Nitrogen Compounds (as N)—less than 0.0001%-0.0003%
         pH of 5% solution at 25° C.—5.0-9.0
         Phosphate ($PO_3$)—less than 5 ppm
         Potassium (K)—0.001%-0.005%
         Sulfate ($SO_4$)—0.003%-0.004%
   Potassium Chloride, Fisher Chemicals, packaged in gray plastic 3 Kg bottles. The potassium chloride, in crystalline form, is characterized as follows:
      Potassium Chloride, Certified A.C.S.
         Bromide—0.01%
         Chlorate and Nitrate (as $NO_3$)—less than 0.003%
         Nitrogen Compounds (as N)—less than 0.001%
         Phosphate—less than 5 ppm
         Sulfate—less than 0.001%
         Barium 0.001%
         Calcium and $R_2O_3$ Precipitate—less than 0.002%

Heavy Metals (as Pb)—less than 5 ppm
Iron—less than 2 ppm
Sodium—less than 0.005%
Magnesium—less than 0.001%
Iodide—less than 0.002%
pH of 5% solution at 25° C.—5.4 to 8.6
Insoluable Matter—less than 0.005%

Humboldt Bunsen burner, with Coleman propane fuel.

Sodium lamp, Stonco 70 watt high pressure sodium security wall light fitted with a parabolic aluminum reflector directing the light away from the housing and an aluminum foil cone light guide fitted around the sodium bulb, with distal end formed around uniform diameter (about 1.8 cm). The sodium lamp was mounted overhead with the bulb oriented vertically and with the tip of the bulb about 15 inches (about 38 cm) from the crystallization dishes.

Figure 97H:
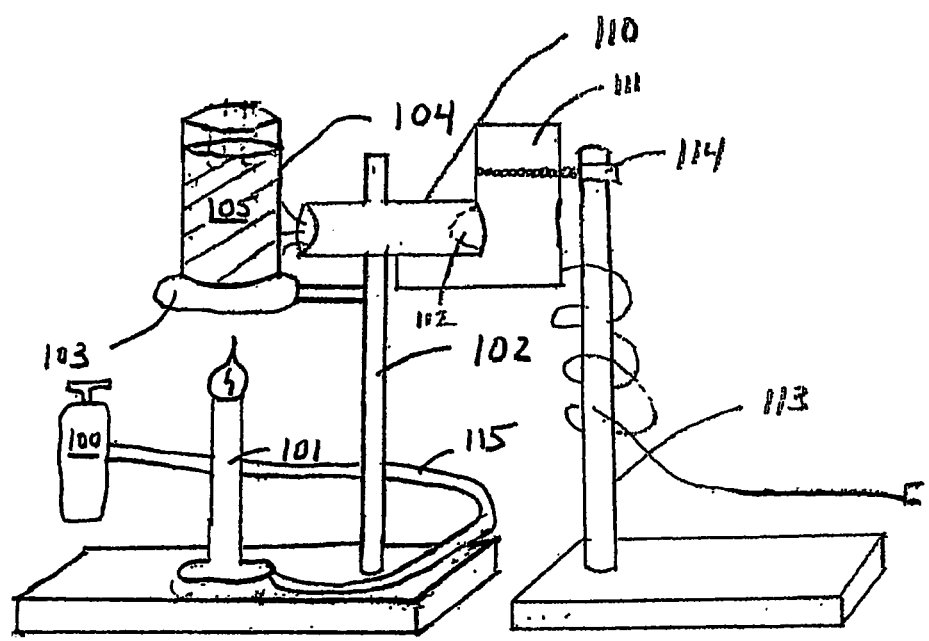

Potassium lamp, Thermo Oriel 10 watt spectral line potassium lamp #65070 with Thermo Oriel lamp mount #65160 and Thermo Oriel spectral lamp power supply #65150. The potassium lamp was mounted overhead with the rectangular bulb oriented horizontally at about 9 inches (about 23 cm) from the crystallization dishes (as shown in FIG. 97h).

Crystallization dishes, Pyrex 270 ml capacity, Corning 3140, Ace Glass 8465-12.

b) Preparation of Solutions

Water was heated with a Bunsen burner from room temperature to about 55° C. Salt was added to the solution which was stirred with a glass stir rod until no more salt would dissolve. The solution was allowed to equilibrate overnight (about 18 hours) before being decanted and filtered for use in a crystallization procedure.

Example 6a

Classical KCl solution was filtered and about 100 ml was placed into each of nine (9) crystallization dishes. Dish #'s 1-3 were placed in the dark, shielded room under the potassium lamp. Cardboard shields were placed between the potassium lamp and Dish #'s 4-6 which then received only very low levels of an ambient potassium spectrum. Dish #'s 7-9 were placed onto a counter in another room with overhead ambient fluorescent lighting.

Results: Control crystals grew small cubic crystals (see FIG. 98w). The solution was exposed to a low ambient potassium lamp light and grew about 25 crystals which showed some twinning. Most crystals were about 3-5 mm cubic, and the largest crystal (about 12 mm cubic) is shown in FIGS. 98x and 98y. The solution under the potassium lamp grew about 15 large crystals, with cubes, triangular rods, polycrystalline masses, and twinned crystals (see FIGS. 98z and 98aa).

Example 6b

Classical NaCl solution was filtered and about 100 ml was placed into each of 3 crystallization dishes. Dish #1 was placed in the dark, shielded room under the potassium lamp. Dish #2 was placed behind a cardboard shield with only low ambient levels of the potassium lamp. Dish #3 was placed in an office under fluorescent lights.

Results: All dishes produced small cubic crystals: about 2.8 grams in dish #1 under the potassium lamp; about 0.6 grams in dish #2 with ambient potassium lamp light; and about 0.89 grams in dish #3 under fluorescent lights.

Example 6c

Classical KCl solution was filtered and about 100 ml was placed into eight (8) crystallization dishes. Dish #'s 1-3 were placed into the dark, shielded room under the potassium lamp. Dishes #'s 4-6 were placed into the same dark, shielded room under the sodium lamp. Cardboard shields were placed between the potassium and sodium lamps to prevent cross-illumination. Dish #7 was placed in an aluminum foil-covered bucket in the shielded room. Dish #8 was placed onto a file cabinet in an office, about 40 inches beneath fluorescent overhead lights (about 1.12 mW/cm$^2$).

Results:

There were different crystal sizes and morphologies observed:

1) Potassium lamp—Several cubic and twinned hoppers, about 1.6×1.6×0.7 cm in length for the largest crystal which grew under the main part of the potassium bulb;

2) Sodium lamp—Cubic and twinned hoppers, many rods and glassy sheets, the largest of which was about 2×2×1 cm in length, grew directly under the sodium bulb (see FIG. 98ab and FIG. 98ac);

3) Foil bucket—no growth; and

4) Fluorescent office—many small cubes, about 2-3 mm, a few rods and sheets.

Average weights per dish were: 1) potassium lamp, about 1.5 grams; 2) sodium lamp, about 2.9 grams; 3) foil bucket 0.0 grams; and 6) fluorescent office about 0.97 grams.

Example 7

Increase in Measured pH in a NaCl/Water Solution Due to a Sodium Spectral Pattern This Example demonstrates the effects of conditioning a conditionable participant (distilled water) with a conditioning energy (sodium lamp) by dissolving crystalline sodium chloride (NaCl) into the water and monitoring pH changes.

a) Equipment and Materials

The following reference numerals refer to those items shown schematically in FIGS. 99, 100 and 101, which setups are referred to in the following Examples 7a-7f. FIG. 102 shows the pH electrode 109 in greater detail. Like reference numerals have been used whenever possible.

100—Bernzomatic propane fuel.
101—Humboldt Bunsen burner.
102—Ring stand.
103—Cast iron hot plate from Fisher Scientific.
104—1000 ml Pyrex™ cylindrical beaker.
105—A solution of water, or of sodium chloride and water.

Sodium Chloride, Fisher Chemicals, packaged in gray plastic 3 Kg bottles. The sodium chloride, in crystalline form, is characterized as follows:

Sodium Chloride, Certified A.C.S.
Barium (Ba) (about 0.001%)—P.T.
Bromide (Br)—less than 0.01%
Calcium (Ca)—less than 0.0002%-0.0007%
Chlorate and Nitrate (as NO$_3$)—less than 0.0006%-0.0009%
Heavy Metals (as Pb)—less than 0.2 ppm-0.4 ppm
Insoluble Matter—less than 0.001%-0.006%
Iodide (I)—less than 0.0002%-0.0004%
Iron (Fe)—less than 0.2 ppm-0.4 ppm
Magnesium (Mg)—less than 0.001%-0.0003%
Nitrogen Compounds (as N)—less than 0.0001%-0.0003%
pH of 5% solution at 25° C.—5.0-9.0
Phosphate (PO$_3$)—less than 5 ppm
Potassium (K)—0.001%-0.005%
Sulfate (SO$_4$)—0.003%-0.004%

Distilled Water—American Fare, contained in one (1) gallon translucent, colorless, plastic jugs, processed by distillation, microfiltration and ozonation. Source, Greeneville Municipal Water supply, Greeneville, Tenn. Stored in cardboard boxes in a dark, shielded room prior to use in the experiments described in Examples 7a, 7b and 7c.

106—Support structure for pH meter.

107—An AR20 "pH/mV/° C./Conductivity" meter from Accumet Research (Fisher Catalog No. 13-636-AR20 2000/2001 Catalog).

108—Temperature probe for pH meter.

109—pH Electrode for AR20 pH meter (Fisher 2000-2001 Catalog #13-620-285); and shown in greater detail in FIG. 102.

110—Aluminum foil tube made from kitchen grade aluminum foil, medium duty.

111—Stonco 70 watt high-pressure sodium security wall fixture (TLW Series Twilighter Wallprism model) fitted with a parabolic aluminum reflector which directs the light from the housing.

112—sodium lamp, Stonco 70 watt high-pressure sodium security wall light, fitted with a parabolic aluminum reflector directing the light away from the housing. The sodium bulb was a Type S62 lamp, 120V, 601H, 1.5 A made in Hungary by Jemanamjjasond. The lamp was located about 12 cm from the beaker side.

113—Ring stand.

114—Chain clamp.

Experimental Procedure

Example 7a

Figure 99:
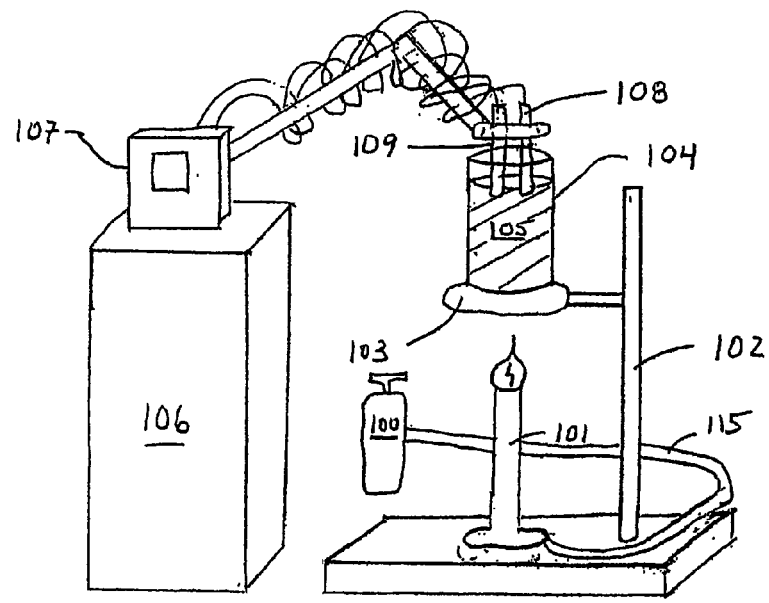

FIG. 99 is a schematic of the experimental apparatus used to generate baseline measured pH information at about 55° C. as a function of time. In this Example 7a, the Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 102. The pH meter was elevated to a convenient height by the use of a support structure 106.

The AR20 meter 107, which used the pH electrode 109 (the electrode being shown in more detail in FIG. 102), were together calibrated by using two different buffer solutions. The first buffer solution had a pH of 4.00+/−0.01 at 25° C., and was a solution of potassium bipthalate. A second buffer solution had a pH of 7.00+/−0.01 at 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the readings from the pH electrode.

The pH of the distilled water in the beaker 104 was first measured at room temperature and then heated to about 55° C. in about 15-20 minutes by use of the Bunsen burner heating the hot plate 103 and the hot plate 103 radiating (e.g., by radiation and/or conduction) its conditioning energy to the beaker 104 containing the distilled water. The water temperature was monitored by the Accumet meter 107. Once a temperature of about 55° C. was obtained, about 50 grams of sodium chloride (certified A.C.S. and as discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 30-45 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted into the solution 105 upon completion of the stirring.

FIG. 103a shows the results of three (3) separate experiments corresponding to the experimental apparatus of FIG. 99. The plotted data show the change in measured pH of the solution 105 as a function of time from room temperature to about 55° C. In particular, the pH of the distilled water alone was first measured at room temperature and then measured at about 55° C., and thereafter the pH of the solution 105 was measured about every two minutes for about 20 minutes after the addition and dissolution of sodium chloride. The time measurements were all at intervals of about two minutes up to about 20 minutes with a final measurement being taken after about 40 minutes.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 7.6 meters×12.1 meters). The fluorescent lamps produce a widely broadened and noisy mercury spectrum.

Example 7b

Figure 100:
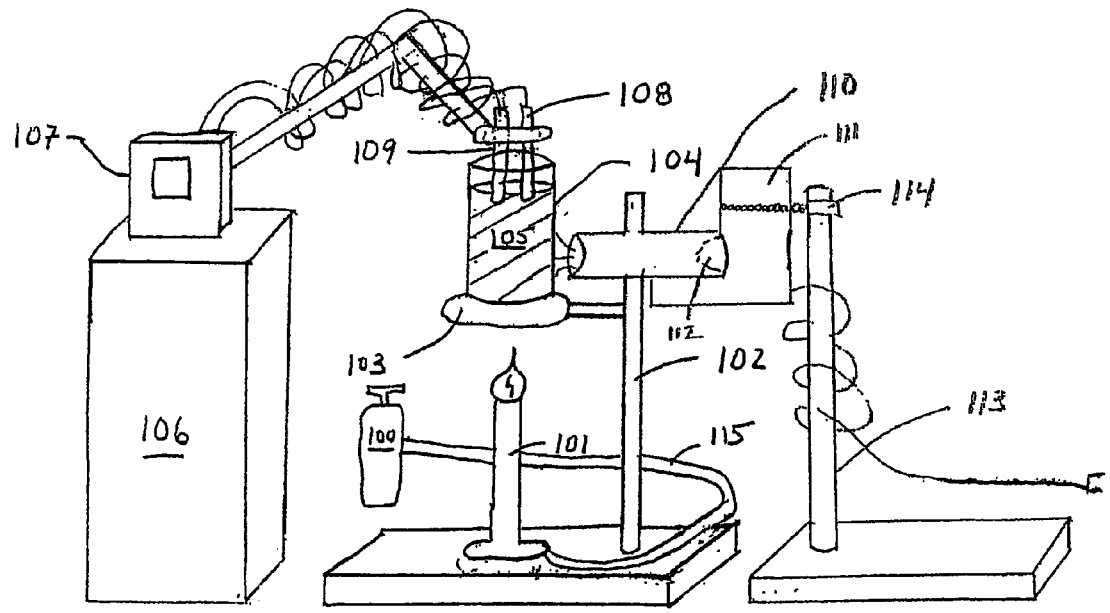
FIG. 100 shows a schematic of the experimental set-up which corresponds to a Bunsen burner heating a solution of sodium chloride and water on a hot plate, and a sodium lamp emitting an electromagnetic spectral pattern into the side of a beaker, which is discussed in Example 7b.

FIG. 100 is a schematic of the experimental apparatus used to generate measured pH information at about 55° C. as a function of time. In this Example 7b, the Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 102. The pH meter was elevated to a convenient height by the use of a support structure 106.

The AR20 meter 107, which used the pH electrode 109 (the electrode being shown in more detail in FIG. 102) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

The pH of the distilled water in the beaker 104 was first measured at room temperature and then heated to about 55° C. in about 15-20 minutes by use of the Bunsen burner heating the hot plate 103. The water temperature was monitored by the Accumet meter 107. Once a temperature of about 55° C. was obtained, about 50 grams of sodium chloride (certified A.C.S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 3045 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

A ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch away from the side of the beaker 104. The tube 110 measured about eight (8) inches long and was about 3½ inches in diameter. The end of the sodium light bulb 112 was about five (5) inches from the end of the tube 110. In this Example 18b, the sodium light bulb 112 was actuated at about the same time that the electrodes 108 and 109 were reinserted into the solution 105 which is after the sodium chloride had been mixed into and dissolved in the distilled water. The light fixture 111 was fixed to the ring stand 113 by use of a chain clamp 114.

FIG. 103b shows the results of three (3) separate experiments corresponding to the experimental apparatus of FIG. 100. The plotted data show the change in measured pH of the solution 105 as a function of time from room temperature to about 55° C. In particular, the pH of the distilled water alone was first measured at room temperature and then measured at about 55° C., and thereafter measured about every two minutes after the addition and dissolution of sodium chloride and the activation of the high pressure sodium light 112. The time measurements were all at intervals of about two minutes for about 20 minutes with a final measurement being taken after about 40 minutes.

All experimental conditions described in this Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 7.6 meters×12.1 meters). The fluorescent lamps produce a widely broadened and noisy mercury spectrum.

Example 7c

Figure 101:
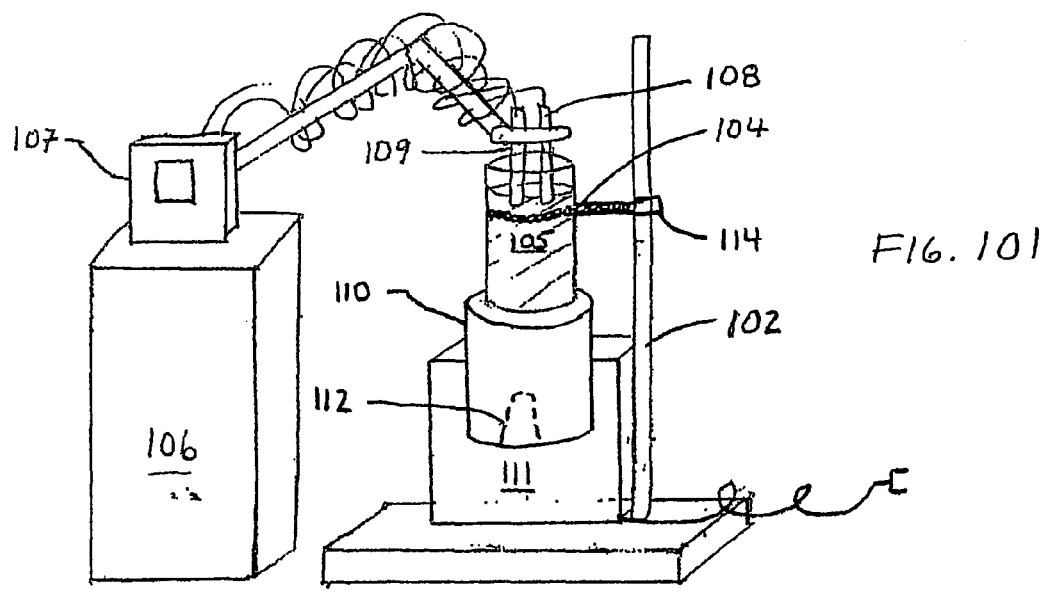
FIG. 101 shows a schematic of the experimental set-up which corresponds to a sodium lamp heating a solution of sodium chloride and water from the bottom of a beaker, which is discussed in Example 7c.
Figure 102:
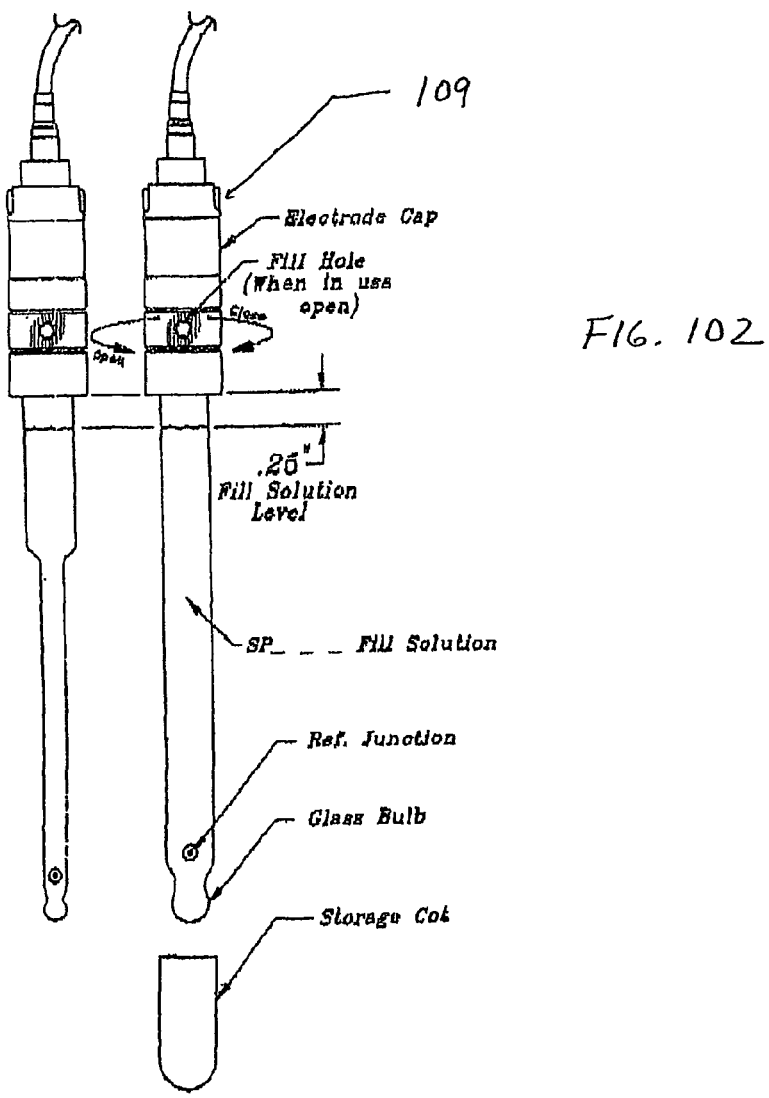
FIG. 102 shows a schematic of the pH electrode 109 used with the Accumet AR20 meter 107.

FIG. 101 is a schematic of the experimental apparatus used to generate measured pH information where the temperature of the distilled water in the beaker 104, and later in the solution 105, in the beaker 104 was heated exclusively by use of a high pressure sodium bulb 112 contained in a fixture 111.

The AR20 meter 107, which used the pH electrode 109 (the electrode being shown in more detail in FIG. 102) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

This Example 7c differs from the previous Examples 7a and 7b in that no Bunsen burner was provided for heating. In this regard, heat was generated from the energy emitted by the combination of the high-pressure sodium bulb 112, and the fixture 111. In particular, the energy was transmitted to the bottom of the beaker 104 initially containing the distilled water, and later to the solution 105, through the use of the aluminum foil tube 110. Specifically, the ring stand 102 supported the beaker 104 by the use of the chain clamp 114. The beaker 104 was initially lowered into the aluminum foil tube 110 such that approximately 150-200 ml of the distilled water contained in the beaker 104 was physically located inside of the aluminum foil tube 110. The tube 110 measured about seven (7) inches long and was about four (4) inches in diameter. The top end of the sodium light bulb 112 was about four (4) inches from the end of the tube 110. Once the distilled water temperature achieved about 55° C. after about 1¼-1½ hours, the sodium chloride was added, as discussed above. The chain clamp 114 was then raised vertically slightly upon the ring stand 102 so that the bottom of the beaker 104 was now positioned slightly outside of the aluminum foil tube 110 (as shown in FIG. 101). Experience caused the precise final location of the bottom of the beaker 104 to be about ½ inch-¾ inch above the end of the aluminum foil tube 110. The primary difference between this Example 7c and the previous two Examples 7a and 7b is that the only energy provided to the distilled water and the solution 105 came from the combination of the sodium bulb 112 and the fixture 111 by radiation and convection.

Figure 103C:
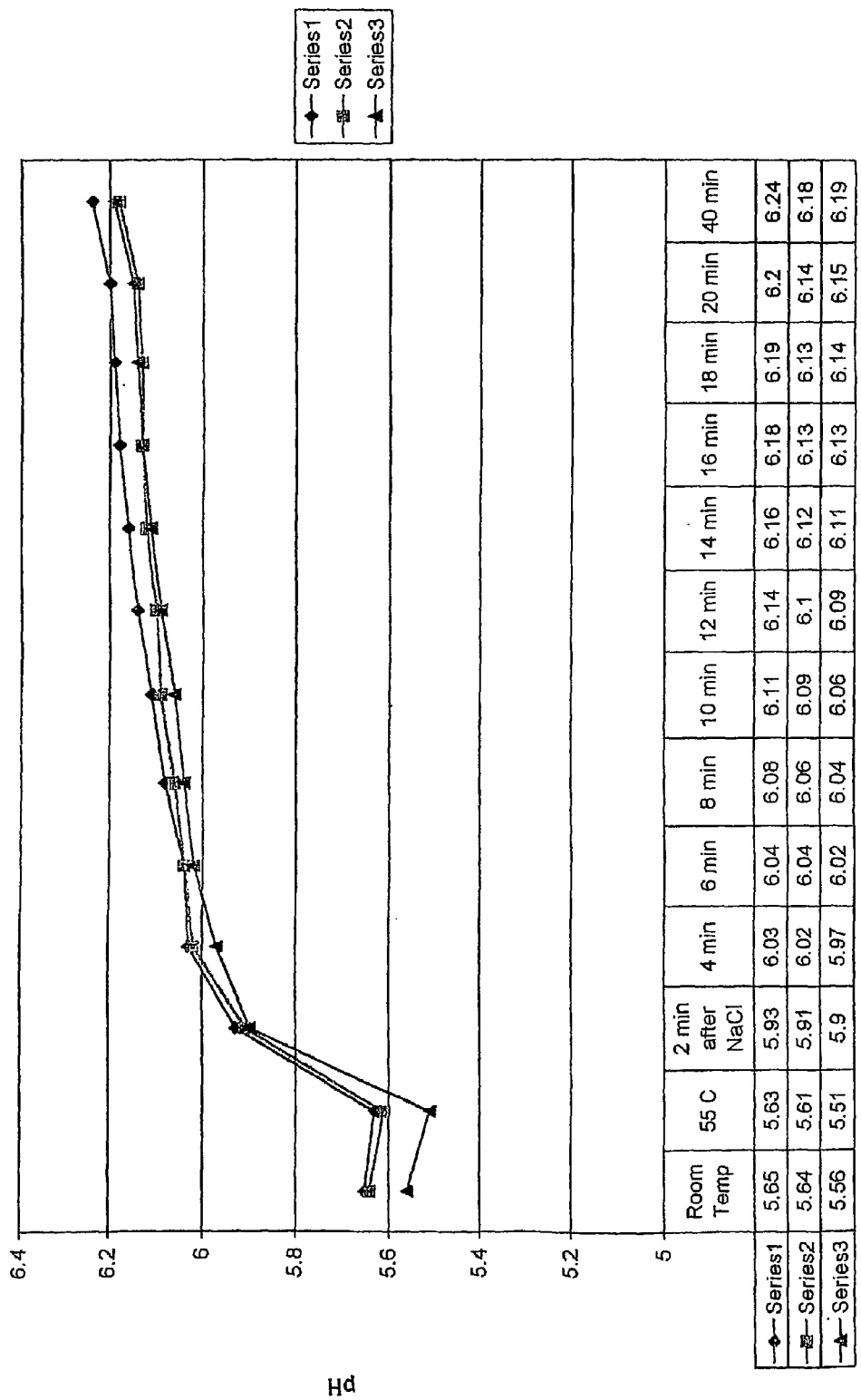
FIG. 103c is a graph of the experimental data which shows pH as a function of time and corresponds to the experimental set-up of Example 7c.
Figure 103:
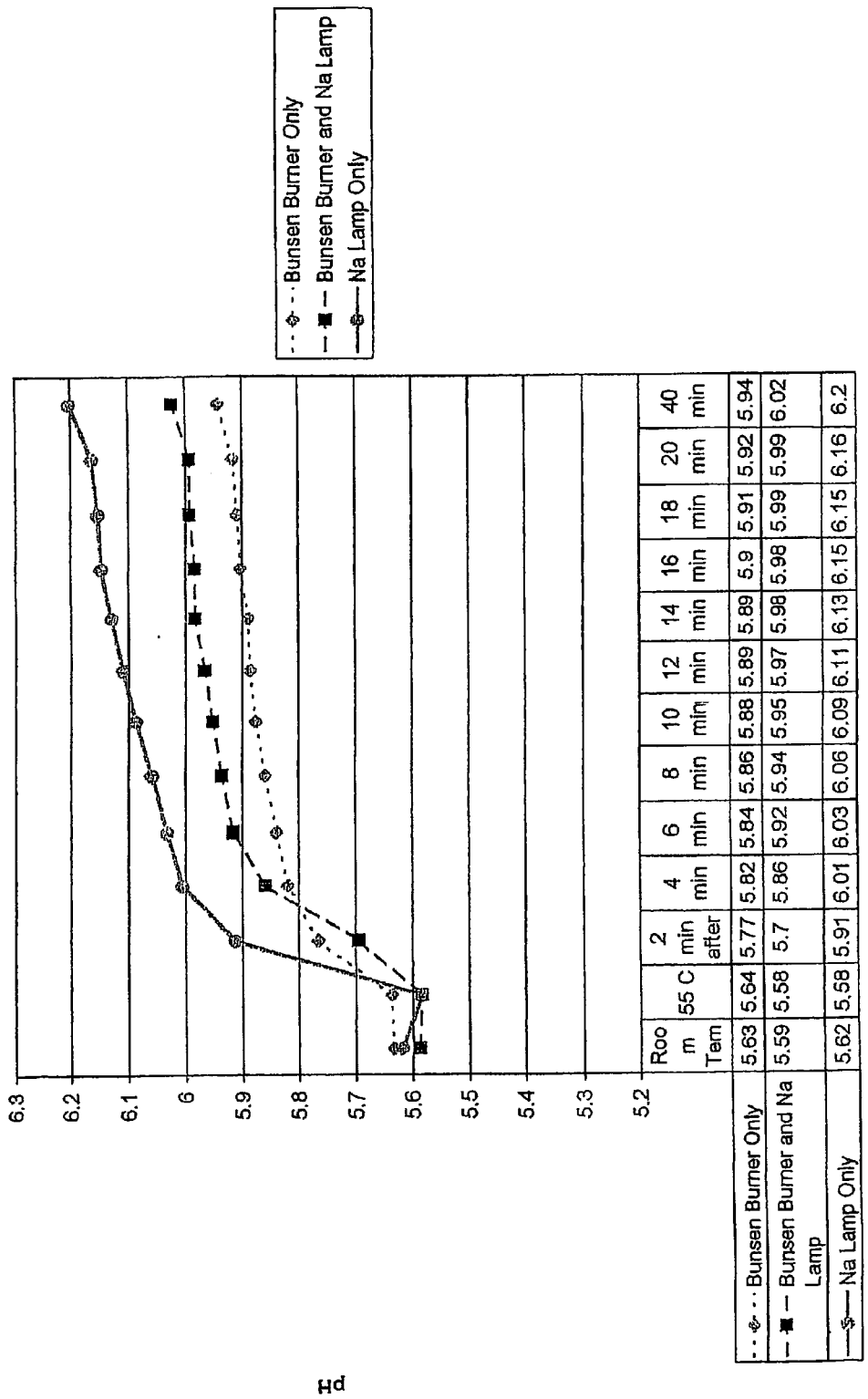

FIG. 103c shows the results of three (3) separate experiments corresponding to the experimental apparatus of FIG. 101. The plotted data show the change in measured pH of the solution 105 as a function of time at a temperature of about 55° C. In particular, the pH of the distilled water alone was first measured at room temperature and then measured at about 55° C., and thereafter the pH of the solution 105 was measured about every two minutes after the addition and dissolution of sodium chloride. The time measurements were all at intervals of about two minutes for 20 minutes, with a final measurement being taken at about 40 minutes.

All experimental conditions described in this Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) of lamps present in a room which measured approximately 25 feet by 40 feet (about 7.6 meters×12.1 meters). The fluorescent lamps produce a widely broadened and noisy mercury spectrum.

Example 7d

FIG. 100 is a schematic of the experimental apparatus used to generate measured pH information at about 55° C. as a function of time. In this Example 7d, a ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch (about 2.0 cm to about 2.5 cm) away from the side of the beaker 104. The tube 110 measured about eight (8) inches (about 2.4 meters) long and was about 3½ inches (about 8.5 cm) in diameter. The top end of the sodium light bulb 112 was about five (5) inches (about 12.5 cm) from the end of the tube 110. In this Example 7d, the sodium light bulb 112 was actuated about 40 minutes before heating the water with the Bunsen burner and irradiated the solution continuously throughout the pH measurements. The light fixture 111 was fixed to the ring stand 113 by use of a chain clamp 114.

The Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 102. The pH meter was elevated to a convenient height by the use of a support structure 106.

The AR20 meter 107, which used the pH electrode 109 (the electrode being shown in more detail in FIG. 102) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

The pH of the distilled water in the beaker 104 was first measured at room temperature before actuating the sodium lamp. After the 40 minute sodium lamp conditioning, the water was then heated to about 55° C. in about 15-20 minutes by use of the Bunsen burner heating the hot plate 103. The water temperature was monitored by the Accumet meter 107. Once a temperature of about 55° C. was obtained, about 50 grams of sodium chloride (certified A.C.S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 3045 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

Figure 103E:
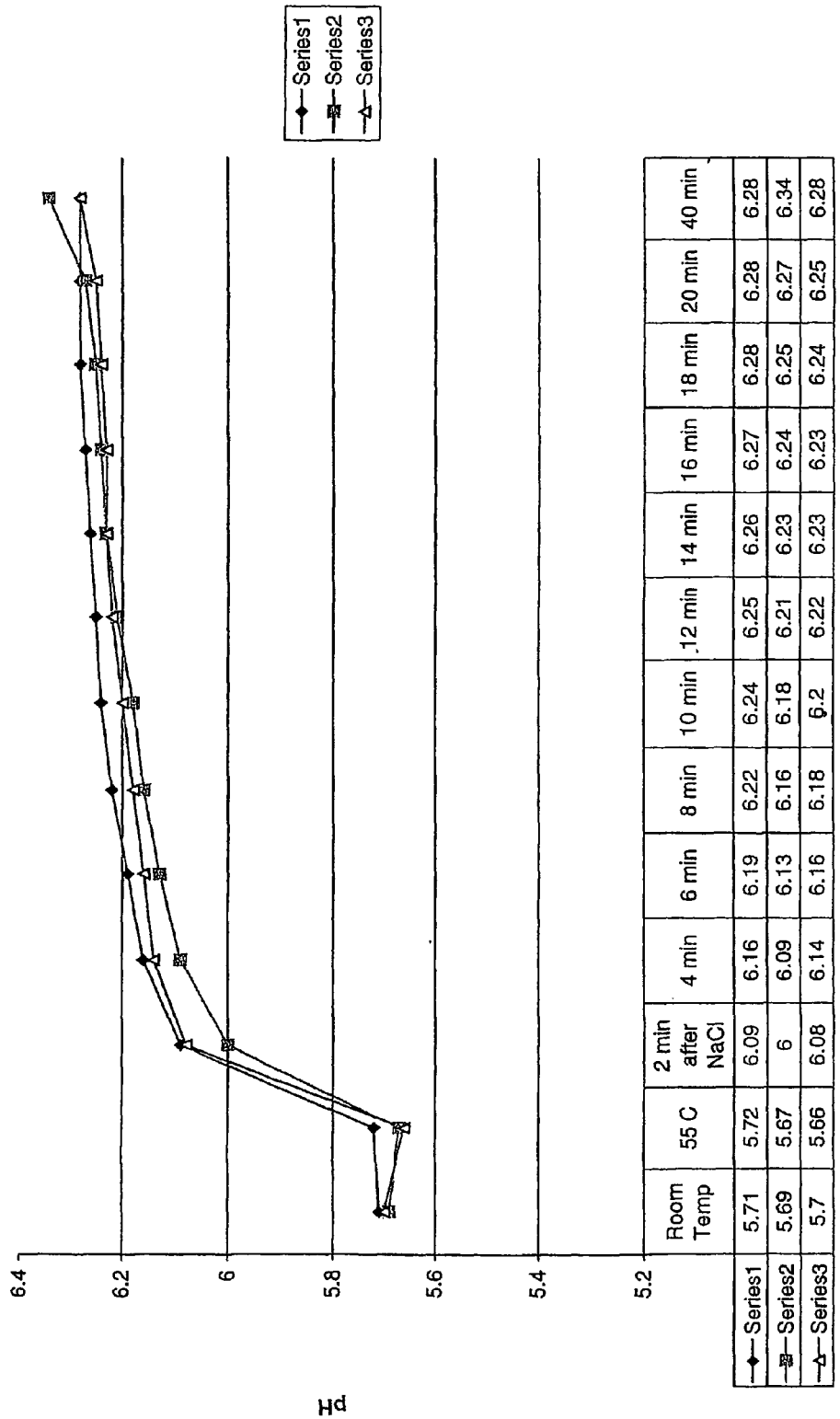
Figure 103:
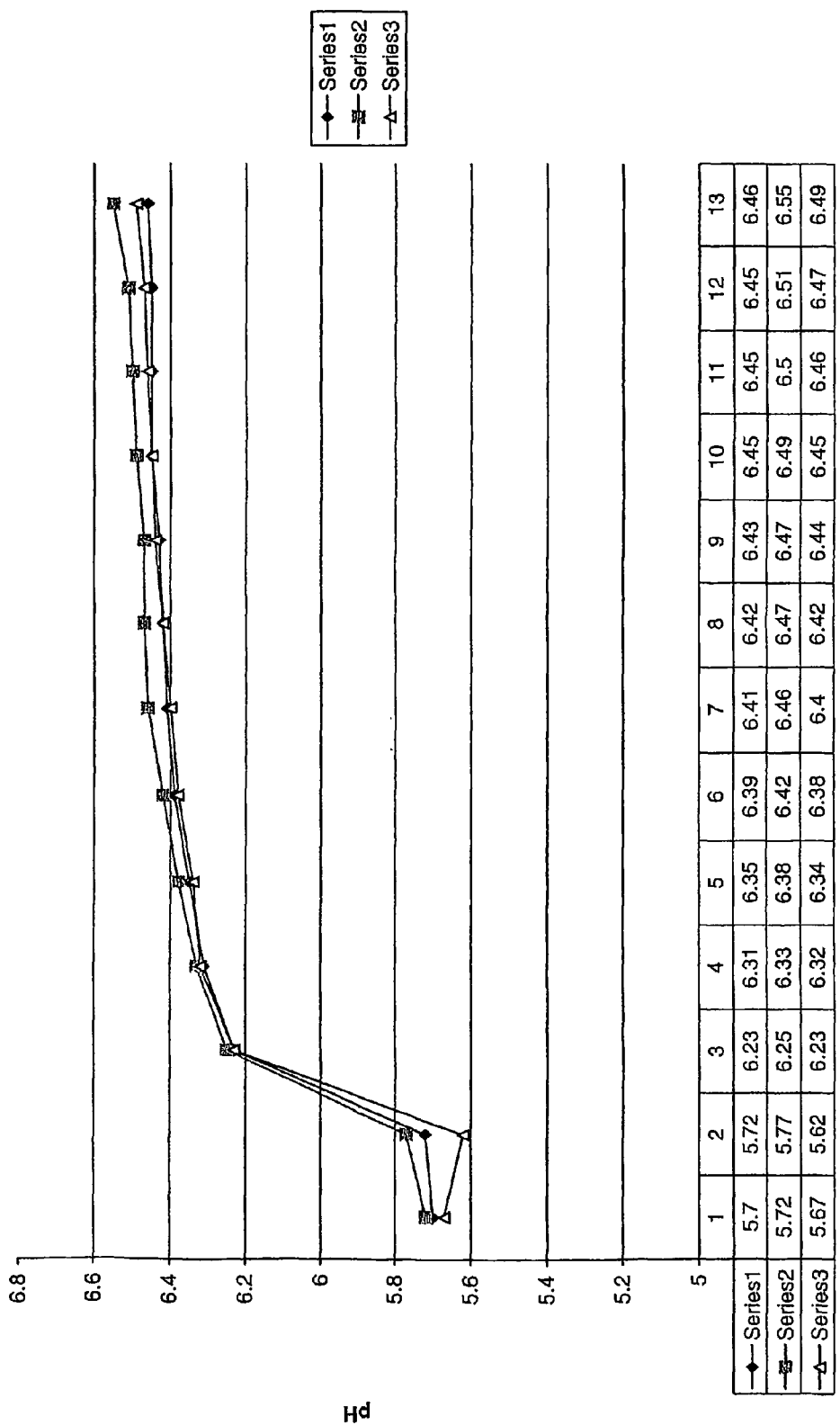
Figure 103:
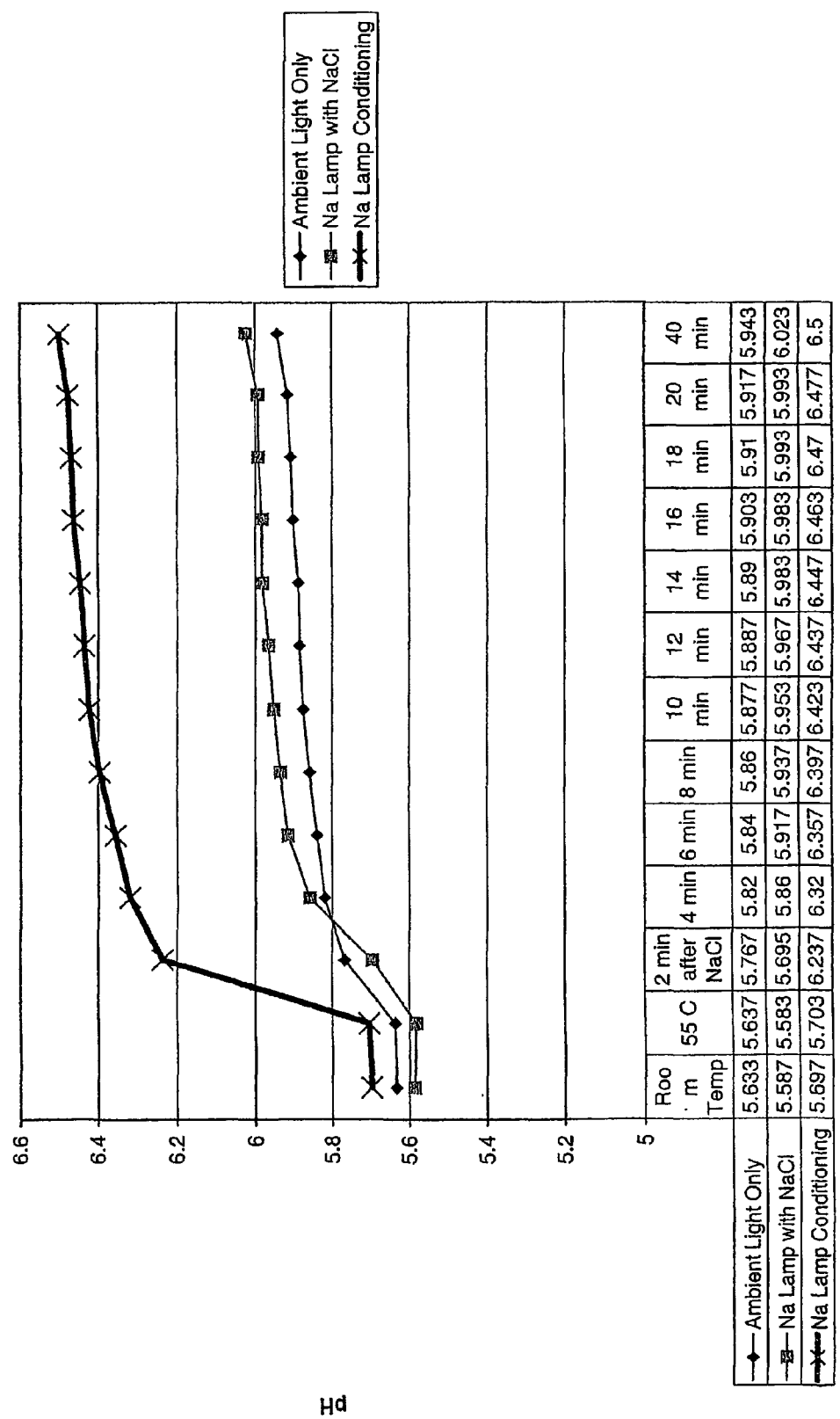
Figure 103:
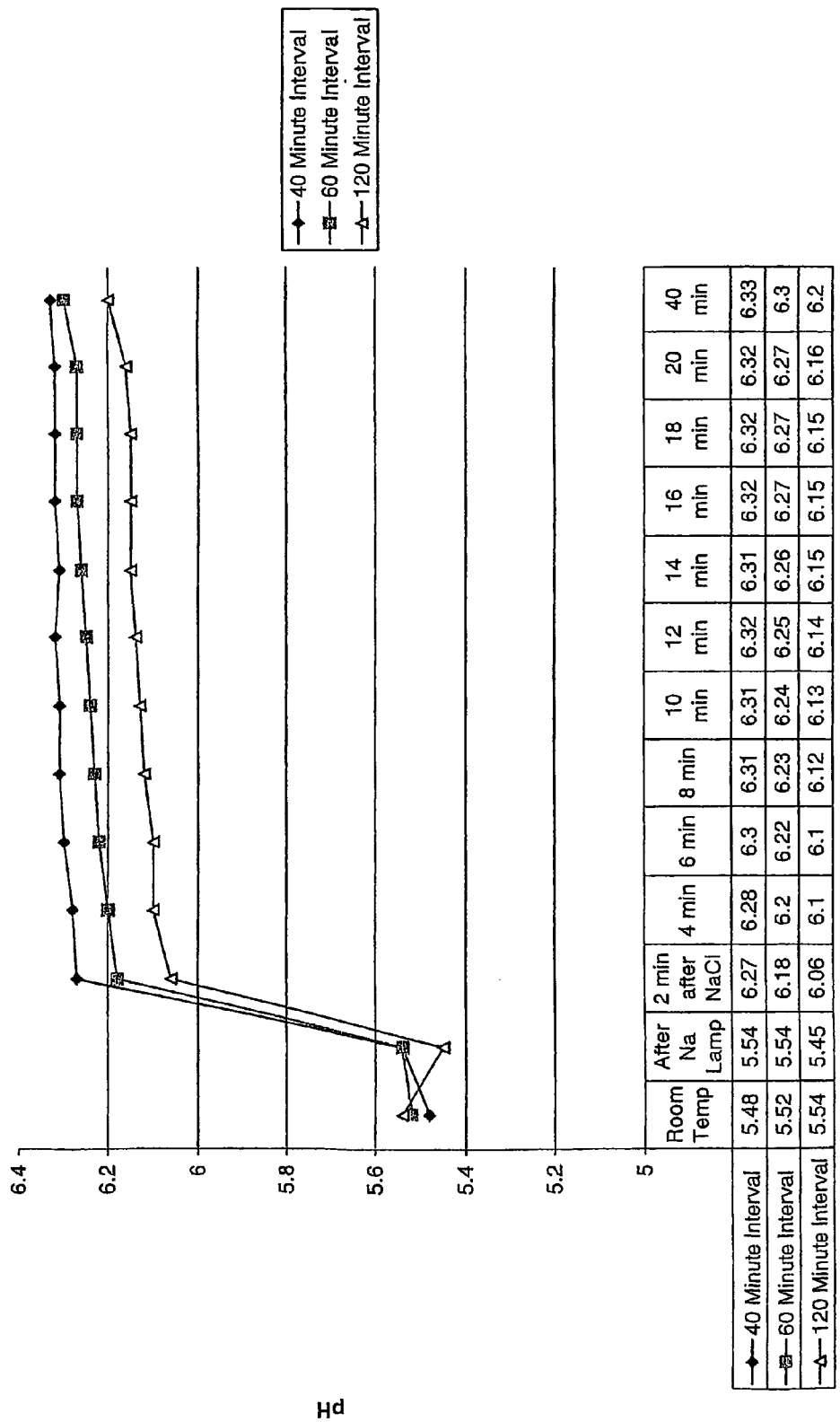
Figure 103:
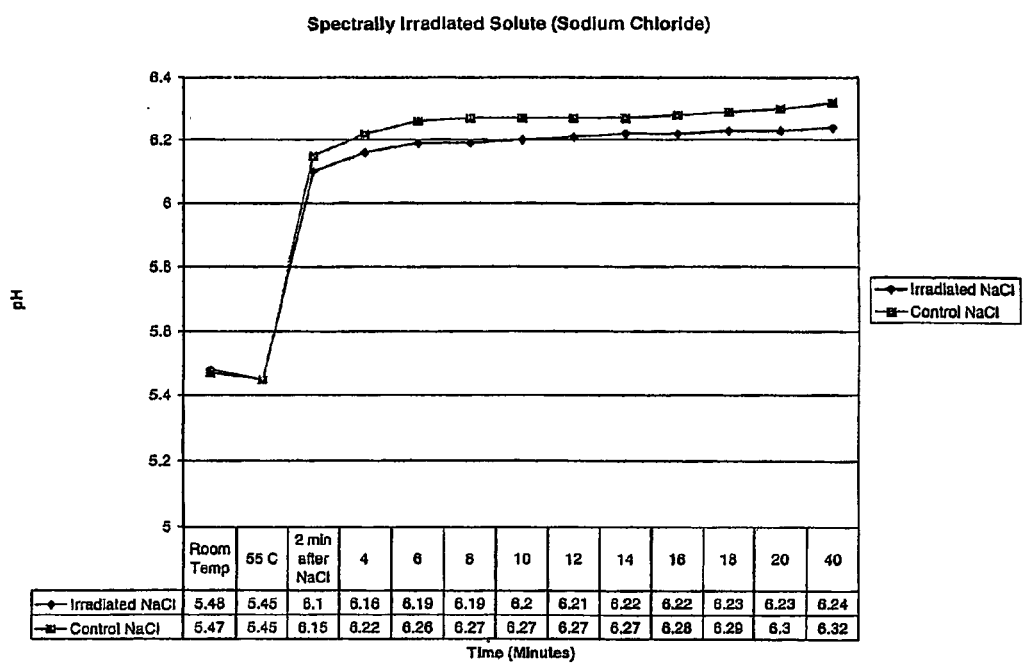

FIG. 103e shows the results of three (3) separate experiments corresponding to the experimental apparatus of FIG. 100. The plotted data show the change in measured pH of the solution 105 as a function of time at room temperature to about 55° C. In particular, the pH of the distilled water alone was first measured at room temperature and then measured at about 55° C., and thereafter measured about every two minutes after the addition and dissolution of sodium chloride and the activation of the high pressure sodium light 112. The time measurements were all at intervals of about two minutes for 20 minutes with a final measurement being taken at about 40 minutes.

All experimental conditions described in this Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 feet above the laboratory counter on which the experimental set-up was located. There were six (6) pairs of lamps present in a room which measured approximately 25 feet by 40 feet (about 2.6 meters×12.1 meters). The fluorescent light produce a widely broadened and noisy mercury spectrum.

Example 7e

FIG. 100 is a schematic of the experimental apparatus used to generate measured pH information at about 55° C. as a function of time. In this Example 7e, a ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch (about 2.0 cm to about 2.5 cm) away from the side of the beaker 104. The tube 110 measured about eight (8) inches (about 2.4 cm) long and was about 3½ inches (about 8.5 cm) in diameter. The top end of the sodium light bulb 112 was about five (5) inches (about 12.5 cm) from the end of the tube 110. In this Example 7e, the sodium light bulb 112 was actuated about 40 minutes and then terminated, before heating the water with the Bunsen burner. The light fixture 111 was fixed to the ring stand 113 by use of a chain clamp 114.

The Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 102. The pH meter was elevated to a convenient height by the use of a support structure 106.

The AR20 meter 107, which used the pH electrode 109 (the electrode being shown in more detail in FIG. 102) were together calibrated by using two different buffer solutions. The first buffer solution had a pH of 4.00+/−0.01 at about 25° C., and was a solution of potassium bipthalate. A second buffer solution had a pH of about 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

The pH of the distilled water in the beaker 104 was first measured at room temperature, before actuating the sodium lamp conditioning. After the 40 minutes of sodium lamp conditioning of the water, the water was then heated to about 55° C. in about 15-20 minutes by use of the Bunsen burner heating the hot plate 103. The water temperature was monitored by the Accumet meter 107. Once a temperature of about 55° C. was obtained, about 50 grams of sodium chloride (certified A.C.S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 3045 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

FIG. 103*f* shows the results of three (3) separate experiments corresponding to the experimental apparatus of FIG. 100. The plotted data show the change in measured pH of the solution 105 as a function of time from room temperature to about 55° C. In particular, the pH of the distilled water alone was first measured at room temperature and then measured at about 55° C., and thereafter measured about every two minutes after the addition and dissolution of sodium chloride and the activation of the high pressure sodium light 112. The time measurements were all at intervals of about two minutes for about 20 minutes with a final measurement being taken at about 40 minutes.

FIG. 103*g* shows the averages calculated from the data from each of the three (3) series of experiments from each of Examples 7a, 7b and 7e.

All experimental conditions described in this Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 7.6 meters×12.1 meters). The fluorescent lamps produce a widely broadened and noisy mercury spectrum.

Example 7f

FIG. 100 is a schematic of the experimental apparatus used to generate measured pH information at about 55° C. as a function of time. In this Example 7f, a ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch (about 1 cm to about 1.5 cm) away from the side of the beaker 104. The tube 110 measured about eight (8) inches long (about 20 cm) and was about 3½ inches (about 8.5 cm) in diameter. The top end of the sodium light bulb 112 was about five (5) inches (about 12.5 cm) from the end of the tube 110. In this Example 7f, the sodium light bulb 112 was actuated about 40 minutes, terminated, and pH was measured. The light fixture 111 was fixed to the ring stand 113 by use of a chain clamp 114.

The Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 102. The pH meter was elevated to a convenient height by the use of a support structure 106.

The AR20 meter 107, which used the pH electrode 109 (the electrode being shown in more detail in FIG. 102) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

The pH of the distilled water in the beaker 104 was first measured at room temperature, before actuating the sodium lamp conditioning. After the 40 minutes sodium lamp conditioning of the water, the following time intervals elapsed before heating the water to 55° C. with the Bunsen burner: 1) 0 minutes; 2) 20 minutes; 3) 40 minutes; 4) 60 minutes; and 5) 120 minutes. The water was then heated to about 55° C. in about 5 minutes by use of the Bunsen burner heating the hot plate 103. The water temperature was monitored by the Accumet meter 107. Once a temperature of about 55° C. was obtained, about 50 grams of sodium chloride (certified A.C.S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 3045 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

FIG. 103*h* shows the results of three (3) separate experiments (#'s 3, 4, and 5) corresponding to the experimental apparatus of FIG. 100, representing decay curves for the sodium lamp conditioning effect in water. The plotted data show the change in measured pH of the solution 105 as a function of time from room temperature to about 55° C. (curves 7f1, 7f2 and 7f3 were essentially identical). In particular, the pH of the distilled water alone was first measured at room temperature and then measured when the sodium lamp was terminated, and thereafter measured about every two minutes after the addition and dissolution of sodium chloride. The time measurements were all at intervals of about two (2) minutes for 20 minutes, with a final measurement being taken at about 40 minutes.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 2.6 meters×12.1 meters).). The fluorescent lamps produce a widely broadened and noisy mercury spectrum.

Discussion of Examples 7a, 7b, 7c, 7d, 7e and 7f

FIG. 103*d* shows the averages calculated from the data from each of the three (3) series of experiments from each of Examples 7a, 7b and 7c. The data show that the Bunsen burner—only heating corresponding to Example 7a and FIG. 99 had the smallest overall measured rise in pH after a period of time of approximately 40 minutes. The data generated from Example 7b, and corresponding to FIG. 100, showed an intermediate rise in measured pH with time after about 40 minutes. In Example 7b, the sodium spectral pattern was added only at the point when the solution 105 had attained a temperature of about 55° C.

The greatest overall increase in measured pH from a time of about 240 minutes was shown in the data corresponding to Example 7c, which corresponds to the experimental apparatus shown in FIG. 101. In this Example 7c, the distilled water in the beaker 104, was exposed to the sodium spectral pattern emitted from the sodium light bulb 112 for the longest amount of time (e.g., energy was provided to the distilled water and the solution 105 exclusively through the combination of the sodium light bulb 112 and the fixture 111) which was about 1¼-1½ hours to heat the water to about 55° C. and then for an additional 40 minutes while the pH measurements were made.

Accordingly, the data shown in FIG. 103*d* clearly show the effect of a sodium spectral pattern upon the measured pH of the sodium chloride/water solution 105, as measured by an AR20 meter from Accumet Research used in combination with a pH electrode 109 (as shown in more detail in FIG. 102).

FIG. 103*g* shows the averages calculated from the data from each of the three (3) series of experiments from each of Examples 7a, 7b and 7e. The data show that the Bunsen burner-only heating corresponding to Example 7a and FIG. 99 had the smallest overall measured rise in pH after a period of time of approximately 40 minutes. The data generated from Example 7b, and corresponding to FIG. 100, showed an intermediate rise in measured pH with time after about 40 minutes. In Example 7e, the water was conditioned by the sodium spectral pattern, after which it was heated to 55° C. and the NaCl was added and dissolved.

The greatest overall increase in measured pH from a time of about 240 minutes was shown in the data corresponding to Example 7e, which corresponds to the experimental apparatus shown in FIG. 100. In this Example 7e, the distilled water in the beaker 104, was exposed to the conditioning sodium spectral pattern emitted from the sodium light bulb 112 for about forty (40) minutes (e.g., conditioning energy was provided to the distilled water 105 exclusively with the sodium light bulb 112 for about 40 minutes).

Accordingly, the data shown in FIG. 103*g* clearly show the pH effect of a conditioning sodium spectral pattern upon distilled water, which is later used to make a sodium chloride/water solution 105, as measured by an AR20 meter from Accumet Research used in combination with a pH electrode 109 (as shown in more detail in FIG. 102).

FIG. 103*h* shows the experimental data from each of the three (3) experiments from Example 7f3, 7f4, and 7f5. The data (7f5) show that the 120 minute interval between conditioning of the distilled water and dissolution of the NaCl salt had the smallest overall measured rise in pH after a period of time of approximately 40 minutes. The data generated from Example 7f4, after about a 60 minute interval between conditioning of the distilled water and dissolution of the NaCl salt, showed an intermediate rise in measured pH with time after about 40 minutes. In Example 7f3, the water was conditioned by the sodium spectral pattern, and the interval between conditioning and dissolution of the NaCl salt was only about 40 minutes. This curve was essentially identical to the curve for 20 minutes and the normalized curve for zero minutes. Example 7f3 showed the greatest rise in pH.

Accordingly, the data shown in FIG. 103*h* clearly show a time-related decay effect of a conditioning sodium spectral pattern upon distilled water, which is later used to make a sodium chloride/water solution 105, as measured by an AR20 meter from Accumet Research used in combination with a pH electrode 109 (as shown in more detail in FIG. 102). The conditioning effects of a sodium spectral pattern upon distilled water remained in the water for a period of time approximately equal to the conditioning time. After an interval of 1.5 times the conditioning time, the conditioning effects of a sodium spectral pattern upon distilled water were beginning to decline. Finally, after an interval of 3.0 times the conditioning time, the conditioning effects of a sodium spectral pattern upon distilled water declined still further.

Example 7g

Changes in pH Due to Effects of Na Lamp Conditioned NaCl on pH

Sodium chloride (about 50 grams) was spread into a thin layer under a sodium lamp in an otherwise dark room overnight. The next day the salt was used in a pH experiment.

Overhead fluorescent lighting was present continuously throughout both experiments. Water (about 800 ml) was placed in a 1000 ml beaker and the pH was measured. The water was next heated to about 55° C. and pH was measured again. The water temperature was maintained at about 55° C. for the remainder of the experiment. NaCl (about 50 grams) was added and stirred with a glass stir rod. Ten additional pH measurements were taken about every two (2) minutes after the addition of the NaCl, for a total of about 20 minutes. Final pH was measured about 40 minutes after addition of the NaCl. FIG. 103*i* shows pH as a function of time for two experiments where sodium chloride solute was dissolved in water.

One series of pH tests was performed on a solution made with the regular salt (which had not been conditioned), and one series of tests was performed on the solution made with the conditioned salt.

Results: The pH increased more when the salt had been conditioned with its own Na spectral energy pattern. This same effect was seen in other similar experiments. When significantly larger amounts of salt in a much thicker layer were irradiated with the same intensity, this effect was not nearly so pronounced, or was not seen at all.

In this Example, targeted spectral energies were used to change the material properties of a solid upon subsequent phase change into a liquid solution.

Example 8

Studies of Solubility Rates in Conditioned Water

For the following Examples 8a-8d, the below-listed Equipment, materials and experimental procedures were utilized (unless stated differently in each Example).
a) Equipment and Materials
Pyrex 1000 ml beakers, Corning.
Pyrex 600 ml beakers, Corning.
Pyrex Petri dishes; model 3160-102, 100×20 mm.
Ohaus portable standard scale LS200, 0.1 to 100.0 grams.
Toastmaster cool touch griddle (TG15W).
Distilled Water—American Fare, contained in one (1) gallon translucent, colorless, plastic jugs, processed by distillation, microfiltration and ozonation. Source, Greeneville Municipal Water supply, Greeneville, Tenn. Stored in cardboard boxes in a dark, shielded room prior to use in the experiments described in Examples 8a, 8b and 8c.
Forma Scientific Incubator; Model 3157, Water-jacketed; 28° C. internal temperature, opaque door and walls, nearly completely light blocking with internal light average 0.82 mW/cm$^2$. Chamber capacity about 5.6 cubic feet.
Fisher brand Salimeters; Models 11-605 (1.0% divisions), 11-606 (0.5% divisions); specialized salinity and sodium chloride hydrometers; length 12". Calibrated for 60° F.
Fisher brand Specific Gravity Hydrometer; Model 11-520E. Length 12". Calibrated for 60° F., with 0.01 s.g. divisions.
Fisher brand Sugar Hydrometer, Model 11-6080; length 12". Calibrated for 60° F., in 0.1% divisions.
Ambient Lighting—All experimental conditions described in these Examples occurred in the presence of standard fluorescent lighting. The fluorescent lamps were Sylvania Cool White Deluxe Fluorescent Lamps, 75 watts and were each about eight (8) feet long (about 2.4 meters long). The lamps were suspended in pairs approximately 3.5 meters above the laboratory counter on which the experimental set-up was located. There were six (6) pairs of lamps present in a room which measured approximately 25 feet by 40 feet (7.6 meters× 12.1 meters). The fluorescent lamps produce a widely broadened and noisy mercury spectrum.
Fisher 50 ml pipettes TD 20° C. serological/Drummond pipet-aid.
Kymex immersion tube (2.3 cm×30 cm) tapered bottom with rubber stopper.
E-Z high purity solvent acetone; contains acetone CAS #67-64-1, E. E. Zimmeman Co.
Glass stir rod.
Sodium Chloride, Fisher Chemicals, packaged in gray plastic 3 Kg bottles. The sodium chloride, in crystalline form, is characterized as follows:
  Sodium Chloride: Certified A.C.S.
    Barium (Ba) (about 0.001%)—P.T.
    Bromide (Br)—less than 0.01%
    Calcium (Ca)—less than 0.0002%-0.0007%
    Chlorate and Nitrate (as $NO_3$)—less than 0.0006%-0.0009%
    Heavy Metals (as Pb)—less than 0.2 ppm-0.4 ppm
    Insoluble Matter—less than 0.001%-0.006%
    Iodide (I)—less than 0.0002%-0.0004%
    Iron (Fe)—less than 0.2 ppm-0.4 ppm
    Magnesium (Mg)—less than 0.001%-0.0003%
    Nitrogen Compounds (as N)—less than 0.0001%-0.0003%
    pH of 5% solution at 25° C.—5.0-9.0
    Phosphate ($PO_3$)—less than 5 ppm
    Potassium (K)—0.001%-0.005%
    Sulfate ($SO_4$)—0.003%-0.004%
Sucrose, Table sugar 4 g/1 tsp, Kroger Brand.
Sodium lamp, Stonco, 70 watt high-pressure sodium security wall light fitted with a parabolic aluminum reflector directing the light down and away from the housing, oriented vertically above a flat, horizontal testing surface, with the bulb about 9 inches (about 23 cm) from the horizontal test surface.

Example 8a

Sodium Chloride Solubility in Water at Room Temperature (22° C.)

Distilled water (about 500 ml, at about 20° C.) was placed into each of six beakers (each about 1000 ml in size). One Beaker "EE" was placed under a sodium lamp 112, as configured in FIG. 97f, while the other Beaker "FF" functioning as the control was placed in an incubator at about 28° C. Approximately, one hour later, about 500 ml of water was again placed into two separate beakers. Beaker "CC" was placed under another sodium lamp as Beaker "EE"; and Beaker "DD" was placed into the same incubator as Beaker "FF". The process was repeated a third time, about one hour later. Specifically, Beaker "AA" was placed under another sodium lamp as Beakers "EE" and "CC"; and Becker "BB" was placed into the same incubator as Beaker "FF" and "DD". Thus, the result was three sets of beakers exposed to the sodium lamp and three sets of beakers in the incubator, one set each for one, two, or three hours. Water temperatures were as follows:

1) Beaker AA sodium lamp about 1 hour, at about 21° C.;
2) Beaker CC sodium lamp about 2 hours, at about 22° C.;
3) Beaker EE sodium lamp about 3 hours, at about 23° C.;
4) Beaker BB, a control beaker, about 1 hour, at about 21° C.;
5) Beaker DD, a control beaker, about 2 hours, at about 22° C.; and
6) Beaker FF, a control beaker, about 3 hours, at about 23° C.

Sodium chloride (about 250 grams) was then added to each beaker and stirred. The beakers were covered with wax paper, placed in a darkened cabinet, and covered with a thick, black, opaque, light-blocking drape.

Twenty hours later the solutions in the beakers were filtered over their salt into 1000 ml beakers. Two hours later each of the solutions (about 85 ml) was pipetted into the Kimex hydrometer testing tube, and temperature and hydrometer measurements were determined. The solutions were finally pipetted (about 50 ml) into each of five petri dishes, dried, and the dry sodium chloride weight per 100 ml solution determined.

Results: The rate of NaCl dissolution increased with exposure of the solvent water to the conditioning sodium lamp, as compared to unconditioned control water. After two hours exposure to the sodium lamp, the conditioned water dissolved approximately 7% more NaCl than the unconditioned control water. After three hours exposure to the sodium lamp, the conditioned water dissolved approximately 9% more NaCl than the unconditioned control water.

The rate of NaCl dissolution also increased with increasing time of exposure to the sodium lamp from one hour to two hours. After about two hours conditioned water dissolved about 3.5% more NaCl than the one hour conditioned water.

| Beaker AA Sodium Lamp 1 Hour | | Beaker BB Control 1 Hour | |
|---|---|---|---|
| Temperature | 22° C. | Temperature | 22° C. |
| Salinity | 82 | Salinity | 80% |
| Specific gravity | 1.163 | Specific gravity | 1.155 |
| NaCl Percent | 21.5% | NaCl Percent | 20.75% |
| Weight | 27.0 g/100 ml | Weight | 26.2 g/100 ml |

| Beaker CC Na Lamp Two Hours | | Beaker DD Control 2 Hours | |
|---|---|---|---|
| Temperature | 22° C. | Temperature | 22 ° C. |
| Salinity | 83+% | Salinity | 77% |
| Specific gravity | 1.160 | Specific gravity | 1.145 |
| NaCl Percent | 21.5% | NaCl Percent | 20.0% |
| Weight | 27.8 g/100 ml | Weight | 25.2 g/100 ml |

| Beaker EE Na Lamp Three Hours | | Beaker FF Control 3 Hours | |
|---|---|---|---|
| Temperature | 22° C. | Temperature | 22° C. |
| Salinity | 80.5% | Salinity | 74% |
| Specific gravity | 1.155 | Specific gravity | 1.135 |
| NaCl Percent | 21.0% | NaCl Percent | 19.0% |
| Weight | 26.0 g/100 ml | Weight | 23.8 g/100 ml |

Example 8b

Sodium Chloride Solubility in Water at Elevated Temperature (55° C.)

Distilled water (about 500 ml, at about 20° C.) was placed in each of two beakers 104 as shown in FIG. 92 (about 1000 ml) and heated to about 55° C. on an iron ringplate 103, over a Bunsen burner 101. One beaker 105 was then irradiated with a sodium lamp 112 from the side (as shown in FIG. 97h), while the other control water beaker 105 was exposed simply to the ambient laboratory lighting. One hour later, water was placed into a second set of beakers 105, which were treated exactly the same as the first set of beakers. The process was repeated a third time with a third set of beakers 105, one hour later, producing three sets of beakers, each set having been exposed to the sodium lamp or just ambient lighting for about one hour, two hours or three hours. Temperatures were maintained at about 55° C. for all three sets of beakers for the entire time prior to sodium chloride being added thereto.

Specifically, sodium chloride (about 250 grams) was added to each beaker and stirred after the treatments discussed above occurred. Each of the six the beakers were covered with wax paper, placed in a darkened cabinet, and covered with a thick, black, opaque, light-blocking, cloth drape.

Twenty hours later the solutions in the beakers were filtered over their salt into 1000 ml beakers. Each of the solutions (about 85 ml) was pipetted into the Kimex hydrometer testing tube, and temperature and hydrometer measurements were determined.

Results: Results were virtually identical for all six solutions, which were all fully saturated. Temperature was about 23.5° C., salinity was about 99.5-100%, specific gravity was about 1.195 and NaCl percent was about 25.5-26%.

Example 8c

Sugar Solubility in Water at Room Temperature (22° C.)

Distilled water (about 500 ml, at about 20° C.) was placed in each of two beakers (each about 1000 ml). One beaker "KK" was placed under a sodium lamp 112 for about three hours, as configured in FIG. 97f, while the other Beaker "IL" functioning as the control was placed in an incubator for about three hours at an internal temperature of about 28° C.

Sugar (about 300 grams) was then added to each beaker and stirred. The beakers were covered with wax paper, placed in a darkened cabinet, and covered with a thick, black, opaque, light-blocking, cloth drape.

Twenty hours later the solutions in the beakers were filtered over their crystals into 2000 ml beakers. Each of the solutions (about 85 ml) was pipetted into a hydrometer testing tube, and temperature and hydrometer measurements were determined.

Results: The rate of sucrose dissolution increased with exposure of the solvent water to the sodium lamp, as compared to unconditioned control water. After three hours exposure to the sodium lamp, the conditioned water dissolved about 2.4% more sucrose by weight than the unconditioned control water.

| KK Na Lamp Three Hours | | LL Control 3 Hours | |
|---|---|---|---|
| Temperature | 23.5° C. | Temperature | 23.5° C. |
| Specific Gravity | 1.170 | Specific Gravity | 1.150 |
| Percent sugar by weight | 39.1% | Percent sugar by weight | 36.7% |

Example 8d

Phenyl Salicylate Solubility in Acetone at Room Temperature (22° C.)

Acetone (about 1 ml) was pipetted into small glass test tubes and stoppers placed in the tube. The neon electronic spectrum was resonant with the vibrational overtones of acetone. Tubes were conditioned under a neon lamp; (about 8 mW/cm$^2$) in an otherwise dark room for about 1.5 hours at about 28° C. ambient temperature. Tubes were also placed simultaneously in an incubator at about 28° C. for about 1.5 hours.

Phenyl salicylate (about 3.50 grams) was added to each tube leaving a layer undissolved on the bottom of each tube. The solutions were allowed to equilibrate overnight (about 20 hours). Solution was filtered over the crystals and 0.500 ml pipetted into fresh tubes.

After the acetone evaporated, dry weights of phenyl salicylate per ml dissolved in conditioned and unconditioned acetone were determined.

Results: Average amounts of phenyl salicylate dissolved in conditioned acetone was 0.78 g/ml. Average amount dissolved in unconditioned acetone was 0.68 g/ml.

Example 9

For the following Examples 9a and 9b, the below-listed Equipment, materials and experimental procedures were utilized (unless stated differently in each Example).

Mercury-Silver Metal Alloy Crystallization a) Equipment and Materials

Distilled water—American Fare, contained in one (1) gallon translucent, colorless, plastic jugs, processed by distillation, microfiltration and ozonation. Source, Greenville Municipal Water supply, Greenville, Tenn.

Forma Scientific incubator; Model 3157; Water-jacketed; 28° C. internal temperature, opaque door and walls, nearly completely light blocking with internal light, average 0.82 mW/cm².

Silver nitrate ($AgNO_3$) crystals: Fisher chemicals, certified A.C.S, in brown glass bottle, 100 gm, product #S181-1001; Lot #017010.

Mercury reagent; Fisher M141, Lot # 014856; ACS mercury metal.

Test tubes; Fisherbrand, disposable culture tubes; 12×75 mm; Borosilicate glass; Cat. #14-961-26.

Mercury Vapor Lamp; GE; 175 watts; HR 175D×39; oriented vertically above a flat testing surface, with spectral emissions traveling down along the vertical axis of the test tubes from top to bottom.

Ambient lighting—All experimental conditions described in the Examples occurred in the presence of standard fluorescent lighting. The fluorescent lamps were Sylvania Cool White Deluxe Fluorescent Lamps, 75 watts, and were each about eight (8) feet long (about 2.4 meters long). The lamps were suspended in pairs approximately 3.5 meters above the laboratory counter on which the experimental set-up was located. There were six (6) pairs of lamps present in a room which measured approximately 25 feet by 40 feet (7.6 meters×12.1 meters). The fluorescent lamps produce a widely broadened and noisy mercury spectrum.

Radiant Power Energy Meter; ThermoOriel; Model 70260, 190 nm to 10 μm.

Sodium lamp, Stonco, 70 watt high-pressure sodium security wall light fitted with a parabolic aluminum reflector directing the light down and away from the housing, oriented vertically above a flat, horizontal testing surface, with the bulb about 8.75 inches (intensity about 14.0 mW/cm²) from the horizontal test surface.

Example 9a

Spectral Enhancement of Mercury-Silver Metal Alloy Crystallization

Silver nitrate (about 2.0 grams) was added to about 80 ml distilled water (stored in white, semi-opaque plastic one-gallon jugs in cardboard boxes with thick black opaque drapes, in a darkened, shielded room). The solution was allowed to equilibrate for about 1.5 hours in ambient laboratory lighting before pipetting about two (2) ml into each of 36 small test tubes. Mercury (about 2 drops) was added to each tube. Eighteen of the test tubes were placed into the incubator as controls at about 28° C. Eighteen test tubes were placed on a black non-reflective surface about 14 inches (about 35 cm) from the mercury lamp (47 mW/cm²). Ambient room temperature was about 28° C., in an otherwise dark room.

About four hours later the ambient temperature under the mercury lamp was noted to be about 30° C. and the test tubes on the black non-reflective surface were moved to a distance of about 29.5 inches (about 75 cm) from the mercury lamp at a light intensity of about 4.5 mW/cm², where ambient temperature remained at about 28° C. Crystals in test tubes under the mercury lamp measured up to about 10 mm long at this time, while crystals in the incubator measured up to about 3 mm long.

Figure 104A:
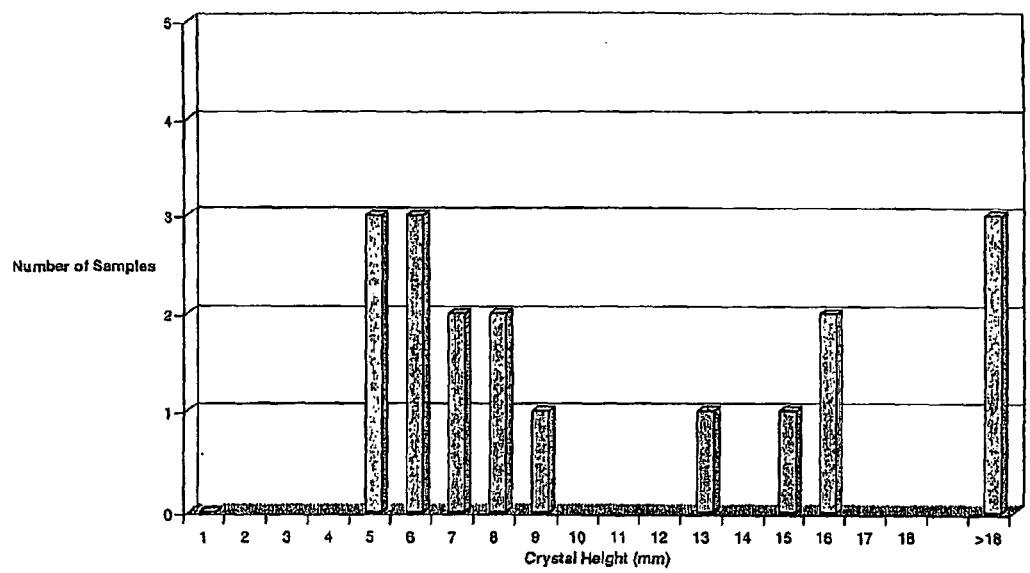
Figure 104B:
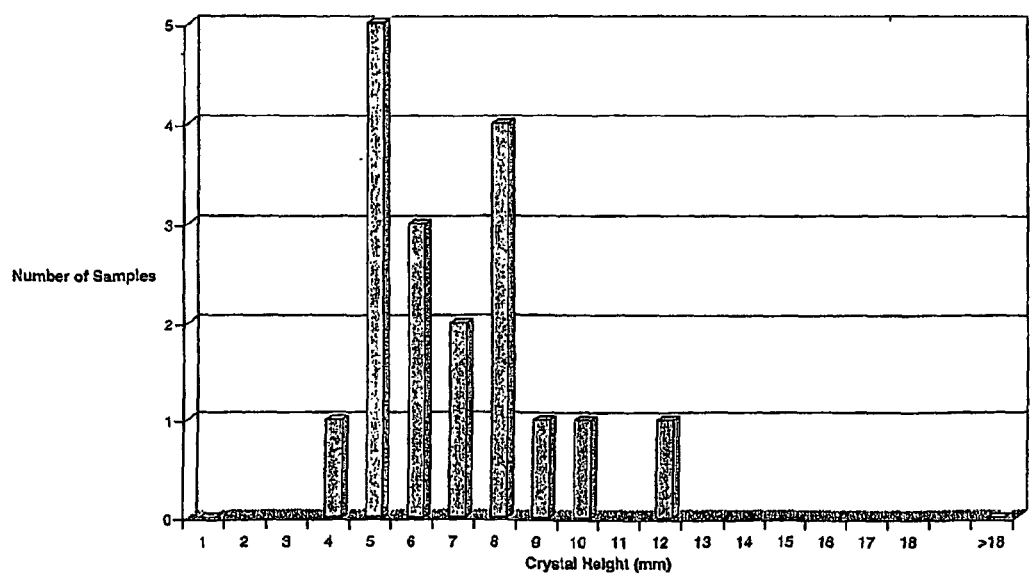
Figure 105A:
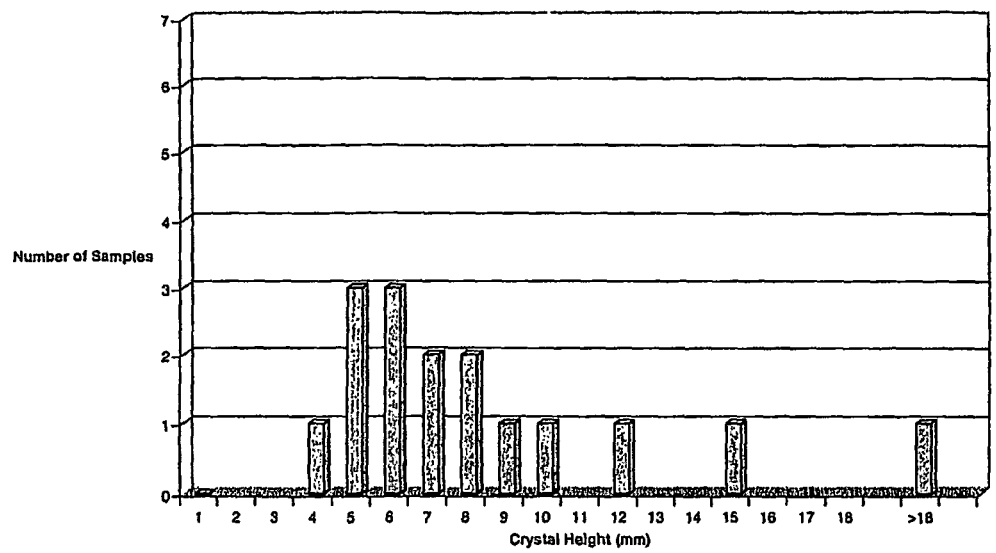
Figure 105B:
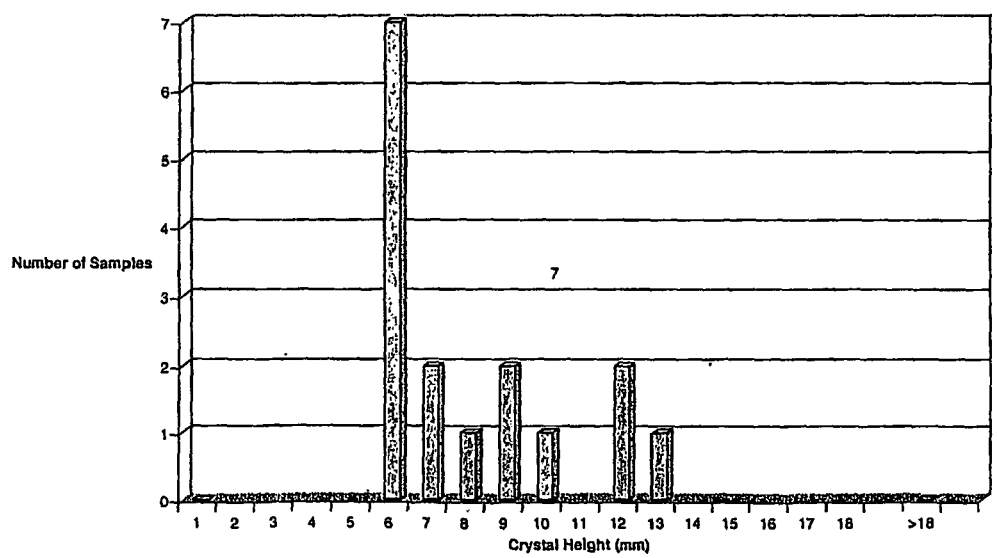
Figure 105C:
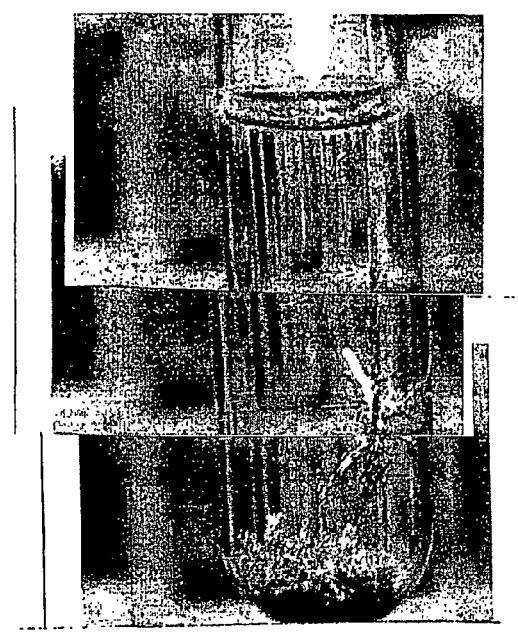
Figure 105F:
Figure 105G:
Figure 105H:
Figure 105I:
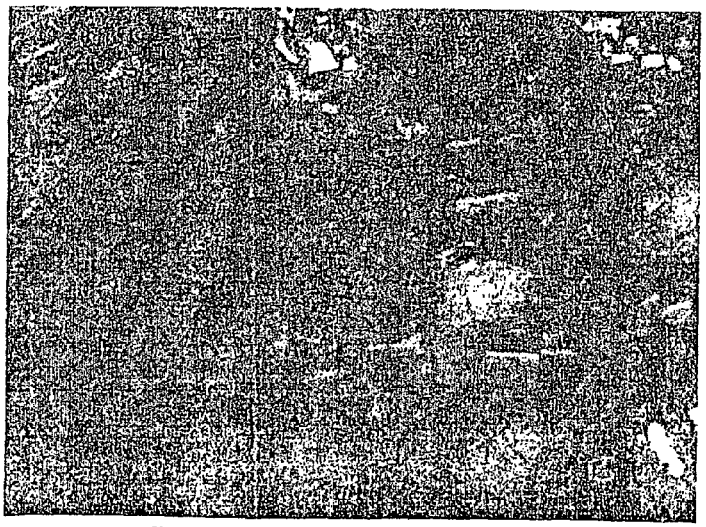

Results: The crystals were evaluated after about 20 hours after the addition of the mercury. Photomicrographs were taken at about 10× magnification (not shown herein). Heights of the crystals formed were determined from measurements taken from the photomicrographs and plotted in graphs shown in FIGS. 104a and 104b. The average height of the incubator control metal alloy crystals was about 7 mm, with branched dendrites in one tube. The average height of the mercury spectrally irradiated metal alloy crystals was about 12 mm, with branched dendrites in 7 tubes, six of which contained excessively branched dendrites. Three of the spectrally grown crystals were about 22-25 mm high (an exemplary photograph of the dendritic formation is shown in FIG. 105c). The mercury spectral pattern catalyzed enhanced growth of the mercury-silver alloy and morphology was significantly different.

In this Example, targeted spectral energy was used to affect phase change and structure.

Example 9b

Mercury-Silver Metal Alloy Crystallization Using Water Conditioned for One Hour

Distilled water (about 40 ml) at about 18° C. (stored in a white, semi-opaque plastic one-gallon jug in a dark, shielded cabinet) was pipetted into a 125 ml Pyrex beaker and was conditioned by irradiation under a sodium lamp for about one hour. Another 125 ml Pyrex beaker with distilled water (about 40 ml) at about 18° C. was placed into the incubator at 28° C. at the same time. At the end of about one hour, water temperatures in both beakers were 21° C. and the volume unchanged. Silver nitrate (about 1.00 gram) was added to each beaker. The solutions (about 2 ml) were each pipetted into 16 small test tubes and mercury (about 100 μl) was added to each tube. All of the test tubes were placed in the incubator at about 28° C.

Results: The crystals were evaluated after about 17 hours after addition of the mercury. Photomicrographs were taken at about 10× magnification (not shown herein). The heights of the formed crystals were determined from measurements taken from the photomicrographs and plotted in graphs shown in FIGS. 105a and 105b. The average height of the control metal alloy crystals was about 8 mm, the tallest being about 13 mm, and one tube contained a simple branched dendritic crystal. The average height of the mercury-silver metal alloy crystals grown from conditioned water was about 9 mm, the tallest about 25 mm. Three tubes contained excessively branched dendritic crystals.

Growth of the mercury-silver alloy was slightly greater in the solution made with sodium lamp conditioned water, and morphology was different compared to the control solution.

Example 10

Protein Crystals and Phase Changes

For the following Examples 10a-10b the below listed Equipment, materials and experimental procedures were utilized (unless stated otherwise in the Example).

a) Equipment and Materials

Distilled Water—the water is distilled water from American Fare, contained in one (1) gallon translucent, colorless, plastic jugs and was processed by a combination of distillation, microfiltration and ozonation. The original source for the water was the Greeneville Municipal water supply in Greeneville, Tenn. The plastic jugs were stored in a darkened and electromagnetic shielded room prior to use in the experiments described in Examples 10a, 10b and 10c.

Sodium lamp, Stonco 70 watt high-pressure sodium security wall light fitted with a parabolic aluminum reflector directing the light away from the housing. Ring stand and beaker suspension chain (i.e., similar to the apparatus shown in FIG. 94). Sodium lamps placed on table in an irradiation room (room measuring about 11 feet×14 feet), no electronics products and no other lights sources in the room, temperature 28°±2 C.

Forma Scientific incubator; Model 3157, water jacketed, 28° C., with solid opaque sides and door which was nearly completely light blocking; with the internal light having an average intensity of about 0.82 mW/cm$^2$.

Protein; Sigma Lysozyme Grade I from chicken egg white; EC 3.2.1.17: Material # L6876, Lot 051K7028, 1 Gram: 58,100 units/mg protein.

Emerald Biostructures Inc., combinatorial clover crystallization plates, First Generation Combi Plates, 24 reservoirs with 4 wells per reservoir for sitting drop crystallization, Crystal Clear sealing tape (EBS-CBT).

Reservoir: Hampton Research Grid Screen Sodium Chloride; # HR2-219.

Reservoir: Hampton Research Crystal Screen 2, Macromolecular Crystallization Kit; #HR2-112.

Hampton Research, Sodium acetate, 3.0 M, solution made from sodium acetate trihydrate, HR2-543.

Binocular microscope.

Intel computerized microscope.

Ambient Lighting—All experimental conditions described in these Examples occurred in the presence of standard fluorescent lighting. The fluorescent lamps were Sylvania Cool White Deluxe Fluorescent Lamps, 75 watts and were each about eight (8) feet long (about 2.4 meters long). The lamps were suspended in pairs approximately 3.5 meters above the laboratory counter on which the experimental set-up was located. There were six (6) pairs of lamps present in a room which measured approximately 25 feet by 40 feet (7.6 meters× 12.1 meters). The fluorescent lamps produce a widely broadened and noisy mercury spectrum.

Example 10a

Altered Protein Crystallization and Phase Changes

Lysozyme (about 1 gram) was dissolved in about 0.1 M sodium acetate to a sample concentration of about 50 mg/ml. Grid screen sodium chloride (about 1.3 ml) was pipetted into the reservoirs of two combi plates. Protein sample (about 30 μl) was pipetted into each of the four wells and reservoir solution (about 30 μl) was pipetted over the protein sample for a total of about 60 μl per drop. Drop mixing was accomplished with one micropipette aspiration per well. Plates were sealed with sealing tape. One plate was placed in the incubator, and one plate was placed under a sodium lamp.

Results:
Two Days
- A4—(0.1 M HEPES pH 7.0, 1.0 M sodium chloride). The incubator plate showed single crystals (less than about 0.2 mm) in 2 wells and clear drop in 2 wells. The sodium lamp plate showed all clear drops.
- B1—(0.1 M citric acid pH 4.0, 2.0 M sodium chloride). The incubator plate showed precipitate in 2 wells and single crystals (less than about 0.2 mm) in 2 wells. The sodium lamp wells contained clear drops.

6 Days
- A1—(0.1 M Citric acid pH 4.0, 1.0 M sodium chloride). The incubator plate showed clear drops. Two of four wells in the sodium lamp plate precipitated.
- A3—(0.1 M MES pH 6.0, 1.0 M sodium chloride). The incubator plate contained clear drops, while one of four sodium lamp wells contained needles.
- A4—The incubator plate contained small crystals (less than about 0.2 mm) in all four wells, while the sodium lamp plate still contained clear drops.
- B1—The incubator plate contained precipitate in three wells and single crystals (less than about 0.2 mm) in only one well. The sodium lamp plate also contained precipitate in three wells and new single crystals (less than about 0.2 mm) in one well.
- B2—(0.1 M/citric acid pH 5.0, 2.0 M sodium chloride). The incubator plate contained clear drops, while all four wells in the sodium lamp plate contained precipitate.

9 Days
- A1—The incubator plate contained clear drops in all four wells. The sodium lamp plate contained precipitate in all four wells.
- A2—(0.1 M citric acid pH 5.0, 1.0 M sodium chloride). The incubator plate contained clear drops in all 4 wells. The sodium lamp plate contained precipitate in three of four wells.
- A3—The incubator plate still contained clear drops in all four wells. The sodium lamp plate contained needles again in one well, precipitate in two wells, and clear drop in the fourth.
- A4—The incubator plate contained single crystals (less than about 0.2 mm and a few up to about 0.5 mm largest dimension) in all four wells again. The sodium lamp plate contained new needles in two wells, and new single crystals (greater then about 0.2 mm, up to about 1×2 mm) in two wells.
- B1—The incubator plate contained precipitate in 3 wells and single crystals (less than about 0.2 mm) in only one well again. The sodium lamp plate also contained precipitate in only two wells, new needles in one well, and single crystals (greater than about 0.2 mm) in one well.
- B2—Both plates contained precipitate in all four wells.

Crystals from A4 were dried and stored in containers in a desiccation chamber.

Example 10b

Altered Protein Crystal Growth and Phase

Lysozyme (about 1 gram) was dissolved in 0.1 M sodium acetate to a sample concentration of 50 about mg/ml. Crystal Screen 2 (#'s 1-18) (about 1.3 ml) was pipetted into the first 18 reservoirs of two combi plates. Protein sample (about 30 μl) was pipetted into each of the four wells and reservoir solution (about 30 μl) was pipetted over the protein sample for a total of about 60 μl drop. Drop mixing was accomplished with one micropipette aspiration per well. Plates were sealed with sealing tape. One plate was placed in the incubator, and one plate was placed under a sodium lamp.

Results:
Two Days
- —Tube #14—(about 0.2 M potassium sodium tartrate tetrahydrate, 0.1 M tri-sodium citrate dihydrate pH 5.6, and 2.0 M ammonium sulfate). The incubator contained clear drops in all 4 wells. The sodium lamp plate contained precipitate in two out of four wells.

Six Days

Tube #1—(about 2.0 M sodium chloride, 10% w/v PEG 6000). The incubator plate contained clear drops in all four wells. The sodium lamp plate contained clear drop in three wells, and single crystals (greater than about 0.2 mm) in one well.

Tube #2—(about 0.01 M Hexadecyltrimethylammonium bromide, 0.5 M sodium chloride, 0.01 magnesium chloride hexahydrate). The incubator plate contained precipitate in two wells and needles in two wells. The sodium lamp plate contained clear drops in two wells and rods in two wells.

Tube #9—(buffer about 0.1 M Sodium Acetate trihydrate pH 4.6, precipitant 2.0 M sodium chloride). The incubator plate contained single crystals (less than about 0.2 mm) in all four wells. The sodium lamp plate contained precipitate in all four wells.

Tube #14—Both plates contained precipitate in all four wells.

Nine Days

Tube #1—The incubator plate contained clear drops in two wells, and precipitate in two wells. The sodium lamp plate contained clear drops in two wells, needles in one well, and needles and single crystals (greater than about 0.2 mm) in one well.

Tube #2—The incubator plate contained precipitate in two wells and needles in two wells. The sodium lamp plate contained clear drop in only one well, needles in one well, and rods (greater than about 0.2 mm) in two wells.

Tube #9—The incubator plate contained single crystals (greater than about 0.2 mm) in all 4 wells. The sodium lamp plate again contained precipitate in all 4 wells.

Example 10c

Altered Protein Crystal Growth and Phase

Lysozyme (about 1 gram) was dissolved in about 0.1 M sodium acetate to a sample concentration of about 50 mg/ml. Crystal Screen 2 (#9) (1.2 ml) was pipetted into two reservoirs on each of two combi plates. Protein sample (about 30 μl) was pipetted into each of the four wells and reservoir solution (about 30 μl) was pipetted over the protein sample for a total of about 60 μl per drop. Drop mixing was accomplished with one micropipette aspiration per well. Plates were sealed with sealing tape. One plate was placed in the incubator, and one plate was placed under a sodium lamp 112, similar to the lamp shown in FIG. 94.

Results:

Two Days

Tube #9 (buffer about 0.1 M sodium acetate trihydrate, pH 4.6, preciptant 2.0 M sodium chloride). The incubator plate contained single crystals (less than 0.2 mm) in all four wells of both reservoirs (i.e., eight total wells). The sodium lamp plate contained precipitate in all four wells of both reservoirs (i.e., eight total wells).

Example 10d

Enhanced Protein Crystallization

Lysozyme (about 1 gram) was dissolved in about 0.1 M sodium acetate to a sample concentration of about 50 mg/ml. Grid screen A4 (0.1 M HEPES, pH 7.0, 1.0M sodium chloride) about 1.3 ml was pipetted into two reservoirs each of two combi plates. Protein sample (30 μl) was pipetted into each of the four wells and reservoir solution (about 30 μl) was pipetted over the protein sample for a total of about 60 μl per drop. Drop mixing was accomplished with one micropipette aspiration per well. Plates were sealed with sealing tape. One plate was placed in the incubator at about 28° C., and one plate was placed under a sodium lamp at about 28° C.

Results:

Two Days:

Clear drops in all wells on both plates.

Six Days:

Three of the eight sodium lamp wells grew large (greater than about 1.0 mm) single protein crystals (FIG. 105*d*). On the control plate, two of the eight wells grew several small (less than about 0.1 mm) crystals (FIG. 105*e*).

Conclusion: The sodium lamp irradiation produced varying effects on lysozyme protein crystal growth depending on the reagents used, including:

1. Increased precipitation.
2. Decreased precipitation.
3. Increased rate of precipitation.
4. Delayed single crystal growth followed by growth of larger single crystals.
5. Increased growth rate of large, single crystals.
6. Altered morphology of crystals.

Differences were noted between the incubator and sodium lamp primarily for reservoir solutions containing sodium or potassium. Differences were minimal when the reservoir solution did not contain sodium or potassium.

Example 11

For the following Examples 11a-e the below listed Equipment, materials and experimental procedures were utilized (unless stated otherwise in the Example).

a) Equipment and Materials

Sodium Chloride, Fisher Chemicals, packaged in gray plastic 3 Kg bottles. The sodium chloride, in crystalline form, is characterized as follows:

Sodium Chloride: Certified A.C.S.
  Barium (Ba) (about 0.001%)—P.T.
  Bromide (Br)—less than 0.01%
  Calcium (Ca)—less than 0.0002%-0.0007%
  Chlorate and Nitrate (as $NO_3$)—less than 0.0006%-0.0009%
  Heavy Metals (as Pb)—less than 0.2 ppm-0.4 ppm
  Insoluble Matter—less than 0.001%-0.006%
  Iodide (I)—less than 0.0002%-0.0004%
  Iron (Fe)—less than 0.2 ppm-0.4 ppm
  Magnesium (Mg)—less than 0.001%-0.0003%
  Nitrogen Compounds (as N)—less than 0.0001%-0.0003%
  pH of 5% solution at 25° C.—5.0-9.0
  Phosphate ($PO_3$)—less than 5 ppm
  Potassium (K)—0.001%-0.005%
  Sulfate ($SO_4$)—0.003%-0.004%

Potassium Chloride, Fisher Chemicals, packaged in gray plastic 3 Kg bottles. The potassium chloride, in crystalline form, is characterized as follows:

Potassium Chloride, Certified A.C.S.
Certificate of Lot Analysis
  Bromide—0.01%
  Chlorate and Nitrate (as $NO_3$)—less than 0.003%
  Nitrogen Compounds (as N)—less than 0.001%
  Phosphate—less than 5 ppm
  Sulfate—less than 0.001%
  Barium 0.001%
  Calcium and $R_2O_3$ Precipitate—less than 0.002%
  Heavy Metals (as Pb)—less than 5 ppm
  Iron—less than 2 ppm Sodium—less than 0.005%
Magnesium—less than 0.001%
Iodide—less than 0.002%
pH of 5% solution at 25° C.—5.4 to 8.6
Insoluable Matter—less than 0.005%
Sterile water by Bio Whittaker (prepared by ultrafiltration, reverse osmosis, deionization, and distillation) in one liter plastic bottles.
Sodium lamp, Stonco, 70 watt high-pressure sodium security wall light fitted with a parabolic aluminum reflector directing the light down and away from the housing, oriented vertically above a flat, horizontal testing surface, with the bulb about 8.75 inches (intensity about 14.0 mW/cm) the from horizontal test surface.
Humboldt Bunsen burner.
Ring stand and Fisher cast iron ring and heating plate.
Crystallization dishes, Pyrex 270 ml capacity, Corning 3140, Ace Glass 8465-12.
Shielded room in a darkened room, Ace Shielded Room Ace, Philadelphia, Pa., U.S. Model A6H3-16, copper mesh, with a width of about eight feet, a length of about 17 feet and a height of about eight feet (about 2.4 meters×5.2 meters×2.4 meters).
Ambient Lighting—All experimental conditions described in the Examples occurred in the presence of standard fluorescent lighting. The fluorescent lamps were Sylvania Cool White Deluxe Fluorescent Lamps, 75 watts and were each about eight (8) feet long (about 2.4 meters long). The lamps were suspended in pairs approximately 3.5 meters above the laboratory counter on which the experimental set-up was located. There were six (6) pairs of lamps present in a room which measured approximately 25 feet by 40 feet (7.6 meters×12.1 meters). The fluorescent lamps produce a widely broadened and noisy mercury spectrum.
Aluminum foil, plastic containers.
Black plastic, plastic container.
Potassium lamp, Thermo Oriel 10 watt spectral line potassium lamp #65070 with Thermo Oriel lamp mount #65160 and Thermo Oriel spectral lamp power supply #65150. The potassium lamp was mounted overhead with the rectangular bulb oriented horizontally at about 9 inches (about 23 cm) from the crystallization dishes (as shown in FIG. 97h).
American Fare distilled water, in one gallon semi-opaque colorless plastic jugs, processed by distillation, microfiltration and ozonation. Source: Greenville Municipal water supply, Greenville, Tenn. Stored in shielded, darkened room, in cardboard boxes.
Pyrex 1000 ml beakers.
Pyrex 400 ml beakers.
Pyrex 2000 ml bealers.
Grounded, dark enclosure, about 6 feet by about 3 feet by about 1½ feet metal cabinet (24 gauge metal), flat, black paint inside.
Microwave horn, Maury Microwave, Model P230B, SN# s959, 12.4-18.0 GHz (10.0-18.7), 8725 A, 3.5 mm.
Microwave spectroscopy system, Hewlett Packard; HP 8350B Sweep Oscillator, HP8510B Network analyzer, and HP 8513A Reflection Transmission Test set.
Forma Scientific incubator; model 3157, water jacketed, 28° C., with solid opaque sides and door, average internal light intensity about 0.82 mW/cm$^2$).
Computer microscope manufactured by Intel, Model Qx3.

Example 11a

Sodium Chloride/Potassium Chloride 1:1 Molar Saturated Solution

Saturated sodium chloride (NaCl)/potassium chloride (KCl) 1:1 molar solution was prepared by heating distilled/deionized water (about 1600 ml) in a 2000 ml Pyrex beaker to about 55° C. NaCl (about 29 grams) and KCl (about 37 grams) were mixed dry and added in about 66 gram amounts for a total mixture weight of about 726 grams, until no more would dissolve, under ambient laboratory lighting. The beaker was wrapped in black plastic, stored in a cabinet, and allowed to equilibrate overnight (about 18 hours).

The saturated solution was filtered at room temperature at about 100 ml and was placed into each of 13 crystallization dishes. The dishes were treated as follows:
three under the potassium lamp in the shielded room surrounded by 1 meter tall light blocking barriers (the potassium lamp was suspended on a ring stand such that the lamp portion in the rectangular-shaped housing was about 9 inches above the sample beakers);
three under the sodium lamp (apparatus similar to that shown in FIG. 94) in the shielded room surrounded by about 1 meter tall light blocking barriers;
two in an opaque plastic container with light blocked by an entire covering of aluminum foil, in the shielded room;
two in an opaque plastic container with light blocked by an entire covering of black plastic in the shielded room;
three under fluorescent lights (the fluorescent lamps produce a widely broadened and noisy mercury spectrum).

The solutions were allowed to crystallize overnight.

Results: All dishes had crystalline masses covering the bottom. Weights were about as follows:

|  | Average Weight (g) per Dish |
| --- | --- |
| Potassium Lamp | 14.94 |
| Sodium Lamp | 15.03 |
| Al Foil Covered Container | 5.75 |
| Black Plastic Covered Container | 5.50 |
| Fluorescent Lights | 13.87 |

Elemental analysis for sodium and potassium was performed on the mixed NaCl/KCl crystals. Results were:

|  | Percent K by Weight | Percent Na by Weight |
| --- | --- | --- |
| Potassium Lamp | 52.1 | 1.15 |
| Sodium Lamp | 50.8 | 1.61 |
| Al Foil Covered Container | 51.9 | 1.10 |
| Black Plastic Covered Container | 51.9 | 1.63 |
| Fluorescent Lights | 51.7 | 1.55 |

The presence of spectral light frequencies (potassium lamp, sodium lamp, and fluorescent lights) enhanced the rate of crystallization for both sodium and potassium, compared to conditions in which light was blocked (aluminum foil and black plastic covered containers).

The potassium lamp inhibited NaCl crystallization preferentially in favor of KCl. Similarly, the sodium lamp enhanced crystallization of NaCl relative to KCl.

The aluminum-foil covered container inhibited crystallization of NaCl, without affecting KCl crystallization.

Example 11b

Sodium Chloride/Potassium Chloride 1:1 Molar Unsaturated Solution

Saturated sodium chloride (NaCl)/potassium chloride (KCl) 1:1 molar solution was prepared by heating distilled/deionized water (about 1600 ml) in a 2000 ml Pyrex beaker to about 55° C. NaCl (about 29 grams) and KCl (about 37 grams) were mixed dry and added in about 66 gram amounts for a total mixture weight of about 660 grams under ambient laboratory lighting. The beaker was wrapped in black plastic, stored in a cabinet, and allowed to equilibrate overnight (about 18 hours).

The unsaturated solution was filtered at room temperature and 100 ml was placed in each of 13 crystallization dishes. Dishes were treated as follows:
- three under the potassium lamp in the shielded room surrounded by about 1 meter tall light blocking barriers (the potassium lamp was suspended on a ring stand such that the lamp portion in the rectangular-shaped housing was about 9 inches above the sample beakers);
- three under the sodium lamp (apparatus similar to that shown in FIG. 94) in the shielded room surrounded by 1 meter tall light blocking barriers;
- two in an opaque plastic container with light blocked by an entire covering of aluminum foil, in the shielded room;
- two in an opaque plastic container with light blocked by an entire covering of black plastic in the shielded room;
- three under fluorescent lights (the fluorescent lamps produce a widely broadened and noisy mercury spectrum).

The solutions were allowed to crystallize overnight and were evaluated after about 20 hours.

Results: Weights and morphologies of crystals grown from unsaturated solution were as follows:

|   | Average Weight (g) per Dish | Morphology |
|---|---|---|
| Potassium Lamp | 3.4 | more than 50 cubic crystals, 3-4 mm cubic |
| Sodium Lamp | 3.9 | more than 50 cubic crystals, up to 5 mm cubic |
| Al Foil Covered Container | 1.2 | about 15 crystals, 3-10 mm in size |
| Black Plastic Covered Container | 1.1 | 8 crystals, 6-15 mm |
| Fluorescent Lights | 2.8 | more than 50 crystals, 1-2 mm in one dish, 5-10 mm in two dishes |

Elemental analysis for sodium and potassium was performed via ICP (Baird) on the mixed NaCl/KCl crystals. Results were:

|   | Percent K by Weight | Percent Na by Weight |
|---|---|---|
| Potassium Lamp | 51.4 | 1.45 |
| Sodium Lamp | 51.1 | 1.36 |
| Aluminum-Foil Covered Container | 51.6 | 1.17 |
| Black Plastic Covered Container | 50.1 | 1.88 |
| Fluorescent Lights | 50.5 | 1.83 |

The presence of spectral light frequencies (potassium lamp, sodium lamp, and fluorescent lights) in a less saturated solution again enhanced the overall rates of crystallization and nucleation, compared to conditions in which light was blocked (aluminum foil and black plastic covered containers). Individual crystals were larger in those same light-blocked conditions, with significantly less nucleation.

The potassium and sodium lamps did not exhibit preferential crystallization in this unsaturated solution.

The aluminum foil-covered container again exhibited inhibition of NaCl crystallization, relative to KCl crystallization.

Conversely, crystallization of Na was enhanced in the unsaturated solution under fluorescent lights and in the plastic container with light blocking black plastic. (It was noted after the fact that the plastic container with light blocking black plastic had been placed directly adjacent to a bundle of electrical cords.)

Example 11c

Sodium Chloride/Potassium Chloride 1:1 Molar Unsaturated Solution

Saturated sodium chloride (NaCl)/potassium chloride (KCl) 1:1 molar solution was prepared as above in Example 11a dissolving a total of about 528 grams mixed salts in about 1600 ml distilled/deionized water. Dishes were prepared and treated as above and allowed to crystallize overnight, however there was no crystal growth in any of the dishes.

Example 11d

Sodium Chloride/Potassium Chloride 1:1 Molar Unsaturated Solution

Saturated sodium chloride (NaCl)/potassium chloride (KCl) 1:1 molar solution was prepared by heating distilled/deionized water (about 1600 ml) in a 2000 ml Pyrex beaker to about 55° C. NaCl (about 29 grams) and KCl (about 37 grams) were mixed dry and added in about 66 gram amounts for a total mixture weight of about 594 grams under ambient laboratory lighting. The beaker was wrapped in black plastic, stored in a cabinet, and allowed to equilibrate overnight (about 18 hours).

The unsaturated solution was filtered at room temperature and 100 ml was placed in each of 14 crystallization dishes. Dishes were treated as follows:
- three under the potassium lamp in the shielded room surrounded by 1 meter tall light blocking barriers (the potassium lamp was suspended on a ring stand such that the lamp portion in the rectangular-shaped housing was about 9 inches above the sample beakers);
- three under the sodium lamp (apparatus similar to that shown in FIG. 94) in the shielded room surrounded by 1 meter tall light blocking barriers;
- two in an opaque plastic container with light blocked by an entire covering of aluminum foil, in the shielded room;
- two in an opaque plastic container with light blocked by an entire covering of loose black plastic; and
- two under fluorescent lights.

The solutions were allowed to crystallize overnight and were evaluated after about 20 hours.

Results: Weights and morphologies of crystals grown from unsaturated solution were as follows:

|  | Average Weight (g) per Dish | Morphology |
| --- | --- | --- |
| Potassium Lamp | 0.15 | 3 cubes 4-7 mm, one flat sheet 1 × 2 cm |
| Sodium Lamp | 0.9 | more than 5 cubic crystals, about 5-10 mm in size |
| Aluminum-Foil Covered Container | | No growth |
| Loose Black Plastic Covered Container | | No growth |
| Fluorescent Lights | 0.1 | about 4 cubic crystals, about 3-5 mm in size |

Elemental analysis for sodium and potassium was performed via ICP (Baird) on the mixed NaCl/KCl crystals. Results were:

|  | Percent K by Weight | Percent Na by Weight |
| --- | --- | --- |
| Potassium Lamp | 51.8 | 0.71 |
| Sodium Lamp | 52.1 | 0.99 |
| Fluorescent Lights | 51.1 | 0.79 |

The presence of spectral light frequencies (potassium lamp, sodium lamp, and fluorescent lights) in this much less saturated solution again enhanced the overall rates of crystallization and nucleation, compared to conditions in which light was blocked (aluminum foil and black plastic-covered containers). Crystallization growth rate was greatest with the sodium lamp. Nucleation was approximately equal with all light irradiation.

The potassium and sodium lamps exhibited slight preferential crystallization in this very unsaturated solution.

Example 12

Mixed Microwave Crystals

For the following Examples 12a and 12b the below-listed Equipment, materials and experimental procedures were utilized (unless stated otherwise in the Example).
  a) Equipment and Materials
  American Fare distilled water, in one gallon semi-opaque colorless plastic jugs, processed by distillation, microfiltration and ozonation. Source: Greenville Municipal water supply, Greenville, Tenn. Stored in shielded, darkened room, in cardboard boxes.
  Pyrex 1000 ml beakers.
  Pyrex 400 ml beakers.
  Sodium Chloride, Fisher Chemicals, packaged in gray plastic 3 Kg bottles. The sodium chloride, in crystalline form, is characterized as follows:
    Sodium Chloride: Certified A.C.S.
      Barium (Ba) (about 0.001%)—P.T.
      Bromide (Br)—less than 0.01%
      Calcium (Ca)—less than 0.0002%-0.0007%
      Chlorate and Nitrate (as $NO_3$)—less than 0.0006%-0.0009%
      Heavy Metals (as Pb)—less than 0.2 ppm-0.4 ppm
      Insoluble Matter—less than 0.001%-0.006%
      Iodide (I)—less than 0.0002%-0.0004%
      Iron (Fe)—less than 0.2 ppm-0.4 ppm
      Magnesium (Mg)—less than 0.001%-0.0003%
      Nitrogen Compounds (as N)—less than 0.0001%-0.0003%
      pH of 5% solution at 25° C.—5.0-9.0
      Phosphate $PO_3$)—less than 5 ppm
      Potassium (K)—0.001%-0.005%
      Sulfate ($SO_4$)—0.003%-0.004%
  Potassium Chloride, Fisher Chemicals, packaged in gray plastic 3 Kg bottles. The potassium chloride, in crystalline form, is characterized as follows:
    Potassium Chloride, Certified A.C.S.
    Certificate of Lot Analysis
      Bromide—0.01%
      Chlorate and Nitrate (as $NO_3$)—less than 0.003%
      Nitrogen Compounds (as N)—less than 0.001%
      Phosphate—less than 5 ppm
      Sulfate—less than 0.001%
      Barium 0.001%
      Calcium and $R_2O_3$ Precipitate—less than 0.002%
      Heavy Metals (as Pb)—less than 5 ppm
      Iron—less than 2 ppm
      Sodium—less than 0.005%
      Magnesium—less than 0.001%
      Iodide—less than 0.002%
      pH of 5% solution at 25° C.—5.4 to 8.6
      Insoluable Matter—less than 0.005%
  Grounded, dark enclosures (2) about 6 feet by 3 feet×1½ feet metal cabinets (24 gauge metal); flat, black paint inside.
  Microwave horn, Maury Microwave, Model P230B, SN# s959, 12.4-18.0 GHz (10.0-18.7), 8725 A, 3.5 mm.
  Microwave spectroscopy system, Hewlett Packard; HP 8350B Sweep Oscillator, HP 8510B Network analyzer, and HP 8513A Reflection Transmission Test set.
  Sodium lamp, Stonco, 70 watt high-pressure sodium security wall light fitted with a parabolic aluminum reflector directing the light down and away from the housing, oriented vertically above a flat, horizontal testing surface, with the bulb about 9 inches (23 cm) from the horizontal test surface.
  Humboldt Bunsen burner with Bernzomatic propane fuel.
  Ring stand and Fisher cast iron ring and heating plate.
  Crystallization dishes, Pyrex, 90×50 mm, part no. 3140.
  Forma Scientific Incubator; Model # 3157; Single chamber/water-jacketed incubator with CHIP CO2 control; chamber capacity-5.6 cubic feet, opaque walls and door with an average internal light intensity of about 0.82 mW/cm².
  Computer microscope; manufactured by Intel, model Qx3.

Example 12a

Sodium Chloride/Potassium Chloride 1:1 Molar Saturated Solution and Sodium Chloride Microwave Rotational Frequency A saturated sodium chloride (NaCl)/potassium chloride (KCl) 1:1 molar solution was prepared by heating distilled water (about 800 ml) in a 1000 ml Pyrex beaker to about 55° C. NaCl (about 29 grams) and KCl (about 37 grams) were mixed dry and added in about 66 gram amounts, until no more would dissolve, under ambient laboratory lighting. The beaker was wrapped in black plastic, stored in a cabinet, and allowed to equilibrate overnight about 18 hours.

The saturated solution was filtered at room temperature and about 100 ml was placed into each of 4 crystallization dishes. Two of the dishes were placed in the shielded, dark control enclosure and two were placed in the second shielded, dark enclosure for microwave irradiation, parameter $S_{11}$, sweeping from 13.073719 GHz to 13.073721 in a very narrow resonance peak. Microwave Dish "A" was immediately adjacent to the microwave horn, and microwave Dish "B" was adjacent to dish A, and in line with the microwave horn.

After about 17 hours, the microwave irradiation was terminated and the crystals were evaluated. Temperatures in both cabinets were about 21° C.

Results: Crystals were similar in size and morphology. Weights for total crystals differed however, with the control crystals weighing more. Microwave crystals exhibited reduced crystallization rates relative to controls.

|  | Weight of Crystals (g) |
| --- | --- |
| Microwave Dish A | 3.2 |
| Microwave Dish B | 3.1 |
| Control Dish A | 3.4 |
| Control Dish B | 3.5 |

Example 12b

Sodium Chloride/Potassium Chloride 1:3 Molar Saturated Solution and Sodium Chloride Microwave Rotational Frequency Saturated sodium chloride (NaCl)/potassium chloride (KCl) solution, 1:4 by weight (approximately 1:3 molar) was prepared by heating distilled water (about 800 ml) in a 1000 ml Pyrex beaker to about 55° C. NaCl (about 75 grams) and KCl (about 300 grams) were mixed dry and then added to the water with undissolved salt remaining in the water under ambient laboratory lighting. The beaker was wrapped in black plastic, stored in a cabinet, and allowed to equilibrate overnight about 18 hours.

The saturated solution was filtered at room temperature and about 100 ml was placed into each of 8 crystallization dishes. Dishes were treated as follows:

Two dishes in the shielded, dark control enclosure (about 22° C.)

Two dishes in the second shielded, dark enclosure (about 22° C.) for microwave irradiation, parameter $S_{11}$, sweeping more broadly from 13.0736 GHz to 13.0738. Microwave Dish "A" was immediately adjacent to the microwave horn, and microwave Dish "B" was adjacent to dish A, and in line with the microwave horn.

Two dishes in the incubator (about 28° C.)

Two dishes under a sodium lamp (about 28° C.) as shown in FIG. 94.

Microwave irradiation was terminated after about 12 hours and the shielded controls were placed in the same enclosure with the microwave dishes. After about 5 more hours all the crystallization dishes were assessed. Photomicrographs corresponding to the grown crystals are shown in FIGS. 105*f*-105*i*. Dry crystal weights were also obtained.

Results: Weights and morphologies were:

|  | Weight of Crystals (g) | Morphology |
| --- | --- | --- |
| Microwave A (FIG. 105f) | 2.2 | Many cubic crystals |
| Microwave B | 2.0 | with some flat sheets |
| Shielded Control A (FIG. 105g) | 2.5 | Many flat sheets |
| Shielded Control B | 2.6 | with some cubic crystals |
| Na Lamp A (FIG. 105h) | 6.2 | Mostly cubic crystals |
| Na Lamp B | 5.9 |  |
| Incubator Control A (FIG. 105i) | 1.2 | Mostly flat sheets |
| Incubator Control B | 0.9 |  |

A broader microwave resonance curve was used in the experiment. Differences between the microwave crystal weights and the shielded control weights were more pronounced, with crystallization during microwave irradiation being 18% less.

Morphology differences between the crystals were more pronounced, as shown in FIGS. 105*f*-105*i*, as well and revealed a continuum from spectrally irradiated crystals to controls.

Example 13

Conductivity

For the following Example 13, the below-listed Equipment, materials and experimental procedures were utilized.
a) Equipment and Materials Accumet Research AR20 ph/Conductivity Meter, calibrated with reference solutions prior to all experiments.

Traceable Conductivity Calibration Standard—Catalog # 09-328-3

MicroMHOS/cm—1,004.

Microseimens/cm—1,004.

OmhS/cm—99.

PPM D. S.—669.

Accuracy @ 25° C. (+/−0.25%).

Size—16 oz (473 ml).

Analysis #—2713.

Conductivity probe # 13-620-155 with thermocouple.

Humboldt Bunsen burner with Bernozomatic propane fuel.

Ring stand and Fisher cast iron ring and heating plate.

sodium lamp, Stonco 70 watt high-pressure sodium security wall light, fitted with a parabolic aluminum reflector directing the light away from the housing. The sodium bulb was a Type S62 lamp, 120V, 60 Hz, 1.5 A made in Hungary by Jemanamjjasond. The lamp was located about 12 cm from the beaker side.

Sterile water—Bio Whittaker, contained in one liter clear, plastic bottles, processed by ultrafiltration, reverse osmosis, deionization, and distillation.

Example 13a

Conductivity of Sodium Chloride Aqueous Solution

Procedures similar to those discussed in detail in Example 7 were followed with the following specific differences.

Water (about 800 ml) was placed in a 1000 ml beaker and room temperature measurements were obtained for conductivity (S/cm), dissolved solids (ppm), and resistance (kOhms), after allowing about 10 minutes for the probe to equilibrate to the water. The water was then heated to about 56.1° C., and measurements were repeated. Sodium chloride (about 0.01 gram) was added and stirred with a glass stir rod for about 30 seconds. Measurements of conductivity were obtained about every 2 minutes for about 20 minutes, and a final measurement was taken at about 40 minutes. Dissolved solids and resistance measurements were also obtained at about 4 minutes, at about 14 minutes, and at about 20 minutes after adding the salt.

The experimental apparatuses used to obtain data are shown in FIGS. 99 and 100. A conditioning probe was substituted for the pH probe of Example 7.

Four sets of parameters were evaluated, with three tests within each set:
1. Bunsen burner heating only (apparatus corresponding to FIG. 99);
2. Sodium lamp irradiation of water about 40 minutes before adding the salt (apparatus corresponding to FIG. 100);
3. Sodium lamp irradiation of water about 40 minutes after adding the salt (apparatus corresponding to FIG. 100);
4. Sodium lamp irradiation of water about 40 minutes before and after adding the salt (apparatus corresponding to FIG. 100).

Results: Conductivity appears to be increased with sodium lamp irradiation after addition of the sodium chloride.

FIG. 106a is a graph of the experimental data which shows conductivity as a function of time for three separate sets of Bunsen burner-only data.

FIG. 106b is a graph of the experimental data which shows conductivity as a function of temperature (two separate data points only) for Bunsen burner-only data.

FIG. 106c is a graph of the experimental data which shows conductivity as a function of time for three separate sets of Bunsen burner-only data, the plot beginning with the data point generated two minutes after sodium chloride was added to the water.

FIG. 106d is a graph of the experimental data which shows conductivity as a function of time for three separate sets of data corresponding to the water being conditioned by the sodium lamp for about 40 minutes before the sodium chloride was dissolved therein.

FIG. 106e is a graph of the experimental data which shows conductivity as a function of temperature (two separate data points only), corresponding to the water being conditioned by the sodium lamp for about 40 minutes before the sodium chloride was dissolved therein.

FIG. 106f is a graph of the experimental data which shows conductivity as a function of time for three separate sets of data corresponding to the water being conditioned by the sodium lamp for about 40 minutes before the sodium chloride was dissolved therein, the plot beginning with the data point generated two minutes after sodium chloride was added to the water.

FIG. 106g is a graph of the experimental data which shows conductivity as a function of time for three separate sets of data corresponding to the solution of sodium chloride and water being irradiated with a spectral energy pattern of a sodium lamp beginning when the sodium chloride was added to the water.

FIG. 106h is a graph of the experimental data which shows conductivity as a function of temperature (two separate data points only) corresponding to the solution of sodium chloride and water being irradiated with a spectral energy pattern of a sodium lamp beginning when the sodium chloride was added to the water.

FIG. 106i is a graph of the experimental data which shows conductivity as a function of time for three separate sets of data corresponding to the solution of sodium chloride and water being irradiated with a spectral energy pattern of a sodium lamp beginning when the sodium chloride was added to the water, the plot beginning with the data point generated two minutes after sodium chloride was added to the water.

FIG. 106j is a graph of the experimental data which shows conductivity as a function of time for three separate sets of data corresponding to the water being conditioned by the sodium lamp spectral conditioning pattern for about 40 minutes before the sodium chloride was added to the water; and continually irradiating the water with the sodium light spectral pattern while sodium chloride is added thereto and remaining on while all conductivity measurements were taken.

FIG. 106k is a graph of the experimental data which shows conductivity as a function of temperature (two separate data points only) for three sets of data, corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

FIG. 106l is a graph of the experimental data which shows conductivity as a function of time for three separate sets of data corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken, the plot beginning with the data point generated two minutes after sodium chloride was added to the water.

FIG. 106m is a graph of the experimental data which superimposes averages from the data in FIGS. 106a, 106d, 106g and 106j.

FIG. 106n is a graph of the experimental data which superimposes averages from the data in FIGS. 106b, 106e, 106h and 106k.

FIG. 106o is a graph of the experimental data which superimposes averages from the data in FIGS. 106c, 106f, 106i and 106j.

In this Example, targeted spectral patterns and/or targeted spectral conditioning patterns were used to change the material properties of a solvent and/or solvent/solute system.

Example 14

Batteries

For the following Examples 14a and 14b the following Equipment, materials and experimental procedures were utilized.
a) Equipment and Materials
One or more sodium lamps, Stonco 70 watt high-pressure sodium security wall light, fitted with a parabolic aluminum reflector directing the light away from the housing. The sodium bulb was a Type S62 lamp, 120V, 60 Hz, 1.5 A made in Hungary by Jemanamjjasond. One or more sodium lamps was/were mounted at various angles, and location(s) as specified in each experiment. Unless stated differently in the Example, the lamp was located at about 15 inches (about 38 cm) from the beakers or dishes to maintain substantially consistent intensities.
Sterile water—Bio Whittaker, contained in one liter clear, plastic bottles, processed by ultrafiltration, reverse osmosis, deionization, and distillation.
Sodium Chloride, Fisher Chemicals, packaged in gray plastic 3 Kg bottles. The sodium chloride, in crystalline form, is characterized as follows:
Sodium Chloride: Certified A.C.S.
Barium (Ba) (about 0.001%)—P.T.

Bromide (Br)—less than 0.01%
Calcium (Ca)—less than 0.0002%-0.0007%
Chlorate and Nitrate (as $NO_3$)—less than 0.0006%-0.0009%
Heavy Metals (as Pb)—less than 0.2 ppm-0.4 ppm
Insoluble Matter—less than 0.001%-0.006%
Iodide (I)—less than 0.0002%-0.0004%
Iron (Fe)—less than 0.2 ppm-0.4 ppm
Magnesium (Mg)—less than 0.001%-0.0003%
Nitrogen Compounds (as N)—less than 0.0001%-0.0003%
pH of 5% solution at 25° C.—5.0-9.0
Phosphate ($PO_3$)—less than 5 ppm
Potassium (K)—0.001%-0.005%
Sulfate ($SO_4$)—0.003%-0.004%
Battery anodes by Sovietski; #150400; primarily magnesium and aluminum.

Battery/flashlight assembly: Aqueous sodium chloride (NaCl) electrolyte powered flashlight by Sovietski; #150400; double cathode/anode configuration.

Sodium (Na) Lamp, Stonco 70 watt high-pressure sodium security wall light fitted with a parabolic aluminum reflector directing the light away from the housing, oriented horizontally with a cylindrical aluminum foil light guide about 9 cm in diameter.

Receptacle, clear plastic box about 7.5×5.75×3.75 inches.

American Fare distilled water, in one gallon semi-opaque colorless plastic jugs, processed by distillation, microfiltration and ozonation. Source: Greenville Municipal water supply, Greenville, Tenn. Stored in shielded, darkened room, in cardboard boxes.

Grounded, dark enclosure about 6 feet×3 feet×1½ feet metal cabinet (24 gauge metal), flat, black paint inside.

Load box Ammeter/Voltmeter (Fuel Cell Store) Heliocentris #DBGMNR29126811 with 10 ohm load.

FisherBrand Dual Channel Thermometer with Offset.

2000 ml Pyrex beaker.

Example 14a

Enhanced Sodium Chloride Battery Current with Sodium Spectral Irradiation

FIG. 107 shows an aqueous NaCl battery/flashlight assembly 308. Two assemblies 308 were placed side-by-side in a grounded, dark enclosure. Electrolyte 310 was distilled water (about 1700 ml) and NaCl (about 97 g) mixed at the same time at room temperature in 2000 ml Pyrex beakers. Thermometer wires 309 were placed on the bottom center of the electrolyte receptacles 307. FIG. 108 shows Sodium lamp 112 in a housing 111 with an aluminum foil cylinder 110, with the sodium lamp 112 positioned about 18 cm to the outside side of each electrolyte receptacle 307 allowing delivery of sodium spectral irradiation through the outside of the receptacle 307, into the electrolyte solution 310, and onto the outside of the anode plate 306.

The electrolyte receptacles 307 were filled with electrolyte 310, the anode/cathode assembly 301 was lowered into the electrolyte 310, and the flashlights 303 of each assembly 308 were turned on throughout the experiment. Initial measurements of current (mAmps) and temperature were performed and then measured again every 40 minutes.

The sodium lamp was cycled as follows:
1. Off first 40 minutes;
2. On second 40 minutes;
3. Off third 40 minutes;
4. On fourth 40 minutes.

Results: As shown in FIG. 109, the standard initial current increase occurred with the sodium lamp turned off. The current increase continued with the sodium lamp turned on during the second 40 minutes. When the sodium lamp was turned off at 80 minutes however, the current stopped increasing and stayed essentially the same to 120 minutes. When the sodium lamp was turned on again at 120 minutes, the current again increased. Finally, when the sodium lamp was turned off again the current remained the same.

These current characteristics were not related to temperature. Although the temperature increased between 80 and 120 minutes and between 160 and 200 minutes, when the sodium lamp was off, the current did not increase, suggesting that current increase was not due to an increase in temperature.

Example 14b

Enhanced Sodium Chloride Battery Current with Sodium Spectral Irradiation

FIG. 107 shows an aqueous NaCl battery/flashlight assembly 308. Two assemblies 308 were placed side-by-side in a grounded, dark enclosure. Electrolyte 310 was distilled water (about 1700 ml) and NaCl (about 97 g) mixed at the same time at room temperature in 2000 ml Pyrex beakers. FIG. 108 shows Sodium lamp 112 in a housing 111 with an aluminum foil cylinder 110 with the sodium lamp 112 that was positioned about 18 cm to the outside side of each electrolyte receptacle 307 allowing delivery of sodium spectral irradiation through the outside of the receptacle 307, into the electrolyte solution 310, and onto the outside of the anode plate 306.

The electrolyte receptacles 307 were filled with electrolyte 310, the anode/cathode assembly 301 was lowered into the electrolyte 310, and the flashlights 303 of each assembly 308 were turned on throughout the experiment. Initial measurements of current (mAmps) and temperature were performed and then measured again every 10 minutes. Movement of charged species in this battery is accomplished by phase changes entailing dissolution of metal atoms on the anode, followed by migration across the electrolyte, and ending with bonding crystallization onto the cathode. The spectral energy pattern used in this Example enhanced these phase changes.

The sodium lamp was cycled as follows:
1. Off 040 minutes;
2. Off 40-70 minutes;
2. On 70-110 minutes;
3. Off 110-150 minutes;
4. On 150-190 minutes.

Results: As shown in FIG. 110, the standard initial current increase occurred with the sodium lamp turned off. Rate of rise of current had slowed by about 70 minutes. The current increased faster with the sodium lamp turned on between 70 and 110 minutes. When the sodium lamp was turned off at from 110-150 minutes, the rate of current increase went down. When the sodium lamp was turned on again at 150 minutes, the rate of current increase went up again.

In these examples, the spectral energy pattern of sodium was used to increase current in an electrolyte.

Example 15

Corrosion

Corrosion of Steel Razor Blades in Aqueous Solutions

For the following Examples 15a and 15b, the following Equipment, materials and experimental procedures were utilized.

a) Equipment and Materials

Sterile water, BioWhittaker, contained in one liter clear, plastic bottles, processed by ultrafiltration, reverse osmosis, deionization, and distillation.

Stanley Utility blades 11-921, 1095 Carbon steel.

Sodium Lamp, Stonco 70 watt high-pressure sodium security wall light, fitted with a parabolic aluminum reflector directing light away from the housing. The sodium bulb Type S62 lamp, 120 V, 60 Hz, 1.5 Å made in Hungary by Jemanamjjasond.

Example 15 a

Ten steel razor blades 311 were placed in a beaker 104 in distilled deionized water 105 for about 48 hours. Five razor blades 311b were kept in the dark, and five razor blades 311a were exposed only to the sodium electronic spectrum, which is resonant with water vibrational overtones. FIG. 94 shows the experimental apparatus used in this experiment. FIG. 111 shows the differences in amounts of corrosion between blades 311a and 311b.

Results: Razor blades kept in the dark had virtually no corrosion. Razor blades exposed to sodium electronic/water vibrational overtones displayed corrosion on more than 90% of the surface.

Example 15b

Twelve razor blades 311 were placed in beakers 104, in sodium chloride solution 105 (25 g/100 ml). Six razor blades (311b) were kept in total darkness and six razor blades (311a) were exposed only to the sodium electronic/water vibrational overtones from a sodium lamp. FIG. 94 shows the experimental apparatus used in this experiment.

Results: Razor blades kept in the dark (not shown) had mild corrosion over 20-25% of their surfaces. Razor blades exposed to sodium electronic/water vibrational overtones exhibited moderate corrosion (not shown) over 70-75% of their surfaces.

Example 16

Replacing a Physical Catalyst with a Spectral Catalyst in a Gas Phase Reaction

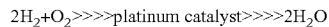

$2H_2 + O_2 \ggg \text{platinum catalyst} \ggg 2H_2O$

Water can be produced by the method of exposing $H_2$ and $O_2$ to a physical platinum (Pt) catalyst but there is always the possibility of producing a potentially dangerous explosive risk, This experiment replaced the physical platinum catalyst with a spectral catalyst comprising the spectral pattern of the physical platinum catalyst, which resonates with and transfers energy to the hydrogen and hydroxy intermediates.

To demonstrate that oxygen and hydrogen can combine to form water utilizing a spectral catalyst, electrolysis of water was performed to provide stoichiometric amounts of oxygen and hydrogen starting gases. A triple neck flask was fitted with two (2) rubber stoppers on the outside necks, each fitted with platinum electrodes encased in glass for a four (4) inch length. The flask was filled with distilled water and a pinch of salt so that only the glass-encased portion of the electrode was exposed to air, and the unencased portion of the electrode was completely under water. The central neck was connected via a rubber stopper to vacuum tubing, which led to a Drierite column to remove any water from the produced gases.

After vacuum removal of all gases in the system (to about 700 mm Hg), electrolysis was conducted using a 12 V power source attached to the two electrodes. Electrolysis was commenced with the subsequent production of hydrogen and oxygen gases in stoichiometric amounts. The gases passed through the Drierite column, through vacuum tubing connected to positive and negative pressure gauges and into a sealed 1,000 ml, round quartz flask. A strip of filter paper, which contained dried cobalt, had been placed in the bottom of the sealed flask. Initially the cobalt paper was blue, indicating the absence of water in the flask. A similar cobalt test strip exposed to the ambient air was also blue.

The traditional physical platinum catalyst was replaced by spectral catalyst platinum electronic frequencies (with their attendant fine and hyperfine frequencies) from a Fisher Scientific Hollow Cathode Platinum Lamp which was positioned approximately one inch (about 2 cm) from the flask. This allowed the oxygen and hydrogen gases in the round quartz flask to be irradiated with emissions from the spectral catalyst. A Cathodeon Hollow Cathode Lamp Supply C610 was used to power the Pt lamp at 80% maximum current (12 mAmps). The reaction flask was cooled using dry ice in a Styrofoam container positioned directly beneath the round quartz flask, offsetting any effects of heat from the Pt lamp. The Pt lamp was turned on and within two days of irradiation, a noticeable pink color was evident on the cobalt paper strip indicating the presence of water in the round quartz flask. The cobalt test strip exposed to ambient air in the lab remained blue. Over the next four to five days, the pink colored area on the cobalt strip became brighter and larger. Upon discontinuation of the Pt emission, $H_2O$ diffused out of the cobalt strip and was taken up by the Drierite column. Over the next four to five days, the pink coloration of the cobalt strip in the quartz flask faded. The cobalt strip exposed to the ambient air remained blue.

In this Example, targeted spectral energies were used to affect chemical reactions in a gas phase.

Example 17

Replacing a Physical Catalyst with a Spectrl Catalyst in a Liquid Phase Reaction

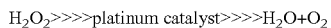

$H_2O_2 \ggg \text{platinum catalyst} \ggg H_2O + O_2$

The decomposition of hydrogen peroxide is an extremely slow reaction in the absence of catalysts. Accordingly, an experiment was performed which showed that the physical catalyst, finely divided platinum, could be replaced with the spectral catalyst having the spectral pattern of platinum. Hydrogen peroxide, 3%, filled two (2) nippled quartz tubes. (the nippled quartz tubes consisted of a lower portion about 17 mm internal diameter and about 150 mm in length, narrowing over about a 10 mm length to an upper capillary portion being about 2.0 mm internal diameter and about 140 mm in length and were made from PhotoVac Laser quartz tubing). Both quartz tubes were inverted in 50 ml beaker reservoirs filled with (3%) hydrogen peroxide to about 40 ml and were shielded from incident light (cardboard cylinders covered with aluminum foil). One of the light shielded tubes was used as a control. The other shielded tube was exposed to a Fisher Scientific Hollow Cathode Lamp for platinum (Pt) using a Cathodeon Hollow Cathode Lamp Supply C610, at 80% maximum current (12 mA). The experiment was performed several times with an exposure time ranging from about 24 to about 96 hours. The shielded tubes were monitored for increases in temperature (there was none) to assure that any reaction was not due to thermal effects. In a typical experiment the nippled tubes were prepared with hydrogen peroxide (3%) as described above herein. Both tubes were shielded from light, and the Pt tube was exposed to platinum spectral emissions, as described above, for about 24 hours. Gas production in the control tube A measured about four (4) mm in length in the capillary (i.e., about 12.5 mm$^3$), while gas in the Pt (tube B) measured about 50 mm (i.e., about 157 mm$^3$) The platinum spectral catalyst thus increased the reaction rate about 12.5 times.

The tubes were then switched and tube A was exposed to the platinum spectral catalyst, for about 24 hours, while tube B served as the control. Gas production in the control (tube B) measured about 2 mm in length in the capillary (i.e., about 6 mm$^3$) while gas in the Pt tube (tube A) measured about 36 mm (i.e., about 113 mm$^3$), yielding about a 19 fold difference in reaction rate.

As a negative control, to confirm that any lamp would not cause the same result, the experiment was repeated with a sodium lamp at 6 mA (80% of the maximum current). Na in a traditional reaction would be a reactant with water releasing hydrogen gas, not a catalyst of hydrogen peroxide breakdown. The control tube measured gas to be about 4 mm in length (i.e., about 12 mm$^3$) in the capillary portion, while the Na tube gas measured to be about 1 mm in length (i.e., about 3 mm$^3$). This indicated that while spectral emissions can substitute for catalysts, they cannot yet substitute for reactants. Also, it indicated that the simple effect of using a hollow cathode tube emitting heat and energy into the hydrogen peroxide was not the cause of the gas bubble formation, but instead, the spectral pattern of Pt replacing the physical catalyst caused the reaction.

In this Example, targeted spectral energies were used to affect a chemical reaction in a liquid phase and subsequent transformation to a gas phase.

Example 18

Replacing a Physical Catalyst with a Spectral Catalyst in a Solid Phase Reaction It is well known that certain microorganisms have a toxic reaction to silver (Ag). The silver electronic spectrum consists of essentially two ultraviolet frequencies that fall between UV-A and UV-B. It is now understood through this invention, that the high intensity spectral frequencies produced in the silver electronic spectrum are ultraviolet frequencies that inhibit bacterial growth (by creation of free radicals and by causing bacterial DNA damage). These UV frequencies are essentially harmless to mammalian cells. Thus, it was theorized that the known medicinal and antimicrobial uses of silver are due to a spectral catalyst effect. In this regard, an experiment was conducted which showed that the spectral catalyst emitting the spectrum of silver demonstrated a toxic or inhibitory effect on microorganisms.

Bacterial cultures were placed onto standard growth medium in two petri dishes (one control and one Ag) using standard plating techniques covering the entire dish. Each dish was placed at the bottom of a light shielding cylindrical chamber. A light shielding foil-covered, cardboard disc with a patterned slit was placed over each culture plate. A Fisher Scientific Hollow Cathode Lamp for Silver (Ag) was inserted through the top of the Ag exposure chamber so that only the spectral emission pattern from the silver lamp was irradiating the bacteria on the Ag culture plate (i.e., through the patterned slit). A Cathodeon Hollow Cathode Lamp Supply C610 was used to power the Ag lamp at about 80% maximum current (3.6 mA). The control plate was not exposed to emissions of an Ag lamp, and ambient light was blocked. Both control and Ag plates were maintained at room temperature (e.g., about 70-74° F.) during the silver spectral emission exposure time, which ranged from about 12-24 hours in the various experiments. Afterwards, both plates were incubated using standard techniques (37° C., aerobic Forma Scientific Model 3157, Water-Jacketed Incubator) for about 24 hours.

The following bacteria (obtained from the Microbiology Laboratory at People's Hospital in Mansfield, Ohio, US), were studied for effects of the Ag lamp spectral emissions:
 1. *E. coli;*
 2. *Strep. pneumoniae;*
 3. *Staph. aureus*; and
 4. *Salmonella typhi.*

This group included both Gram$^+$ and Gram$^-$ species, as well as cocci and rods.

Results were as follows:
 1. Controls—all controls showed full growth covering the culture plates;
 2. The Ag plates
  areas unexposed to the Ag spectral emission pattern showed full growth.
  areas exposed to the Ag spectral emission pattern showed:
   a. *E. coli*—no growth;
   b. *Strep. pneumoniae*—no growth;
   c. *Staph. aureus*—no growth; and
   d. *Salmonella tyhli*—inhibited growth.

In this Example, targeted spectral energies were used to catalyze chemical reactions in biological organisms. These reactions inhibited growth of the biological organisms.

Example 19

Replacing a Physical Catalyst with a Spectral Catalyst, and Comparing Results to Physical Catalyst Results in a Biologic Preparation To further demonstrate that certain susceptible organisms which have a toxic reaction to silver would have a similar reaction to the spectral catalyst emitting the spectrum of silver, cultures were obtained from the American Type Culture Collection (ATCC) which included *Escherichia coli* #25922, and *Klebsiella pneumonia*, subsp *Pneumoniae,* # 13883. Control and Ag plate cultures were performed as described above. After incubation, plates were examined using a binocular microscope. The *E. coli* exhibited moderate resistance to the bactericidal effects of the spectral silver emission, while the *Klebsiella* exhibited moderate sensitivity. All controls exhibited full growth.

Accordingly, an experiment was performed which demonstrated a similar result using the physical silver catalyst as was obtained with the Ag spectral catalyst. Sterile test discs were soaked in an 80 ppm, colloidal silver solution. The same two (2) organisms were again plated, as described above. Colloidal silver test discs were placed on each Ag plate, while the control plates had none. The plates were incubated as described above and examined under the binocular microscope. The colloidal silver *E. coli* exhibited moderate resistance to the bactericidal effects of the physical colloidal silver, while the *Klebsiella* again exhibited moderate sensitivity. All controls exhibited full growth.

Example 20

Augmenting a Physical Catalyst with a Spectral Catalyst

To demonstrate that oxygen and hydrogen can combine to form water utilizing a spectral catalyst to augment a physical catalyst, electrolysis of water was performed to provide the necessary oxygen and hydrogen starting gases, as in Example 1.

Two quartz flasks (A and B) were connected separately after the Drierite column, each with its own set of vacuum and pressure gauges. Platinum powder (about 31 mg) was placed in each flask. The flasks were filled with electrolytically produced stoichiometric amounts of $H_2$ and $O_2$ to 120 mm Hg. The flasks were separated by a stopcock from the electrolysis system and from each other. The pressure in each flask was recorded over time as the reaction proceeded over the physical platinum catalyst. The reaction combines three (3) moles of gases, (i.e., two (2) moles $H_2$ and one (1) mole $O_2$), to produce two (2) moles $H_2O$. This decrease in molarity, and hence progress of the reaction, can be monitored by a decrease in pressure "P" which is proportional, via the ideal gas law, ($PV=nRT$), to molarity "n". A baseline rate of reaction was thus obtained. Additionally, the test was repeated filling each flask with $H_2$ and $O_2$ to 220 mm Hg. Catalysis of the reaction by only the physical catalyst yielded two baseline reaction curves which were in good agreement between flasks A and B, and for both the 110 mm and 220 mm Hg tests.

Next, the traditional physical platinum catalyst in flask A was augmented with spectral catalyst platinum emissions from two (2) parallel Fisher Scientific Hollow Cathode Platinum Lamps, as in Example 1, which were positioned approximately two (2) cm from flask A. The test was repeated as described above, separating the two (2) flasks from each other and monitoring the rate of the reaction via the pressure decrease in each. Flask B served as a control flask. In flask A, the oxygen and hydrogen gases, as well as the physical platinum catalyst, were directly irradiated with emissions from the Pt lamp spectral catalyst.

Rate of reaction in the control flask B, was in good agreement with previous baseline rates. Rate of reaction in flask "A", wherein physical platinum catalyst was augmented with the platinum spectral pattern, exhibited an overall mean increase of 60%, with a maximal increase of 70% over the baseline and flask B.

In this Example, targeted spectral energies were used to change the chemical reaction properties of a solid catalyst in a gas phase (heterogeneous) reaction system.

Example 21

Replacing a Physical Catalyst with a Fine Structure Heterodyned Frequency and Replacing a Physical Catalyst with a Fine Structure Frequency the Alpha Rotation-Vibration Constant Water was electrolyzed to produce stoichiometric amounts of hydrogen and oxygen gases as described above herein. Additionally, a dry ice cooled stainless steel coil was placed immediately after the Drierite column. After vacuum removal of all gases in the system, electrolysis was accomplished using a 12 V power source attached to the two electrodes, resulting in a production of hydrogen and oxygen gases. After passing through the Drierite column, the hydrogen and oxygen gases passed through vacuum tubing connected to positive and negative pressure gauges, through the dry ice cooled stainless steel coil and then to a 1,000 ml round, quartz flask. A strip of filter paper impregnated with dry (blue) cobalt was in the bottom of the quartz flask, as an indicator of the presence or absence of water.

The entire system was vacuum evacuated to a pressure of about 700 mm Hg below atmospheric pressure. Electrolysis was performed, producing hydrogen and oxygen gases in stoichiometric amounts, to result in a pressure of about 220 mm Hg above atmospheric pressure. The center of the quartz flask, now containing hydrogen and oxygen gases, was irradiated for approximately 12 hours with continuous microwave electromagnetic radiation emitted from a Hewlett Packard microwave spectroscopy system which included an HP 83350B Sweep Oscillator, an HP 8510B Network Analyzer and an HP 8513A Reflection Transmission Test Set. The frequency used was 21.4 GHz, which corresponds to a fine splitting constant, the alpha rotation-vibration constant, of the hydroxy intermediate, and is thus a harmonic resonant heterodyne for the hydroxy radical. The cobalt strip changed strongly in color to pink which indicated the presence of water in the quartz flask, whose creation was catalyzed by a harmonic resonant heterodyne frequency for the hydroxy radical.

In this Example, targeted spectral energies were used to control a gas phase chemical reaction.

Example 22

Replacing a Physical Catalyst with a Hyperfine Splitting Frequency

An experimental dark room was prepared, in which there is no ambient light, and which can be totally darkened. A shielded, ground room (Ace Shielded Room, Ace, Philadelphia, Pa., US, Model A6H3-16; 8 feet wide, 17 feet long, and 8 feet high (about 2. meters×5.2 meters×2.4 meters) copper mesh) was installed inside the dark room.

Hydrogen peroxide (3%) was placed in nippled quartz tubes, which were then inverted in beakers filled with (3%) hydrogen peroxide, as described in greater detail herein. The tubes were allowed to rest for about 18 hours in the dark room, covered with non-metallic light blocking hoods (so that the room could be entered without exposing the tubes to light). Baseline measurements of gases in the nippled tubes were then performed.

Three nippled RF tubes were placed on a wooden grid table in the shielded room, in the center of grids 4, 54, and 127; corresponding to distances of about 107 cm, 187 cm, and 312 cm respectively, from a frequency-emitting antenna (copper tubing 15 mm diameter, 4.7 m octagonal circumference, with the center frequency at approximately 6.5 MHz. A 25 watt, 17 MHz signal was sent to the antenna. This frequency corresponds to a hyperfine splitting frequency of the hydrogen atom, which is a transient in the dissociation of hydrogen peroxide. The antenna was pulsed continuously by a BK Precision RF Signal Generator Model 2005A, and amplified by an Amplifier Research amplifier, Model 25A-100. A control tube was placed on a wooden cart immediately adjacent to the shielded room, in the dark room. All tubes were covered with non-metallic light blocking hoods.

After about 18 hours, gas production from dissociation of hydrogen peroxide and resultant oxygen formation in the nippled tubes was measured. The RF tube closest to the antenna produced 11 mm length gas in the capillary (34 $mm^3$), the tube intermediate to the antenna produced a 5 mm length (10 $mm^3$) gas, and the RF tube farthest from the antenna produced no gas. The control tube produced 1 mm gas. Thus, it can be concluded that the RF hyperfine splitting frequency for hydrogen increased the reaction rate approximately five (5) to ten (10) times.

In this Example, targeted spectral energy was used to control a chemical reaction in a liquid phase, resulting in a transformation to a gas phase.

Example 23

Replacing a Physical Catalyst with a Magnetic Field

Hydrogen peroxide (15%) was placed in nippled quartz tubes, which were then inverted in beakers filled with (15%) hydrogen peroxide, as described above. The tubes were allowed to rest for about four (4) hours on a wooden table in a shielded cage, in a dark room. Baseline measurements of gases in the nippled tubes were then performed.

Remaining in the shielded cage, in the dark room, two (2) control tubes were left on a wooden table as controls. Two (2) magnetic field tubes were placed on the center platform of an ETS Helmholtz single axis coil, Model 6402, 1.06 gauss/Ampere, pulsed at about 83 Hz by a BK Precision 20 MHz Sweep/Function Generator, Model 4040. The voltage output of the function generator was adjusted to produce an alternating magnetic field of about 19.5 milliGauss on the center platform of the Helmholtz Coil, as measured by a Holaday Model HI-3627, three (3) axis ELF magnetic field meter and probe. Hydrogen atoms, which are a transient in the dissociation of hydrogen peroxide, exhibit nuclear magnetic resonance via Zeeman splitting at this applied frequency and applied magnetic field strength. Thus, frequency of the alternating magnetic field was resonant with the hydrogen transients.

After about 18 hours, gas production from dissociation of hydrogen peroxide and resultant oxygen formation in the nippled tubes was measured. The control tubes averaged about 180 mm gas formation (540 mm$^3$) while the tubes exposed to the alternating magnetic field produced about 810 mm gas (2,430 mm$^3$), resulting in an increase in the reaction rate of approximately four (4) times.

Example 24

Negatively Catalyzing a Reaction with an Electric Field

Hydrogen peroxide (15%) was placed in four (4) nippled quartz tubes which were inverted in hydrogen peroxide (15%) filled beakers, as described in greater detail above herein. The tubes were placed on a wooden table, in a shielded room, in a dark room. After four (4) hours, baseline measurements were taken of the gas in the capillary portion of the tubes.

An Amplifier Research self-contained electromagnetic mode cell ("TEM") Model TC1510A had been placed in the dark, shielded room. A sine wave signal of about 133 MHz was provided to the TEM cell by a BK Precision RF Signal Generator, Model 2005A, and an Amplifier Research amplifier, Model 25A100. Output levels on the signal generator and amplifier wave adjusted to produce an electric field (E-field) of about five (5) V/m in the center of the TEM cell, as measured with a Holaday Industries electric field probe, Model HI-4433GRE, placed in the center of the lower chamber.

Two of the hydrogen peroxide filled tubes were placed in the center of the upper chamber of the TEM cell, about 35 cm from the wall of the shielded room. The other two (2) tubes served as controls and were placed on a wooden table, also about 35 cm from the same wall of the shielded, dark room, and removed from the immediate vicinity of the TEM cell, so that there was no ambient electric field, as confirmed by E-field probe measurements.

The 133 MHz alternating sine wave signal delivered to the TEM cell was well above the typical line width frequency at room temperature (e.g., about 100 KHz) and was theorized to be resonant with an n=20 Rydberg state of the hydrogen atom as derived from $$\Delta E = c E^{3/4}$$

where E is the change in energy in cm$^{-1}$, c is 7.51+/−0.02 for the hydrogen state n=20 and E is the electric field intensity in (Kv/cm)$^2$.

After about five (5) hours of exposure to the electric field, the mean gas production in the tubes subjected to the E-field was about 17.5 mm, while mean gas production in the control tubes was about 58 mm.

While not wishing to be bound by any particular theory or explanation, it is believed that the alternating electric field resonated with an upper energy level in the hydrogen atoms, producing a negative Stark effect, and thereby negatively catalyzing the reaction.

Example 25

Augmentation of a Physical Catalyst by Irradiating Reactants/Transients with a Spectral Catalyst Hydrogen and oxygen gases were produced in stoichiometric amounts by electrolysis, as previously described in greater detail above herein. A stainless steel coil cooled in dry ice was placed immediately after the Drierite column. Positive and negative pressure gauges were connected after the coil, and then a 1,000 ml round quartz flask was sequentially connected with a second set of pressure gauges.

At the beginning of each experimental run, the entire system was vacuum evacuated to a pressure of about minus 650 mm Hg. The system was sealed for about 15 minutes to confirm the maintenance of the generated vacuum and integrity of the connections. Electrolysis of water to produce hydrogen and oxygen gases was performed, as described previously.

Initially, about 10 mg of finely divided platinum was placed into the round quartz flask. Reactant gases were allowed to react over the platinum and the reaction rate was monitored by increasing the rate of pressure drop over time, as previously described. The starting pressure was approximately in the mid-90's mm Hg positive pressure, and the ending pressure was approximately in the low 30's over the amount of time that measurements were taken. Two (2) control runs were performed, with reaction rates of about 0.47 mm Hg/minute and about 0.48 mm Hg/minute.

For the third run, a single platinum lamp was applied, as previously described, except that the operating current was reduced to about eight (8) mA and the lamp was positioned through the center of the flask to irradiate only the reactant/transient gases, and not the physical platinum catalyst. The reaction rate was determined, as described above, and was found to be about 0.63 mm Hg/minute, an increase of 34%.

Example 26

Apparent Poisoning of a Reaction by the Spectral Pattern of a physical poison

The conversion of hydrogen and oxygen gases to water, over a stepped platinum physical catalyst, is known to be poisoned by gold. Addition of gold to this platinum catalyzed reaction reduces reaction rates by about 95%. The gold blocks only about one sixth of the platinum binding sites, which according to prior art, would need to be blocked to poison the physical catalyst to this degree. Thus, it was theorized that a spectral interaction of the physical gold with the physical platinum and/or reaction system could also be responsible for the poisoning effects of gold on the reaction. It was further theorized that addition of the gold spectral pattern to the reaction catalyzed by physical platinum could also poison the reaction.

Hydrogen and oxygen gases were produced by electrolysis, as described above in greater detail. Finely directed platinum, about 15 mg, was added to the round quartz flask.

Starting pressures were about in the 90's mm Hg positive pressure, and ending pressures were about in the 20's mm Hg over the amount of time that measurements were taken. Reaction rates were determined as previously described. The first control run revealed a reaction rate of about 0.81 mm Hg/minute.

In the second run, a Fisher Hollow Cathode Gold lamp was applied, as previously described, at an operating frequency of about eight (8) mA, (80% maximum current), through about the center of the round flask. The reaction rate increased to about 0.87 mm Hg/minute.

A third run was then performed on the same reaction flask and physical platinum that had been in the flask exposed to the gold spectral pattern. The reaction rate decreased to about 0.75 mm Hg/minute.

In this Example, targeted spectral energies were used to control an environmental reaction condition (poison) and change the chemical reaction properties of a physical catalyst in a heterogeneous catalyst reaction system.

In these experiments, targeted spectral energies were used to change the chemical and material properties of solutions, resulting in altered electrochemical reaction rates and corrosion of solids.

What is claimed is:

1. A method for conditioning at least one conditionable participant in a crystallization reaction system comprising:
    applying at least one electromagnetic conditioning frequency to at least one conditionable participant to cause at least one of the formation, stimulation and stabilization of at least one conditioned participant, whereby said at least one electromagnetic conditioning frequency comprises at least one frequency selected from the group consisting of direct resonance conditioning frequencies, harmonic resonance conditioning frequencies and non-harmonic heterodyne conditioning resonance frequencies wherein said conditioned participant resonantly transfers energy with at least one participant in said crystallization reaction system; and
    using said conditioned participant in said crystallization reaction system to enhance the rate of at least one reaction in said crystallization reaction system.

2. The method of claim 1, further comprising applying at least one spectral energy pattern to said crystallization reaction system.

3. The method of claim 2, wherein a rate of at least one reaction in said crystallization reaction system is accelerated.

\* \* \* \* \*